United States Patent
Bit et al.

(10) Patent No.: US 10,442,786 B2
(45) Date of Patent: Oct. 15, 2019

(54) BENZIMIDAZOLE DERIVATIVES AS BROMODOMAIN INHIBITORS

(71) Applicant: GLAXOSMITHKLINE INTELLECTUAL PROPERTY DEVELOPMENT LIMITED, Brentford, Middlesex (GB)

(72) Inventors: Rino Antonio Bit, Stevenage (GB); John Alexander Brown, Stevenage (GB); Philip G. Humphreys, Stevenage (GB); Katherine Louise Jones, Stevenage (GB)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 7 days.

(21) Appl. No.: 15/559,556

(22) PCT Filed: Mar. 17, 2016

(86) PCT No.: PCT/EP2016/055792
§ 371 (c)(1),
(2) Date: Sep. 19, 2017

(87) PCT Pub. No.: WO2016/146738
PCT Pub. Date: Sep. 22, 2016

(65) Prior Publication Data
US 2018/0044317 A1  Feb. 15, 2018

(30) Foreign Application Priority Data
Mar. 19, 2015  (GB) .................... 1504689.9

(51) Int. Cl.
| | |
|---|---|
| *C07D 401/04* | (2006.01) |
| *C07D 401/14* | (2006.01) |
| *C07D 405/14* | (2006.01) |
| *C07D 413/14* | (2006.01) |
| *A61P 29/00* | (2006.01) |
| *A61P 35/00* | (2006.01) |
| *A61P 37/00* | (2006.01) |

(52) U.S. Cl.
CPC ............ *C07D 401/04* (2013.01); *A61P 29/00* (2018.01); *A61P 35/00* (2018.01); *A61P 37/00* (2018.01); *C07D 401/14* (2013.01); *C07D 405/14* (2013.01); *C07D 413/14* (2013.01); *C07B 2200/13* (2013.01)

(58) Field of Classification Search
CPC .................................................. C07D 401/04
See application file for complete search history.

(56) References Cited

U.S. PATENT DOCUMENTS

2014/0336190 A1  11/2014  Aktoudianakis
2015/0051208 A1  2/2015  Engelhardt

FOREIGN PATENT DOCUMENTS

| WO | WO 2007/117399 A2 | 10/2007 | |
|---|---|---|---|
| WO | WO 2012/047538 A1 | 4/2012 | |
| WO | WO 2014/145051 A1 | 9/2014 | |
| WO | WO 2014/160873 A1 | 10/2014 | |
| WO | WO-2016146755 A1 * | 9/2016 | ........... C07D 405/14 |

OTHER PUBLICATIONS

Garnier, Jean-Marc, et al. "BET Bromodomain Inhibitors: a patent review." Expert Opin. Ther. Patents (2014), vol. 24, Issue 2, pp. 185-199. (Year: 2014).*
Goldbergova, M.P., et al. "RANTES, MCP-1 chemokines and factors describing rheumatoid arthritis." Molecular Immunology. (2012), vol. 52, pp. 273-278. (Year: 2012).*
WebMD. "Rheumatoid Arthritis Health Center." (Jan. 17, 2013). Accessed Oct. 15, 2018. Available from: < https://web.archive.org/web/20130117044355/https://www.webmd.com/rheumatoid-arthritis/rheumatoid-arthritis-prevention >. (Year: 2013).*

* cited by examiner

*Primary Examiner* — Andrew D Kosar
*Assistant Examiner* — John S Kenyon
(74) *Attorney, Agent, or Firm* — Donald Huddler; Duke M. Fitch; Edward R. Gimmi

(57) ABSTRACT

Compounds of formula (I) and salts thereof:

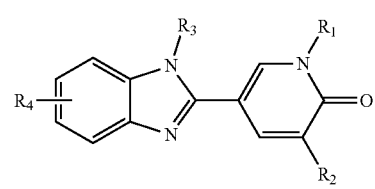

wherein $R_1$, $R_2$, $R_3$, $R_4$ are defined herein. Compounds of formula (I) and salts thereof have been found to inhibit the binding of the BET family of bromodomain proteins to, for example, acetylated lysine residues and thus may have use in therapy, for example in the treatment of autoimmune and inflammatory diseases, such as rheumatoid arthritis; and cancers.

22 Claims, No Drawings

BENZIMIDAZOLE DERIVATIVES AS BROMODOMAIN INHIBITORS

This application is a § 371 of International Application No. PCT/EP2016/055792, filed 17 Mar. 2016, which claims the priority of GB 1504689.9, filed 19 Mar. 2015, which are incorporated herein in their entireties.

FIELD OF THE INVENTION

The present invention relates to compounds, processes for their preparation, compositions containing them, and to their use in the treatment of various disorders in particular inflammatory and autoimmune diseases, such as rheumatoid arthritis; and cancers.

BACKGROUND TO THE INVENTION

The genomes of eukaryotic organisms are highly organised within the nucleus of the cell. The long strands of duplex DNA are wrapped around an octomer of histone proteins (most usually comprising two copies of histones H2A, H2B, H3 and H4) to form a nucleosome. This basic unit is then further compressed by the aggregation and folding of nucleosomes to form a highly condensed chromatin structure. A range of different states of condensation are possible, and the tightness of this structure varies during the cell cycle, being most compact during the process of cell division. Chromatin structure plays a critical role in regulating gene transcription, which cannot occur efficiently from highly condensed chromatin. The chromatin structure is controlled by a series of post translational modifications to histone proteins, notably histones H3 and H4, and most commonly within the histone tails which extend beyond the core nucleosome structure. These modifications include acetylation, methylation, phosphorylation, ubiquitinylation, SUMOylation. These epigenetic marks are written and erased by specific enzymes, which place tags on specific residues within the histone tail, thereby forming an epigenetic code, which is then interpreted by the cell to allow regulation of gene expression.

Histone acetylation is most usually associated with the activation of gene transcription, as the modification relaxes the interaction of the DNA and the histone octomer by changing the electrostatics. In addition to this physical change, specific proteins recognise and bind to acetylated lysine residues within histones to read the epigenetic code. Bromodomains are small (~110 amino acid) distinct domains within proteins that bind to acetylated lysine resides commonly but not exclusively in the context of histones. There is a family of around 50 proteins known to contain bromodomains, and they have a range of functions within the cell.

The BET family of bromodomain containing proteins comprises 4 proteins (BRD2, BRD3, BRD4 and BRDT) which contain tandem bromodomains capable of binding to two acetylated lysine residues in close proximity, increasing the specificity of the interaction. Numbering from the N-terminal end of each BET protein the tandem bromodomains are typically labelled Binding Domain 1 (BD1) and Binding Domain 2 (BD2) (Chung et al, *J Med. Chem.*, 2011, 54, 3827-3838). Inhibiting the binding of a BET protein to acetylated lysine residues has the potential to ameliorate progression of several diseases, including but not limited to, cancer (Dawson M. A. et al, *Nature*, 2011: 478(7370):529-33; Wyce, A. et al, *Oncotarget*. 2013: 4(12):2419-29), sepsis (Nicodeme E. et al, *Nature*, 2010: 468(7327):1119-23), autoimmune and inflammatory diseases such as rheumatoid arthritis and multiple sclerosis (Mele D. A. et al, *Journal of Experimental Medicine*, 2013: 210(11):2181-90), heart failure (Anand P. et al, *Cell*, 2013: 154(3):569-82), and lung fibrosis (Tang X et al, *Molecular Pharmacology*, 2013: 83(1):283-293).

There exists a need for chemical compounds which inhibit the activity of bromodomains, in particular compounds that inhibit the binding of BET proteins to acetylated lysine residues and hence have utility in the treatment of, for example, autoimmune and inflammatory diseases, and cancers.

SUMMARY OF THE INVENTION

In a first aspect, the present invention is directed to compounds of formula (I) and salts thereof:

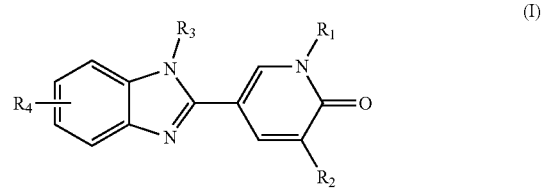

wherein
$R_1$ and $R_2$ are each independently hydrogen or methyl with the proviso that at least one of $R_1$ and $R_2$ is methyl;
$R_3$ is $C_{1-6}$alkyl, $C_{1-6}$alkoxy, cycloalkyl, heterocycloalkyl, or —$CHR_5(CH_2)_aR_6$;
$R_4$ is attached at the 5 or 6 position of the benzimidazole and represents

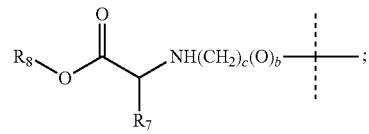

$R_5$ is hydrogen, $C_{1-3}$alkyl, $C_{1-3}$alkoxy, or —$(CH_2)_dOR_9$;
$R_6$ is hydrogen, $C_{1-3}$alkyl, $C_{1-3}$alkoxy, —$(CH_2)_eOR_{10}$, hydroxyl, —$NR_{11}R_{12}$, halo, cycloalkyl, heterocycloalkyl, aryl, or heteroaryl, wherein said $C_{1-3}$alkyl, $C_{1-3}$alkoxy, —$(CH_2)_eOR_{10}$, cycloalkyl, heterocycloalkyl, aryl or heteroaryl may be optionally substituted with one or two substituents independently selected from the group consisting of $C_{1-3}$alkyl, $C_{1-3}$alkoxy, halo, —$CH_2OH$, —COOH, and —$COCH_3$;
$R_7$ is hydrogen, $C_{1-6}$alkyl, —$(CH_2)_g$cycloalkyl, —$(CH_2)_h$heterocycloalkyl, or —$CR_{13}R_{14}R_{15}$;
$R_8$ is hydrogen, $C_{1-6}$alkyl, cycloalkyl, heterocycloalkyl, or —$CHR_{16}R_{17}$ wherein said $C_{1-6}$alkyl is optionally substituted with $C_{1-3}$alkoxy, and wherein $R_{16}$ is hydrogen or $C_{1-3}$alkyl and $R_{17}$ is cycloalkyl or heterocycloalkyl;
$R_9$, $R_{10}$, $R_{11}$, $R_{12}$, $R_{14}$, $R_{15}$, and $R_{18}$ are each independently hydrogen or $C_{1-3}$alkyl;
$R_{13}$ is hydrogen, hydroxyl, —$CH_2OR_{18}$, halo, —COOH, —$CONH_2$, 1H-imidazol-4-yl, —SH, —SeH, $C_{1-3}$alkyl, $C_{1-3}$alkoxy, phenyl, or 4-hydroxyphenyl, wherein said $C_{1-3}$alkyl or $C_{1-3}$alkoxy may be optionally substituted with halo or hydroxyl, —$NHC(=NH_2)NH_2$, —$NH_2$, —COOH, —$CONH_2$, or —$SCH_3$;

a is 0, 1, 2 or 3;
b is 0 or 1;
c is 1, 2 or 3 with the proviso that when b is 1, c is 2 or 3;
d and e are each independently 1 or 2; and
g and h are each independently 0, 1 or 2.

Compounds of formula (I) and salts thereof have been found to inhibit the binding of bromodomain proteins; in particular, the binding of the BET family of bromodomain proteins to, for example, acetylated lysine residues. Compounds of formula (I), or pharmaceutically acceptable salts thereof, may thus have use in therapy, for example in the treatment of autoimmune and inflammatory diseases, such as rheumatoid arthritis; and cancers.

The present invention is further directed to methods of treatment of autoimmune and inflammatory diseases and cancers through inhibition of the function of bromodomain proteins, for example members of the BET family of bromodomain proteins, which comprises administering to a subject in need thereof, a therapeutically effective amount of a compound of formula (I), or a pharmaceutically acceptable salt thereof.

In a further aspect, the present invention is directed to pharmaceutical compositions comprising a compound of formula (I), or a pharmaceutically acceptable salt thereof, and one or more pharmaceutically acceptable excipients.

DETAILED DESCRIPTION OF THE INVENTION

Definitions

As used herein, the term "bromodomain" refers to evolutionary and structurally conserved modules (approximately 110 amino acids in length) that bind acetylatedlysine residues, such as those on the N-terminal tails of histones. They are protein domains that are found as part of much larger bromodomain containing proteins (BCPs), many of which have roles in regulating gene transcription and/or chromatin remodelling. The human genome encodes for at least 57 bromodomains.

As used herein, the term "BET" refers to the bromodomain and extraterminal domain family of bromodomain containing proteins which include BRD2, BRD3, BRD4 and BRDT.

As used herein, the term "BET inhibitor" refers to a compound that is capable of inhibiting the binding of one or more BET family bromodomain containing proteins (e.g. BRD2, BRD3, BRD4 or BRDT) to, for example, acetylated lysine residues.

As used herein, the term "alkyl" refers to a saturated hydrocarbon chain, straight or branched, having the specified number of carbon atoms. For example, $C_{1-6}$ alkyl refers to an alkyl group having from 1 to 6 carbon atoms. Unless otherwise stated, alkyl groups are unsubstituted. The term "alkyl" includes, but is not limited to, methyl, ethyl, propyl (n-propyl and isopropyl), butyl (n-butyl, sec-butyl, isobutyl and tert-butyl), pentyl, and hexyl.

As used herein, the term "alkoxy" refers to an —O-alkyl group wherein "alkyl" is defined above.

As used herein, the term "cycloalkyl" refers to a saturated, monocyclic, hydrocarbon ring having 3 (cyclopropyl), 4 (cyclobutyl), 5 (cyclopentyl), 6 (cyclohexyl) or 7 (cycloheptyl) carbon atoms.

As used herein, the term "heterocycloalkyl" refers to a saturated or unsaturated 3 to 7 membered monocyclic or bicyclic ring, which must contain 1 or 2 non-carbon atoms, which are selected from nitrogen, oxygen, and sulfur. Heterocycloalkyl groups may contain one or more C(O), S(O) or $SO_2$ groups. However, heterocycloalkyl groups are not aromatic. Heterocycloalkyl groups containing more than one heteroatom may contain different heteroatoms. "5 or 6 membered heterocycloalkyl" refers to a saturated or unsaturated 5 or 6 membered monocyclic ring, which must contain 1 or 2 non-carbon atoms, which are selected from nitrogen, oxygen, and sulfur. Heterocycloalkyl includes, but is not limited to, pyrrolidine, piperidine, piperazine, oxetane, tetrahydrofuran, tetrahydro-2H-pyran, morpholine, morpholine-3-one, piperidin-2-one, pyrimidine-2,4(1H,3H)-dione, thiomorpholine, and thiomorpholine 1,1-dioxide.

As used herein, the term "aryl" refers to a monocyclic or bicyclic, hydrocarbon, aromatic radical. Aryl includes, for example, phenyl and naphthyl.

As used herein, the term "heteroaryl" refers to a monocyclic or bicyclic, aromatic radical containing one or more heteroatoms selected from S, N and O. Illustrative examples of heteroaryl useful in the present invention include, but are not limited to, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, triazinyl, benzofuranyl, isobenzofuryl, 2,3-dihydrobenzofuryl, 1,3-benzodioxolyl, dihydrobenzodioxinyl, benzothienyl, indolizinyl, indolyl, isoindolyl, dihydroindolyl, benzimidazolyl, dihydrobenzimidazolyl, benzoxazolyl, dihydrobenzoxazolyl, benzthiazolyl, benzoisothiazolyl, dihydrobenzoisothiazolyl, indazolyl, imidazopyridinyl, pyrazolopyridinyl, benzotriazolyl, triazolopyridinyl, purinyl, quinolinyl, tetrahydroquinolinyl, isoquinolinyl, tetrahydroisoquinolinyl, quinoxalinyl, cinnolinyl, phthalazinyl, quinazolinyl, 1,5-naphthyridinyl, 1,6-naphthyridinyl, 1,7-naphthyridinyl, 1,8-naphthyridinyl, and pteridinyl.

As used herein, the phrase "optionally substituted" indicates that a group may be unsubstituted or substituted with one or more substituents as defined herein. "Substituted" in reference to a group indicates that a hydrogen atom attached to a member atom within a group is replaced by one of the defined substituents.

As used herein, the term "pharmaceutically acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively. Furthermore, pharmaceutically-acceptable salts of the compound of formula (I) may be prepared during further processing of the free acid or base form, for example in situ during manufacture into a pharmaceutical formulation.

As used herein, the phrase "attached at the 5 or 6 position of the benzimidazole" refers to attachment of the specified substituent at the 5 or 6 position as denoted in the structure below:

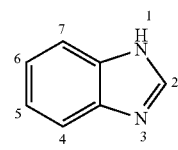

As used herein, the term "treatment" refers to prophylaxis of the condition, ameliorating or stabilising the specified condition, reducing or eliminating the symptoms of the condition, slowing or eliminating the progression of the condition, and preventing or delaying reoccurrence of the condition in a previously afflicted patient or subject. In one embodiment, treatment refers to ameliorating or stabilising a specified condition, reducing or eliminating the symptoms of the condition, or slowing or eliminating the progression of the condition.

As used herein, the term "therapeutically effective amount" refers to the quantity of a compound of formula (I), or a pharmaceutically acceptable salt thereof, which will elicit the desired biological response in an animal or human body.

As used herein, the term "subject" refers to an animal or human body.

It is to be understood that references herein to "compound(s) of the invention" mean a compound of formula (I) as the free base, or as a salt, for example a pharmaceutically acceptable salt.

STATEMENT OF THE INVENTION

In a first aspect, the present invention provides compounds of formula (I), or salts thereof:

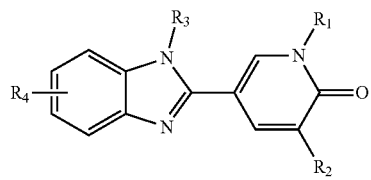

(I)

wherein
$R_1$ and $R_2$ are each independently hydrogen or methyl with the proviso that at least one of $R_1$ and $R_2$ is methyl;
$R_3$ is $C_{1-6}$alkyl, $C_{1-6}$alkoxy, cycloalkyl, heterocycloalkyl, or —$CHR_5(CH_2)_aR_6$;
$R_4$ is attached at the 5 or 6 position of the benzimidazole and represents

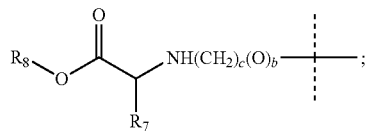

$R_5$ is hydrogen, $C_{1-3}$alkyl, $C_{1-3}$alkoxy, or —$(CH_2)_dOR_9$;
$R_6$ is hydrogen, $C_{1-3}$alkyl, $C_{1-3}$alkoxy, —$(CH_2)_eOR_{10}$, hydroxyl, —$NR_{11}R_{12}$, halo, cycloalkyl, heterocycloalkyl, aryl, or heteroaryl, wherein said $C_{1-3}$alkyl, $C_{1-3}$alkoxy, —$(CH_2)_eOR_{10}$, cycloalkyl, heterocycloalkyl, aryl or heteroaryl may be optionally substituted with one or two substituents independently selected from the group consisting of $C_{1-3}$alkyl, $C_{1-3}$alkoxy, halo, —$CH_2OH$, —COOH, and —$COCH_3$;
$R_7$ is hydrogen, $C_{1-6}$alkyl, —$(CH_2)_g$cycloalkyl, —$(CH_2)_h$heterocycloalkyl, or —$CR_{13}R_{14}R_{15}$;
$R_8$ is hydrogen, $C_{1-6}$alkyl, cycloalkyl, heterocycloalkyl, or —$CHR_{16}R_{17}$ wherein said $C_{1-6}$alkyl is optionally substituted with $C_{1-3}$alkoxy, and wherein $R_{16}$ is hydrogen or $C_{1-3}$alkyl and $R_{17}$ is cycloalkyl or heterocycloalkyl;

$R_9$, $R_{10}$, $R_{11}$, $R_{12}$, $R_{14}$, $R_{15}$, and $R_{18}$ are each independently hydrogen or $C_{1-3}$alkyl;
$R_{13}$ is hydrogen, hydroxyl, $CH_2OR_{18}$, halo, —COOH, —$CONH_2$, 1H-imidazol-4-yl, —SH, —SeH, $C_{1-3}$alkyl, $C_{1-3}$alkoxy, phenyl, or 4-hydroxyphenyl, wherein said $C_{1-3}$alkyl or $C_{1-3}$alkoxy may be optionally substituted with halo or hydroxyl, —NHC(=NH$_2$)NH$_2$, —NH$_2$, —COOH, —$CONH_2$, or —$SCH_3$;
a is 0, 1, 2 or 3;
b is 0 or 1;
c is 1, 2 or 3 with the proviso that when b is 1, c is 2 or 3;
d and e are each independently 1 or 2; and
g and h are each independently 0, 1 or 2.

In a further aspect of the present invention, $R_1$ and $R_2$ are each methyl.

In a further embodiment, $R_3$ represents 5 or 6 membered heterocycloalkyl or the group —$CHR_5R_6$ wherein $R_5$ represents hydrogen or $C_{1-3}$alkyl and $R_6$ represents 5 or 6 membered heterocycloalkyl, further wherein said heterocycloalkyl may be optionally substituted with $C_{1-3}$alkyl, or $C(O)CH_3$.

In a further embodiment, $R_6$ is selected from the group consisting of:

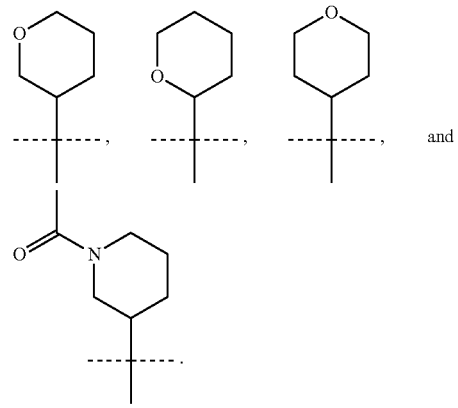

and

In a further embodiment of the present invention, $R_6$ is:

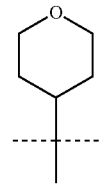

In a further embodiment of the present invention, $R_3$ is the group —$CHR_5R_6$ wherein $R_5$ is hydrogen and $R_6$ is

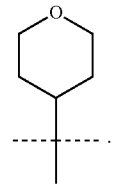

In a further embodiment of the present invention, $R_3$ is selected from the group consisting of:

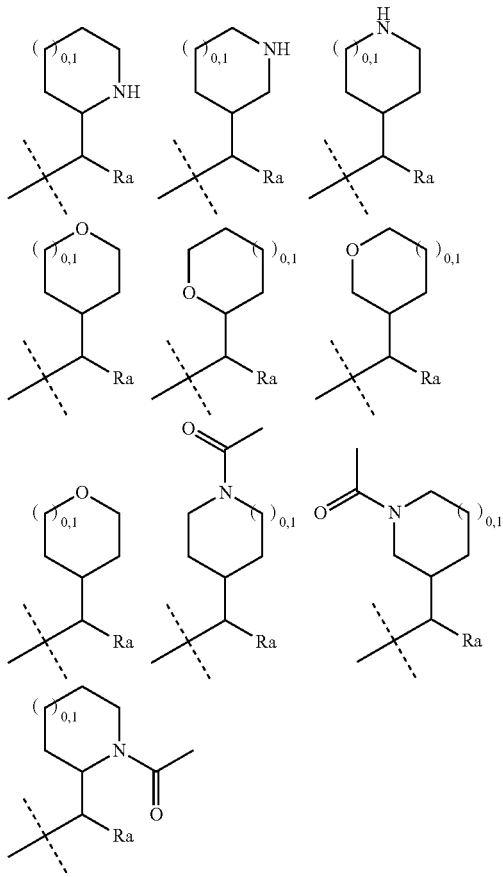

wherein Ra represent hydrogen or $C_{1-3}$alkyl.

In a further aspect of the present invention, $R_5$ is hydrogen.

In a further aspect of the present invention, $R_3$ is the group —$CHR_5(CH_2)_aR_6$, and further wherein $R_5$ is —$(CH_2)_dOR_9$, a is 0 and $R_6$ is —$(CH_2)_eOR_{10}$.

In a further aspect of the present invention, $R_5$ and R % each represent —$CH_2OCH_3$.

In a further aspect of the present invention, $R_4$ is attached at the 5 position of the benzimidazole.

In a further aspect of the present invention, b is 0.

In a further aspect of the present invention, c is 1.

In a further aspect of the present invention, $R_4$ represents:

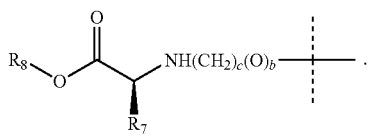

In a further aspect of the present invention, $R_7$ is hydrogen, methyl, isopropyl, sec-butyl, isobutyl, —$CH_2$-phenyl, —$CH_2$-4-hydroxyphenyl, —$CH_2OH$, —$CH(CH_3)OH$, —$CH_2SH$, —$CH_2SeH$, —$(CH_2)_2SCH_3$, —$CH_2COOH$, —$(CH_2)_2COOH$, —$CH_2CONH_2$, —$(CH_2)_2CONH_2$, —$(CH_2)_4NH_2$, —$(CH_2)_3NHC(=NH_2)NH_2$, or —$CH_2$-1H-imidazol-4-yl.

In a further aspect of the present invention, $R_7$ is isopropyl, sec-butyl, or —$CH(CH_3)OH$.

In a further aspect of the present invention, $R_7$ is —$CH(CH_3)OH$.

In a further aspect of the present invention, $R_7$ is (R)-1-hydroxyethyl.

In a further aspect of the present invention, $R_8$ is hydrogen.

In a further aspect of the present invention, $R_8$ is $C_{1-6}$alkyl or cycloalkyl.

In a further aspect of the present invention, $R_8$ is isopropyl, isobutyl or cyclopentyl.

In a further aspect of the present invention, $R_8$ is isopropyl.

The present invention covers all combinations of substituent groups referred to herein above.

In a further aspect, the present invention provides a compound of formula (Ia):

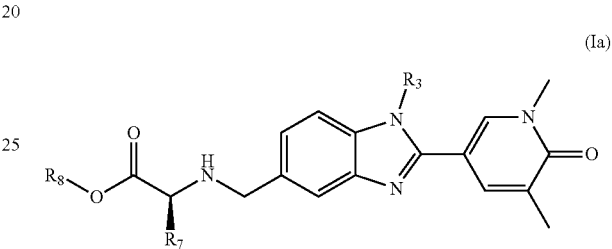

(Ia)

wherein $R_3$ is cycloalkyl, heterocycloalkyl, or the group —$CHR_5(CH_2)_aR_6$;

$R_5$ is hydrogen, $C_{1-3}$alkyl, or $C_{1-3}$alkoxy;

$R_6$ is cycloalkyl or heterocycloalkyl, wherein said cycloalkyl or heterocycloalkyl may be optionally substituted with one or two substituents selected from the group consisting of $C_{1-3}$alkyl, $C_{1-3}$alkoxy, halo, —$CH_2OH$, —COOH, and —$COCH_3$;

$R_7$ is hydrogen, $C_{1-6}$alkyl, —$(CH_2)_g$cycloalkyl, —$(CH_2)_h$heterocycloalkyl, or —$CR_{13}R_{14}R_{15}$;

$R_8$ is hydrogen, $C_{1-6}$alkyl, cycloalkyl or heterocycloalkyl, wherein said $C_{1-6}$alkyl is optionally substituted with $C_{1-3}$alkoxy;

$R_{13}$ is hydrogen, hydroxyl, —$CH_2OR_{18}$, halo, —COOH, —$CONH_2$, 1H-imidazol-4-yl, —SH, —SeH, $C_{1-3}$alkyl, $C_{1-3}$alkoxy, phenyl, or 4-hydroxyphenyl wherein said $C_{1-3}$alkyl or $C_{1-3}$alkoxy may be optionally substituted with halo, hydroxyl, —$NHC(=NH_2)NH_2$, —$NH_2$, —COOH, —$CONH_2$, or —$SCH_3$;

$R_{14}$, $R_{15}$ and $R_{18}$ are each independently hydrogen or $C_{1-3}$alkyl; and a, g and h are each independently 0, 1 or 2.

In a further aspect, the present invention provides a compound of formula (Ib):

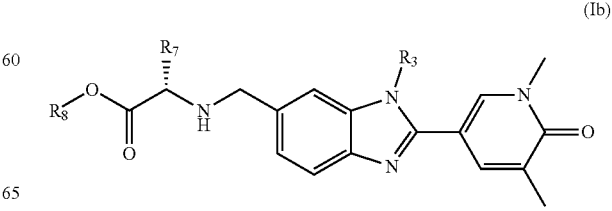

(Ib)

wherein $R_3$ is cycloalkyl, heterocycloalkyl, or the group —CHR$_5$(CH$_2$)$_a$R$_6$;

$R_5$ is hydrogen, C$_{1-3}$alkyl, or C$_{1-3}$alkoxy;

$R_6$ is cycloalkyl or heterocycloalkyl, wherein said cycloalkyl or heterocycloalkyl may be optionally substituted with one or two substituents selected from the group consisting of C$_{1-3}$alkyl, C$_{1-3}$alkoxy, halo, —CH$_2$OH, —COOH, and —COCH$_3$;

$R_7$ is hydrogen, C$_{1-6}$alkyl, —(CH$_2$)$_g$cycloalkyl, —(CH$_2$)$_h$heterocycloalkyl, or —CR$_{13}$R$_{14}$R$_{15}$;

$R_8$ is hydrogen, C$_{1-6}$alkyl, cycloalkyl, or heterocycloalkyl, wherein said C$_{1-6}$alkyl is optionally substituted with C$_{1-3}$alkoxy;

$R_{13}$ is hydrogen, hydroxyl, —CH$_2$OR$_{18}$, halo, —COOH, —CONH$_2$, 1H-imidazol-4-yl, —SH, —SeH, C$_{1-3}$alkyl, C$_{1-3}$alkoxy, phenyl, or 4-hydroxyphenyl wherein said C$_{1-3}$alkyl or C$_{1-3}$alkoxy may be optionally substituted with halo, hydroxyl, —NHC(=NH$_2$)NH$_2$, —NH$_2$, —COOH, —CONH$_2$, or —SCH$_3$;

$R_{14}$, $R_{15}$ and $R_{18}$ are each independently hydrogen or C$_{1-3}$alkyl; and a, g and h are each independently 0, 1 or 2.

In a further aspect, the present invention provides a compound of formula (Ia):

(Ia)

wherein $R_3$ is C$_{1-6}$alkyl, C$_{1-6}$alkoxy, cycloalkyl, heterocycloalkyl, or —CHR$_5$(CH$_2$)$_a$R$_6$;

$R_5$ is hydrogen, C$_{1-3}$alkyl, C$_{1-3}$alkoxy, or —(CH$_2$)$_d$OR$_9$;

$R_6$ is hydrogen, C$_{1-3}$alkyl, C$_{1-3}$alkoxy, —(CH$_2$)$_e$OR$_{10}$, hydroxyl, —NR$_{11}$R$_{12}$, halo, cycloalkyl, heterocycloalkyl, aryl, or heteroaryl, wherein said C$_{1-3}$alkyl, C$_{1-3}$alkoxy, —(CH$_2$)$_e$OR$_{10}$, cycloalkyl, heterocycloalkyl, aryl or heteroaryl may be optionally substituted with one or two substituents independently selected from the group consisting of C$_{1-3}$alkyl, C$_{1-3}$alkoxy, halo, —CH$_2$OH, —COOH, and —COCH$_3$;

$R_7$ is C$_{1-6}$alkyl, —CH$_2$OH, —CH$_2$OCH$_3$, —(CH$_2$)$_2$OCH$_3$, —CH(CH$_3$)OH, or —C(CH$_3$)$_2$OH;

$R_8$ is hydrogen, C$_{1-6}$alkyl, cycloalkyl, or heterocycloalkyl, wherein said C$_{1-6}$alkyl is optionally substituted with C$_{1-3}$alkoxy;

$R_9$, $R_{10}$, $R_{11}$, and $R_{12}$ are each independently hydrogen or C$_{1-3}$alkyl;

a is 0, 1 or 2; and d and e are each independently 1 or 2.

In a further aspect, the present invention provides a compound of formula (Ib):

(Ib)

wherein $R_3$ is C$_{1-6}$alkyl, C$_{1-6}$alkoxy, cycloalkyl, heterocycloalkyl, or —CHR$_5$(CH$_2$)$_a$R$_6$;

$R_5$ is hydrogen, C$_{1-3}$alkyl, C$_{1-3}$alkoxy, or —(CH$_2$)$_d$OR$_9$;

$R_6$ is hydrogen, C$_{1-3}$alkyl, C$_{1-3}$alkoxy, —(CH$_2$)$_e$OR$_{10}$, hydroxyl, —NR$_{11}$R$_{12}$, halo, cycloalkyl, heterocycloalkyl, aryl, or heteroaryl, wherein said C$_{1-3}$alkyl, C$_{1-3}$alkoxy, —(CH$_2$)$_e$OR$_{10}$, cycloalkyl, heterocycloalkyl, aryl or heteroaryl may be optionally substituted with one or two substituents independently selected from the group consisting of C$_{1-3}$alkyl, C$_{1-3}$alkoxy, halo, —CH$_2$OH, —COOH, and —COCH$_3$;

$R_7$ is C$_{1-6}$alkyl, —CH$_2$OH, —CH$_2$OCH$_3$, —(CH$_2$)$_2$OCH$_3$, —CH(CH$_3$)OH, or —C(CH$_3$)$_2$OH;

$R_8$ is hydrogen, C$_{1-6}$alkyl, cycloalkyl, or heterocycloalkyl, wherein said C$_{1-6}$alkyl is optionally substituted with C$_{1-3}$alkoxy;

$R_9$, $R_{10}$, $R_{11}$, and $R_{12}$ are each independently hydrogen or C$_{1-3}$alkyl;

a is 0, 1 or 2; and d and e are each independently 1 or 2.

In a further aspect, the present invention provides a compound of formula (Ia):

(Ia)

wherein $R_3$ is cycloalkyl, heterocycloalkyl, or —CHR$_5$(CH$_2$)$_a$R %;

$R_5$ is hydrogen or C$_{1-3}$alkyl;

$R_6$ is cycloalkyl or heterocycloalkyl, wherein said cycloalkyl or heterocycloalkyl may be optionally substituted with one or two substituents independently selected from the group consisting of C$_{1-3}$alkyl, C$_{1-3}$alkoxy, halo, —CH$_2$OH, —COOH, and —COCH$_3$;

$R_7$ is C$_{1-6}$alkyl, —CH$_2$OH, —CH$_2$OCH$_3$, —(CH$_2$)$_2$OCH$_3$, —CH(CH$_3$)OH, or —C(CH$_3$)$_2$OH;

$R_8$ is hydrogen, C$_{1-6}$alkyl, cycloalkyl, or heterocycloalkyl, wherein said C$_{1-6}$alkyl is optionally substituted with C$_{1-3}$alkoxy; and a is 0, 1 or 2.

In a further aspect, the present invention provides a compound of formula (Ib):

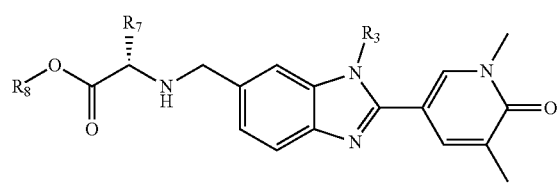
(Ib)

wherein $R_3$ is cycloalkyl, heterocycloalkyl, or —$CHR_5(CH_2)_aR_6$;

$R_5$ is hydrogen or $C_{1-3}$alkyl;

$R_6$ is cycloalkyl or heterocycloalkyl, wherein said cycloalkyl or heterocycloalkyl may be optionally substituted with one or two substituents independently selected from the group consisting of $C_{1-3}$alkyl, $C_{1-3}$alkoxy, halo, —$CH_2OH$, —COOH, and —$COCH_3$;

$R_7$ is $C_{1-6}$alkyl, —$CH_2OH$, —$CH_2OCH_3$, —$(CH_2)_2OCH_3$, —$CH(CH_3)OH$, or —$C(CH_3)_2OH$;

$R_8$ is hydrogen, $C_{1-6}$alkyl, cycloalkyl, or heterocycloalkyl, wherein said $C_{1-6}$alkyl is optionally substituted with $C_{1-3}$alkoxy; and a is 0, 1 or 2.

In a further aspect, the present invention provides a compound of formula (Ia):

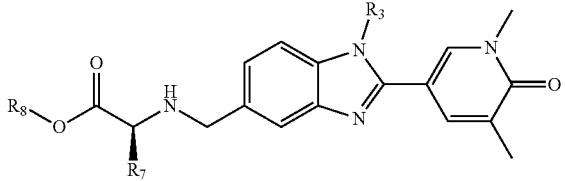
(Ia)

wherein $R_3$ is selected from the group consisting of:

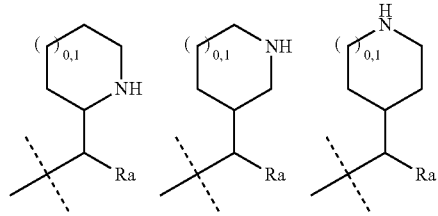

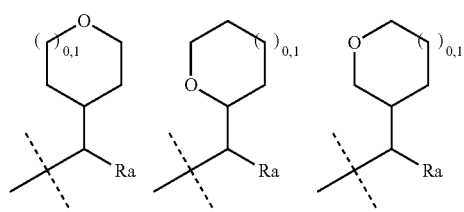

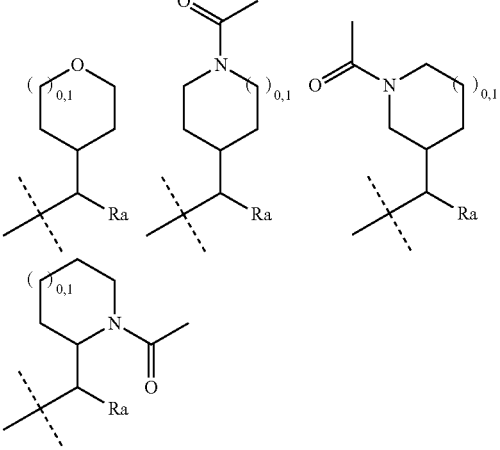

wherein Ra is hydrogen or $C_{1-3}$alkyl;

$R_7$ is isopropyl, sec-butyl, or —$CH(CH_3)OH$; and $R_8$ is isopropyl, isobutyl, sec-butyl, tert-butyl, cyclobutyl, cyclopentyl, or —$CH_2OCH_3$.

In a further aspect, the present invention provides a compound of formula (Ib):

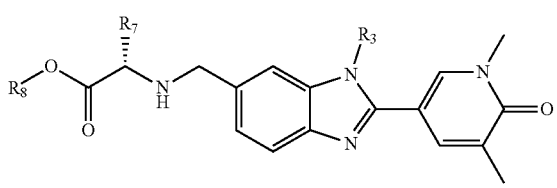
(Ib)

wherein $R_3$ is selected from the group consisting of:

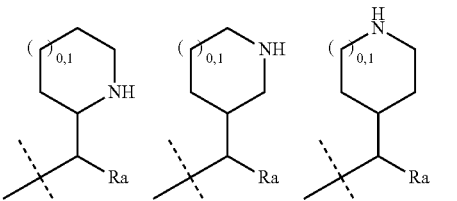

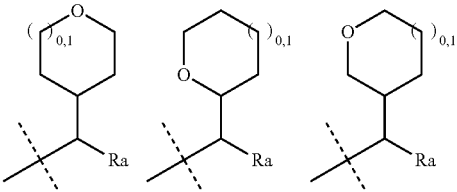

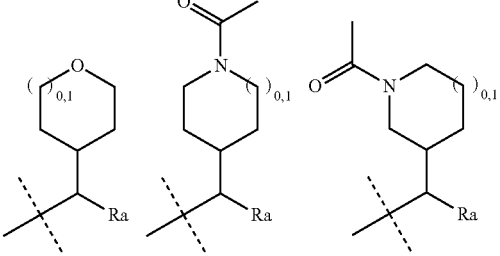

-continued

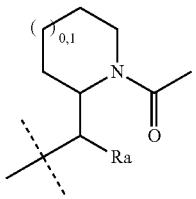

wherein Ra is hydrogen or $C_{1-3}$alkyl;
$R_7$ is isopropyl, sec-butyl, or —CH(CH$_3$)OH; and
$R_8$ is isopropyl, isobutyl, sec-butyl, tert-butyl, cyclobutyl, cyclopentyl, or —CH$_2$OCH$_3$.

In a further aspect, the present invention provides a compound of formula (Ic):

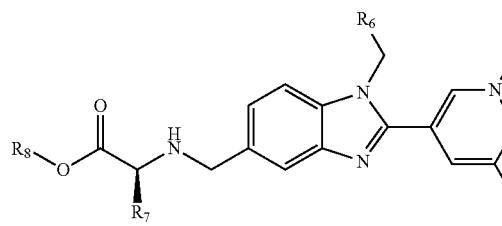

(Ic)

wherein R % is selected from the group consisting of:

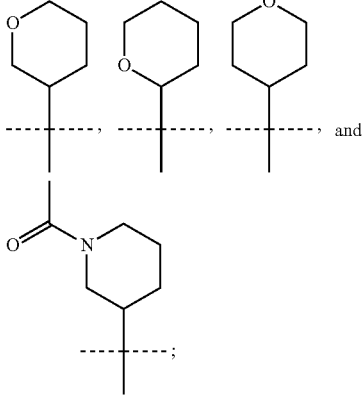

$R_7$ is isopropyl, sec-butyl, or —CH(CH$_3$)OH; and
$R_8$ is hydrogen, $C_{3-6}$alkyl or cycloalkyl.

In a further aspect, the present invention provides a compound of formula (Id):

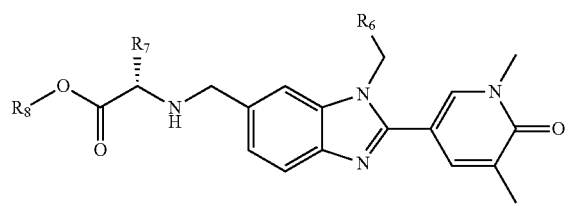

(Id)

wherein $R_6$ is selected from the group consisting of:

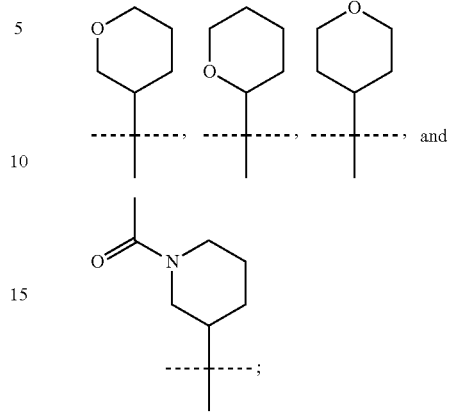

$R_7$ is isopropyl, sec-butyl, or —CH(CH$_3$)OH; and
$R_8$ is hydrogen, $C_{3-6}$alkyl or cycloalkyl.

In a further aspect, the present invention provides a compound of formula (Ic):

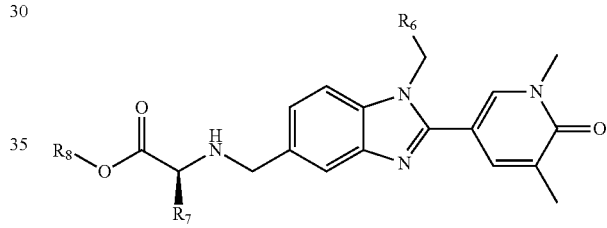

(Ic)

wherein $R_6$ is selected from the group consisting of:

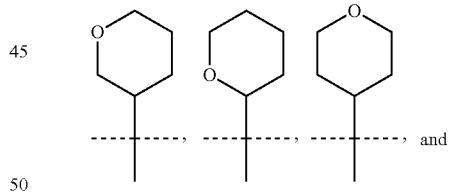

$R_7$ is isopropyl, sec-butyl, or —CH(CH$_3$)OH; and
$R_8$ is isopropyl, isobutyl or cyclopentyl.

In a further aspect, the present invention provides a compound of formula (Id):

(Id)

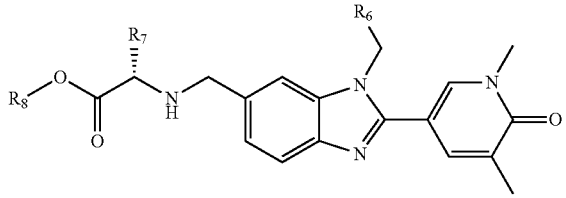

wherein R₆ is selected from the group consisting of:

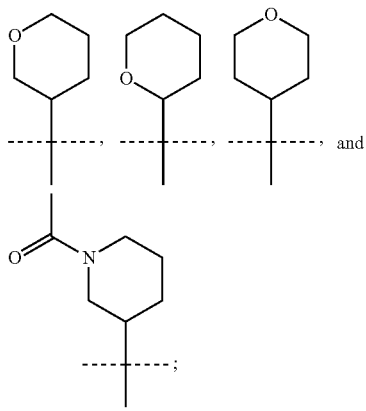

R₇ is isopropyl, sec-butyl, or —CH(CH₃)OH; and
R₈ is isopropyl, isobutyl or cyclopentyl.

In a further embodiment, the present invention is directed to compounds of formula (I) and salts thereof:

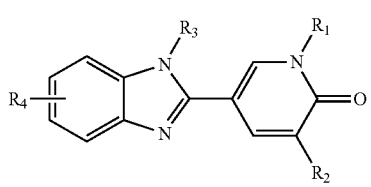
(I)

wherein
$R_1$ and $R_2$ are each independently hydrogen or methyl with the proviso that at least one of $R_1$ and $R_2$ is methyl;
$R_3$ is $C_{1-6}$alkyl, $C_{1-6}$alkoxy, cycloalkyl, heterocycloalkyl, or —CHR₅(CH₂)ₐR₆;
$R_4$ is attached at the 5 or 6 position of the benzimidazole and represents

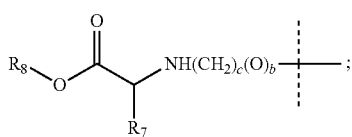

$R_5$ is hydrogen, $C_{1-3}$alkyl, $C_{1-3}$alkoxy, or —(CH₂)$_d$OR₉;
$R_6$ is hydrogen, $C_{1-3}$alkyl, $C_{1-3}$alkoxy, —(CH₂)$_e$OR₁₀, hydroxyl, —NR₁₁R₁₂, halo, cycloalkyl, heterocycloalkyl, aryl, or heteroaryl, wherein said $C_{1-3}$alkyl, $C_{1-3}$alkoxy, —(CH₂)$_e$OR₁₀, cycloalkyl, heterocycloalkyl, aryl or heteroaryl may be optionally substituted with one or two substituents independently selected from the group consisting of $C_{1-3}$alkyl, $C_{1-3}$alkoxy, halo, —CH₂OH, —COOH, and —COCH₃;
$R_7$ is hydrogen, $C_{1-6}$alkyl, —(CH₂)$_g$cycloalkyl, —(CH₂)$_h$heterocycloalkyl, or —CR₁₃R₁₄R₁₅;
$R_8$ is $C_{1-6}$alkyl, cycloalkyl, heterocycloalkyl, or —CHR₁₆R₁₇ wherein said $C_{1-6}$alkyl is optionally substituted with $C_{1-3}$alkoxy, and wherein R₁₆ is hydrogen or $C_{1-3}$alkyl and R₁₇ is cycloalkyl or heterocycloalkyl;
$R_9$, $R_{10}$, $R_{11}$, $R_{12}$, $R_{14}$, $R_{15}$, and $R_{18}$ are each independently hydrogen or $C_{1-3}$alkyl;
$R_{13}$ is hydrogen, hydroxyl, —CH₂OR₁₈, halo, —COOH, —CONH₂, 1H-imidazol-4-yl, —SH, —SeH, $C_{1-3}$alkyl, $C_{1-3}$alkoxy, phenyl, or 4-hydroxyphenyl, wherein said $C_{1-3}$alkyl or $C_{1-3}$alkoxy may be optionally substituted with halo or hydroxyl, —NHC(=NH₂)NH₂, —NH₂, —COOH, —CONH₂, or —SCH₃;
a is 0, 1, 2 or 3;
b is 0 or 1;
c is 1, 2 or 3 with the proviso that when b is 1, c is 2 or 3;
d and e are each independently 1 or 2; and
g and h are each independently 0, 1 or 2.

Specific examples of compounds of formula (I) are:
tert-butyl (2S,3R)-2-{[(1-{[(3R)-1-acetylpiperidin-3-yl]methyl}-2-(1,5-dimethyl-6-oxo-1,6-dihydropyridin-3-yl)-1H-1,3-benzodiazol-6-yl)methyl]amino}-3-hydroxybutanoate;
tert-butyl (2S,3R)-2-({[2-(1,5-dimethyl-6-oxo-1,6-dihydropyridin-3-yl)-1-(oxan-4-ylmethyl)-1H-1,3-benzodiazol-6-yl]methyl}amino)-3-hydroxybutanoate;
2-methylpropyl (2S)-2-[(2-{[2-(1,5-dimethyl-6-oxo-1,6-dihydropyridin-3-yl)-1-(oxan-4-ylmethyl)-1H-1,3-benzodiazol-5-yl]oxy}ethyl)amino]-3-hydroxybutanoate;
2-methylpropyl (2S,3R)-2-({[2-(1,5-dimethyl-6-oxo-1,6-dihydropyridin-3-yl)-1-[(3S)-oxan-3-ylmethyl]-1H-1,3-benzodiazol-5-yl]methyl}amino)-3-hydroxybutanoate;
tert-butyl (2S,3R)-2-{[(1-{[(3R)-1-acetylpiperidin-3-yl]methyl}-2-(1,5-dimethyl-6-oxo-1,6-dihydropyridin-3-yl)-1H-1,3-benzodiazol-5-yl)methyl]amino}-3-hydroxybutanoate;
propan-2-yl (2S,3R)-2-{[(1-{[(3R)-1-acetylpiperidin-3-yl]methyl}-2-(1,5-dimethyl-6-oxo-1,6-dihydropyridin-3-yl)-1H-1,3-benzodiazol-5-yl)methyl]amino}-3-hydroxybutanoate;
2-methylpropyl (2S,3R)-2-({[2-(1,5-dimethyl-6-oxo-1,6-dihydropyridin-3-yl)-1-(oxan-3-ylmethyl)-1H-1,3-benzodiazol-5-yl]methyl}amino)-3-hydroxybutanoate;
cyclopentyl (2S)-2-[(2-{[2-(1,5-dimethyl-6-oxo-1,6-dihydropyridin-3-yl)-1-(oxan-4-ylmethyl)-1H-1,3-benzodiazol-5-yl]oxy}ethyl)amino]propanoate;
propan-2-yl (2S)-2-[(2-{[2-(1,5-dimethyl-6-oxo-1,6-dihydropyridin-3-yl)-1-(oxan-4-ylmethyl)-1H-1,3-benzodiazol-5-yl]oxy}ethyl)amino]-3-hydroxybutanoate;
propan-2-yl (2S,3R)-2-{[(1-{[(3R)-1-acetylpiperidin-3-yl]methyl}-2-(1,5-dimethyl-6-oxo-1,6-dihydropyridin-3-yl)-1H-1,3-benzodiazol-6-yl)methyl]amino}-3-hydroxybutanoate;
propan-2-yl (2S,3R)-2-({[2-(1,5-dimethyl-6-oxo-1,6-dihydropyridin-3-yl)-1-[(3R)-oxan-3-ylmethyl]-1H-1,3-benzodiazol-6-yl]methyl}amino)-3-hydroxybutanoate;
cyclobutyl (2S,3R)-2-{[(1-{[(3R)-1-acetylpiperidin-3-yl]methyl}-2-(1,5-dimethyl-6-oxo-1,6-dihydropyridin-3-yl)-1H-1,3-benzodiazol-5-yl)methyl]amino}-3-hydroxybutanoate;

propan-2-yl (2S)-2-{[(1-{[(3R)-1-acetylpiperidin-3-yl]methyl}-2-(1,5-dimethyl-6-oxo-1,6-dihydropyridin-3-yl)-1H-1,3-benzodiazol-5-yl)methyl]amino}-3-methylbutanoate;

cyclopentyl (2S)-2-[(2-{[2-(1,5-dimethyl-6-oxo-1,6-dihydropyridin-3-yl)-1-(oxan-4-ylmethyl)-1H-1,3-benzodiazol-5-yl]oxy}ethyl)amino]-3-methoxypropanoate;

2,2-dimethylpropyl (2S,3R)-2-({[2-(1,5-dimethyl-6-oxo-1,6-dihydropyridin-3-yl)-1-(oxan-4-ylmethyl)-1H-1,3-benzodiazol-6-yl]methyl}amino)-3-hydroxybutanoate;

propan-2-yl (2S,3R)-2-({[2-(1,5-dimethyl-6-oxo-1,6-dihydropyridin-3-yl)-1-[(3R)-oxan-3-ylmethyl]-1H-1,3-benzodiazol-5-yl]methyl}amino)-3-hydroxybutanoate;

cyclobutyl (2S,3R)-2-[(2-{[2-(1,5-dimethyl-6-oxo-1,6-dihydropyridin-3-yl)-1-(oxan-4-ylmethyl)-1H-1,3-benzodiazol-5-yl]oxy}ethyl)amino]-3-hydroxybutanoate;

cyclopentyl (2S)-2-[(2-{[2-(1,5-dimethyl-6-oxo-1,6-dihydropyridin-3-yl)-1-(oxan-4-ylmethyl)-1H-1,3-benzodiazol-6-yl]oxy}ethyl)amino]propanoate;

propan-2-yl (2S,3R)-2-({[2-(1,5-dimethyl-6-oxo-1,6-dihydropyridin-3-yl)-1-(oxan-3-ylmethyl)-1H-1,3-benzodiazol-5-yl]methyl}amino)-3-hydroxybutanoate;

propan-2-yl (2S,3R)-2-{[(1-{[(3S)-1-acetylpiperidin-3-yl]methyl}-2-(1,5-dimethyl-6-oxo-1,6-dihydropyridin-3-yl)-1H-1,3-benzodiazol-6-yl)methyl]amino}-3-hydroxybutanoate;

propan-2-yl (2S,3R)-2-({[2-(1,5-dimethyl-6-oxo-1,6-dihydropyridin-3-yl)-1-[(3R)-oxan-3-ylmethyl]-1H-1,3-benzodiazol-6-yl]methyl}amino)-3-hydroxybutanoate;

propan-2-yl (2S,3R)-2-({[2-(1,5-dimethyl-6-oxo-1,6-dihydropyridin-3-yl)-1-[(3R)-oxan-3-ylmethyl]-1H-1,3-benzodiazol-5-yl]methyl}amino)-3-hydroxybutanoate;

cyclobutyl (2R,3S)-2-({[2-(1,5-dimethyl-6-oxo-1,6-dihydropyridin-3-yl)-1-[(3R)-oxan-3-ylmethyl]-1H-1,3-benzodiazol-6-yl]methyl}amino)-3-hydroxybutanoate;

(3S)-oxolan-3-yl (2S,3R)-2-[(2-{[2-(1,5-dimethyl-6-oxo-1,6-dihydropyridin-3-yl)-1-(oxan-4-ylmethyl)-1H-1,3-benzodiazol-5-yl]oxy}ethyl)amino]-3-hydroxybutanoate;

cyclopentyl (2S,3R)-2-({[2-(1,5-dimethyl-6-oxo-1,6-dihydropyridin-3-yl)-1-(oxan-4-ylmethyl)-1H-1,3-benzodiazol-6-yl]methyl}amino)-3-hydroxybutanoate;

(2S)-butan-2-yl (2S,3R)-2-({[2-(1,5-dimethyl-6-oxo-1,6-dihydropyridin-3-yl)-1-(oxan-4-ylmethyl)-1H-1,3-benzodiazol-5-yl]methyl}amino)-3-hydroxybutanoate;

cyclopentyl (2S)-2-[(2-{[2-(1,5-dimethyl-6-oxo-1,6-dihydropyridin-3-yl)-1-(oxan-4-ylmethyl)-1H-1,3-benzodiazol-6-yl]oxy}ethyl)amino]-3-methoxypropanoate;

(3S)-oxolan-3-yl (2S)-2-[(2-{[2-(1,5-dimethyl-6-oxo-1,6-dihydropyridin-3-yl)-1-(oxan-4-ylmethyl)-1H-1,3-benzodiazol-6-yl]oxy}ethyl)amino]-3-methylbutanoate;

(2S)-1-methoxypropan-2-yl (2S)-2-[(2-{[2-(1,5-dimethyl-6-oxo-1,6-dihydropyridin-3-yl)-1-(oxan-4-ylmethyl)-1H-1,3-benzodiazol-6-yl]oxy}ethyl)amino]-3-methylbutanoate;

2-methylpropyl (2S,3R)-2-({[2-(1,5-dimethyl-6-oxo-1,6-dihydropyridin-3-yl)-1-[(3R)-oxan-3-ylmethyl]-1H-1,3-benzodiazol-5-yl]methyl}amino)-3-hydroxybutanoate;

2-methylpropyl (2S,3R)-2-({[2-(1,5-dimethyl-6-oxo-1,6-dihydropyridin-3-yl)-1-[(2S)-oxan-2-ylmethyl]-1H-1,3-benzodiazol-5-yl]methyl}amino)-3-hydroxybutanoate;

tert-butyl (2S,3R)-2-({[2-(1,5-dimethyl-6-oxo-1,6-dihydropyridin-3-yl)-1-(oxan-2-ylmethyl)-1H-1,3-benzodiazol-6-yl]methyl}amino)-3-hydroxybutanoate;

2-methylpropyl (2S,3R)-2-{[(1-{[(3S)-1-acetylpiperidin-3-yl]methyl}-2-(1,5-dimethyl-6-oxo-1,6-dihydropyridin-3-yl)-1H-1,3-benzodiazol-6-yl)methyl]amino}-3-hydroxybutanoate;

propan-2-yl (2S,3R)-2-({[2-(1,5-dimethyl-6-oxo-1,6-dihydropyridin-3-yl)-1-(oxan-2-ylmethyl)-1H-1,3-benzodiazol-5-yl]methyl}amino)-3-hydroxybutanoate;

propan-2-yl (2S,3R)-2-({[2-(1,5-dimethyl-6-oxo-1,6-dihydropyridin-3-yl)-1-[(2R)-oxan-2-ylmethyl]-1H-1,3-benzodiazol-6-yl]methyl}amino)-3-hydroxybutanoate;

2-methylpropyl (2S,3R)-2-({[2-(1,5-dimethyl-6-oxo-1,6-dihydropyridin-3-yl)-1-[(2R)-oxan-2-ylmethyl]-1H-1,3-benzodiazol-6-yl]methyl}amino)-3-hydroxybutanoate;

tert-butyl (2S,3R)-2-({[2-(1,5-dimethyl-6-oxo-1,6-dihydropyridin-3-yl)-1-[(2R)-oxan-2-ylmethyl]-1H-1,3-benzodiazol-6-yl]methyl}amino)-3-hydroxybutanoate;

tert-butyl (2S,3R)-2-({[2-(1,5-dimethyl-6-oxo-1,6-dihydropyridin-3-yl)-1-[(2R)-oxan-2-ylmethyl]-1H-1,3-benzodiazol-6-yl]methyl}amino)-3-hydroxybutanoate;

2-methylpropyl (2S,3R)-2-({[2-(1,5-dimethyl-6-oxo-1,6-dihydropyridin-3-yl)-1-[(2R)-oxan-2-ylmethyl]-1H-1,3-benzodiazol-6-yl]methyl}amino)-3-hydroxybutanoate;

propan-2-yl (2S,3R)-2-({[1-(1,3-dimethoxypropan-2-yl)-2-(1,5-dimethyl-6-oxo-1,6-dihydropyridin-3-yl)-1H-1,3-benzodiazol-6-yl]methyl}amino)-3-hydroxybutanoate;

cyclobutyl (2R,3S)-2-({[2-(1,5-dimethyl-6-oxo-1,6-dihydropyridin-3-yl)-1-[(3R)-oxan-3-ylmethyl]-1H-1,3-benzodiazol-6-yl]methyl}amino)-3-hydroxybutanoate;

tert-butyl (2S,3R)-2-[(2-{[2-(1,5-dimethyl-6-oxo-1,6-dihydropyridin-3-yl)-1-(oxan-4-ylmethyl)-1H-1,3-benzodiazol-5-yl]oxy}ethyl)amino]-3-hydroxybutanoate;

propan-2-yl (2S,3R)-2-({[2-(1,5-dimethyl-6-oxo-1,6-dihydropyridin-3-yl)-1-[(1R)-1-(oxan-4-yl)ethyl]-1H-1,3-benzodiazol-5-yl]methyl}amino)-3-hydroxybutanoate;

tert-butyl (2S,3R)-2-({[2-(1,5-dimethyl-6-oxo-1,6-dihydropyridin-3-yl)-1-[(1R)-1-(oxan-4-yl)ethyl]-1H-1,3-benzodiazol-5-yl]methyl}amino)-3-hydroxybutanoate;

propan-2-yl (2S,3R)-2-({2-[2-(1,5-dimethyl-6-oxo-1,6-dihydropyridin-3-yl)-1-(oxan-4-ylmethyl)-1H-1,3-benzodiazol-5-yl]ethyl}amino)-3-hydroxybutanoate;

2,2-dimethylpropyl (2S,3R)-2-({[2-(1,5-dimethyl-6-oxo-1,6-dihydropyridin-3-yl)-1-(oxan-4-ylmethyl)-1H-1,3-benzodiazol-5-yl]methyl}amino)-3-hydroxybutanoate;

cyclopentyl (2S,3R)-2-({[2-(1,5-dimethyl-6-oxo-1,6-dihydropyridin-3-yl)-1-(oxan-4-ylmethyl)-1H-1,3-benzodiazol-5-yl]methyl}amino)-3-hydroxybutanoate;

2-methylpropyl (2S,3R)-2-({[2-(1,5-dimethyl-6-oxo-1,6-dihydropyridin-3-yl)-1-(oxan-2-ylmethyl)-1H-1,3-benzodiazol-5-yl]methyl}amino)-3-hydroxybutanoate;

2-methylpropyl (2S,3R)-2-({[2-(1,5-dimethyl-6-oxo-1,6-dihydropyridin-3-yl)-1-(oxan-4-ylmethyl)-1H-1,3-benzodiazol-6-yl]methyl}amino)-3-hydroxybutanoate;

propan-2-yl (2S)-2-[(2-{[2-(1,5-dimethyl-6-oxo-1,6-dihydropyridin-3-yl)-1-(oxan-4-ylmethyl)-1H-1,3-benzodiazol-6-yl]oxy}ethyl)amino]-3-hydroxybutanoate;

2-hydroxy-2-methylpropyl (2S,3R)-2-({[2-(1,5-dimethyl-6-oxo-1,6-dihydropyridin-3-yl)-1-(oxan-4-ylmethyl)-1H-1,3-benzodiazol-6-yl]methyl}amino)-3-hydroxybutanoate;

propan-2-yl (2S,3R)-2-({[2-(1,5-dimethyl-6-oxo-1,6-dihydropyridin-3-yl)-1-(oxan-2-ylmethyl)-1H-1,3-benzodiazol-6-yl]methyl}amino)-3-hydroxybutanoate;

2-methylpropyl (2S,3R)-2-({[2-(1,5-dimethyl-6-oxo-1,6-dihydropyridin-3-yl)-1-(oxan-2-ylmethyl)-1H-1,3-benzodiazol-6-yl]methyl}amino)-3-hydroxybutanoate;

tert-butyl (2S,3R)-2-{[(1-{[(3S)-1-acetylpiperidin-3-yl]methyl}-2-(1,5-dimethyl-6-oxo-1,6-dihydropyridin-3-yl)-1H-1,3-benzodiazol-6-yl)methyl]amino}-3-hydroxybutanoate;

propan-2-yl (2S,3R)-2-({[2-(1,5-dimethyl-6-oxo-1,6-dihydropyridin-3-yl)-1-[(2R)-oxan-2-ylmethyl]-1H-1,3-benzodiazol-6-yl]methyl}amino)-3-hydroxybutanoate;

propan-2-yl (2S,3R)-2-({[2-(1,5-dimethyl-6-oxo-1,6-dihydropyridin-3-yl)-1-[(2S)-oxan-2-ylmethyl]-1H-1,3-benzodiazol-5-yl]methyl}amino)-3-hydroxybutanoate;

propan-2-yl (2S,3R)-2-({[2-(1,5-dimethyl-6-oxo-1,6-dihydropyridin-3-yl)-1-[(2S)-oxan-2-ylmethyl]-1H-1,3-benzodiazol-5-yl]methyl}amino)-3-hydroxybutanoate;

propan-2-yl (2S,3R)-2-({[1-(1,3-dimethoxypropan-2-yl)-2-(1,5-dimethyl-6-oxo-1,6-dihydropyridin-3-yl)-1H-1,3-benzodiazol-5-yl]methyl}amino)-3-hydroxybutanoate;

cyclobutyl (2S,3R)-2-({[1-(1,3-dimethoxypropan-2-yl)-2-(1,5-dimethyl-6-oxo-1,6-dihydropyridin-3-yl)-1H-1,3-benzodiazol-5-yl]methyl}amino)-3-hydroxybutanoate;

tert-butyl (2S,3R)-2-({[1-(1,3-dimethoxypropan-2-yl)-2-(1,5-dimethyl-6-oxo-1,6-dihydropyridin-3-yl)-1H-1,3-benzodiazol-5-yl]methyl}amino)-3-hydroxybutanoate;

cyclobutyl (2S,3R)-2-({[2-(1,5-dimethyl-6-oxo-1,6-dihydropyridin-3-yl)-1-(1-methoxybutan-2-yl)-1H-1,3-benzodiazol-5-yl]methyl}amino)-3-hydroxybutanoate;

propan-2-yl (2S,3R)-2-({[2-(1,5-dimethyl-6-oxo-1,6-dihydropyridin-3-yl)-1-(1-methoxybutan-2-yl)-1H-1,3-benzodiazol-5-yl]methyl}amino)-3-hydroxybutanoate;

propan-2-yl (2S,3R)-2-{[(1-{[(3S)-1-acetylpiperidin-3-yl]methyl}-2-(1,5-dimethyl-6-oxo-1,6-dihydropyridin-3-yl)-1H-1,3-benzodiazol-5-yl)methyl]amino}-3-hydroxybutanoate;

cyclobutyl (2S,3R)-2-{[(1-{[(3S)-1-acetylpiperidin-3-yl]methyl}-2-(1,5-dimethyl-6-oxo-1,6-dihydropyridin-3-yl)-1H-1,3-benzodiazol-5-yl)methyl]amino}-3-hydroxybutanoate;

tert-butyl (2S,3R)-2-{[(1-{[(3S)-1-acetylpiperidin-3-yl]methyl}-2-(1,5-dimethyl-6-oxo-1,6-dihydropyridin-3-yl)-1H-1,3-benzodiazol-5-yl)methyl]amino}-3-hydroxybutanoate;

propan-2-yl (2S)-4-chloro-2-({[2-(1,5-dimethyl-6-oxo-1,6-dihydropyridin-3-yl)-1-(oxan-4-ylmethyl)-1H-1,3-benzodiazol-5-yl]methyl}amino)butanoate;

cyclopentyl (2S)-2-({[2-(1,5-dimethyl-6-oxo-1,6-dihydropyridin-3-yl)-1-(oxan-4-ylmethyl)-1H-1,3-benzodiazol-5-yl]methyl}amino)-4-methylpentanoate;

2-methylpropyl (2S,3R)-2-({[2-(1,5-dimethyl-6-oxo-1,6-dihydropyridin-3-yl)-1-(oxan-4-ylmethyl)-1H-1,3-benzodiazol-5-yl]methyl}amino)-3-hydroxybutanoate;

(3S)-oxolan-3-yl (2S,3R)-2-({[2-(1,5-dimethyl-6-oxo-1,6-dihydropyridin-3-yl)-1-(oxan-4-ylmethyl)-1H-1,3-benzodiazol-5-yl]methyl}amino)-3-hydroxybutanoate;

propan-2-yl (2S,3R)-2-({[2-(1,5-dimethyl-6-oxo-1,6-dihydropyridin-3-yl)-1-(oxan-4-ylmethyl)-1H-1,3-benzodiazol-5-yl]methyl}amino)-3-hydroxybutanoate;

propan-2-yl (2S,3R)-2-({[2-(1,5-dimethyl-6-oxo-1,6-dihydropyridin-3-yl)-1-(oxan-4-ylmethyl)-1H-1,3-benzodiazol-5-yl]methyl}amino)-3-hydroxybutanoate;

2-methylpropyl (2S,3R)-2-({[2-(1,5-dimethyl-6-oxo-1,6-dihydropyridin-3-yl)-1-{[(2R)-4-methylmorpholin-2-yl]methyl}-1H-1,3-benzodiazol-5-yl]methyl}amino)-3-hydroxybutanoate;

(3S)-oxolan-3-yl (2S,3R)-2-({[2-(1,5-dimethyl-6-oxo-1,6-dihydropyridin-3-yl)-1-(oxan-4-ylmethyl)-1H-1,3-benzodiazol-6-yl]methyl}amino)-3-hydroxybutanoate;

propan-2-yl (2S,3R)-2-({[2-(1,5-dimethyl-6-oxo-1,6-dihydropyridin-3-yl)-1-(oxan-4-ylmethyl)-1H-1,3-benzodiazol-6-yl]methyl}amino)-3-hydroxybutanoate;

cyclobutyl (2S,3R)-2-({[2-(1,5-dimethyl-6-oxo-1,6-dihydropyridin-3-yl)-1-(oxan-4-ylmethyl)-1H-1,3-benzodiazol-6-yl]methyl}amino)-3-hydroxybutanoate;

2-methylpropyl (2S,3R)-2-({[2-(1,5-dimethyl-6-oxo-1,6-dihydropyridin-3-yl)-1-[(2S)-oxan-2-ylmethyl]-1H-1,3-benzodiazol-5-yl]methyl}amino)-3-hydroxybutanoate;

propan-2-yl (2S,3R)-2-({[2-(1,5-dimethyl-6-oxo-1,6-dihydropyridin-3-yl)-1-[(3S)-piperidin-3-ylmethyl]-1H-1,3-benzodiazol-6-yl]methyl}amino)-3-hydroxybutanoate;

(3S)-oxolan-3-yl (2S,3R)-2-({[2-(1,5-dimethyl-6-oxo-1,6-dihydropyridin-3-yl)-1-(oxan-2-ylmethyl)-1H-1,3-benzodiazol-6-yl]methyl}amino)-3-hydroxybutanoate;

(3S)-oxolan-3-yl (2S,3R)-2-({[2-(1,5-dimethyl-6-oxo-1,6-dihydropyridin-3-yl)-1-[(2R)-oxan-2-ylmethyl]-1H-1,3-benzodiazol-6-yl]methyl}amino)-3-hydroxybutanoate;

(3S)-oxolan-3-yl (2S,3R)-2-({[2-(1,5-dimethyl-6-oxo-1,6-dihydropyridin-3-yl)-1-[(2R)-oxan-2-ylmethyl]-1H-1,3-benzodiazol-6-yl]methyl}amino)-3-hydroxybutanoate;

tert-butyl (2S,3R)-2-({[2-(1,5-dimethyl-6-oxo-1,6-dihydropyridin-3-yl)-1-(1-methoxybutan-2-yl)-1H-1,3-benzodiazol-5-yl]methyl}amino)-3-hydroxybutanoate;

tert-butyl (2S,3R)-2-({[2-(1,5-dimethyl-6-oxo-1,6-dihydropyridin-3-yl)-1-[1-(oxan-4-yl)ethyl]-1H-1,3-benzodiazol-5-yl]methyl}amino)-3-hydroxybutanoate;

tert-butyl (2S,3R)-2-({2-[2-(1,5-dimethyl-6-oxo-1,6-dihydropyridin-3-yl)-1-(oxan-4-ylmethyl)-1H-1,3-benzodiazol-5-yl]ethyl}amino)-3-hydroxybutanoate;

cyclopentyl (2S)-2-({[2-(1,5-dimethyl-6-oxo-1,6-dihydropyridin-3-yl)-1-[(2S)-1-methoxypropan-2-yl]-1H-1,3-benzodiazol-5-yl]methyl}amino)-3-methoxypropanoate;

tert-butyl (2S,3R)-2-({[2-(1,5-dimethyl-6-oxo-1,6-dihydropyridin-3-yl)-1-[(3S)-piperidin-3-ylmethyl]-1H-1,3-benzodiazol-6-yl]methyl}amino)-3-hydroxybutanoate;

2-methylpropyl (2S)-2-[(2-{[2-(1,5-dimethyl-6-oxo-1,6-dihydropyridin-3-yl)-1-[(2S)-1-methoxypropan-2-yl]-1H-1,3-benzodiazol-5-yl]oxy}ethyl)amino]-3-methoxypropanoate;

cyclopentyl (2S)-2-({[2-(1,5-dimethyl-6-oxo-1,6-dihydropyridin-3-yl)-1-(oxan-4-ylmethyl)-1H-1,3-benzodiazol-5-yl]methyl}amino)-3-hydroxypropanoate;

tert-butyl (2S,3R)-2-({[2-(1,5-dimethyl-6-oxo-1,6-dihydropyridin-3-yl)-1-(1-methoxybutan-2-yl)-1H-1,3-benzodiazol-5-yl]methyl}amino)-3-hydroxybutanoate;

propan-2-yl (2S,3R)-2-({[2-(1,5-dimethyl-6-oxo-1,6-dihydropyridin-3-yl)-1-[1-(oxan-4-yl)ethyl]-1H-1,3-benzodiazol-5-yl]methyl}amino)-3-hydroxybutanoate;

propan-2-yl (2S,3R)-2-({[2-(1,5-dimethyl-6-oxo-1,6-dihydropyridin-3-yl)-1-[(3S)-oxolan-3-ylmethyl]-1H-1,3-benzodiazol-6-yl]methyl}amino)-3-hydroxybutanoate;

tert-butyl (2S,3R)-2-({[2-(1,5-dimethyl-6-oxo-1,6-dihydropyridin-3-yl)-1-[(3S)-oxolan-3-ylmethyl]-1H-1,3-benzodiazol-6-yl]methyl}amino)-3-hydroxybutanoate;

2-methylpropyl (2S,3R)-2-({[2-(1,5-dimethyl-6-oxo-1,6-dihydropyridin-3-yl)-1-[(4-methylmorpholin-2-yl)methyl]-1H-1,3-benzodiazol-5-yl]methyl}amino)-3-hydroxybutanoate;

2-methylpropyl (2S)-2-[(2-{[2-(1,5-dimethyl-6-oxo-1,6-dihydropyridin-3-yl)-1-(oxan-4-ylmethyl)-1H-1,3-benzodiazol-6-yl]oxy}ethyl)amino]-3-hydroxybutanoate;

(3S)-oxolan-3-yl (2S,3R)-2-({[2-(1,5-dimethyl-6-oxo-1,6-dihydropyridin-3-yl)-1-(oxan-4-ylmethyl)-1H-1,3-benzodiazol-5-yl]methyl}amino)-3-methoxybutanoate;

2-methylpropyl (2S,3R)-2-({[2-(1,5-dimethyl-6-oxo-1,6-dihydropyridin-3-yl)-1-[(2S)-1-methoxypropan-2-yl]-1H-1,3-benzodiazol-6-yl]methyl}amino)-3-hydroxybutanoate;

propan-2-yl (2S,3R)-3-hydroxy-2-({[2-(5-methyl-6-oxo-1,6-dihydropyridin-3-yl)-1-[(3R)-oxan-3-ylmethyl]-1H-1,3-benzodiazol-5-yl]methyl}amino)butanoate;

(3S)-oxolan-3-yl (2S,3S)-2-({[2-(1,5-dimethyl-6-oxo-1,6-dihydropyridin-3-yl)-1-(oxan-4-ylmethyl)-1H-1,3-benzodiazol-5-yl]methyl}amino)-3-hydroxybutanoate;

propan-2-yl (2S,3R)-2-({[2-(1,5-dimethyl-6-oxo-1,6-dihydropyridin-3-yl)-1-[(2S)-1-methoxypropan-2-yl]-1H-1,3-benzodiazol-6-yl]methyl}amino)-3-hydroxybutanoate;

tert-butyl (2S,3R)-2-({[2-(1,5-dimethyl-6-oxo-1,6-dihydropyridin-3-yl)-1-[(2S)-1-methoxypropan-2-yl]-1H-1,3-benzodiazol-6-yl]methyl}amino)-3-hydroxybutanoate;

propan-2-yl (2S,3R)-2-[(2-{[2-(1,5-dimethyl-6-oxo-1,6-dihydropyridin-3-yl)-1-[(2S)-1-methoxypropan-2-yl]-1H-1,3-benzodiazol-5-yl]oxy}ethyl)amino]-3-hydroxybutanoate;

tert-butyl (2S,3R)-2-({[2-(1,5-dimethyl-6-oxo-1,6-dihydropyridin-3-yl)-1-(oxolan-3-ylmethyl)-1H-1,3-benzodiazol-5-yl]methyl}amino)-3-hydroxybutanoate;

propan-2-yl (2S,3R)-2-({[2-(1,5-dimethyl-6-oxo-1,6-dihydropyridin-3-yl)-1-(1-methoxybutan-2-yl)-1H-1,3-benzodiazol-5-yl]methyl}amino)-3-hydroxybutanoate;

cyclobutyl (2S,3R)-2-({[2-(1,5-dimethyl-6-oxo-1,6-dihydropyridin-3-yl)-1-(1-methoxybutan-2-yl)-1H-1,3-benzodiazol-5-yl]methyl}amino)-3-hydroxybutanoate;

tert-butyl (2S,3R)-2-({[2-(1,5-dimethyl-6-oxo-1,6-dihydropyridin-3-yl)-1-[(3R)-oxolan-3-ylmethyl]-1H-1,3-benzodiazol-5-yl]methyl}amino)-3-hydroxybutanoate;

propan-2-yl (2S,3R)-2-({[2-(1,5-dimethyl-6-oxo-1,6-dihydropyridin-3-yl)-1-[(3R)-oxolan-3-ylmethyl]-1H-1,3-benzodiazol-5-yl]methyl}amino)-3-hydroxybutanoate;

propan-2-yl (2S,3R)-2-({[2-(1,5-dimethyl-6-oxo-1,6-dihydropyridin-3-yl)-1-(oxolan-3-ylmethyl)-1H-1,3-benzodiazol-6-yl]methyl}amino)-3-hydroxybutanoate; and propan-2-yl (2S,3R)-2-({[2-(1,5-dimethyl-6-oxo-1,6-dihydropyridin-3-yl)-1-(1-methoxybutan-2-yl)-1H-1,3-benzodiazol-5-yl]methyl}amino)-3-hydroxybutanoate, or salts thereof.

In a further embodiment, the present invention provides a compound, or a salt thereof, which is selected from the group consisting of:

tert-butyl (2S,3R)-2-{[(1-{[(3R)-1-acetylpiperidin-3-yl]methyl}-2-(1,5-dimethyl-6-oxo-1,6-dihydropyridin-3-yl)-1H-1,3-benzodiazol-6-yl)methyl]amino}-3-hydroxybutanoate;

tert-butyl (2S,3R)-2-({[2-(1,5-dimethyl-6-oxo-1,6-dihydropyridin-3-yl)-1-(oxan-4-ylmethyl)-1H-1,3-benzodiazol-6-yl]methyl}amino)-3-hydroxybutanoate;

2-methylpropyl (2S)-2-[(2-{[2-(1,5-dimethyl-6-oxo-1,6-dihydropyridin-3-yl)-1-(oxan-4-ylmethyl)-1H-1,3-benzodiazol-5-yl]oxy}ethyl)amino]-3-hydroxybutanoate;

2-methylpropyl (2S,3R)-2-({[2-(1,5-dimethyl-6-oxo-1,6-dihydropyridin-3-yl)-1-[(3S)-oxan-3-ylmethyl]-1H-1,3-benzodiazol-5-yl]methyl}amino)-3-hydroxybutanoate;

tert-butyl (2S,3R)-2-{[(1-{[(3R)-1-acetylpiperidin-3-yl]methyl}-2-(1,5-dimethyl-6-oxo-1,6-dihydropyridin-3-yl)-1H-1,3-benzodiazol-5-yl)methyl]amino}-3-hydroxybutanoate;

propan-2-yl (2S,3R)-2-{[(1-{[(3R)-1-acetylpiperidin-3-yl]methyl}-2-(1,5-dimethyl-6-oxo-1,6-dihydropyridin-3-yl)-1H-1,3-benzodiazol-5-yl)methyl]amino}-3-hydroxybutanoate;

2-methylpropyl (2S,3R)-2-({[2-(1,5-dimethyl-6-oxo-1,6-dihydropyridin-3-yl)-1-(oxan-3-ylmethyl)-1H-1,3-benzodiazol-5-yl]methyl}amino)-3-hydroxybutanoate;

cyclopentyl (2S)-2-[(2-{[2-(1,5-dimethyl-6-oxo-1,6-dihydropyridin-3-yl)-1-(oxan-4-ylmethyl)-1H-1,3-benzodiazol-5-yl]oxy}ethyl)amino]propanoate;

propan-2-yl (2S,3R)-2-[(2-{[2-(1,5-dimethyl-6-oxo-1,6-dihydropyridin-3-yl)-1-(oxan-4-ylmethyl)-1H-1,3-benzodiazol-5-yl]oxy}ethyl)amino]-3-hydroxybutanoate;

propan-2-yl (2S,3R)-2-{[(1-{[(3R)-1-acetylpiperidin-3-yl]methyl}-2-(1,5-dimethyl-6-oxo-1,6-dihydropyridin-3-yl)-1H-1,3-benzodiazol-6-yl)methyl]amino}-3-hydroxybutanoate;

propan-2-yl (2S,3R)-2-({[2-(1,5-dimethyl-6-oxo-1,6-dihydropyridin-3-yl)-1-[(3R)-oxan-3-ylmethyl]-1H-1,3-benzodiazol-6-yl]methyl}amino)-3-hydroxybutanoate;

cyclobutyl (2S,3R)-2-{[(1-{[(3R)-1-acetylpiperidin-3-yl]methyl}-2-(1,5-dimethyl-6-oxo-1,6-dihydropyridin-3-yl)-1H-1,3-benzodiazol-5-yl)methyl]amino}-3-hydroxybutanoate;

propan-2-yl (2S)-2-{[(1-{[(3R)-1-acetylpiperidin-3-yl]methyl}-2-(1,5-dimethyl-6-oxo-1,6-dihydropyridin-3-yl)-1H-1,3-benzodiazol-5-yl)methyl]amino}-3-methylbutanoate;

cyclopentyl (2S)-2-[(2-{[2-(1,5-dimethyl-6-oxo-1,6-dihydropyridin-3-yl)-1-(oxan-4-ylmethyl)-1H-1,3-benzodiazol-5-yl]oxy}ethyl)amino]-3-methoxypropanoate;

2,2-dimethylpropyl (2S,3R)-2-({[2-(1,5-dimethyl-6-oxo-1,6-dihydropyridin-3-yl)-1-(oxan-4-ylmethyl)-1H-1,3-benzodiazol-6-yl]methyl}amino)-3-hydroxybutanoate;

propan-2-yl (2S,3R)-2-({[2-(1,5-dimethyl-6-oxo-1,6-dihydropyridin-3-yl)-1-[(3R)-oxan-3-ylmethyl]-1H-1,3-benzodiazol-5-yl]methyl}amino)-3-hydroxybutanoate;

cyclobutyl (2S,3R)-2-[(2-{[2-(1,5-dimethyl-6-oxo-1,6-dihydropyridin-3-yl)-1-(oxan-4-ylmethyl)-1H-1,3-benzodiazol-5-yl]oxy}ethyl)amino]-3-hydroxybutanoate;

cyclopentyl (2S)-2-[(2-{[2-(1,5-dimethyl-6-oxo-1,6-dihydropyridin-3-yl)-1-(oxan-4-ylmethyl)-1H-1,3-benzodiazol-6-yl]oxy}ethyl)amino]propanoate;

propan-2-yl (2S,3R)-2-({[2-(1,5-dimethyl-6-oxo-1,6-dihydropyridin-3-yl)-1-(oxan-3-ylmethyl)-1H-1,3-benzodiazol-5-yl]methyl}amino)-3-hydroxybutanoate;

propan-2-yl (2S,3R)-2-{[(1-{[(3S)-1-acetylpiperidin-3-yl]methyl}-2-(1,5-dimethyl-6-oxo-1,6-dihydropyridin-3-yl)-1H-1,3-benzodiazol-6-yl)methyl]amino}-3-hydroxybutanoate;

propan-2-yl (2S,3R)-2-({[2-(1,5-dimethyl-6-oxo-1,6-dihydropyridin-3-yl)-1-[(3R)-oxan-3-ylmethyl]-1H-1,3-benzodiazol-6-yl]methyl}amino)-3-hydroxybutanoate;

propan-2-yl (2S,3R)-2-({[2-(1,5-dimethyl-6-oxo-1,6-dihydropyridin-3-yl)-1-[(3R)-oxan-3-ylmethyl]-1H-1,3-benzodiazol-5-yl]methyl}amino)-3-hydroxybutanoate;

cyclobutyl (2R,3S)-2-({[2-(1,5-dimethyl-6-oxo-1,6-dihydropyridin-3-yl)-1-[(3R)-oxan-3-ylmethyl]-1H-1,3-benzodiazol-6-yl]methyl}amino)-3-hydroxybutanoate; and (3S)-oxolan-3-yl (2S,3R)-2-[(2-{[2-(1,5-dimethyl-6-oxo-1,6-dihydropyridin-3-yl)-1-(oxan-4-ylmethyl)-1H-1,3-benzodiazol-5-yl]oxy}ethyl)amino]-3-hydroxybutanoate.

In a further embodiment, the present invention provides a compound which is (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate, of formula:

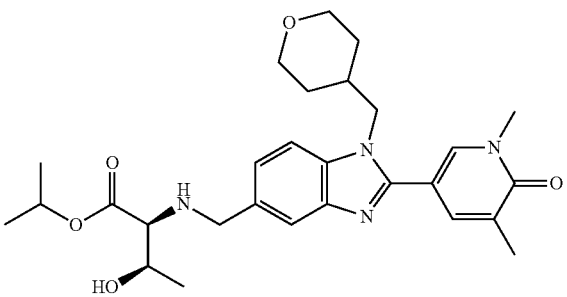 [SMILES: Cc1cc(-c2nc3cc(CN[C@H](C(=O)OC(C)C)[C@@H](C)O)ccc3n2CC2CCOCC2)cn(C)c1=O]

or a salt thereof.

In a further embodiment, the present invention provides a compound which is (2S,3R)-2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoic acid, of formula:

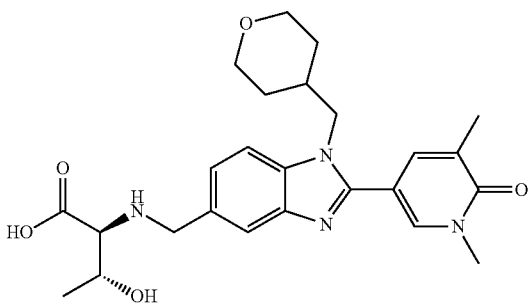 [SMILES: Cc1cc(-c2nc3cc(CN[C@H](C(=O)O)[C@@H](C)O)ccc3n2CC2CCOCC2)cn(C)c1=O]

or a salt thereof.

In a further embodiment, the present invention provides a compound which is (2S,3R)-Isopropyl 2-(((1-(1,3-dimethoxypropan-2-yl)-2-(1,5-dimethyl-6-oxo-1,6-dihydropyridin-3-yl)-1-benzo[d]imidazol-5-yl)methyl)amino)-3-hydroxybutanoate, of formula:

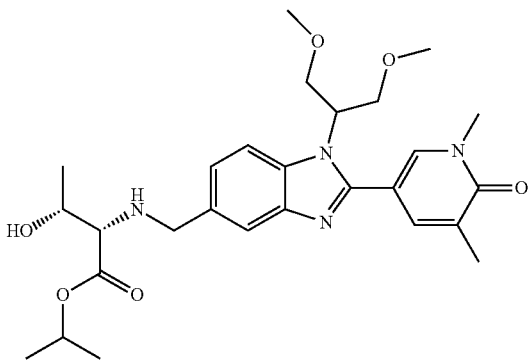 [SMILES: COCC(COC)n1c(-c2cc(C)c(=O)n(C)c2)nc2cc(CN[C@H](C(=O)OC(C)C)[C@@H](C)O)ccc21]

or a salt thereof.

In a further embodiment, the present invention provides a compound which is (2S,3R)-2-(((1-(1,3-dimethoxypropan-2-yl)-2-(1,5-dimethyl-6-oxo-1,6-dihydropyridin-3-yl)-1H-benzo[d]imidazol-5-yl)methyl)amino)-3-hydroxybutanoic acid, of formula:

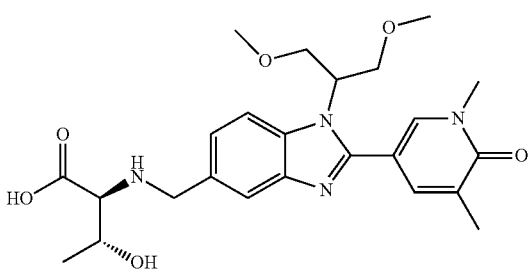 [SMILES: COCC(COC)n1c(-c2cc(C)c(=O)n(C)c2)nc2cc(CN[C@H](C(=O)O)[C@@H](C)O)ccc21]

or a salt thereof.

In a further embodiment of the present invention, a compound of formula (I) is in the form of a free base. In one embodiment, the compound of formula (I) in the form of a free base is any one of the compounds of Examples 1 to 324.

Salts of the compounds of formula (I) include pharmaceutically acceptable salts and salts which may not be pharmaceutically acceptable but may be useful in the preparation of compounds of formula (I) and pharmaceutically acceptable salts thereof.

In one embodiment of the present invention, a compound of formula (I) is in the form of a pharmaceutically acceptable salt. In one embodiment, the compound of any of Example 1 to 324 is in the form of a pharmaceutically acceptable salt.

Compounds of formula (I) may contain an acidic or basic functional group and, thus, the skilled artisan will appreciate that pharmaceutically acceptable salts of the compounds of formula (I) may be prepared. Pharmaceutically acceptable salts of compounds of the invention may possess, for example, improved stability, solubility, and/or crystallinity, facilitating development as a medicine.

Compounds of formula (I) may contain a basic functional group and may be capable of forming pharmaceutically acceptable acid addition salts by treatment with an suitable acid (inorganic or organic acid). Representative pharmaceutically acceptable acid addition salts include hydrochloride, hydrobromide, nitrate, sulfate, bisulfate, sulfamate, phosphate, acetate, hydroxyacetate, phenylacetate, propionate, butyrate, isobutyrate, valerate, maleate, hydroxymaleate, acrylate, fumarate, maleate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, naphthoate, hydroxynaphthoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate. In another embodiment, the pharmaceutically acceptable salt is the 1,2-ethanedisulphonic acid (edisylate) salt.

Compounds of formula (I) may contain an acidic functional group and suitable pharmaceutically-acceptable salts include salts of such acidic functional groups. Representative salts include pharmaceutically acceptable metal salts such as sodium, potassium, lithium, calcium, magnesium, aluminum, and zinc salts; pharmaceutically acceptable organic primary, secondary, and tertiary amines including aliphatic amines, aromatic amines, aliphatic diamines, and hydroxy alkylamines such as methylamine, ethylamine, 2-hydroxyethylamine, diethylamine, TEA, ethylenediamine, ethanolamine, diethanolamine, and cyclohexylamine.

In one embodiment, there is provided a compound which is the 1,2-ethanedisulphonic acid salt of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxy butanoate, of formula:

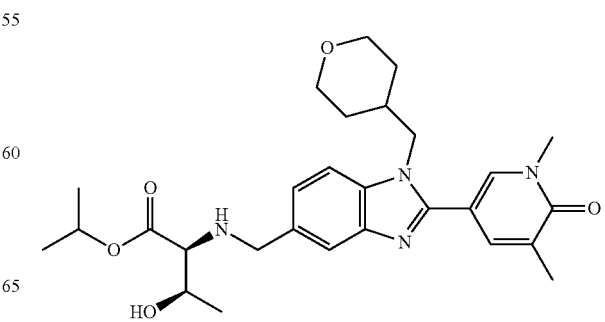

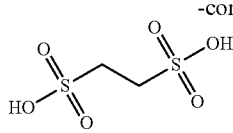

In one embodiment, there is provided a crystalline solid state form of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate, 1,2-ethanedisulphonic acid salt.

In a further embodiment, there is provided a crystalline solid state form of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate, 1,2-ethanedisulphonic acid salt characterised by an X-ray powder diffraction (XRPD) pattern having significant diffraction peaks at 2θ values shown in Table 1.

TABLE 1

XRPD peak table for the 1,2-ethanedisulphonic acid salt of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate

| Position/°2θ | d-spacing [Å] |
|---|---|
| 5.4 | 16.5 |
| 8.8 | 10.1 |
| 9.9 | 8.9 |
| 11.0 | 8.1 |
| 11.6 | 7.7 |
| 13.5 | 6.6 |
| 13.8 | 6.4 |
| 15.0 | 5.9 |
| 15.7 | 5.6 |
| 16.0 | 5.6 |
| 16.9 | 5.2 |
| 18.0 | 4.9 |
| 18.4 | 4.8 |
| 18.6 | 4.8 |
| 19.2 | 4.6 |
| 19.4 | 4.6 |
| 19.8 | 4.5 |
| 20.4 | 4.3 |
| 20.9 | 4.3 |
| 21.1 | 4.2 |
| 21.3 | 4.2 |
| 22.0 | 4.0 |
| 22.4 | 4.0 |
| 22.9 | 3.9 |
| 23.4 | 3.8 |
| 24.9 | 3.6 |
| 25.1 | 3.5 |
| 25.7 | 3.5 |
| 25.9 | 3.4 |
| 26.4 | 3.4 |
| 26.7 | 3.3 |
| 26.9 | 3.3 |
| 27.5 | 3.2 |
| 28.1 | 3.2 |
| 28.5 | 3.1 |
| 30.2 | 3.0 |
| 32.2 | 2.8 |
| 32.9 | 2.7 |
| 33.2 | 2.7 |
| 33.6 | 2.7 |
| 34.3 | 2.6 |
| 34.8 | 2.6 |
| 35.4 | 2.5 |
| 35.7 | 2.5 |
| 36.4 | 2.5 |
| 37.8 | 2.4 |
| 38.3 | 2.4 |

TABLE 1-continued

XRPD peak table for the 1,2-ethanedisulphonic acid salt of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate

| Position/°2θ | d-spacing [Å] |
|---|---|
| 38.7 | 2.3 |
| 39.1 | 2.3 |

In a further embodiment, there is provided a crystalline solid state form of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate, 1,2-ethanedisulphonic acid salt characterised by an X-ray powder diffraction (XRPD) pattern having significant diffraction peaks at 2θ values, +0.1° 2 θ experimental error, of 5.4, 8.8, 9.9, 11.6, 13.8, 16.9, 18.0, 16.6, 19.1, 19.4, 19.8, 20.4, 20.9, 21.3, 22.0, 22.4, 22.9, 23.4, 24.9, and 25.1 degrees.

For a review on suitable salts see Berge et al., *J. Pharm. Sci.*, 66:1-19 (1977). The invention includes within its scope all possible stoichiometric and non-stoichiometric forms of the salts of the compounds of formula (I).

Salts may be formed using techniques well-known in the art, for example by precipitation from solution followed by filtration, or by evaporation of the solvent.

It will be appreciated that many organic compounds can form complexes with solvents in which they are reacted or from which they are precipitated or crystallised. These complexes are known as "solvates". For example, a complex with water is known as a "hydrate". Solvents with high boiling points and/or solvents with a high propensity to form hydrogen bonds such as water, ethanol, iso-propyl alcohol, and N-methyl pyrrolidinone may be used to form solvates. Methods for the identification of solvated include, but are not limited to, NMR and microanalysis. Compounds of formula (I), or salts thereof, may exist is solvated and unsolvated form.

Certain of the compounds of the invention may exist in tautomeric forms. It will be understood that the present invention encompasses all of the tautomers of the compounds of the invention whether as individual tautomers or as mixtures thereof.

The compounds of the invention may be in crystalline or amorphous form. The most thermodynamically stable crystalline form of a compound of the invention is of particular interest.

Crystalline forms of compounds of the invention may be characterised and differentiated using a number of conventional analytical techniques, including, but not limited to, X-ray powder diffraction (XRPD), infrared spectroscopy (IR), Raman spectroscopy, differential scanning calorimetry (DSC), thermogravimetric analysis (TGA) and solid-state nuclear magnetic resonance (ssNMR).

The present invention also includes all suitable isotopic variations of a compound of formula (I) or a pharmaceutically acceptable salt thereof. An isotopic variation of a compound of formula (I), or a pharmaceutically acceptable salt thereof, is defined as one in which at least one atom is replaced by an atom having the same atomic number but an atomic mass different from the atomic mass usually found in nature. Examples of isotopes that can be incorporated into compounds of the invention include isotopes of hydrogen, carbon, nitrogen, oxygen, fluorine and chlorine such as $^{2}H$, $^{3}H$, $^{13}C$, $^{14}C$, $^{15}N$, $^{17}O$, $^{18}O$, $^{18}F$ and $^{36}Cl$, respectively. Certain isotopic variations of a compound of formula (I) or a salt or solvate thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of a compound of formula (I), or a pharmaceutically salt thereof, can generally be prepared by conventional procedures such as by the illustrative methods or by the preparations described in the Examples hereafter using appropriate isotopic variations of suitable reagents.

The compounds of formula (I) and pharmaceutically acceptable salts thereof may contain one or more asymmetric center (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in a compound of formula (I), or in any chemical structure illustrated herein, is not specified the structure is intended to encompass all individual stereoisomers and all mixtures thereof. Thus, compounds of formula (I) and pharmaceutically acceptable salts thereof containing one or more chiral center may be used as racemic mixtures, enantiomerically enriched mixtures, or as enantiomerically pure individual stereoisomers.

Individual stereoisomers of a compound of formula (I), or a pharmaceutically acceptable salt thereof, which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

Certain compounds of the invention described herein possess an alpha amino acid ester that facilitates penetration of the compound through the cell wall. When inside the cell, the ester is hydrolysed by intracellular carboxyesterases to release the parent acid. Due to its charge, the parent acid has reduced permeability and is thus retained within the cell, where it becomes more concentrated leading to increased potency and duration of action. Even though compounds of the invention comprising an alpha amino acid ester are converted to their corresponding carboxylic acid by intracellular esterases, both the esters and their corresponding acids function as inhibitors of the BET family of bromodomain containing proteins. In one embodiment, a compound of the invention is capable of inhibiting the binding of one or more of the four known BET family bromodomain containing proteins (e.g. BRD2, BRD3, BRD4 and BRDt) to, for example, an acetylated lysine residue. In a further embodiment, the compound of formula (I), or a pharmaceutically acceptable salt thereof, is capable of inhibiting the binding of BRD4 to its cognate acetylated lysine residue. The compounds of the invention may possess an improved profile over known BET inhibitors, for example, certain compounds may have one or more of the following properties:

(i) potent BET inhibitory activity;
(ii) selectivity over other known bromodomain containing proteins outside of the BET family of proteins;
(iii) selectivity for a particular BET family member over other BET family members;
(iv) selectivity for one Binding Domain (i.e. BD1 over BD2 or vice versa) for any given BET family member;
(v) improved developability (e.g. desirable solubility profile, pharmacokinetics and pharmacodynamics); or
(vi) a reduced side-effect profile.

Further, certain compounds of the invention may inhibit other known bromodomain containing proteins that are outside of the BET family of proteins, such as, for example, bromodomain adjacent to zinc finger domain protein 2A (BAZ2A).

The compounds of the invention comprise a $R_4$ substituent attached at either the 5- or 6-position of the benzimidazole core, which represents an alpha amino acid ester group and also captures the corresponding carboxylic acids. The particular structure of the alpha amino acid esters of $R_4$ ensures that the ester is hydrolysed by cells containing carboxyesterase hCE-1, and not by cells that contain other carboxyesterases (such as hCE-2 and hCE-3) but not hCE-1. This property enables selective targeting of the compounds of the invention to cells that express hCE-1, such as macrophages, monocytes and dendritic cells.

Carboxyesterases hCE-2 and hCE-3 have a ubiquitous expression pattern, whereas hCE-1 is highly expressed in liver, lung and bone marrow but is, importantly, only found in certain types of cell, such as monocytes, macrophages and dendritic cells.

The structure of the alpha amino acid ester group, in particular the substitution pattern at positions $R_7$ and $R_8$, can determine the rate of hydrolysis of the compound within cells that contain hCE-1, and the desired rate of hydrolysis may differ depending on the selected route of administration.

hCE-1 is present in hepatocytes and, thus, for orally administered compounds, ester groups that have a slower rate of hydrolysis are desirable to ensure that a sufficient amount of the compound enters the bloodstream after first pass metabolism.

In one embodiment of the present invention, a desirable rate of hydrolysis for an orally administered compound may be obtained if $R_7$ represents cycloalkyl, heterocycloalkyl, or —$CR_{13}R_{14}R_{15}$ wherein $R_{13}$ is hydrogen, hydroxyl, —$CH_2OH$, —$CH_2C_{1-3}$alkyl, halo, $C_{1-3}$alkyl, or $C_{1-3}$alkoxy wherein said $C_{1-3}$alkyl or $C_{1-3}$alkoxy may be optionally substituted with halo or hydroxyl; and $R_{14}$, and $R_{15}$ are independently hydrogen or $C_{1-3}$alkyl, with the proviso that at least two of $R_{13}$, $R_{14}$ and $R_{15}$ are not hydrogen. In a further embodiment, $R_7$ represents isopropyl, —CH(CH$_3$)OH, sec-butyl, tert-butyl, tert-pentyl, sec-pentyl, 3-pentyl or cycloalkyl. Similarly, $R_8$ may represent —$CHR_{16}R_{17}$ wherein $R_{16}$ is $C_{1-3}$alkyl and $R_{17}$ is $C_{1-6}$alkyl, cycloalkyl, heterocycloalkyl, wherein said $C_{1-6}$alkyl is optionally substituted with $C_{1-3}$alkoxy, or $R_{16}$ and $R_{17}$ together with the carbon atom to which they attach form a cycloalkyl or heterocycloalkyl. In a further embodiment, $R_8$ represents isopropyl, sec-butyl, sec-pentyl, 3-pentyl, or cycloalkyl.

In one embodiment, the present invention is also includes each corresponding acid of the exemplified covalent conjugates that comprise an alpha amino acid ester (i.e. the covalent conjugates of Examples 1 to 324 that comprises an alpha amino acid ester).

Statement of Use

Compounds of formula (I), or pharmaceutically acceptable salts thereof, are BET inhibitors and thus may have therapeutic utility in the treatment of a variety of diseases or conditions related to systemic or tissue inflammation, inflammatory responses to infection or hypoxia, cellular activation and proliferation, lipid metabolism, fibrosis and in the prevention and treatment of viral infections.

BET inhibitors may be useful in the treatment of a wide variety of acute or chronic autoimmune or inflammatory conditions such as rheumatoid arthritis, osteoarthritis, acute gout, psoriasis, systemic lupus erythematosus, pulmonary arterial hypertension (PAH), multiple sclerosis, inflammatory bowel disease (Crohn's disease and Ulcerative colitis), asthma, chronic obstructive airways disease, pneumonitis, myocarditis, pericarditis, myositis, eczema, dermatitis (including atopic dermatitis), alopecia, vitiligo, bullous skin diseases, nephritis, vasculitis, hypercholesterolemia, atherosclerosis, Alzheimer's disease, depression, Sjögren's syndrome, sialoadenitis, central retinal vein occlusion, branched retinal vein occlusion, Irvine-Gass syndrome (post cataract and post-surgical), retinitis pigmentosa, pars planitis, birdshot retinochoroidopathy, epiretinal membrane, cystic macular edema, parafoveal telengiectasis, tractional maculopathies, vitreomacular traction syndromes, retinal detachment, neuroretinitis, idiopathic macular edema, retinitis, dry eye (keratoconjunctivitis Sicca), vernal keratoconjunctivitis, atopic keratoconjunctivitis, uveitis (such as anterior uveitis, pan uveitis, posterior uveitis, uveitis-associated macular edema), scleritis, diabetic retinopathy, diabetic macula edema, age-related macular dystrophy, hepatitis, pancreatitis, primary biliary cirrhosis, sclerosing cholangitis, Addison's disease, hypophysitis, thyroiditis, type I diabetes, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, pyoderma gangrenosum, vasculitis with organ involvement and acute rejection of transplanted organs. The use of BET inhibitors for the treatment of rheumatoid arthritis is of particular interest.

In one embodiment, the acute or chronic autoimmune or inflammatory condition is a disorder of lipid metabolism via the regulation of APO-A1 such as hypercholesterolemia, atherosclerosis and Alzheimer's disease.

In another embodiment, the acute or chronic autoimmune or inflammatory condition is a respiratory disorder such as asthma or chronic obstructive airways disease.

In another embodiment, the acute or chronic autoimmune or inflammatory condition is a systemic inflammatory disorder such as rheumatoid arthritis, osteoarthritis, acute gout, psoriasis, systemic lupus erythematosus, multiple sclerosis or inflammatory bowel disease (Crohn's disease and ulcerative colitis).

In another embodiment, the acute or chronic autoimmune or inflammatory condition is multiple sclerosis.

In a further embodiment, the acute or chronic autoimmune or inflammatory condition is Type I diabetes.

BET inhibitors may be useful in the treatment of diseases or conditions which involve inflammatory responses to infections with bacteria, viruses, fungi, parasites or their toxins, such as sepsis, acute sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus. In one embodiment, the disease or condition which involves an inflammatory response to an infection with bacteria, a virus, fungi, a parasite or their toxins is acute sepsis.

BET inhibitors may be useful in the treatment of conditions associated with ischaemia-reperfusion injury such as myocardial infarction, cerebro-vascular ischaemia (stroke), acute coronary syndromes, renal reperfusion injury, organ transplantation, coronary artery bypass grafting, cardiopulmonary bypass procedures, pulmonary, renal, hepatic, gastro-intestinal or peripheral limb embolism.

BET inhibitors may be useful in the treatment of fibrotic conditions such as idiopathic pulmonary fibrosis, renal fibrosis, post-operative stricture, keloid scar formation, scleroderma (including morphea), cardiac fibrosis and cystic fibrosis.

BET inhibitors may be useful in the treatment of viral infections such as herpes simplex infections and reactivations, cold sores, herpes zoster infections and reactivations, chickenpox, shingles, human papilloma virus (HPV), human immunodeficiency virus (HIV), cervical neoplasia, adenovirus infections, including acute respiratory disease, poxvirus infections such as cowpox and smallpox and African swine fever virus. In one embodiment, the viral infection is a HPV infection of skin or cervical epithelia. In another embodiment, the viral infection is a latent HIV infection.

BET inhibitors may be useful in the treatment of cancer, including hematological (such as leukaemia, lymphoma and multiple myeloma), epithelial including lung, breast and colon carcinomas, midline carcinomas, mesenchymal, hepatic, renal and neurological tumours.

BET inhibitors may be useful in the treatment of one or more cancers selected from brain cancer (gliomas), glioblastomas, Bannayan-Zonana syndrome, Cowden disease, Lhermitte-Duclos disease, breast cancer, inflammatory breast cancer, colorectal cancer, Wilm's tumor, Ewing's sarcoma, rhabdomyosarcoma, ependymoma, medulloblastoma, colon cancer, head and neck cancer, kidney cancer, lung cancer, liver cancer, melanoma, squamous cell carcinoma, ovarian cancer, pancreatic cancer, prostate cancer, sarcoma cancer, osteosarcoma, giant cell tumor of bone, thyroid cancer, lymphoblastic T-cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T-cell leukemia, plasmacytoma, immunoblastic large cell leukemia, mantle cell leukemia, multiple myeloma, megakaryoblastic leukemia, acute megakaryocytic leukemia, promyelocytic leukemia, mixed lineage leukaemia, erythroleukemia, malignant lymphoma, Hodgkins lymphoma, non-Hodgkins lymphoma, lymphoblastic T-cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), NUT-midline carcinoma and testicular cancer.

In one embodiment, the cancer is a leukaemia, for example a leukaemia selected from acute monocytic leukemia, acute myelogenous leukemia, chronic myelogenous leukemia, chronic lymphocytic leukemia and mixed lineage leukaemia (MLL). In another embodiment, the cancer is NUT-midline carcinoma. In another embodiment, the cancer is multiple myeloma. In another embodiment, the cancer is a lung cancer such as small cell lung cancer (SCLC). In another embodiment, the cancer is a neuroblastoma. In another embodiment, the cancer is Burkitt's lymphoma. In another embodiment, the cancer is cervical cancer. In another embodiment, the cancer is esophageal cancer. In another embodiment, the cancer is ovarian cancer. In another embodiment, the cancer is breast cancer. In another embodiment, the cancer is colorectal cancer.

In one embodiment, the disease or condition for which a BET inhibitor is indicated is selected from diseases associated with systemic inflammatory response syndrome, such as sepsis, burns, pancreatitis, major trauma, haemorrhage and ischaemia. In this embodiment, the BET inhibitor would be administered at the point of diagnosis to reduce the incidence of SIRS, the onset of shock, multi-organ dysfunction syndrome, which includes the onset of acute lung injury, ARDS, acute renal, hepatic, cardiac or gastro-intestinal injury and mortality. In another embodiment, the BET inhibitor would be administered prior to surgical or other procedures associated with a high risk of sepsis, haemorrhage, extensive tissue damage, SIRS or MODS (multiple organ dysfunction syndrome). In a particular embodiment, the disease or condition for which a BET inhibitor is indicated is sepsis, sepsis syndrome, septic shock and endotoxaemia. In another embodiment, the BET inhibitor is indicated for the treatment of acute or chronic pancreatitis. In another embodiment, the BET inhibitor is indicated for the treatment of burns.

In a further aspect, the present invention also provides a compound of formula (I) or a pharmaceutically acceptable salt thereof for use in therapy.

In a further aspect, the present invention provides (2S, 3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate, of formula:

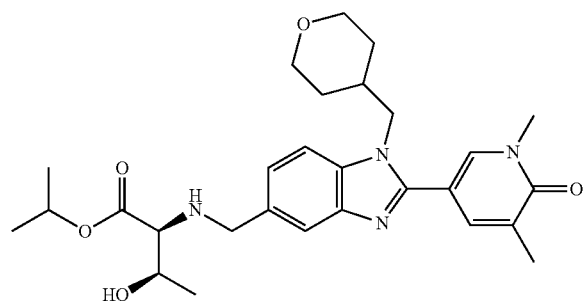 [SMILES: Cc1cc(-c2nc3cc(CN[C@H](C(=O)OC(C)C)[C@@H](C)O)ccc3n2CC2CCOCC2)cn(C)c1=O]

or a pharmaceutically acceptable salt thereof, for use in therapy.

In a further aspect, the present invention provides the 1,2-ethanedisulphonic acid salt of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate, of formula:

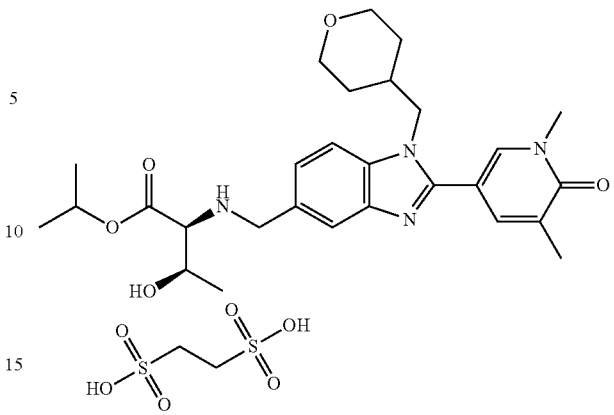

for use in therapy.

In a further aspect, the present invention provides (2S, 3R)-isopropyl 2-(((1-(1,3-dimethoxypropan-2-yl)-2-(1,5-dimethyl-6-oxo-1,6-dihydropyridin-3-yl)-1H-benzo[d]imidazol-5-yl)methyl)amino)-3-hydroxybutanoate, of formula:

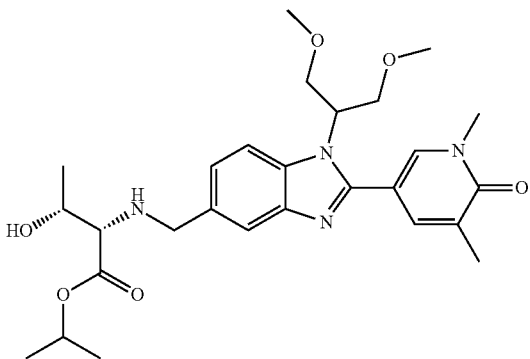 [SMILES: COCC(COC)n1c(-c2cc(C)c(=O)n(C)c2)nc2cc(CN[C@H](C(=O)OC(C)C)[C@@H](C)O)ccc21]

or a pharmaceutically acceptable salt thereof, for use in therapy.

In a further aspect, the present invention provides a compound of formula (I) or a pharmaceutically acceptable salt thereof for use in the treatment of diseases or conditions for which a bromodomain inhibitor, in particular a BET inhibitor, is indicated, including each and all of the above listed indications.

In a further aspect, the present invention also provides a compound of formula (I), or a pharmaceutically acceptable salt thereof, for use in the treatment of autoimmune and inflammatory diseases, and cancer.

In a further aspect, the present invention provides a compound of formula (I), or a pharmaceutically acceptable salt thereof, for use in the treatment of rheumatoid arthritis.

In a further aspect, the present invention is directed to a method of treatment of an autoimmune or inflammatory disease or cancer, which comprises administering to a subject in need thereof, a therapeutically effective amount of a compound of formula (I), or a pharmaceutically acceptable salt thereof.

In yet a further aspect, the present invention is directed to a method of treating rheumatoid arthritis, which comprises administering to a subject in need thereof, a therapeutically effective amount of a compound of formula (I), or a pharmaceutically acceptable salt thereof.

In a further aspect, the present invention is directed to the use of a compound of formula (I), or a pharmaceutically acceptable salt thereof, in the manufacture of a medicament for use in the treatment of an autoimmune or inflammatory disease, or cancer.

In a further aspect, the present invention is directed to the use of a compound of formula (I), or a pharmaceutically acceptable salt thereof, in the manufacture of a medicament for use in the treatment of rheumatoid arthritis.

Pharmaceutical Compositions/Routes of Administration/Dosages

While it is possible that for use in therapy, a compound of formula (I) as well as pharmaceutically acceptable salts thereof may be administered as the raw chemical, it is common to present the active ingredient as a pharmaceutical composition.

In a further aspect, there is provided a pharmaceutical composition comprising a compound of formula (I), or a pharmaceutically acceptable salt thereof, and one or more pharmaceutically acceptable excipients. In a further aspect, there is provided a pharmaceutical composition comprising a compound of formula (I), or a pharmaceutically acceptable salt thereof, and a pharmaceutically acceptable excipient.

In a further aspect, there is provided a pharmaceutical composition comprising (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate, of formula:

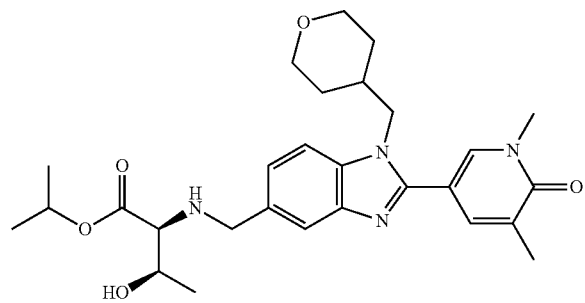 [SMILES: Cc1cc(-c2nc3cc(CN[C@H](C(=O)OC(C)C)[C@@H](C)O)ccc3n2CC2CCOCC2)cn(C)c1=O]

or a pharmaceutically acceptable salt thereof, and one or more pharmaceutically acceptable excipients.

In a further aspect, there is provided a pharmaceutical composition comprising the 1,2-ethanedisulphonic acid salt of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate, of formula:

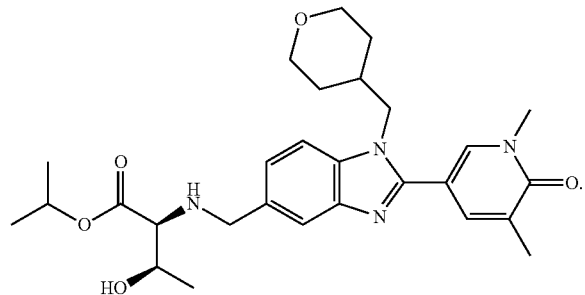

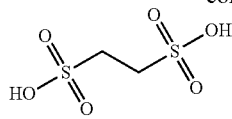

In a further aspect, there is provided a pharmaceutical composition comprising (2S,3R)-Isopropyl 2-(((1-(1,3-dimethoxypropan-2-yl)-2-(1,5-dimethyl-6-oxo-1,6-dihydropyridin-3-yl)-1H-benzo[d]imidazol-5-yl)methyl)amino)-3-hydroxybutanoate, of formula:

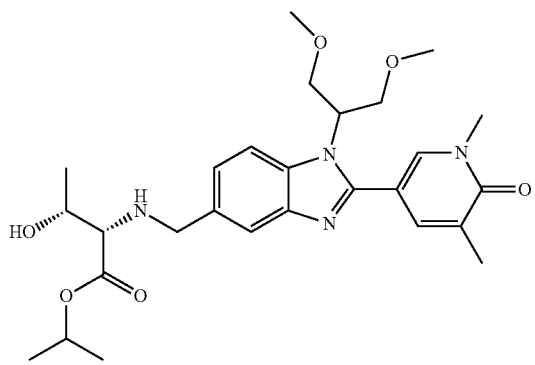 [SMILES: COCC(COC)n1c(-c2cc(C)c(=O)n(C)c2)nc2cc(CN[C@H](C(=O)OC(C)C)[C@@H](C)O)ccc21]

or a pharmaceutically acceptable salt thereof, and one or more pharmaceutically acceptable excipients.

The excipient(s) must be pharmaceutically acceptable and be compatible with the other ingredients of the composition. In accordance with another aspect of the invention there is also provided a process for the preparation of a pharmaceutical composition including admixing a compound of formula (I), or a pharmaceutically acceptable salt thereof, with one or more pharmaceutically acceptable excipients. The pharmaceutical composition can be used in the treatment of any of the diseases described herein.

Since the compounds of formula (I) are intended for use in pharmaceutical compositions it will be readily understood that they are each preferably provided in substantially pure form, for example, at least 85% pure, especially at least 98% pure (% in a weight for weight basis).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day.

Pharmaceutical compositions may be adapted for administration by any appropriate route, for example by the oral (including buccal or sublingual), rectal, inhaled, intranasal, topical (including buccal, sublingual or transdermal), ocular (including topical, intraocular, subconjunctival, episcleral, sub-Tenon), vaginal or parenteral (including subcutaneous, intramuscular, intravenous or intradermal) route. Such compositions may be prepared by any method known in the art of pharmacy, for example by bringing into association the active ingredient with the excipient(s).

In one aspect, the pharmaceutical composition is adapted for oral administration.

In a further aspect, a compound of the invention may be formulated in such a way as to facilitate delivery of said compound intracellularly.

Pharmaceutical compositions adapted for oral administration may be presented as discrete units such as tablets or capsules; powders or granules; solutions or suspensions in aqueous or non-aqueous liquids; edible foams or whips; or oil-in-water liquid emulsions or water-in-oil liquid emulsions.

Powders suitable for incorporating into tablets or capsules may be prepared by reducing the compound to a suitable fine size (e.g. by micronisation) and mixing with a similarly prepared pharmaceutical excipient such as an edible carbohydrate, for example, starch or mannitol. Flavoring, preservative, dispersing and coloring agents, for example, may also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, glidants, lubricants, sweetening agents, flavours, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of formula (I) and pharmaceutically acceptable salts thereof can also be combined with a free flowing inert excipient and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added. Compositions for oral administration may be designed to provide a modified release profile so as to sustain or otherwise control the release of the therapeutically active agent.

Where appropriate, dosage unit compositions for oral administration can be microencapsulated. The composition may be prepared to prolong or sustain the release as for example by coating or embedding particulate material in polymers, wax or the like.

Pharmaceutical compositions for nasal or inhaled administration may conveniently be formulated as aerosols, solutions, suspensions, gels or dry powders.

For pharmaceutical compositions suitable for and/or adapted for inhaled administration, it is preferred that a compound of formula (I) or a pharmaceutically acceptable salt thereof, is in a particle-size-reduced form e.g. obtained by micronisation. The preferable particle size of the size-reduced (e.g. micronised) compound or salt is defined by a D50 value of about 0.5 to about 10 microns (for example as measured using laser diffraction).

For pharmaceutical compositions suitable for and/or adapted for inhaled administration, the pharmaceutical composition may be a dry powder composition or an aerosol formulation, comprising a solution or fine suspension of the active substance in a pharmaceutically acceptable aqueous or non-aqueous solvent. Dry powder compositions can comprise a powder base such as lactose, glucose, trehalose, mannitol or starch, the compounds of formulae (I) or a pharmaceutically acceptable salt thereof (preferably in particle-size-reduced form, e.g. in micronised form), and optionally a performance modifier such as L-leucine or another amino acid and/or metal salt of stearic acid such as magnesium or calcium stearate. Preferably, the dry powder inhalable composition comprises a dry powder blend of lactose e.g. lactose monohydrate and the compound of formula (I) or a salt thereof.

In one embodiment, a dry powder composition suitable for inhaled administration may be incorporated into a plurality of sealed dose containers provided on medicament pack(s) mounted inside a suitable inhalation device. The containers may be rupturable, peelable or otherwise openable one-at-a-time and the doses of the dry powder composition administered by inhalation on a mouthpiece of the inhalation device, as known in the art. The medicament pack may take a number of different forms, for instance a disk-shape or an elongate strip. Representative inhalation devices are the DISKHALER™ inhaler device, the DISKUS™ inhalation device, and the ELLIPTA™ inhalation device, marketed by GlaxoSmithKline. The DISKUS™ inhalation device is, for example, described in GB 2242134A, and the ELLIPTA™ inhalation device is, for example, described in WO 03/061743 A1 WO 2007/012871 A1 and/or WO2007/068896.

Pharmaceutical compositions adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Pharmaceutical compositions adapted for topical administration may be formulated as ointments, creams, suspensions, emulsions, lotions, powders, solutions, pastes, gels, foams, sprays, aerosols or oils. Such pharmaceutical compositions may include conventional additives which include, but are not limited to, preservatives, solvents to assist drug penetration, co-solvents, emollients, propellants, viscosity modifying agents (gelling agents), surfactants and carriers. In one embodiment there is provided a pharmaceutical composition adapted for topical administration which comprises between 0.01-10%, or between 0.01-1% of a compound of formula (I)-(XVI), or a pharmaceutically acceptable salt thereof, by weight of the composition.

For treatments of the eye or other external tissues, for example mouth and skin, the compositions are preferably applied as a topical ointment, cream, gel, spray or foam. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administrations to the eye include eye drops wherein the active ingredient is dissolved or suspended in a suitable carrier, especially an aqueous solvent.

A therapeutically effective amount of a compound of formula (I) or a pharmaceutically acceptable salt thereof, will depend upon a number of factors including, for example, the age and weight of the subject, the precise condition requiring treatment and its severity, the nature of the formulation, and the route of administration, and will ultimately be at the discretion of the attendant physician or veterinarian. In the pharmaceutical composition, each dosage unit for oral administration preferably contains from 0.01 to 1000 mg, more preferably 0.5 to 100 mg, of a compound of formula (I) or a pharmaceutically acceptable salt thereof, calculated as the free base.

The compounds of formula (I) and pharmaceutically acceptable salts thereof may be employed alone or in combination with other therapeutic agents. Combination therapies according to the present invention thus comprise the administration of at least one compound of formula (I) or a pharmaceutically acceptable salt thereof, and the use of at least one other therapeutically active agent. A compound of formula (I) or pharmaceutically acceptable salt thereof, and the other therapeutically active agent(s) may be administered together in a single pharmaceutical composition or separately and, when administered separately this may occur simultaneously or sequentially in any order.

In a further aspect, there is provided a combination product comprising a compound of formula (I) or a pharmaceutically acceptable salt thereof, together with one or more other therapeutically active agents, and optionally one or more pharmaceutically acceptable excipients.

It will be clear to a person skilled in the art that, where appropriate, the other therapeutic ingredient(s) may be used in the form of salts, for example as alkali metal or amine salts or as acid addition salts, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable excipient.

General Synthetic Routes

The compounds of formula (I) and salts thereof may be prepared by the methodology described hereinafter, constituting further aspects of this invention.

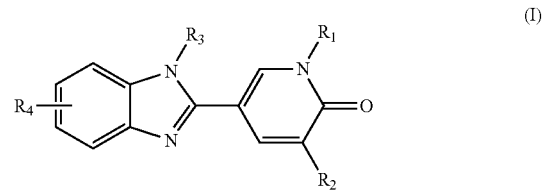

Accordingly, there is provided a process for the preparation of a compound of formula (I), which process comprises the alkylation of a compound of formula (II):

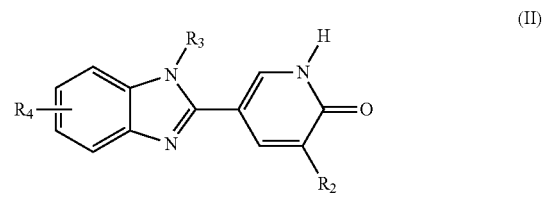

Wherein $R_2$, $R_3$ and $R_4$ are as defined hereinbefore for a compound of formula (I). For example, a compound of formula (II) could be dissolved in a solvent such as N,N-dimethylformamide, then treated with a suitable base in the presence of an alkyl halide and heated at a suitable temperature for an appropriate time to give, after purification, compounds of the formula (I) wherein $R_1$, $R_2$, $R_3$ and $R_4$ are as defined hereinbefore for a compound of formula (I).

There is provided a process for the preparation of a compound of formula (I), which process comprises cyclisation of a compound of formula (III):

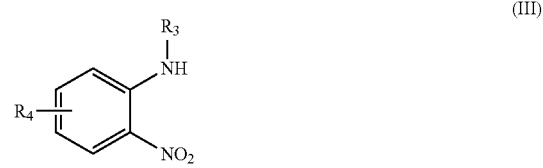

Wherein $R_3$ and $R_4$ are as defined hereinbefore for a compound of formula (I). For example, a compound of formula (III) could be dissolved in a solvent mixture such as ethanol/water, then treated with a suitable aldehyde of formula (IV) in the presence of sodium dithionite and heated at a suitable temperature for an appropriate time to give, after purification, compounds of the formula (I). The aldehydes mentioned above are of general formula (IV) wherein $R_1$ and $R_2$ are as defined for a compound of formula (I).

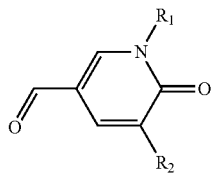

(IV)

There is provided a process for the preparation of a compound of formula (III), which process comprises the nucleophilic functionalisation of a compound of formula (V):

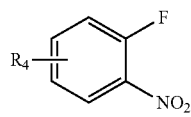

(V)

Wherein $R_4$ is as defined hereinbefore for a compound of formula (I). For example, a compound of formula (V) could be dissolved in a solvent such as tetrahydrofuran then treated with a suitable amine containing $R_3$ as defined hereinbefore for a compound of formula (I) in the presence of a suitable base such as triethylamine. The mixture would then be heated at a suitable temperature for an appropriate time to give, after purification, compounds of the formula (III).

There is provided a process for the preparation of a compound of formula (V), which process comprises the reductive amination of a compound of formula (VI):

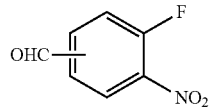

(VI)

Wherein (VI) is dissolved in a suitable solvent such as dicloromethane to which is added an appropriately functionalised amine and an additive such as acetic acid. The mixture would be stirred at an appropriate temperature for a specific time prior to the addition of a reducing agent such as sodium triacetoxyborohydride. The mixture would be stirred for an appropriate time to give, after purification, compounds of formula (V) wherein $R_4$ is as defined hereinbefore for a compound of formula (I).

There is provided a process for the preparation of a compound of formula (VII), which process comprises the functionalisation of a compound of formula (VIII):

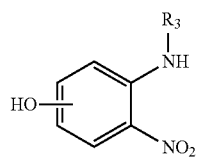

(VII)

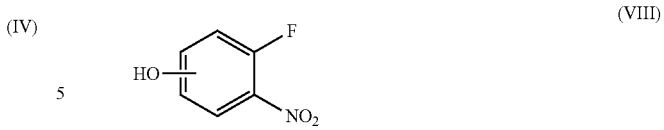

(VIII)

Wherein a compound of formula (VIII) could be dissolved in a solvent such as dioxane, and then treated with a suitable amine containing $R_3$ as defined hereinbefore for a compound of formula (I) in the presence of a suitable base such as triethylamine. The mixture would then be heated at a suitable temperature for an appropriate time to give, after purification, compounds of the formula (VII). The resulting compounds of general formula (VII) could then be reacted with aldehydes of formula (IV) in the presence of sodium dithionite in a suitable solvent mixture such as ethanol/water at a suitable temperature for an appropriate time to give, after purification, compounds of the formula (IX).

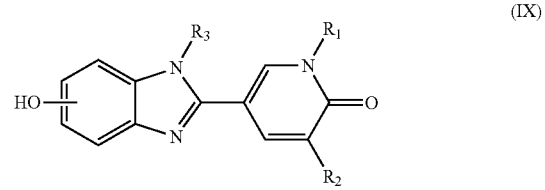

(IX)

The resulting compounds could then be further elaborated via sequential alkylation, oxidation and reductive amination procedures by someone skilled in the art to give further functionalised molecules fitting the general formula (I) wherein $R_1$, $R_2$, $R_3$ and $R_4$ are as defined hereinbefore for a compound of formula (I).

There is provided a process for the preparation of a compound of formula (I), which process comprises the functionalisation of a compound of formula (X):

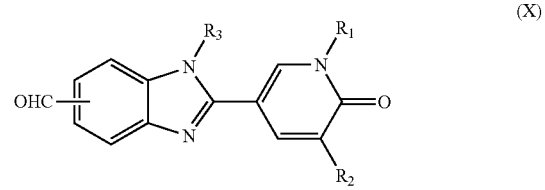

(X)

Wherein $R_1$, $R_2$ and $R_3$ are as defined hereinbefore for a compound of formula (I). For example, a compound of formula (X) could be dissolved in a solvent mixture comprising acetonitrile and water, then treated with a suitable base in the presence of trimethylsulfonium iodide and heated at a suitable temperature for an appropriate time to give, after workup, functionalised intermediate compounds. These compounds could then be further elaborated by, for example, dissolution in a suitable solvent such as tetrahydrofuran and addition of a Lewis acid such as boron trifluoride diethyl etherate. After stirring at an appropriate temperature for an appropriate time, addition of a functionalised amine, a base and a reducing agent such as sodium triacetoxyborohydride would give, after the appropriate reaction time, work up and purification, compounds of general formula (I) wherein $R_1$, $R_2$, $R_3$ and $R_4$ are as defined hereinbefore for a compound of formula (I).

There is provided a process for the preparation of a compound of formula (X), which process comprises the functionalisation of a compound of formula (XI):

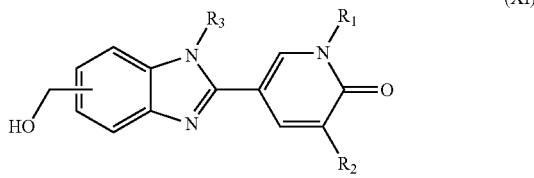

(XI)

Wherein R₁, R₂ and R₃ are as defined hereinbefore for a compound of formula (I). For example, a compound of formula (XI) could be dissolved in a solvent such as dichloromethane and treated with an appropriate oxidant for an appropriate time to give, after purification, compounds of the formula (X).

There is provided a process for the preparation of a compound of formula (XII), which process comprises the functionalisation of a compound of formula (XIII):

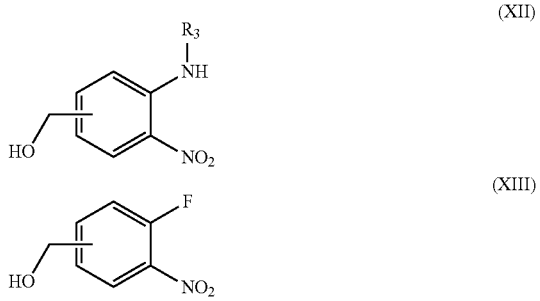

(XII)

(XIII)

Wherein a compound of formula (XIII) could be dissolved in a solvent such as tetrahydrofuran, then treated with a suitable amine containing R₃ as defined hereinbefore for a compound of formula (I) in the presence of a suitable base such as triethylamine. The mixture would then be heated at a suitable temperature for an appropriate time to give, after purification, compounds of the formula (XII). The resulting compounds of general formula (XII) could then be reacted with aldehydes of formula (IV) in the presence of sodium dithionite in a suitable solvent mixture such as ethanol/water at a suitable temperature for an appropriate time to give, after purification, compounds of the formula (XI), wherein R₁, R₂ and R₃ are as defined hereinbefore for a compound of formula (I).

Further to this, there is provided a process for the preparation of a compound of formula (I), which process comprises the functionalisation of a compound of formula (X) wherein R₁, R₂ and R₃ are as defined hereinbefore for a compound of formula (I). For example, a compound of formula (X) could be dissolved in a solvent such as dichloromethane before being treated with an appropriately functionalised amine in the presence of an additive such as triethylamine. After the appropriate reaction time, the resulting intermediate could be reduced following addition of a reducing agent such as sodium triacetoxyborohydride at an appropriate time and temperature, subsequent work up and purification of the mixture would give compounds of general formula (I) wherein $R_1$, $R_2$, $R_3$ and $R_4$ are as defined hereinbefore for a compound of formula (I).

Additionally, a process is provided for the preparation of compounds of formula (I) wherein $R_1$, $R_2$, $R_3$ and $R_4$ are as defined hereinbefore for a compound of formula (I) and $R_4$ contains a functionalised carboxylic acid. For example, a compound of general formula (I) could be dissolved in a solvent mixture such as tetrahydrofuran/methanol/water then treated with a base such as lithium hydroxide for an appropriate time to give, after purification, a compound of general formula (I) wherein $R_1$, $R_2$, $R_3$ and $R_4$ are as defined hereinbefore for a compound of formula (I).

Compounds IV, VI, VIII, and XIII are commercially available from, for example, Sigma Aldrich.

EXAMPLES

Thus the following Examples serve to illustrate their preparation but are not to be considered as limiting the scope of the invention in any way.

In the Intermediate and Example preparations, use of the phrase "prepared from: Intermediate X" or "prepared from Example Y" indicate where to find an example preparation for the compounds used (e.g. Intermediate X or Example Y), rather than the exact preparation necessarily used.

Abbreviations

Ac Acetyl
Bn Benzyl
BOC tert-Butyloxycarbonyl
dba Dibenzylideneacetone
DCM Dichloromethane
DIPEA N,N-diisopropylethylamine
DMAP 4-Dimethylaminopyridine
DMF N,N-dimethylformamide
DMSO Dimethylsulfoxide
EDC N-(3-Dimethylaminopropyl)-N-ethylcarbodiimide
ee Enantiomeric excess
Et Ethyl
EtOAc Ethyl acetate
EtOH Ethanol
H or hr Hour(s)
HATU O-(7-Azabenzotriazol-1-yl)-N,N,N,N-tetramethyluronium hexafluorophosphate
HOBt Hydroxybenzotriazole
HPLC High-performance liquid chromatography
IC₅₀ Half maximal inhibitory concentration
IPA Isopropyl alcohol
LCMS Liquid chromatography-mass spectrometry
MDAP Mass-directed auto-preparative HPLC
Me Methyl
MPER Mammalian protein extraction reagent
MS Mass spectrometry
nBuLi n-Butyllithium
NMP N-Methyl-2-pyrrolidone
NMR Nuclear magnetic resonance
Pd/C Palladium on carbon
Pd(PPh₃)₄ Tetrakis(triphenylphosphine)palladium(0)
Ph Phenyl
ppm Parts per million
pTSA para-Toluene sulfonic acid
rt Retention time
SCX Sulfonic acid, strong cation exchange
SPE Solid phase extraction
tBu Tertiary butyl
TFA Trifluoroacetic acid
$t_{RET}$ Retention time
THF Tetrahydrofuran UV Ultraviolet
Experimental Details
NMR
¹H NMR spectra were recorded in either CDCl₃ or DMSO-d₆ on either a Bruker DPX 400 or Bruker Avance DRX, Varian Unity 400 spectrometer or JEOL Delta all working at 400 MHz. The internal standard used was either tetramethylsilane or the residual protonated solvent at 7.25 ppm for CDCl₃ or 2.50 ppm for DMSO-d₆.

LCMS
System A
Column: 50 mm×2.1 mm ID, 1.7 μm Acquity UPLC BEH C$_{18}$
Flow Rate: 1 mL/min.
Temp: 40° C.
UV detection range: 210 to 350 nm
Mass spectrum: Recorded on a mass spectrometer using alternative-scan positive and negative mode electrospray ionisation
Solvents: A: 0.1% v/v formic acid in water
B: 0.1% v/v formic acid acetonitrile
Gradient:

| Time (min.) | A % | B % |
| --- | --- | --- |
| 0 | 97 | 3 |
| 1.5 | 0 | 100 |
| 1.9 | 0 | 100 |
| 2.0 | 97 | 3 |

System B
Column: 50 mm×2.1 mm ID, 1.7 m Acquity UPLC BEH C$_{18}$
Flow Rate: 1 mL/min.
Temp: 40° C.
UV detection range: 210 to 350 nm
Mass spectrum: Recorded on a mass spectrometer using alternative-scan positive and negative mode electrospray ionisation
Solvents: A: 10 mM ammonium bicarbonate in water adjusted to pH10 with ammonia solution
B: acetonitrile
Gradient:

| Time (min.) | A % | B % |
| --- | --- | --- |
| 0 | 99 | 1 |
| 1.5 | 3 | 97 |
| 1.9 | 3 | 97 |
| 2.0 | 0 | 100 |

System C
Column: 50 mm×2.1 mm ID, 1.7 m Acquity UPLC CSH C$_{18}$
Flow Rate: 1 mL/min.
Temp: 40° C.
UV detection range: 210 to 350 nm
Mass spectrum: Recorded on a mass spectrometer using alternative-scan positive and negative mode electrospray ionisation
The solvents employed were:
A=0.1% v/v solution of Trifluoroacetic Acid in Water.
B=0.1% v/v solution of Trifluoroacetic Acid in Acetonitrile.
Gradient:

| Time (min.) | A % | B % |
| --- | --- | --- |
| 0 | 95 | 5 |
| 1.5 | 5 | 95 |
| 1.9 | 5 | 95 |
| 2.0 | 95 | 5 |

System D
Column: 50 mm×2.1 mm ID, 1.7 m Acquity UPLC CSH C$_{18}$
Flow Rate: 1 mL/min.
Temp: 40° C.
UV detection range: 210 to 350 nm
Mass spectrum: Recorded on a mass spectrometer using alternative-scan positive and negative mode electrospray ionisation
The solvents employed were:
A=10 mM ammonium bicarbonate in water adjusted to pH10 with ammonia solution.
B=Acetonitrile.
Gradient:

| Time (min.) | A % | B % |
| --- | --- | --- |
| 0 | 97 | 3 |
| 1.5 | 5 | 95 |
| 1.9 | 5 | 95 |
| 2.0 | 97 | 3 |

System E
Column: XBridge BEH C18 (50 mm×4.6 mm, 2.5 μm)
Flow Rate: 1.3 mL/min.
Temp: 35° C.
Solvents: A: 5 mM Ammonium Bicarbonate in water (pH 10)
B: Acetonitrile
Gradient:

| Time (min.) | A % | B % |
| --- | --- | --- |
| 0 | 95 | 5 |
| 0.5 | 95 | 5 |
| 1 | 85 | 15 |
| 3.3 | 2 | 98 |
| 6.0 | 2 | 98 |
| 6.1 | 95 | 5 |
| 6.5 | 95 | 5 |

System F
Column: Acquity BEH C18 (50 mm×2.1 mm, 1.7 μm)
Flow Rate: 0.6 mL/min.
Temp: 35° C.
Solvents: A: 0.1% Formic Acid in water
B: 0.1% Formic Acid in acetonitrile
Gradient:

| Time (min.) | A % | B % |
| --- | --- | --- |
| 0 | 97 | 3 |
| 0.4 | 97 | 3 |
| 3.2 | 2 | 98 |
| 3.8 | 2 | 98 |
| 4.2 | 97 | 3 |
| 4.5 | 97 | 3 |

System G
Column: Acquity BEH C18 (50 mm×2.1 mm, 1.7 μm)
Flow Rate: 0.45 mL/min.
Temp: 35° C.
Solvents: A: 0.05% Formic Acid in acetonitrile
B: 0.05% Formic Acid in water
Gradient:

| Time (min.) | A % | B % |
|---|---|---|
| 0 | 3 | 97 |
| 0.4 | 3 | 97 |
| 7.5 | 98 | 2 |
| 9.5 | 98 | 2 |
| 9.6 | 3 | 97 |
| 10 | 3 | 97 |

System H
Column: XBridge BEH C18 (50 mm×4.6 mm, 2.5 μm)
Flow Rate: 1.3 mL/min.
Temp: 35° C.
Solvents: A: 5 mM Ammonium Bicarbonate in water (pH 10)
B: Acetonitrile
Gradient:

| Time (min.) | A % | B % |
|---|---|---|
| 0 | 95 | 5 |
| 0.5 | 95 | 5 |
| 1 | 85 | 15 |
| 6.0 | 2 | 98 |
| 9.0 | 2 | 98 |
| 9.5 | 95 | 5 |
| 10 | 95 | 5 |

System I
Column: 50 mm×2.1 mm ID, 1.7 μm Acquity UPLC CSH $C_{18}$
Flow Rate: 1 mL/min.
Temp: 40° C.
UV detection range: 210 to 350 nm
Mass spectrum: Recorded on a mass spectrometer using alternative-scan positive and negative mode electrospray ionisation
Solvents: A: 0.1% v/v formic acid in water
B: 0.1% v/v formic acid acetonitrile
Gradient:

| Time (min.) | A % | B % |
|---|---|---|
| 0 | 97 | 3 |
| 1.5 | 5 | 95 |
| 1.9 | 5 | 95 |
| 2.0 | 97 | 3 |

System J
Column: 50 mm×2.1 mm ID, 1.7 μm Acquity UPLC CSH $C_{18}$
Flow Rate: 1 mL/min.
Temp: 40° C.
UV detection range: 210 to 350 nm
Mass spectrum: Recorded on a mass spectrometer using alternative-scan positive and negative mode electrospray ionisation
Solvents: A: 10 mM ammonium bicarbonate in water adjusted to pH10 with ammonia solution
B: acetonitrile
Gradient:

| Time (min.) | A % | B % |
|---|---|---|
| 0 | 97 | 3 |
| 0.05 | 97 | 3 |
| 1.5 | 5 | 95 |
| 1.9 | 5 | 95 |
| 2.0 | 97 | 3 |

Mass Directed Autopreparative HPLC (MDAP)
Mass directed autopreparative HPLC was undertaken under the conditions given below. The UV detection was an averaged signal from wavelength of 210 nm to 350 nm and mass spectra were recorded on a mass spectrometer using alternate-scan positive and negative mode electrospray ionization.
Method A
Method A was conducted on a Sunfire $C_{18}$ column (typically 150 mm×30 mm i.d. 5 μm packing diameter) at ambient temperature. The solvents employed were:
A=0.1% v/v solution of formic acid in water
B=0.1% v/v solution of formic acid in acetonitrile.
Method B
Method B was conducted on an XBridge $C_{18}$ column (typically 100 mm×30 mm i.d. 5 μm packing diameter) at ambient temperature. The solvents employed were:
A=10 mM aqueous ammonium bicarbonate adjusted to pH 10 with ammonia solution.
B=acetonitrile.

Intermediate Preparation

Intermediate 1:
5-Methyl-6-oxo-1,6-dihydropyridine-3-carbaldehyde

5-Bromo-3-methylpyridin-2(1H)-one (commercially available from, for example, Sigma Aldrich) (1.5 g, 7.98 mmol) was added to a flask which was purged with nitrogen. Anhydrous THF (75 mL) was added and the solution was stirred under nitrogen, in dry-ice/acetone bath for 20 min. 1.6 M n-Butyllithium in hexanes (14.96 mL, 23.93 mmol) was added dropwise to the mixture and the reaction mixture was stirred under nitrogen in dry-ice/acetone bath for 3 hours. Anhydrous DMF (14.83 mL, 191 mmol) was added dropwise and the reaction mixture was stirred under nitrogen in dry-ice/acetone bath for 1 hour. It was quenched using saturated aqueous ammonium chloride solution (30 mL) and allowed to warm to room temperature. The resulting slurry was partitioned between EtOAc (100 mL) and water (100 mL) and the layers were separated. The organic layer was washed with brine (50 mL), dried, and evaporated under reduced pressure to give a pale yellow solid. The solid was triturated with diethyl ether and the solid filtered was collected as the title compound (Batch 1, 210.8 mg). The aqueous layers from the previous extractions were combined and re-extracted with DCM (4×75 mL and 4×100 mL). The combined organic layers were dried and evaporated under reduced pressure to give a pale yellow liquid. The liquid residue was azeotroped with toluene (2×30 mL) and the solvents were removed under reduced pressure to give a yellow solid. The solid was triturated with diethyl ether, and the solid filtered was collected as the title compound (Batch 2, 452.4 mg). The total yield of the reaction was 61%. Batch 1: LCMS (System A): $t_{RET}$=0.41 min, MH$^+$=138. Batch 2: LCMS (System A): $t_{RET}$=0.41 min, MH$^+$=138.

Intermediate 2: 1,5-Dimethyl-6-oxo-1,6-dihydropyridine-3-carbaldehyde

A mixture of 5-methyl-6-oxo-1,6-dihydropyridine-3-carbaldehyde (For an example preparation see Intermediate 1, 5 g, 36.5 mmol) and potassium carbonate (10.08 g, 72.9 mmol) in DMF (50 mL) was cooled in an ice/water bath, and methyl iodide (5.70 mL, 91 mmol) added dropwise. The reaction mixture was stirred for 15 min under nitrogen and then allowed to warm to room temperature and stirred for a further 2.5 hours. The solid was removed by filtration and the resulting solution evaporated under reduced pressure. The residue was partitioned between EtOAc (2×150 mL) and 1:1 water:saturated brine solution (150 mL). The organic layers were combined, dried using a hydrophobic frit, and evaporated under reduced pressure. The sample was loaded in DCM and purified by silica gel column chromatography (100 g column) using a gradient of 0-50% EtOAc in cyclohexane. The appropriate fractions were combined and evaporated under reduced pressure to give the title compound (4.4 g, 80% yield) as an off-white solid. LCMS (System A): $t_{RE}$T=0.46 min, MH$^+$=152.

Intermediate 3: (S)-cyclopentyl 2-amino-4-methylpentanoate 4-methylbenzenesulfonate A round bottom flask was charged with (S)-2-amino-4-methylpentanoic acid (5 g, 38.1 mmol), Cyclohexane (100 mL), tosic acid monohydrate (9.43 g, 49.6 mmol) and cyclopentanol (35 mL, 386 mmol). A Dean-Stark condensor was fitted and the mixture warmed to 130° C. to effect complete dissolution. The mixture was stirred at this temperature over the weekend before being allowed to stand at room temperature for 7 days. The precipitated solid was isolated by filtration and washed sequentially with cyclohexane and ethyl acetate. The solid was dried in vacuo to give the title compound (5.56 g) as a white solid. $^1$H NMR (400 MHz, METHANOL-d$_4$) δ 7.62-7.79 (m, 2H), 7.25 (d, J=7.83 Hz, 2H), 5.15-5.42 (m, 1H), 3.97 (t, J=6.97 Hz, 1H), 2.39 (s, 3H), 1.42-2.10 (m, 11H), 1.02 (d, J=7.09 Hz, 6H).

Intermediate 4: (2S)-tetrahydrofuran-3-yl 2-((tert-butoxycarbonyl)amino)-3-methylbutanoate A mixture of (S)-2-((tert-butoxycarbonyl)amino)-3-methylbutanoic acid (2.5 g, 11.51 mmol), diisopropylethylamine (2.97 g, 4.02 mL, 23.01 mmol), 1-hydroxybenzotriazole hydrate (2.12 g, 13.84 mmol), EDC (2.65 g, 13.81 mmol), and tetrahydrofuran-3-ol (10.14 g, 9.33 mL, 115 mmol) in DMF (20 mL) was stirred at room temperature overnight. The reaction mixture was partitioned between ethyl acetate (50 mL) and saturated NaHCO$_3$ (50 mL). The organic phase was washed with 1M hydrochloric acid (50 mL), water (50 mL) and brine (50 mL). The organic phase was dried and evaporated to give the title compound (3.19 g) as a colourless oil. $^1$H NMR (400 MHz, CHLOROFORM-d) δ 5.34 (d, J=1.71 Hz, 1H), 4.93-5.09 (m, 1H), 4.16-4.26 (m, 1H), 3.72-3.97 (m, 4H), 2.07-2.23 (m, 2H), 1.44 (s, 9H), 0.82-1.02 (m, 6H).

Intermediate 5: (2S)-tetrahydrofuran-3-yl 2-amino-3-methylbutanoate hydrochloride A solution of (2S)-tetrahydrofuran-3-yl 2-((tert-butoxycarbonyl)amino)-3-methylbutanoate (For a preparation see Intermediate 4, 3.1 g, 10.79 mmol) in dioxan (5 mL) was treated with 4M hydrogen chloride in dioxan (10 mL, 40 mmol). The reaction mixture was stirred at room temperature for 24 hours. The solvent was evaporated and the residue azeotroped with toluene (×3) to give the title compound (1.81 g), as a light brown oil. The crude product was used in subsequent reactions without purification.

Intermediate 6: (2S,3R)-2-hydroxy-2-methylpropyl 2-((tert-butoxycarbonyl)amino)-3-hydroxybutanoate In a microwave vial, 2,2-dimethyloxirane (2.058 mL, 23.17 mmol) was added to a mixture of (2S,3R)-2-((tert-butoxycarbonyl)amino)-3-hydroxybutanoic acid (1.016 g, 4.63 mmol) and sodium bicarbonate (2.038 g, 24.26 mmol). The resulting mixture was heated under microwave irradiation at 120° C. for 30 min. Mixture was filtered on a bond eluent filter, using EtOAc as eluent. Volatiles were removed under reduced pressure to afford 1.75 g of a clear oil as a crude product. The crude product was purified by silica gel column chromatography (50 g Silica column), eluted with a 0-100% EtOAc in Cyclohexane gradient over 10 column volumes. The appropriate fractions were combined, and the volatiles were removed under reduced pressure to afford the title compound (0.8 g) as a clear oil. The product was used crude in the next step without further purification.

Intermediate 7: (2S,3R)-2-hydroxy-2-methylpropyl 2-amino-3-hydroxybutanoate 4.0M HCl in Dioxane (1 mL, 32.9 mmol) was added to (2S,3R)-2-hydroxy-2-methylpropyl 2-((tert-butoxycarbonyl)amino)-3-hydroxybutanoate (For a preparation see Intermediate 6, 85 mg, 0.292 mmol) and the resulting mixture was stirred at r.t. for 2.5 hours. The volatiles were removed under reduced pressure and the oil was triturated with Et$_2$O to give the title compound (55.8 mg). Intermediate was used crude in following step without purification.

Intermediate 8: (2S,3R)—(S)-tetrahydrofuran-3-yl 2-((tert-butoxycarbonyl)amino)-3-methoxybutanoate (2S,3R)-2-((tert-butoxycarbonyl)amino)-3-methoxybutanoic acid (5000 mg, 21.44 mmol), EDC (4931 mg, 25.7 mmol), DMAP (262 mg, 2.144 mmol) and HOBt (3939 mg, 25.7 mmol) was dissolved in DIPEA (7.49 mL, 42.9 mmol) and DMF (25 mL). The solution was stirred for 30 minutes prior to adding (S)-tetrahydrofuran-3-ol (17.39 mL, 215 mmol). The reaction mixture was stirred overnight. The reaction mixture was partitioned between ethyl acetate (150 mL) and saturated solution of sodium bicarbonate (150 mL). The organic fraction was isolated and the aqueous layer was re-extracted twice with ethyl acetate (2×150 mL). The organic fractions were combined, passed through a hydrophobic frit and concentrated under reduced pressure. The resultant oil was dissolved in DCM (3 mL) and the solution was split into two which in turn were loaded onto silica columns (100 g columns). The product was eluted with a gradient of 20-70% of ethyl acetate in cyclohexane. The appropriate fractions were combined and dried in a vacuum oven to give the title compound (2156 mg). $^1$H NMR (400 MHz, DMSO-d$_6$) δ 5.84-5.99 (m, 1H), 5.25-5.33 (m, 1H), 4.11 (dd, J=4.04, 8.59 Hz, 1H), 3.72-3.89 (m, 4H), 3.68 (s, 1H), 3.26 (s, 3H), 2.12-2.26 (m, 1H), 1.86-2.00 (m, 1H), 1.38-1.46 (m, 9H), 1.11-1.16 (m, 3H).

Intermediate 9: (2S,3R)—(S)-tetrahydrofuran-3-yl 2-amino-3-methoxybutanoate hydrochloride (2S,3R)—(S)-tetrahydrofuran-3-yl 2-((tert-butoxycarbonyl) amino)-3-methoxybutanoate (For a preparation see Intermediate 8, 5910 mg, 17.53 mmol) was dissolved in HCl (5M in IPA) (35.1 mL, 176 mmol) and the reaction mixture was stirred overnight. The solvent was removed under reduced pressure and the resulting oil was placed in a vacuum oven overnight to yield the title compound (3890 mg, 93% yield) as an orange crystalline solid which was used in the subsequent step without further purification.

Intermediate 10: (2S,3R)-Neopentyl 2-amino-3-hydroxybutanoate 4-methylbenzenesulfonate To a suspension of (2S,3R)-2-amino-3-hydroxybutanoic acid (2.27 g, 19.06 mmol) and 4-methylbenzenesulfonic acid monohydrate (4.71 g, 24.77 mmol) in cyclohexane (100 mL) was added 2,2-dimethylpropan-1-ol (13.44 g, 152 mmol). The reaction mixture was fitted with a Dean-Stark condenser and heated at 130° C. overnight. A white slurry was formed upon cooling to room temperature, and it was evaporated under reduced pressure to remove the solvent. The white solid was dissolved in minimum amount of hot EtOAc and the clear solution was allowed to cool and then placed in an ice/water bath. No crystallisation occurred. The solution was evaporated under reduced pressure and dried in a vacuum oven for four nights. The resultant solid was recrystallised from EtOAc and allowed to cool, whereupon a white solid was formed. The resulting white solid was removed by filtration, washed with a little cold EtOAc, and dried in a vacuum oven to give the title compound (6.0 g) as a white solid. $^1$H NMR ($d_6$-DMSO, 293 K): δ 0.94 (s, 9H) 1.22 (d, J=6.3 Hz, 3H) 2.29 (s, 3H) 3.84 (d, J=10.4 Hz, 1H) 3.92 (d, J=10.6 Hz, 1H) 3.99 (d, J=3.8 Hz, 1H) 4.13-4.20 (m, 1H) 5.61 (d, J=4.3 Hz, 1H) 7.11 (m, J=7.8 Hz, 2H) 7.48 (m, J=8.1 Hz, 2H) 8.22 (br.s., 3H).

Intermediate 11: (2S,3R)-Isobutyl 2-amino-3-hydroxybutanoate 4-methylbenzenesulfonate To a suspension of (2S,3R)-2-amino-3-hydroxybutanoic acid (2.5 g, 20.99 mmol) and 4-methylbenzenesulfonic acid monohydrate (5.19 g, 27.3 mmol) in cyclohexane (100 mL) was added 2-methylpropan-1-ol (15.50 mL, 168 mmol). The reaction mixture was fitted with a Dean-Stark condenser and heated at 130° C. overnight. The reaction mixture was allowed to cool to room temperature and the solvent removed under reduced pressure. The resulting colourless liquid was dried in a vacuum oven for three nights. Initially, recrystallisation was attempted using EtOAc, but the sample remained in solution and therefore the solvent was removed under reduced pressure. Trituration in diethyl ether was carried out twice, the resulting white solid was removed by filtration and dried in a vacuum oven to give the title compound (2.2 g,) as a white solid. $^1$H NMR ($d_6$-DMSO, 293 K): δ 0.92 (d, J=6.6 Hz, 6H) 1.21 (d, J=6.6 Hz, 3H) 1.82-1.99 (m, 1H) 2.29 (s, 3H) 3.92-4.00 (m, 3H) 4.11-4.17 (m, 1H) 7.11 (d, J=7.8 Hz, 2H) 7.48 (d, J=8.1 Hz, 2H) 8.23 (br.s., 3H).

Intermediate 12: (S)-isopropyl 2-amino-3-methylbutanoate 4-methylbenzenesulfonate (S)-2-amino-3-methylbutanoic acid (2.5 g, 21.34 mmol), tosic acid (5.28 g, 27.7 mmol) and propan-2-o1 (15 mL, 196 mmol) were dissolved in cyclohexane (100 mL) and heated to 130° C. for 22 hrs. Solution was allowed to cool to room temperature at which point a white solid precipitated. This mixture was filtered under vacuum and the solid washed several times with hexane. Solid was then placed in a vacuum oven at 40° C. for 3 hrs. This solid was then added to cyclohexane (100 mL) along with tosic acid (1.76 g, 9.2 mmol) and propan-2-ol (3.94 g, 5.3 mmol). Mixture was then heated to 130° C. for 20 hrs. Mixture was allowed to cool to room temperature and filtered under gravity. White solid was then placed in a vacuum oven at 40° C. for 24 hrs to give the title compound (5.98 g). $^1$H NMR (400 MHz, METHANOL-$d_4$) δ 7.65-7.78 (m, 2H), 7.25 (d, J=7.83 Hz, 2H), 5.10-5.19 (m, 1H), 3.87 (d, J=4.40 Hz, 1H), 2.39 (s, 3H), 2.23-2.33 (m, 1H), 1.34 (d, J=6.11 Hz, 6H), 1.09 (dd, J=3.55, 6.97 Hz, 6H).

Intermediate 13: (S)-Cyclopentyl 2-aminobutanoate 4-methylbenzenesulfonate (S)-2-Aminobutanoic acid (3.0 g, 29.1 mmol), cyclopentanol (20.5 g, 238 mmol) and 4-methylbenzenesulfonic acid monohydrate (7.19 g, 37.8 mmol) were added to cyclohexane (100 mL) and the reaction mixture was heated to 125° C., whereupon complete dissolution was achieved. It was then heated at this temperature for 24 hours. After cooling to room temperature, the volatile components were removed from the slurry under reduced pressure to give a white solid. The solid was recrystallised from the minimum amount of hot EtOAc. The resulting crystals were filtered and washed with a little cold EtOAc to give the title compound (6.30 g, 18.35 mmol, 63% yield) as a white solid. $^1$H NMR ($d_6$-DMSO, 293 K): δ 0.92 (t, J=7.5 Hz, 3H) 1.52-1.73 (m, 6H) 1.73-1.95 (m, 4H) 2.29 (s, 3H) 3.90-4.01 (m, 1H) 5.18-5.22 (m, 1H) 7.11 (d, J=7.8 Hz, 2H) 7.48 (d, J=8.1 Hz, 1H) 8.26 (br.s., 3H).

The following Intermediates were prepared in a similar manner to Intermediate 13 using the appropriate commercially available amino acid and alcohol starting materials:

Intermediate 14: (S)-tetrahydro-2H-pyran-4-yl 2-amino-4-methylpentanoate 4-methylbenzenesulfonate $^1$H NMR ($d_6$-DMSO, 293 K): δ 0.90 (d, J=2.9 Hz, 3H) 0.92 (d, J=2.9 Hz, 3H) 1.49-1.78 (m, 5H) 1.84-1.93 (m, 1H) 2.29 (s, 3H) 3.46-3.54 (m, 2H) 3.76-3.82 (m, 2H) 3.89-4.18 (m, 1H) 4.98-5.05 (m, 1H) 5.75 (s, 1H) 7.11 (m, J=8.1 Hz, 2H) 7.48 (m, J=8.1 Hz, 2H) 8.29 (br.s., 3H), Yield: 2.8 g, 68%

Intermediate 15: (S)-Neopentyl 2-amino-3-methylbutanoate 4-methylbenzenesulfonate $^1$H NMR ($d_6$-DMSO, 293 K): δ 0.94 (s, 9H), 0.97 (d, J=7.1 Hz, 3H), 1.01 (d, J=6.9 Hz, 3H) 2.02-2.24 (m, 1H) 2.29 (s, 3H) 3.86 (d, J=10.3 Hz, 1H), 3.90 (d, J=10.3 Hz, 1H) 3.98 (d, J=4.7 Hz, 1H) 7.11 (d, J=7.8 Hz, 2H) 7.48 (d, J=8.1 Hz, 2H) 8.03-8.46 (br.s., 3H) Yield 3.9 g, 56%

Intermediate 16: (S)-Tetrahydro-2H-pyran-4-yl 2-amino-4-methylpentanoate 4-methylbenzenesulfonate $^1$H NMR ($d_6$-DMSO, 293 K): δ 0.90 (d, J=2.9 Hz, 3H) 0.92 (d, J=2.9 Hz, 3H) 1.49-1.78 (m, 5H) 1.84-1.93 (m, 1H)

2.29 (s, 3H) 3.46-3.54 (m, 2H) 3.76-3.82 (m, 2H) 3.89-4.18 (m, 1H) 4.98-5.05 (m, 1H) 5.75 (s, 1H) 7.11 (m, J=8.1 Hz, 2H) 7.48 (m, J=8.1 Hz, 2H) 8.29 (br.s., 3H) Yield: 2.8 g, 63%

Intermediate 17: (2S)-Tetrahydrofuran-3-yl 2-amino-4-methylpentanoate 4-methylbenzenesulfonate $^1$H NMR (d$_6$-DMSO, 293 K): δ 0.90 (d, J=2.2 Hz, 2H) 0.91 (d, J=2.2 Hz, 2H) 1.54-1.77 (m, 3H) 1.86-2.00 (m, 1H) 2.13-2.25 (m, 1H) 2.29 (s, 3H) 3.69-3.87 (m, 4H) 3.95-4.02 (m, 1H) 5.33-5.39 (m, 1H) 7.11 (d, J=8.1 Hz, 2H) 7.47 (d, J=8.1 Hz, 2H) 8.28 (br.s., 3H) Yield: 3.37 g, 59%

Intermediate 18: (2S)-1-Methoxypropan-2-yl 2-amino-4-methylpentanoate 4-methylbenzenesulfonate (Mixture of Diastereomers)

$^1$H NMR (d$_6$-DMSO, 293 K): δ 0.85-1.01 (m, 6H) 1.19 (d, J=4.7 Hz, 1.3H) 1.21 (d, J=4.9 Hz, 1.8H) 1.50-1.68 (m, 2H) 1.68-1.85 (m, 1H) 2.29 (s, 3H) 3.25 (s, 1.7H) 3.27 (s, 1.2H) 3.36-3.51 (m, 2H) 3.93-4.02 (m, 1H) 5.03-5.17 (m, 1H) 7.11 (d, J=7.8 Hz, 2H) 7.48 (d, J=8.1 Hz, 2H) 8.29 (br.s., 3H) Yield: 950 mg, 15%

Intermediate 19: (S)-Neopentyl 2-amino-4-methylpentanoate 4-methylbenzenesulfonate $^1$H NMR (d$_6$-DMSO, 293 K): δ 0.90 (d, J=3.7 Hz, 2H) 0.91-0.94 (m, 12H) 1.54-1.81 (m, 3H) 2.29 (s, 3H) 3.84 (d, J=10.5 Hz, 1H) 3.89 (d, J=10.5 Hz, 1H) 3.98-4.08 (m, 1H) 7.11 (d, J=7.8 Hz, 2H) 7.48 (d, J=8.1 Hz, 2H) 8.20-8.41 (br.s., 3H) Yield: 4.91 g, 86%

Intermediate 20: (S)-Cyclobutyl 2-amino-4-methylpentanoate 4-methylbenzenesulfonate $^1$H NMR (d$_6$-DMSO, 293 K): δ 0.90 (d, J=2.0 Hz, 3H) 0.91 (d, J=2.0 Hz, 3H) 1.54-1.84 (m, 5H) 1.96-2.15 (m, 2H) 2.23-2.39 (m, 5H) 3.97 (t, J=7.1 Hz, 1H) 4.98-5.06 (m, 1H) 7.11 (m, J=7.8 Hz, 2H) 7.48 (m, J=8.1 Hz, 2H) 8.27 (br.s., 3H) Yield: 5.7 g, 92%

Intermediate 21: (S)-Isopropyl 2-amino-4-methylpentanoate 4-methylbenzenesulfonate $^1$H NMR (d$_6$-DMSO, 293 K): δ 0.89 (d, J=2.0 Hz, 3H) 0.91 (d, J=2.3 Hz, 3H) 1.22-1.26 (m, 6H) 1.54-1.66 (m, 2H) 1.67-1.81 (m, 1H) 2.29 (s, 3H) 3.93 (t, J=7.1 Hz, 1H) 4.91-5.10 (m, 1H) 7.12 (m, J=8.1 Hz, 2H) 7.48 (m, J=8.1 Hz, 2H) 8.27 (br.s., 3H) Yield 4.2 g, 70%

Intermediate 22: (S)-Cyclopentyl 2-amino-2-(tetrahydro-2H-pyran-4-yl)acetate 4-methylbenzenesulfonate $^1$H NMR (d$_6$-DMSO, 293 K): δ 1.19-1.36 (m, 1H) 1.40-1.53 (m, 2H) 1.53-1.74 (m, 7H) 1.82-1.92 (m, 2H) 1.97-2.11 (m, 1H) 2.29 (s, 3H) 3.20-3.31 (m, 2H) 3.81-3.96 (m, 3H) 5.19-5.24 (s, 1H) 7.11 (d, J=7.8 Hz, 2H) 7.48 (d, J=8.1 Hz, 2H) 8.30 (br.s., 3H) Yield: 1.77 g, 35%

Intermediate 23: (S)-Cyclopentyl 2-amino-4-methoxybutanoate 4-methylbenzenesulfonate $^1$H NMR (d$_6$-DMSO, 293 K): δ 1.49-1.62 (m, 2H) 1.62-1.77 (m, 4H) 1.76-1.92 (m, 2H) 2.00 (q, J=6.1 Hz, 2H) 2.29 (s, 3H) 3.22 (s, 3H) 3.40-3.43 (m, partially obscured by solvent peak) 3.92-4.09 (m, 1H) 5.16-5.20 (m, 1H) 7.11 (d, J=7.8 Hz, 2H) 7.48 (d, J=8.1 Hz, 2H) 8.24 (br.s., 3H) Yield: 4.70 g, 56%

Intermediate 24: (S)-Cyclopentyl 2-amino-3-methylbutanoate 4-methylbenzenesulfonate (S)-2-Amino-3-methylbutanoic acid (800 mg, 6.83 mmol), cyclopentanol (5.07 ml, 55.9 mmol) and 4-methylbenzenesulfonic acid monohydrate (1.689 g, 8.88 mmol) were suspended in cyclohexane (15 mL) and the reaction mixture was heated to 95° C. with a Dean-Stark condenser attached. Complete dissolution was achieved, and the reaction mixture was heated at 95° C. overnight. No water had been collected in the Dean-Stark apparatus. The temperature of the reaction mixture was raised to 110° C., and the reaction mixture was heated at 110° C. overnight. The reaction mixture was cooled to room temperature to give a white slurry. The solvent was removed under reduced pressure to give a white solid. This crude material was dissolved in a minimum volume of hot EtOAc and the solution was allowed to cool. The resulting white solid was filtered, washed with a small amount of EtOAc, and dried to give the title compound (1.89 g, 5.28 mmol, 77% yield) as an off-white solid. $^1$H NMR (d$_6$-DMSO, 293 K): δ 0.94 (d, J=7.1 Hz, 3H) 0.96 (d, J=7.1 Hz, 3H) 1.54-1.76 (m, 6H) 1.81-1.95 (m, 2H) 2.05-2.20 (m, 1H) 2.29 (s, 3H) 3.85-3.90 (m, 1H) 5.20-5.24 (m, 1H) 7.11 (d, J=7.8 Hz, 2H) 7.47 (d, J=8.1 Hz, 2H) 8.23 (br.s., 3H).

Intermediate 25: (2S,3R)-Isobutyl 2-amino-3-hydroxybutanoate 4-methylbenzenesulfonate To a suspension of (2S,3R)-2-amino-3-hydroxybutanoic acid (2.5 g, 20.99 mmol) and 4-methylbenzenesulfonic acid monohydrate (5.19 g, 27.3 mmol) in cyclohexane (100 mL) was added 2-methylpropan-1-ol (15.50 ml, 168 mmol). The reaction mixture was fitted with a Dean-Stark condenser and heated at 130° C. overnight. The reaction mixture was allowed to cool to room temperature and the solvent removed under reduced pressure. The resulting colourless liquid was dried in a vacuum oven for three nights. Initially, recrystallisation was attempted using EtOAc, but the sample remained in solution and therefore the solvent was removed under reduced pressure. Trituration in diethyl ether was again unsuccessful, so the sample (with ether still present) was stood overnight open to the air, with a pasteur pipette and spatula left in the gum to attempt to induce crystallisation. A small amount of solid had formed around the spatula and pipette, so trituration in diethyl ether was again attempted, and was this time successful. The resulting white solid was removed by filtration and dried in a vacuum oven to give the title compound (2.2 g, 6.33 mmol, 30% yield) as a white solid. $^1$H NMR (d$_6$-DMSO, 293 K): δ 0.92 (d, J=6.6 Hz, 6H) 1.21 (d, J=6.6 Hz, 3H) 1.82-1.99 (m, 1H) 2.29 (s, 3H) 3.92-4.00 (m, 3H) 4.11-4.17 (m, 1H) 7.11 (d, J=7.8 Hz, 2H) 7.48 (d, J=8.1 Hz, 2H) 8.23 (br.s., 3H).

Intermediate 26: Cyclopentyl 1-aminocyclobutanecarboxylate 4-methylbenzenesulfonate 1-Aminocyclobutanecarboxylic acid (1.66 g, 14.42 mmol), 4-methylbenzenesulfonic acid monohydrate (3.57 g, 18.74 mmol) and cyclopentanol (10.16 g, 118 mmol) were added to cyclohexane (100 mL) and the reaction mixture was heated to 130° C. Full dissolution was achieved, and the reaction mixture was heated at this temperature for 3 days. The solvent had evaporated due to the condenser not being fitted properly. The resulting pale brown solid was recrystallised from EtOAc, filtered, washed, and dried to give the tosic acid salt of the starting material amino acid. This recovered starting material (3.7726 g, 13.13 mmol), cyclopentanol (10.16 g, 118 mmol) and 4-methylbenzenesulfonic acid monohydrate (0.823 g, 4.33 mmol) were added to cyclohexane (100 mL) and the reaction mixture was heated at 130° C. for 5 days. The resulting slurry was evaporated under reduced pressure and dried in a vacuum oven. The solid was recrystallised from hot EtOAc, filtered, washed, and dried to give the title compound (3.31 g, 9.31 mmol, 65% yield) as a white solid. $^1$H NMR (d$_6$-DMSO, 293 K): δ 1.55-1.65 (m, 2H) 1.65-1.77 (m, 4H) 1.81-1.93 (m, 2H) 1.97-2.05 (m, 2H) 2.29 (s, 3H) 2.30-2.39 (m, 2H) 2.39-2.49 (m, 2H) 5.21-5.25 (m, 1H) 7.12 (d, J=8.3 Hz, 2H) 7.48 (d, J=8.1 Hz, 2H) 8.50 (br.s., 3H).

Intermediate 27: (2S,3S)-2-(((benzyloxy)carbonyl)amino)-3-hydroxybutanoic acid To a stirred solution of (2S,3S)-2-amino-3-hydroxybutanoic acid (1 g, 8.39 mmol) and potassium carbonate (2.90 g, 20.99 mmol) in water (18 mL) was added at 0° C. benzyl carbonochloridate (1.438 mL, 10.07 mmol). The reaction mixture was stirred at room temperature for 21 h. The reaction mixture was washed by Et$_2$O and the aqueous acidified to pH 0 by addition of 2M aq. HCl. The resulting milky white solution was extracted 3 times by EtOAc, concentrated in vacuo to give a colourless oil. Toluene was added to the oil and concentrated in vacuo to give the title compound (1.80 g) as a colourless oil. LCMS (System A): $t_{RET}$=0.68 min, MH$^+$=254.

Intermediate 28: (2S,3S)—(S)-tetrahydrofuran-3-yl 2-(((benzyloxy)carbonyl)amino)-3-hydroxybutanoate To a stirred solution of (2S,3S)-2-(((benzyloxy)carbonyl)amino)-3-hydroxybutanoic acid (for a preparation see Intermediate 27, 0.920 g, 3.45 mmol) in DMF (5 mL) was added (S)-tetrahydrofuran-3-ol (2.343 mL, 34.5 mmol), EDC (0.794 g, 4.14 mmol), DIPEA (1.205 mL, 6.90 mmol), DMAP (0.417 g, 3.42 mmol) and 1-hydroxybenzotriazole hydrate (0.634 g, 4.14 mmol). The resulting solution was stirred overnight and the reaction mixture was partitioned between EtOAc and aq. sat. NaHCO$_3$. The organic phase was washed with 2M HCl, passed through a hydrophobic frit, and concentrated in vacuo to give a colourless oil. The oil was dissolved in DCM and purified by silica gel chromatography eluting with Cyclohexane:EtOAc (15-75%). The appropriate fractions were combined and evaporated in vacuo to give the title compound as a colourless oil. The total yield of the reaction was 46%. LCMS (System A): $t_{RET}$=0.79 min, MH$^+$=324.

Intermediate 29: (2S,3S)—(S)-tetrahydrofuran-3-yl 2-amino-3-hydroxybutanoate Hydrochloride To a vacuum degassed black suspension of (2S,3S)-(S)-tetrahydrofuran-3-yl 2-(((benzyloxy)carbonyl)amino)-3-hydroxybutanoate (for a preparation see Intermediate 28 0.508 g, 1.571 mmol) and 10% Pd/C (0.167 g, 0.157 mmol) in Ethanol (20 mL) was added a hydrogen atmosphere. The reaction mixture was stirred for 5 h 30 min, passed through a celite cartridge, concentrated in vacuo and dried under a stream of nitrogen to obtain a brown oil. Et2O (2 mL) and 1M HCl in Et2O (1.46 mL) were added to the brown oil, concentrated under a stream of nitrogen, and dried in vacuo to give the title compound as a brown solid. Compound used at this purity.

Intermediate 30: (S)-(S)-Tetrahydrofuran-3-yl 2-amino-4-methylpentanoate

Tosic acid monohydrate (7.73 g, 40.6 mmol) was added to a stirred suspension of L-leucine (4.1 g, 31.3 mmol) and (S)-(+)-3-Hydroxytetrahydrofuran (10 mL, 147 mmol) in cyclohexane (105 mL). The resulting suspension was heated 110° C. with Dean-Stark apparatus for 2 days and cooled to room temperature with stirring. The resulting solid was slurried in additional cyclohexane (100 mL), filtered and dried in vacuo to a brown solid (18 g). The solid was slurried in toluene (100 mL) and heated to 60° C. The resulting solution was cooled to room temperature, filtered and the combined filtrates from the toluene and cyclohexane washes were combined with the filtered solid. The resulting suspension was washed (3× aqueous saturated sodium bicarbonate, 1× brine), dried over MgSO$_4$, and evaporated in vacuo to a brown oil. The oil was loaded on to an SPE (silica, 100 g) and eluted with 0-5% (2 M ammonia in methanol) in DCM. The clean, product containing fractions were evaporated in vacuo to give the title compound (2.58 g) as a light brown oil. LCMS (System C): $t_{RET}$=0.49 min, MH$^+$=202

Intermediate 31: (2S,3R)-Isopropyl 2-amino-3-hydroxybutanoate 4-methylbenzenesulfonate To a suspension of (2S,3R)-2-amino-3-hydroxybutanoic acid (commercially available from, for example, Sigma Aldrich) (10 g, 84 mmol) in cyclohexane (100 mL), 2-propanol (51.7 mL, 672 mmol) and 4-methylbenzenesulfonic acid hydrate (20.76 g, 109 mmol) was added at room temperature. A Dean-Stark apparatus was fitted and the reaction mixture was stirred at 105° C. for 4 days. The reaction mixture was evaporated in vacuo to give a colourless oil (53 g). The oil was recristalysed from EtOAc (20 mL) to obtain a white solid (49 g). The solid was dried in a vacuum oven overnight to obtain the title compound (31.9 g) as a waxy white solid. Intermediate is ~85% pure, used at this purity level in subsequent reactions. $^1$H NMR (d$_6$-DMSO): δ 1.20 (d, J=6.6 Hz, 3H), 1.25 (dd, J=3.2, 6.4 Hz, 6H), 2.29 (s, 3H), 3.82-3.92 (m, 1H), 4.05-4.16 (m, 2H), 5.02 (m, 1H), 7.11 (d, J=7.9 Hz, 2H), 7.42-7.51 (m, 2H), 8.20 (br. s., 3H).

Intermediate 31a: (2S,3R)-isopropyl 2-amino-3-hydroxybutanoate hydrochloride (2S,3R)-isopropyl 2-amino-3-hydroxybutanoate 4-methylbenzenesulfonic acid salt (for an example preparation see Intermediate 31) (90 g) was dissolved in water (200 mL) and basified with saturated sodium carbonate solution (200 mL), then extracted with dichloromethane (5×200 mL) and the organic layer dried and evaporated in vacuo to give a pale yellow oil. The product was dissolved in dichloromethane and 4.0M hydrogen chloride in dioxan (100 mL) was added, then the mixture was stirred for 1 hour, then evaporated in vacuo and dried in a vacuum oven overnight to give (2S, 3R)-isopropyl 2-amino-3-hydroxybutanoate hydrochloride (33.5 g, 169 mmol) as a colourless crystalline solid. $^1$H NMR (400 MHz, DMSO-$d_6$) δ ppm 8.44 (br s, 3H), 5.65 (d, J=10 Hz, 1H), 4.95-5.04 (m, 1H), 4.04-4.13 (m, 1H), 3.80 (d, J=10 Hz, 1H), 1.18-1.29 (m, 9H).

Intermediate 32: (2S,3R)-Cyclobutyl 2-amino-3-hydroxybutanoate 4-methylbenzenesulfonate (2S,3R)-2-amino-3-hydroxybutanoic acid (15 g, 126 mmol), cyclobutanol (72.6 g, 1007 mmol) and p-toluenesulfonic acid monohydrate (31.1 g, 164 mmol) were combined in cyclohexane (480 mL) and heated to 140° C. for four nights with Dean-Stark apparatus attached. In total 8.4 mL water was removed. The reaction was concentrated in vacuo. The residue was triturated with $Et_2O$ (115 mL) for 2 hours. The resulting solid was collected by filtration and washed with $Et_2O$ (~50 mL) then dried in a vacuum oven to give the title compound (40.0064 g, 110 mmol) as a white solid. $^1$H NMR ($d_6$-DMSO): δ 1.20 (d, J=6.6 Hz, 3H), 1.54-1.71 (m, 1H), 1.71-1.88 (m, 1H), 1.98-2.16 (m, 2H), 2.23-2.38 (m, 5H), 3.92 (d, J=3.9 Hz, 1H), 4.06-4.21 (m, 1H), 4.98-5.06 (m, 1H), 5.63 (d, J=4.4 Hz, 1H), 7.11 (d, J=7.8 Hz, 2H), 7.41-7.52 (m, 2H), 8.21 (br. s., 2H).

Intermediate 33: (2S,3R)—(S)-sec-Butyl 2-((tert-butoxycarbonyl)amino)-3-hydroxybutanoate To a solution of (2S,3R)-2-((tert-butoxycarbonyl)amino)-3-hydroxybutanoic acid (2.95 g, 13.46 mmol) in DMF (10 mL) was added HOBT (2.473 g, 16.15 mmol), EDC (3.10 g, 16.15 mmol), DMAP (0.164 g, 1.346 mmol) and DIPEA (4.70 mL, 26.9 mmol). The reaction mixture was stirred at room temperature for 4 nights. The reaction mixture was concentrated under reduced pressure, and the residue partitioned between EtOAc (2×150 mL) and saturated aqueous sodium bicarbonate solution (150 mL). The organic layers were combined, washed with 2 M aqueous hydrochloric acid (150 mL) and brine (150 mL), dried using a hydrophobic frit, and evaporated under reduced pressure. The sample was loaded in DCM and purified by SPE (silica, 100 g) using a gradient of 0-100% EtOAc in cyclohexane. The appropriate fractions were combined and evaporated under reduced pressure to give the title compound (2.0 g, 7.26 mmol) as a colourless gum. LCMS (System B): $t_{RET}$=1.01 min, MH$^+$=276

Intermediate 34: (2S,3R)—(S)-sec-Butyl 2-amino-3-hydroxybutanoate hydrochloride

To a solution of (2S,3R)—(S)-sec-butyl 2-((tert-butoxycarbonyl)amino)-3-hydroxybutanoate (For an example preparation see Intermediate 33, 2.0 g, 7.26 mmol) in 1,4-dioxane (16 mL) was added 4 M hydrochloric acid in 1,4-dioxane (4.41 mL, 145 mmol) and the reaction mixture stirred at room temperature overnight. The reaction mixture evaporated under reduced pressure. The material was dissolved in 1,4-dioxane (4 mL) and 4 M hydrochloric acid in 1,4-dioxane (4.41 mL, 145 mmol) was added. The reaction mixture was stirred at room temperature for 3 nights. The reaction mixture was evaporated under reduced pressure to leave the title compound (1.5 g, 7.09 mmol) as a light brown gum. $^1$H NMR ($d_6$-DMSO): 0.89 (t, J=7.5 Hz, 3H), 1.22 (s, 3H), 1.23 (s, 3H), 1.53-1.65 (m, 2H), 3.87 (d, J=3.8 Hz, 1H), 4.10-4.17 (m, 1H), 4.81-4.91 (m, 1H), 5.50-5.73 (br.s., 1H), 8.36 (br.s., 3H).

Intermediate 35: (2S)-tetrahydrofuran-3-yl 2-aminobutanoate hydrochloride

A solution of (2S)-tetrahydrofuran-3-yl 2-((tert-butoxycarbonyl)amino)butanoate (for a preparation see intermediate 36, 3.0 g, 10.98 mmol) in dioxan (5 mL) was treated with 4M hydrogen chloride in dioxan (10 mL, 40 mmol). The reaction mixture was stirred at room temperature for 24 hours. The solvent was evaporated and the residue azeotroped with toluene (×3) to give the title compound (1.87 g, 8.92 mmol, 81% yield), as a colourless solid. $^1$H NMR (400 MHz, DMSO-d6) δ ppm 8.55 (br s, 3H), 5.32-5.38 (m, 1H), 3.92-3.96 (m, 1H), 3.70-3.84 (m, 4H). 2.13-2.24 (m, 2H), 1.88-2.00 (m, 1H), 1.78-1.87 (m, 1H), 0.92 (t, J=12.0 Hz, 3H).

Intermediate 36: (2S)-tetrahydrofuran-3-yl 2-((tert-butoxycarbonyl)amino)butanoate A mixture of (S)-2-((tert-butoxycarbonyl)amino)butanoic acid (2.5 g, 12.3 mmol), diisopropylethylamine (3.18 g, 4.3 mL, 24.6 mmol), 1-hydroxybenzotriazole hydrate (2.26 g, 14.76 mmol), EDC (2.83 g, 14.76 mmol), and tetrahydrofuran-3-ol (10.84 g, 9.97 mL, 123 mmol) in DMF (20 mL) was stirred at room temperature overnight. The reaction mixture was partitioned between ethyl acetate (50 mL) and saturated NaHCO$_3$ (50 mL). The organic phase was washed with 1M hydrochloric acid (50 mL), water (50 mL) and brine (50 mL). The organic phase was dried and evaporated to give the title compound (3.07 g, 11.23 mmol, 91% yield), as a colourless oil. $^1$H NMR (400 MHz, DMSO-d6) δ ppm 5.30-5.34 (m, 1H), 5.00-5.04 (m, 1H), 4.16-4.22 (m, 1H), 3.92-3.94 (m, 1H), 2.12-2.22 (m, 1H). 1.93-2.03 (m, 1H), 1.78-1.84 (m, 1H), 1.60-1.69 (m, 1H), 1.43 (s, 9H), 0.92 (t, J=12.0 Hz, 3H).

Intermediate 37: (2S)-1-methoxypropan-2-yl 2-aminobutanoate hydrochloride

A solution of (2S)-1-methoxypropan-2-yl 2-((tert-butoxycarbonyl)amino)butanoate (for a preparation see intermediate 38, 2.98 g, 10.82 mmol) in dioxan (5 mL) was treated with 4M hydrogen chloride in dioxan (10 mL, 40 mmol). The reaction mixture was stirred at room temperature for 24 hours. The solvent was evaporated and the residue azeotroped with toluene (×3) to give (2S)-1-methoxypropan-2-yl 2-aminobutanoate hydrochloride (2.13 g, 10.06 mmol, 93% yield) as a light brown oil. $^1$H NMR (400 MHz, DMSO-d6) δ ppm 8.64 (br s, 3H), 5.04-5.13 (m, 1H), 3.89-3.93 (m, 1H), 3.56 (s, 3H), 3.25 (d, J=10.0 Hz, 2H) 1.79-1.90 (m, 2H), 1.18 (dd, J=12 Hz, 4 Hz, 3H), 0.93 (dt, J=10.0 Hz, 4 Hz, 3H).

Intermediate 38: (2S)-1-methoxypropan-2-yl 2-((tert-butoxycarbonyl)amino)butanoate A mixture of (S)-2-((tert-butoxycarbonyl)amino)butanoic acid (2.5 g, 12.3 mmol), diisopropylethylamine (3.18 g, 4.3 mL, 24.6 mmol), 1-hydroxybenzotriazole hydrate (HOBt) (2.26 g, 14.76 mmol), EDC (2.83 g, 14.76 mmol), and 1-methoxy-2-propanol (11.09 g, 12.02 mL, 123 mmol) in DMF (20 mL) was stirred at room temperature overnight. The reaction mixture was partitioned between ethyl acetate (50 mL) and saturated NaHCO$_3$ (50 mL). The organic phase was washed with 1M hydrochloric acid (50 mL), water (50 mL) and brine (50 mL). The organic phase was dried and evaporated to give the title compound (2.98 g, 10.82 mmol, 88% yield), as a colourless oil. $^1$H NMR (400 MHz, CDCl$_3$) δ ppm 5.05-5.15 (m, 2H), 4.20-4.30 (m, 1H), 3.37-3.48 (m, 2H), 3.34 (d, J=10.0 Hz, 1H), 1.80-1.90 (m, 1H). 1.64-1.72 (m, 1H), 1.78-1.84 (m, 1H), 1.44 (s, 9H), 1.22-1.27 (m, 3H), 0.89-0.96 (m, 3H).

Intermediate 39: (2S,3R)—(S)-Tetrahydrofuran-3-yl 2-((tert-butoxycarbonyl)amino)-3-hydroxybutanoate To a solution of (2S,3R)-2-((tert-butoxycarbonyl)amino)-3-hydroxybutanoic acid (5 g, 22.8 mmol) in N,N-dimethylformamide (22.5 mL) was added diisopropylethylamine (7.97 mL, 45.6 mmol), 1-hydroxybenzotriazole hydrate (4.19 g, 27.4 mmol), EDC (5.25 g, 27.4 mmol), DMAP (0.28 g, 2.26 mmol) and (S)-tetrahydrofuran-3-ol (18.3 mL, 228 mmol). The reaction mixture was stirred at RT for 72 h. The reaction mixture was partitioned between ethyl acetate (200 mL) and saturated aqueous sodium hydrogen carbonate (200 mL). The organic phase was separated and washed with 2M aqueous HCl (160 mL), water (160 mL) and brine (160 mL). The organic phase was dried and evaporated to give the crude product as a clear oil. The oil was dissolved in dichloromethane (2 mL) and loaded onto 2×100 g SNAP silica column. The crude material on silica was purified by Biotage SP4 using a gradient of 10-50% ethyl acetate in cyclohexane over 24 CV. Fractions containing pure product were collected and the solvent removed under reduced pressure and further dried under high vacuum overnight to yield (2S,3R)—(S)-tetrahydrofuran-3-yl 2-((tert-butoxycarbonyl)amino)-3-hydroxybutanoate (2.81 g, 9.42 mmol, 41% yield) as a clear gum. $^1$H NMR δ (500 MHz, CDCl$_3$) ppm: 5.38 (1H, t, J=5.4 Hz), 5.29 (1H, d, J=7.7 Hz), 4.36-4.27 (1H, m), 4.23 (1H, d, J=8.5 Hz), 3.98-3.81 (4H, m), 2.25-2.13 (1H, m), 2.10-2.01 (1H, m), 1.64 (1H, br. s), 1.46 (9H, s), 1.26 (3H, d, J=6.6 Hz).

Intermediate 40: (2S,3R)—(S)-tetrahydrofuran-3-yl 2-amino-3-hydroxybutanoate, hydrochloride To a solution of (2S,3R)—(S)-tetrahydrofuran-3-yl 2-((tert-butoxycarbonyl)amino)-3-hydroxybutanoate (for a preparation see Intermediate 39, 570 mg, 1.97 mmol) in 1,4-dioxane (5.5 mL) at room temperature was added hydrochloric acid (4 M in dioxane) (1.97 mL, 7.88 mmol). The reaction mixture was stirred at room temperature for 16 h. The reaction (monitored by TLC) showed conversion, but not to completion. An additional portion of hydrochloric acid (4 M in dioxane) (1.97 mL, 7.88 mmol) was added and stirred for 6 h. Hydrochloric acid (4 M in dioxane) (1.97 mL, 7.88 mmol) was again added, stirred for 2 h and left to stand overnight. The solvent was removed in vacuo and the product further dried in the vacuum oven to yield (2S,3R)—(S)-tetrahydrofuran-3-yl 2-amino-3-hydroxybutanoate, hydrochloride (470 mg, 1.979 mmol, 100% yield) as a yellow gum. $^1$H NMR δ (400 MHz, DMSO-d6) ppm: 8.46 (3H, br. s.), 5.66 (1H, br. s.), 5.35 (1H, td, J=4.2, 2.3 Hz), 4.17-4.08 (1H, m), 3.89 (1H, d, J=3.8 Hz), 3.85-3.69 (4H, m), 2.24-2.13 (1H, m), 2.00-1.91 (1H, m), 1.22 (3H, d, J=6.6 Hz).

Intermediate 41: (2S)-1-methoxypropan-2-yl 2-amino-3-methylbutanoate hydrochloride A solution of (2S)-1-methoxypropan-2-yl 2-((tert-butoxycarbonyl)amino)-3-methylbutanoate (for a preparation see Intermediate 42, 3.13 g, 10.82 mmol) in dioxan (5 mL) was treated with 4M hydrogen chloride in dioxan (10 mL, 40 mmol). The reaction mixture was stirred at room temperature for 24 hours. The solvent was evaporated and the residue azeotroped with toluene (×3) to give the title compound (1.84 g, 8.15 mmol, 75% yield) as a light brown oil. $^1$H NMR (400 MHz, DMSO-d6) δ ppm 8.64 (br s, 3H), 5.05-5.15 (m, 1H), 3.78-3.81 (m, 1H), 3.33-3.43 (m, 2H), 3.23-3.25 (m, 3H), 2.15-2.24 (m, 1H), 1.19 (dd, J=12 Hz, 4 Hz, 3H), 0.98-1.02 (m, 3H), 0.94 (dd, J=10.0 Hz, 3 Hz, 3H).

Intermediate 42: ((2S)-1-methoxypropan-2-yl 2-((tert-butoxycarbonyl)amino)-3-methylbutanoate A mixture of (S)-2-((tert-butoxycarbonyl)amino)-3-methylbutanoic acid (2.5 g, 11.51 mmol), diisopropylethylamine (2.97 g, 4.02 mL, 23.01 mmol), 1-hydroxybenzotriazole hydrate (2.12 g, 13.84 mmol), EDC (2.65 g, 13.81 mmol), and 1-methoxypropan-2-ol (10.37 g, 11.25 mL, 115 mmol) in DMF (20 mL) was stirred at room temperature overnight. The reaction mixture was partitioned between ethyl acetate (50 mL) and saturated NaHCO$_3$ (50 mL). The organic phase was washed with 1M hydrochloric acid (50 mL), water (50 mL) and brine (50 mL). The organic phase was dried and evaporated to give the title compound (3.13 g, 10.82 mmol, 94% yield), as a colourless oil. $^1$H NMR (400 MHz, CDCl$_3$) δ ppm 5.00-5.15 (m, 2H), 4.16-4.22 (m, 1H), 3.34-3.47 (m, 2H), 3.30-3.33 (m, 3H), 1.41 (s, 9H), 1.21 (d, J=12 Hz, 3H), 0.94 (d, J=12 Hz, 3H), 0.84-0.88 (m, 3H).

Intermediate 43: (2S)-1-methoxypropan-2-yl 2-amino-3,3-dimethylbutanoate hydrochloride 4M Hydrogen chloride in dioxan (10 mL, 40 mmol) was added to (2S)-1-methoxypropan-2-yl 2-((tert-butoxycarbonyl)amino)-3,3-dimethylbutanoate (for a preparation see Intermediate 44, 2.6 g, 8.63 mmol). The reaction mixture was stirred at room temperature for 24 hours. The solvent was evaporated and the residue azeotroped with toluene (×3) to give the title compound (1.83 g, 7.63 mmol, 89% yield) as a pale yellow oil. $^1$H NMR (400 MHz, DMSO-d6) δ ppm 8.55 (br s, 3H), 5.05-5.16 (m, 1H), 3.32-3.45 (m, 3H), 3.23-3.25 (m, 3H), 1.19 (m, 3H), 1.02 (s, 9H).

Intermediate 44: (2S)-1-methoxypropan-2-yl 2-((tert-butoxycarbonyl)amino)-3,3-dimethylbutanoate A mixture of (S)-2-((tert-butoxycarbonyl)amino)-3,3-dimethylbutanoic acid (2.5 g, 10.8 mmol), diisopropylethylamine (2.79 g, 3.78 mL, 21.6 mmol), 1-hydroxybenzotriazole hydrate (1.99 g, 12.97 mmol), EDC (2.49 g, 12.97 mmol), and 1-methoxypropan-2-ol (9.74 g, 10.57 mL, 108 mmol) in DMF (20 mL) was stirred at room temperature overnight. The reaction mixture was partitioned between ethyl acetate (50 mL) and saturated NaHCO$_3$ (50 mL). The organic phase was washed with 1M hydrochloric acid (50 mL), water (50 mL) and brine (50 mL). The organic phase was dried and evaporated to give the title compound (2.65 g, 8.73 mmol, 81% yield) as a colourless oil. $^1$H NMR (400 MHz, CDCl$_3$)

δ ppm 5.08-5.18 (m, 2H), 4.04-4.11 (m, 1H), 3.32-3.48 (m, 5H), 1.43 (s, 9H), 1.23 (d, J=12 Hz, 3H), 0.97 (s, 9H).

Intermediate 45: (2S)-tetrahydrofuran-3-yl 2-amino-3,3-dimethylbutanoate hydrochloride 4M hydrogen chloride in dioxan (10 mL, 40 mmol) was added to (2S)-tetrahydrofuran-3-yl 2-((tert-butoxycarbonyl)amino)-3,3-dimethylbutanoate (for a preparation see Intermediate 46, 2.6 g, 8.63 mmol). The reaction mixture was stirred at room temperature for 24 hours. The solvent was evaporated and the residue azeotroped with toluene (×3) to give the title compound ((1.78 g, 7.49 mmol, 87% yield) as a colourless hygroscopic solid. $^1$H NMR (400 MHz, DMSO-d6) δ ppm 8.58 (br s, 3H), 5.33-5.37 (m, 1H), 3.65-3.84 (m, 5H), 2.12-2.22 (m, 1H), 1.94-2.03 (m, 1H), 1.01 (s, 9H).

Intermediate 46: (2S)-tetrahydrofuran-3-yl 2-((tert-butoxycarbonyl)amino)-3,3-dimethylbutanoate A mixture of (S)-2-((tert-butoxycarbonyl)amino)-3,3-dimethylbutanoic acid (2.5 g, 10.8 mmol), diisopropylethylamine (2.79 g, 3.78 mL, 21.6 mmol), 1-hydroxybenzotriazole hydrate (1.99 g, 12.97 mmol), EDC (2.49 g, 12.97 mmol), and tetrahydrofuran-3-ol (9.52 g, 8.76 mL, 123 mmol) in DMF (20 mL) was stirred at room temperature overnight. The reaction mixture was partitioned between ethyl acetate (50 mL) and saturated NaHCO$_3$ (50 mL). The organic phase was washed with 1M hydrochloric acid (50 mL), water (50 mL) and brine (50 mL). The organic phase was dried and evaporated to give the title compound (2.7 g, 8.96 mmol, 83% yield) as a colourless oil. $^1$H NMR (400 MHz, CDCl$_3$) δ ppm 5.30-5.35 (m, 1H), 5.05-5.12 (m, 1H), 3.79-4.09 (m, 4H), 1.97-2.22 (m, 2H), 1.43 (s, 9H), 0.97 (s, 9H).

Intermediate 47: (2S)-tetrahydrofuran-3-yl 2-amino-3-hydroxy-3-methylbutanoate hydrochloride A solution of (2S)-tetrahydrofuran-3-yl 2-((tert-butoxycarbonyl)amino)-3-hydroxy-3-methylbutanoate (for a preparation see Intermediate 48, 320 mg, 1.05 mmol) in dioxan (2 mL) was treated with 4M hydrogen chloride in dioxan (2 mL, 8 mmol). The reaction mixture was stirred at room temperature for 24 hours. The solvent was evaporated. The residue was triturated with diethyl ether, a gum formed. The supernatant was decanted off and the residual solvent evaporated to give the title compound (250 mg, 1.043 mmol, 99% yield) as a colourless foam. $^1$H NMR (400 MHz, DMSO-d6) δ ppm 8.41 (br s, 3H), 5.49-5.56 (m, 1H), 5.32-5.38 (m, 1H), 3.70-3.85 (m, 5H), 2.11-2.23 (m, 1H), 1.93-2.02 (m, 1H), 1.29-1.34 (m, 3H), 1.16-1.19 (m, 3H).

Intermediate 48: (2S)-tetrahydrofuran-3-yl 2-((tert-butoxycarbonyl)amino)-3-hydroxy-3-methylbutanoate A solution of (S)-2-((tert-butoxycarbonyl)amino)-3-hydroxy-3-methylbutanoic acid (250 mg, 1.072 mmol) in tetrahydrofuran (5 mL) was treated with triphenylphosphine (309 mg, 1.18 mmol) and diisopropyl azodicarboxylate (238 mg, 229 μL, 1.18 mmol). The mixture was stirred at room temperature for 5 minutes then tetrahydrofuran-3-ol (472 mg, 434 μL, 5.36 mmol) was added. The reaction mixture was stirred at room temperature for 18 hours. The solvent was evaporated. The residue was dissolved in ethyl acetate (15 mL). The solution was washed with water (2×10 mL) and brine (10 mL). The organic phase was dried and evaporated. The residue was chromatographed [40% ethyl acetate/hexane] to give the title compound (142 mg, 0.468 mmol, 43.7% yield) as a colourless oil. $^1$H NMR (400 MHz, CDCl$_3$) δ ppm 5.33-5.44 (m, 2H), 4.14-4.20 (m, 1H), 3.83-3.97 (m, 4H), 2.13-2.25 (m, 1H), 2.00-2.12 (m, 1H), 1.44 (s, 9H), 1.26-1.29 (m, 6H).

Intermediate 49: (S)-(S)-tetrahydrofuran-3-yl 2-amino-3-methylbutanoate hydrochloride A solution of (S)-(S)-tetrahydrofuran-3-yl 2-((tert-butoxycarbonyl)amino)-3-methylbutanoate (for a preparation see Intermediate 50, 2.73 g, 9.50 mmol) in ethyl acetate (5 mL) was treated with 4M hydrogen chloride in dioxan (5 mL). The reaction mixture was stirred at room temperature for 24 hours. The solvent was evaporated. Attempted trituration with diethyl ether did not give a solid. The solvent was evaporated to give the title compound (1.98 g, 8.85 mmol, 93% yield) as a colourless oil. Sample solidified on standing at room temperature for several days. $^1$H NMR (400 MHz, DMSO-d6) δ ppm 8.69 (br s, 3H), 5.32-5.37 (m, 1H), 3.70-3.84 (m, 5H), 2.12-2.24 (m, 2H), 1.93-2.02 (m, 1H), 0.99 (t, J=12 Hz, 3H), 0.94 (t, J=12 Hz, 3H).

Intermediate 50: (S)-(S)-tetrahydrofuran-3-yl 2-((tert-butoxycarbonyl)amino)-3-methylbutanoate A mixture of (S)-2-((tert-butoxycarbonyl)amino)-3-methylbutanoic acid (2.5 g, 11.51 mmol), diisopropylethylamine (2.97 g, 4.02 mL, 23.01 mmol), 1-hydroxybenzotriazole hydrate (HOBt) (2.12 g, 13.84 mmol), EDC (2.65 g, 13.81 mmol), and (S)-tetrahydrofuran-3-ol (5.07 g, 3.91 mL, 57.5 mmol) in DMF (20 mL) was stirred at room temperature overnight. The reaction mixture was partitioned between ethyl acetate (50 mL) and saturated NaHCO$_3$ (50 mL). The organic phase was washed with 1M hydrochloric acid (50 mL), water (50 mL) and brine (50 mL). The organic phase was dried and evaporated to give the title compound (2.73 g, 9.50 mmol, 83% yield), as a colourless oil. $^1$H NMR (400 MHz, CDCl$_3$) δ ppm 5.30-5.35 (m, 1H), 4.90-5.04 (m, 1H), 4.16-4.20 (m, 1H), 3.75-3.93 (m, 4H), 2.08-2.22 (m, 2H), 1.98-2.07 (m, 1H), 1.43 (s, 9H), 0.95 (t, J=12 Hz, 3H), 0.88 (t, J=12 Hz, 3H).

Intermediate 51: (S)-cyclopentyl 2-amino-3-hydroxy-3-methylbutanoate hydrochloride A solution of (S)-cyclopentyl 2-((tert-butoxycarbonyl)amino)-3-hydroxy-3-methyl butanoate (for a preparation see Intermediate 52, 330 mg, 1.09 mmol) in ethyl acetate (2 mL) was treated with 4M HCl in dioxan (2 mL). The reaction mixture was stirred at room temperature overnight. The solvent was evaporated. Attempted trituration with hexane/diethyl ether did not give pure product. The compound was dissolved in methanol and loaded onto an SCX column. The column was washed with methanol then eluted with 2M ammonia in methanol. The NH$_3$/methanol fractions were evaporated. The residue was dissolved in diethyl ether (5 mL) and the solution was treated with 1M hydrogen chloride in diethyl ether (0.5 mL). The solvent was evaporated to give the title compound (258 mg, 1.085 mmol, 99% yield) as a hygroscopic colourless gum. $^1$H NMR (400 MHz, DMSO-d6) δ ppm 8.33 (br s, 3H), 5.50-5.54 (m, 1H), 5.17-5.23 (m, 1H), 3.68-3.77 (m, 1H), 3.30-3.37 (m, 1H), 1.78-1.89 (m, 2H), 1.53-1.74 (m, 5H), 1.17 (s, 6H).

Intermediate 52: (S)-cyclopentyl 2-((tert-butoxycarbonyl)amino)-3-hydroxy-3-methylbutanoate A solution of (S)-2-((tert-butoxycarbonyl)amino)-3-hydroxy-3-methylbutanoic acid (500 mg, 2.14 mmol) in tetrahydrofuran (5 mL) was treated with triphenylphosphine (618 mg, 2.36 mmol) and diisopropylazodicarboxylate (477 mg, 458 μL, 2.36 mmol). The reaction mixture was stirred at room temperature for 10 minutes then cyclopentanol (923 mg, 973 μL, 10.72 mmol) was added. The reaction mixture was stirred at room temperature for 24 hours. The solvent was evaporated. The residue was dissolved in ethyl acetate (10 mL). The solution was washed with saturated NaHCO$_3$ solution (10 mL), 1M hydrochloric acid (10 mL), water (10 mL) and brine (10 mL). The organic phase was dried and evaporated. The residue was chromatographed [30% ethyl acetate/hexane] to give the title compound (330 mg, 1.095 mmol, 51.1% yield) as a colourless gummy solid. $^1$H NMR (400 MHz, CDCl$_3$) δ ppm 6.48 (br s, 1H), 5.20-5.43 (m, 1H), 4.93-5.01 (m, 1H), 4.05-4.36 (m, 1H), 1.50-1.88 (m, 6H), 1.45 (s, 6H), 1.23-1.27 (m, 9H).

Intermediate 53: (2S)-1-methoxypropan-2-yl 2-amino-3-hydroxy-3-methylbutanoate hydrochloride A solution of (2S)-1-methoxypropan-2-yl 2-((tert-butoxycarbonyl)amino)-3-hydroxy-3-methylbutanoate (for a preparation see Intermediate 54, 480 mg, 1.57 mmol) in ethyl acetate (2 mL) was treated with 4M HCl in dioxan (2 mL). The reaction mixture was stirred at room temperature overnight. The solvent was evaporated. The compound was dissolved in methanol and loaded onto an SCX column. The column was washed with methanol then eluted with 2M ammonia in methanol. The NH$_3$/methanol fractions were evaporated. The residue was dissolved in diethyl ether (5 mL) and the solution was treated with 1M hydrogen chloride in diethyl ether (0.5 mL). The solvent was evaporated to give the title compound (315 mg, 1.303 mmol, 83% yield) as a hygroscopic colourless gum. $^1$H NMR (400 MHz, DMSO-d6) δ ppm 8.27 (br s, 3H), 5.48-5.54 (m, 1H), 5.06-5.16 (m, 1H), 3.74-3.82 (m, 1H), 3.38-3.47 (m, 1H), 3.27 and 3.25 (2×s, 3H. OMe) 1.36 and 1.32 (2×s, 3H), 1.20 (d, J=8 Hz, 3H), 1.17 and 1.14 (2×s, 3H).

Intermediate 54: (2S)-1-methoxypropan-2-yl 2-((tert-butoxycarbonyl)amino)-3-hydroxy-3-methylbutanoate A solution of (S)-2-((tert-butoxycarbonyl)amino)-3-hydroxy-3-methylbutanoic acid (500 mg, 2.14 mmol) in tetrahydrofuran (5 mL) was treated with triphenylphosphine (618 mg, 2.36 mmol) and diisopropylazodicarboxylate (477 mg, 458 μL, 2.36 mmol). The reaction mixture was stirred room temperature for 10 minutes then 1-methoxypropan-2-ol (966 mg, 1.05 mL, 10.72 mmol) was added. The reaction mixture was stirred at room temperature for 24 hours. The solvent was evaporated. The residue was dissolved in ethyl acetate (10 mL). The solution was washed with saturated NaHCO$_3$ solution (10 mL), 1M hydrochloric acid (10 mL), water (10 mL) and brine (10 mL). The organic phase was dried and evaporated. The residue was chromatographed [40% ethyl acetate/hexane]. Hexane (10 mL) was added to the product and stirred for 30 minutes. The solid was filtered off, washed with hexane and dried to give the title compound (487 mg, 1.595 mmol, 74.4% yield), as a colourless solid. $^1$H NMR (400 MHz, CDCl$_3$) δ ppm 5.16-5.43 (m, 1H), 4.10-4.30 (m, 1H), 2.38-2.50 (m, 2H), 3.35 and 3.37 (2×s, 3H), 1.60 (s, 3H), 1.45 (s, 3H), 1.25-1.29 (m, 12H).

Intermediate 55: (S)-cyclopentyl 2-amino-2-cyclopropylacetate 20 v/v piperidine in DMF (1 mL) was added to a solution of (S)-cyclopentyl 2-((((9H-fluoren-9-yl)methoxy)carbonyl)amino)-2-cyclopropylacetate (for a preparation see Intermediate 56, 240 mg, 0.59 mmol) in DMF (1 mL). The reaction mixture was stirred at room temperature for 18 hours. The reaction mixture was partitioned between ethyl acetate (15 mL) and water (15 mL). The organic phase was separated, washed with water (2×10 mL), dried and evaporated. The residue was dissolved in methanol and loaded on to an SCX column. The column was washed with methanol (3CV) and then eluted with 2M ammonia in methanol (5CV). The ammonia/MeOH fraction was evaporated. The residue was dissolved in dichloromethane (2 mL). 1.0M Hydrogen chloride in diethyl ether (1 mL) was added. The solvent was evaporated and the residue triturated with diethyl ether to give a solid. The solid was dissolved in ethyl acetate (20 mL) and the solution washed with saturated NaHCO$_3$ and brine. The organic phase was dried and evaporated. The residue was chromatographed [0-4% methanol/dichloromethane] to give the title compound (43 mg, 0.235 mmol, 39.6% yield) as a colourless oil. $^1$H NMR (400 MHz, CDCl$_3$) δ ppm 5.18-5.25 (m, 1H), 2.78-2.82 (m, 1H), 1.80-1.93 (m, 2H), 1.56-1.78 (m, 6H), 0.93-1.03 (m, 1H), 0.41-0.58 (m, 2H), 0.27-0.34 (m, 1H).

Intermediate 56: (S)-cyclopentyl 2-((((9H-fluoren-9-yl)methoxy)carbonyl)amino)-2-cyclopropylacetate Dicyclohexylcarbodiimide (147 mg, 0.711 mmol) was added to a stirred solution of (S)-2-((((9H-fluoren-9-yl)methoxy)carbonyl)amino)-2-cyclopropylacetic acid (200 mg, 0.593 mmol) in cyclopentanol (2 mL, large excess). The reaction mixture was stirred at room temperature for 24 hours. The reaction mixture was partitioned between ethyl acetate (20 mL) and water (20 mL). The organic phase was separated, washed with water and brine. Dried and evaporated. The residue was chromatographed [10-30% ethyl acetate/hexane] to give the title compound (246 mg, 0.607 mmol, 102% yield) as a colourless solid. LCMS (System A): $t_{RET}$=1.42 min; MH$^+$ 406.

Intermediate 57: (S)-cyclopentyl 2-amino-3-cyclopropylpropanoate 20 v/v piperidine in DMF (1 mL) was added to (S)-cyclopentyl 2-((((9H-fluoren-9-yl)methoxy)carbonyl)amino)-3-cyclopropylpropanoate (for a preparation see Intermediate 58, 270 mg, 0.59 mmol). The reaction mixture was stirred at room temperature for 18 hours. The reaction mixture was partitioned between ethyl acetate (15 mL) and saturated NaHCO$_3$ solution (15 mL). The organic phase was separated, washed with water (2×10 mL), and brine (10 mL). The organic phase was dried and evaporated. The residue was chromatographed [0-4% methanol/dichloromethane] to give the title compound (48 mg, 0.243 mmol, 37.8% yield) as a colourless oil. $^1$H NMR (400 MHz, CDCl$_3$) δ ppm 5.11-5.18 (m, 1H), 3.42-3.46 (m, 1H), 3.24-3.28 (m, 1H), 1.76-1.86 (m, 1H), 1.45-1.77 (m, 8H), 0.65-0.75 (m, 1H), 0.38-0.46 (m, 2H), 0.04-0.08 (m, 2H).

Intermediate 58: (S)-cyclopentyl 2-((((9H-fluoren-9-yl)methoxy)carbonyl)amino)-3-cyclopropylpropanoate Cyclopentanol (2 mL, large excess) was added to (S)-2-((((9H-fluoren-9-yl)methoxy)carbonyl)amino)-3-cyclopropylpropanoic acid (250 mg, 0.711 mmol). The mixture was stirred and treated with N-Ethoxycarbonyl-2-ethoxy-1,2-dihydroquinoline (EEDQ) (211 mg, 0.854 mmol). The reaction mixture was stirred at room temperature for 24 hours. The reaction mixture was partitioned between ethyl acetate (10 mL) and saturated NaHCO$_3$ solution (10 mL). The organic phase was separated, washed with water and brine. Dried and evaporated. The residue was chromatographed [10-30% ethyl acetate/hexane] to give the title compound (270 mg, 0.644 mmol, 90% yield).
LCMS (System A): t$_{RET}$=1.45 min; MH$^+$ 420.

Intermediate 59: (R)-cyclopentyl 2-amino-3-cyclopropylpropanoate 20 v/v piperidine in DMF (1 mL) was added to (R)-cyclopentyl 2-((((9H-fluoren-9-yl)methoxy)carbonyl)amino)-3-cyclopropylpropanoate (for a preparation see Intermediate 60, 258 mg, 0.615 mmol). The reaction mixture was stirred at room temperature for 18 hours. The reaction mixture was partitioned between ethyl acetate (15 mL) and saturated NaHCO$_3$ solution (15 mL). The organic phase was separated, washed with water (2×10 mL), and brine (10 mL). The organic phase was dried and evaporated. The residue was chromatographed [0-4% methanol/dichloromethane] to give the title compound (59 mg, 0.299 mmol, 48.6% yield) as a colourless oil. $^1$H NMR (400 MHz, CDCl$_3$) δ ppm 5.11-5.18 (m, 1H), 3.42-3.46 (m, 1H), 3.24-3.28 (m, 1H), 1.76-1.86 (m, 1H), 1.45-1.77 (m, 8H), 0.65-0.75 (m, 1H), 0.38-0.46 (m, 2H), 0.04-0.08 (m, 2H).

Intermediate 60: (R)-cyclopentyl 2-((((9H-fluoren-9-yl)methoxy)carbonyl)amino)-3-cyclopropylpropanoate Cyclopentanol (2 mL, large excess) was added to (R)-2-((((9H-fluoren-9-yl)methoxy)carbonyl)amino)-3-cyclopropylpropanoic acid (250 mg, 0.711 mmol). The mixture was stirred and treated with N-Ethoxycarbonyl-2-ethoxy-1,2-dihydroquinoline (EEDQ) (211 mg, 0.854 mmol). The reaction mixture was stirred at room temperature for 24 hours. The reaction mixture was partitioned between ethyl acetate (10 mL) and saturated NaHCO$_3$ solution (10 mL). The organic phase was separated, washed with water and brine. Dried and evaporated. The residue was chromatographed [10-30% ethyl acetate/hexane] to give the title compound (258 mg, 0.615 mmol, 86% yield) as a colourless oil. LCMS (System A): t$_{RET}$=1.45 min; MH$^+$ 420.

Intermediate 61: (S)-cyclopentyl 2-aminopropanoate hydrochloride (S)-cyclopentyl 2-((tert-butoxycarbonyl)amino)propanoate (for a preparation see Intermediate 62, 4.145 g, 16.11 mmol) was dissolved in 1,4-dioxane (25 mL) and then 4M hydrogen chloride in dioxane (25 mL, 100 mmol) was added to the mixture and the flask was stirred at 25° C. for 18 h. The solvent was removed in vacuo. The product was suspended in ethyl acetate and the solvent evaporated (×4) until having a white solid identified as the title compound (2.801 g, 14.46 mmol, 90% yield). $^1$H NMR (400 MHz, methanol-d$_4$) δ ppm 5.28-5.34 (m, 1H), 4.00-4.08 (q, J=8 Hz, 1H), 1.90-2.00 (m, 1H), 1.64-1.84 (m, 6H), 1.52 (d, J=8 Hz, 3H).

Intermediate 62: (S)-cyclopentyl 2-((tert-butoxycarbonyl)amino)propanoate (S)-2-((tert-butoxycarbonyl)amino)propanoic acid (5 g, 26.4 mmol) and cyclopentanol (24.01 mL, 264 mmol) was dissolved in toluene (250 mL). Then 2-(tributylphosphoranylidene)acetonitrile (14.46 mL, 52.9 mmol) was added to the reaction mixture and refluxed for 60 hours. The reaction mixture was cooled to room temperature. Then 100 mL of ethyl acetate was added to the reaction mixture. Then it was washed, first with 250 mL of a solution saturated sodium bicarbonate, and in a second time with 250 mL of brine. The organic layer was dried over MgSO$_4$ and afterward the solvent removed in vacuo. The solid was then dissolved in MeOH and ran through a 100 g SCX column. The column were washed first with methanol, and then with NH$_3$ in MeOH. According to the TLC, we found out that the desired product was in the first methanolic phase. The solvent was removed to get a pale yellow oil, which was chromatographed [0-30% Ethyl acetate in Cyclohexane]. Appropriate fractions were combined and the solvent removed to give the title compound (4.145 g, 16.11 mmol, 61.0% yield) as a pale yellow oil. $^1$H NMR (400 MHz, methanol-d$_4$) δ ppm 5.13-5.19 (m, 1H), 4.00-4.13 (m, 1H), 1.80-1.90 (m, 5H), 1.43 (s, 9H), 1.31 (d, J=8 Hz, 3H).

Intermediate 63: (S)-(S)-1-methoxypropan-2-yl 2-amino-3-methylbutanoate hydrochloride (S)-(S)-1-methoxypropan-2-yl 2-((tert-butoxycarbonyl)amino)-3-methylbutanoate (for a preparation see Intermediate 64, 1.2 g, 4.15 mmol) was dissolved in ethyl acetate (2 mL), the solution was treated with 4M hydrogen chloride in dioxan (2 mL). The reaction mixture was stirred at room temperature overnight. The solvent was evaporated to give the title compound (725 mg, 3.21 mmol, 77% yield) as a colourless gum. $^1$H NMR (400 MHz, CDCl$_3$) δ ppm 8.80 (br s, 3H), 5.19-5.27 (m, 1H), 3.39-3.53 (m, 2H), 3.33 (s, 3H), 2.43-2.53 (m, 1H), 1.28 (d, J=8 Hz, 3H), 1.13-1.18 (m, 6H).

Intermediate 64: (S)-(S)-1-methoxypropan-2-yl 2-((tert-butoxycarbonyl)amino)-3-methylbutanoate A mixture of (S)-2-((tert-butoxycarbonyl)amino)-3-methylbutanoic acid (1.0 g, 4.60 mmol), diisopropylethylamine (1.19 g, 1.608 mL, 9.21 mmol), 1-hydroxybenzotriazole hydrate (846 mg, 5.52 mmol), EDC (1.06 g, 5.53 mmol), and (S)-1-methoxypropan-2-ol (1.037 g, 1.127 mL, 11.5 mmol) in DMF (5 mL) was stirred at room temperature overnight. The reaction mixture was partitioned between ethyl acetate (15 mL) and saturated NaHCO$_3$ solution (15 mL). The organic phase was washed with 1M hydrochloric acid (15 mL), water (15 mL) and brine (15 mL). The organic phase was dried and evaporated to give the title compound (1.23 g, 4.25 mmol, 92% yield), as a colourless oil. $^1$H NMR (400 MHz, CDCl$_3$) δ ppm 5.13-5.19 (m, 1H), 5.06-5.10 (m, 1H (NH?)), 4.19-4.23 (m, 1H), 3.36-3.46 (m, 2H), 3.33 (s, 3H), 2.10-2.18 (m, 1H), 1.45 (s, 9H), 1.23-1.27 (m, 3H), 0.88-1.02 (m, 6H).

Intermediate 65: (S)-isopropyl 2-amino-3-methylbutanoate, 4-methylbenzenesulphonate (S)-2-amino-3-methylbutanoic acid (2.5 g, 21.34 mmol), tosic acid (5.28 g, 27.7 mmol) and propan-2-o1 (15 mL, 196 mmol) were dissolved in cyclohexane (100 mL) and heated to 130° C. for 22 hrs. The solution was allowed to cool to room temperature at which point a white solid precipitated. This mixture was filtered under vacuum and the solid washed several times with hexane. Solid was then placed in a vacuum oven at 40° C. for 3 hours. This solid was then added to cyclohexane (100 mL) along with tosic acid (1.76 g, 9.2 mmol) and propan-2-ol (3.94 g, 65.3 mmol). Mixture was then heated to 130° C. for 20 hours. Mixture was allowed to cool to room temperature and filtered under gravity. White solid was then placed in a vacuum oven at 40° C. for 24 hours to give the title compound (5.977 g, 18.09 mmol, 85% yield). $^1$H NMR (400 MHz, DMSO-d$_6$) δ ppm 8.24 (br s, 3H), 7.48 (d, J=12 Hz, 2H), 7.11 (d, J=12 Hz, 2H), 4.99-5.09 (m, 1H), 3.85-3.91 (m, 1H), 2.28 (s, 3H), 2.09-2.19 (m, 1H), 1.23-1.28 (m, 6H), 0.94-1.00 (m, 6H).

Intermediate 66: (S)-isobutyl 2-amino-3-methoxypropanoate, hydrochloride

10% Palladium on carbon, 50% water paste (350 mg, 20% wt) was added to a stirred solution of (S)-isobutyl 2-(((benzyloxy)carbonyl)amino)-3-methoxypropanoate (for a preparation see Intermediate 67, 1.75 g, 5.66 mmol) and ammonium formate (1.78 g, 28.3 mmol) in isopropanol (50 mL). The reaction mixture was stirred at 90° C. for 2 hours. The reaction mixture was cooled to room temperature and filtered through 'celite'. The solvent was evaporated from the filtrate. The residue was dissolved in ethyl acetate (10 mL) and treated with 1M hydrogen chloride in diethyl ether (6.0 mL, 6 mmol). The solvent was evaporated and the residue was triturated with diethyl ether to give the title compound (840 mg, 3.97 mmol, 70.1% yield), as a pale yellow solid. $^1$H NMR (400 MHz, DMSO-d$_6$) δ ppm 8.68 (br s, 3H), 4.32 (br s, 1H), 4.01-4.06 (m, 1H), 3.88-3.94 (m, 1H), 1.92 (heptet, J=8 Hz, 1H), 0.91 (d, J=8 Hz, 6H).

Intermediate 67: (S)-isobutyl 2-(((benzyloxy)carbonyl)amino)-3-methoxypropanoate A mixture of (S)-2-(((benzyloxy)carbonyl)amino)-3-methoxypropanoic acid (1.6 g, 6.32 mmol), N-ethylmorpholine (1.45 g, 1.60 mL, 12.64 mmol), N-hydoxybenzotriazole hydrate (1.16 g, 7.58 mmol), EDC (1.45 g, 7.58 mmol) and isobutanol (2.34 g, 2.92 mL, 31.6 mmol) in dichloromethane (20 mL) was stirred at room temperature overnight. The solvent was evaporated. The residue was partitioned between ethyl acetate (25 mL) and saturated NaHCO$_3$ (25 mL). The organic phase was separated, washed with 2M hydrochloric acid, water and brine. The organic phase was dried and evaporated. The residue was azeotroped with toluene to give the title compound (1.81 g, 5.85 mmol, 93% yield), as a colourless oil. $^1$H NMR (400 MHz, CDCl$_3$) δ ppm 7.15-7.40 (m, 5H), 5.6-5.65 (m, 1H, (NH?)), 5.14 (s, 2H), 4.47-4.52 (m, 1H), 3.89-4.04 (m, 2H), 3.81-3.87 (m, 1H), 3.61-3.68 (m, 1H), 1.96 (heptet, J=8 Hz, 1H), 0.94 (d, J=8 Hz, 6H).

Intermediate 68: (S)-2-(((benzyloxy)carbonyl)amino)-3-methoxypropanoic acid

Stage i).
Ref: Tetrahedron Asymmetry 9(1988)3841.
A mixture of Z-Ser-OH (1.0 g, 4.18 mmol), silver(I) oxide (4.84 g, 20.9 mmol) and iodomethane (5.93 g, 2.61 mL, 41.8 mmol) in acetonitrile (20 mL) was stirred at room temperature overnight. The reaction mixture was filtered through 'celite' and the solvent was evaporated from the filtrate to give stage i) product as a light yellow oil.

Stage ii).

Stage i) product was dissolved in tetrahydrofuran (5 mL) and methanol (5 mL). The solution was treated with 1M lithium hydroxide solution (10 mL). The reaction mixture was stirred at room temperature for 24 hours. The methanol and THF were evaporated. The residue was diluted with water (10 mL) and acidified with 2M hydrochloric acid. The mixture was extracted with ethyl acetate (3×20 mL). The combined extracts were dried and evaporated to give the title compound (869 mg, 3.43 mmol, 82% yield), as a colourless gum. LCMS (System A): $t_{RET}$=0.75 min; MH$^+$ 254.

Intermediate 69: (S)-isopropyl 2-amino-4-chlorobutanoate

Thionyl chloride (2.0 g, 1.23 mL, 16.8 mmol) was added slowly to a stirred solution of L-homoserine (1.0 g, 8.4 mmol) in isopropanol (15 mL). The reaction mixture was stirred at 60° C. overnight. The reaction mixture was cooled and the solvent was evaporated. The residue was triturated with diethyl ether to give a mixture. The solid was partitioned between ethyl acetate (25 mL) and saturated NaHCO$_3$ (25 mL). The aqueous layer was extracted with ethyl acetate (2×25 mL). The combined organics were dried and evaporated to give the title compound (160 mg, 0.891 mmol, 10.61% yield), as a colourless oil. $^1$H NMR (400 MHz, CDCl$_3$) δ ppm 5.03 (heptet, J=8 Hz, 1H), 3.63-3.77 (m, 2H), 3.55-3.59 (m, 1H), 2.14-2.23 (m, 1H) 1.84-1.95 (m, 1H), 1.25 (d, J=8 Hz, 3H), 1.23 (d, J=8 Hz, 3H).

Intermediate 70: (4-(Ethylamino)-3-nitrophenyl)methanol (4-fluoro-3-nitrophenyl)methanol (500 mg, 2.92 mmol), 70% ethanamine in water (286 µl, 2.92 mmol) and DIPEA (1531 µl, 8.77 mmol) were dissolved in tetrahydrofuran (THF) (3 mL) and the reaction mixture was heated in a Biotage Initiator microwave using initial high absorption setting to 120° C. for 3 hours. The reaction mixture was partitioned between DCM (25 mL) and saturated sodium hydrogen carbonate solution (25 mL). The layers were separated and the aqueous layer was extracted with DCM (2×25 mL). The organic layers were combined, dried using a hydrophobic frit and evaporated under reduced pressure. The crude sample was loaded in dichloromethane and purified by silica gel column chromatography (50 g silica) using a gradient of 0-5% dichloromethane-2M ammonia in methanol over 10 column volumes. The appropriate fractions were combined and evaporated under reduced pressure to give the title compound (4-(ethylamino)-3-nitrophenyl)methanol (524.3 mg, 2.67 mmol, 91% yield) as an orange solid. LCMS (System A): $t_{RET}$=0.80 min; MH$^+$ 197. $^1$H NMR δ (400 MHz, D6-DMSO): 1.22, (t, J=7 Hz, 3H), 3.34-3.42, (m, 2H), 4.39, (d, J=5 Hz, 2H), 5.18, (t, J=6 Hz, H), 7.03, (d, J=9 Hz, H), 7.48, (dd, J=6 Hz, J=3 Hz, H), 7.98-8.01, (m, H), 8.02-8.07, (m, H).

The following Intermediates were prepared in a similar manner to Intermediate 70 using the appropriate commercially available amines:

(In the tables, details of the LCMS system used, retention time ($t_{RET}$), MH+, reaction yield and % yield are provided for each Intermediate).

Intermediate 71: (4-(methylamino)-3-nitrophenyl) methanol (Prepared from: (4-fluoro-3-nitrophenyl) methanol (Commercially Available))

System A, 0.64 min, MH+=183; Yield: 2.25 g, 106% (>100% yield due to impurities)

Intermediate 72: (4-(isopropylamino)-3-nitrophenyl) methanol (Prepared from: (4-fluoro-3-nitrophenyl) methanol (Commercially Available))

System A, 0.87 min, MH+=211; Yield: 2.49 g, 101% (>100% yield due to trace solvent present in product)

Intermediate 73: (S)-(3-nitro-4-(((tetrahydrofuran-2-yl)methyl)amino)phenyl)methanol (Prepared from: (4-fluoro-3-nitrophenyl)methanol (Commercially Available))

System B, 0.80 min, MH+=253; Yield: 1.90 g, 92%

Intermediate 74: (R)-(3-nitro-4-(((tetrahydrofuran-2-yl)methyl)amino)phenyl)methanol (Prepared from: (4-fluoro-3-nitrophenyl)methanol (Commercially Available))

System B, 0.80 min, MH+=253; Yield: 1.99 g, 96%

Intermediate 75: (4-nitro-3-(((tetrahydro-2H-pyran-4-yl)methyl)amino)phenyl)methanol (Prepared from: (3-fluoro-4-nitrophenyl)methanol (Commercially Available))

System B, 0.81 min, MH+=267 Yield; 9.42 g, 121% (Sample contains impurities, carried through without further purification)

Intermediate 76: (rac)-(4-(((1,4-dioxan-2-yl)methyl)amino)-3-nitrophenyl)methanol (Prepared from: (4-fluoro-3-nitrophenyl)methanol (Commercially Available))

System B, 0.70 min, MH+=269 Yield: 1.96 g, 53%

Intermediate 78: (S)-(3-((1-methoxypropan-2-yl)amino)-4-nitrophenyl)methanol (Prepared from: (3-fluoro-4-nitrophenyl)methanol (Commercially Available))

System A, 0.80 min, MH+=241 Yield: 494 mg, 23%

Intermediate 79: (S)-(4-nitro-3-(((tetrahydrofuran-2-yl)methyl)amino)phenyl)methanol (Prepared from: (3-fluoro-4-nitrophenyl)methanol (Commercially Available))

System A, 0.87 min, MH+=253; Yield: 8.49 g, 126% (Sample contains impurities, carried through without further purification)

Intermediate 80: (R)-tert-butyl 3-(((5-(hydroxymethyl)-2-nitrophenyl)amino)methyl)piperidine-1-carboxylate (Prepared from: (3-fluoro-4-nitrophenyl)methanol (Commercially Available))

System C, 1.13 min, MH+=366; Yield: 4.98 g, 93%

Intermediate 81: (S)-tert-butyl 3-(((5-(hydroxymethyl)-2-nitrophenyl)amino)methyl)piperidine-1-carboxylate (Prepared from: (3-fluoro-4-nitrophenyl)methanol (Commercially Available))

System B, 1.18 min, MH+=366; Yield: 2.74 g, 103% (Sample contains impurities, carried through without further purification)

Intermediate 82: (4-((1-methoxybutan-2-yl)amino)-3-nitrophenyl)methanol (Prepared from: (4-fluoro-3-nitrophenyl)methanol (Commercially Available))

System A, 0.95 min, 255 Yield: 7.18 g, 97%

Intermediate 83: (4-nitro-3-(((tetrahydrofuran-3-yl)methyl)amino)phenyl)methanol (Prepared from: (3-fluoro-4-nitrophenyl)methanol (Commercially Available))

System A, 0.79 min, MH+=253; Yield: 3.9 g, 88%

Intermediate 84: (S)-tert-butyl 3-(((4-(hydroxymethyl)-2-nitrophenyl)amino)methyl)piperidine-1-carboxylate DIPEA (7.65 mL, 43.8 mmol) was added to a stirred solution of 4-Fluoro-3-nitrobenzyl alcohol (2.50 g, 14.61 mmol) and (3S)-3-(aminomethyl)piperidine (4.70 g, 21.91 mmol in 2-Methyltetrahydrofuran (15 mL). The solution was heated to 80° C. overnight, the reaction mixture cooled to room temperature and the resulting solid partitioned between EtOAc and sat. aq. NaHCO$_3$. The aqueous layer was removed and the organic layer washed (1×sat. aq. NaHCO$_3$, 1× brine). The organic portion was dried over MgSO$_4$ and evaporated in vacuo to an orange oil. The residue was dissolved in DCM and purified by silica gel chromatography eluting with cyclohexane:EtOAc (10-66%). The product containing fractions were evaporated in vacuo to an orange oil foam. The oil was dissolved in TBME and evaporated in vacuo to an orange oil to give the title compound as an orange oil (5.52 g). The total yield of the reaction was 88%. LCMS (System C): $t_{RET}$=1.27 min, MH+=366.

The following Intermediates were prepared in a similar manner to Intermediate 84 using the appropriate commercially available amines:

Intermediate 85: (4-nitro-3-((tetrahydro-2H-pyran-4-yl)amino)phenyl)methanol (Prepared from: (3-fluoro-4-nitrophenyl)methanol (Commercially Available))

System A, 0.80 min, MH+=253, Yield: 1.19 g, 77%

Intermediate 86: (4-nitro-3-(((tetrahydro-2H-pyran-2-yl)methyl)amino)phenyl)methanol (Prepared from: (3-fluoro-4-nitrophenyl)methanol (Commercially Available))

System A, 0.97 min, MH+=267 Yield: 1.41 g, 93%

Intermediate 87: (3-nitro-4-((1-(tetrahydro-2H-pyran-4-yl)ethyl)amino)phenyl)methanol (Prepared from: (3-fluoro-4-nitrophenyl)methanol (Commercially Available))

System A, 0.89 min, MH+=281 Yield: 1.06 g, 75%

Intermediate 88: (R)-tert-butyl 3-(((4-(hydroxymethyl)-2-nitrophenyl)amino)methyl)piperidine-1-carboxylate (Prepared from: (3-fluoro-4-nitrophenyl)methanol (Commercially Available))

System A, 1.14 min, MH+=366; Yield: 4.41 g, 78%

Intermediate 89: 5-(1-ethyl-5-(hydroxymethyl)-1H-benzo[d]imidazol-2-yl)-3-methylpyridin-2(1H)-one 4-(ethylamino)-(3-nitrophenyl)methanol (For a preparation see Intermediate 70, 520 mg, 2.65 mmol), 5-methyl-6-oxo-1,6-dihydropyridine-3-carbaldehyde (For a preparation see Intermediate 1, 363 mg, 2.65 mmol) and sodium dithionite (1384 mg, 7.95 mmol) were added to Ethanol (8 mL) and Water (4 mL). The reaction mixture was heated in a microwave to 1000° C. for 5 hours. The reaction mixture was partitioned between 25% propan-2-ol in DCM solution (25 mL) and saturated sodium hydrogen carbonate solution (25 mL) and the layers were separated. The aqueous layer was extracted with 25% propan-2-ol in DCM solution (3×25 mL). The organic layers were combined, dried using a hydrophobic frit and evaporated under reduced pressure. The sample was loaded in DCM and purified by silica gel column chromatography (50 g silica) using a gradient of 2-12% DCM-2M ammonia in methanol over 10 column volumes followed by holding at 12% DCM-2M ammonia in methanol for 5 column volumes. The appropriate fractions were combined and evaporated under reduced pressure to give the title compound (295.1 mg) as a white solid. LCMS (System B): $t_{RET}$=060 min, MH+=284.

The following Intermediates were prepared in a similar way to Intermediate 89, using either 5-Methyl-6-oxo-1,6-dihydropyridine-3-carbaldehyde (Intermediate 1) or 1,5-Dimethyl-6-oxo-1,6-dihydropyridine-3-carbaldehyde (Intermediate 2) as appropriate:

Intermediate 90: 5-(5-(hydroxymethyl)-1-methyl-1H-benzo[d]imidazol-2-yl)-1,3-dimethylpyridin-2(1H)-one (Prepared from: Intermediate 71)

System B, 0.59 min, 284 Yield: 0.7 g, 36%

Intermediate 91: 5-(5-(hydroxymethyl)-1-isopropyl-1H-benzo[d]imidazol-2-yl)-1,3-dimethylpyridin-2(1H)-one (Prepared from: Intermediate 72)

System A, 0.52 min, MH+=312; Yield: 722 mg, 33%

Intermediate 92: (S)-5-(5-(hydroxymethyl)-1-((tetrahydrofuran-2-yl)methyl)-1H-benzo[d]imidazol-2-yl)-3-methylpyridin-2(1H-one (Prepared from: Intermediate 73)

System B, 0.63 min, MH+=340; Yield: 941 mg, 37%

Intermediate 93: (R)-5-(5-(hydroxymethyl)-1-((tetrahydrofuran-2-yl)methyl)-1H-benzo[d]imidazol-2-yl)-3-methylpyridin-2(1H-one (Prepared from: Intermediate 74)

System B, 0.63 min, MH+=340; Yield: 168 mg, 6.3%

Intermediate 94: 5-(6-(hydroxymethyl)-1-((tetrahydro-2H-pyran-4-yl)methyl)-1H-benzo[d]imidazol-2-yl)-1,3-dimethylpyridin-2(1H)-one (Prepared from: Intermediate 75)

System B, 0.61 min, MH+=368; Yield: 4.5 g, 95%

Intermediate 95: (rac)-5-(1-((1,4-dioxan-2-yl)methyl)-5-(hydroxymethyl)-1H-benzo[d]imidazol-2-yl)-3-methylpyridin-2(1H)-one (Prepared from: Intermediate 76)

System C, 0.44 min, MH+=356; Yield: 1.2 g, 30%

Intermediate 97: (S)-5-(6-(hydroxymethyl)-1-(1-methoxypropan-2-yl)-1H-benzo[d]imidazol-2-yl)-1,3-dimethylpyridin-2(1H)-one (Prepared from: Intermediate 78)

System B, 0.67 min, MH+=342; Yield: 1.85 g, 55%

Intermediate 98: (S)-5-(6-(hydroxymethyl)-1-((tetrahydrofuran-2-yl)methyl)-1H-benzo[d]imidazol-2-yl)-1,3-dimethylpyridin-2(1H)-one (Prepared from: Intermediate 79)

System B, 0.67 min, MH+=354; Yield: 2.3 g, 58%

Intermediate 99: (R)-tert-butyl 3-((2-(1,5-dimethyl-6-oxo-1,6-dihydropyridin-3-yl)-6-(hydroxymethyl)-1H-benzo[d]imidazol-1-yl)methyl)piperidine-1-carboxylate (Prepared from: Intermediate 80)

System C, 0.66 min, MH+=467; Yield: 1.78 g, 56%

Intermediate 100: (S)-tert-butyl 3-((2-(1,5-dimethyl-6-oxo-1,6-dihydropyridin-3-yl)-6-(hydroxymethyl)-1H-benzo[d]imidazol-1-yl)methyl)piperidine-1-carboxylate (Prepared from: Intermediate 81)

System A, 0.69 min, MH+=467; Yield: 811 mg, 19%

Intermediate 101: 5-(5-(hydroxymethyl)-1-(1-methoxybutan-2-yl)-1H-benzo[d]imidazol-2-yl)-1,3-dimethylpyridin-2(1H)-one (Prepared from: Intermediate 82)

System A, 0.55 min, MH+=356; Yield: 2.76 g, 28%

Intermediate 102: 5-(6-(hydroxymethyl)-1-((tetrahydrofuran-3-yl)methyl)-1H-benzo[d]imidazol-2-yl)-1,3-dimethylpyridin-2(1H)-one (Prepared from: Intermediate 83)

System B, 0.64 min, MH+=354; Yield: 1.88 g, 34%

Intermediate 103: (S)-tert-butyl 3-((2-(1,5-dimethyl-6-oxo-1,6-dihydropyridin-3-yl)-5-(hydroxymethyl)-1H-benzo[d]imidazol-1-yl)methyl)piperidine-1-carboxylate Sodium hydrosulfite (7.89 g, 45.3 mmol) was added to a suspension of (S)-tert-butyl 3-(((4-(hydroxymethyl)-2-nitrophenyl)amino)methyl)piperidine-1-carboxylate (For an example preparation see Intermediate 84) (5.52 g, 15.11 mmol) and 1,5-dimethyl-6-oxo-1,6-dihydropyridine-3-carbaldehyde (for a preparation see Intermediate 2, 2.97 g, 19.64 mmol) in a mixture of water (20 mL) and ethanol (40 mL). The resulting suspension was heated to 80° C. for 6 h, cooled to room temperature and left for 1.5 days. The mixture was partitioned between sat. aq. NaHCO$_3$ (200 mL) and DCM: IPA (3:1, 200 mL). The organic layer was removed and the aqueous layer extracted [2×DCM:IPA (3:1, 200 mL)]. The combined organic layers were dried over MgSO$_4$ and evaporated in vacuo to a pale brown foam. The residue was dissolved in DCM, purified by silica gel chromatography eluting with EtOAc:EtOH (12.5-25%). The product containing fractions were evaporated in vacuo to a pale brown foam and slurried with TBME and cyclohexane. The resulting suspension was evaporated in vacuo to give the title compound as a white solid. The total yield of the reaction was 49%. LCMS (System C): $t_{RET}$=0.68 min, MH$^+$=467.

The following Intermediates were prepared in a similar manner to Intermediate 103:

Intermediate 104: (4-nitro-3-((tetrahydro-2H-pyran-4-yl)amino)phenyl)methanol (Prepared from: Intermediate 2 and Intermediate 85)

System A, 0.44 min, MH$^+$=354; Yield: 0.723 g, 40%

Intermediate 105: 5-(6-(hydroxymethyl)-1-((tetrahydro-2H-pyran-2-yl)methyl)-1H-benzo[d]imidazol-2-yl)-1,3-dimethylpyridin-2(1H)-one (Prepared from: Intermediate 2 and Intermediate 86)

System A, 0.55 min, MH$^+$=368; Yield: 0.723 g, 40%

Intermediate 106: 5-(5-(hydroxymethyl)-1-(1-(tetrahydro-2H-pyran-4-yl)ethyl)-1H-benzo[d]imidazol-2-yl)-1,3-dimethylpyridin-2(1H)-one (Prepared from: Intermediate 2 and Intermediate 87)

System A, 0.50 min, MH$^+$=382; Yield: 0.416 g, 27%

Intermediate 107: 5-(1-(1,3-dimethoxypropan-2-yl)-6-(hydroxymethyl)-1H-benzo[d]imidazol-2-yl)-1,3-dimethylpyridin-2(1H)-one (Prepared from: Intermediate 2 and Intermediate 180)

System B, 0.67 min, MH$^+$=372; Yield: 2.038 g, 29%

Intermediate 108: (R)-tert-butyl 3-((2-(1,5-dimethyl-6-oxo-1,6-dihydropyridin-3-yl)-5-(hydroxymethyl)-1H-benzo[d]imidazol-1-yl)methyl)piperidine-1-carboxylate (Prepared from: Intermediate 2 and Intermediate 88)

System A, 0.71 min, MH$^+$=467; Yield: 2.96 g, 50%

Intermediate 109: (R)-5-(5-(hydroxymethyl)-1-(piperidin-3-ylmethyl)-1H-benzo[d]imidazol-2-yl)-1,3-dimethylpyridin-2(1H)-one A solution of 5M HCl in IPA (40 mL, 200 mmol) was added to (S)-tert-butyl 3-((2-(1,5-dimethyl-6-oxo-1,6-dihydropyridin-3-yl)-5-(hydroxymethyl)-1H-benzo[d]imidazol-1-yl)methyl)piperidine-1-carboxylate (for a preparation see Intermediate 103, 1.8 g, 3.86 mmol) and the suspension stirred for 4 h. The reaction mixture was evaporated in vacuo to a brown oil. The residue was dissolved in MeOH and loaded on to a 20 g SCX cartridge. The cartridge was eluted with MeOH (200 mL), followed by 2M methanolic ammonia (100 mL). The basic fractions were evaporated in vacuo to give the title compound as a pale yellow foam (1.389 g). The total yield of the reaction was 98%.

LCMS (System B): $t_{RET}$=0.61 min, MH$^+$=367.

The following Intermediate was prepared in a similar manner to Intermediate 109:

Intermediate 110: (S)-5-(5-(hydroxymethyl)-1-(piperidin-3-ylmethyl)-1H-benzo[d]imidazol-2-yl)-1,3-dimethylpyridin-2(1H)-one, Hydrochloride (Prepared from: Intermediate 108)

System A, 0.60 min, MH$^+$=367; Yield: 1.4 g, 97%

Intermediate 111: (S)-5-(1-((1-acetylpiperidin-3-yl)methyl)-5-(hydroxymethyl)-1H-benzo[d]imidazol-2-yl)-1,3-dimethylpyridin-2(1H)-one Acetic anhydride (0.382 mL, 4.05 mmol) was added to a suspension of (R)-5-(5-(hydroxymethyl)-1-(piperidin-3-yl-methyl)-1H-benzo[d]imidazol-2-yl)-1,3-dimethylpyridin-2(1H)-one (for a preparation see Intermediate 109, 1.35 g, 3.68 mmol) in 2-Methyltetrahydrofuran (30 mL). The resulting suspension was stirred for 2 h. The reaction mixture was partitioned between 2-MeTHF (200 mL) and sat. aq. NaHCO$_3$ (25 mL). The organic layer was washed (1×sat. aq. NaHCO$_3$ [25 mL]), dried over MgSO$_4$ and evaporated in vacuo to a white solid (~0.3 g). The combined aqueous layers were extracted (3×DCM [50 mL]) and the organic layers added to the residue from the 2-MeTHF evaporation. The resulting solution was evaporated in vacuo to a white solid. The solid was dissolved in DCM, and purified by silica gel chromatography eluting with DCM:2M methanolic ammonia (0-5%). The product containing fractions were evaporated in vacuo to a give the title compound as a white solid (1.353 g). The total yield was 90%. LCMS (System C): $t_{RET}$=0.44 min, MH$^+$=409.

Intermediate 112: (R)-5-(1-((1-acetylpiperidin-3-yl)methyl)-5-(hydroxymethyl)-1H-benzo[d]imidazol-2-yl)-1,3-dimethylpyridin-2(1H)-one To a stirred suspension of (S)-5-(5-(hydroxymethyl)-1-(piperidin-3-ylmethyl)-1H-benzo[d]imidazol-2-yl)-1,3-dimethylpyridin-2(1H)-one hydrochloride (for a preparation see Intermediate 109, 1.49 g, 3.37 mmol) in dichloromethane (10 mL) was added DIPEA (3.53 mL, 20.19 mmol). To the resulting yellow solution was added acetyl chloride (0.718 mL, 10.10 mmol) and stirred for 1.5 h. 2M aq. NaOH (10 mL, 20.00 mmol) was added, the reaction mixture stirred vigorously for 30 min, and the organic layer removed. The aqueous was extracted 3 times with DCM and the combined organic phases passed through a hydrophobic frit and concentrated in vacuo to give a brown paste. The residue was dissolved in THF (10 mL) and 2M aq. NaOH (10 mL, 20.00 mmol) was added. The reaction mixture was stirred for 30 min. The reaction mixture was partitioned between Water and DCM and the organic layer removed. The aqueous phases was extracted 3 times with DCM. Sat. aq. NaHCO$_3$ and DCM:IPA (3:1) were added to the aqueous layer and the organic removed. The aqueous layer was extracted 3 times and the combined organic phases were passed through a hydrophobic frit, concentrated and dried in vacuo to give a yellow solid. The crude solid was dissolved in DCM, purified by silica gel chromatography, eluting with 2M Methanolic ammonia:DCM (2.5-12.5%, 15 CV). The appropriate fractions were combined and evaporated in vacuo to give the title compound as a yellow solid (1.01 g). The total yield of the reaction was 73%. LCMS (System A): $t_{RET}$=0.47 min, MH$^+$=409.

Intermediate 113: 1-ethyl-2-(5-methyl-6-oxo-1,6-dihydropyridin-3-yl)-1H-benzo[d]imidazole-5-carbaldehyde 5-(1-ethyl-5-(hydroxymethyl)-1H-benzo[d]imidazol-2-yl)-3-methylpyridin-2(1H)-one (For a preparation see Intermediate 89, 290 mg, 1.024 mmol) and 45% by weight 2-iodoxybenzoic acid (701 mg, 1.126 mmol) were added to DCM (5 mL) and the suspension was stirred under nitrogen for 4 days. The reaction mixture was partitioned between saturated sodium hydrogen carbonate solution (30 mL) and DCM (30 mL) and the layers were separated. The aqueous layer was extracted with DCM (3×30 mL). The organic layers were combined and concentrated under reduced pressure. It was again partitioned between saturated sodium hydrogen carbonate solution (50 mL) and DCM (50 mL). The layers were separated and the aqueous layer was extracted with DCM (3×50 mL). The combined organic layers were dried using a hydrophobic frit and was concentrated under reduced pressure to give the title compound (263 mg) as an off-white solid. LCMS (System B): $t_{RET}$=0.67 min, MH$^+$=282

The following Intermediates were prepared in a similar way to Intermediate 113:

Intermediate 114: (S)-2-(5-methyl-6-oxo-1,6-dihydropyridin-3-yl)-1-((tetrahydrofuran-2-yl)methyl)-1H-benzo[d]imidazole-5-carbaldehyde (Prepared from: Intermediate 92 (S)-5-(5-(hydroxymethyl)-1-((tetrahydrofuran-2-yl)methyl)-1H-benzo[d]imidazol-2-yl)-3-methylpyridin-2(1H)-one)

System B, 0.70 min, MH$^+$=338; Yield: 1.04 g, 85%

Intermediate 115: (R)-2-(1,5-dimethyl-6-oxo-1,6-dihydropyridin-3-yl)-1-((tetrahydrofuran-2-yl)methyl)-1H-benzo[d]imidazole-5-carbaldehyde (Prepared from: Intermediate 93)

System B, 0.70 min, MH$^+$=338; Yield: 147 mg, 63%

Intermediate 117: 2-(1,5-dimethyl-6-oxo-1,6-dihydropyridin-3-yl)-1-(1-methoxybutan-2-yl)-1H-benzo[d]imidazole-5-carbaldehyde (Prepared from: Intermediate 101)

System A, 0.82 min, MH$^+$=354; Yield: 2.60 g, 95%

Intermediate 118: (S)-2-(1,5-dimethyl-6-oxo-1,6-dihydropyridin-3-yl)-1-((tetrahydrofuran-2-yl)methyl)-1H-benzo[d]imidazole-5-carbaldehyde A suspension of (S)-2-(5-methyl-6-oxo-1,6-dihydropyridin-3-yl)-1-((tetrahydrofuran-2-yl)methyl)-1H-benzo[d]imidazole-5-carbaldehyde (For a preparation see Intermediate 114, 500 mg, 1.260 mmol) and Potassium carbonate (348 mg, 2.52 mmol) in DMF (5 mL) was stirred for 1.15 h prior to adding iodomethane (0.095 mL, 1.512 mmol). The reaction mixture was stirred over the weekend. The reaction mixture was concentrated under reduced pressure and the residue was partitioned between 3:1 chloroform:isopropanol (125 mL) and saturated solution of sodium bicarbonate (125 mL). The organic layer was isolated and the aqueous fraction was re-extracted three times with 3:1 chloroform:isopropanol (3×125 mL). The organic fractions were combined, passed through a hydrophobic frit and concentrated under reduced pressure. The residue was dissolved in 10% ethanol in ethyl acetate and loaded onto a silica column (50 g). The products were eluted with a gradient of 0-30% ethanol in ethyl acetate. The appropriate fractions were combined and concentrated under reduced pressure to give the title compound (121 mg) as a light brown solid. LCMS (System B): $t_{RET}$=0.75 min, MH$^+$=352

Intermediate 119: (R)-2-(1,5-dimethyl-6-oxo-1,6-dihydropyridin-3-yl)-1-((tetrahydrofuran-2-yl)methyl)-1H-benzo[d]imidazole-5-carbaldehyde (R)-2-(5-methyl-6-oxo-1,6-dihydropyridin-3-yl)-1-((tetrahydrofuran-2-yl)methyl)-1H-benzo[d]imidazole-5-carbaldehyde (For a preparation see Intermediate 115, 149 mg, 0.353 mmol) was dissolved in DMF (2.5 mL) and Potassium carbonate (98 mg, 0.707 mmol) was added. The reaction mixture was stirred for one hour prior to adding Iodomethane (0.027 mL, 0.424 mmol). The flask containing the reaction mixture was sealed. The reaction mixture was stirred overnight. The reaction mixture was diluted with isopropanol and filtered through a celite cartridge (2.5 g) which had been preconditioned with the solvent. 4 CV of isopropanol were passed through the column. The washings were combined and concentrated under reduced pressure. The residue was dissolved in a minimum amount of DCM and loaded onto a silica column (25 g) and eluted with a gradient of 0-20% ethanol in ethyl acetate. The appropriate fractions were combined and concentrated under reduced pressure to give the title compound (56 mg) as a colourless gum. LCMS (System B): $t_{RET}$=0.75 min, MH$^+$=352

Intermediate 120: 1-((1,4-dioxan-2-yl)methyl)-2-(1,5-dimethyl-6-oxo-1,6-dihydropyridin-3-yl)-1H-benzo[d]imidazole-5-carbaldehyde (Single Enantiomer of Unknown Configuration)

Potassium carbonate (368 mg, 2.66 mmol) was added in a single portion to a suspension of 1-((1,4-dioxan-2-yl)methyl)-2-(5-methyl-6-oxo-1,6-dihydropyridin-3-yl)-1H-benzo[d]imidazole-5-carbaldehyde (For a preparation see Intermediate 122, 470 mg, 1.330 mmol) in DMF (15 mL). The mixture was then cooled in a water-ice bath and iodomethane (0.108 mL, 1.729 mmol) was added dropwise. When the addition was completed, the bath was removed and the reaction mixture stirred at rt overnight (18 hr). The solvent was removed under reduced pressure. The solid was then partitioned between NaHCO$_3$ (100 mL) and DCM:iPrOH 3:1 (100 mL). The separated aqueous phase was extracted with DCM:iPrOH 3:1 (3×100 mL). The combined organic phases where passed through a hydrophobic frit and evaporated to obtain the title compound (476 mg) as a pale yellow solid. LCMS (System B): $t_{RET}$=0.70 min, MH$^+$=368.

Intermediate 121: 2-(1,5-dimethyl-6-oxo-1,6-dihydropyridin-3-yl)-1-((tetrahydro-2H-pyran-4-yl)methyl)-1H-benzo[d]imidazole-6-carbaldehyde Manganese dioxide (11 g, 108 mmol) was added in a single portion to a stirred solution of 5-(6-(hydroxymethyl)-1-((tetrahydro-2H-pyran-4-yl)methyl)-1H-benzo[d]imidazol-2-yl)-1,3-dimethylpyridin-2(1H)-one (For a preparation see Intermediate 94, 3.3 g, 8.98 mmol) in chloroform (150 mL) at rt. The resultant suspension was stirred rapidly overnight (18 hr). Further manganese dioxide (2 g, 19.55 mmol) was added and the reaction mixture was stirred for 0.5 hr longer. 20 mL of the reaction mixture was filtrated through celite and the solvent evaporated to obtain the title compound (424 mg) as colourless oil. LCMS (System B): $t_{RET}$=0.72 min, MH$^+$=367

Intermediate 122: 1-((1,4-dioxan-2-yl)methyl)-2-(5-methyl-6-oxo-1,6-dihydropyridin-3-yl)-1H-benzo[d]imidazole-5-carbaldehyde (Single Unknown Enantiomer)

Manganese dioxide (2232 mg, 21.82 mmol) was added in a single portion to a stirred suspension of 5-(1-((1,4-dioxan-2-yl)methyl)-5-(hydroxymethyl)-1H-benzo[d]imidazol-2-yl)-3-methylpyridin-2(1H)-one (For a preparation see Intermediate 138a, 554 mg, 1.559 mmol) in chloroform (25 mL) at rt. The resultant suspension was stirred rapidly for 4 hr and was leaved to stand overnight. The suspension was filtered through Celite and flushed with DCM (2×30 mL), MeOH (5×30 mL) and DCM:iPr 3:1 (2×30 mL). The filtrate was evaporated under vacuo and 1 hr in the vacuum oven to obtain the title compound (470 mg) as a pale yellow solid. LCMS (System B): $t_{RET}$=0.65 min, MH$^+$=354
The following Intermediates were prepared in a similar way to Intermediate 122:

Intermediate 123: (S)-2-(1,5-dimethyl-6-oxo-1,6-dihydropyridin-3-yl)-1-(1-methoxypropan-2-yl)-1H-benzo[d]imidazole-6-carbaldehyde (Prepared from: Intermediate 97)

System A, 0.71 min, MH$^+$=340; Yield: 1.56 g, 87%

Intermediate 124: (S)-2-(1,5-dimethyl-6-oxo-1,6-dihydropyridin-3-yl)-1-((tetrahydrofuran-2-yl)methyl)-1H-benzo[d]imidazole-6-carbaldehyde (Prepared from: Intermediate 98)

System B, 0.80 min, MH$^+$=352; Yield: 2.29 g, 100%

Intermediate 125: (R)-1-((1-acetylpiperidin-3-yl)methyl)-2-(1,5-dimethyl-6-oxo-1,6-dihydropyridin-3-yl)-1H-benzo[d]imidazole-6-carbaldehyde (Prepared from: Intermediate 141)

System B, 0.73 min, MH$^+$=407; Yield: 535 mg, 79%

Intermediate 126: (R)-tert-butyl 3-((2-(1,5-dimethyl-6-oxo-1,6-dihydropyridin-3-yl)-6-formyl-1H-benzo[d]imidazol-1-yl)methyl)piperidine-1-carboxylate (Prepared from: Intermediate 99)

System C, 0.80 min, MH$^+$=465; Yield: 897 mg, 90%

Intermediate 127: (S)-1-((1-acetylpiperidin-3-yl)methyl)-2-(1,5-dimethyl-6-oxo-1,6-dihydropyridin-3-yl)-1H-benzo[d]imidazole-6-carbaldehyde (Prepared from: Intermediate 142)

System B, 0.73 min, MH$^+$=407; Yield: 217 mg, 95%

Intermediate 128: (S)-tert-butyl 3-((2-(1,5-dimethyl-6-oxo-1,6-dihydropyridin-3-yl)-6-formyl-1H-benzo[d]imidazol-1-yl)methyl)piperidine-1-carboxylate (Prepared from: Intermediate 100)

System B, 1.00 min, MH$^+$=465; Yield: 79 mg, 64%

Intermediate 129: 2-(1,5-dimethyl-6-oxo-1,6-dihydropyridin-3-yl)-1-((tetrahydrofuran-3-yl)methyl)-1H-benzo[d]imidazole-6-carbaldehyde (Prepared from: Intermediate 102)

System B, 0.74 min, MH$^+$=352; Yield: 1.79 g, 96%

Intermediate 130: (S)-tert-butyl 3-((2-(1,5-dimethyl-6-oxo-1,6-dihydropyridin-3-yl)-5-formyl-1H-benzo[d]imidazol-1-yl)methyl)piperidine-1-carboxylate Manganese dioxide (2.98 g, 34.3 mmol) was added to a solution of (S)-tert-butyl 3-((2-(1,5-dimethyl-6-oxo-1,6-dihydropyridin-3-yl)-5-(hydroxymethyl)-1H-benzo[d]imidazol-1-yl)methyl)piperidine-1-carboxylate (1.6 g, 3.43 mmol) (for an example preparation see Intermediate 103) in chloroform (60 mL). The suspension was stirred for 3 h and stirring stopped over the weekend. The suspension was filtered and evaporated in vacuo to give the title compound as a brown solid (1.299 g). The total yield for the reaction was 82%. LCMS (System C): $t_{RET}$=0.83 min, MH$^+$=465.
The following Intermediates were prepared in a similar manner to Intermediate 130:

Intermediate 131: 2-(1,5-dimethyl-6-oxo-1,6-dihydropyridin-3-yl)-1-(tetrahydro-2H-pyran-4-yl)-1H-benzo[d]imidazole-6-carbaldehyde (Prepared from: Intermediate 104)

System A, 0.67 min, MH$^+$=351 Yield: 0.657 g, 87%

Intermediate 132: 2-(1,5-dimethyl-6-oxo-1,6-dihydropyridin-3-yl)-1-((tetrahydro-2H-pyran-2-yl)methyl)-1H-benzo[d]imidazole-6-carbaldehyde (Prepared from: Intermediate 105)

System A, 0.84 min, MH$^+$=366; Yield: 0.983 g, 94%

Intermediate 133: 2-(1,5-dimethyl-6-oxo-1,6-dihydropyridin-3-yl)-1-(1-(tetrahydro-2H-pyran-4-yl)ethyl)-1H-benzo[d]imidazole-5-carbaldehyde (Prepared from: Intermediate 106)

System A, 0.74 min, MH$^+$=380; Yield: 0.376 g, 88%

Intermediate 134: 1-(1,3-dimethoxypropan-2-yl)-2-(1,5-dimethyl-6-oxo-1,6-dihydropyridin-3-yl)-1H-benzo[d]imidazole-6-carbaldehyde (Prepared from: Intermediate 107)

System B, 0.80 min, MH$^+$=370; yield not recorded)

Intermediate 135: (S)-1-((1-acetylpiperidin-3-yl)methyl)-2-(1,5-dimethyl-6-oxo-1,6-dihydropyridin-3-yl)-1H-benzo[d]imidazole-5-carbaldehyde (Prepared from: Intermediate 111)

System C, 0.55 min, MH$^+$=407; Yield: 1.41 g, 94%

Intermediate 136: (R)-1-((1-acetylpiperidin-3-yl)methyl)-2-(1,5-dimethyl-6-oxo-1,6-dihydropyridin-3-yl)-1H-benzo[d]imidazole-5-carbaldehyde (Prepared from: Intermediate 112)

System A, 0.65 min, MH$^+$=407; Yield: 958 mg, 91%

Intermediate 137: (2S,3R)-Cyclopentyl 2-amino-3-hydroxybutanoate, 4-methylbenzenesulphonic acid salt To a suspension of (2S,3R)-2-amino-3-hydroxybutanoic acid (20 g, 168 mmol) in cyclohexane (200 mL), cyclopentanol (116 g, 1343 mmol) and 4-methylbenzenesulfonic acid (37.6 g, 218 mmol) at room temperature were added. The reaction mixture was stirred at 100° C. for 24 hr. The reaction mixture was evaporated in vacuo to give the crude product as a brown oil. The brown oil was allowed to cool and the resulting crystals filtered, washed with EtOAc (50 mL) to give (2S,3R)-cyclopentyl 2-amino-3-hydroxybutanoate, 4-methylbenzenesulphonic acid salt (50.06 g, 136 mmol, 81% yield) as a white solid. $^1$H NMR δ (400 MHz, DMSO-d$_6$) ppm: 8.20 (3H, br. s.), 7.48 (2H, d, J=8.1 Hz), 7.12 (2H, d, J=7.8 Hz), 5.63 (1H, d, J=4.4 Hz), 5.20 (1H, t, J=5.6 Hz), 4.18-4.03 (1H, m), 3.89 (1H, d, J=3.4 Hz), 2.30 (3H, s), 1.94-1.78 (2H, m), 1.77-1.50 (6H, m), 1.20 (3H, d, J=6.6 Hz).

Intermediate 138a and 138b: 5-(1-((1,4-dioxan-2-yl)methyl)-5-(hydroxymethyl)-1H-benzo[d]imidazol-2-yl)-3-methylpyridin-2(1H)-one (rac)-5-(1-((1,4-dioxan-2-yl)methyl)-5-(hydroxymethyl)-1H-benzo[d]imidazol-2-yl)-3-methylpyridin-2(1H)-one (for a preparation see Intermediate 95, 1.2 g) was separated into it's two corresponding enantiomers by chiral chromatography, using a 30 mm×25 cm Chiralcel OD-H column, eluting with 40% EtOH/Heptane at a flowrate of 30 mL/min, wavelength of detection=215 nm.
Isomer 1: (Intermediate 138a) 563 mg obtained as a solid
LCMS (System A): $t_{RET}$=0.44 min, MH$^+$=356
Analysed for chiral purity on 4.6 mmid×25 cm Chiralcel OD-H column, eluting with 40% EtOH/Heptane at a flowrate of 1.0 mL/min, wavelength of detection=215 nm.
Chiral purity found to be >99.5%.
Isomer 2: (Intermediate 138b) 598 mg obtained as a solid
LCMS (System A): $t_{RET}$=0.41 min, MH$^+$=356
Analysed for chiral purity on 4.6 mmid×25 cm Chiralcel OD-H column, eluting with 40% EtOH/Heptane at a flowrate of 1.0 mL/min, wavelength of detection=215 nm.
Chiral purity found to be 99.1%.

Intermediate 139: (S)-5-(6-(hydroxymethyl)-1-(piperidin-3-ylmethyl)-1H-benzo[d]imidazol-2-yl)-1,3-dimethylpyridin-2(1H-one 5M HCl in IPA (15 mL) was added to (R)-tert-butyl 3-((2-(1,5-dimethyl-6-oxo-1,6-dihydropyridin-3-yl)-6-(hydroxymethyl)-1H-benzo[d]imidazol-1-yl)methyl)piperidine-1-carboxylate (For a preparation see Intermediate 99, 850 mg, 1.82 mmol). The resulting solution was stirred for 3 h and evaporated in vacuo to a brown solid. The residue was dissolved in MeOH, loaded on to a 10 g SCX cartridge and eluted with MeOH, followed by 2M methanolic ammonia. The basic fractions were evaporated in vacuo to give the title compound (617 mg) as a white foam. LCMS (System C): $t_{RET}$=0.33 min, MH$^+$=367.

Intermediate 140: (R)-(1-((1-acetylpiperidin-3-yl)methyl)-2-(1,5-dimethyl-6-oxo-1,6-dihydropyridin-3-yl)-1H-benzo[d]imidazol-6-yl)methyl acetate (S)-5-(6-(hydroxymethyl)-1-(piperidin-3-ylmethyl)-1H-benzo[d]imidazol-2-yl)-1,3-dimethylpyridin-2(1H)-one (For a preparation see Intermediate 139, 617 mg, 1.68 mmol) was dissolved in DCM (5 mL). DIPEA (0.618 mL, 3.54 mmol) and acetyl chloride (0.253 mL, 3.54 mmol) were added and the reaction stirred under nitrogen at rt for 3.5 hr. 0.2 eq of DIPEA (0.059 mL, 0.336 mmol) and 0.2 eq of acetyl chloride (0.024 mL, 0.336 mmol) were added and the reaction was stirred under nitrogen overnight (16 hr). 0.4 eq of DIPEA (0.118 mL, 0.672 mmol) and 0.4 eq of acetyl chloride (0.048 mL, 0.672 mmol) were added and the reaction was stirred under nitrogen for 1 hr. 5 mL of aq. NaOH 2M were added and the suspension was vigorously stirred for 30 min. The separated aqueous phase was extracted with DCM (3×10 mL). The combined organic phases were passed through a hydrophobic frit to obtain the title compound (796 mg) as a yellow paste. LCMS (System A): $t_{RET}$=0.62 min, MH$^+$=451.

Intermediate 141: (R)-5-(1-((1-acetylpiperidin-3-yl)methyl)-6-(hydroxymethyl)-1H benzo[d]imidazol-2-yl)-1,3-dimethylpyridin-2(1H)-one (R)-(1-((1-acetylpiperidin-3-yl)methyl)-2-(1,5-dimethyl-6-oxo-1,6-dihydropyridin-3-yl)-1H-benzo[d]imidazol-6-yl)methyl acetate (For a preparation see Intermediate 140, 796 mg, 1.77 mmol) was dissolved in tetrahydrofuran (2 mL) and MeOH (2 mL) and aqueous NaOH 2M (0.883 mL, 1.77 mmol) was added. The reaction mixture was stirred for 10 min at rt. The reaction mixture was neutralized to pH=7 with aq. sol. HCl 2M and diluted with Water (10 mL) and DCM:iPrOH 3:1 (10 mL). The separated aqueous phase was extracted with DCM:iPrOH 3:1 (3×10 mL). The combined organic phases were passed through a hydrophobic frit and evaporated to obtain the title compound (683 mg) as a yellow oil. LCMS (System A): $t_{RET}$=0.46 min, MH$^+$=409.

Intermediate 142: (S)-5-(1-((1-acetylpiperidin-3-yl)methyl)-6-(hydroxymethyl)-1H-benzo[d]imidazol-2-yl)-1,3-dimethylpyridin-2(1H)-one (R)-5-(6-(hydroxymethyl)-1-(piperidin-3-ylmethyl)-1H-benzo[d]imidazol-2-yl)-1,3-dimethylpyridin-2(1H)-one
(For a preparation see Intermediate 170, 284 mg, 0.775 mmol) was dissolved in DCM (5 mL) and cooled in a water/ice bath prior addition of DIPEA (0.108 mL, 0.620 mmol) followed by dropwise addition of acetyl chloride (0.044 mL, 0.620 mmol). The reaction mixture was stirred for 5 min, then the bath was removed and the reaction mixture was allowed to warm up to rt and stirred for 2 hr. The reaction mixture was partitioned between DCM:iPrOH 3:1 (10 mL) and NaHCO$_3$ (10 mL). The separated aqueous phase was extracted with DCM:iPrOH 3:1 (3×10 mL). The combined organic fractions were passed though a hydrofobic frit and evaporated to obtain the crude product, 300 mg. The samples were dissolved in MeOH 3 mL and purified by MDAP (Method B). The solvent was dried down to give the title compound (230 mg) as a white solid. LCMS (System B): $t_{RET}$=0.64 min, MH$^+$=409.

Intermediate 143: (2S)-cyclopentyl 4-methyl-2-((4-(((4-methylmorpholin-2-yl)methyl)amino)-3-nitrobenzyl)amino)pentanoate (4-methylmorpholin-2-yl)methanamine (665 mg, 5.11 mmol) and DIPEA (0.892 mL, 5.11 mmol) were added to a solution of (S)-cyclopentyl 2-((4-fluoro-3-nitrobenzyl)amino)-4-methylpentanoate (for a preparation see Intermediate 144, 600 mg, 1.703 mmol) in tetrahydrofuran (12 mL).

The reaction mixture was heated in a Biotage Initiator microwave using initial high absorption setting to 120° C. for a total of 90 mins. DCM (30 mL) and saturated sodium hydrogen carbonate solution (30 mL) were added and the layers were separated. The aqueous layer was extracted with DCM (2×30 mL) and the organic layers were combined, dried and evaporated under reduced pressure to give an orange liquid. The sample was loaded in dichloromethane and purified by silica gel column chromatography (50 g silica) using a gradient of 0-10% dichloromethane-methanol over 15 column volumes followed by holding at 10% dichloromethane-methanol for 5 column volumes. The appropriate fractions were combined and evaporated under reduced pressure to give the title compound (693.6 mg, 1.499 mmol, 88% yield) as an orange gum. LCMS (System A): $t_{RET}$=0.70 min, $MH^+$=463

Intermediate 144: (S)-cyclopentyl 2-((4-fluoro-3-nitrobenzyl)amino)-4-methylpentanoate 4-fluoro-3-nitrobenzaldehyde (2 g, 11.83 mmol) and (S)-cyclopentyl 2-amino-4-methylpentanoate 4-methylbenzenesulfonate (for a preparation see Intermediate 3, 4.83 g, 13.01 mmol) were dissolved in DCM (50 mL) and to this, acetic acid (2.031 mL, 35.5 mmol) was added. The reaction mixture was stirred under nitrogen for 1.5 hours. sodium triacetoxyborohydride (5.01 g, 23.65 mmol) was added in portions and the reaction mixture was stirred under nitrogen overnight. Saturated aqueous sodium hydrogen carbonate solution (100 mL) was added slowly and the reaction mixture was stirred until the fizzing had stopped. The resulting suspension was extracted with DCM (3×100 mL). The combined organic layers were dried and evaporated under reduced pressure to give a yellow oil. The crude sample was loaded in dichloromethane and purified by Biotage SP4 SNAP 100 g silica using a gradient of 0-50% cyclohexane-ethyl acetate over 10 column volumes followed by holding at 50% cyclohexane-ethyl acetate for 10 column volumes. The appropriate fractions were combined and evaporated under reduced pressure to give the title compound (2.64 g, 7.48 mmol, 63.3% yield) as a yellow oil. LCMS (System A): $t_{RET}$=0.97 min, $MH^+$=353.

Intermediate 145: (2S)-cyclopentyl 2-((4-(((4-methylmorpholin-2-yl)methyl)amino)-3-nitrobenzyl)amino)propanoate (S)-cyclopentyl 2-((4-fluoro-3-nitrobenzyl)amino)propanoate (for a preparation see Intermediate 146, 490 mg, 1.579 mmol), (4-methylmorpholin-2-yl)methanamine (617 mg, 4.74 mmol) and DIPEA (0.827 mL, 4.74 mmol) were dissolved in THF (12 mL) and the reaction mixture was heated in a Biotage Initiator microwave using initial high absorption setting to 120° C. for a total of 90 minutes. The reaction mixture was partitioned between saturated sodium hydrogen carbonate solution (40 mL) and DCM (40 mL) and the layers were separated. The aqueous layer was washed with DCM (3×40 mL) and the combined organic layers were dried using a hydrophobic frit and evaporated under reduced pressure to give an orange oil. The sample was loaded in dichloromethane and purified by silica gel column chromatography (50 g silica) using a gradient of 0-12% dichloromethane-2M ammonia in methanol over 10 column volumes followed by holding at 12% dichloromethane-2M ammonia in methanol for 5 column volumes. The appropriate fractions were combined and evaporated under reduced pressure to give the title compound (649.8 mg, 1.545 mmol, 98% yield) as an orange oil. LCMS (System A): $t_{RET}$=1.12 min, $MH^+$=421

Intermediate 146: (S)-cyclopentyl 2-((4-fluoro-3-nitrobenzyl)amino)-4-methylpentanoate 4-fluoro-3-nitrobenzaldehyde (500 mg, 2.96 mmol) and (S)-cyclopentyl 2-aminopropanoate hydrochloride (for a preparation see Intermediate 61, 630 mg, 3.25 mmol) were dissolved in Dichloromethane (DCM) (15 mL) and to this solution, acetic acid (0.508 mL, 8.87 mmol) was added. The reaction mixture was stirred under nitrogen for 1 hour. sodium triacetoxyborohydride (1.253 g, 5.91 mmol) was added to the reaction mixture and it was stirred under nitrogen at room temperature overnight. Saturated sodium hydrogen carbonate solution (40 mL) was slowly added to the solution until the fizzing stopped. This solution was then extracted with DCM (4×40 mL) and the organic layers were combined, dried using a hydrophobic frit and the solvent was removed under reduced pressure to give a yellow oil. The sample was loaded in dichloromethane and purified by silica gel column chromatography (50 g silica) using a gradient of 35-65% cyclohexane-ethyl acetate over 10 column volumes followed by holding at 65% cyclohexane-ethyl acetate for 5 column volumes. The appropriate fractions were combined and evaporated under reduced pressure to give the title compound (496.5 mg, 1.600 mmol, 54.1% yield) as a yellow oil. LCMS (System A): $t_{RET}$=0.75 min, $MH^+$=311

Intermediate 147: (2S)-cyclopentyl 3-methyl-2-((4-(((4-methylmorpholin-2-yl)methyl)amino)-3-nitrobenzyl)amino)butanoate (4-methylmorpholin-2-yl)methanamine (666 mg, 5.12 mmol) and DIPEA (0.893 mL, 5.12 mmol) were added to a solution of (S)-cyclopentyl 2-((4-fluoro-3-nitrobenzyl)amino)-3-methylbutanoate (for a preparation see Intermediate 148, 577 mg, 1.705 mmol) in THF (12 mL) and the reaction mixture was heated in a Biotage Initiator microwave using initial high absorption setting to 120° C. for a total of 90 minutes. The reaction mixture was partitioned between DCM (40 mL) and saturated sodium hydrogen carbonate solution (40 mL) and the layers were separated. The aqueous layer was extracted with DCM (2×40 mL) and the combined organic layers were dried using a hydrophobic frit and evaporated under reduced pressure to give an orange oil. The sample was loaded in dichloromethane and purified by silica gel column chromatography (50 g silica) using a gradient of 0-7% dichloromethane-2M ammonia in methanol over 10 column volumes followed by holding at 7% dichloromethane-2M ammonia in methanol for 5 column volumes. The appropriate fractions were combined and evaporated under reduced pressure to give the title compound (760.6 mg, 1.696 mmol, 99% yield) as an orange oil. LCMS (System B): $t_{RET}$=1.33 min, $MH^+$=449.

Intermediate 148: (S)-cyclopentyl 2-((4-fluoro-3-nitrobenzyl)amino)-3-methylbutanoate 4-fluoro-3-nitrobenzaldehyde (500 mg, 2.96 mmol) and (S)-cyclopentyl 2-amino-3-methylbutanoate 4-methylbenzenesulfonate (1.163 g, 3.25 mmol, for a preparation see Intermediate 24) were dissolved in Dichloromethane (DCM) (20 mL) and the reaction mixture was stirred under nitrogen for 1 hour. Sodium triacetoxyborohydride (1.253 g, 5.91 mmol)

was added and the reaction mixture was stirred under nitrogen at room temperature for 2 hours. Saturated aqueous sodium hydrogen carbonate solution (50 mL) was added to the reaction mixture in portions till the fizzing stopped. The resulting suspension was extracted with DCM (4×50 mL) and the organic layers were combined, dried using a hydrophobic frit and evaporated under reduced pressure to give a pale yellow oil. The sample was loaded in dichloromethane and purified by silica gel column chromatography (50 g silica) using a gradient of 0-1% dichloromethane-methanol over 10 column volumes followed by holding at 1% dichloromethane-methanol for 5 column volumes. The appropriate fractions were combined and evaporated under reduced pressure to give the title compound (581 mg, 1.717 mmol, 35.9% yield) as a pale yellow oil. LCMS (System A): $t_{RET}$=0.95 min, MH$^+$=339.

Intermediate 149: (S)-cyclopentyl 4-methyl-2-((4-(((1-methylpiperidin-4-yl)methyl)amino)-3-nitrobenzyl)amino)pentanoate (S)-cyclopentyl 2-((4-fluoro-3-nitrobenzyl)amino)-4-methylpentanoate (for a preparation see Intermediate 144, 500 mg, 1.419 mmol), (1-methylpiperidin-4-yl)methanamine (546 mg, 4.26 mmol) and DIPEA (0.743 mL, 4.26 mmol) were added to Tetrahydrofuran (THF) (12 mL) and the reaction mixture was heated in a Biotage Initiator microwave using initial high absorption setting to 120° C. for 1 hour. The reaction mixture was partitioned between DCM (40 mL) and saturated sodium hydrogen carbonate solution (40 mL) and the layers were separated. The aqueous layer was extracted with DCM (2×40 mL) and the combined organic layers were dried and evaporated under reduced pressure to give a yellow oil. The sample was loaded in dichloromethane and purified by silica gel column chromatography (50 g silica) using a gradient of 0-10% dichloromethane-2M ammonia in methanol over 10 column volumes followed by holding at 10% dichloromethane-2M ammonia in methanol for 5 column volumes. The appropriate fractions were combined and evaporated under reduced pressure to give the title compound (595.5 mg, 1.293 mmol, 91% yield) as an orange gum. LCMS (System A): $t_{RET}$=0.69 min, MH$^+$=461.

Intermediate 150: 5-(5-(hydroxymethyl)-1-((4-methylmorpholin-2-yl)methyl)-1H-benzo[d]imidazol-2-yl)-3-methylpyridin-2(1H)-one Three identical mixtures of (4-(((4-methylmorpholin-2-yl)methyl)amino)-3-nitrophenyl)methanol (1 g, 3.55 mmol, for a preparation see Intermediate 166), 5-methyl-6-oxo-1,6-dihydropyridine-3-carbaldehyde (504 mg, 3.68 mmol, for a preparation see Intermediate 1) and sodium dithionite (2 g, 11.5 mmol) in ethanol (8 mL) and water (4 mL) were heated in a Biotage Initiator microwave using initial high absorption setting to 100° C. for 5 hours. The reaction mixtures were combined and partitioned between saturated sodium hydrogen carbonate solution (100 mL) and 25% propan-2-ol in chloroform (100 mL). The layers were separated and the aqueous layer was extracted with 25% propan-2-ol in chloroform (4×100 mL). The organic layers were combined, dried using a hydrophobic frit and evaporated under reduced pressure to give a white solid. The sample was loaded in dichloromethane and purified by Biotage SP4 SNAP 2×100 g silica using a gradient of 5-15% dichloromethane-2M ammonia in methanol over 15 column volumes followed by holding at 15% dichloromethane-2M ammonia in methanol for 5 column volumes. The appropriate fractions were combined and evaporated under reduced pressure to give the title compound 5-(5-(hydroxymethyl)-1-((4-methylmorpholin-2-yl)methyl)-1H-benzo[d]imidazol-2-yl)-3-methylpyridin-2(1H)-one (1.745 g, 4.74 mmol, 44.4% yield) as an off-white solid. LCMS (System B): $t_{RET}$=0.58 min, MH$^+$=369.

Intermediate 151: 2-(5-methyl-6-oxo-1,6-dihydropyridin-3-yl)-1-((tetrahydro-2H-pyran-4-yl)methyl)-1H-benzo[d]imidazole-5-carbaldehyde 5-(5-(hydroxymethyl)-1-((tetrahydro-2H-pyran-4-yl)methyl)-1H-benzo[d]imidazol-2-yl)-3-methylpyridin-2(1H)-one (for a preparation see Intermediate 152, 1.67 g, 4.73 mmol) was fully dissolved in Dimethyl Sulfoxide (DMSO) (25 mL) before adding 2-iodoxybenzoic acid (3.23 g, 5.20 mmol) and stirring under nitrogen for 2 hours. The reaction mixture was diluted with water (100 mL) and the white solid which precipitated out was removed by filtration and kept aside. The filtrate was extracted with ethyl acetate (3×100 mL) and then with 25% methanol in DCM solution (4×100 mL). The solid obtained from earlier filtration was suspended in 25% methanol in DCM (100 mL) and saturated sodium hydrogen carbonate solution (100 mL) was added. The layers were separated and the aqueous layer was extracted with 25% methanol in DCM solution (4×100 mL). All the organic layers were combined, dried using a hydrophobic frit and evaporated under reduced pressure to give a white solid which was then loaded as a suspension in methanol/dichloromethane and purified by silica gel column chromatography (100 g silica) using a gradient of 0-10% dichloromethane-methanol over 10 column volumes followed by holding at 10% dichloromethane-methanol for 10 column volumes. The pure fractions were combined and evaporated under reduced pressure to give the title compound (1.1487 g, 3.27 mmol, 69.2% yield) as an off-white solid. LCMS (System B): $t_{RET}$=0.68 min, MH$^+$=352.

Intermediate 152: 5-(5-(hydroxymethyl)-1-((tetrahydro-2H-pyran-4-yl)methyl)-1H-benzo[d]imidazol-2-yl)-3-methylpyridin-2(1H)-one Four identical mixtures of (3-nitro-4-(((tetrahydro-2H-pyran-4-yl)methyl)amino)phenyl)methanol (for a preparation see Intermediate 77, 1.15 g, 4.3 mmol), 5-methyl-6-oxo-1,6-dihydropyridine-3-carbaldehyde (592 mg, 4.3 mmol, for a preparation see intermediate 1) and sodium dithionite (2.25 g, 13.0 mmol) in Ethanol (8 mL) and Water (4 mL) were heated in a Biotage Initiator microwave using initial high absorption setting to 1000° C. for 5 hours. All four reaction mixtures were combined and partitioned between saturated sodium hydrogen carbonate solution (100 mL) and 25% propan-2-ol in DCM (100 mL). The layers were separated and the aqueous layer was extracted with 25% propan-2-ol in DCM (3×100 mL). The organic layers were combined, dried using a hydrophobic frit and evaporated under reduced pressure to give a white solid. The sample was loaded in dichloromethane and purified by silica gel column chromatography (2×100 g silica) using a gradient of 0-10% dichloromethane-2M ammonia in methanol over 15 column volumes followed by holding at 10% dichloromethane-2M ammonia in methanol for 10 column volumes. The appropriate fractions were combined and evaporated under reduced pressure to give the title com-

Intermediate 153: 1-((1-methyl-5-oxopyrrolidin-3-yl)methyl)-2-(5-methyl-6-oxo-1,6-dihydropyridin-3-yl)-1H-benzo[d]imidazole-5-carbaldehyde 45% by weight 2-iodoxybenzoic acid (695 mg, 1.117 mmol) was added in portions to a suspension of 5-(5-(hydroxymethyl)-1-((1-methyl-5-oxopyrrolidin-3-yl)methyl)-1H-benzo[d]imidazol-2-yl)-3-methylpyridin-2(1H)-one (for a preparation see Intermediate 154, 372 mg, 1.015 mmol) in DCM (5 mL) and the reaction mixture was stirred under nitrogen for 3 days. The reaction mixture was partitioned between DCM and saturated sodium hydrogen carbonate solution. The aqueous layer was extracted with DCM (6×40 mL). The organic layers were combined, dried using a hydrophobic frit and evaporated under reduced pressure to give the title compound (272 mg, 0.746 mmol, 73.5% yield) as an off-white solid. LCMS (System B): $t_{RET}$=0.58 min, MH$^+$=365

Intermediate 154: 5-(5-(hydroxymethyl)-1-((1-methyl-5-oxopyrrolidin-3-yl)methyl)-1H-benzo[d]imidazol-2-yl)-3-methylpyridin-2(1H)-one 4-(((4-(hydroxymethyl)-2-nitrophenyl)amino)methyl)-1-methylpyrrolidin-2-one (for a preparation see Intermediate 155, 710 mg, 2.54 mmol), 5-methyl-6-oxo-1,6-dihydropyridine-3-carbaldehyde (for a preparation see intermediate 1, 349 mg, 2.54 mmol) and sodium dithionite (1328 mg, 7.63 mmol) were added to ethanol (8 mL) and water (4 mL) and the reaction mixture was heated in a Biotage Initiator microwave using initial high absorption setting to 1000° C. for 5 hours. The reaction mixture was partitioned between saturated sodium hydrogen carbonate solution (30 mL) and DCM (30 mL). The aqueous layer was extracted with DCM (3×30 mL). The organic layers were combined, dried using a hydrophobic frit and evaporated under reduced pressure. The sample was loaded in dichloromethane and purified by silica gel column chromatography (50 g silica) using a gradient of 5-20% dichloromethane-2M ammonia in methanol over 15 column volumes followed by holding at 20% dichloromethane-2M ammonia in methanol for 5 column volumes. The appropriate fractions were combined and evaporated under reduced pressure to give the title compound (378 mg, 1.032 mmol, 40.6% yield) as a colourless gum. LCMS (System B): $t_{RET}$=0.51 min, MH$^+$=365.

Intermediate 155: 4-(((4-(hydroxymethyl)-2-nitrophenyl)amino)methyl)-1-methylpyrrolidin-2-one (4-fluoro-3-nitrophenyl)methanol (500 mg, 2.92 mmol), 4-(aminomethyl)-1-methylpyrrolidin-2-one (562 mg, 4.38 mmol) and DIPEA (1.531 mL, 8.77 mmol) were added to tetrahydrofuran (THF) (2 mL) and the reaction mixture was heated in a Biotage Initiator microwave using initial high absorption setting to 120° C. for 4 hours. The reaction mixture was partitioned between DCM (25 mL) and saturated sodium hydrogen carbonate (25 mL). The layers were separated and the aqueous layer was extracted with DCM (3×25 mL). The organic layers were combined, dried using a hydrophobic frit and evaporated under reduced pressure. The sample was loaded in dichloromethane and purified by silica gel column chromatography (50 g silica) using a gradient of 0-10% dichloromethane-2M ammonia in methanol over 10 column volumes followed by holding at 10% dichloromethane-2M ammonia in methanol for 5 column volumes. The appropriate fractions were combined and evaporated under reduced pressure to give the title compound (713.7 mg, 2.56 mmol, 87% yield) as an orange solid. LCMS (System B): $t_{RET}$=0.61 min, MH$^+$=262.

Intermediate 156: 1-((1-acetylpyrrolidin-3-yl)methyl)-2-(5-methyl-6-oxo-1,6-dihydropyridin-3-yl)-1H-benzo[d]imidazole-5-carbaldehyde 5-(1-((1-acetylpyrrolidin-3-yl)methyl)-5-(hydroxymethyl)-1H-benzo[d]imidazol-2-yl)-3-methylpyridin-2(1H)-one (For a preparation see Intermediate 157, 135 mg, 0.355 mmol) was suspended in DCM (5 mL) and 45% by weight 2-iodoxybenzoic acid (243 mg, 0.390 mmol) was added. The reaction mixture was stirred at room temperature for 40 hours. The reaction mixture was partitioned between DCM (25 mL) and saturated sodium hydrogen carbonate solution (25 mL) and the aqueous layer was extracted with DCM (4×25 mL). The combined organic layers were dried using hydrophobic frit and concentrated under reduced pressure. The sample was partitioned again between DCM (25 mL) and saturated sodium hydrogen carbonate solution (25 mL) and the aqueous layer was extracted with DCM (8×25 mL). The combined organic layers were dried using a hydrophobic frit and solvent was removed under reduced pressure to give the title compound (132.1 mg, 0.349 mmol, 98% yield) as an off-white solid. LCMS (System B): $t_{RET}$=0.59 min, MH$^+$=264.

Intermediate 157: 5-(1-((1-acetylpyrrolidin-3-yl)methyl)-5-(hydroxymethyl)-1H-benzo[d]imidazol-2-yl)-3-methylpyridin-2(1H)-one A solution of 5-(5-(hydroxymethyl)-1-(pyrrolidin-3-ylmethyl)-1H-benzo[d]imidazol-2-yl)-3-methylpyridin-2(1H)-one (For a preparation see Intermediate 158, 150 mg, 0.443 mmol) in DCM (5 mL) and pyridine (0.108 mL, 1.330 mmol) was cooled to −5° C. and stirred for 30 minutes. acetyl chloride (0.032 mL, 0.443 mmol), was added and the reaction mixture was stirred at room temperature for 3 days. The reaction mixture was partitioned between water (20 mL) and DCM (20 mL) and the aqueous layer was extracted with DCM (3×20 mL). The combined organic layers were dried using a hydrophobic frit and evaporated under reduced pressure to give crude material (181.8 mg). This was suspended in THF (2 mL) and methanol (2 mL) and 1M aqueous lithium hydroxide solution (1.29 mL, 1.29 mmol) was added and the reaction mixture was stirred at 62° C. for 24 hours. The reaction mixture was partitioned between water (30 mL) and 25% propan-2-ol in DCM solution (30 mL). The aqueous layer was extracted with 25% propan-2-ol in DCM solution (3×30 mL). The combined organic layers were dried using a hydrophobic frit and evaporated under reduced pressure to give the title compound (136.9 mg, 0.360 mmol, 81% yield) as a pale yellow solid. LCMS (System B): $t_{RET}$=0.54 min, MH$^+$=381.

Intermediate 158: 5-(1-((1-acetylpyrrolidin-3-yl)methyl)-5-(hydroxymethyl)-1H-benzo[d]imidazol-2-yl)-3-methylpyridin-2(1H)-one tert-butyl 3-((5-(hydroxymethyl)-2-(5-methyl-6-oxo-1,6-dihydropyridin-3-yl)-1H-benzo[d]imidazol-1-yl)methyl)pyrrolidine-1-carboxylate (for a preparation see Intermediate 159, 420 mg, 0.958 mmol) was dissolved in DCM (7 mL) and 4M hydrochloric acid in 1,4-dioxane (0.958 mL, 3.83 mmol) was added. The reaction mixture was stirred under nitrogen for 5 hours. The volatiles were removed by evaporation under reduced pressure and the sample was loaded in dichloromethane/methanol onto an SCX 10 g cartridge. Elutions of methanol, followed by 2M ammonia in methanol solution were used to purify the product. Appropriate fractions were combined, and concentrated to dryness. The product was purified again on an SCX 10 g cartridge initially washed with methanol, followed by 33%, 50%, 66% and 100% 2M ammonia in methanol solution elutions. The appropriate fractions were combined and evaporated under reduced pressure to give the crude product (309 mg, 0.913 mmol, 95% yield) as a pale yellow solid. The sample was dissolved in DMSO (3×1 mL) and purified by MDAP (Method B). The solvent was evaporated under reduced pressure to give the title compound (163 mg, 0.482 mmol, 50.3% yield) as a white solid. LCMS (System B): $t_{RET}$=0.48 min, MH+=339.

Intermediate 159: tert-butyl 3-((5-(hydroxymethyl)-2-(5-methyl-6-oxo-1,6-dihydropyridin-3-yl)-1H-benzo[d]imidazol-1-yl)methyl)pyrrolidine-1-carboxylate tert-butyl 3-(((4-(hydroxymethyl)-2-nitrophenyl)amino)methyl)pyrrolidine-1-carboxylate (for a preparation see Intermediate 160, 1.0345 g, 2.94 mmol), 5-methyl-6-oxo-1,6-dihydropyridine-3-carbaldehyde (for a preparation see intermediate 1, 0.404 g, 2.94 mmol) and sodium dithionite (1.538 g, 8.83 mmol) were added to ethanol (8 mL) and water (4 mL). The reaction mixture was heated in a Biotage Initiator microwave using initial high absorption setting to 1000° C. for 5 hours. The reaction mixture was partitioned between 25% propan-2-ol in DCM solution (30 mL) and saturated sodium hydrogen carbonate solution (30 mL) and the layers were separated. The aqueous layer was extracted with 25% propan-2-ol in DCM solution (3×30 mL). The organic layers were combined, dried using a hydrophobic frit and evaporated under reduced pressure. The sample was loaded in dichloromethane and purified by Biotage SP4 SNAP 50 g silica using a gradient of 2-12% dichloromethane-2M ammonia in methanol over 10 column volumes followed by holding at 12% dichloromethane-2M ammonia in methanol for 5 column volumes. The appropriate fractions were combined and evaporated under reduced pressure to give the title compound (428.9 mg, 0.978 mmol, 33.2% yield) as a colourless gum. LCMS (System B): $t_{RET}$=0.78 min, MH+=439.

Intermediate 160: tert-butyl 3-(((4-(hydroxymethyl)-2-nitrophenyl)amino)methyl)pyrrolidine-1-carboxylate (4-fluoro-3-nitrophenyl)methanol (521 mg, 3.04 mmol), tert-butyl 3-(aminomethyl)pyrrolidine-1-carboxylate (850 mg, 4.24 mmol) and DIPEA (1.595 mL, 9.13 mmol) were added to tetrahydrofuran (THF) (3 mL) and the reaction mixture was heated in a Biotage Initiator microwave using initial high absorption setting to 120° C. for 3.5 hours. The reaction mixture was partitioned between DCM (25 mL) and saturated sodium hydrogen carbonate solution (25 mL) and the layers were separated. The aqueous layer was extracted with DCM (4×25 mL) and the combined organic layers were dried using a hydrophobic frit and evaporated under reduced pressure. The sample was loaded in dichloromethane and purified by silica gel column chromatography (50 g silica) using a gradient of 0-3% dichloromethane-2M ammonia in methanol over 10 column volumes. The appropriate fractions were combined and evaporated under reduced pressure to give the title compound (1.0781 g, 3.07 mmol, 101% yield) as an orange oil. LCMS (System B): $t_{RET}$=1.03 min, MH+=350.

Intermediate 161: 2-(1,5-dimethyl-6-oxo-1,6-dihydropyridin-3-yl)-1-(tetrahydro-2H-pyran-4-yl)-1H-benzo[d]imidazole-5-carbaldehyde A round bottom flask was charged with 5-(5-(hydroxymethyl)-1-(tetrahydro-2H-pyran-4-yl)-1H-benzo[d]imidazol-2-yl)-1,3-dimethylpyridin-2(1H)-one (for a preparation see Intermediate 162, 360 mg, 1.019 mmol), DCM (20 mL) and Dess-Martin periodinane (432 mg, 1.019 mmol). The mixture was stirred at room temperature overnight. The mixture was diluted with DCM and saturated sodium bicarbonate added before the layers were mixed and separated. The organics were washed with brine before being passed through a hydrophobic frit and concentrated in vacuo to give an off-white solid. The sample was loaded in dichloromethane and purified by silica gel column chromatography (25 g silica) using a gradient of 0-100% ethyl acetate-cyclohexane over 15 CV followed by 0-10% dichloromethane-methanol for 15 CV. The appropriate fractions were combined and evaporated in vacuo to give the title compound (345 mg, 0.884 mmol, 87% yield) as a white solid. LCMS (System A): $t_{RET}$=0.65 min, MH+=352.

Intermediate 162: 5-(5-(hydroxymethyl)-1-(tetrahydro-2H-pyran-4-yl)-1H-benzo[d]imidazol-2-yl)-1,3-dimethylpyridin-2(1H)-one A round bottom flask was charged with 1,5-dimethyl-6-oxo-1,6-dihydropyridine-3-carbaldehyde (for a preparation see Intermediate 2, 574 mg, 3.23 mmol), sodium hydrosulfite (1.8 g, 10.34 mmol), water (10 mL), and a solution of (3-nitro-4-((tetrahydro-2H-pyran-4-yl)amino)phenyl)methanol (for a preparation see intermediate 163, 740 mg, 2.93 mmol) in ethanol (20 mL). The vessel was fitted with an air condensor and the slurry heated at 1000° C. overnight. The mixture was diluted with water and EtOAc, the layers mixed and separated before the organic layer was passed through a hydrophobic frit and concentrated in vacuo to give a yellow oil. The sample was loaded in dichloromethane and purified by silica gel column chromatography (25 g silica) using a gradient of 0-100% ethyl acetate-cyclohexane over 15 CV followed by 0-10% 2M ammonia in methanol-dichloromethane for 15CV. The appropriate fractions were combined and evaporated in vacuo to give the title compound (360 mg, 1.019 mmol, 34.7% yield) as a colourless oil. LCMS (System A): $t_{RET}$=0.47 min, MH+=354.

Intermediate 163: (3-nitro-4-((tetrahydro-2H-pyran-4-yl)amino)phenyl)methanol

A round bottom flask was charged with (4-fluoro-3-nitrophenyl)methanol (1 g, 5.84 mmol), tetrahydro-2H-pyran-4-amine, hydrochloride (0.9 g, 6.54 mmol, J&W PharmLab), DMF (10 mL) and DIPEA (4.1 mL, 23.48 mmol). An air condensor was fitted and the slurry warmed to 70° C. overnight. The mixture was cooled to room temperature, diluted with EtOAc and the organics washed with 1M HCl followed by brine before being passed through a hydrophobic frit. The filtrate was concentrated in vacuo to give an orange oil. The sample was loaded in dichloromethane and purified by silica gel column chromatography (50 g silica)

using a gradient of 0-100% ethyl acetate-cyclohexane over 15 CV. The appropriate fractions were combined and evaporated in vacuo to give an orange oil. The sample was dissolved in EtOAc before being washed with 10% LiCl solution. the organics were passed through a hydrophobic frit before being concentrated in vacuo to give the title compound (740 mg, 2.93 mmol, 50.2% yield) as an orange solid. LCMS (System A): $t_{RET}$=0.71 min, MH$^+$=253.

Intermediate 164: 2-(1,5-dimethyl-6-oxo-1,6-dihydropyridin-3-yl)-1-((4-methylmorpholin-2-yl)methyl)-1H-benzo[d]imidazole-5-carbaldehyde 5-(5-(hydroxymethyl)-1-((4-methylmorpholin-2-yl)methyl)-1H-benzo[d]imidazol-2-yl)-1,3-dimethylpyridin-2(1H)-one (for a preparation see Intermediate 165, 506 mg, 1.323 mmol) was dissolved in dichloromethane (DCM) (5 mL) and Dess-Martin periodinane (561 mg, 1.323 mmol) added. This mixture was stirred under nitrogen for 18 hrs. The mixture was then partitioned between ethyl acetate (100 mL) and saturated sodium bicarbonate (100 mL) and the phases separated. The aqueous phase was then extracted twice with ethyl acetate (100 mL×2) and the organics combined. Organics were then washed with brine (100 mL) and dried using a hydrophobic frit. Solvent was then removed in vacuo yielding the title compound (457 mg, 1.201 mmol, 91% yield) as an off-white solid. LCMS (System B): $t_{RET}$=0.68 min, MH$^+$=381.

Intermediate 165: 5-(5-(hydroxymethyl)-1-((4-methylmorpholin-2-yl)methyl)-1H-benzo[d]imidazol-2-yl)-1,3-dimethylpyridin-2(1H)-one (4-(((4-methylmorpholin-2-yl)methyl)amino)-3-nitrophenyl)methanol (for a preparation see Intermediate 166, 1.6 g, 5.69 mmol), 1,5-dimethyl-6-oxo-1,6-dihydropyridine-3-carbaldehyde (for a preparation see Intermediate 2, 0.860 g, 5.69 mmol) and sodium dithionite (2.97 g, 17.06 mmol) was added to a microwave vial along with ethanol (8 mL) and water (8 mL) and heated to 1000° C. for 5 hrs. The sample was then partitioned between ethyl acetate (75 mL) and saturated sodium carbonate (75 mL) and the phases separated. The organic phases was retained and aqueous phase extracted twice with ethyl acetate (75 mL×2). The organics were then combined, dried using a hydrophobic frit then solvents removed in vacuo. This yielded a pale yellow solid. This was dissolved in dichloromethane. The sample was loaded onto a Biotage SNAP 100 g Silica cartridge and eluted using a gradient of 0%-10% methanolic ammonia/DCM followed by 10%-15% methanolic ammonia/DCM. The appropriate fractions were then combined yielding the title compound (506 mg, 1.323 mmol, 23.26% yield) as a yellow oil. LCMS (System B): $t_{RET}$=0.61 min, MH$^+$=383.

Intermediate 166: (4-(((4-methylmorpholin-2-yl)methyl)amino)-3-nitrophenyl)methanol (4-fluoro-3-nitrophenyl)methanol (1.041 g, 6.08 mmol) and (4-methylmorpholin-2-yl)methanamine (2.376 g, 18.25 mmol) were dissolved in THF (5 mL) and treated with N,N-diisopropylethylamine (3.19 mL, 18.25 mmol). This mixture was heated in a microwave reactor at 120° C. for 1 hr. The dark orange mixture was then partitioned between ethyl acetate (75 mL) and saturated sodium bicarbonate (75 mL). The phases were then separated and the aqueous phase extracted twice with ethyl acetate (75 mL×2). The organics were then combined and dried using a hydrophobic frit then solvents removed in vacuo. This yielded the title compound (1.6 g, 5.69 mmol, 93% yield) as an orange solid. LCMS (System B): $t_{RET}$=0.69 min, MH$^+$=282.

Intermediate 167: 2-(1,5-dimethyl-6-oxo-1,6-dihydropyridin-3-yl)-1-((4-methylmorpholin-3-yl)methyl)-1H-benzo[d]imidazole-5-carbaldehyde 5-(5-(hydroxymethyl)-1-((4-methylmorpholin-3-yl)methyl)-1H-benzo[d]imidazol-2-yl)-1,3-dimethylpyridin-2(1H)-one (for a preparation see Intermediate 168, 473 mg, 1.237 mmol) was dissolved in DCM and Dess-Martin periodinane (525 mg, 1.237 mmol) added. This mixture was stirred at room temperature for 20 hrs. Saturated sodium bicarbonate (100 mL) was then added and the mixture stirred for 15 min. To the mixture was added ethyl acetate (100 mL) and the phases separated. The aqueous phase was then extracted twice with ethyl acetate (100 mL×2). The organics were then combined, dried using a hydrophobic frit then solvent removed in vacuo; to yield the crude title compound (450 mg, 1.18 mmol, 96% yield) as a yellow solid which was used without further purification. LCMS (System B): $t_{RET}$=0.65 min, MH$^+$=381.

Intermediate 168: 5-(5-(hydroxymethyl)-1-((4-methylmorpholin-3-yl)methyl)-1H-benzo[d]imidazol-2-yl)-1,3-dimethylpyridin-2(1H)-one (4-(((4-methylmorpholin-3-yl)methyl)amino)-3-nitrophenyl)methanol (for a preparation see Intermediate 169, 2.83 g, 10.06 mmol) and 1,5-dimethyl-6-oxo-1,6-dihydropyridine-3-carbaldehyde (for a preparation see Intermediate 2, 1.977 g, 13.08 mmol) were dissolved in ethanol (16 mL) along with sodium dithionite (5.25 g, 30.2 mmol) and water (16 mL). The mixtures were heated in a microwave reactor for 5 hrs at 120° C. The yellow mixture was then partitioned between ethyl acetate (150 mL) and saturated sodium bicarbonate (150 mL) and the phases separated. The aqueous phase was extracted twice with ethyl acetate (150 mL×2) and the organics combined. The organics were then dried using a hydrophobic frit. The solvent was then removed in vacuo yielding a yellow oil. The yellow oil was dissolved in dichloromethane and loaded onto a biotage SNAP 100 g silica column and eluted using a gradient of 0%-15% 2M methanolic ammonia/DCM. Appropriate fractions were combined and solvents removed in vacuo to yield the title compound (473 mg, 1.24 mmol, 12.3% yield) as a yellow oil. LCMS (System B): $t_{RET}$=0.58 min, MH$^+$=383.

Intermediate 169: (4-(((4-methylmorpholin-3-yl)methyl)amino)-3-nitrophenyl)methanol (4-fluoro-3-nitrophenyl)methanol (1.77 g, 10.34 mmol, Aldrich) and (4-methylmorpholin-3-yl)methanamine (4.14 mL, 31.0 mmol, Chess Fine Organics) were dissolved in tetrahydrofuran (THF) (5 mL) and treated with N,N-diisopropylethylamine (5.42 mL, 31.0 mmol). This mixture was heated in a microwave reactor at 120° C. for 1 hr. The dark orange mixture was then partitioned between ethyl acetate (150 mL) and saturated sodium bicarbonate (150 mL). The phases were then separated and the aqueous phase extracted twice with ethyl acetate (150 mL×2). The organics were then combined and dried using a hydrophobic frit then solvents removed in vacuo. This yielded the title compound (4-(((4-methylmorpholin-3-yl)methyl)amino)-3-nitrophenyl)

methanol (2.83 g, 10.06 mmol, 97% yield) as a dark red oil. LCMS (System B): $t_{RET}$=0.70 min, MH$^+$=282.

Intermediate 170: (R)-5-(6-(hydroxymethyl)-1-(piperidin-3-ylmethyl)-1H-benzo[d]imidazol-2-yl)-1,3-dimethylpyridin-2(1H)-one HCl 5 M in IPA (9 ml, 45.0 mmol) was added to (S)-tert-butyl 3-((2-(1,5-dimethyl-6-oxo-1,6-dihydropyridin-3-yl)-6-(hydroxymethyl)-1H-benzo[d]imidazol-1-yl)methyl)piperidine-1-carboxylate (525 mg, 0.979 mmol, for a preparation see Intermediate 100) and the resulting solution was stirred at rt for 2 hr. After this time the solution was evaporated under reduced pressure to obtain a pale pink-white solid. The solid was dissolved in MeOH and loaded into an SCX-2 cartridge (20 g). The cartridge was flushed with MeOH (3×CV) followed by 2 M Ammonia in MeOH (3×CV). The basic fractions were combined to obtain the title compound N31482-98-1, 287 mg, 80% yield as a pale yellow oil. LCMS (System B): $t_{RET}$=0.59 min, MH$^+$=367.

Intermediate 171: (3-((cyclopropylmethyl)amino)-4-nitrophenyl)methanol (3-fluoro-4-nitrophenyl)methanol (1 g, 5.84 mmol) was dissolved in 2-methyl tetrahydrofuran (10 mL) and DIPEA (3.06 mL, 17.52 mmol) and cyclopropylmethylamine (0.76 mL, 8.76 mmol) were added. The resulting mixture was stirred at 80° C. overnight.
The reaction mixture was partitioned between DCM and saturated aqueous sodium hydrogen carbonate solution. The aqueous layer was extracted with DCM. The combined organics were washed with saturated aqueous sodium hydrogen carbonate solution, dried using a hydrophobic frit and evaporated in vacuo to give an orange oil which solidified on standing (1.65 g). The crude product was purified by chromatography on silica (100 g) using a 0-50% ethyl acetate/cyclohexane gradient. Appropriate fractions were combined and evaporated to give the title compound (1.28 g) as a bright orange solid. LCMS (System A): $t_{RET}$=0.98 min; MH$^+$=223.

Intermediate 172: 5-(1-(cyclopropylmethyl)-6-(hydroxymethyl)-1H-benzo[d]imidazol-2-yl)-1,3-dimethylpyridin-2(1H-one (3-((cyclopropylmethyl)amino)-4-nitrophenyl)methanol (for a preparation see Intermediate 171, 1.28 g, 5.76 mmol,) and 1,5-dimethyl-6-oxo-1,6-dihydropyridine-3-carbaldehyde (for a preparation see Intermediate 2 N31961-84-1, 1.13 g, 7.49 mmol) were dissolved in ethanol (20 mL) and water (10 mL). Sodium dithionate (3.56 g, 17.28 mmol) was added and the reaction was heated at 80° C. for 2 hours. The reaction mixture was partitioned between ethyl acetate and saturated aqueous sodium bicarbonate solution. The organic layer was washed with saturated aqueous sodium bicarbonate solution, dried using a hydrophobic frit and evaporated to give the title compound (1.39 g) a beige solid. LCMS (System A): $t_{RET}$=0.49 min; MH$^+$=324.

Intermediate 173: 1-(cyclopropylmethyl)-2-(1,5-dimethyl-6-oxo-1,6-dihydropyridin-3-yl)-1H benzo[d]imidazole-6-carbaldehyde 5-(1-(cyclopropylmethyl)-6-(hydroxymethyl)-1H-benzo[d]imidazol-2-yl)-1,3-dimethylpyridin-2(1H)-one (for a preparation see Intermediate 172, 1.38 g, 4.27 mmol) was dissolved in chloroform (50 mL) and manganese dioxide (3.71 g, 42.7 mmol) was added. The resulting suspension was stirred at room temperature under nitrogen overnight. The reaction mixture was filtered through celite and evaporated to give the title compound (1.38 g) as a pale yellow oil, which solidified on standing. LCMS (System A): $t_{RET}$=0.76 min; MH$^+$=322.

Intermediate 174: (4-nitro-3-(((tetrahydro-2H-pyran-3-yl)methyl)amino)phenyl)methanol (tetrahydro-2H-pyran-3-yl)methanamine hydrochloride (1.33 g, 8.77 mmol, Enamine) was added to a mixture of (3-fluoro-4-nitrophenyl)methanol (1 g, 5.84 mmol, Apollo) and DIPEA (4.08 mL, 23.36 mmol) in 2-methyl tetrahydrofuran (10 mL). The resulting mixture was stirred at 80° C. overnight. The reaction mixture was partitioned between DCM and saturated aqueous sodium hydrogen carbonate solution. The aqueous layer was extracted with DCM. The combined organics were washed with saturated aqueous sodium hydrogen carbonate solution, dried using a hydrophobic frit and evaporated in vacuo to give an orange oil (1.74 g). The crude product was purified by chromatography on silica (100 g) using a 0-100% ethyl acetate/cyclohexane gradient. Appropriate fractions were combined and evaporated to give the title compound (1.35 g) as an orange oil. LCMS (System A): $t_{RET}$=0.88 min; MH$^+$=267.

Intermediate 175 and 176: 5-(6-(hydroxymethyl)-1-((tetrahydro-2H-pyran-3-yl)methyl)-1H benzo[d]imidazol-2-yl)-1,3-dimethylpyridin-2(1H)-one (4-nitro-3-(((tetrahydro-2H-pyran-3-yl)methyl)amino)phenyl)methanol (for a preparation see Intermediate 174, 134 g, 5.03 mmol) and 1,5-dimethyl-6-oxo-1,6-dihydropyridine-3-carbaldehyde (for a preparation see Intermediate 2, 0.99 g, 6.54 mmol) were dissolved in ethanol (20 mL) and water (10 mL). Sodium dithionate (3.11, 15.09 mmol) was added and the reaction was heated at 80° C. for 2 hours. The reaction mixture was partitioned between ethyl acetate and sat. aqueous sodium bicarbonate solution. The organic layer was washed with sat. aqueous sodium bicarbonate solution, dried using a hydrophobic frit and evaporated to give a beige solid (1.01 g). The crude product was purified by chromatography on silica (100 g) using a 0-50% (20% ammonia methanol in dichloromethane)/dichloromethane gradient. Appropriate fractions were combined and evaporated to give a colourless oil (0.99 g) which solidified on standing. LCMS (System A): $t_{RET}$=0.47 min; MH$^+$=328. This material was separated into its two component enantiomers by preparative chiral HPLC. The racemate was dissolved in ethanol and purified by chiral chromatography (stationary phase: Chiralpak AD-H (250× 30 mm, 5 micron), mobile phase: hexane/ethanol (+0.2% v/v isopropylamine)). Appropriate fractions were combined and evaporated to give the two enantiomers: Intermediate 175: 426 mg, yellow solid. LCMS (System A): $t_{RET}$=0.47 mins; MH$^+$=368. Intermediate 176: 488 mg, yellow solid. LCMS (System A): $t_{RET}$=0.47 mins; MH$^+$=368. Absolute stereochemistry was not assigned.

Intermediate 177a: 2-(1,5-dimethyl-6-oxo-1,6-dihydropyridin-3-yl)-1-((tetrahydro-2H-pyran-3-yl)methyl)-1H-benzo[d]imidazole-6-carbaldehyde (Isomer 1)

5-(6-(hydroxymethyl)-1-((tetrahydro-2H-pyran-3-yl)methyl)-1H-benzo[d]imidazol-2-yl)-1,3-dimethylpyridin-2

(1H)-one (for a preparation see Intermediate 175 [isomer 1], 423 mg, 1.151 mmol) was dissolved in chloroform (10 mL) and manganese dioxide (1 g, 11.50 mmol) was added. The resulting suspension was stirred at room temperature under nitrogen for 6 hours. The reaction mixture was filtered through celite and evaporated to give the title compound (400 mg) as a pale yellow solid. LCMS (System A): $t_{RET}$=0.73 mins; MH$^+$=366.

Intermediate 177b: 2-(1,5-dimethyl-6-oxo-1,6-dihydropyridin-3-yl)-1-((tetrahydro-2H-pyran-3-yl) methyl)-1H-benzo[d]imidazole-6-carbaldehyde (Isomer 2)

5-(6-(hydroxymethyl)-1-((tetrahydro-2H-pyran-3-yl) methyl)-1H-benzo[d]imidazol-2-yl)-1,3-dimethylpyridin-2 (1H)-one (for a preparation see Intermediate 176, [Isomer 2], 484 mg, 1.317 mmol) was dissolved in chloroform (10 mL) and manganese dioxide (1.14 g, 13.11 mmol) was added. The resulting suspension was stirred at room temperature under nitrogen overnight. LCMS showed ~15% starting material remained. A further portion of manganese dioxide (0.6 g, 6.90 mmol) was added and the reaction was stirred at room temperature, under nitrogen, for 5 hours. The reaction mixture was filtered through celite and evaporated to give the title compound (422 mg) as a yellow solid. LCMS (System A): $t_{RET}$=0.73 mins; MH$^+$=366.

Intermediate 178:
1-(tetrahydro-2H-pyran-4-yl)ethanamine, Hydrochloride

A black suspension of N-(4-methoxybenzyl)-1-(tetrahydro-2H-pyran-4-yl)ethanamine (for a preparation see Intermediate 179, 4.95 g, 18.86 mmol) and 10% w/w palladium on carbon (0.401 g, 1.886 mmol) in ethanol (100 mL) was stirred under hydrogen for 2 days. The reaction mixture was passed through celite column, rinsed with EtOH, and 2M aq. HCl (10 mL) added. The resulting solution was stirred for 20 min, and evaporated in vacuo to afford the title compound as a white solid. The total yield of the reaction was 80%. 8.13 (br.s, 8.13, 3H), 3.88 (dd, J=3.5, 11.0 Hz, 2H), 3.24 (tdd, 2.0, 4.0, 12.0 Hz, 2H), 3.06-2.92 (m, 1H), 1.79-1.66 (m, 1H), 1.66-1.52 (m, 2H), 1.34-1.19 (m, 2H), 1.16 (d, J=6.5 Hz, 3H).

Intermediate 179: N-(4-methoxybenzyl)-1-(tetrahydro-2H-pyran-4-yl)ethanamine

To a stirred solution of 1-(tetrahydro-2H-pyran-4-yl)ethanone (3.2 g, 24.97 mmol) in DCM) (50 mL was added (4-methoxyphenyl)methanamine (6.87 g, 50.1 mmol). The resulting yellow solution was stirred for 4.5 h and sodium triacetoxyborohydride (10 g, 48.6 mmol) added. The white suspension was stirred. The reaction mixture was partitioned between DCM and aq. sat. NaHCO$_3$. The organic layer was removed and the aqueous extracted 3 times with DCM. The combined organic phases were passed through a hydrophobic frit and concentrated in vacuo to give a yellow oil. The oil was dissolved in DCM, purified by silica gel chromatography eluting with EtOAc:EtOH (7.5-25%) and evaporated in vacuo to give the title compound as a yellow oil. The total yield of the reaction was 80%. LCMS (System A): $t_{RET}$=1.27 min, MH$^+$=366.

Intermediate 180: 3-((1,3-dimethoxypropan-2-yl) amino)-4-nitrophenyl)methanol (1,4-dioxan-2-yl)methanamine (3.08 g, 26.3 mmol) was added to a mixture of (3-fluoro-4-nitrophenyl)methanol (4.1 g, 24 mmol), DIPEA (9.18 mL, 52.6 mmol) in THF (30 mL). The resulting mixture was stirred at 80° C. overnight. The reaction mixture was partitioned between DCM (100 mL) and saturated aqueous sodium hydrogen carbonate solution (100 mL) and the layers separated. The aqueous layer was extracted with DCM (3×100 mL) and the combined organic layers were passed through a phase separator and evaporated in vacuo to afford ~10 g of a crude mixture of the title compound. Used at this purity in next step. LCMS (System A): $t_{RET}$=0.88 min, MH$^+$=271.

Intermediate 181: (S)-cyclopentyl 4-methyl-2-((4-((1-methylpiperidin-4-yl)amino)-3-nitrobenzyl) amino)pentanoate To a solution of (S)-cyclopentyl 2-((4-fluoro-3-nitrobenzyl) amino)-4-methylpentanoate (For a preparation see Intermediate 144, 500 mg, 1.419 mmol) in THF (9 mL) was added 1-methylpiperidin-4-amine (486 mg, 4.26 mmol) and DIPEA (0.743 mL, 4.26 mmol), and the reaction mixture heated in a microwave to 120° C. for a total of 90 mins. Further 1-methylpiperidin-4-amine (486 mg, 4.26 mmol) was added and the reaction mixture heated for a further 30 mins at 120° C. The reaction mixture was partitioned between DCM (2×100 mL) and saturated aqueous sodium bicarbonate solution (100 mL). The organic layers were combined, dried using a hydrophobic frit and evaporated under reduced pressure. The sample was loaded in dichloromethane and purified by silica gel column chromatography using a gradient of 0-5% DCM-2M ammonia in methanol over 10 column volumes followed by holding at 5% DCM-2M ammonia in methanol for 5 column volumes. The appropriate fractions were combined and evaporated under reduced pressure to give the title compound (456 mg) as an orange gum. LCMS (System A): $t_{RET}$=0.70 min, MH$^+$=447. The following Intermediates were prepared in a similar manner to Intermediate 181 using the appropriate commercially available amine, and the appropriate fluorophenyl intermediate as shown in the table below:

Intermediate 182: (S)-cyclopentyl 4-methyl-2-((3-nitro-4-((((tetrahydro-2H-pyran-4-yl)methyl)amino) benzyl)amino)pentanoate (Prepared from: Intermediate 144)

System A, 0.98 min, MH$^+$=448; Yield: 603 mg, 85%

Intermediate 183: (2S)-cyclopentyl 4-methyl-2-((4-(((4-methylmorpholin-2-yl)methyl)amino)-3-nitrobenzyl)amino)pentanoate (Prepared from: Intermediate 144)

System B, 1.37 min, MH$^+$=463; Yield: 1.250 g, 98%

Intermediate 184: (S)-cyclopentyl 2-((4-((2-methoxyethyl)amino)-3-nitrobenzyl)amino)-4-methylpentanoate (Prepared from: Intermediate 144)

System A, 0.94 min, MH$^+$=408; Yield: 353 mg, 61%

Intermediate 185: (S)-cyclopentyl 2-((4-((2-(dimethylamino)ethyl)amino)-3-nitrobenzyl)amino)-4-methylpentanoate (Prepared from: Intermediate 144)

System A, 0.69 min, MH$^+$=421 Yield: 543 mg, 91%

Intermediate 186: (S)-cyclopentyl 2-((4-((3-hydroxypropyl)amino)-3-nitrobenzyl)amino)-4-methylpentanoate (Prepared from: Intermediate 144)

System A, 0.85 min, MH$^+$=408; Yield: 445 mg, 77%

Intermediate 187: (S)-cyclopentyl 4-methyl-2-((4-(methylamino)-3-nitrobenzyl)amino)pentanoate (Prepared from: Intermediate 144)

System A, 0.89 min, MH$^+$=354; Yield: 171 mg, 40%

Intermediate 188: (S)-Tert-butyl 2-((4-fluoro-3-nitrobenzyl)amino)-4-methylpentanoate To a solution of 4-fluoro-3-nitrobenzaldehyde (1 g, 5.91 mmol) and (S)-tert-butyl 2-amino-4-methylpentanoate hydrochloride (1.46 g, 6.50 mmol) in DCM (25 mL) was added acetic acid (1.016 mL, 17.74 mmol) and the reaction mixture stirred under nitrogen for 1 hour. Sodium triacetoxyborohydride (2.507 g, 11.83 mmol) was added portionwise, and the reaction mixture stirred at room temperature overnight. Saturated aqueous sodium bicarbonate solution (50 mL) was added slowly, and stirring continued until fizzing had stopped. The resulting suspension was extracted with DCM (3×50 mL). The organic layers were combined, dried using a hydrophobic frit and evaporated under reduced pressure. The sample was loaded in DCM and purified by SPE (silica, 100 g) using a gradient of 0-50% EtOAc in cyclohexane. The appropriate fractions were combined and evaporated under reduced pressure to give the title compound (1.66 g, 4.88 mmol) as a yellow gum. LCMS (System A): $t_{RET}$=0.95 min, MH$^+$=341.

Intermediate 189: (S)-tert-Butyl 4-methyl-2-((4-((1-methylpiperidin-4-yl)amino)-3-nitrobenzyl)amino) pentanoate To a solution of (S)-tert-butyl 2-((4-fluoro-3-nitrobenzyl)amino)-4-methylpentanoate (For an example preparation see Intermediate 188, 250 mg, 0.734 mmol) in THF (3.5 mL) was added 1-methylpiperidin-4-amine (252 mg, 2.203 mmol) and DIPEA (0.385 mL, 2.203 mmol), and the reaction mixture heated under microwave conditions to 120° C. for 30 min. The reaction mixture was partitioned between DCM (2×20 mL) and saturated aqueous sodium bicarbonate solution (20 mL). The organic layers were combined, dried using a hydrophobic frit and blown down under a stream of nitrogen. The sample was loaded in DCM and purified by SPE (silica, 25 g) using a gradient of 0-10% (2 M ammonia in MeOH) in DCM. The appropriate fractions were combined and evaporated under reduced pressure to give the title compound (127 mg, 0.292 mmol). LCMS (System B): $t_{RET}$=1.09 min, MH$^+$=435.

Intermediate 190: (S)-Cyclopentyl 4-methyl-2-((4-nitro-3-(((tetrahydro-2H-pyran-4-yl)methyl)amino) benzyl)amino)pentanoate A solution of 3-fluoro-4-nitrobenzaldehyde (500 mg, 2.96 mmol) and (S)-cyclopentyl 2-amino-4-methylpentanoate 4-methylbenzenesulfonate (For an example preparation see Intermediate 3, 1208 mg, 3.25 mmol) in DCM (20 mL) was stirred under nitrogen for 1.5 hours. Sodium triacetoxyborohydride (1253 mg, 5.91 mmol) was added portionwise, and the reaction mixture stirred at room temperature overnight. Saturated aqueous sodium bicarbonate solution (50 mL) was added slowly, and the reaction stirring continued until fizzing had stopped. The resulting suspension was extracted with DCM (3×50 mL). The organic layers were combined, dried using a hydrophobic frit and evaporated under reduced pressure. The sample was loaded in dichloromethane and purified by SPE (silica, 50 g) using a gradient of 0-50% EtOAc in cyclohexane. The appropriate fractions were combined and blown down under a stream of nitrogen to give a yellow gum. To this material in THF (4 mL) was added (tetrahydro-2H-pyran-4-yl)methanamine (260 mg, 2.257 mmol) and DIPEA (0.395 mL, 2.259 mmol), and the reaction mixture heated under microwave conditions at 120° C. for 30 min. The reaction mixture was partitioned between dichloromethane (3×50 mL) and saturated aqueous sodium bicarbonate solution (50 mL). The organic layers were combined, dried using a hydrophobic frit and blown down under a stream of nitrogen. The sample was loaded in dichloromethane and purified by SPE (silica, 50 g) using a gradient of 0-5% (2 M ammonia in MeOH) in DCM. The appropriate fractions were combined and blown down under a stream of nitrogen to give the crude product. The crude product was again partitioned between dichloromethane (3×50 mL) and saturated aqueous sodium bicarbonate solution (50 mL). The organic layers were combined, dried using a hydrophobic frit and blown down under a stream of nitrogen to give the title compound (522 mg, 1.166 mmol). LCMS (System B): $t_{RET}$=1.49 min, MH$^+$=448

Intermediate 191: (S)-Neopentyl 2-(((benzyloxy) carbonyl)amino)-3-hydroxypropanoate To a solution of (S)-2-(((benzyloxy)carbonyl)amino)-3-hydroxypropanoic acid (2.27 g, 9.49 mmol), EDC (2.18 g, 11.39 mmol) and HOBT (1.74 g, 11.39 mmol) in DMF (20 mL) was added DIPEA (3.31 mL, 18.98 mmol) and 2,2-dimethylpropan-1-ol (8.36 g, 95 mmol), and the reaction mixture stirred under nitrogen at room temperature overnight. The reaction mixture was partitioned between ethyl acetate (50 mL) and saturated aqueous sodium bicarbonate solution (50 mL). The organic layer was then washed with 1 M aqueous hydrochloric acid (50 mL), water (50 mL) and brine (50 mL). The organic layer was then dried using a hydrophobic frit and blown down under a stream of nitrogen. The sample was loaded in dichloromethane and purified by SPE (silica, 100 g) using a gradient of 0-50% EtOAc in cyclohexane. The appropriate fractions were combined and evaporated under reduced pressure to give the title compound (951 mg, 3.07 mmol) as a white solid. LCMS (System B): $t_{RET}$=1.06 min, MH$^+$=310.

Intermediate 192: (S)-Neopentyl 2-amino-3-methoxypropanoate

To a mixture of (S)-neopentyl 2-(((benzyloxy)carbonyl) amino)-3-hydroxypropanoate (For an example preparation see Intermediate 191, 947 mg, 3.06 mmol) and silver oxide (1064 mg, 4.59 mmol) in dry acetonitrile (20 mL) was added methyl iodide (1.914 mL, 30.6 mmol), and the reaction mixture heated at 90° C. under nitrogen for two nights. The reaction mixture was allowed to cool to room temperature, and the solid removed by filtration. The resulting solution was evaporated under reduced pressure. The sample was loaded in dichloromethane and purified by SPE (silica, 50 g) using a gradient of 0-25% EtOAc in cyclohexane. The appropriate fractions were combined and evaporated under reduced pressure. A solution of this material (347 mg) in ethanol (10 mL) was hydrogenated using an H-cube (settings: 20° C., 1 bar, 1 mL/min flow rate) and 10% Pd/C CatCart 30 as the catalyst. The reaction mixture was blown down under a stream of nitrogen and dried in a vacuum oven to give the title compound (199 mg, 1.052 mmol). LCMS (System B): $t_{RET}$=0.81 min, MH$^+$=190 no UV chromophore.

Intermediate 193: (3-Nitro-4-((oxetan-3-ylmethyl) amino)phenyl)methanol

A round bottom flask was charged with (4-fluoro-3-nitrophenyl)methanol (770 mg, 4.50 mmol), oxetan-3-ylmethanamine hydrochloride (753 mg, 6.09 mmol), THF (10 mL) and DIPEA (2.3 mL, 13.17 mmol). An air condensor was fitted and the slurry warmed to 62° C. overnight. The mixture was cooled to room temperature before DMF (2 mL) was added. The mixture was warmed to 70° C. for 4 days. The mixture was cooled to room temperature, diluted with EtOAc and the organics washed with water followed by brine before being passed through a hydrophobic frit. The filtrate was concentrated in vacuo to give an orange oil. The sample was loaded in dichloromethane and purified by SPE (silica, 25 g) using a gradient of 0-100% EtOAc in cyclohexane. The appropriate fractions were combined and evaporated in vacuo to give the title compound (584 mg, 2.451 mmol) as an orange solid. LCMS (System A): $t_{RET}$=0.61 min, MH$^+$=239.

Intermediate 194: 5-(5-(Hydroxymethyl)-1-(oxetan-3-ylmethyl)-1H-benzo[d]imidazol-2-yl)-3-methylpyridin-2(1H)-one A microwave vial was charged with 5-methyl-6-oxo-1,6-dihydropyridine-3-carbaldehyde (For an example preparation see Intermediate 1, 504 mg, 3.68 mmol), sodium hydrosulfite (1.5 g, 8.62 mmol), water (5.00 mL), and a solution of (3-nitro-4-((oxetan-3-ylmethyl)amino)phenyl) methanol (For an example preparation see Intermediate 193, 584 mg, 2.451 mmol) in ethanol (10 mL). The vial was capped and the slurry irradiated at 100° C. for 5 hours. The mixture was diluted with water and chloroform/IPA (3:1), the layers mixed and separated before the organic layer was passed through a hydrophobic frit and concentrated in vacuo to give a yellow oil. The sample was loaded in dichloromethane and purified by SPE (silica, 25 g) using a gradient of 0-100% EtOAc in cyclohexane. The appropriate fractions were combined and evaporated in vacuo to give the title compound (178 mg, 0.547 mmol) as a colourless oil which solidified. LCMS (System A): $t_{RET}$=0.40 min, MH$^+$=326.

Intermediate 195: 2-(5-Methyl-6-oxo-1,6-dihydropyridin-3-yl)-1-(oxetan-3-ylmethyl)-1H-benzo[d] imidazole-5-carbaldehyde To a solution of 5-(5-(hydroxymethyl)-1-(oxetan-3-ylmethyl)-1H-benzo[d]imidazol-2-yl)-3-methylpyridin-2(1H)-one (For an example preparation see Intermediate 194, 180 mg, 0.553 mmol) in DCM (15 mL) was added 45% iodoxybenzoic acid (stabilised by benzoic acid and isophthalic acid) (379 mg, 0.609 mmol), portionwise. The reaction mixture was stirred at room temperature for 4 nights. The reaction mixture was partitioned between 10% isopropanol in dichloromethane (100 mL) and saturated aqueous sodium bicarbonate solution (3×100 mL). The organic layer was passed through a hydrophobic frit and blown down under a stream of nitrogen to give the title compound (152 mg, 0.470 mmol) as a pale yellow gum. LCMS (System B): $t_{RET}$=0.60 min, MH$^+$=324.

Intermediate 196: (S)-Cyclopentyl 2-amino-3-methoxypropanoate (S)-2-amino-3-methoxypropanoic acid hydrochloride (3.3131 g, 21.30 mmol) was added to cyclopentanol (30 mL) and the suspension was brought to −5° C. using a dry ice/acetone bath. After stirring at this temperature for ten minutes, thionyl chloride (3.57 mL, 49.0 mmol) was added dropwise. The suspension was left stirring and allowed to warm up to room temperature. The reaction mixture was warmed to 60° C. and stirred at this temperature for 24 hours. Volatiles were removed from the reaction mixture under reduced pressure. Hot EtOAc was added with the intention of performing a recrystallisation. The material did not dissolve so the suspension was filtered off, washed on the filter, and dried in a vacuum oven to give the title compound (4.49 g, 0.24 mmol) as a white solid. $^1$H NMR (d$_6$-DMSO, 293 K): δ 1.51-1.76 (m, 6H) 1.76-1.92 (m, 2H) 3.29 (s, 3H) 3.75 (d, J=3.4 Hz, 2H) 4.21 (t, J=3.4 Hz, 1H) 5.17-5.21 (m, 1H) 8.64 (br.s., 3H).

Intermediate 197: 5-(1-Ethyl-5-(hydroxymethyl)-1H-benzo[d]imidazol-2-yl)-1,3-dimethylpyridin-2 (1H)-one To a mixture of 1,5-dimethyl-6-oxo-1,6-dihydropyridine-3-carbaldehyde (For an example preparation see Intermediate 2, 1 g, 6.62 mmol) and sodium hydrosulfite (3.46 g, 19.85 mmol) was added a solution of (4-(ethylamino)-3-nitrophenyl)methanol (For an example preparation see Intermediate 70, 1.298 g, 6.62 mmol) in ethanol (30 mL), followed by water (15 mL). The reaction mixture was heated at 80° C. overnight. The reaction mixture was partitioned between saturated aqueous sodium hydrogen carbonate solution (150 mL) and 3:1 chloroform:isopropanol (3×150 mL). The organic layers were combined, dried using a hydrophobic frit and evaporated under reduced pressure. The sample was loaded in dichloromethane and purified by SPE (silica, 100 g) silica using a gradient of 0-12% (2 M ammonia in methanol) in DCM. The appropriate fractions were combined and evaporated under reduced pressure to give the title compound (1.05 g, 3.53 mmol) as an off-white foam. LCMS (System B): $t_{RET}$=0.64 min, MH$^+$=298

Intermediate 198: 2-(1,5-Dimethyl-6-oxo-1,6-dihydropyridin-3-yl)-1-ethyl-1H benzo[d]imidazole-5-carbaldehyde To a solution of 5-(1-ethyl-5-(hydroxymethyl)-1H-benzo[d] imidazol-2-yl)-1,3-dimethylpyridin-2(1H)-one (For an example preparation see Intermediate 197, 1.05 g, 3.53 mmol) in DCM (50 mL) was added 45% iodoxybenzoic acid (stabilised by benzoic acid and isophthalic acid) (2.417 g, 3.88 mmol), portionwise. The reaction mixture was stirred at room temperature for 4 nights. The reaction mixture was partitioned between 10% isopropanol in dichloromethane (250 mL) and saturated aqueous sodium bicarbonate solution (3×200 mL). The organic layer was dried using a hydrophobic frit and blown down under a stream of nitrogen to give the title compound (856 mg, 2.90 mmol) as a pale yellow solid. LCMS (System B): $t_{RET}$=0.72 min, MH$^+$=296.

Intermediate 199: (4-((2-Methoxyethyl)amino)-3-nitrophenyl)methanol

A round bottom flask was charged with (4-fluoro-3-nitrophenyl)methanol (3.2 g, 18.70 mmol), 2-methoxyethanamine (2.107 g, 28.0 mmol), THF (30 mL) and DIPEA (9.80 mL, 56.1 mmol). An air condensor was fitted and the slurry warmed to 62° C. overnight. The mixture was cooled to room temperature and diluted with EtOAc. The organics were washed with water before being passed through a hydrophobic frit and concentrated in vacuo to give an orange oil. The sample was loaded in dichloromethane and purified by SPE (silica, 100 g) using a gradient of 0-80% EtOAc in cyclohexane. The appropriate fractions were combined and evaporated in vacuo to give the title compound (3.48 g, 15.38 mmol) as a orange oil which solidified. LCMS (System A): $t_{RET}$=0.70 min, MH$^+$=227.

Intermediate 200: 5-(5-(Hydroxymethyl)-1-(2-methoxyethyl)-1H-benzo[d]imidazol-2-yl)-3-methylpyridin-2(1H-one A round bottom flask was charged with 5-methyl-6-oxo-1,6-dihydropyridine-3-carbaldehyde (For an example preparation see Intermediate 1, 2.53 g, 18.46 mmol), sodium hydrosulfite (9.37 g, 53.8 mmol), water (25.00 mL), and a solution of (4-((2-methoxyethyl)amino)-3-nitrophenyl)methanol (For an example preparation see Intermediate 199, 3.48 g, 15.38 mmol) in ethanol (50 mL). The vessel was fitted with an air condensor and warmed to 100° C. overnight. The mixture was diluted with water and chloroform/IPA (3:1), the layers mixed and separated before the organic layer was passed through a hydrophobic frit and concentrated in vacuo to give a white solid. The sample was loaded in dichloromethane and purified by SPE (silica, 25 g) using a gradient of 0-100% EtOAc in cyclohexane. The appropriate fractions were combined and evaporated in vacuo to give the title compound (3.58 g, 11.42 mmol) as a colourless oil which solidified. LCMS (System A): $t_{RET}$=0.44 min, MH$^+$=314.

Intermediate 201: 1-(2-Methoxyethyl)-2-(5-methyl-6-oxo-1,6-dihydropyridin-3-yl)-1H benzo[d]imidazole-5-carbaldehyde To a solution of 5-(5-(hydroxymethyl)-1-(2-methoxyethyl)-1H-benzo[d]imidazol-2-yl)-3-methylpyridin-2(1H)-one (For and example preparation see Intermediate 200, 3.38 g, 10.79 mmol) in DCM (150 mL) was added 45% iodoxybenzoic acid (stabilised by benzoic acid and isophthalic acid) (7.38 g, 11.87 mmol), portionwise. The reaction mixture was stirred at room temperature for 4 nights. The reaction mixture was partitioned between DCM (200 mL) and saturated aqueous sodium bicarbonate solution (200 mL). The aqueous layer contained a large amount of solid, so was further extracted with 10% isopropanol in dichloromethane (2×200 mL). The organic layers were combined, washed with aqueous sodium bicarbonate solution (2×200 mL), dried using a hydrophobic frit and evaporated under reduced pressure to give the title compound (2.7 g, 8.67 mmol) as a pale brown solid. LCMS (System B): $t_{RET}$=0.66 min, MH$^+$=312.

Intermediate 202: 5-(5-(Hydroxymethyl)-1-(2-methoxyethyl)-1H-benzo[d]imidazol-2-yl)-1,3-dimethylpyridin-2(1H)-one To a mixture of 1,5-dimethyl-6-oxo-1,6-dihydropyridine-3-carbaldehyde (For an example preparation see Intermediate 2, 1 g, 6.62 mmol) and sodium hydrosulfite (3.46 g, 19.85 mmol) was added a solution of (4-((2-methoxyethyl)amino)-3-nitrophenyl)methanol (For an example preparation see Intermediate 199, 1.497 g, 6.62 mmol) in ethanol (30 mL), followed by water (15 mL). The reaction mixture was heated at 80° C. overnight. The reaction mixture was partitioned between saturated aqueous sodium hydrogen carbonate solution (150 mL) and 3:1 chloroform:isopropanol (3×150 mL). The organic layers were combined, dried using a hydrophobic frit and evaporated under reduced pressure. The sample was loaded in dichloromethane and purified by SPE (silica, 100 g) using a gradient of 0-12% (2 M ammonia in methanol) in DCM. The appropriate fractions were combined and evaporated under reduced pressure to give the title compound (2.0 g, 6.11 mmol) as an off-white foam. LCMS (System B): $t_{RET}$=0.62 min, MH$^+$=328.

Intermediate 203: 2-(1,5-Dimethyl-6-oxo-1,6-dihydropyridin-3-yl)-1-(2-methoxyethyl)-1H-benzo[d]imidazole-5-carbaldehyde To a solution of 5-(5-(hydroxymethyl)-1-(2-methoxyethyl)-1H-benzo[d]imidazol-2-yl)-1,3-dimethylpyridin-2(1H)-one (For an example preparation see Intermediate 202, 2.0 g, 6.11 mmol) in DCM (50 mL) was added 45% iodoxybenzoic acid (stabilised by benzoic acid and isophthalic acid) (4.18 g, 6.72 mmol), portionwise. The reaction mixture was stirred at room temperature for 2 nights. The reaction mixture was partitioned between 10% isopropanol in dichloromethane (200 mL) and saturated aqueous sodium bicarbonate solution (3×200 mL). The organic layer was dried using a hydrophobic frit and evaporated under reduced pressure to give the title compound (975 mg, 3.00 mmol) as a pale yellow solid. LCMS (System B): $t_{RET}$=0.71 min, MH$^+$=326.

Intermediate 204: (4-((2-(Dimethylamino)ethyl)amino)-3-nitrophenyl)methanol

A mixture of (4-fluoro-3-nitrophenyl)methanol (2.5 g, 14.61 mmol), N1,N1-dimethylethane-1,2-diamine (3.19 mL, 29.2 mmol) and DIPEA (7.65 mL, 43.8 mmol) in THF (20 mL) in two equal portions was under microwave conditions (initial high absorption setting) at 120° C. for 30 min. The reaction mixture was partitioned between dichloromethane (3×150 mL) and saturated aqueous sodium bicarbonate solution (150 mL). The organic layers were combined, dried using a hydrophobic frit and evaporated under reduced pressure. The sample was loaded in dichloromethane and purified by SPE (silica, 100 g). The appropriate fractions were combined and evaporated under reduced pressure to give the title compound (3.32 g, 13.88 mmol) as a dark orange gum. LCMS (System B): $t_{RET}$=0.73 min, MH$^+$=240.

Intermediate 205: 5-(1-(2-(Dimethylamino)ethyl)-5-(hydroxymethyl)-1H-benzo[d]imidazol-2-yl)-3-methylpyridin-2(1H-one To a mixture of 5-methyl-6-oxo-1,6-dihydropyridine-3-carbaldehyde (For an example preparation see Intermediate 1, 3.3 g, 24.06 mmol) and sodium hydrosulfite (7.20 g, 41.4 mmol) was added a solution of (4-((2-(dimethylamino)ethyl)amino)-3-nitrophenyl)methanol (For an example preparation see Intermediate 204, 3.3 g, 13.79 mmol) in ethanol (26 mL), followed by water (13 mL). The reaction mixture was heated, in two equal portions, under microwave conditions (initial high absorption setting) at 100° C. for 5 hours. The reaction mixture was partitioned between saturated aqueous sodium hydrogen carbonate solution (100 mL) and dichloromethane (2×100 mL), followed by further extraction of the aqueous layer with 3:1 chloroform:isopropanol (3×100 mL). The organic layers were combined and evaporated under reduced pressure. The sample was loaded in methanol/dichloromethane (and the column dried in a vacuum oven) and purified by SPE (silica, 100 g) using a gradient of 0-50% (2 M ammonia in methanol) in DCM. The appropriate fractions were combined and evaporated under reduced pressure. The sample was dried in a vacuum oven to give the title compound (1.75 g, 5.36 mmol). LCMS (System B): $t_{RET}$=0.58 min, MH$^+$=327.

Intermediate 206: 1-(2-(Dimethylamino)ethyl)-2-(5-methyl-6-oxo-1,6-dihydropyridin-3-yl)-1H-benzo[d]imidazole-5-carbaldehyde To a solution of 5-(1-(2-(dimethylamino)ethyl)-5-(hydroxymethyl)-1H-benzo[d]imidazol-2-yl)-3-methylpyridin-2(1H)-one (For an example preparation see Intermediate 205, 1.31 g, 4.01 mmol) in DCM (50 mL) was added 45% iodoxybenzoic acid (stabilised by benzoic acid and isophthalic acid) (2.75 g, 4.41 mmol), portionwise. The reaction mixture was stirred at room temperature for 5 nights. Further 45% iodoxybenzoic acid (stabilised by benzoic acid and isophthalic acid) (1.38 g, 2.21 mmol) was added, followed by DMSO (10 mL). The reaction mixture was stirred at room temperature for a further 7 nights. The reaction mixture was partitioned between 10% isopropanol in dichloromethane (150 mL) and saturated aqueous sodium bicarbonate solution (3×150 mL). The organic layers were combined, dried using a hydrophobic frit and blown down under a stream of nitrogen to give the title compound (758 mg, 2.337 mmol) as an off-white solid. LCMS (System B): $t_{RET}$=0.66 min, MH$^+$=325.

Intermediate 207: 5-(5-(Hydroxymethyl)-1-methyl-1H-benzo[d]imidazol-2-yl)-3-methylpyridin-2(1H)-one (4-(Methylamino)-3-nitrophenyl)methanol (For an example preparation see Intermediate 1, 5.32 g, 29.2 mmol), 5-methyl-6-oxo-1,6-dihydropyridine-3-carbaldehyde (For an example preparation see Intermediate 71, 4.00 g, 29.2 mmol) and sodium dithionite (15.25 g, 88 mmol) were dissolved in ethanol (75 mL), water (37.5 mL) and refluxed over 14 h. Thereby, the mixture was partitioned through the addition of 200 mL of saturated sodium bicarbonate and 200 mL of ethyl acetate. The organic phase was isolated and the aqueous extracted twice with 200 mL of ethyl acetate. The organics were combined, dried over magnesium sulfate, solvent removed. The residue was triturated with diethyl ether and filtered to give the title compound (1.519 g, 5.64 mmol) as a pale yellow solid. LCMS (System A): $t_{RET}$=0.39 min, MH$^+$=270.

Intermediate 208: 1-Methyl-2-(5-methyl-6-oxo-1,6-dihydropyridin-3-yl)-1H benzo[d]imidazole-5-carbaldehyde To a solution of 5-(5-(hydroxymethyl)-1-methyl-1H-benzo[d]imidazol-2-yl)-3-methylpyridin-2(1H)-one (For an example preparation see Intermediate 207, 1.88 g, 6.98 mmol) in DCM (50 mL) was added 45% iodoxybenzoic acid (stabilised by benzoic acid and isophthalic acid) (4.78 g, 7.68 mmol), portionwise. The reaction mixture was stirred at room temperature for 4 nights. DMSO (10 mL) was added and the reaction mixture stirred at room temperature for a further 1 night. The reaction mixture was partitioned between dichloromethane (100 mL) and saturated aqueous sodium bicarbonate solution (3×100 mL). The organic layer was dried using a hydrophobic frit and evaporated under reduced pressure to give the title compound (655 mg, 2.451 mmol) as a dark brown solid. LCMS (System B): $t_{RET}$=0.61 min, MH$^+$=268.

Intermediate 209: (3-Nitro-4-(((tetrahydro-2H-pyran-3-yl)methyl)amino)phenyl)methanol A solution of (tetrahydro-2H-pyran-3-yl)methanamine (4.11 mL, 32.1 mmol), (4-fluoro-3-nitrophenyl)methanol (2200 mg, 12.86 mmol) and N-ethyl-N-isopropylpropan-2-amine (11.23 mL, 64.3 mmol) in THF (30 mL) was degassed and heated under nitrogen at 60° C. overnight. The solvent was removed under reduced pressure and the residue was partitioned between ethyl acetate (150 mL) and a saturated solution of sodium bicarbonate (150 mL). The organic fraction was isolated and the aqueous layer was re-extracted twice with ethyl acetate (2×150 mL). The organic fractions were combined, passed through a hydrophobic frit and concentrated under reduced pressure. The residue was dissolved in a minimum amount of dichloromethane purified by SPE (silice, 2×100 g), eluted with a gradient of 0-70% EtOAc in cyclohexane. The product containing fractions were combined and concentrated under reduced pressure to yield the title compound (2731 mg) as an orange solid. LCMS (System B): $t_{RET}$=0.82 min, MH$^+$=267.

Intermediate 210: 5-(5-(Hydroxymethyl)-1-((tetrahydro-2H-pyran-3-yl)methyl)-1H benzo[d]imidazol-2-yl)-3-methylpyridin-2(1H)-one A solution of (3-nitro-4-(((tetrahydro-2H-pyran-3-yl)methyl)amino)phenyl)methanol (For an example preparation see Intermediate 1, 2600 mg, 9.76 mmol), 5-methyl-6-oxo-1,6-dihydropyridine-3-carbaldehyde (For an example preparation see Intermediate 209, 1339 mg, 9.76 mmol) and sodium dithionite (5100 mg, 29.3 mmol) in ethanol (30 mL) and water (15 mL) was degassed. The reaction mixture was heated under nitrogen at 800° C. overnight. The reaction mixture was allowed to cool down to room temperature and then partitioned between 3:1 chloroform:isopropanol (150 mL) and a saturated solution of sodium bicarbonate (150 mL). The organic fraction was isolated and the aqueous layer was re-extracted twice with 3:1 chloroform:isopropanol (2×150 mL). The organic fractions were combined, passed through a hydrophobic frit and concentrated under reduced pressure. The residue was dissolved in a minimum amount of 10% methanol in ethyl acetate. The solution was loaded onto two SPE columns (100 g, silica) and the solvents in which the product was loaded onto the columns allowed to evaporate. The product was then eluted with a gradient of 0-30% EtOH in EtOAc. The product containing fractions were combined and concentrated under reduced pressure to yield the title compound (1500 mg) as a white solid. LCMS (System B): $t_{RET}$=0.63 min, MH$^+$=354.

Intermediate 211: 2-(5-Methyl-6-oxo-1,6-dihydropyridin-3-yl)-1-((tetrahydro-2H-pyran-3-yl)methyl)-1H-benzo[d]imidazole-5-carbaldehyde A suspension of 45% 2-iodoxybenzoic acid (stabilised by benzoic and isonapthalic acids) (6603 mg, 10.61 mmol) and 5-(5-(hydroxymethyl)-1-((tetrahydro-2H-pyran-3-yl)methyl)-1H-benzo[d]imidazol-2-yl)-3-methylpyridin-2(1H)-one (For an example preparation see Intermediate 210, 1500 mg, 4.24 mmol) was stirred at room temperature for 3 days under nitrogen. The reaction mixture was partitioned between 3:1 chloroform:isopropanol (75 mL) and a saturated solution of sodium bicarbonate (75 mL). The organic layer was isolated and the aqueous fraction was re-extracted twice with 3:1 chloroform:isopropanol (2×75 mL). The organic fractions were combined, passed through a hydrophobic frit and concentrated under reduced pressure. The material was partitioned between 3:1 chloroform:isopropanol (75 mL) and saturated solution of sodium bicarbonate (75 mL). The organic layer was isolated and the aqueous fraction was re-extracted twice with 3:1 chloroform:isopropanol (2×75 mL). The organic fractions were combined, passed through a hydrophobic frit, concentrated under reduced pressure, and dried under vacuum for 7 days to yield the title compound (1487 mg) as a light pink solid. LCMS (System B): $t_{RET}$=0.70 min, MH$^+$=352.

Intermediate 212: 2-(1,5-Dimethyl-6-oxo-1,6-dihydropyridin-3-yl)-1-((tetrahydro-2H-pyran-3-yl)methyl)-1H-benzo[d]imidazole-5-carbaldehyde A solution of 2-(5-methyl-6-oxo-1,6-dihydropyridin-3-yl)-1-((tetrahydro-2H-pyran-3-yl)methyl)-1H-benzo[d]imidazole-5-carbaldehyde (For an example preparation see Intermediate 211, 700 mg, 1.992 mmol) in DMF (10 mL) was treated with potassium carbonate (551 mg, 3.98 mmol) and the reaction mixture was stirred for 2 hours. Iodomethane (0.149 mL, 2.390 mmol) was added and the mixture was stirred overnight. The solvent was removed under reduced pressure and the residue was partitioned between 3:1 chloroform:isopropanol (75 mL) and a saturated solution of sodium bicarbonate (75 mL). The organic layer was isolated and the aqueous fraction was re-extracted twice with 3:1 chloroform:isopropanol (2×75 mL). The organic fractions were combined, passed through a hydrophobic frit and concentrated under reduced pressure. The resulting gum was dissolved in a minimum amount of 10% methanol in EtOAc and loaded onto an SPE column (50 g, silica). The product was eluted with a gradient of 0-30% EtOH in EtOAc. Product containing fractions were combined and concentrated under reduced pressure to yield the title compound (451 mg) as a brown solid. LCMS (System A): $t_{RET}$=0.73 min, MH$^+$=366.

Intermediate 213: (S)-(4-((1-Methoxypropan-2-yl)amino)-3-nitrophenyl)methanol

To a solution of (4-fluoro-3-nitrophenyl)methanol (2 g, 11.69 mmol) in THF (10 mL) was added (S)-1-methoxypropan-2-amine (1.851 mL, 17.53 mmol) and DIPEA (6.12 mL, 35.1 mmol) and the reaction mixture was heated under microwave conditions (initial high absorption setting) at 120° C. for 30 min. The reaction mixture was partitioned between dichloromethane (3×150 mL) and saturated aqueous sodium bicarbonate solution (150 mL). The organic layers were combined, dried using a hydrophobic frit and evaporated under reduced pressure. The sample was loaded in dichloromethane and purified by SPE (silica, 100 g) using a gradient of 0-25% EtOAc in cyclohexane. The appropriate fractions were combined and evaporated under reduced pressure to give the title compound (1.4 g, 5.83 mmol) as a orange gum. LCMS (System B): $t_{RET}$=0.82 min, MH$^+$=241.

Intermediate 214: (S)-5-(5-(Hydroxymethyl)-1-(1-methoxypropan-2-yl)-1H-benzo[d]imidazol-2-yl)-1,3-dimethylpyridin-2(1H)-one To a mixture of 1,5-dimethyl-6-oxo-1,6-dihydropyridine-3-carbaldehyde (For an example preparation see Intermediate 2, 0.881 g, 5.83 mmol) and sodium hydrosulfite (3.04 g, 17.48 mmol) was added a solution of (S)-(4-((1-methoxypropan-2-yl)amino)-3-nitrophenyl)methanol (For an example preparation see Intermediate 213, 1.4 g, 5.83 mmol) in ethanol (30 mL), followed by Water (15 mL). The reaction mixture was heated at 800° C. overnight. The reaction mixture was partitioned between saturated aqueous sodium hydrogen carbonate solution (150 mL) and ethyl acetate (3×150 mL), followed by 3:1 chloroform:isopropanol (3×150 mL). The organic layers were combined, dried using a hydrophobic frit and evaporated under reduced pressure. The sample was loaded in dichloromethane and purified by SPE (silica, 100 g) using a gradient of 0-25% EtOAc in cyclohexane. The appropriate fractions were combined and evaporated under reduced pressure to give the title compound (580 mg, 1.699 mmol) as a off-white foam. LCMS (System B): $t_{RET}$=0.67 min, MH$^+$=342

Intermediate 215: (S)-2-(1,5-Dimethyl-6-oxo-1,6-dihydropyridin-3-yl)-1-(1-methoxypropan-2-yl)-1H-benzo[d]imidazole-5-carbaldehyde To a solution of (S)-5-(5-(hydroxymethyl)-1-(1-methoxypropan-2-yl)-1H-benzo[d]imidazol-2-yl)-1,3-dimethylpyridin-2(1H)-one (For an example preparation see Intermediate 214, 577 mg, 1.690 mmol) in DCM (25 mL) was added 45% iodoxybenzoic acid (stabilised by benzoic acid and isophthalic acid) (1157 mg, 1.859 mmol), portionwise. The reaction mixture was stirred at room temperature for 3 nights. The reaction mixture was partitioned between 10% isopropanol in dichloromethane (200 mL) and saturated aqueous sodium bicarbonate solution (3×200 mL). The organic layer was dried using a hydrophobic frit and evaporated under reduced pressure to give the title compound (630 mg, 1.856 mmol) as an off-white foam. LCMS (System B): $t_{RET}$=0.76 min, MH$^+$=340.

Intermediate 216: (R)-(4-((1-Methoxypropan-2-yl)amino)-3-nitrophenyl)methanol

To a solution of (4-fluoro-3-nitrophenyl)methanol (5 g, 29.2 mmol) in THF (40 mL) was added (R)-1-methoxypropan-2-amine hydrochloride (5.50 g, 43.8 mmol) and DIPEA (22.96 mL, 131 mmol) and the reaction mixture was heated at 60° C. overnight. The reaction mixture was partitioned between dichloromethane (3×250 mL) and saturated aqueous sodium bicarbonate solution (150 mL). The organic layers were combined, dried using a hydrophobic frit and evaporated under reduced pressure. The sample was loaded in dichloromethane and purified by SPE (silica, 2×100 g), using a gradient of 0-25% EtOAc in cyclohezane. The appropriate fractions were combined and evaporated under reduced pressure to give the title compound (1.7 g, 7.08 mmol) as an orange gum. LCMS (System B): $t_{RET}$=0.81 min, MH$^+$=241.

Intermediate 217: (R)-5-(5-(Hydroxymethyl)-1-(1-methoxypropan-2-yl)-1H-benzo[d]imidazol-2-yl)-1,3-dimethylpyridin-2(1H-one To a mixture of 1,5-dimethyl-6-oxo-1,6-dihydropyridine-3-carbaldehyde (For an example preparation see Intermediate 2, 0.629 g, 4.16 mmol) and sodium hydrosulfite (2.174 g, 12.49 mmol) was added a solution of (R)-(4-((1-methoxypropan-2-yl)amino)-3-nitrophenyl)methanol (For an example preparation see Intermediate 216, 1 g, 4.16 mmol) in ethanol (30 mL), followed by water (15 mL). The reaction mixture was heated at 90° C. for 6 hours. The reaction mixture was partitioned between saturated aqueous sodium hydrogen carbonate solution (150 mL) and ethyl acetate (3×150 mL), followed by 3:1 chloroform:isopropanol (3×150 mL). The organic layers were combined, dried using a hydrophobic frit and evaporated under reduced pressure. The sample was loaded in dichloromethane and purified by SPE (silica, 100 g) using a gradient of 0-100% EtOAc in cyclohexane, followed by a gradient of 0-100% (25% EtOH in EtOAc) in cyclohexane. The appropriate fractions were combined and evaporated under reduced pressure to give the title compound (393 mg, 1.151 mmol) as an off-white foam. LCMS (System B): $t_{RET}$=0.67 min, $MH^+$=342.

Intermediate 218: (R)-2-(1,5-dimethyl-6-oxo-1,6-dihydropyridin-3-yl)-1-(1-methoxypropan-2-yl)-1H-benzo[d]imidazole-5-carbaldehyde To a solution of (R)-5-(5-(hydroxymethyl)-1-(1-methoxypropan-2-yl)-1H-benzo[d]imidazol-2-yl)-1,3-dimethylpyridin-2(1H)-one (For an example preparation see Intermediate 217, 390 mg, 1.142 mmol) in DCM (25 mL) was added 45% iodoxybenzoic acid (stabilised by benzoic acid and isophthalic acid) (782 mg, 1.257 mmol), portionwise. The reaction mixture was stirred at room temperature for 3 nights. The reaction mixture was partitioned between 3:1 chloroform:IPA (200 mL) and saturated aqueous sodium bicarbonate solution (3×200 mL). The organic layer was dried using a hydrophobic frit and evaporated under reduced pressure. The sample was dissolved in 3:1 chloroform:IPA (200 mL) and washed with saturated aqueous sodium bicarbonate solution (3×200 mL). The organic layer was dried using a hydrophobic frit and evaporated under reduced pressure to give the title compound (554 mg, 1.632 mmol, 143% yield), in approximately 70% purity. LCMS (System B): $t_{RE}T$=0.76 min, $MH^+$=340.

Intermediate 219: (3-Nitro-4-(((tetrahydrofuran-3-yl)methyl)amino)phenyl)methanol (Tetrahydrofuran-3-yl)methanamine (1.711 mL, 16.36 mmol) was dissolved in THF (5 mL), and DIPEA (5.00 mL, 28.6 mmol) and (4-fluoro-3-nitrophenyl)methanol (1400 mg, 8.18 mmol) were added. The reaction mixture was heated for 2.5 h under microwave conditions at 125° C. The reaction mixture was partitioned between a saturated solution of sodium bicarbonate (100 mL) and ethyl acetate (100 mL). The organic layer was isolated and the aqueous fraction was extracted twice with ethyl acetate (2×100 mL). The organic fractions were combined, passed through a hydrophobic frit and concentrated under reduced pressure. The residue was dissolved in a minimum amount of DCM and purified by SPE (silica, 100 g), eluted with a gradient of 0-65% EtOAc in cyclohexane. The purest fractions were combined and concentrated under reduced pressure to give the title compound (1719 mg) as an orange gum. LCMS (System B): $t_{RET}$=0.78 min, $MH^+$=253.

Intermediate 220: 5-(5-(Hydroxymethyl)-1-((tetrahydrofuran-3-yl)methyl)-1H-benzo[d]imidazol-2-yl)-1,3-dimethylpyridin-2(1H)-one (3-Nitro-4-((((tetrahydrofuran-3-yl)methyl)amino)phenyl)methanol (For an example preparation see Intermediate 219, 1719 mg, 6.81 mmol) was dissolved in ethanol (16.00 mL) and water (8 mL) and 1,5-dimethyl-6-oxo-1,6-dihydropyridine-3-carbaldehyde (For an example preparation see Intermediate 2, 1145 mg, 6.81 mmol) was added. The reaction mixture was heated under nitrogen until it reached the reaction temperature (80° C.) and sodium dithionite (3559 mg, 20.44 mmol) was added. The reaction mixture was stirred under nitrogen for 4 hours. The reaction mixture was concentrated under reduced pressure and the residue was partitioned between 10% IPA/DCM (100 mL) and a saturated solution of sodium bicarbonate (100 mL). The organic layer was isolated, the aqueous fraction was extracted with 10% IPA/DCM (2×100 mL). The organic fractions were combined, passed through a hydrophobic frit and concentrated under reduced pressure. The residue was dissolved in a minimum amount of DCM and purified by SPE (100 g, silica), eluted with a gradient of 0-25% EtOH in EtOAc. The appropriate fractions were combined and concentrated under reduced pressure to give the title compound (1189 mg) as a white solid. LCMS (System B): $t_{RET}$=0.65 min, $MH^+$=354.

Intermediate 221: 2-(1,5-Dimethyl-6-oxo-1,6-dihydropyridin-3-yl)-1-((tetrahydrofuran-3-yl)methyl)-1H-benzo[b]imidazole-5-carbaldehyde 5-(5-(Hydroxymethyl)-1-((tetrahydrofuran-3-yl)methyl)-1H benzo[d]imidazol-2-yl)-1,3-dimethylpyridin-2(1H)-one (For an example preparation see Intermediate 220, 1189 mg, 3.36 mmol) was dissolved in DCM (20 mL). IBX (45 wt %, stabilised by benzoic and naphthalic acids) (5234 mg, 8.41 mmol) was added and the reaction mixture was stirred for 3 days. The reaction mixture was partitioned between 10% IPA/DCM (50 mL) and a saturated solution of sodium bicarbonate (50 mL). The organic layer was isolated and the aqueous fraction was extracted twice with 10% IPA/DCM (2×50 mL). The organic fractions were combined and washed with a saturated solution of sodium bicarbonate (75 mL). The organic layer was isolated, passed through a hydrophobic frit and concentrated under reduced pressure. The residue was placed in a vacuum oven for 30 minutes to give the title compound (1271 mg) as a white solid. LCMS (System B): $t_{RET}$=0.73 min, $MH^+$=352.

Intermediate 222: (4-((1,3-Dimethoxypropan-2-yl)amino)-3-nitrophenyl)methanol

To a solution of (4-fluoro-3-nitrophenyl)methanol (16 g, 93 mmol) in THF (80 mL) was added 1,3-dimethoxypropan-2-amine (10 g, 84 mmol) and DIPEA (15 mL, 86 mmol). The mixture was split into seven portions and heated under microwave conditions at 100° C. for 7 hours. The reaction mixture was partitioned between ethyl acetate (3×500 mL) and saturated aqueous sodium bicarbonate solution (750 mL). The organic layers were combined, washed with saturated brine (500 mL), and evaporated under reduced pressure. The sample was loaded in dichloromethane and purified SPE (silica, 100 g) using a gradient of 0-80% EtOAc in cyclohexane. The appropriate fractions were combined and evaporated under reduced pressure to give a the title compound (12.0 g, 44.4 mmol). LCMS (System B): $t_{RET}$=0.85 min, $MH^+$=271. Less pure fractions were combined and evaporated. The sample was loaded in dichloromethane and purified by SPE (silica, 100 g) using a gradient of 0-50% EtOAc in cyclohexane. The appropriate fractions were combined and evaporated under reduced pressure to give the title compound (3.7 g, 13.69 mmol). LCMS (System J): $t_{RET}$=0.85 min, $MH^+$=271.

Intermediate 223: 5-(1-(1,3-Dimethoxypropan-2-yl)-5-(hydroxymethyl)-1H-benzo[d]imidazol-2-yl)-1,3-dimethylpyridin-2(1H)-one To a solution of (4-((1,3-dimethoxypropan-2-yl)amino)-3-nitrophenyl)methanol (For an example preparation see Intermediate 222, 12 g, 44.4 mmol) in ethanol (160 mL) was added sodium hydrosulfite (27.5 g, 133 mmol) and 1,5-dimethyl-6-oxo-1,6-dihydropyridine-3-carbaldehyde (For an example preparation see Intermediate 2, 8.39 g, 55.5 mmol), followed by water. The reaction mixture was heated at 70° C. for two hours The reaction mixture was concentrated to approximately half the volume under reduced pressure, and the resulting liquid partitioned between 3:1 chloroform:isopropanol (3×300 mL) and saturated aqueous sodium bicarbonate solution (300 mL). The organic layers were combined, dried using a hydrophobic frit and evaporated under reduced pressure. Crude material from a similar reaction (an additional 40% scale) was added at this stage. The sample was loaded in DCM and purified by SPE (silica, 3×340 g) using a gradient of 0-100% (25% EtOH in EtOAc) in cyclohexane. The appropriate fractions were combined and evaporated under reduced pressure to give the title compound (7.5 g, 20.19 mmol) as an off-white foam. LCMS (System J): $t_{RET}$=0.70 min, $MH^+$=372.

Intermediate 224: 1-(1,3-Dimethoxypropan-2-yl)-2-(1,5-dimethyl-6-oxo-1,6-dihydropyridin-3-yl)-1H-benzo[d]imidazole-5-carbaldehyde To a solution of 5-(1-(1,3-dimethoxypropan-2-yl)-5-(hydroxymethyl)-1H-benzo[d]imidazol-2-yl)-1,3-dimethylpyridin-2(1H)-one (For an example preparation see Intermediate 223, 7.5 g, 20.19 mmol) in DCM (400 mL) was added 45% iodoxybenzoic acid (stabilised by benzoic acid and isophthalic acid) (13.82 g, 22.21 mmol) and the reaction mixture stirred at room temperature for 3 nights. Saturated aqueous sodium bicarbonate solution (400 mL) was added slowly, and the mixture stirred until bubbling had stopped. The organic layer was removed, and the aqueous reextracted with 3:1 chloroform:isopropanol (2×400 mL). The organic layers were combined, dried using a hydrophobic frit and evaporated under reduced pressure to give the title compound (7.3 g, 19.76 mmol). LCMS (System J): $t_{RET}$=0.81 min, $MH^+$=370.

Intermediate 225: 2-(1,5-dimethyl-6-oxo-1,6-dihydropyridin-3-yl)-1-((tetrahydro-2H-pyran-2-yl)methyl)-1H-benzo[d]imidazole-5-carbaldehyde 5-(5-(hydroxymethyl)-1-((tetrahydro-2H-pyran-2-yl)methyl)-1H-benzo[d]imidazol-2-yl)-1,3-dimethylpyridin-2(1H)-one (for a preparation see Intermediate 226) (600 mg, 1.633 mmol) and Dess-Martin periodinane (693 mg, 1.633 mmol) were dissolved in DCM (5 mL) and stirred under nitrogen for 2 hrs. Dess-Martin periodinane (291 mg, 0.544 mmol) was then added and the mixture stirred for a further 30 min. Saturated sodium bicarbonate solution (25 mL) was then added and the mixture stirred for 25 minutes then left standing overnight. To the mixture was added dichloromethane (25 mL) and the phases separated. The aqueous phase was then extracted with dichloromethane (25 mL×2) and the organics combined. The organic phase was then washed with brine (30 mL×2) and the organics combined and dried over a hydrophobic frit. Solvents were then removed in vacuo yielding the title compound (550 mg, 1.505 mmol, 92% yield) as an off-white solid. LCMS (System B): $t_{RET}$=0.87 min; $MH^+$ 366.

Intermediate 226: 5-(5-(hydroxymethyl)-1-((tetrahydro-2H-pyran-2-yl)methyl)-1H-benzo[d]imidazol-2-yl)-1,3-dimethylpyridin-2(1H)-one (3-Nitro-4-(((tetrahydro-2H-pyran-2-yl)methyl)amino)phenyl)methanol (for a preparation see Intermediate 227, 2.9 g, 10.89 mmol), 1,5-dimethyl-6-oxo-1,6-dihydropyridine-3-carbaldehyde (for a preparation see Intermediate 2, 2.469 g, 16.34 mmol) and sodium dithionite (5.69 g, 32.7 mmol) were added to flask along with ethanol (35 mL). This mixture was heated to 90° C. and stirred for 15 minutes. Water (35 mL) was then added and the mixture stirred under nitrogen for 20 hours. The mixture was allowed to cool to room temperature. The mixture was then partitioned between 3:1 dichloromethane:isopropyl alcohol (100 mL) and water (100 mL) and the phases separated. Aqueous phase was extracted with 3:1 dichloromethane:isopropyl alcohol (100 mL×2) and the organics combined. Organic phase was then dried using a hydrophobic frit and solvents removed in vacuo yielding the title compound (1.99 g, 5.42 mmol, 49.7% yield) as an off-white solid. LCMS (System B): $t_{RET}$=0.77 min; $MH^+$ 368.

Intermediate 227: (3-nitro-4-(((tetrahydro-2H-pyran-2-yl)methyl)amino)phenyl)methanol (4-fluoro-3-nitrophenyl)methanol (1.985 g, 11.60 mmol) and (tetrahydro-2H-pyran-2-yl)methanamine (4.44 mL, 34.7 mmol) were dissolved in THF (10 mL) and N,N Diisopropylethylamine (6.08 mL, 34.8 mmol) added. Mixture was heated in a microwave reactor at 120° C. for 1 hr. The orange mixture was then partitioned between ethyl acetate (100 mL) and saturated sodium bicarbonate (100 mL). The phases were separated and the aqueous layer extracted twice with ethyl acetate (100 mL). The organics were then combined, dried using a hydrophobic frit and solvents removed in vacuo. This yielded the title compound as a bright orange solid. Excessively high yield must be due to a misweighing of a starting material. LCMS (System B): $t_{RET}$=0.92 min; $MH^+$ 267.

Intermediate 228: 2-((2-(1,5-dimethyl-6-oxo-1,6-dihydropyridin-3-yl)-1-ethyl-1H-benzo[d]imidazol-5-yl)oxy)acetaldehyde Dess-Martin periodinane (143 mg, 0.34 mmol) was added portionwise to a stirred solution of 5-(1-ethyl-5-(2-hydroxyethoxy)-1H-benzo[d]imidazol-2-yl)-1,3-dimethylpyridin-2 (1H)-one (for a preparation see Intermediate 229, 100 mg, 0.31 mmol) in dichloromethane (10 mL). The reaction mixture was stirred at room temperature under nitrogen for 4 hours. A further portion of Dess-Martin periodinane (143 mg, 0.34 mmol) was added portionwise and the reaction mixture was stirred at room temperature overnight. 10% sodium thiosulphate solution (20 mL) was added. The organic phase was separated and the aqueous phase was extracted with dichloromethane (2×10 mL). The combined extracts were washed with saturated $NaHCO_3$ solution, dried and evaporated. The residue title compound (99 mg, 0.305 mmol, 100% yield) was used in the next steps without further purification. 100% yield assumed. LCMS (System B): $t_{RET}$=0.67 min; $M+18^+$ 344.

Intermediate 229: 5-(1-ethyl-5-(2-hydroxyethoxy)-1H-benzo[d]imidazol-2-yl)-1,3-dimethylpyridin-2(1H)-one A mixture of 5-(1-ethyl-5-hydroxy-1H-benzo[d]imidazol-2-yl)-1,3-dimethylpyridin-2(1H)-one (for a preparation see Intermediate 230, 600 mg, 2.12 mmol), 2-bromoethanol (291 mg, 165 μL, 2.33 mmol) and potassium carbonate (878 mg, 6.35 mmol) in DMF (3 mL) was heated at 800° C. for 3 days. The reaction mixture was allowed to cool to room temperature and partitioned between ethyl acetate (25 mL) and water (15 mL). The organic phase was separated, dried and evaporated. The residue was chromatographed [0-10% ethanol/ethyl acetate] to give the title compound (105 mg, 0.321 mmol, 15.15% yield), as an off-white solid. LCMS (System B): $t_{RET}$=0.66 min; MH$^+$ 328.

Intermediate 230: 5-(1-ethyl-5-hydroxy-1H-benzo[d]imidazol-2-yl)-1,3-dimethylpyridin-2(1H)-one Sodium dithionite (2.72 g, 15.64 mmol) was added to a mixture of 4-(ethylamino)-3-nitrophenol (for a preparation see Intermediate 231, 950 mg, 5.21 mmol) and 1,5-dimethyl-6-oxo-1,6-dihydropyridine-3-carbaldehyde (for a preparation see Intermediate 2, 985 mg, 6.52 mmol) in ethanol (20 mL) and water (10 mL). The reaction mixture was stirred at 800° C. overnight. The reaction mixture was cooled to room temperature and the ethanol was evaporated. Ethyl acetate (100 mL) and saturated NaHCO$_3$ solution (50 mL) were added to the residue. A solid was formed. The solid was filtered off and dried to give the title compound (1.2 g, 4.24 mmol, 81% yield), as a colourless solid. LCMS (System A): $t_{RET}$=0.46 min; MH$^+$ 284.

Intermediate 231: 4-(ethylamino)-3-nitrophenol and Intermediate 232: 3-nitro-4-(((tetrahydro-2H-pyran-4-yl)methyl)amino)phenol A mixture of 4-amino-3-nitrophenol (5.06 g, 32.9 mmol), tetrahydro-2H-pyran-4-carbaldehyde (3.0 g, 26.3 mmol), and acetic acid (1.97 g, 1.88 mL, 32.9 mmol) in dichloromethane (100 mL) was stirred at room temperature for 1 hour. Sodium triacetoxyborohydride (16.71 g, 79 mmol) was added over 5 minutes. After complete addition the reaction mixture was stirred at room temperature for 24 hours. Saturated NaHCO$_3$ solution (100 mL) was added carefully (gas evolved) and the mixture stirred at room temperature for 30 minutes. The organic phase was separated. The aqueous phase was extracted with dichloromethane (3×50 mL). The combined organics were dried and evaporated. The residue was chromatographed [0-15% ethanol/ethyl acetate] to give; 4-(ethylamino)-3-nitrophenol (950 mg, 5.21 mmol, 19.84% yield), as an orange solid (unexpected product from reduction of acetanilide formed by reaction of triacetoxyborohydride with starting material). LCMS (System A): $t_{RET}$=0.87 min; MH$^+$ 183. Plus N31507-32-A3, 3-nitro-4-(((tetrahydro-2H-pyran-4-yl)methyl)amino)phenol (450 mg, 1.784 mmol, 6.79% yield) as an orange solid. LCMS (System A): $t_{RET}$=0.85 min; MH$^+$ 253.

Intermediate 233: (R)-2-(1,5-dimethyl-6-oxo-1,6-dihydropyridin-3-yl)-1-(1-hydroxypropan-2-yl)-1H-benzo[d]imidazole-5-carbaldehyde To (R)-5-(5-(hydroxymethyl)-1-(1-hydroxypropan-2-yl)-1H-benzo[d]imidazol-2-yl)-1,3-dimethylpyridin-2(1H)-one (for a preparation see Intermediate 234, 500 mg, 1.527 mmol) and Dess-Martin Periodinane (648 mg, 1.527 mmol) was added dichloromethane (DCM) (20 mL). Mixture was stirred under nitrogen for 20 hrs; LCMS showed remaining starting material so Dess-Martin Periodinane (65 mg, 0.157 mmol) was added and the mixture stirred for 3 hrs. To the mixture was added saturated sodium bicarbonate (100 mL) and it was stirred for 30 min. Dichloromethane (80 mL) was then added and the phases separated. The aqueous phase was then extracted with dichloromethane (100 mL×2). The combined organics were then washed with brine (100 mL) then dried using a hydrophobic frit. Solvents were then removed in vacuo yielding the title compound (460 mg, 1.414 mmol, 93%) as a yellow solid. LCMS (System A): $t_{RET}$=0.65 min; MH$^+$ 326.

Intermediate 234: (R)-5-(5-(hydroxymethyl)-1-(1-hydroxypropan-2-yl)-1H-benzo[d]imidazol-2-yl)-1,3-dimethylpyridin-2(1H)-one (R)-2-((4-(hydroxymethyl)-2-nitrophenyl)amino)propan-1-ol (for a preparation see Intermediate 235, 1.902 g, 8.41 mmol) and 1,5-dimethyl-6-oxo-1,6-dihydropyridine-3-carbaldehyde (for a preparation see Intermediate 2, 1.906 g, 12.61 mmol) were dissolved in ethanol (30 mL) and water (15 mL) and heated to 90° C. for 15 minutes. Sodium dithionite (4.39 g, 25.2 mmol) was then added and the mixture stirred for 20 hours under nitrogen. The mixture was then allowed to cool to room temperature. The mixture was then partitioned between 2:1 dichloromethane:isopropanol (75 mL) and water (70 mL). Phases were separated and the aqueous phase extracted with 2:1 dichloromethane:isopropanol (75 mL×2). Organics were then dried over a hydrophobic frit then solvents removed in vacuo. This yielded a yellow oil which was dissolved in dichloromethane and loaded onto a SNAP 100 g Silica column. This was eluted running a gradient of 0%-30% ethanol/ethyl acetate. Appropriate fractions were combined and solvents removed in vacuo to give the title compound (1.139 g, 3.48 mmol, 41.4% yield) as a white solid. LCMS (System B): $t_{RET}$=0.58 min; MH$^+$ 328.

Intermediate 235: (R)-2-((4-(hydroxymethyl)-2-nitrophenyl)amino)propan-1-ol (4-fluoro-3-nitrophenyl)methanol (1.5 g, 8.77 mmol) and (R)-2-aminopropan-1-ol (2.047 mL, 26.3 mmol) were dissolved in tetrahydrofuran (THF) (5 mL) and N,N-diisopropylethylamine (4.59 mL, 26.3 mmol) was added. Mixture was then heated in a microwave reactor at 120° C. for 1 hr. The orange mixture was then partitioned between ethyl acetate (80 mL) and saturated sodium bicarbonate (80 mL) and the phases separated. Aqueous phase was then extracted with ethyl acetate (80 mL×2) and the organics combined. The organic phase was then dried using a hydrophobic frit then solvents removed in vacuo to give the title compound (1.904 g, 8.41 mmol, 96% yield) as an orange/red solid. LCMS (System B): $t_{RET}$=0.63 min; MH$^+$ 227.

Intermediate 236: (S)-2-(1,5-dimethyl-6-oxo-1,6-dihydropyridin-3-yl)-1-(1-hydroxypropan-2-yl)-1H-benzo[d]imidazole-5-carbaldehyde (S)-5-(5-(hydroxymethyl)-1-(1-hydroxypropan-2-yl)-1H-benzo[d]imidazol-2-yl)-1,3-dimethylpyridin-2(1H)-one (for a preparation see Intermediate 237, 808 mg, 2.468 mmol) and Dess-Martin periodinane (1047 mg, 2.468 mmol) were dissolved in DCM (30 mL) and the mixture stirred for 3 hours. Dess-Martin Periodinane (104.7 mg, 0.247 mmol) was added. The mixture was then stirred overnight then sodium hydroxide solution (2M, 5 mL) and saturated sodium bicarbonate solution (20 mL) were then added and the mixture stirred for 3 hrs. To the mixture was then added dichloromethane (60 mL) and water (60 mL) and the phases separated. The aqueous phase was then extracted three times with dichloromethane (60 mL) and the organics combined. Combined organics were then dried using a hydrophobic frit, then solvents removed in vacuo. This yielded the title compound (592 mg, 1.82 mmol, 74%) as a yellow solid. LCMS (System B): $t_{RET}$=0.64 min; MH+ 326.

Intermediate 237: (S)-5-5-(hydroxymethyl)-1-(1-hydroxypropan-2-yl)-1H-benzo[d]imidazol-2-yl)-1,3-dimethylpyridin-2(1H)-one (S)-2-((4-(hydroxymethyl)-2-nitrophenyl)amino)propan-1-ol (for a preparation see Intermediate 238, 1.8 g, 7.96 mmol), 1,5-dimethyl-6-oxo-1,6-dihydropyridine-3-carbaldehyde (for a preparation see Intermediate 2, 1.323 g, 8.75 mmol) and sodium dithionite (4.16 g, 23.87 mmol) were dissolved in ethanol (30 mL) and water (15 mL) and the mixture heated to 90° C. for 20 hours. The mixture was then partitioned between dichloromethane:isopropanol (2:1; 100 mL) and water (100 mL) and the phases separated. Aqueous phase was then extracted twice with dichloromethane:isopropanol (2:1; 100 mL) and the organics combined and dried. The solvents were then removed in vacuo. Residue was then dissolved in dichloromethane and loaded onto a Biotage SNAP 100 g Silica column and eluted using a gradient of 0%-25% ethanol/ethyl acetate. Appropriate fractions were then combined and solvents removed in vacuo. This yielded the title compound (808 mg, 2.468 mmol, 31.0% yield) as a white solid. LCMS (System A): $t_{RET}$=0.40 min; MH+ 328.

Intermediate 238: (S)-2-((4-(hydroxymethyl)-2-nitrophenyl)amino)propan-1-ol 4-fluoro-3-(nitrophenyl)methanol (2 g, 11.69 mmol) was dissolved in tetrahydrofuran (5 mL) and DIPEA (6.12 mL, 35.1 mmol) and (S)-2-aminopropan-1-ol (2.73 mL, 35.1 mmol) added. This mixture was heated to 120° C. in a microwave reactor for 1 hour. The orange mixture was then partitioned between ethyl acetate (80 mL) and saturated sodium bicarbonate (80 mL). Phases were then separated and the aqueous phase was then extracted twice with ethyl acetate (80 mL). Organics were then combined, dried using a hydrophobic frit then solvents removed in vacuo. To the oil was added cyclohexane and the mixture left to stand for 16 hrs. Mixture was then stirred for 2.5 hrs then the solvent was decanted. The mixture was then dissolved in dichloromethane/methanol then solvents removed in vacuo. This yielded the title compound (1.8 g, 7.96 mmol, 68.1% yield) as a red/orange oil. LCMS (System B): $t_{RET}$=0.63 min; MH+ 328.

Intermediate 239: 2-((2-(1,5-dimethyl-6-oxo-1,6-dihydropyridin-3-yl)-1-((tetrahydro-2H-pyran-4-yl)methyl)-1H-benzo[d]imidazol-6-yl)oxy)acetaldehyde Dess-Martin periodinane (1.12 g, 2.64 mmol) was added portionwise to a stirred solution of 5-(6-(2-hydroxyethoxy)-1-((tetrahydro-2H-pyran-4-yl)methyl)-1H-benzo[d]imidazol-2-yl)-1,3-dimethylpyridin-2(1H)-one (for a preparation see Intermediate 240, 700 mg, 1.76 mmol) in dichloromethane (25 mL). After complete addition the reaction mixture was stirred at room temperature for 24 hours. 10% aq. Sodium thiosulphate solution (25 mL) was added and the mixture stirred for 15 minutes. The organic phase was separated. The aqueous phase was extracted with dichloromethane (2×20 mL). The combined organics were washed with saturated NaHCO₃ solution (20 mL). The organic phase was dried and evaporated to give the title compound (696 mg, 1.761 mmol, 100% yield), as a light brown oil. LCMS (System B): $t_{RET}$=0.57 min; M+18+ 414.

Intermediate 240: 5-(6-(2-hydroxyethoxy)-1-((tetrahydro-2H-pyran-4-yl)methyl)-1H-benzo[d]imidazol-2-yl)-1,3-dimethylpyridin-2(1H)-one A mixture of 5-(6-hydroxy-1-((tetrahydro-2H-pyran-4-yl)methyl)-1H-benzo[d]imidazol-2-yl)-1,3-dimethylpyridin-2(1H)-one (for a preparation see Intermediate 241, 2.0 g, 5.66 mmol), 2-bromoethanol (778 mg, 442 μL, 6.22 mmol) and potassium carbonate (2.346 g, 16.98 mmol) in dry DMF (15 mL) was stirred at 1100° C. for 24 hours. The reaction mixture was cooled to room temperature, then partitioned between ethyl acetate (50 mL) and water (50 mL). The organic phase was separated and the aqueous phase was extracted with ethyl acetate (3×25 mL). The combined organics were dried and evaporated. The residue was chromatographed [5-25% ethanol/ethyl acetate] to give the title compound (720 mg, 1.811 mmol, 32.0% yield), as a colourless solid. LCMS (System B): $t_{RET}$=0.63 min; MH+ 398.

Intermediate 241: 5-(6-hydroxy-1-((tetrahydro-2H-pyran-4-yl)methyl)-1H-benzo[d]imidazol-2-yl)-1,3-dimethylpyridin-2(1H)-one Sodium dithionite (7.04 g, 40.4 mmol) was added portionwise to a stirred mixture of 4-nitro-3-(((tetrahydro-2H-pyran-4-yl)methyl)amino)phenol (for a preparation see Intermediate 242, 3.4 g. 13.48 mmol) and 1,5-dimethyl-6-oxo-1,6-dihydropyridine-3-carbaldehyde (for a preparation see Intermediate 2, 2.45 g, 16.21 mmol) in ethanol (50 mL) and water (25 mL). After complete addition the reaction mixture was refluxed for 4 hours. The reaction mixture was cooled and the ethanol was evaporated. The residue was partitioned between ethyl acetate (50 mL) and water (50 mL). The organic phase was separated and the aqueous phase was extracted with ethyl acetate (3×25 mL). The combined organics were dried and evaporated. The residue was chromatographed [5-20% ethanol/ethyl acetate] to give the title compound (3.77 g, 10.67 mmol, 79% yield), as a colourless solid. LCMS (System B): $t_{RET}$=0.61 min; MH+ 354.

Intermediate 242: 4-nitro-3-(((tetrahydro-2H-pyran-4-yl)methyl)amino)phenol

A mixture of 3-fluoro-4-nitrophenol (3.0 g, 19.1 mmol), (tetrahydro-2H-pyran-4-yl)methanamine (3.30 g, 28.6 mmol), and diisopropylethylamine (3.70 g, 5.0 mL, 28.6 mmol) in dioxan (50 mL) was refluxed for 3 hours. The reaction mixture was cooled to room temperature and the solvent was evaporated. The residue was chromatographed [50-75% ethyl acetate/cyclohexane] to give the title compound (3.42 g, 13.56 mmol, 71.0% yield), as an orange solid. LCMS (System A): $t_{RET}$=0.86 min; MH+ 253.

Intermediate 243: 5-(1-(2-hydroxyethyl)-5-(hydroxymethyl)-1H-benzo[d]imidazol-2-yl)-1,3-dimethylpyridin-2(1H)-one 1,5-dimethyl-6-oxo-1,6-dihydropyridine-3-carbaldehyde (for a preparation see Intermediate 2, 1.726 g, 11.42 mmol), 2-((4-(hydroxymethyl)-2-nitrophenyl)amino)ethanol for a preparation see Intermediate 244, 2.203 g, 10.38 mmol) and sodium dithionite (5.42 g, 31.1 mmol) were dissolved in ethanol (30 mL) and water (15 mL) and stirred at 90° C. for 48 hours. Mixture was then allowed to cool to room temperature then 3:1 DCM/isopropanol (100 mL) and water (100 mL) added. Phases were separated then the aqueous phase extracted twice with 3:1 DCM/isopropanol (100 mL). Organics were combined then dried using a hydrophobic frit then solvents removed in vacuo. The yellow residue produced was then loaded onto a Biotage SNAP 100 g silica column then eluted with 0%-25% ethanol/ethyl acetate. Appropriate fractions were combined and solvents removed in vacuo. This yielded the title compound (975 mg, 3.11 mmol, 30.0% yield) as a white solid. LCMS (System B): $t_{RET}$=0.57 min; MH$^+$ 314.

Intermediate 244:
2-((4-(hydroxymethyl)-2-nitrophenyl)amino)ethanol (4-fluoro-3-nitrophenyl)methanol (2 g, 11.69 mmol) was dissolved in tetrahydrofuran (5 mL) then 2-aminoethanol (2.120 mL, 35.1 mmol) and N,N-Diisopropylethylamine (6.12 mL, 35.1 mmol) were added. This mixture was heated in a microwave reactor at 120° C. for 1 hour. LCMS analysis showed presence of starting material and the sample was heated in the microwave reactor at 120° C. for 30 min. Mixture was then partitioned between ethyl acetate (75 mL) and saturated sodium bicarbonate (75 mL) and the phases separated. Aqueous phase was then extracted twice with ethyl acetate (75 mL) and the organics combined and retained. The aqueous phase was then extracted with 1:1 mixture of isopropanol/dichloromethane (75 mL) and the organic phase combined with the previous organics. Organics were dried over a hydrophobic frit and solvents removed in vacuo. This yielded the title compound (2.203 g, 10.38 mmol, 89% yield) as an orange/red solid. LCMS (System A): $t_{RET}$=0.57 min; MH$^+$ 213.

Intermediate 245: 2-(5-methyl-6-oxo-1,6-dihydropyridin-3-yl)-1-((tetrahydro-2H-pyran-2-yl)methyl)-1H-benzo[d]imidazole-5-carbaldehyde To 5-(5-(hydroxymethyl)-1-((tetrahydro-2H-pyran-2-yl)methyl)-1H-benzo[d]imidazol-2-yl)-3-methylpyridin-2(1H)-one (for a preparation see Intermediate 246, 1046 mg, 2.96 mmol) and Dess-Martin periodinane (1255 mg, 2.96 mmol) was added Dichloromethane (20 mL) and the mixture stirred for 20 hours. LCMS analysis of the brown mixture showed presence of starting material therefore Dess-Martin Periodinane (126 mg, 0.296 mmol) was added and the mixture stirred for 3 hours. To the mixture was added saturated sodium bicarbonate solution (100 mL) and dichloromethane (80 mL) and the phases separated. Organics were then extracted twice with dichloromethane (100 mL) and organics combined. Organics were then washed with brine (100 mL) then dried using a hydrophobic frit. Solvents were removed in vacuo producing the crude title compound (1.2 g, 3.41 mmol, 115% yield) as an off-white solid with some evidence of remaining Dess-Martin Periodinane residues. No purification attempted as product is an intermediate. Compound appeared as a pale brown solid. LCMS (System A): $t_{RET}$=0.76 min; MH$^+$ 352.

Intermediate 246: 5-(5-(hydroxymethyl)-1-((tetrahydro-2H-pyran-2-yl)methyl)-1H-benzo[d]imidazol-2-yl)-3-methylpyridin-2(1M-one (3-nitro-4-(((tetrahydro-2H-pyran-2-yl)methyl)amino)phenyl)methanol (for a preparation see Intermediate 227, 2.7 g, 10.14 mmol) and 5-methyl-6-oxo-1,6-dihydropyridine-3-carbaldehyde (for a preparation see Intermediate 1, 1.808 g, 13.18 mmol) were dissolved in ethanol (35 mL) and water (35.0 mL) and heated to 90° C. Sodium dithionite (5.30 g, 30.4 mmol) was then added and the mixture stirred for 20 hours. Mixture was allowed to cool to room temperature then partitioned between 3:1 dichloromethane:isopropanol (160 mL) and sodium bicarbonate (160 mL) and phases separated. Organic phase was then extracted twice with 3:1 dichloromethane:isopropanol (160 mL). The organics were then combined, dried using a hydrophobic frit and solvents removed in vacuo. This yielded a yellow residue which solidified after being last to stand in air. An attempt was made to dissolve the sample in 25% ethanol/ethyl acetate, however, the solid was quite insoluble. The mixture was thus filtered under gravity and the residue washed with 25% ethanol/ethyl acetate. The solid was dried in air then dried further in vacuum oven at 40° C. for 1 hour to give the title compound (1.05 g, 2.97 mmol, 29.3% yield) as an off white solid. LCMS (System A): $t_{RET}$=0.52 min; MH$^+$ 354.

Intermediate 247: (S)-2-((2-(1,5-dimethyl-6-oxo-1,6-dihydropyridin-3-yl)-1-(1-methoxypropan-2-yl)-1H-benzo[d]imidazol-5-yl)oxy)acetaldehyde Dess-Martin periodinane (320 mg, 0.75 mmol) was added portionwise to a stirred solution of (S)-5-(5-(2-hydroxyethoxy)-1-(1-methoxypropan-2-yl)-1H-benzo[d]imidazol-2-yl)-1,3-dimethylpyridin-2(1H)-one (for a preparation see Intermediate 248, 140 mg, 0.38 mmol) in dichloromethane (10 mL). The reaction mixture was stirred at room temperature overnight. 10% sodium thiosulphate solution (20 mL) was added and the mixture stirred for 15 minutes. The organic phase was separated. The aqeuous phase was extracted with dichloromethane (2×10 mL). The combined organics were washed with saturated NaHCO$_3$ (10 mL), dried and evaporated to give the title compound (139 mg, 0.377 mmol, 100% yield), as a colourless gum. Quantitative yield assumed used in next steps without further purification. LCMS (System B): $t_{RET}$=0.66 min; M+18$^+$ 388.

Intermediate 248: (S)-5-(5-(2-hydroxyethoxy)-1-(1-methoxypropan-2-yl)-1H-benzo[d]imidazol-2-yl)-1,3-dimethylpyridin-2(1H)-one A mixture of (S)-5-(5-hydroxy-1-(1-methoxypropan-2-yl)-1H-benzo[d]imidazol-2-yl)-1,3-dimethylpyridin-2(1H)-one (for a preparation see Intermediate 249, 1.25 g, 3.82 mmol), 2-bromoethanol (525 mg, 298·L, 4.2 mmol) and potassium carbonate (1.58 g, 11.45 mmol) in DMF (50 mL) was stirred at 130° C. for 48 hours. The reaction mixture was cooled and the solvent was evaporated. The residue was suspended in ethyl acetate (50 mL) and filtered through 'celite'. The solvent was evaporated from the filtrate. The residue was purified by silica gel column chromatography [10-25% ethanol/ethyl acetate] to give the title compound (140 mg, 0.377 mmol, 9.87% yield), as a yellow gum. LCMS (System B): $t_{RET}$=0.75 min; MH$^+$ 372.

Intermediate 249: (S)-5-(5-hydroxy-1-(1-methoxypropan-2-yl)-1H-benzo[d]imidazol-2-yl)-1,3-dimethylpyridin-2(1H)-one A solution of (S)-4-((1-methoxypropan-2-yl)amino)-3-nitrophenol (for a preparation see Intermediate 250, 1.3 g, 5.75 mmol) and 1,5-dimethyl-6-oxo-1,6-dihydropyridine-3-carbaldehyde (for a preparation see Intermediate 2, N-Me pyridone aldehyde, 1.04 g, 6.90 mmol) in ethanol (30 mL) and water (15 mL) was treated with sodium dithionite (3.00 g, 17.24 mmol) added portion wise over 5 minutes. After complete addition the reaction mixture was refluxed for 4 hours. The reaction mixture was allowed to cool to room temperature. The ethanol was evaporated. The residue was partitioned between ethyl acetate (50 mL) and water (25 mL). The organic phase was separated. The aqueous phase was extracted with ethyl acetate (2×25 mL). The combined organics were dried and evaporated. The residue was chromatographed [5-20% ethanol/ethyl acetate] to give the title compound (1.27 g, 3.88 mmol, 67.5% yield), as an off white solid. LCMS (System A): $t_{RET}$=0.46 min; MH+ 328.

Intermediate 250: (S)-4-((1-methoxypropan-2-yl)amino)-3-nitrophenol

A mixture of 4-fluoro-3-nitrophenol (1.0 g, 6.37 mmol), (S)-1-methoxypropan-2-amine (1.13 g, 1.35 mL, 12.73 mmol) and diisopropylethylamine (1.65 g, 2.22 mL, 12.73 mmol) in dioxan (10 mL) was refluxed for 2 hours. The solvent was evaporated, the residue was dissolved in N/methyl-2-pyrrolidone (10 mL). The mixture was heated in a microwave at 1800° C. for 4 hours. The cooled reaction mixture was partitioned between ethyl acetate (50 mL) and water (25 mL). The organic phase was separated, washed with water (2×25 mL), dried and evaporated. The residue was chromatographed [10-40% ethyl acetate/cyclohexane] to give the title compound (1.31 g, 5.79 mmol, 91% yield), as an orange solid. LCMS (System A): $t_{RET}$=0.89 min; MH+ 227.

Intermediate 251: 2-(5-methyl-6-oxo-1,6-dihydropyridin-3-yl)-1-((tetrahydrofuran-3-yl)methyl)-1H-benzo[d]imidazole-5-carbaldehyde (Enantiomer 1, a Single Enantiomer of Unknown Configuration)

Dess-Martin periodinane (625 mg, 1.47 mmol) was added portionwise to a stirred solution of 5-(5-(hydroxymethyl)-1-((tetrahydrofuran-3-yl)methyl)-1H-benzo[d]imidazol-2-yl)-3-methylpyridin-2(1H)-one (Enantiomer 1, for a preparation see Intermediate 252, 250 mg, 0.74 mmol) in dichloromethane (10 mL). The reaction mixture was stirred at room temperature overnight. 10% sodium thiosulphate solution (20 mL) was added and the mixture stirred for 15 minutes. The organic phase was separated. The aqueous phase was extracted with dichloromethane (2×10 mL). The combined organics were washed with saturated NaHCO$_3$ solution (10 mL), dried and evaporated to give the title compound (249 mg, 0.737 mmol, 100% yield), as a colourless gum. Quantitative yield assumed. LCMS (System B): $t_{RET}$=0.67 min; MH+ 338.

Intermediate 252: 5-(5-(hydroxymethyl)-1-((tetrahydrofuran-3-yl)methyl)-1H-benzo[d]imidazol-2-yl)-3-methylpyridin-2(1H)-one (Enantiomer 1) and Intermediate 253: 5-(5-(hydroxymethyl)-1-((tetrahydrofuran-3-yl)methyl)-1H-benzo[d]imidazol-2-yl)-3-methylpyridin-2(1-one (Enantiomer 2)

Chiral separation of Intermediate 254:
Analytical Method: Approx 0.5 mg dissolved in 50% EtOH/Heptane (1 mL) 20 ul injected on column (40% EtOH/Heptane, f=1.0 mL/min, wavelength 215 nm, 4. Ref 550, 100, Column 4.6 mmid×25 cm Chiralpak IA)

Prep Method: Approx 2.25 g dissolved in 12 mL of EtOH+heat. Injection; 2 mL of the solution was injected onto the column (40% EtOH/Heptane, f=30 mL/min, wavelength 215 nm, 4.
Ref 550,100, Column 30 mm×25 cm Chiralpak IA)
Intermediate 252 (Enantiomer 1) Rt=11.5 min.>99% ee by UV.
Intermediate 253 (Enantiomer 2) Rt=16.5 min.>99% ee by UV.

Intermediate 254: 5-(5-(hydroxymethyl)-1-((tetrahydrofuran-3-yl)methyl)-1H-benzo[d]imidazol-2-yl)-3-methylpyridin-2(1H)-one Sodium dithionite (7.66 g, 44.0 mmol) was added in three single portions to a suspension of (3-nitro-4-(((tetrahydrofuran-3-yl)methyl)amino)phenyl)methanol (for a preparation see Intermediate 219, 3.7 g, 14.67 mmol) and 5-methyl-6-oxo-1,6-dihydropyridine-3-carbaldehyde (for a preparation see Intermediate 1, 2.51 g, 15.56 mmol) in ethanol (60 mL) and water (30 mL). The reaction mixture was stirred at 80° C. overnight. The reaction mixture was cooled to room temperature and the ethanol was evaporated. The mixture was partitioned between DCM:iPrOH 3:1 (150 mL) and NaHCO$_3$ (100 mL). The separated aqueous phase was extracted with DCM:iPrOH 3:1 (3×150 mL). The combined organic phases were passed through a hydrophobic frit and evaporated to obtain a pale yellow oil. The sample was loaded in 20% MeOH/DCM and purified by chromatography (Biotage SP4) on SNAP 100 g silica column using a 10-20% MeOH/DCM gradient. The appropriate fractions were combined and dried down to give the title compound (2.37 g, 6.98 mmol, 48%) as a pale yellow oil. LCMS (System C): $t_{RET}$=0.42 min; MH+ 340.

Intermediate 255: 2-(5-methyl-6-oxo-1,6-dihydropyridin-3-yl)-1-((tetrahydrofuran-3-yl)methyl)-1H-benzo[d]imidazole-5-carbaldehyde (Enantiomer 2)

Dess-Martin periodinane (625 mg, 1.47 mmol) was added portionwise to a stirred solution of 5-(5-(hydroxymethyl)-1-((tetrahydrofuran-3-yl)methyl)-1H-benzo[d]imidazol-2-yl)-3-methylpyridin-2(1H)-one (Enantiomer 2, for a preparation see Intermediate 253, 250 mg, 0.74 mmol) in dichloromethane (10 mL). The reaction mixture was stirred at room temperature overnight. 10% sodium thiosulphate solution (20 mL) was added and the mixture stirred for 15 minutes. The organic phase was separated. The aqeuous phase was extracted with dichloromethane (2×10 mL). The combined organics were washed with saturated NaHCO$_3$ solution (10 mL), dried and evaporated to give the title compound (249 mg, 0.737 mmol, 100% yield), as a colourless gum. Quantitative yield assumed. Used without further purification in next steps. LCMS (System B): $t_{RET}$=0.67 min; MH+ 338.

Intermediate 256: 2-(1,5-dimethyl-6-oxo-1,6-dihydropyridin-3-yl)-1-(2-methoxypropyl)-1H-benzo[d]imidazole-5-carbaldehyde 5-(5-(hydroxymethyl)-1-(2-methoxypropyl)-1H-benzo[d]imidazol-2-yl)-1,3-dimethylpyridin-2(1H)-one (for a preparation see Intermediate 257, 2.153 g, 6.31 mmol) was dissolved in dichloromethane (15 mL) then Dess-Martin periodinane (2.67 g, 6.31 mmol) was added. Mixture was stirred under nitrogen for 1 hour. To the mixture was added sodium bicarbonate (200 mL) and dichloromethane (200 mL). This mixture was stirred for 1.5 hours then phase separation attempted. The organics from the separation were retained. 2M HCl (100 mL) was added. The organic phase was separated and dried using a hydrophobic frit, and solvents removed in vacuo. This yielded a brown residue, the crude title compound. LC-MS purity was ~45%. LCMS (System A): $t_{RET}$=0.73 min; MH+ 340.

Intermediate 257: 5-(5-(hydroxymethyl)-1-(2-methoxypropyl)-1H-benzo[d]imidazol-2-yl)-1,3-dimethylpyridin-2(1H)-one (4-((2-methoxypropyl)amino)-3-nitrophenyl)methanol (for a preparation see Intermediate 258, 2.8152 g, 11.72 mmol) and 1,5-dimethyl-6-oxo-1,6-dihydropyridine-3-carbaldehyde (for a preparation see Intermediate 2, 1.948 g, 12.89 mmol) were dissolved in ethanol (50 mL) and water (25 mL) and heated to 90° C. under nitrogen for 1 hour. Sodium dithionite (8.16 g, 46.9 mmol) was then added and the mixture stirred under nitrogen for 1.5 hours at 90° C. The mixture was then partitioned between saturated sodium bicarbonate (100 mL) and 3:1 dichloromethane:isopropanol (100 mL) and the phases separated. Aqueous phase was then extracted twice with 3:1 dichloromethane:isopropanol (100 mL) the organics were combined then dried over a hydrophobic frit. Solvents were then removed in vacuo leaving a yellow residue. Residue was dissolved in dichloromethane, split into two portions and loaded onto two Biotage SNAP 100 g Silica columns. Each column was eluted running a gradient of 0%-25% ethanol/ethyl acetate. Appropriate fractions were then combined and solvents removed in vacuo. This yielded the title compound (2.1253 g, 6.23 mmol, 53.1% yield) as a brown solid. LCMS (System A): $t_{RET}$=0.48 min; MH+ 342.

Intermediate 258: (4-((2-methoxypropyl)amino)-3-nitrophenyl)methanol (4-fluoro-3-nitrophenyl)methanol (2.72 g, 15.89 mmol), 2-methoxypropan-1-amine, hydrochloride (2.99 g, 23.84 mmol), and diisopropylethylamine (13.88 mL, 79 mmol) were added to tetrahydrofuran (10 mL) and split into two equal portions. Each portion was placed in a 20 mL microwave vial and heated to 120° C. for 1 hour in a microwave reactor. Starting material was still present therefore sample was heated in the microwave reactor for 30 minutes at 120° C. The mixtures were combined and partitioned between ethyl acetate (150 mL) and saturated sodium bicarbonate (150 mL). Aqueous phase was then extracted twice with ethyl acetate (150 mL), organics combined and dried using a hydrophobic frit. Solvents were then removed in vacuo yielding a red oil. The oil was dissolved in dichloromethane and loaded onto two Biotage SNAP 100 g Silica columns. Each column was eluted using a gradient of 10%-50% ethyl acetate/cyclohexane. Appropriate fractions were combined yielding the title compound (2.8152 g, 11.72 mmol, 73.7% yield) as an orange solid. LCMS (System A): $t_{RET}$=0.82 min; MH+ 241.

Intermediate 259: 5-(5-hydroxy-1-((tetrahydro-2H-pyran-4-yl)methyl)-1H-benzo[d]imidazol-2-yl)-1,3-dimethylpyridin-2(1H)-one 3-nitro-4-(((tetrahydro-2H-pyran-4-yl)methyl)amino)phenol (for a preparation see Intermediate 232, 3.68 g, 14.59 mmol), 1,5-dimethyl-6-oxo-1,6-dihydropyridine-3-carbaldehyde (for a preparation see Intermediate 1, 2.205 g, 14.59 mmol) and sodium hydrosulfite (7.62 g, 43.8 mmol) were stirred in Ethanol (64.8 mL) under nitrogen. Water (32.4 mL) was added and the reaction mixture was stirred at 90° C. under nitrogen overnight. The reaction mixture was cooled down to room temperature and concentrated under reduced pressure to ⅓ of its volume. The residue was taken in DCM and washed with water. The organics were dried over a phase separator and concentrated under reduced pressure. The red solid was purified by silica gel column chromatography eluted with 0-25% EtOH in ethyl acetate. The fractions were concentrated under reduced pressure to give the title compound (3.48 g). LCMS (System B): $t_{RET}$=0.67 min, MH+=354.

Intermediate 260: 5-(5-(2-hydroxyethoxy)-1-((tetrahydro-2H-pyran-4-yl)methyl)-1H-benzo[d]imidazol-2-yl)-1,3-dimethylpyridin-2(1H)-one 5-(5-hydroxy-1-((tetrahydro-2H-pyran-4-yl)methyl)-1H-benzo[d]imidazol-2-yl)-1,3-dimethylpyridin-2(1H)-one (for a preparation see Intermediate 259, 0.75 g, 2.122 mmol), 2-bromoethanol (0.318 g, 2.55 mmol) and K$_2$CO$_3$ (0.880 g, 6.37 mmol) in dry DMF (7.07 mL) were stirred at 120° C. under nitrogen. After 18 hrs, 2-bromoethanol (0.318 g, 2.55 mmol) was added and the reaction mixture was stirred at 120° C. for 7 hrs. The mixture was allowed to cool down to room temperature. Water and ethyl acetate were added and the layers were separated. The organics were washed with water, dried through a hydrophobic frit and concentrated under reduced pressure. The residue was purified by flash column chromatography eluted with 5-25% ethanol in ethyl acetate to give the title compound as a white solid (0.18 g). LCMS (System B): $t_{RET}$=0.70 min, MH+=398.

Intermediate 261: 2-((2-(1,5-dimethyl-6-oxo-1,6-dihydropyridin-3-yl)-1-((tetrahydro-2H-pyran-4-yl)methyl)-1H-benzo[d]imidazol-5-yl)oxy)acetaldehyde 5-(5-(2-hydroxyethoxy)-1-((tetrahydro-2H-pyran-4-yl)methyl)-1H-benzo[d]imidazol-2-yl)-1,3-dimethylpyridin-2(1H)-one (for a preparation see Intermediate 260, 0.18 g, 0.453 mmol) was dissolved in DCM (8 mL) under nitrogen atmosphere. Dess-martin periodinane (0.288 g, 0.679 mmol) was added. The reaction mixture was stirred at room temperature overnight. A saturated solution of sodium thiosulfate (20 mL) was added and the mixture was stirred at room temperature for 15 min. The mixture was diluted with DCM and the layers separated. The aqueous was extracted with DCM. The organics were combined and washed with a saturated sodium bicarbonate solution, dried through a phase separator and concentrated to give the title compound as a yellow solid. Further experiments were carried out on the crude material. LCMS (System B): $t_{RET}$=0.65 min, MH+=396.

Intermediate 262: (2S,3R)-isopropyl 2-(2-(4-fluoro-3-nitrophenyl)acetamido)-hydroxybutanoate 2-(4-fluoro-3-nitrophenyl)acetic acid (2 g, 10.04 mmol), (2S,3R)-isopropyl 2-amino-3-hydroxybutanoate, 4-Methylbenzenesulphonic acid salt (for a preparation see Intermediate 31, 4.02 g, 12.05 mmol), pyridine (2.437 mL, 30.1 mmol) and n-propylphosphonic acid anhydride, cyclic trimer (8.88 mL, 15.07 mmol) in Ethyl acetate (45 mL) were stirred at room temperature overnight. Pyridine (2.437 mL, 30.1 mmol) was added and the reaction mixture further stirred at room temperature for 18 hrs. The reaction mixture was diluted with water. The layers were separated. The aqueous were extracted with ethyl acetate. The organics were washed with brine and then water, dried over a phase separator and concentrated. The residue was purified by flash column chromatography eluted with 0-10% ethanol in ethyl acetate. The fractions were concentrated to give the title compound (31% yield). LCMS (System B): $t_{RET}$=0.90 min, MH$^+$=343.

The following Intermediate was prepared in a similar manner to intermediate 262:

Intermediate 263: (2S,3R)-tert-butyl 2-(2-(4-fluoro-3-nitrophenyl)acetamido)-3-hydroxybutanoate (Prepared from Commercially Available Starting Materials)

System B, 0.96 min, MH$^+$=355.

Intermediate 264: (2S,3R)-isopropyl 3-hydroxy-2-(2-(3-nitro-4-(((tetrahydro-2H-pyran-4-yl)methyl)amino)phenyl)acetamido)butanoate (2S,3R)-isopropyl 2-(2-(4-fluoro-3-nitrophenyl)acetamido)-3-hydroxybutanoate (for a preparation see Intermediate 262, 1.51 g, 4.41 mmol), DIPEA (2.311 mL, 13.23 mmol) and (tetrahydro-2H-pyran-4-yl)methanamine (0.762 g, 6.62 mmol) in THF (40 mL) were stirred under nitrogen at 60° C. overnight. DIPEA (2.311 mL, 13.23 mmol) and (tetrahydro-2H-pyran-4-yl)methanamine (0.2 mL) were added and the reaction mixture was heated at 600° C. for two hours. The reaction mixture was concentrated under reduced pressure. The residue was taken in DCM and washed with water. The organics were dried over a phase separator and concentrated to give an orange oil. The oil was purified by flash column chromatography eluted with 25-100% ethyl acetate in cyclohexane. The fractions were concentrated to give the title compound (58% yield).

LCMS (System B): $t_{RET}$=0.95 min, MH$^+$=438.

The following Intermediate was prepared in a similar way to Intermediate 264:

Intermediate 265: (2S,3R)-tert-butyl 3-hydroxy-2-(2-(3-nitro-4-(((tetrahydro-2H-pyran-4-yl)methyl)amino)phenyl)acetamido)butanoate (Prepared from: Intermediate 263)

System B, 1.00 min, MH$^+$=452.

Intermediate 266: 1,3-dimethyl-5-(5-(oxiran-2-yl)-1-((tetrahydro-2H-pyran-4-yl)methyl)-1H-benzo[d]imidazol-2-yl)pyridin-2(1H)-one 2-(1,5-dimethyl-6-oxo-1,6-dihydropyridin-3-yl)-1-((tetrahydro-2H-pyran-4-yl)methyl)-1H-benzo[d]imidazole-5-carbaldehyde (for a preparation see Intermediate 116, 0.100 g, 0.274 mmol), trimethylsulfonium iodide (0.057 g, 0.279 mmol) and potassium hydroxide (0.092 g, 1.642 mmol) were stirred in Acetonitrile (2.72 mL) and Water (0.014 mL) under nitrogen at 65° C. for 4 hours. The reaction was cooled down to room temperature, diluted with ethyl acetate and water. The organics were washed with sodium bicarbonate. The organics were then dried over a phase separator and concentrated under reduced pressure to give the title compound as a white solid (49% yield). LCMS (System B): $t_{RET}$=0.79 min, MH$^+$=389.

Intermediate 267: (R)-tert-butyl 3-((2-(1,5-dimethyl-6-oxo-1,6-dihydropyridin-3-yl)-6-(((((2S,3R)-3-hydroxy-1-isopropoxy-1-oxobutan-2-yl)amino)methyl)-1H-benzo[d]imidazol-1-yl)methyl)piperidine-1-carboxylate Sodium triacetoxyborohydride (68 mg, 0.33 mmol) was added to a stirred solution of (R)-tert-butyl 3-((2-(1,5-dimethyl-6-oxo-1,6-dihydropyridin-3-yl)-6-formyl-1H-benzo[d]imidazol-1-yl)methyl)piperidine-1-carboxylate (for a preparation see Intermediate 126, 100 mg, 0.22 mmol) and (2S,3R)-isopropyl 2-amino-3-hydroxybutanoate 4-methylbenzenesulfonate (For a preparation see Intermediate 31, 86 mg, 0.26 mmol). The resulting suspension was stirred overnight. Further (2S,3R)-isopropyl 2-amino-3-hydroxybutanoate 4-methylbenzenesulfonate (86 mg, 0.26 mmol) and Sodium triacetoxyborohydride (68 mg, 0.33 mmol) were added and the suspension stirred for 2 h. The reaction mixture was solubilised with MeOH and loaded on to a 5 g SCX cartridge. The cartridge was eluted with MeOH, followed by 2M methanolic ammonia. The basic fractions were evaporated in vacuo to a colourless gum and purified by MDAP (Method B). The product containing fractions were evaporated in vacuo to give the title compound (29 mg) as a white foam. LCMS (System C): $t_{RET}$=0.66 min, MH$^+$=610.

Intermediate 268: (R)-tert-butyl 3-((6-(((((2S,3R)-1-(tert-butoxy)-3-hydroxy-1-oxobutan-2-yl)amino)methyl)-2-(1,5-dimethyl-6-oxo-1,6-dihydropyridin-3-yl)-1H-benzo[d]imidazol-1-yl)methyl)piperidine-1-carboxylate Sodium triacetoxyborohydride (46 mg, 0.22 mmol) was added to a stirred solution of (R)-tert-butyl 3-((2-(1,5-dimethyl-6-oxo-1,6-dihydropyridin-3-yl)-6-formyl-1H-benzo[d]imidazol-1-yl)methyl)piperidine-1-carboxylate (For a preparation see Intermediate 126, 50 mg, 0.11 mmol) and (2S,3R)-tert-butyl 2-amino-3-hydroxybutanoate.HCl (28 mg, 0.13 mmol). The reaction mixture was stirred overnight. (2S,3R)-tert-butyl 2-amino-3-hydroxybutanoate hydrochloride (28 mg, 0.13 mmol) was added, the resulting suspension stirred for 2 h and sodium triacetoxyborohydride (46 mg, 0.22 mmol) added. The resulting suspension was stirred for 1 h. The suspension was solubilised with MeOH and loaded on to a 5 g SCX cartridge. The cartridge was eluted with MeOH, followed by 2M methanolic ammonia. The basic fractions were evaporated in vacuo to a colourless gum and purified by MDAP (Method B). The product containing fractions were evaporated in vacuo to give the title compound (20 mg) as a white foam.

LCMS (System C): $t_{RET}$=0.69 min, MH$^+$=624.

Intermediate 269: (S)-tert-butyl 3-((2-(1,5-dimethyl-6-oxo-1,6-dihydropyridin-3-yl)-6-(((((S)-1-isopropoxy-3-methyl-1-oxobutan-2-yl)amino)methyl)-1H-benzo[d]imidazol-1-yl)methyl)piperidine-1-carboxylate (S)-tert-butyl 3-((2-(1,5-dimethyl-6-oxo-1,6-dihydropyridin-3-yl)-6-formyl-1H-benzo[d]imidazol-1-yl)methyl)piperidine-1-carboxylate (For a preparation see Intermediate 128, 70 mg, 0.151 mmol) was dissolved in DCM (3 mL) and (S)-isopropyl 2-amino-3-methylbutanoate 4-methylbenzenesulfonate (For a preparation see Intermediate 65, N31501-74-A2, 100 mg, 0.301 mmol) was added. The suspension was stirred under nitrogen flow for 1 hr. Sodium triacetoxyborohydride (63.9 mg, 0.301 mmol) was added and the reaction mixture was stirred at rt for 23 hr. (S)-isopropyl 2-amino-3-methylbutanoate 4-methylbenzenesulfonate (49.9 mg, 0.151 mmol) was added and stirred for 30 min prior to addition of sodium triacetoxyborohydride (31.9 mg, 0.151 mmol). The mixture was stirred at rt for 3.5 hr. The reaction mixture was diluted with DCM (20 mL) and NaHCO$_3$ (20 mL) was added. The separated aqueous phase was extracted with DCM (3×20 mL). The combined organic phases were passed through a hydrophobic frit and evaporated to obtain the crude product (124 mg) as a yellow solid. The sample was dissolved in MeOH 2 mL and purified by MDAP (Method B). The solvent was dried down to give the title compound (65 mg) as a yellow-orange solid. LCMS (System B): $t_{RET}$=1.30 min, MH$^+$=608.

Intermediate 270: (S)-tert-butyl 3-((5-(((1-(cyclopentyloxy)-4-methyl-1-oxopentan-2-yl)amino)methyl)-2-(5-methyl-6-oxo-1,6-dihydropyridin-3-yl)-1H-benzo[d]imidazol-1-yl)methyl)azetidine-1-carboxylate A microwave vial was charged with (S)-tert-butyl 3-(((4-(((1-(cyclopentyloxy)-4-methyl-1-oxopentan-2-yl)amino)methyl)-2-nitrophenyl)amino)methyl)azetidine-1-carboxylate (for a preparation see Intermediate 271, 355 mg, 0.684 mmol), THF (12 mL), 5-methyl-6-oxo-1,6-dihydropyridine-3-carbaldehyde (for a preparation see Intermediate 1, 94 mg, 0.684 mmol) and a solution of sodium hydrosulfite (417 mg, 2.396 mmol) in Water (3 mL). The vial was capped and the mixture heated in a microwave using initial normal to 1000° C. for 5 hours. The organic solvent was removed in vacuo and replaced with ethanol (12 mL). The vial was capped and the mixture heated in a microwave to 1000° C. for a total of 5 hours. The mixture was diluted with EtOAc and water, the layers mixed and separated before the organics were passed through a hydrophobic frit and concentrated in vacuo to give a yellow oil. The oil was loaded in dichloromethane and purified by Biotage SP4 SNAP 25 g silica using a gradient of 0-100% ethyl acetate-cyclohexane over 15 CV followed by 0-20% MeOH-DCM over 15 CV. The appropriate fractions were combined and evaporated in vacuo to give the title compound (60 mg, 0.099 mmol, 14.47% yield) as a yellow oil. LCMS (System A): $t_{RET}$=0.88 min; MH$^+$ 606.

Intermediate 271: (S)-tert-butyl 3-(((4-(((1-(cyclopentyloxy)-4-methyl-1-oxopentan-2-yl)amino)methyl)-2-nitrophenyl)amino)methyl)azetidine-1-carboxylate A round bottom flask was charged with (S)-cyclopentyl 2-((4-fluoro-3-nitrobenzyl)amino)-4-methylpentanoate (for a preparation see Intermediate 137, 230 mg, 0.653 mmol), acetonitrile (10 mL), potassium carbonate (180 mg, 1.305 mmol) and tert-butyl 3-(aminomethyl)azetidine-1-carboxylate (146 mg, 0.783 mmol). An air condensor was fitted and the mixture warmed to 800° C. under a blanket of nitrogen for 1 week. The mixture was diluted with water and ethyl acetate, the layers mixed and separated before the organics were washed with brine. The organics were passed through a hydrophobic frit and concentrated in vacuo to give an orange oil. The oil was loaded in dichloromethane and purified by Biotage SP4 SNAP 25 g silica (Si) using a gradient of 0-40% ethyl acetate-cyclohexane over 15 CV. The appropriate fractions were combined and evaporated in vacuo to give the title compound (355 mg, 0.684 mmol, 105% yield) as an orange oil. LCMS (System A): $t_{RET}$=1.07 min; MH$^+$ 519.

Intermediate 272: (S)-tert-butyl 3-((2-(1,5-dimethyl-6-oxo-1,6-dihydropyridin-3-yl)-5-((((S)-1-isopropoxy-3-methyl-1-oxobutan-2-yl)amino)methyl)-1H-benzo[d]imidazol-1-yl)methyl)piperidine-1-carboxylate (S)-tert-butyl 3-((2-(1,5-dimethyl-6-oxo-1,6-dihydropyridin-3-yl)-5-formyl-1H-benzo[d]imidazol-1-yl)methyl)piperidine-1-carboxylate (for an example preparation see intermediate 130, 500 mg, 1.076 mmol) was added to a solution of (S)-isopropyl 2-amino-3-methylbutanoate, phenylmethane sulphonic acid salt (for a preparation see Intermediate 65, 713 mg, 2.153 mmol) in Dichloromethane (DCM) (10 mL). The resulting solution was stirred overnight and sodium triacetoxyborohydride (684 mg, 3.23 mmol) added. The resulting suspension was stirred for 1 h. MeOH (10 mL) was added and the resulting solution loaded on to a 10 g SCX cartridge. The cartridge was eluted with MeOH (50 mL), followed by 2 M methanolic ammonia (50 mL). The basic fractions were evaporated in vacuo to a brown gum. The gum was dissolved in DCM and purified by silica gel chromatography eluting with DCM:2M methanolic ammonia (0-5%). The product containing fractions were evaporated in vacuo to give the title compound. The total yield of the reaction was 28%. LCMS (System C): $t_{RET}$=0.75 min, MH$^+$=608.

Intermediate 273: 2-(1,5-dimethyl-6-oxo-1,6-dihydropyridin-3-yl)-1-methyl-1H-benzo[d]imidazole-5-carbaldehyde 5-(5-(hydroxymethyl)-1-methyl-1H-benzo[d]imidazol-2-yl)-1,3-dimethylpyridin-2(1H)-one (for a preparation see Intermediate 90, 931 mg, 3.29 mmol) was dissolved in dichloromethane (DCM) (52 mL). To the stirred solution was added 2-iodoxybenzoic acid (2249 mg, 3.61 mmol). The mixture was stirred under nitrogen at room temperature for 2.5 hrs then 1,1,1-Triacetoxy-1,1-dihydro-1,2-benziodoxol-3(1H)-one 1,1,1-Triacetoxy-1,1-dihydro-1,2-benziodoxol-3 (1H)-one (1394 mg, 3.29 mmol) was added portion wise to the stirred solution. The mixture was stirred at room temperature overnight. The solution was then partitioned between saturated sodium bicarbonate (200 mL) and dichloromethane (100 mL), the phases separated and the aqueous phase extracted twice with dichloromethane (100 mL×2). The organics were then combined and dried using a hydrophobic frit and the solvent removed under vacuum. To the residue was added a few mLs of dichloromethane followed by a few mLs of 2M NaOH and the solution was stirred for 15 min. The mixture was then partitioned between dichloromethane (50 mL) and saturated sodium bicarbonate (50 mL) and the phases separated taking care not to allow any of the precipitated solid to enter the organic phase. The aqueous phase was then washed twice with dichloromethane (2×50 mL) and the organics combined. The solution was then dried with a hydrophobic frit and the solvent removed under vacuum producing 2-(1,5-dimethyl-6-oxo-1,6-dihydropyridin-3-yl)-1-methyl-1H-benzo[d]imidazole-5-carbaldehyde (438 mg, 1.557 mmol, 47.4% yield) as a pale yellow solid. The precipitated solid was isolated by filtration and dried under suction to yield an additional batch of 2-(1,5-dimethyl-6-oxo-1,6-dihydropyridin-3-yl)-1-methyl-1H- benzo[d]imidazole-5-carbaldehyde (200 mg, 0.710 mmol, 21.6% yield) as a light brown solid. LCMS (System B): $t_{RET}$=0.66 min, MH+=282.

Intermediate 274: 1-ethyl-2-(5-methyl-6-oxo-1,6-dihydropyridin-3-yl)-1H-benzo[d]imidazole-5-carbaldehyde 5-(5-(hydroxymethyl)-1-isopropyl-1H-benzo[d]imidazol-2-yl)-1,3-dimethylpyridin-2(1H)-one (for a preparation see Intermediate 91, 722 mg, 2.319 mmol) was dissolved in dichloromethane (DCM) (5 mL) and then treated with 1,1,1-triacetoxy-1,1-dihydro-1,2-benziodoxol-3(1H)-one (983 mg, 2.319 mmol). The solution was stirred for 1 hr under nitrogen then 2M NaOH (15 mL) added and the solution stirred until the mixture became clear (15 min). The mixture was then partitioned between dichloromethane (150 mL) and saturated sodium bicarbonate (150 mL) and the phases separated. The aqueous layer was then extracted twice with saturated sodium bicarbonate (150 mL×2) and the organics combined. The organic layer was then dried using a hydrophobic frit and solvent removed in vacuo. The residue was then purified using automated chromatography using the following method: 100% ethyl acetate for 2 column volumes, 0%-25% ethanol in ethyl acetate over 15 column volumes then 25% ethanol in ethyl acetate over 2 column volumes. The appropriate fractions were then combined and solvent removed in vacuo to yield 2-(1,5-dimethyl-6-oxo-1,6-dihydropyridin-3-yl)-1-isopropyl-1H-benzo[d]imidazole-5-carbaldehyde (718.7 mg, 2.323 mmol, 100% yield) as a white solid. LCMS (System A): $t_{RET}$=0.70 min, MH+=310.

Intermediate 275: 2-(5-methyl-6-oxo-1,6-dihydropyridin-3-yl)-1-((4-methylmorpholin-2-yl)methyl)-1H-benzo[d]imidazole-5-carbaldehyde A solution of oxalyl chloride (0.124 ml, 1.411 mmol) in dichloromethane (2 mL) was cooled to −78° C. in acetone/dry-ice bath. To this, a solution of DMSO (0.213 ml, 3.01 mmol) in dichloromethane (3 mL) was added and the mixture was stirred at −78° C. for 10 minutes. A suspension of 5-(5-(hydroxymethyl)-1-((4-methylmorpholin-2-yl)methyl)-1H-benzo[d]imidazol-2-yl)-3-methylpyridin-2(1H)-one (400 mg, 1.086 mmol, for a preparation see intermediate 150) in dichloromethane (5 mL) was added and the reaction mixture was stirred at −78° C. for 2 hours. Triethylamine (1.059 ml, 7.60 mmol) was then added and the reaction mixture was warmed up to room temperature. It was stirred under nitrogen at room temperature overnight. The reaction mixture was partitioned between saturated sodium hydrogen carbonate solution (40 mL) and DCM (40 mL) and the layers were separated. The aqueous layer was extracted with DCM (3×40 mL) and then with 25% methanol in DCM (2×40 mL). The organic layers were combined, dried using a hydrophobic frit and evaporated under reduced pressure to give a colourless gum. The sample was loaded in dichloromethane and purified by Biotage SP4 SNAP 25 g silica using a gradient of 0-20% dichloromethane-2M ammonia in methanol over 20 column volumes followed by holding at 20% dichloromethane-2M ammonia in methanol for 5 column volumes. The pure fractions were combined and evaporated under reduced pressure to give a colourless gum. The less pure fractions containing product were combined separately and the solvent was removed under reduced pressure. This impure crude sample was loaded in dichloromethane and repurified by Biotage SP4 SNAP 25 g silica using a gradient of 4-16% dichloromethane-2M ammonia in methanol over 20 column volumes followed by holding at 16% dichloromethane-2M ammonia in methanol for 5 column volumes. The appropriate fractions were combined and evaporated under reduced pressure. This was combined with the pure sample from the earlier run to give the crude product 2-(5-methyl-6-oxo-1,6-dihydropyridin-3-yl)-1-((4-methylmorpholin-2-yl)methyl)-1H-benzo[d]imidazole-5-carbaldehyde (137.8 mg, 0.376 mmol, 34.6% yield) as a pale yellow solid. The sample was loaded in dichloromethane/methanol and repurified by Biotage SP4 SNAP 25 g silica using a gradient of 10-25% methanol-chloroform over 20 column volumes followed by holding at 25% methanol-chloroform for 5 column volumes. The appropriate fractions were combined and evaporated under reduced pressure to give the title compound (53.6 mg, 0.146 mmol, 13.47% yield) as a white solid. LCMS (System B): $t_{RET}$=0.65 min, MH+=367.

Intermediate 276: (S)-Cyclopentyl 2-amino-3-hydroxypropanoate, 4-methylbenzenesulphonic acid salt To a suspension of (S)-2-amino-3-hydroxypropanoic acid (15 g, 143 mmol) in cyclohexane (150 mL), cyclopentanol (98 g, 1142 mmol) and 4-methylbenzenesulfonic acid (32.0 g, 186 mmol) were added at room temperature were added. The reaction mixture was stirred at 100° C. for 24 hr. The reaction mixture was evaporated in vacuo to give the crude products as a brown oil. The brown oil was allowed to cool and the resulting crystals filtered, washed with EtOAc (50 mL) to give (S)-cyclopentyl 2-amino-3-hydroxypropanoate, 4-methylbenzenesulphonic acid salt (38 g, 110 mmol, 77% yield) as a white solid. $^1$H NMR δ (400 MHz, DMSO-$d_6$) ppm: 8.28 (3H, br. s.), 7.47 (2H, d, J=8.1 Hz), 7.11 (2H, d, J=7.8 Hz), 5.55 (1H, br. s.), 5.19 (1H, t, J=5.7 Hz), 3.81 (1H, dd, J=11.4, 3.8 Hz), 3.73 (1H, dd, J=11.4, 2.8 Hz), 2.29 (3H, s), 1.93-1.78 (2H, m), 1.67 (4H, d, J=5.6 Hz), 1.63-1.50 (2H, m).

Intermediate 277: (S)-Cyclopentyl 2-aminopropanoate, 4-methylbenzenesulphonic acid salt A round bottom flask was charged with (S)-2-aminopropanoic acid (20 g, 224 mmol), cyclohexane (101 mL), tosic acid monohydrate (55.5 g, 292 mmol) and cyclopentanol (166 ml, 1836 mmol). A Dean-Stark condensor was fitted and the mixture was stirred at 110° C. for 48 h. The reaction mixture was cooled to room temperature and then the solvent was evaporated in vacuo to give the crude product as a brown liquid. The crude product was dissolved in a minimum volume of hot EtOAc (20 mL). The solution was allowed to cool and the resulting crystals filtered, washed with a small amount of EtOAc (10 mL×3) and dried in an oil vacuum to give (S)-cyclopentyl 2-aminopropanoate, 4-methylbenzenesulphonic acid salt (58 g, 174 mmol, 78% yield) as a white solid. $^1$H NMR δ (400 MHz, DMSO-$d_6$) ppm: 8.23 (3H, br. s.), 7.47 (2H, d, J=8.1 Hz), 7.12 (2H, d, J=7.8 Hz), 5.18 (1H, t, J=5.9 Hz), 4.05 (1H, q, J=6.7 Hz), 2.29 (3H, s), 1.92-1.79 (2H, m), 1.72-1.53 (6H, m), 1.36 (3H, d, J=7.3 Hz).

Intermediate 278: 2-(1,5-dimethyl-6-oxo-1,6-dihydropyridin-3-yl)-1-(2-hydroxyethyl)-1H-benzo[d]imidazole-5-carbaldehyde To 5-(1-(2-hydroxyethyl)-5-(hydroxymethyl)-1H-benzo[d]imidazol-2-yl)-1,3-dimethylpyridin-2(1H)-one (for a preparation see Intermediate 243, 975 mg, 3.11 mmol) and Dess-Martin periodinane (660 mg, 1.556 mmol) was added dichloromethane (40 mL). The mixture was stirred for 1.5 hours then Dess-Martin periodinane (660 mg, 1.556 mmol) was added. The mixture was stirred for an additional 18 hours. Dess-Martin periodinane (66 mg, 0.156 mmol) was added and stirred for 2 hours. Dess-Martin periodinane (66 mg, 0.156 mmol) was added and stirred for 2 hours. Dess-Martin periodinane (75 mg, 0.38 mmol) was then added and the mixture stirred for 2 hours. To the mixture was added 2M aq sodium hydroxide solution (20 mL) and the mixture stirred for 10 minutes until the mixture became clear. Water (20 mL) and dichloromethane (60 mL) were then added and the phases separated. Aqueous phase was then extracted with dichloromethane (100 mL×2) and the organic phases combined and dried using a hydrophobic frit. Solvents were then removed in vacuo. This yielded an off-white solid 2-(1,5-dimethyl-6-oxo-1,6-dihydropyridin-3-yl)-1-(2-hydroxyethyl)-1H-benzo[d]imidazole-5-carbaldehyde (675 mg, 2.168 mmol, 69.7% yield). LCMS (System A): $t_{RET}$=0.53 min; MH$^+$ 312.

Intermediate 279: (S)-(R)-1-methoxypropan-2-yl 2-((tert-butoxycarbonyl)amino)-3-methylbutanoate A mixture of (S)-2-((tert-butoxycarbonyl)amino)-3-methylbutanoic acid (1.0 g, 4.60 mmol), diisopropylethylamine (1.19 g, 1.608 mL, 9.21 mmol), 1-hydroxybenzotriazole hydrate (HOBt) (846 mg, 5.52 mmol), EDC (1.06 g, 5.53 mmol), and (R)-1-methoxypropan-2-ol (1.037 g, 1.127 mL, 11.5 mmol) in DMF (5 mL) was stirred at room temperature overnight. The reaction mixture was partitioned between ethyl acetate (15 mL) and sat'd NaHCO$_3$ (15 mL). The organic phase was washed with 1M hydrochloric acid (15 mL), water (15 mL) and brine (15 mL). The organic phase was dried and evaporated under reduced pressure to give the title compound as a colourless oil (1.2 g, 90% yield). $^1$H NMR (CDCl$_3$): δ 0.89 (m, 3H), 0.96 (m, 3H), 1.24 (d, J=6.6 Hz, 3H), 1.45 (s, 9H), 2.16 (m, 1H), 3.36 (s, 3H), 3.44 (m, 2H), 4.23 (m, 1H), 5.05 (m, 1H), 5.13 (m, 1H).

Intermediate 280: (S)-(R)-1-methoxypropan-2-yl 2-amino-3-methylbutanoate, Hydrochloride (S)-(R)-1-methoxypropan-2-yl 2-((tert-butoxycarbonyl) amino)-3-methylbutanoate (for a preparation see Intermediate 279, 1.15 g, 3.97 mmol) was dissolved in ethyl acetate (2 mL). The solution was treated with 4M hydrogen chloride in dioxan (2 mL). The reaction mixture was stirred at room temperature overnight. The solvent was evaporated to give the title compound as a colourless gum (425 mg, 47.4% yield). $^1$H NMR (CDCl$_3$): δ 1.15 (m, 6H), 1.29 (d, J=6.4 Hz, 3H), 2.47 (m, 1H), 3.35 (s, 3H), 3.47 (m, 2H), 3.95 (m, 1H), 5.18 (m, 1H), 8.79 (m, 3H).

Intermediate 281: (S)-cyclopentyl 2-aminopentanoate hydrochloride (S)-2-aminopentanoic acid (2.5 g, 21.34 mmol) was added to cyclopentanol (30 mL) and the suspension was brought to −5° C. using a dry ice/acetone bath. After stirring at this temperature for ten minutes, thionyl chloride (3.58 mL, 49.1 mmol) was added dropwise. The suspension was left stirring and allowed to warm up to room temperature. It was then stirred at this temperature for 18 hours. The reaction mixture was warmed to 60° C. and stirred at this temperature for 24 hours. The reaction mixture was concentrated under reduced pressure. The product was recrystallised from ethyl acetate, filtered, washed and dried to give the title product (2.62 g, 86% yield) as a white solid. $^1$H NMR (d6-DMSO): δ 0.89 (t, J=7.3 Hz, 3H), 1.31 (m, 1H), 1.42 (m, 1H), 1.67 (m, 8H), 1.86 (m, 2H), 3.91 (m, 1H), 5.19 (m, 1H), 8.49 (m, 3H).

Intermediate 282: (S)-(S)-tetrahydrofuran-3-yl 2-((tert-butoxycarbonyl)amino)-3-methylbutanoate A mixture of (S)-2-((tert-butoxycarbonyl)amino)-3-methylbutanoic acid (2.5 g, 11.51 mmol), diisopropylethylamine (2.97 g, 4.02 mL, 23.01 mmol), 1-hydroxybenzotriazole hydrate (2.12 g, 13.84 mmol), EDC (2.65 g, 13.81 mmol), and (S)-tetrahydrofuran-3-ol (5.07 g, 3.91 mL, 57.5 mmol) in DMF (20 mL) was stirred at room temperature overnight. The reaction mixture was partitioned between ethyl acetate (50 mL) and saturated sodium bicarbonate (50 mL). The organic phase was washed with 1 M hydrochloric acid (50 mL), water (50 mL) and brine (50 mL). The organic phase was dried and evaporated to give the title compound (2.73 g, 9.50 mmol, 83% yield), as a colourless oil. $^1$H NMR (CDCl$_3$): δ 0.90 (d, J=7.1 Hz, 3H) 0.97 (d, J=6.9 Hz, 3H) 1.45 (s, 9H) 2.01-2.09 (m, 1H) 2.10-2.24 (m, 2H) 3.80 (d, J=10.8 Hz, 1H) 3.83-3.97 (m, 3H) 5.04 (d, J=8.8 Hz, 1H) 5.27-5.43 (m, 1H).

Intermediate 283: (S)—(S)-tetrahydrofuran-3-yl 2-amino-3-methylbutanoate hydrochloride A solution of (S)-(S)-tetrahydrofuran-3-yl 2-((tert-butoxycarbonyl)amino)-3-methylbutanoate (for an example preparation see Intermediate 282, 2.73 g, 9.50 mmol) in ethyl acetate (5 mL) was treated with 4 M hydrogen chloride in dioxan (5 mL). The reaction mixture was stirred at room temperature for 24 hours. The solvent was evaporated. Attempted trituration with diethyl ether did not give solid. The solvent was evaporated to give the title compound (1.98 g, 8.85 mmol, 93% yield) as a colourless oil. Sample solidified on standing at room temperature for several days. $^1$H NMR (d$_6$-DMSO): δ 0.95 (d, J=6.9 Hz, 2H) 1.00 (d, J=6.9 Hz, 3H) 1.94-2.02 (m, 1H) 2.13-2.25 (m, 2H) 3.71-3.84 (m, 5H) 5.33-5.37 (m, 1H) 8.70 (br.s., 3H).

Intermediate 284: (S)-3-(1-(tert-butoxycarbonyl)-1H-imidazol-4-yl)-2-((tert-butoxycarbonyl)amino) propanoic acid Solid (S)-2-((tert-butoxycarbonyl)amino)-3-(1H-imidazol-4-yl)propanoic acid (48.27 g, 189 mmol) was dissolved in a solution of sodium bicarbonate (15.89 g, 189 mmol) in water (200 mL) and 1,4-dioxane (500 mL), di-tert-butyl dicarbonate (43.9 mL, 189 mmol) was added at 0° C. The reaction mixture was stirred at 25° C. overnight. The reaction mixture was evaporated and the residue partitioned between water (500 mL) and ether (500 mL). Then to the aqueous was added saturated KHSO$_4$ to adjust pH=4, extracted with ethyl acetate (3×500 mL) and saturated brine (500 mL), dried over sodium sulfate and evaporated in vacuo to give the title compound (40 g, 113 mmol, 60% yield) as a white solid. $^1$H NMR (CDCl$_3$): δ 1.38, 1.60 (2×s, total 18H) 3.16, 3.25 (2×m, total 2H) 4.48 (m, 1H) 5.54 (m, 1H) 7.21 (s, 1H) 8.17 (s, 1H).

Intermediate 285: (S)-tert-butyl 4-(2-((tert-butoxycarbonyl)amino)-3-(cyclopentyloxy)-3-oxopropyl)-1H-imidazole-1-carboxylate To a solution of (S)-3-(1-(tert-butoxycarbonyl)-1H-imidazol-4-yl)-2-((tert-butoxycarbonyl)amino)propanoic acid (For an example preparation see Intermediate 284, 40 g, 1126 mmol) and cyclopentanol (97 g, 1126 mmol) in DCM (200 mL), DCC (232 g, 1126 mmol) and DMAP (13.75 g, 113 mmol) was added. The reaction mixture was stirred at 25° C. overnight. The reaction was filtered through a separatory funnel, rinsed with Dichloromethane (DCM) (200 mL), and the filtrate collected. The filtrate was washed with water (200 mL), saturated brine (200 mL), dried over sodium sulphate and evaporated in vacuo to give the crude product. The crude product was added to a silica gel column and was eluted with Hex/EtOAc=4:1. Collected fractions: the title compound (36 g, 851 mmol, 75.6% yield) as a brown oil. $^1$H NMR (CDCl$_3$): b 1.45 (s, 9H) 1.59-1.71 (m, 11H), 1.8 (m, 6H) 3.05 (d, 2H) 4.52 (m, 1H) 5.21 (m, 1H) 5.70 (d, 1H) 7.16 (s, 1H) 8.03 (s, 1H).

Intermediate 286: (S)-cyclopentyl 2-amino-3-(1H-imidazol-4-yl)propanoate dihydrochloride To solid (S)-tert-butyl 4-(2-((tert-butoxycarbonyl)amino)-3-(cyclopentyloxy)-3-oxopropyl)-1H-imidazole-1-carboxylate (For an example preparation see Intermediate 285, 36 g, 52.7 mmol), 4 M hydrochloric acid in ethyl acetate (400 ml, 1600 mmol) was added. The reaction mixture was stirred at 25° C. for 24 hr. Another hydrochloric in dioxane (400 mL) addition was made and the reaction mixture was stirred at 25° C. for 24 hr. The reaction mixture was filtered, the resulting solid was filtered through a separatory funnel, rinsed with ethyl acetate (25 mL), and collected as a white solid, the title compound (14.3 g) which was assumed to be two HCl salt. The filtrate was evaporated in vacuo to give the crude product. The crude product was triturated with ethyl acetate (50 mL). The resulting solid was filtered through a separatory funnel, rinsed with ethyl acetate (25 mL), and collected the title compound (7.7 g) as an orange solid, which was assumed to be the bis hydrochloride salt. $^1$H NMR (MeOD): δ 1.61-1.78 (m, 6H) 1.95-1.95 (m, 2H) 3.37 (m, 2H) 4.43 (m, 1H) 5.30-5.33 (m, 1H) 7.56 (s, 1H) 9.00 (s, 1H).

Intermediate 287: (2R,3S)-isopropyl 2-amino-3-hydroxybutanoate hydrochloride

Acetyl chloride (17.91 mL, 252 mmol) was added dropwise to propan-2-ol (120 mL, 1557 mmol) while cooling in an ice bath, then the mixture was stirred for 30 min at room temperature. After that (2R,3S)-2-amino-3-hydroxybutanoic acid (10 g, 84 mmol) was added to the reaction mixture and then the reaction mixture was heated at 800° C. for 16 h. The reaction mixture was concentrated under reduced pressure and the resultant residue was azeotroped with toluene (2×50 mL), then triturated with ether (50 mL) and dried to get the title compound (2R,3S)-isopropyl 2-amino-3-hydroxybutanoate hydrochloride (8 g, 48.2% yield) as a white semi solid. LCMS (System G): $t_{RET}$=1.37 min; MH$^+$ 162

Intermediate 288: (2S,3S)-isopropyl 2-amino-3-hydroxybutanoate hydrochloride

Acetyl chloride (4.48 mL, 63.0 mmol) was added dropwise to iPrOH (30.0 mL, 389 mmol) while cooling in an ice bath, the mixture was then stirred for 30 minutes at room temperature before the addition of (2S,3S)-2-amino-3-hydroxybutanoic acid (2.5 g, 20.99 mmol). The mixture was then heated to 80° C. giving a dense white suspension, which clarified on further heating to a clear colourless solution. This was heated overnight. The reaction mixture was cooled and evaporated in vacuo to give a white solid, the residue was azeotroped with toluene (20 mL), then triturated with ether (20 mL), giving the crude title compound (2S,3S)-isopropyl 2-amino-3-hydroxybutanoate hydrochloride (2.69 g, 65% yield) as a white solid. The crude product was used directly in the next step without further purification.
$^1$H NMR (400 MHz, METHANOL-d$_4$) δ 5.27-5.46 (m, 1H), 4.38-4.59 (m, 2H), 4.19-4.27 (m, 1H), 1.29-1.60 (m, 13H (9H from desired compound, plus overlapping isopropanol impurity)) Overall purity is 66% by NMR.

Intermediate 289: (2R,3R)-isopropyl 2-amino-3-hydroxybutanoate hydrochloride

Acetyl chloride (448 μL, 6.30 mmol) was added dropwise to iPrOH (2999 μL, 38.9 mmol) while cooling in an ice bath, the mixture was then stirred for 30 minutes at room temperature before the addition of (2R,3R)-2-amino-3-hydroxybutanoic acid (250 mg, 2.099 mmol). The mixture was then heated to 80° C. giving a dense white suspension, which clarified on further heating to a clear colourless solution. This was heated over the weekend. The reaction mixture was cooled and evaporated in vacuo to give a white solid, the residue was azeotroped with toluene (20 mL), then triturated with ether (20 mL), giving the title compound (2R,3R)-isopropyl 2-amino-3-hydroxybutanoate hydrochloride (169.9 mg, 33%) as a white solid.
$^1$H NMR (400 MHz, CHLOROFORM-d) • 8.35 (br. s., 3H), 5.18 (td, J=6.24, 12.47 Hz, 1H), 4.48-4.65 (m, 1H), 4.31 (m, 1H), 1.38 (d, J=6.60 Hz, 3H), 1.33 (d, J=6.36 Hz, 6H).

Intermediate 290: Isopropyl 2-amino-3-hydroxybutanoate hydrochloride

Acetyl chloride (35.8 ml, 504 mmol) was added drop wise to propan-2-ol (240 ml, 3115 mmol) while cooling in an ice bath, then the mixture was stirred for 30 min at room temperature. After that 2-amino-3-hydroxybutanoic acid (20 g, 168 mmol) was added to the reaction mixture and then reaction mixture was heated at 800° C. for 16 h. The reaction mixture concentrated under reduced pressure and the resultant residue was azeotroped with Toluene (2×100 mL), then triturated with ether (100 mL) and dried to get the title compound isopropyl 2-amino-3-hydroxybutanoate, hydrochloride (24 g, 121 mmol, 72.3% yield) as a white semi solid. LCMS (System G): $t_{RET}$=1.39 min; MH$^+$ 162.

Intermediate 291: 5-(1-(1,3-dimethoxypropan-2-yl)-5-(oxiran-2-yl)-1H-benzo[d]imidazol-2-yl)-1,3-dimethylpyridin-2(1H)-one 1-(1,3-dimethoxypropan-2-yl)-2-(1,5-dimethyl-6-oxo-1,6-dihydropyridin-3-yl)-1H-benzo[d]imidazole-5-carbaldehyde (for an example preparation see Intermediate 224, 2.0 g, 5.41 mmol), trimethyl sulfonium iodide (1.127 g, 5.52 mmol) and potassium hydroxide (1.823 g, 32.5 mmol) in acetonitrile (20 mL)/water (0.5 mL) were stirred under nitrogen at room temperature. The reaction mixture was then stirred at 65° C. for 2 h. The reaction was then quenched with water (20 mL) and extracted with ethyl acetate (50 mL×2), the combined organic layer was washed with brine, dried (Na$_2$SO$_4$), filtered and concentrated to give the title product 5-(1-(1,3-dimethoxypropan-2-yl)-5-(oxiran-2-yl)-1H-benzo[d]imidazol-2-yl)-1,3-dimethylpyridin-2(1H)-one (2.0 g, yield 92%). The crude product was carried through to the next step without further purification. LCMS (System H): $t_{RET}$=4.31 min; MH$^+$ 384.

Intermediate 292: 1,3-dimethyl-5-(5-(oxiran-2-yl)-1-((tetrahydro-2H-pyran-4-yl)methyl)-1H-benzo[d]imidazol-2-yl)pyridin-2(1H)-one To a solution of 2-(1,5-dimethyl-6-oxo-1,6-dihydropyridin-3-yl)-1-((tetrahydro-2H-pyran-4-yl)methyl)-1H-benzo[d]imidazole-5-carbaldehyde (For a preparation see Intermediate 116, 1 g, 2.62 mmol), trimethylsulfonium iodide (0.536 g, 2.62 mmol) in Acetonitrile (15 mL) and water (0.075 mL) stirred under nitrogen at room temp was added neat potassium hydroxide (0.884 g, 15.75 mmol) in one charge at rt. The reaction mixture was stirred at 65° C. for 3 hr. Reaction was diluted with EtOAc (50 mL) and reaction mixture was passed through hydrophobic frit and filtrate was concentrated under reduced pressure to produce a crude residue. The crude residue was diluted with saturated sodium bicarbonate solution (50 mL) and EtOAc (100 mL). The aqueous layer was separated and re-extracted with EtOAc (2×200 mL). The combined organic phases were washed with water (50 mL) and brine solution (50 mL). The organic layer was dried over Na$_2$SO$_4$, filtered and the filtrate was concentrated to afford the crude title compound 1,3-dimethyl-5-(5-(oxiran-2-yl)-1-((tetrahydro-2H-pyran-4-yl)methyl)-1H-benzo[d]imidazol-2-yl)pyridin-2(1H)-one (900 mg, 62.3% yield) as a light yellow solid. The crude product was carried through to the next step without further purification. LCMS (System H): $t_{RET}$=3.28 min; MH$^+$ 380.

Intermediate 77: (3-nitro-4-(((tetrahydro-2H-pyran-4-yl)methyl)amino)phenyl)methanol A solution of (tetrahydro-2H-pyran-4-yl)methanamine (5.23 mL, 40.9 mmol), (4-fluoro-3-nitrophenyl)methanol (3.5 g, 20.45 mmol) and N-ethyl-N-isopropylpropan-2-amine (17.86 mL, 102 mmol) in tetrahydrofuran (THF) (10 mL) was degassed and heated under nitrogen at 60° C. for 5 hours. The reaction mixture was partitioned between ethyl acetate (150 mL) and saturated solution of sodium bicarbonate (150 mL). The organic layer was isolated and the aqueous fraction was re-extracted twice with ethyl acetate (2×150 mL). The organic fractions were combined, passed through a hydrophobic frit and concentrated under reduced pressure. The residue was dissolved in a minimum amount of ethyl acetate and loaded onto a silica column (100 g, SPE). The product was eluted with a gradient of 0-60% of ethyl acetate in cyclohexane. Product containing fractions were combined and concentrated under reduced pressure to yield the title compound (4957 mg, 91% yield) as an orange solid. LCMS (System B): $t_{RET}$=0.79 min; MH$^+$ 267.

Intermediate 96: 5-(5-(hydroxymethyl)-1-((tetrahydro-2H-pyran-4-yl)methyl)-1H-benzo[d]imidazol-2-yl)-1,3-dimethylpyridin-2(1H)-one To a solution of (3-nitro-4-(((tetrahydro-2H-pyran-4-yl)methyl)amino)phenyl)methanol (for an example preparation see Intermediate 77, 2.05 g, 7.70 mmol,) in ethanol (60 mL) was added 1,5-dimethyl-6-oxo-1,6-dihydropyridine-3-carbaldehyde (for an example preparation see Intermediate 2, 1.455 g, 7.70 mmol) and sodium hydrosulfite (4.76 g, 23.09 mmol), followed by water. The reaction mixture was heated at 90° C. for 2 days. The reaction mixture was concentrated to approximately half the volume under reduced pressure, and the resulting liquid partitioned between 3:1 chloroform: isopropanol (3×150 mL) and saturated aqueous sodium bicarbonate solution (150 mL). The organic layers were combined, dried using a hydrophobic frit and evaporated under reduced pressure. The sample was loaded in dichloromethane and purified by Biotage SP4 SNAP 100 g silica using a gradient of 0-25% cyclohexane-(25% ethanol in ethyl acetate) over 10 column volumes followed by holding at 25% cyclohexane-(25% ethanol in ethyl acetate) for 5 column volumes, followed by a gradient of 0-100% cyclohexane-(25% ethanol in ethyl acetate) over 10 column volumes, followed by 25% ethanol in ethyl acetate over 10 column volumes. The appropriate fractions were combined and evaporated under reduced pressure to give the required product 5-(5-(hydroxymethyl)-1-((tetrahydro-2H-pyran-4-yl)methyl)-1H-benzo[d]imidazol-2-yl)-1,3-dimethylpyridin-2(1H)-one (1.22 g, 3.32 mmol, 43.1% yield) as an off-white foam. LCMS (System B): $t_{RET}$=0.63 min; MH$^+$ 368.

Intermediate 116: 2-(1,5-dimethyl-6-oxo-1,6-dihydropyridin-3-yl)-1-((tetrahydro-2H-pyran-4-yl)methyl)-1H-benzo[d]imidazole-5-carbaldehyde 5-(5-(hydroxymethyl)-1-((tetrahydro-2H-pyran-4-yl)methyl)-1H-benzo[d]imidazol-2-yl)-1,3-dimethylpyridin-2(1H)-one (for an example preparation see Intermediate 96, 7 g, 19.05 mmol) was dissolved in dichloromethane (DCM) (200 mL) and manganese dioxide (6.62 g, 76 mmol) was added, the mixture was heated at reflux for 2 h before the mixture was filtered and the solid washed with DCM. The filtrate was evaporated in vacuo to give 2-(1,5-dimethyl-6-oxo-1,6-dihydropyridin-3-yl)-1-((tetrahydro-2H-pyran-4-yl)methyl)-1H-benzo[d]imidazole-5-carbaldehyde (6.6 g, 18.06 mmol, 95% yield) as a pale yellow foam. LCMS (System J): $t_{RET}$=0.75 min; MH$^+$ 366.

Example Preparation

Example 1: (S)-cyclopentyl 4-methyl-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)pentanoate

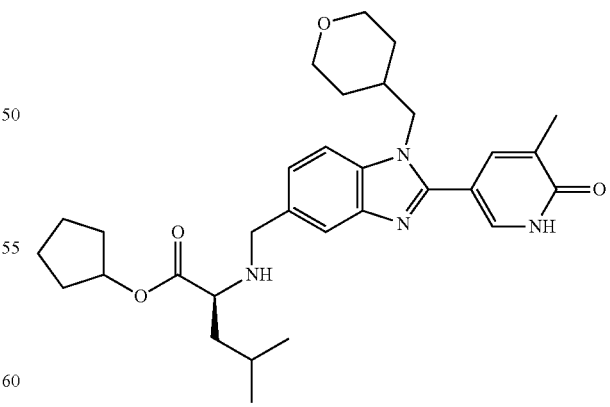

A round bottom flask was charged with 5-methyl-6-oxo-1,6-dihydropyridine-3-carbaldehyde (For an example preparation see Intermediate 1, 203 mg, 1.482 mmol), sodium hydrosulfite (821 mg, 4.72 mmol), Water (10 mL), and a solution of (S)-cyclopentyl-4-methyl-2-((3-nitro-4-(((tetrahydro-2H-pyran-4-yl)methyl)amino)benzyl)amino)pentanoate (For an example preparation, see Intermediate 182, 603 mg, 1.347 mmol) in Ethanol (20 mL). A condensor was fitted and the slurry refluxed at 100° C. overnight. The mixture was diluted with water and EtOAc, the layers mixed and separated before the organic layer was passed through a hydrophobic frit and concentrated in vacuo to give a yellow oil. The sample was loaded in dichloromethane and purified by silica gel column chromatography using a gradient of 0-100% ethyl acetate-cyclohexane over 15 column volumes followed 0-10% 2M ammonia in methanol-dichloromethane for 15 column volumes. The appropriate fractions were combined and evaporated in vacuo to give the title compound (140 mg) as a colourless oil that solidified under high vacuum. LCMS (System A): $t_{RET}$=0.78 min; $MH^+$=535.

The following Examples were prepared in a similar manner to Example 1:
(In the tables, details of the LCMS system used, retention time ($t_{RET}$), $MH^+$, reaction yield and % yield are provided for each Example).

Example 2: (S)-cyclopentyl 4-methyl-2-(((2-(5-methyl-6-oxo-1,6-dihydropyridin-3-yl)-1-(1-methylpiperidin-4-yl)-1H-benzo[d]imidazol-5-yl)methyl)amino)pentanoate (prepared from: Intermediate 181)
System B, 1.10 min, $MH^+$ = 534, Yield: 38 mg, 12%

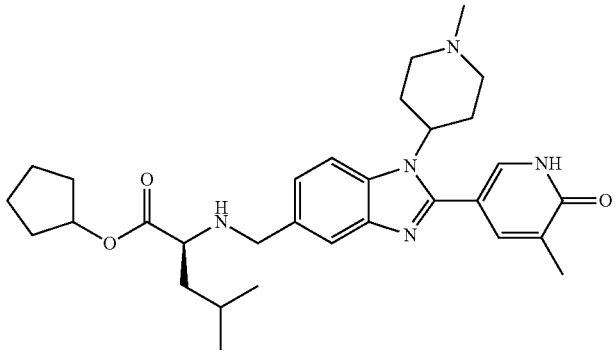 [SMILES: Cc1cc(-c2nc3cc(CN[C@@H](CC(C)C)C(=O)OC4CCCC4)ccc3n2C2CCN(C)CC2)c[nH]c1=O]

Example 3: (S)-cyclopentyl 2-(((1-(2-methoxyethyl)-2-(5-methyl-6-oxo-1,6-dihydropyridin-3-yl)-1H-benzo[d]imidazol-5-yl)methyl)amino)-4-methylpentanoate (prepared from: Intermediate 184)
System A, 0.82 min, $MH^+$ = 495, Yield: 206 mg, 48%

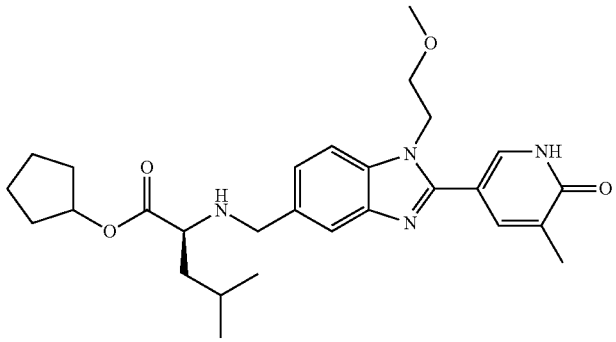 [SMILES: COCCn1c(-c2c[nH]c(=O)c(C)c2)nc2cc(CN[C@@H](CC(C)C)C(=O)OC3CCCC3)ccc21]

Example 4: (S)-cyclopentyl 2-(((1-(2-(dimethylamino)ethyl)-2-(5-methyl-6-oxo-1,6-dihydropyridin-3-yl)-1H-benzo[d]imidazol-5-yl)methyl)amino)-4-methylpentanoate (prepared from: Intermediate 185) System A, 0.69 min, $MH^+$ = 508, Yield: 240 mg, 37%

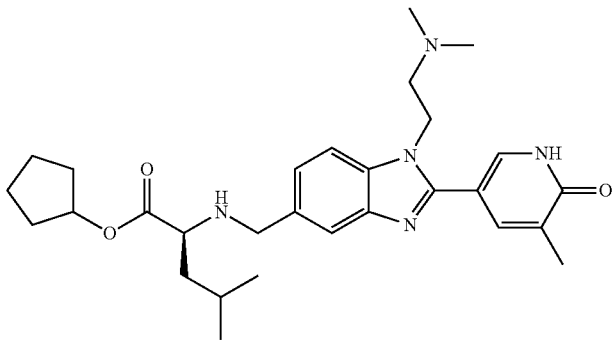 [SMILES: Cc1cc(-c2nc3cc(CN[C@@H](CC(C)C)C(=O)OC4CCCC4)ccc3n2CCN(C)C)c[nH]c1=O]

Example 5: (S)-cyclopentyl 2-(((1-(3-hydroxypropyl)-2-(5-methyl-6-oxo-1,6-dihydropyridin-3-yl)-1H-benzo[d]imidazol-5-yl)methyl)amino)-4-methylpentanoate (prepared from: Intermediate 186)
System A, 0.75 min, $MH^+$ = 495, Yield: 120 mg, 22%

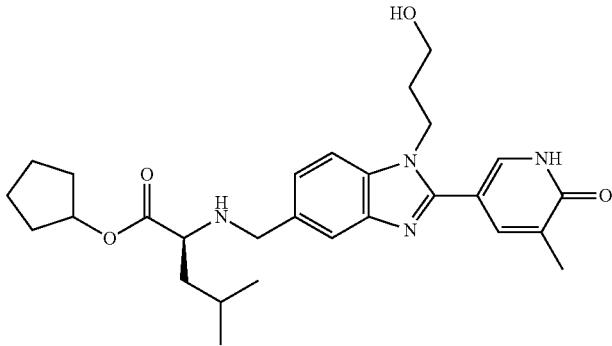 [SMILES: Cc1cc(-c2nc3cc(CN[C@@H](CC(C)C)C(=O)OC4CCCC4)ccc3n2CCCO)c[nH]c1=O]

Example 6: (S)-cyclopentyl 4-methyl-2-(((1-methyl-2-(5-methyl-6-oxo-1,6-dihydropyridin-3-yl)-1H-benzo[d]imidazol-5-yl)methyl)amino)pentanoate (prepared from:
Intermediate 187) System A, 0.73 min, MH⁺ = 451, Yield: 35 mg, 33%

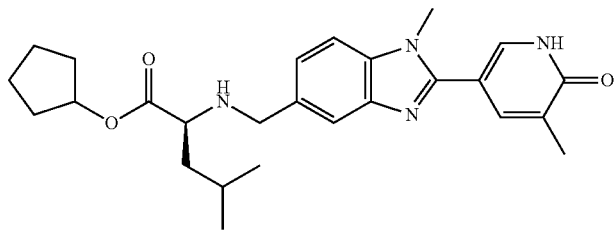 [SMILES: Cc1cc(-c2nc3cc(CN[C@@H](CC(C)C)C(=O)OC4CCCC4)ccc3n2C)c[nH]c1=O]

Example 7: (2S)-cyclopentyl 4-methyl-2-(((2-(5-methyl-6-oxo-1,6-dihydropyridin-3-yl)-1-((4-methylmorpholin-2-yl)methyl)-1H-benzo[d]imidazol-5-yl)methyl)amino)pentanoate (prepared from:
Intermediate 143) System A, 0.65 min, MH⁺ = 550, Yield: 290 mg, 35%

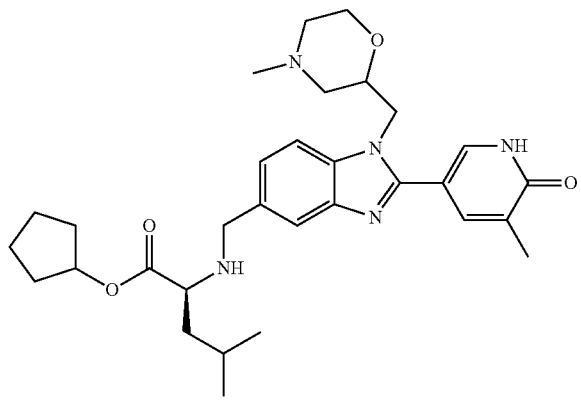 [SMILES: Cc1cc(-c2nc3cc(CN[C@@H](CC(C)C)C(=O)OC4CCCC4)ccc3n2CC2CN(C)CCO2)c[nH]c1=O]

Example 8: (2S)-cyclopentyl 2-(((2-(5-methyl-6-oxo-1,6-dihydropyridin-3-yl)-1-((4-methylmorpholin-2-yl)methyl)-1H-benzo[d]imidazol-5-yl)methyl)amino)propanoate (prepared from:
Intermediate 145) System B, 0.89 min, MH⁺ = 508, Yield: 119 mg, 15%

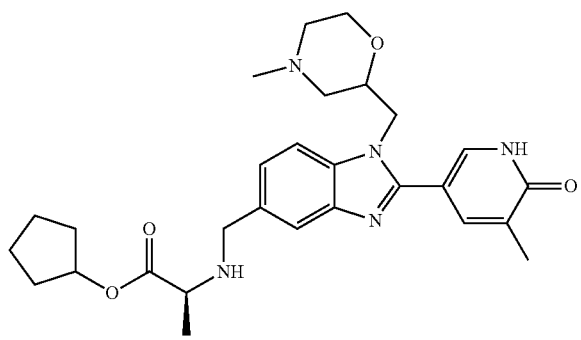 [SMILES: Cc1cc(-c2nc3cc(CN[C@@H](C)C(=O)OC4CCCC4)ccc3n2CC2CN(C)CCO2)c[nH]c1=O]

Example 9: (2S)-cyclopentyl 3-methyl-2-(((2-(5-methyl-6-oxo-1,6-dihydropyridin-3-yl)-1-((4-methylmorpholin-2-yl)methyl)-1H-benzo[d]imidazol-5-yl)methyl)amino)butanoate (prepared from:
Intermediate 147) System B,
1.06 min, MH⁺ = 536, Yield: 348 mg, 38%

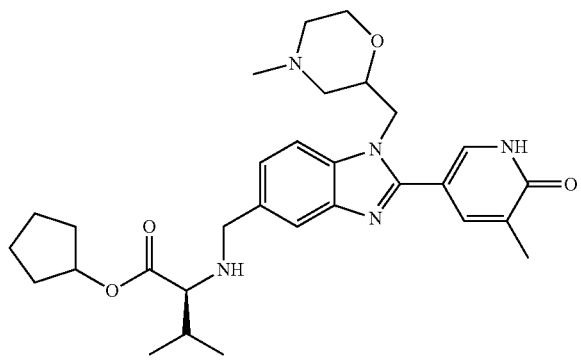 [SMILES: Cc1cc(-c2nc3cc(CN[C@H](C(=O)OC4CCCC4)C(C)C)ccc3n2CC2CN(C)CCO2)c[nH]c1=O]

Example 10: (S)-cyclopentyl 4-methyl-2-(((2-(5-methyl-6-oxo-1,6-dihydropyridin-3-yl)-1-((1-methylpiperidin-4-yl)methyl)-1H-benzo[d]imidazol-5-yl)methyl)amino)pentanoate (prepared from: Intermediate 149) System B, 1.14 min, MH⁺ = 548, Yield: 237 mg, 34%

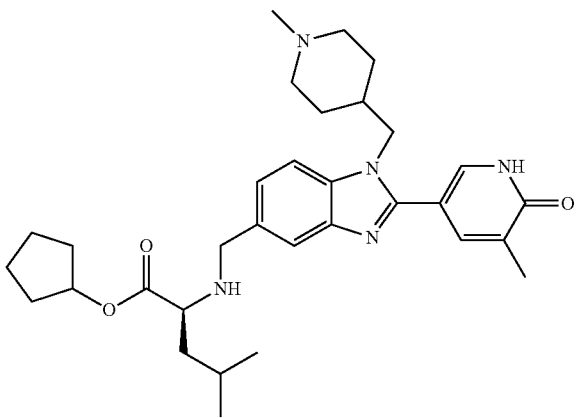 [SMILES: Cc1cc(-c2nc3cc(CN[C@@H](CC(C)C)C(=O)OC4CCCC4)ccc3n2CC2CCN(C)CC2)c[nH]c1=O]

Example 11: (S)-tert-butyl 4-methyl-2-(((2-(5-methyl-6-oxo-1,6-dihydropyridin-3-yl)-1-(1-methylpiperidin-4-yl)-1H-benzo[d]imidazol-5-yl)methyl)amino)pentanoate (prepared from: Intermediate 189) System B, 1.07 min, MH⁺ = 522, Yield: 36 mg, 25%

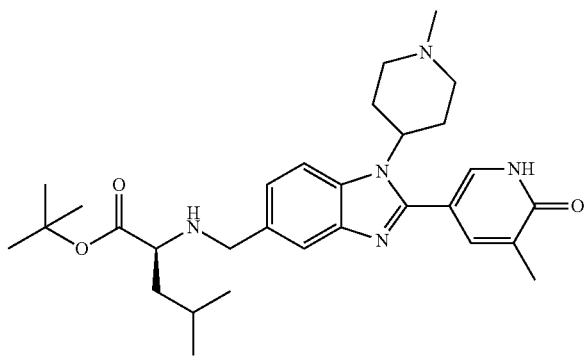 [SMILES: Cc1cc(-c2nc3cc(CN[C@@H](CC(C)C)C(=O)OC(C)(C)C)ccc3n2C2CCN(C)CC2)c[nH]c1=O]

Example 12: (S)-cyclopentyl 4-methyl-2-(((2-(5-methyl-6-oxo-1,6-dihydropyridin-3-yl)-1-((tetrahydro-2H-pyran-4-yl)methyl)-1H-benzo[d]imidazol-6-yl)methyl)amino)pentanoate (prepared from: Intermediate 190) System B, 1.14 min, MH⁺ = 535, Yield: 74 mg, 25%

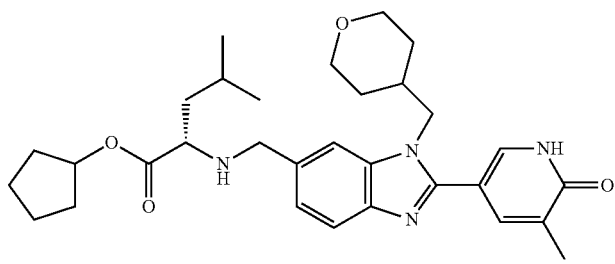 [SMILES: Cc1cc(-c2nc3ccc(CN[C@@H](CC(C)C)C(=O)OC4CCCC4)cc3n2CC2CCOCC2)c[nH]c1=O]

Example 7a and 7b: (S)-cyclopentyl 4-methyl-2-(((2-(5-methyl-6-oxo-1,6-dihydropyridin-3-yl)-1-(((R)-4-methylmorpholin-2-yl)methyl)-1H-benzo[d]imidazol-5-yl)methyl)amino)pentanoate and (S)-cyclopentyl 4-methyl-2-(((2-(5-methyl-6-oxo-1,6-dihydropyridin-3-yl)-1-(((S)-4-methylmorpholin-2-yl)methyl)-1H-benzo[d]imidazol-5-yl)methyl)amino)pentanoate

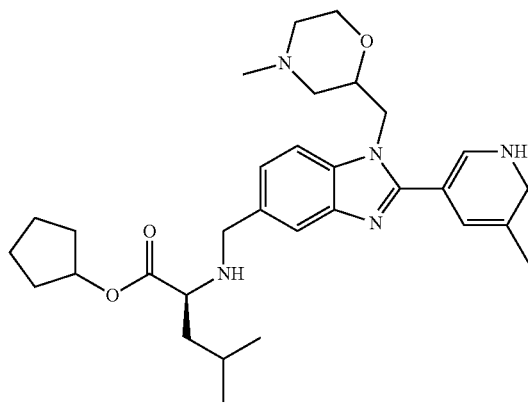

Example 7 (95 mg) was dissolved in Ethanol (2 mL) and purified by chiral chromatography (stationary phase: Chiralpak AD-H 5 μm particles, mobile phase: heptane/ethanol) (N20771-72). The combined fractions containing pure Isomer 1 were concentrated in vacuo and the solid residue was transferred to a weighed flask using a mixture of methanol and dichloromethane, which was removed in vacuo. The material was dried in a vacuum oven at 45° C. for 4 hours and at ambient temperature for 24 hours to give pure Isomer 1 (Example 7a) as a colourless solid (39.8 mg). HPLC-UV: RT 16.73 minutes, ca. 99.7% isomeric purity by area HPLC @ 280 nM. LCMS (System B): $t_{RET}$=1.11 min, MH$^+$=550. The combined fractions containing pure Isomer 2 were concentrated in vacuo and the solid residue was transferred to a weighed flask using a mixture of methanol and dichloromethane, which was removed in vacuo. The material was dried in a vacuum oven at 45° C. for 4 hours and at ambient temperature for 24 hours to give pure Isomer 2 (Example 7b) of the benzimidazole as a colourless solid (41.2 mg). HPLC-UV: RT 21.09 minutes, ca. 99.4% isomeric purity by area HPLC @ 280 nM. LCMS (System B): $t_{RET}$=1.12 min, MH$^+$=550.

Example 13: (2S)-cyclopentyl 2-(((2-(1,5-dimethyl-6-oxo-1,6-dihydropyridin-3-yl)-1-((4-methylmorpholin-2-yl)methyl)-1H-benzo[d]imidazol-5-yl)methyl)amino)-4-methylpentanoate 1,5-dimethyl-6-oxo-1,6-dihydropyridine-3-carbaldehyde (For an example preparation see Intermediate 2, 196 mg, 1.297 mmol) and sodium dithionite (677 mg, 3.89 mmol) were added to a solution of (2S)-cyclopentyl 4-methyl-2-((4-(((4-methylmorpholin-2-yl)methyl)amino)-3-nitrobenzyl)amino)pentanoate (For a preparation see Intermediate 143, 600 mg, 1.297 mmol) in Ethanol (10 mL) and Water (5 mL) and the reaction mixture was heated by microwave irradiation to 1000° C. for 5 hours. The reaction mixture was partitioned between DCM (40 mL) and saturated sodium hydrogen carbonate solution (40 mL) and the layers were separated. The aqueous layer was extracted with DCM (3×40 mL) and the combined organic layers were dried using a hydrophobic frit and evaporated under reduced pressure. The crude sample was purified by silica gel column chromatography using a gradient of 0-10% dichloromethane-2M ammonia in methanol over 10 column volumes followed by 10% dichloromethane-2M ammonia in methanol for 5 column volumes. The appropriate fractions were combined and evaporated under reduced pressure. This crude sample was purified twice by MDAP (Method B) The appropriate fractions were combined and the solvent was evaporated under reduced pressure to give the title compound (202 mg) as an off-white solid. LCMS (System B): $t_{RET}$=1.16 min; MH$^+$=564.

The following Examples were prepared in a similar manner to Example 13:

Example 14: (S)-cyclopentyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-4-methylpentanoate (prepared from: Intermediate 182) System A, 0.85 min, MH+ = 548, Yield 140 mg, 27%

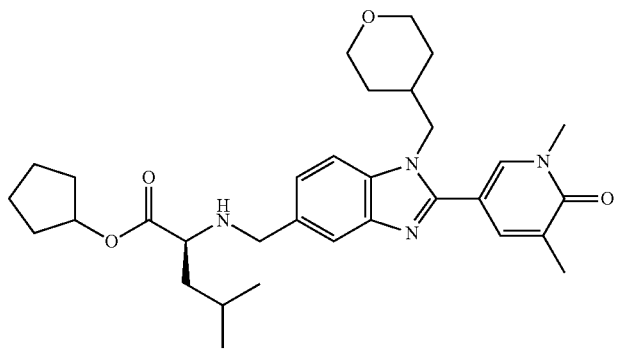 [SMILES: Cc1cc(-c2nc3cc(CN[C@@H](CC(C)C)C(=O)OC4CCCC4)ccc3n2CC2CCOCC2)cn(C)c1=O]

Example 15: (S)-cyclopentyl 2-(((2-(1,5-dimethyl-6-oxo-1,6-dihydropyridin-3-yl)-1-methyl-1H-benzo[d]imidazol-5-yl)methyl)amino)-4-methylpentanoate (prepared from: Intermediate 187) System A, 0.77 min, MH+ = 465, Yield 33 mg, 30%

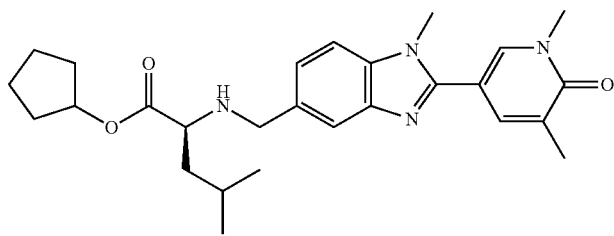 [SMILES: Cc1cc(-c2nc3cc(CN[C@@H](CC(C)C)C(=O)OC4CCCC4)ccc3n2C)cn(C)c1=O]

Example 16: (S)-cyclopentyl 3-methyl-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)butanoate

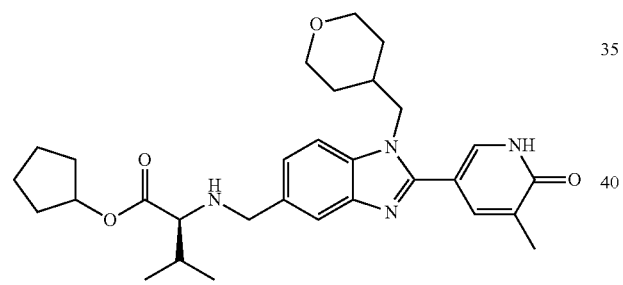

A suspension of 2-(5-methyl-6-oxo-1,6-dihydropyridin-3-yl)-1-((tetrahydro-2H-pyran-4-yl)methyl)-1H-benzo[d]imidazole-5-carbaldehyde (200 mg, 0.569 mmol, Intermediate 151) and (S)-cyclopentyl 2-amino-3-methylbutanoate 4-methylbenzenesulfonate (407 mg, 1.138 mmol, Intermediate 24) in DCM (10 mL) was stirred under nitrogen at room temperature. After 15 minutes, partial dissolution was achieved and sodium triacetoxyborohydride (241 mg, 1.138 mmol) was added to this. The reaction mixture was stirred under nitrogen at room temperature for 2 hours. The reaction mixture was partitioned between DCM (30 mL) and saturated sodium hydrogen carbonate solution (30 mL) and the layers were separated. The aqueous layer was extracted with DCM (3×30 mL) and the organic layers were combined, dried using a hydrophobic frit and evaporated under reduced pressure to give a white solid. The crude sample was dissolved in DMSO (3×1 mL) and purified by MDAP (Method B). The solvent was evaporated under reduced pressure to give the title compound (196.1 mg, 0.377 mmol, 66.2% yield) as a white solid. LCMS (System B): $t_{RET}$=1.11 min, MH+=521.

Example 17: (S)-4-methyl-2-(((2-(5-methyl-6-oxo-1,6-dihydropyridin-3-yl)-1-((tetrahydro-2H-pyran-4-yl)methyl)-1H-benzo[d]imidazol-6-yl)methylamino) pentanoic acid, hydrochloride

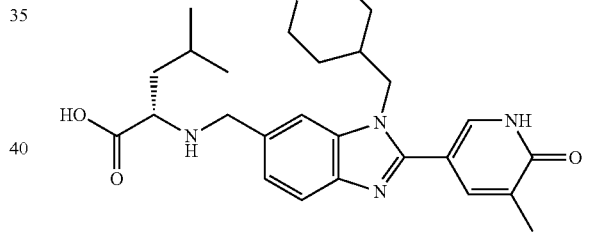

To a solution of (S)-cyclopentyl 4-methyl-2-(((2-(5-methyl-6-oxo-1,6-dihydropyridin-3-yl)-1-((tetrahydro-2H-pyran-4-yl)methyl)-1H-benzo[d]imidazol-6-yl)methyl)amino)pentanoate (For a preparation see Example 12, 35 mg, 0.065 mmol) in Methanol (2 mL) and THF (2 mL) was added 1 M aqueous lithium hydroxide (0.196 mL, 0.196 mmol), and the reaction mixture heated at 50° C. overnight. The reaction mixture was blown down under a stream of nitrogen. The sample was dissolved in 2 M aqueous hydrochloric acid (0.1 mL) and methanol (0.9 mL) and purified by MDAP (Method B). The solvent was blown down under a stream of nitrogen to give a white gum. The sample was suspended in tetrahydrofuran (1 mL) and 2 M aqueous hydrochloric acid (0.5 mL) added to give a clear solution. The mixture was blown down under a stream of nitrogen to give the title compound (22 mg) as an off-white solid. LCMS (System B): $t_{RET}$=0.55 min; MH+ 467.

The following Examples were prepared in a similar manner to Example 17:

Example 18: (S)-2-(((1-ethyl-2-(5-methyl-6-oxo-1,6-dihydropyridin-3-yl)-1H-benzo[d]imidazol-5-yl)methyl)amino)-4-methylpentanoic acid, hydrochloride (prepared from: Example 151) System B, 0.58 min, MH+ = 397, Yield 88 mg, 23%

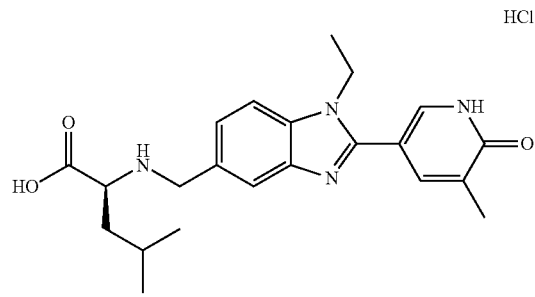 [SMILES: Cl ; CCn1c(-c2c[nH]c(=O)c(C)c2)nc2cc(CN[C@@H](CC(C)C)C(=O)O)ccc21]

Example 19: (S)-2-(((1-(2-methoxyethyl)-2-(5-methyl-6-oxo-1,6-dihydropyridin-3-yl)-1H-benzo[b]imidazol-5-yl)methyl)amino)-4-methylpentanoic acid, hydrochloride (prepared from: Example 3) System A, 0.48 min, MH+ = 427, Yield: 29 mg, 89%

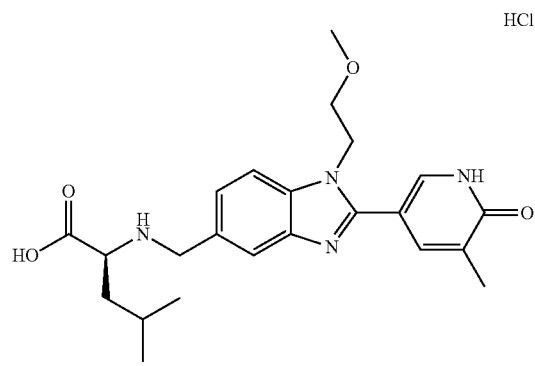 [SMILES: Cl ; COCCn1c(-c2c[nH]c(=O)c(C)c2)nc2cc(CN[C@@H](CC(C)C)C(=O)O)ccc21]

Example 20: (S)-2-(((1-(2-(dimethylamino)ethyl)-2-(5-methyl-6-oxo-1,6-dihydropyridin-3-yl)-1H-benzo[d]imidazol-5-yl)methyl)amino)-4-methylpentanoic acid, hydrochloride (prepared from: Example 4) System A, 0.38 min, MH+ = 440, Yield: 35 mg, 107%, (hygroscopic product)

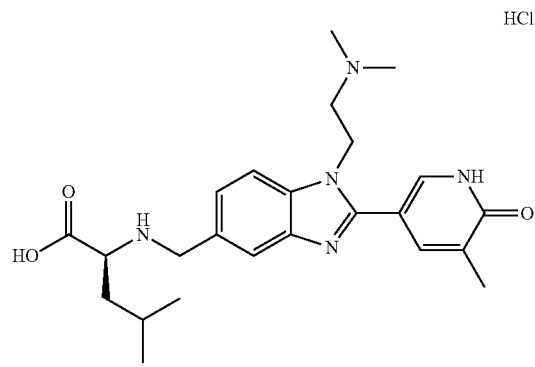 [SMILES: Cl ; Cc1cc(-c2nc3cc(CN[C@@H](CC(C)C)C(=O)O)ccc3n2CCN(C)C)c[nH]c1=O]

Example 21: (S)-2-(((1-(3-hydroxypropyl)-2-(5-methyl-6-oxo-1,6-dihydropyridin-3-yl)-1H-benzo[d]imidazol-5-yl)methyl)amino)-4-methylpentanoic acid, hydrochloride (prepared from: Example 5) System A, 0.42 min, MH+ = 427, Yield: 28 mg, 100%

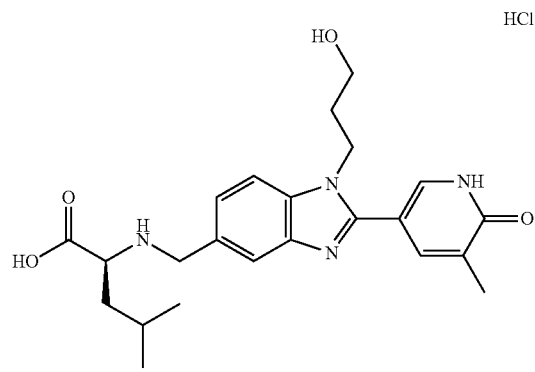 [SMILES: Cl ; Cc1cc(-c2nc3cc(CN[C@@H](CC(C)C)C(=O)O)ccc3n2CCCO)c[nH]c1=O]

Example 22: (S)-2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-4-methylpentanoic acid (prepared from: Example 14) System A, 0.52 min, MH⁺ = 481, Yield: 19 mg, 67%

HCl

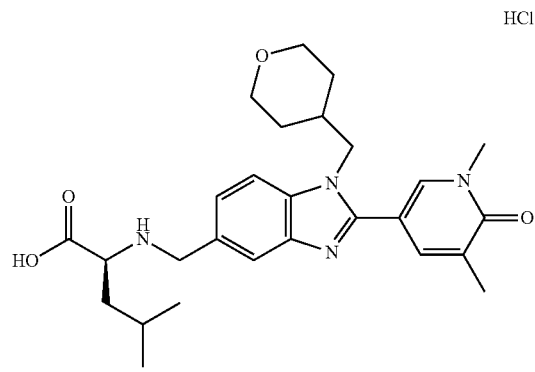 [SMILES: Cl ; Cc1cc(-c2nc3cc(CN[C@@H](CC(C)C)C(=O)O)ccc3n2CC2CCOCC2)cn(C)c1=O]

Example 23: (S)-2-(((2-(1,5-dimethyl-6-oxo-1,6-dihydropyridin-3-yl)-1-methyl-1H-benzo[d]imidazol-5-yl)methyl)amino)-4-methylpentanoic acid, hydrochloride (prepared from: Example 15) System A, 0.45 min, MH⁺ = 397, Yield: 8.7 mg, 93%

HCl

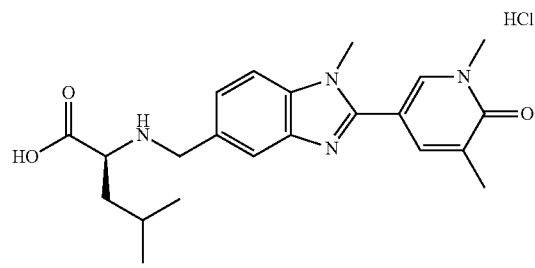 [SMILES: Cl ; Cc1cc(-c2nc3cc(CN[C@@H](CC(C)C)C(=O)O)ccc3n2C)cn(C)c1=O]

Example 24: (S)-4-methyl-2-(((1-methyl-2-(5-methyl-6-oxo-1,6-dihydropyridin-3-yl)-1H-benzo[d]imidazol-5-yl)methyl)amino)pentanoic acid, hydrochloride (prepared from: Example 6) System A, 0.42 min, MH⁺ = 383, Yield: 4.6 mg, 50%

HCl

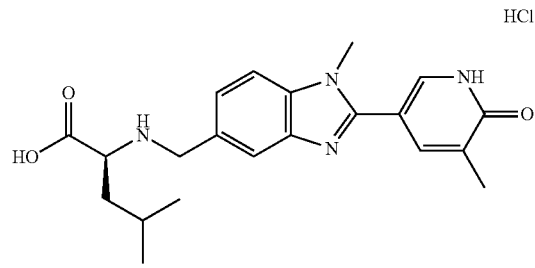 [SMILES: Cl ; Cc1cc(-c2nc3cc(CN[C@@H](CC(C)C)C(=O)O)ccc3n2C)c[nH]c1=O]

Example 25: (S)-2-(((2-(1,5-dimethyl-6-oxo-1,6-dihydropyridin-3-yl)-1-ethyl-1H-benzo[d]imidazol-5-yl)methyl)amino)-3-methoxypropanoic acid, hydrochloride (prepared from: Example 195) System A, 0.43 min, MH⁺ = 399, Yield: 12 mg, 31%

HCl

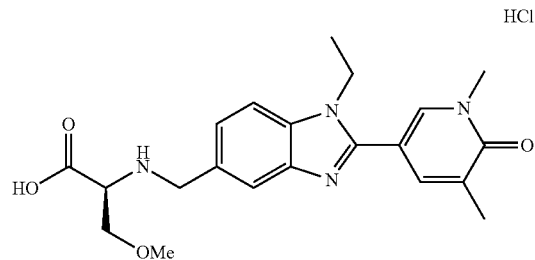 [SMILES: Cl ; CCn1c(-c2cc(C)c(=O)n(C)c2)nc2cc(CN[C@@H](COC)C(=O)O)ccc21]

Example 26: (S)-2-(((2-(1,5-dimethyl-6-oxo-1,6-dihydropyridin-3-yl)-1-ethyl-1H-benzo[d]imidazol-5-yl)methyl)amino)-4-methylpentanoic acid, hydrochloride (prepared from: Example 198) System A, 0.50 min, MH⁺ = 411, Yield: 21 mg, 54%

HCl

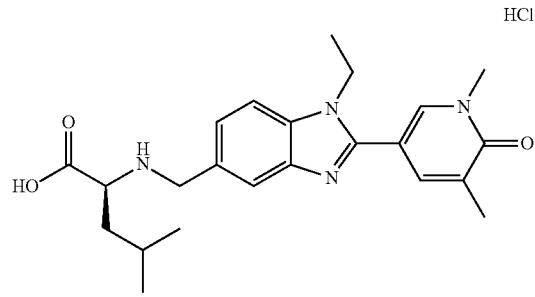 [SMILES: Cl ; CCn1c(-c2cc(C)c(=O)n(C)c2)nc2cc(CN[C@@H](CC(C)C)C(=O)O)ccc21]

Example 27: (S)-2-(((2-(1,5-dimethyl-6-oxo-1,6-dihydropyridin-3-yl)-1-(2-methoxyethyl)-1H-benzo[d]imidazol-5-yl)methyl)amino)-3-methoxypropanoic acid, hydrochloride (prepared from: Example 201) System A, 0.45 min, MH+ = 429, Yield: 22 mg, 55%

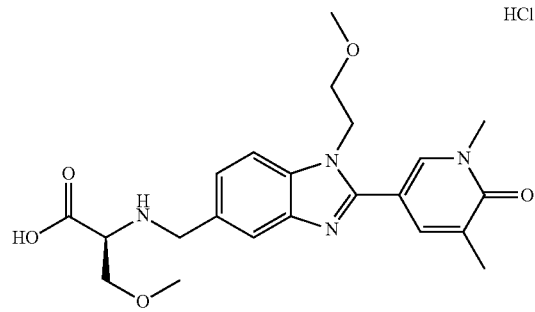 [SMILES: COCCn1c(-c2cc(C)c(=O)n(C)c2)nc2cc(CN[C@@H](COC)C(=O)O)ccc21 ; Cl]

HCl

Example 28: (2S,3R)-2-(((1-ethyl-2-(5-methyl-6-oxo-1,6-dihydropyridin-3-yl)-1H-benzo[d]imidazol-5-yl)methyl)amino)-3-hydroxybutanoic acid, hydrochloride (prepared from: Example 95) System A, 0.38 min, MH+ = 385, Yield: 14 mg, 38%

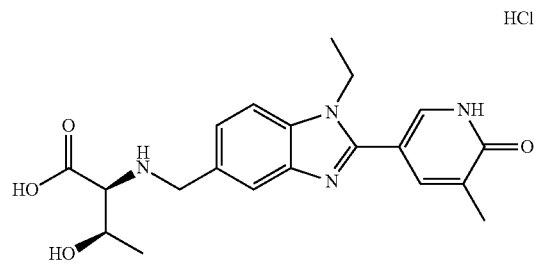 [SMILES: Cl ; CCn1c(-c2c[nH]c(=O)c(C)c2)nc2cc(CN[C@H](C(=O)O)[C@@H](C)O)ccc21]

HCl

Example 29: (2S,3R)-2-(((2-(1,5-dimethyl-6-oxo-1,6-dihydropyridin-3-yl)-1-ethyl-1H-benzo[d]imidazol-5-yl)methyl)amino)-3-hydroxybutanoic acid, hydrochloride (prepared from: Example 199) System A, 0.40 min, MH+ = 399, Yield: 16 mg, 44%

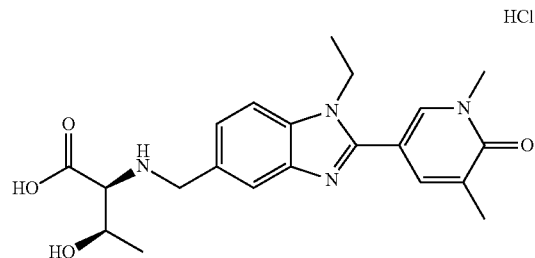 [SMILES: Cl ; CCn1c(-c2cc(C)c(=O)n(C)c2)nc2cc(CN[C@H](C(=O)O)[C@@H](C)O)ccc21]

HCl

Example 30: (2S,3R)-3-hydroxy-2-(((2-(5-methyl-6-oxo-1,6-dihydropyridin-3-yl)-1-(oxeten-3-ylmethyl)-1H-benzo[d]imidazol-5-yl)methyl)amino)butanoic acid hydrochloride (prepared from: Example 200) System A, 0.37 min, MH+ = 427, Yield: 11 mg, 27%

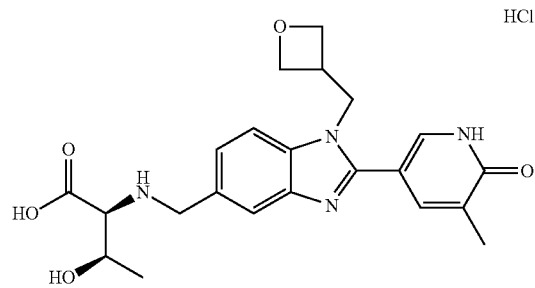 [SMILES: Cl ; Cc1cc(-c2nc3cc(CN[C@H](C(=O)O)[C@@H](C)O)ccc3n2CC2COC2)c[nH]c1=O]

HCl

Example 31: (2S,3R)-3-hydroxy-2-(((1-(2-methoxyethyl)-2-(5-methyl-6-oxo-1,6-dihydropyridin-3-yl)-1H-benzo[d]imidazol-5-yl)methyl)amino)butanoic acid hydrochloride (prepared from: Example 197) System A, 0.39 min, MH+ = 415, Yield: 16 mg, 41%

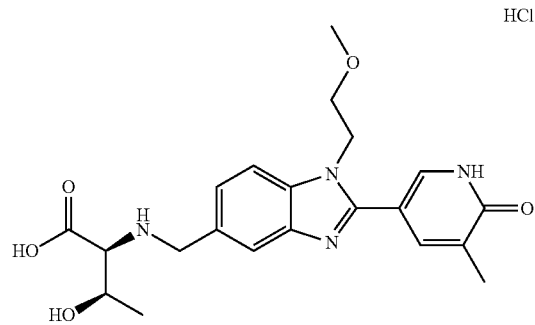 [SMILES: Cl ; COCCn1c(-c2c[nH]c(=O)c(C)c2)nc2cc(CN[C@H](C(=O)O)[C@@H](C)O)ccc21]

HCl

-continued

Example 32: (S)-2-(((2-(1,5-dimethyl-6-oxo-1,6-dihydropyridin-3-yl)-1-methyl-1H-benzo[d]imidazol-5-yl)methyl)amino)-3-methoxypropanoic acid hydrochloride (prepared from: Example 300) System A, 0.37 min, MH+ = 385, Yield: 7.1 mg, 20%

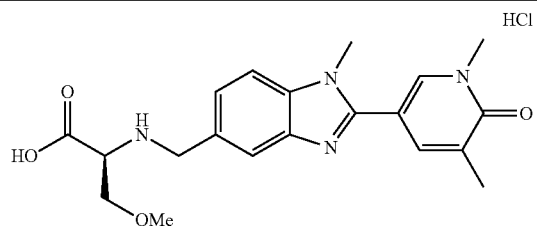

Example 33: (S)-2-(((2-(1,5-dimethyl-6-oxo-1,6-dihydropyridin-3-yl)-1-methyl-1H-benzo[d]imidazol-5-yl)methyl)amino)-3-methylbutanoic acid hydrochloride (prepared from: Example 285) System A, 0.38 min, MH+ = 383, Yield: 3.2 mg, 9%

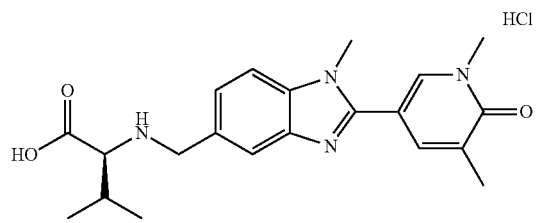 [SMILES: Cl ; Cc1cc(-c2nc3cc(CN[C@H](C(=O)O)C(C)C)ccc3n2C)cn(C)c1=O]

Example 34: (2S,3R)-2-(((2-(1,5-dimethyl-6-oxo-1,6-dihydropyridin-3-yl)-1-methyl-1H-benzo[d]imidazol-5-yl)methyl)amino)-3-hydroxybutanoic acid hydrochloride (prepared from: Example 155) System A, 0.34 min, MH+ = 385, Yield: 1.7 mg, 5%

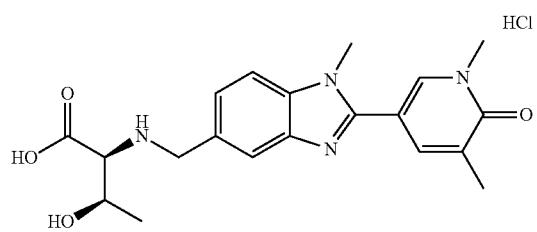 [SMILES: Cl ; Cc1cc(-c2nc3cc(CN[C@H](C(=O)O)[C@@H](C)O)ccc3n2C)cn(C)c1=O]

Example 35: (2S,3R)-2-(((2-(1,5-dimethyl-6-oxo-1,6-dihydropyridin-3-yl)-1-(2-methoxyethyl)-1H-benzo[d]imidazol-5-yl)methyl)amino)-3-hydroxybutanoic acid hydrochloride (prepared from: Example 204) System A, 0.39 min, MH+ = 429, Yield: 10 mg, 25%

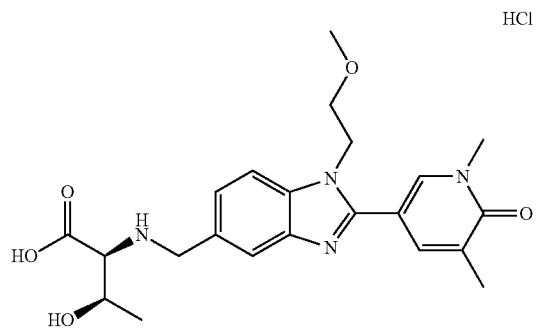 [SMILES: Cl ; COCCn1c(-c2cc(C)c(=O)n(C)c2)nc2cc(CN[C@H](C(=O)O)[C@@H](C)O)ccc21]

Example 36: (2S,3R)-2-(((1-(2-(dimethylamino)ethyl)-2-(5-methyl-6-oxo-1,6-dihydropyridin-3-yl)-1H-benzo[d]imidazol-5-yl)methyl)amino)-3-hydroxybutanoic acid dihydrochloride (prepared from: Example 203) System A, 0.29 min, MH+ = 428, Yield: 6 mg, 13%

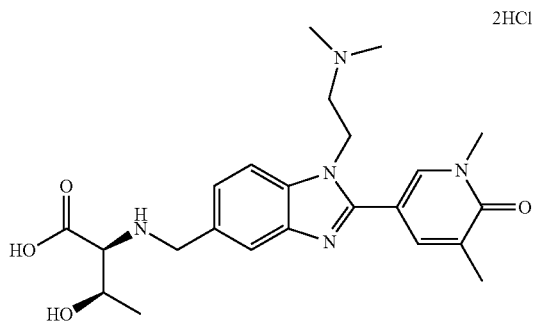 [SMILES: "2HCl" ; Cc1cc(-c2nc3cc(CN[C@H](C(=O)O)[C@@H](C)O)ccc3n2CCN(C)C)cn(C)c1=O]

Example 37: (2S,3R)-2-(((2-(1,5-dimethyl-6-oxo-1,6-dihydropyridin-3-yl)-1-((tetrahydro-2H-pyran-4-yl)methyl)-1H-benzo[d]imidazol-6-yl)methyl)amino)-3-hydroxybutanoic acid hydrochloride (prepared from: Example 105) System J, 0.52 min, MH+ = 469, Yield: 58 mg, 62%

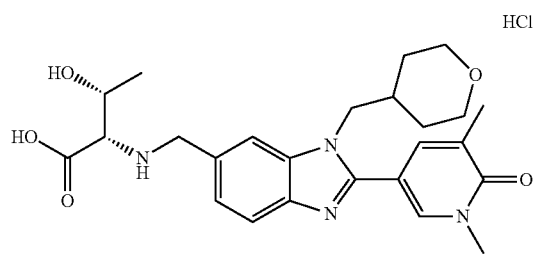 [SMILES: Cl ; Cc1cc(-c2nc3ccc(CN[C@H](C(=O)O)[C@@H](C)O)cc3n2CC2CCOCC2)cn(C)c1=O]

-continued

Example 38: (2S,3R)-2-(((1-((1,4-dioxan-2-yl)methyl)-2-(1,5-dimethyl-6-oxo-1,6-dihydropyridin-3-yl)-1H-benzo[d]imidazol-5-yl)methyl)amino)-3-hydroxybutanoic acid hydrochloride (prepared from: Example 109a) System B, 0.49 min, MH⁻ = 469, Yield: 30 mg, 48%

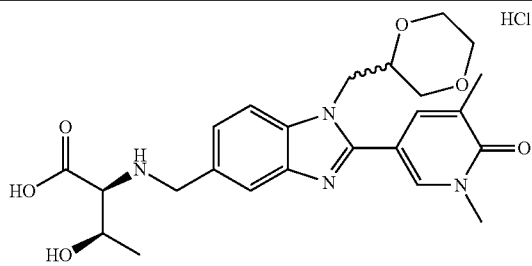

Example 39: (2S,3R)-2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-methoxybutanoic acid hydrochloride (prepared from: Example 114) System J, 0.54 min, MH⁺ = 469 Yield: 81 mg, 46%

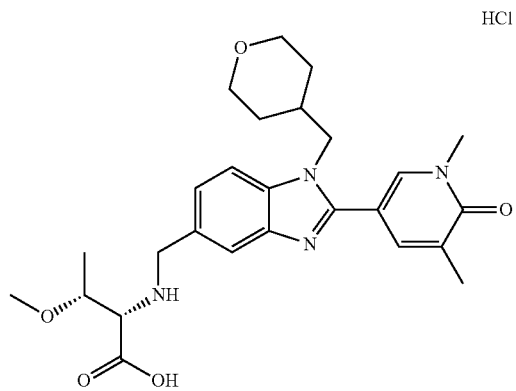 [SMILES: Cl ; CO[C@H](C)[C@H](NCc1ccc2c(c1)nc(-c1cc(C)c(=O)n(C)c1)n2CC1CCOCC1)C(=O)O]

Example 40: (2S,3R)-2-(((1-(((R)-1-acetylpiperidin-3-yl)methyl)-2-(1,5-dimethyl-6-oxo-1,6-dihydropyridin-3-yl)-1H-benzo[d]imidazol-6-yl)methyl)amino)-3-hydroxybutanoic acid hydrochloride (prepared from: Example 124) System J, 0.52 min, MH⁺ = 510, Yield: 21 mg, 77%

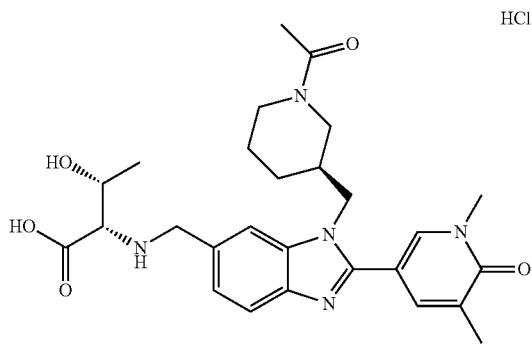 [SMILES: Cl ; CC(=O)N1CCC[C@H](Cn2c(-c3cc(C)c(=O)n(C)c3)nc3ccc(CN[C@H](C(=O)O)[C@@H](C)O)cc32)C1]

Example 41: (2S,3R)-2-(((2-(1,5-dimethyl-6-oxo-1,6-dihydropyridin-3-yl)-1-((S)-piperidin-3-ylmethyl)-1H-benzo[d]imidazol-6-yl)methyl)amino)-3-hydroxybutanoic acid hydrochloride (prepared from: Example 124) System J, 0.49 min, MH⁺ = 468, Yield: 6 mg, 22%

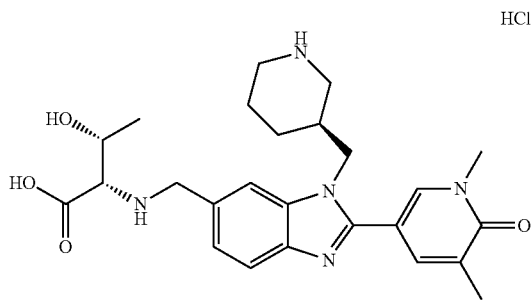 [SMILES: Cl ; Cc1cc(-c2nc3ccc(CN[C@H](C(=O)O)[C@@H](C)O)cc3n2C[C@H]2CCCNC2)cn(C)c1=O]

Example 42a: (2S,3R)-2-(((2-(1,5-dimethyl-6-oxo-1,6-dihydropyridin-3-yl)-1-(2-methoxypropyl)-1H-benzo[d]imidazol-5-yl)methyl)amino)-3-hydroxybutanoic acid hydrochloride (single diastereomer of unknown configuration at marked position, Isomer 1) (prepared from: Example 271b) System J, 0.55 min, MH⁺ = 443, Yield: 65 mg, 50%

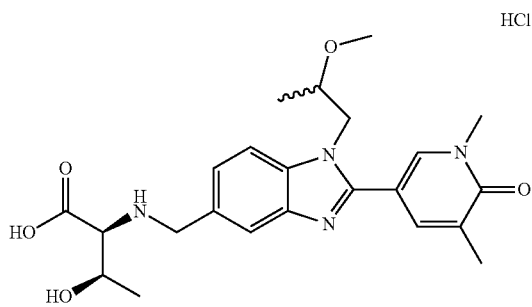 [SMILES: Cl ; COC(C)Cn1c(-c2cc(C)c(=O)n(C)c2)nc2cc(CN[C@H](C(=O)O)[C@@H](C)O)ccc21]

Example 42b: (2S,3R)-2-(((2-(1,5-dimethyl-6-oxo-1,6-dihydropyridin-3-yl)-1-(2-methoxypropyl)-1H-benzo[d]imidazol-5-yl)methyl)amino)-3-hydroxybutanoic acid hydrochloride (single diastereomer of unknown configuration at marked position, Isomer 2) (prepared from: Example 271a) System J, 0.55 min, MH$^+$ = 443, Yield: 50 mg, 38%

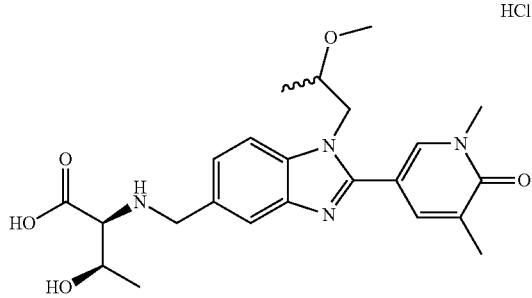 [SMILES: Cl ; COC(C)Cn1c(-c2cc(C)c(=O)n(C)c2)nc2cc(CN[C@H](C(=O)O)[C@@H](C)O)ccc21]

Example 43: (2S,3R)-2-(((1-(((S)-1-acetylpiperidin-3-yl)methyl)-2-(1,5-dimethyl-6-oxo-1,6-dihydropyridin-3-yl)-1H-benzo[d]imidazol-6-yl)methyl)amino)-3-hydroxybutanoic acid hydrochloride (prepared from: Example 128) System J, 0.51 min, MH$^+$ = 510, Yield: 10 mg, 51%

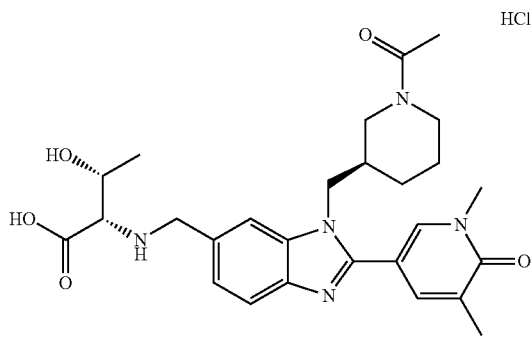 [SMILES: Cl ; CC(=O)N1CCC[C@@H](Cn2c(-c3cc(C)c(=O)n(C)c3)nc3ccc(CN[C@H](C(=O)O)[C@@H](C)O)cc32)C1]

Example 44: (2S,3R)-2-(((2-(1,5-dimethyl-6-oxo-1,6-dihydropyridin-3-yl)-1-(1-methoxybutan-2-yl)-1H-benzo[d]imidazol-5-yl)methyl)amino)-3-hydroxybutanoic acid hydrochloride (Single diastereomer of unknown configuration at marked position) (prepared from: Example 131a) System I, 0.48 min, MH$^+$ = 457, Yield: 13 mg, 67%

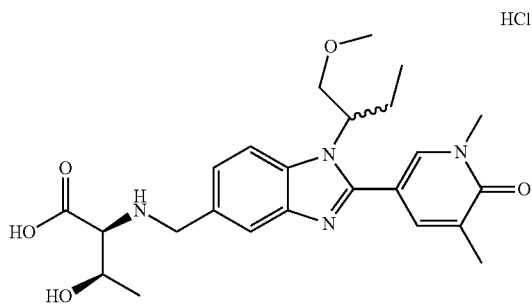 [SMILES: Cl ; CCC(COC)n1c(-c2cc(C)c(=O)n(C)c2)nc2cc(CN[C@H](C(=O)O)[C@@H](C)O)ccc21]

Example 45: (2S)-4-methyl-2-(((2-(5-methyl-6-oxo-1,6-dihydropyridin-3-yl)-1-((4-methylmorpholin-2-yl)methyl)-1H-benzo[d]imidazol-5-yl)methyl)amino)pentanoic acid, bis-hydrochloride (prepared from: Example 7) System B, 0.56 min, MH$^+$ = 482, Yield: 50 mg, 50%

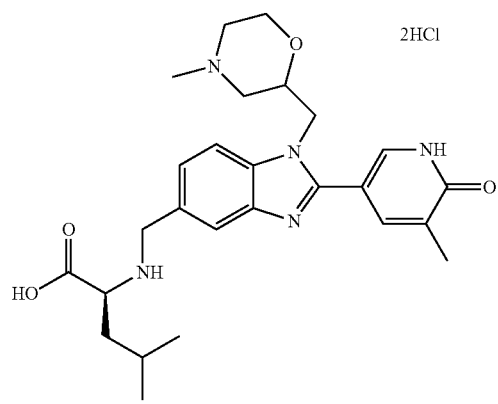 [SMILES: Cc1cc(-c2nc3cc(CN[C@@H](CC(C)C)C(=O)O)ccc3n2CC2CN(C)CCO2)c[nH]c1=O]

Example 46: (2S)-2-(((2-(5-methyl-6-oxo-1,6-dihydropyridin-3-yl)-1-((4-methylmorpholin-2-yl)methyl)-1H-benzo[d]imidazol-5-yl)methyl)amino)propanoic acid, bis hydrochloride (prepared from: Example 8) System B, 0.48 min, MH+ = 440, Yield: 32 mg, 57%

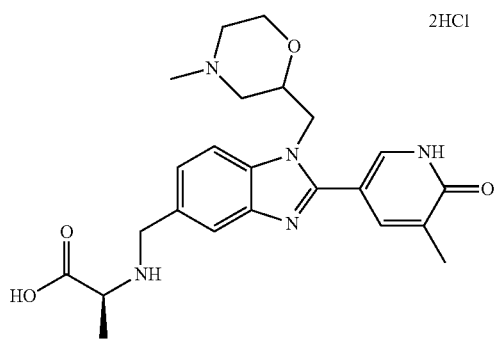 [SMILES: Cc1cc(-c2nc3cc(CN[C@@H](C)C(=O)O)ccc3n2CC2CN(C)CCO2)c[nH]c1=O ; "2HCl"]

Example 47: (2S)-3-methyl-2-(((2-(5-methyl-6-oxo-1,6-dihydropyridin-3-yl)-1-((4-methylmorpholin-2-yl)methyl)-1H-benzo[d]imidazol-5-yl)methyl)amino)butanoic acid, bis hydrochloride (prepared from: Example 9) System B, 0.52 min, MH+ = 468, Yield: 82 mg, 82%

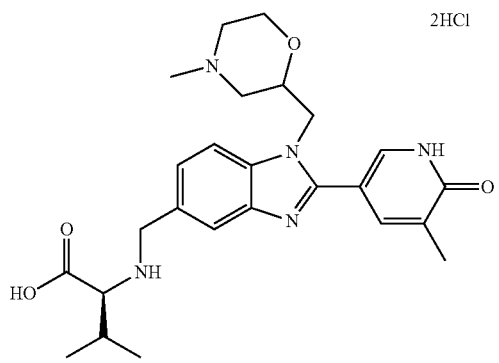 [SMILES: Cc1cc(-c2nc3cc(CN[C@H](C(=O)O)C(C)C)ccc3n2CC2CN(C)CCO2)c[nH]c1=O ; "2HCl"]

Example 48: (S)-4-methyl-2-(((2-(5-methyl-6-oxo-1,6-dihydropyridin-3-yl)-1-((1-methylpiperidin-4-yl)methyl)-1H-benzo[d]imidazol-5-yl)methyl)amino)pentanoic acid, bis hydrochloride (prepared from: Example 10) System B, 0.57 min, MH+ = 480, Yield: 56 mg, 56%

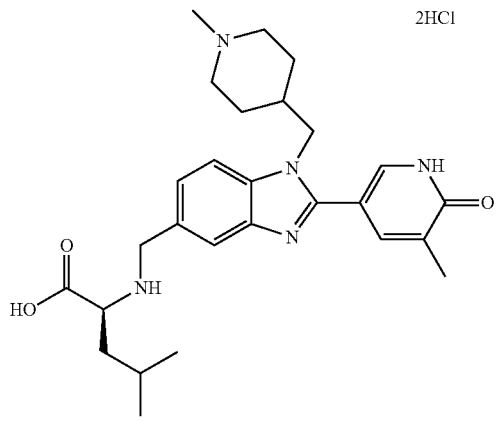 [SMILES: Cc1cc(-c2nc3cc(CN[C@@H](CC(C)C)C(=O)O)ccc3n2CC2CCN(C)CC2)c[nH]c1=O ; "2HCl"]

Example 49: (2S)-2-(((2-(1,5-dimethyl-6-oxo-1,6-dihydropyridin-3-yl)-1-((4-methylmorpholin-2-yl)methyl)-1H-benzo[d]imidazol-5-yl)methyl)amino)-4-methylpentanoic acid, bis hydrochloride (prepared from: Example 13) System B, 0.58 min, MH+ = 496, Yield: 56 mg, 55%

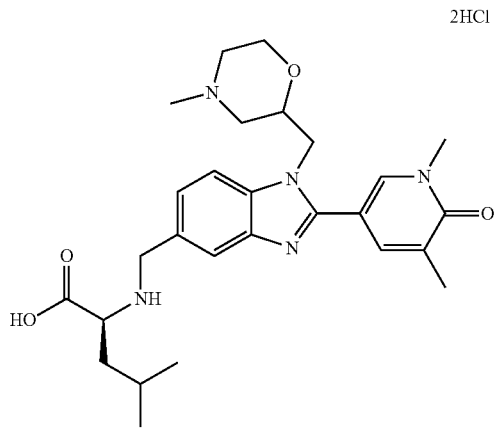 [SMILES: "2HCl" ; Cc1cc(-c2nc3cc(CN[C@@H](CC(C)C)C(=O)O)ccc3n2CC2CN(C)CCO2)cn(C)c1=O]

| | | |
|---|---|---|
| Example 50: (S)-3-methyl-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)butanoic acid, hydrochloride (prepared from: Example 16) System B, 0.53 min, MH+ = 453, Yield: 28 mg, 60% | 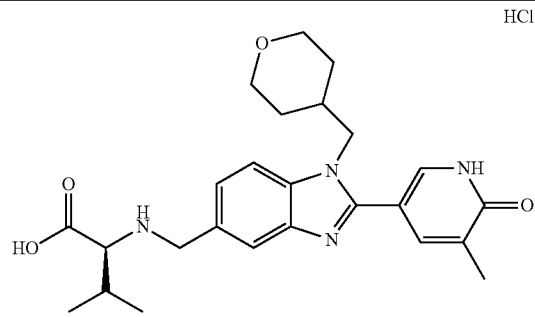 | HCl |
| Example 51: (S)-3-hydroxy-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)propanoic acid, hydrochloride 9prepared from: Example 137) System B, 0.48 min, MH+ = 441, Yield: 33 mg, 70% | 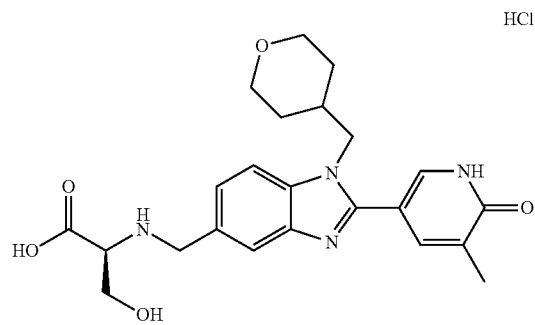 [SMILES: Cl ; Cc1cc(-c2nc3cc(CN[C@@H](CO)C(=O)O)ccc3n2CC2CCOCC2)c[nH]c1=O] | HCl |
| Example 52: (2S,3R)-3-hydroxy-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)butanoic acid, hydrochloride (prepared from: Example 138) System B, 0.49 min, MH+ = 455, Yield: 40 mg, 86% | 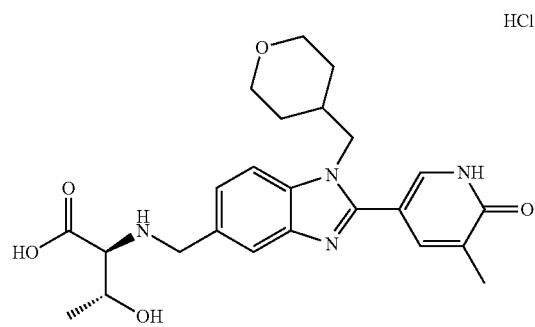 [SMILES: Cl ; Cc1cc(-c2nc3cc(CN[C@H](C(=O)O)[C@@H](C)O)ccc3n2CC2CCOCC2)c[nH]c1=O] | HCl |
| Example 53: (S)-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)propanoic acid, hydrochloride (prepared from: Example 140 ) System B, 0.49 min, MH+ = 425, Yield: 43 mg, 91% | 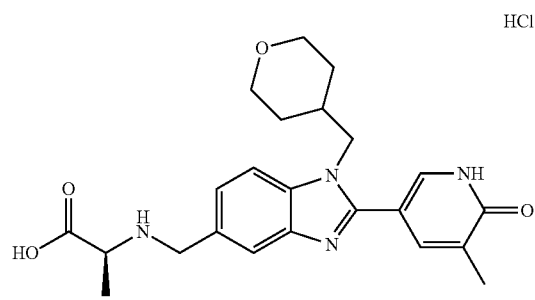 [SMILES: Cl ; Cc1cc(-c2nc3cc(CN[C@@H](C)C(=O)O)ccc3n2CC2CCOCC2)c[nH]c1=O] | HCl |
| Example 54: (S)-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)-2-(tetrahydro-2H-pyran-4-yl)acetic acid, hydrochloride (prepared from: Example 142) System B, 0.51 min, MH+ = 495, Yield: 30 mg, 51% | 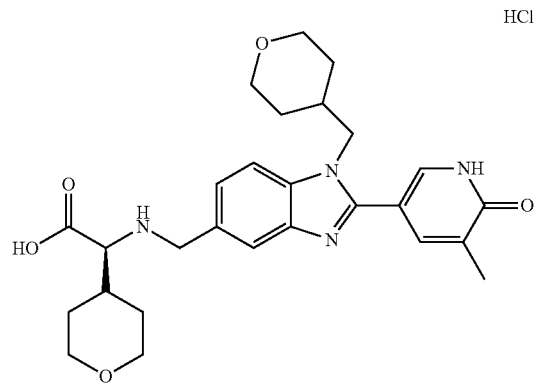 [SMILES: Cl ; Cc1cc(-c2nc3cc(CN[C@H](C(=O)O)C4CCOCC4)ccc3n2CC2CCOCC2)c[nH]c1=O] | HCl |

Example 55: (S)-4-methoxy-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)butanoic acid, hydrochloride (prepared from: Example 143) System B, 0.51 min, MH+ = 469, Yield: 34 mg, 65%

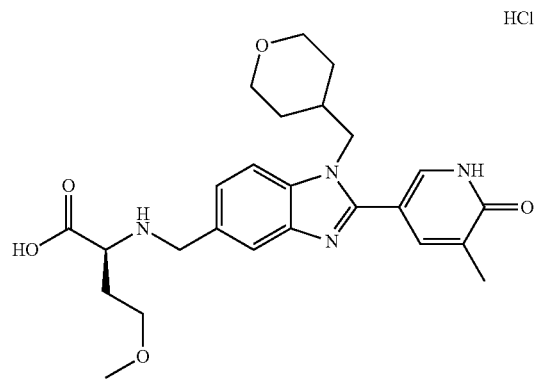 [SMILES: Cl ; COCC[C@H](NCc1ccc2c(c1)nc(-c1c[nH]c(=O)c(C)c1)n2CC1CCOCC1)C(=O)O]

Example 56: (S)-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)butanoic acid, hydrochloride (prepared from: Example 144) System B, 0.50 min, MH+ = 439, Yield: 40 mg, 73%

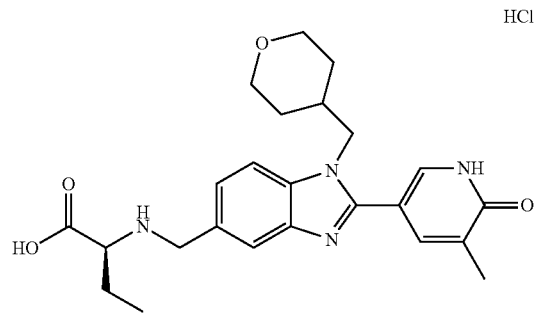 [SMILES: Cl ; CC[C@H](NCc1ccc2c(c1)nc(-c1c[nH]c(=O)c(C)c1)n2CC1CCOCC1)C(=O)O]

Example 57: (S)-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)pentanoic acid, hydrochloride (prepared from: Example 145) System B, 0.54 min, MH+ = 453, Yield: 38 mg, 85%

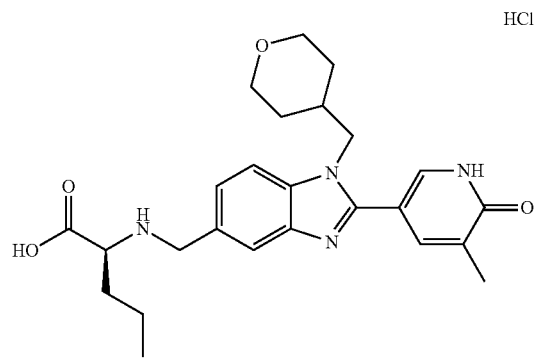 [SMILES: Cl ; CCC[C@H](NCc1ccc2c(c1)nc(-c1c[nH]c(=O)c(C)c1)n2CC1CCOCC1)C(=O)O]

Example 58: (S)-3-methoxy-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)propanoic acid, hydrochloride (prepared from: Example 146) System B, 0.50 min, MH+ = 455, Yield: 34 mg, 72%

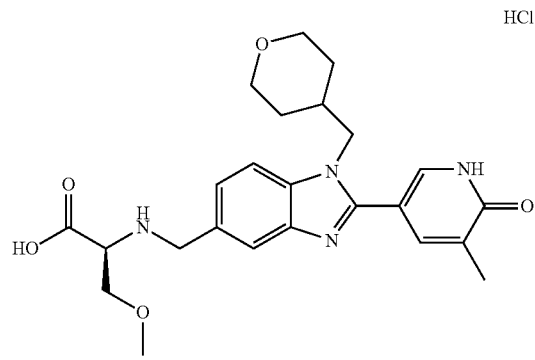

Example 59: (2S,3R)-2-(((2-(1,5-dimethyl-6-oxo-1,6-dihydropyridin-3-yl)-1-((S)-1-methoxypropan-2-yl)-1H-benzo[d]imidazol-5-yl)methyl)amino)-3-hydroxybutanoic acid, hydrochloride (prepared from: Example 218) System A, 0.41 min, MH+ = 443, Yield: 65 mg, 64%

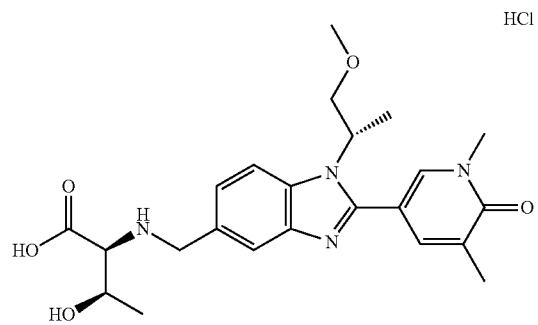 [SMILES: Cl ; COC[C@H](C)n1c(-c2cc(C)c(=O)n(C)c2)nc2cc(CN[C@H](C(=O)O)[C@@H](C)O)ccc21]

Example 60: (S)-4-methyl-2-(((2-(5-methyl-6-oxo-1,6-dihydropyridin-3-yl)-1-(1-methylpiperidin-4-yl)-1H-benzo[d]imidazol-5-yl)methyl)amino)pentanoic acid, bis-hydrochloride (prepared from: Example 2) System B, 0.56 min, MH+ = 466, Yield: 26 mg, 76%

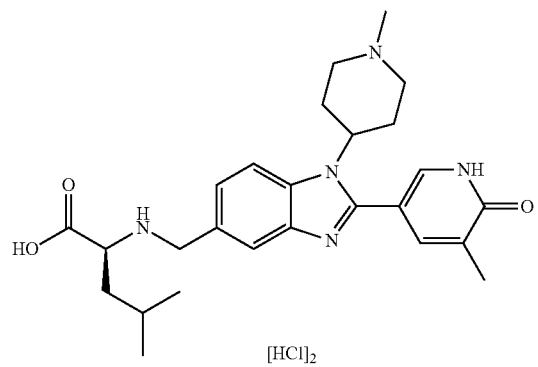

Example 61: (S)-3-(1H-imidazol-5-yl)-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)propanoic acid, bis hydrochloride (prepared from: Example 192) System B, 0.48 min, MH+ = 491, Yield: 26 mg, 76%

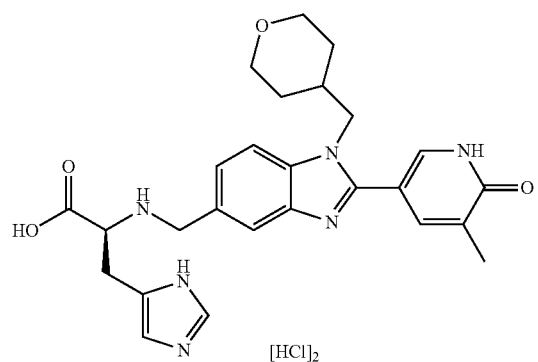

Example 62: (2S,3R)-2-(((2-(1,5-dimethyl-6-oxo-1,6-dihydropyridin-3-yl)-1-(((S)-tetrahydrofuran-2-yl)methyl)-1H-benzo[d]imidazol-5-yl)methyl)amino)-3-hydroxybutanoic acid hydrochloride (prepared from: Example 110) System J, 0.56 min, MH+ = 455, Yield: 57 mg, 73%

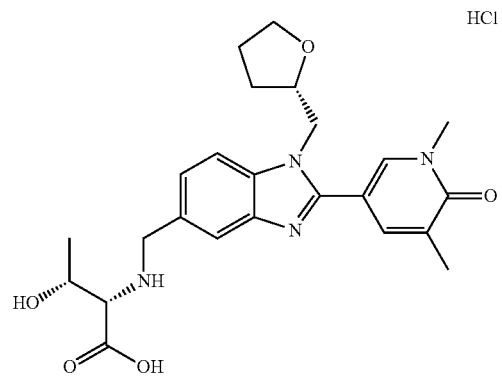 [SMILES: Cl ; Cc1cc(-c2nc3cc(CN[C@H](C(=O)O)[C@@H](C)O)ccc3n2C[C@@H]2CCCO2)cn(C)c1=O]

Example 63: (2S,3R)-2-(((2-(1,5-dimethyl-6-oxo-1,6-dihydropyridin-3-yl)-1-(((R)-tetrahydro-2H-pyran-3-yl)methyl)-1H-benzo[d]imidazol-5-yl)methyl)amino)-3-hydroxybutanoic acid hydrochloride (prepared from: Example 213a) System J, 0.57 min, MH+ = 469, Yield: 16 mg, 48%

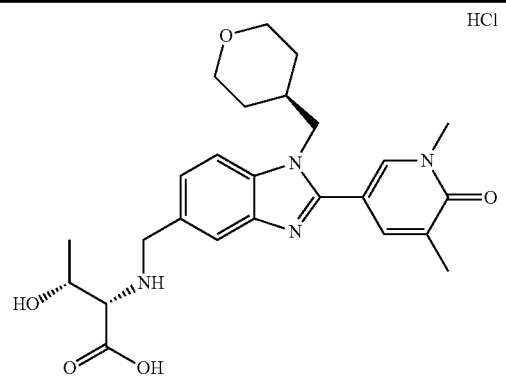

Example 64: (2S,3R)-2-(((2-(1,5-dimethyl-6-oxo-1,6-dihydropyridin-3-yl)-1-(((S)-tetrahydro-2H-pyran-3-yl)methyl)-1H-benzo[d]imidazol-5-yl)methyl)amino)-3-hydroxybutanoic acid hydrochloride (prepared from: Example 213b) System J, 0.57 min, MH+ = 469, Yield: 24 mg, 61%

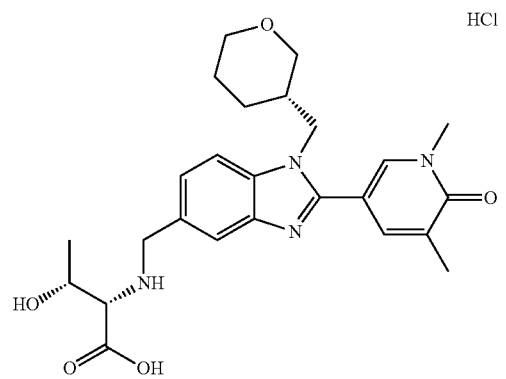 [SMILES: Cl ; Cc1cc(-c2nc3cc(CN[C@H](C(=O)O)[C@@H](C)O)ccc3n2C[C@@H]2CCCOC2)cn(C)c1=O]

Example 65: (S)-2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxypropanoic acid hydrochloride (prepared from: Example 233) System J, 0.52 min, MH+ = 455, Yield: 53 mg, 51%

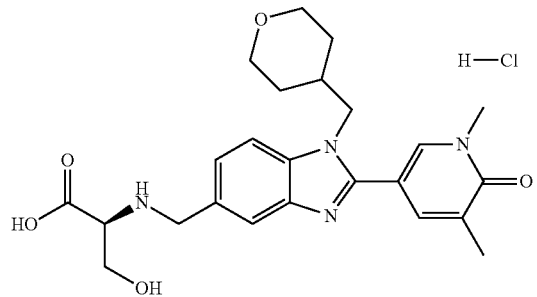

Example 66: (2S,3R)-2-(((1-(1,3-dimethoxypropan-2-yl)-2-(1,5-dimethyl-6-oxo-1,6-dihydropyridin-3-yl)-1H-benzo[d]imidazol-5-yl)methyl)amino)-3-hydroxybutanoic acid hydrochloride (prepared from: Example 305) System J, 0.54 min, MH+ = 473, Yield: 19 mg, 96%

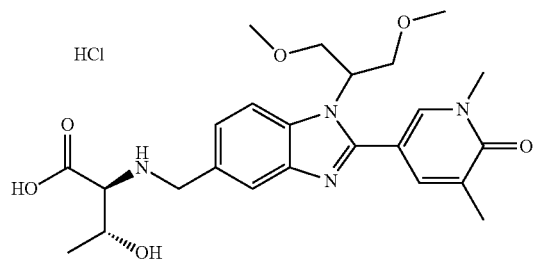 [SMILES: COCC(COC)n1c(-c2cc(C)c(=O)n(C)c2)nc2cc(CN[C@H](C(=O)O)[C@@H](C)O)ccc21 ; Cl]

Example 67: (2S,3R)-2-((2-((2-(1,5-dimethyl-6-oxo-1,6-dihydropyridin-3-yl)-1-((tetrahydro-2H-pyran-4-yl)methyl)-1H-benzo[d]imidazol-5-yl)oxy)ethyl)amino)-3-hydroxybutanoic acid, Hydrochloride (prepared from: Example 276) System J, 0.55 min, MH+ = 499, Yield: 59 mg, 35%

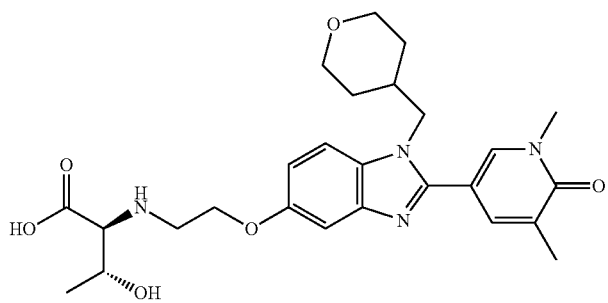 [SMILES: Cc1cc(-c2nc3cc(OCCN[C@H](C(=O)O)[C@@H](C)O)ccc3n2CC2CCOCC2)cn(C)c1=O]

| | |
|---|---|
| Example 68: (2S,3R)-2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoic acid hydrochloride (prepared from: Example 287) System C, 0.41 min, MH⁺ = 469, Yield: 40 mg, 41% | 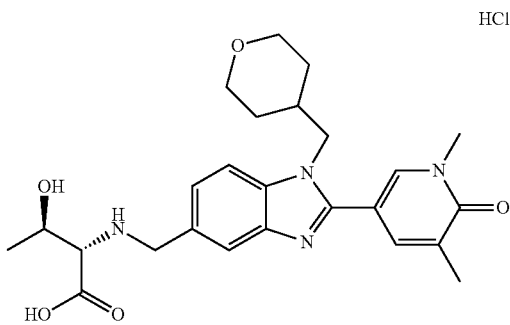 [SMILES: Cl ; Cc1cc(-c2nc3cc(CN[C@H](C(=O)O)[C@@H](C)O)ccc3n2CC2CCOCC2)cn(C)c1=O] |
| Example 69: (2S,3R)-2-(((1-(cyclopropylmethyl)-2-(1,5-dimethyl-6-oxo-1,6-dihydropyridin-3-yl)-1H-benzo[d]imidazol-6-yl)methyl)amino)-3-hydroxybutanoic acid hydrochloride (prepared from: A mixture of Example 170 and Example 169) System I, 0.39 min, MH⁺ = 425, Yield: 38 mg 78% | 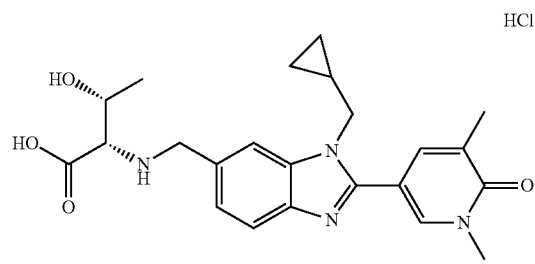 [SMILES: Cl ; Cc1cc(-c2nc3ccc(CN[C@H](C(=O)O)[C@@H](C)O)cc3n2CC2CC2)cn(C)c1=O] |
| Example 70a: (2S,3R)-2-(((2-(1,5-dimethyl-6-oxo-1,6-dihydropyridin-3-yl)-1-((tetrahydro-2H-pyran-3-yl)methyl)-1H-benzo[d]imidazol-6-yl)methyl)amino)-3-hydroxybutanoic acid hydrochloride(Single diastereomer of unknown configuration, Isomer 1) (prepared from: Example 171a) System I, 0.40 mins, MH⁺ = 469, Yield: 22 mg 65% | 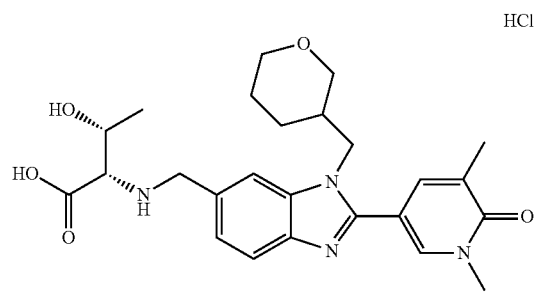 [SMILES: Cl ; Cc1cc(-c2nc3ccc(CN[C@H](C(=O)O)[C@@H](C)O)cc3n2CC2CCCOC2)cn(C)c1=O] |
| Example 70b: (2S,3R)-2-(((2-(1,5-dimethyl-6-oxo-1,6-dihydropyridin-3-yl)-1-((tetrahydro-2H-pyran-3-yl)methyl)-1H-benzo[d]imidazol-6-yl)methyl)amino)-3-hydroxybutanoic acid hydrochloride (Single diastereomer of unknown configuration, Isomer 2) (prepared from: Example 171b) System I, 0.41 mins, MH⁺ = 469, Yield: 16 mg 70% | 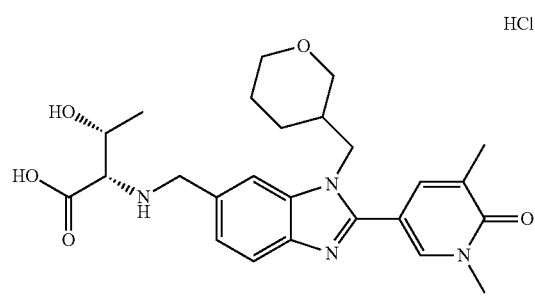 [SMILES: Cl ; Cc1cc(-c2nc3ccc(CN[C@H](C(=O)O)[C@@H](C)O)cc3n2CC2CCCOC2)cn(C)c1=O] |

Example 71: (S)-3,3-dimethyl-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)butanoic acid

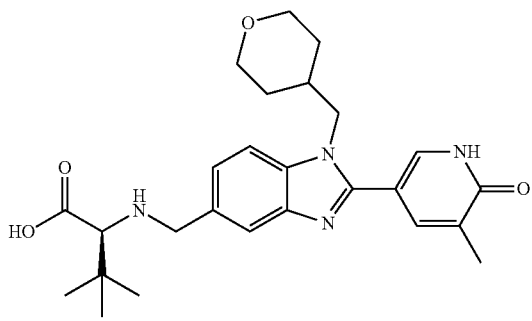 [SMILES: Cc1cc(-c2nc3cc(CN[C@H](C(=O)O)C(C)(C)C)ccc3n2CC2CCOCC2)c[nH]c1=O]

1M aq Lithium hydroxide solution (1.0 mL) was added to a solution of (2S)-tetrahydrofuran-3-yl 3,3-dimethyl-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)butanoate (For a preparation see Example 239, 50 mg, 0.093 mmol) in methanol (0.5 mL) and THF (0.5 mL). The reaction mixture was stirred at 60° C. for 48 hours. The reaction mixture was cooled to room temperature. The solvent was evaporated and the residue purified by MDAP (Method B) to give the title compound (26 mg), as a colourless solid. LCMS (System B): $t_{RET}$=0.57 min; MH$^+$ 467

The following Examples were prepared in a similar manner to Example 71:

Example 72: (2S)-2-(((1-((1-acetylpyrrolidin-3-yl)methyl)-2-(5-methyl-6-oxo-1,6-dihydropyridin-3-yl)-1H-benzo[d]imidazol-5-yl)methyl)amino)-4-methylpentanoic acid (prepared from: Example 153) System B, 0.53 min, MH$^+$ = 494, Yield: 24 mg 97%

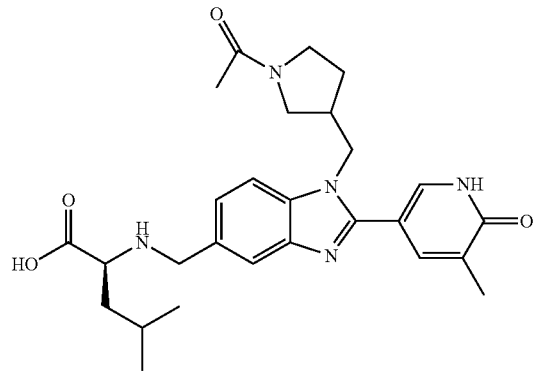 [SMILES: CC(=O)N1CCC(Cn2c(-c3c[nH]c(=O)c(C)c3)nc3cc(CN[C@@H](CC(C)C)C(=O)O)ccc32)C1]

Example 73: (2S,3R)-2-(((2-(1,5-dimethyl-6-oxo-1,6-dihydropyridin-3-yl)-1-((S)-1-methoxypropan-2-yl)-1H-benzo[d]imidazol-6-yl)methyl)amino)-3-hydroxybutanoic acid (prepared from: Example 116) System J, 0.50 min, MH$^+$ = 443, Yield: 61 mg 66%

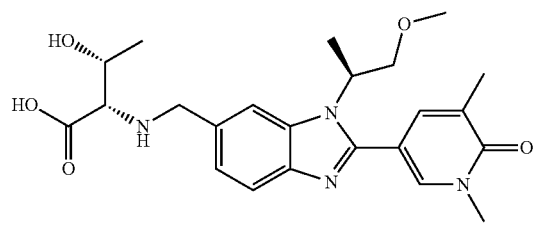 [SMILES: COC[C@H](C)n1c(-c2cc(C)c(=O)n(C)c2)nc2ccc(CN[C@H](C(=O)O)[C@@H](C)O)cc21]

Example 74: (2S,3R)-2-(((2-(1,5-dimethyl-6-oxo-1,6-dihydropyridin-3-yl)-1-((4-methylmorpholin-2-yl)methyl)-1H-benzo[d]imidazol-5-yl)methyl)amino)-3-hydroxybutanoic acid (prepared from: Example 162) System B, 0.51 min, MH$^+$ = 484, Yield: 3.5 mg, 20%

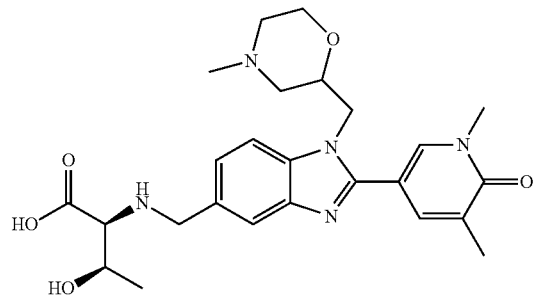 [SMILES: Cc1cc(-c2nc3cc(CN[C@H](C(=O)O)[C@@H](C)O)ccc3n2CC2CN(C)CCO2)cn(C)c1=O]

-continued

Example 75: (2S,3R)-2-(((2-(1,5-dimethyl-6-oxo-1,6-dihydropyridin-3-yl)-1-((4-methylmorpholin-3-yl)methyl)-1H-benzo[d]imidazol-5-yl)methyl)amino)-3-hydroxybutanoic acid (prepared from: Example 165) System B, 0.46 min, MH$^+$ = 484, Yield: 23 mg, 92%

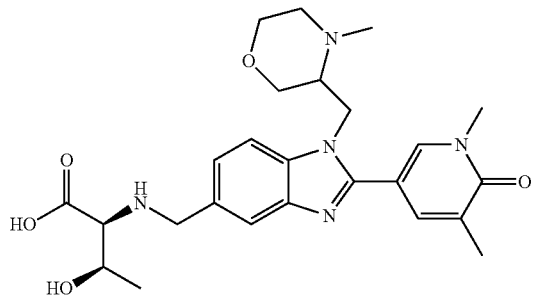 [SMILES: Cc1cc(-c2nc3cc(CN[C@H](C(=O)O)[C@@H](C)O)ccc3n2CC2COCCN2C)cn(C)c1=O]

Example 76: (S)-3-hydroxy-3-methyl-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)butanoic acid (prepared from: Example 240) System B, 0.73 min, MH$^+$ = 539, Yield: 16 mg 74%

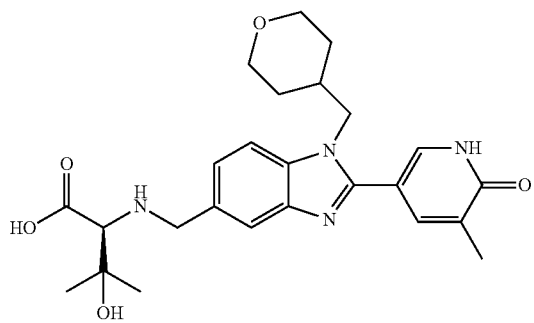 [SMILES: Cc1cc(-c2nc3cc(CN[C@H](C(=O)O)C(C)(C)O)ccc3n2CC2CCOCC2)c[nH]c1=O]

Example 77: (S)-2-cyclopropyl-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)acetic acid (prepared from: Example 245) System B, 0.52 min, MH$^+$ = 451, Yield: 18 mg 83%

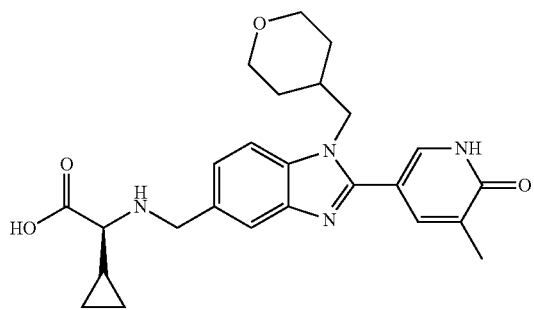 [SMILES: Cc1cc(-c2nc3cc(CN[C@H](C(=O)O)C4CC4)ccc3n2CC2CCOCC2)c[nH]c1=O]

Example 78: (S)-3-cyclopropyl-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)propanoic acid (prepared from: Example 246) System B, 0.54 min, MH$^+$ = 465, Yield: 16 mg 73%

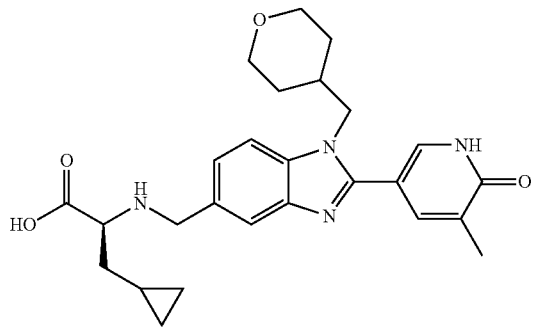

Example 79: (R)-3-cyclopropyl-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)propanoic acid (prepared from: Example 247) System B, 0.55 min, MH$^+$ = 465, Yield: 15 mg 69%

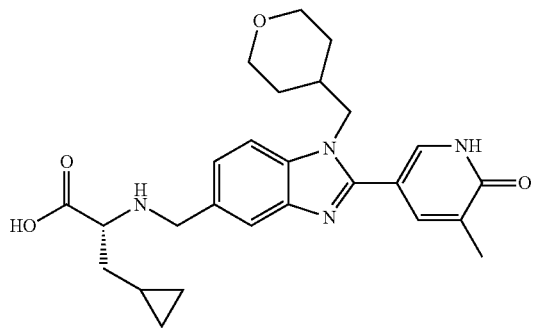 [SMILES: Cc1cc(-c2nc3cc(CN[C@H](CC4CC4)C(=O)O)ccc3n2CC2CCOCC2)c[nH]c1=O]

Example 80: (2S,3R)-2-(((2-(1,5-dimethyl-6-oxo-1,6-dihydropyridin-3-yl)-1-isopropyl-1H-benzo[d]imidazol-5-yl)methyl)amino)-3-hydroxybutanoic acid (prepared from: Example 97) System B, 0.40 min, MH+ = 413, Yield: 27 mg 63%

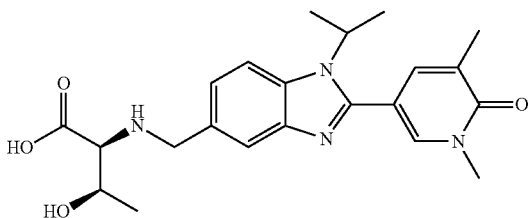 [SMILES: Cc1cc(-c2nc3cc(CN[C@H](C(=O)O)[C@@H](C)O)ccc3n2C(C)C)cn(C)c1=O]

Example 81: (2S)-2-(((2-(1,5-dimethyl-6-oxo-1,6-dihydropyridin-3-yl)-1-((4-methylmorpholin-3-yl)methyl)-1H-benzo[d]imidazol-5-yl)methyl)amino)-3-methoxypropanoic acid (prepared from: Example 166) System B, 0.50 min, MH+ = 484, Yield: 14 mg 52%

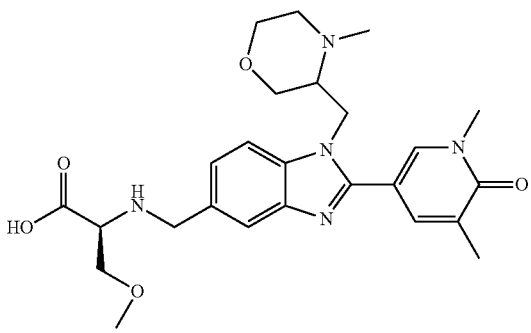 [SMILES: COC[C@H](NCc1ccc2c(c1)nc(-c1cc(C)c(=O)n(C)c1)n2CC1COCCN1C)C(=O)O]

Example 82: (2S,3R)-2-(((2-(1,5-dimethyl-6-oxo-1,6-dihydropyridin-3-yl)-1-((tetrahydro-2H-pyran-2-yl)methyl)-1H-benzo[d]imidazol-5-yl)methyl)amino)-3-hydroxybutanoic acid (prepared from: Example 248) System B, 0.60 min, MH+ = 469, Yield: 15 mg 66%

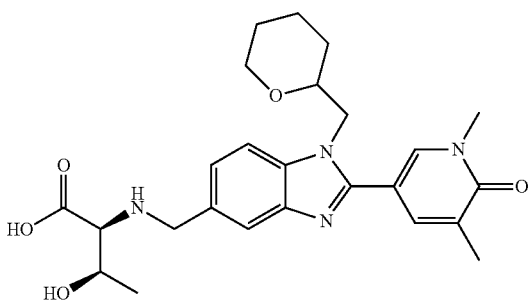 [SMILES: Cc1cc(-c2nc3cc(CN[C@H](C(=O)O)[C@@H](C)O)ccc3n2CC2CCCCO2)cn(C)c1=O]

Example 83: (S)-2-((2-((2-(1,5-dimethyl-6-oxo-1,6-dihydropyridin-3-yl)-1-((tetrahydro-2H-pyran-4-yl)methyl)-1H-benzo[d]imidazol-6-yl)oxy)ethyl)amino)-3-methoxypropanoic acid (prepared from: Example 277) System J, 0.55 min, MH+ = 499, Yield: 12 mg 68%

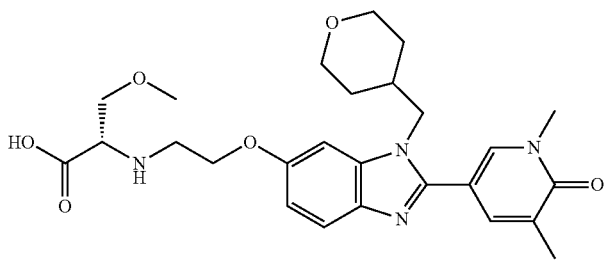 [SMILES: COC[C@H](NCCOc1ccc2nc(-c3cc(C)c(=O)n(C)c3)n(CC3CCOCC3)c2c1)C(=O)O]

Example 84: (S)-2-((2-((2-(1,5-dimethyl-6-oxo-1,6-dihydropyridin-3-yl)-1-((tetrahydro-2H-pyran-4-yl)methyl)-1H-benzo[d]imidazol-6-yl)oxy)ethyl)amino)propanoic acid (prepared from: Example 278) System J, 0.54 min, MH+ = 469, Yield: 14 mg 80%

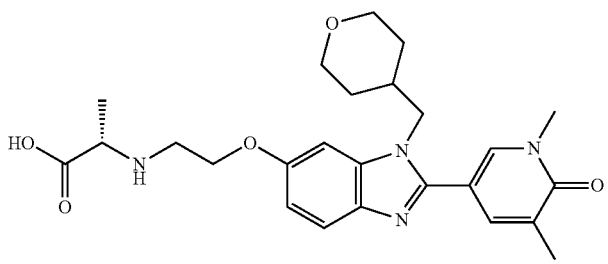 [SMILES: Cc1cc(-c2nc3ccc(OCCN[C@@H](C)C(=O)O)cc3n2CC2CCOCC2)cn(C)c1=O]

| | |
|---|---|
| Example 85: (S)-2-((2-((2-(1,5-dimethyl-6-oxo-1,6-dihydropyridin-3-yl)-1-((tetrahydro-2H-pyran-4-yl)methyl)-1H-benzo[d]imidazol-6-yl)oxy)ethyl)amino)-3-methylbutanoic acid (Prepared from: Example 280) System J, 0.59 min, MH⁺ = 497, Yield: 9 mg 52% | 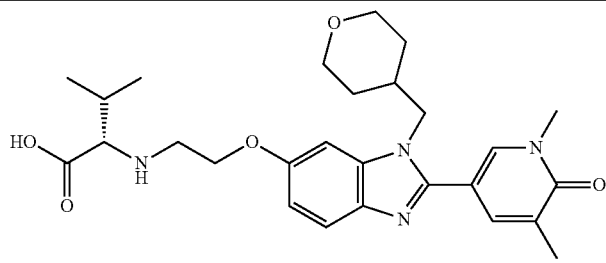 |

Example 86: (2S,3S)-2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoic acid

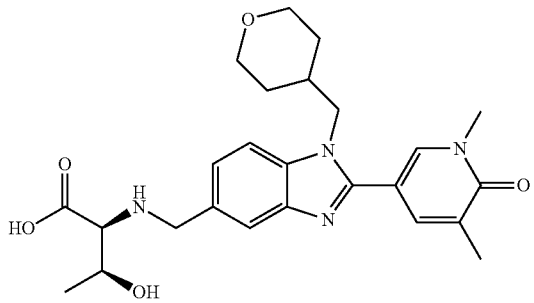 [SMILES: Cc1cc(-c2nc3cc(CN[C@H](C(=O)O)[C@H](C)O)ccc3n2CC2CCOCC2)cn(C)c1=O]

To a stirred solution of (2S,3S)—(S)-tetrahydrofuran-3-yl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate (50.0 mg, 0.093 mmol) (for an example preparation see Example 306) in ethanol (3 mL) was added 1 M lithium hydroxide (0.464 mL, 0.464 mmol). The resulting solution was stirred overnight at 40° C. 2 M HCl (0.300 mL, 0.600 mmol) was added to the reaction mixture and stirred for 30 min. The reaction mixture was loaded onto a SCX Cartridge, eluted with MeOH (15 CV) and followed by 2 M NH₃ in MeOH (15 CV). The basic fraction was concentrated and evaporated in vacuo to give the title compound as a white solid. The total yield of the reaction was 100%. LCMS (System C): $t_{RET}$=0.40 min, MH⁺=469.

The following Examples were prepared in a similar manner to Example 86:

| | |
|---|---|
| Example 87: (2S,3R)-2-(((2-(1,5-dimethyl-6-oxo-1,6-dihydropyridin-3-yl)-1-(tetrahydro-2H-pyran-4-yl)-1H-benzo[d]imidazol-6-yl)methyl)amino)-3-hydroxybutanoic acid (prepared from: Example 173) System J, 0.49 min, MH⁺ = 455, Yield: 18 mg 88% | 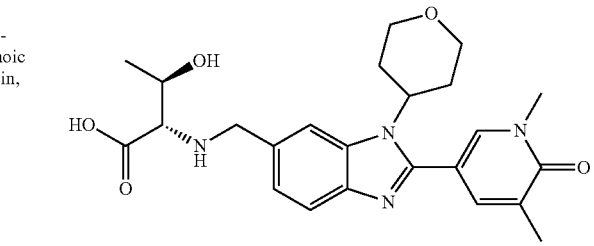 |
| Example 88: (2S,3R)-2-(((2-(1,5-dimethyl-6-oxo-1,6-dihydropyridin-3-yl)-1-((tetrahydro-2H-pyran-2-yl)methyl)-1H-benzo[d]imidazol-6-yl)methyl)amino)-3-hydroxybutanoic acid- diastereomer 2 (prepared from: Intermediate 174b) System I, 0.46 min, MH⁺ = 469, Yield: 28 mg 96% | 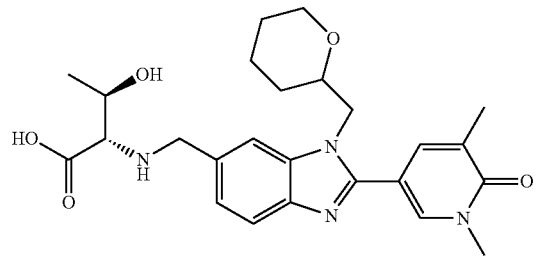 [SMILES: Cc1cc(-c2nc3ccc(CN[C@H](C(=O)O)[C@@H](C)O)cc3n2CC2CCCCO2)cn(C)c1=O] |

Example 89: (2S,3R)-2-(((1-(((S)-1-acetylpiperidin-3-yl)methyl)-2-(1,5-dimethyl-6-oxo-1,6-dihydropyridin-3-yl)-1H-benzo[d]imidazol-5-yl)methyl)amino)-3-hydroxybutanoic acid (prepared from: Intermediate 89)
System C, 0.38 min, MH$^+$ = 510, Yield: 8.7 mg 38%

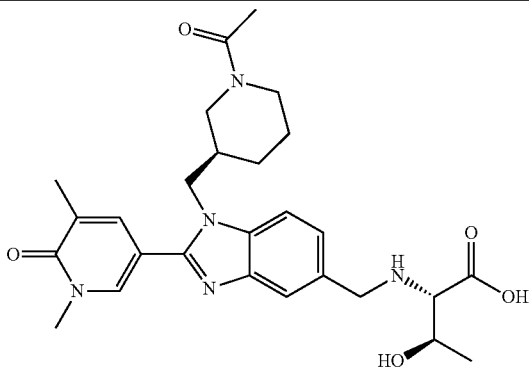

Example 90: (S)-4-methyl-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)pentanoic acid, sodium salt

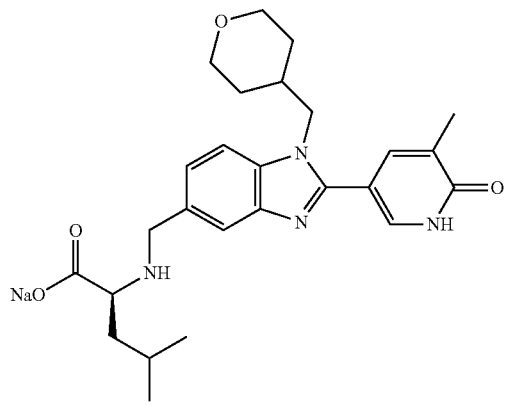

A round bottom flask was charged with (S)-cyclopentyl 4-methyl-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)pentanoate (136 mg, 0.254 mmol, Example 1), tetrahydrofuran (THF) (2 mL), methanol (2 mL), water (1 mL) and lithium hydroxide (15 mg, 0.626 mmol). An air condenser was fitted and the mixture warmed to 500° C. overnight. Lithium hydroxide (15 mg, 0.626 mmol) was added and the mixture heated to 50° C. overnight. The mixture was cooled to room temperature before being concentrated in vacuo to give a white solid. The solid was dissolved in 1:1 MeOH:DMSO 2×1 mL and purified by MDAP (Method A). The relevant fractions were combined and the solvent was evaporated in vacuo to a white solid (86 mg, 0.184 mmol). The solid was slurried in a DCM/MeOH/THF solution (9 mL 1:1:1) prior to the addition of sodium hydroxide (93 μL, 0.186 mmol). The resultant solution was stirred for 5 minutes prior to removal of the volatiles in vacuo to give the title compound (96 mg, 0.19 mmol, 77% yield) as a white solid. LCMS (System A): t$_{RET}$=0.49 min; MH$^+$ 467.

Example 91: (2S,3R)-2-(((2-(1,5-dimethyl-6-oxo-1,6-dihydropyridin-3-yl)-1-((tetrahydro-2H-pyran-2-yl)methyl)-1H-benzo[d]imidazol-6-yl)methyl)amino)-3-hydroxybutanoic acid—Diastereomer 1, hydrochloride

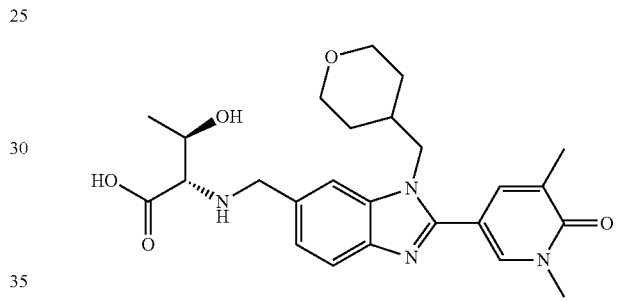

To a stirred solution of (2S,3R)-isopropyl 2-(((2-(1,5-dimethyl-6-oxo-1,6-dihydropyridin-3-yl)-1-((tetrahydro-2H pyran-2-yl)methyl)-1H-benzo[d]imidazol-6-yl)methyl) amino)-3-hydroxybutanoate—diastereomer 1 (174a) (31.5 mg, 0.062 mmol) in Ethanol (2 mL) was added 1M lithium hydroxide (0.308 mL, 0.308 mmol). The resulting reaction mixture was stirred for 2 days at 40° C. The reaction mixture was loaded onto a Biotage SCX Cartridge, eluted with MeOH (15 CV) and 2M methanolic ammonia (15 CV). The basic fraction was evaporated in vacuo to obtain a white solid. To a suspension of the residue in Et$_2$O (0.5 mL) was added 0.5M HCl in Et2O (0.1 mL). The suspension was stirred for 2 h, and evaporated in vacuo to give the title compound as a white solid. The total yield of the reaction was 72%. LCMS (System I): t$_{RET}$=0.46 min, MH$^+$=469.

Example 92: (2S,3R)-tert-butyl 2-(((1-(1,3-dimethoxypropan-2-yl)-2-(1,5-dimethyl-6-oxo-1,6-dihydropyridin-3-yl)-1H-benzo[d]imidazol-6-yl)methyl)amino)-3-hydroxybutanoate

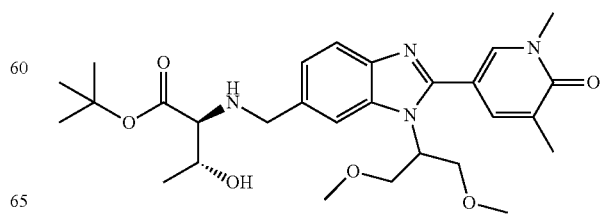

Example 93: (2S,3R)-2-(((1-(1,3-dimethoxypropan-2-yl)-2-(1,5-dimethyl-6-oxo-1,6-dihydropyridin-3-yl)-1H-benzo[d]imidazol-6-yl)methyl)amino)-3-hydroxybutanoic acid

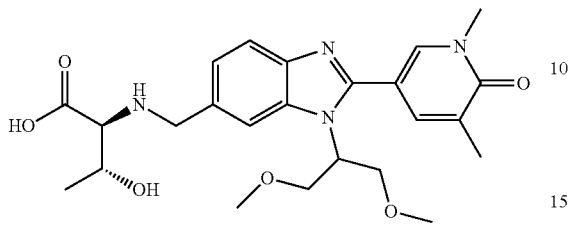

(2S,3R)-tert-butyl 2-amino-3-hydroxybutanoate hydrochloride (115 mg, 0.541 mmol) was added to a stirred solution of 1-(1,3-dimethoxypropan-2-yl)-2-(1,5-dimethyl-6-oxo-1,6-dihydropyridin-3-yl)-1H-benzo[d]imidazole-6-carbaldehyde (134) (100 mg, 0.271 mmol) in DCM (5 mL) under a nitrogen atmosphere for 22 h. Sodium triacetoxyborohydride (172 mg, 0.812 mmol) was added, the resulting suspension stirred for 1 h. MeOH (5 mL) was added, the solution stirred for 5 min and loaded on to a 5 g SCX cartridge. The cartridge was eluted with MeOH (25 mL), followed by 2M methanolic ammonia (25 mL). The basic fractions were evaporated in vacuo to a brown oil and purified by MDAP (method B). 2 M aq. HCl was added (0.5 mL) and the product containing fractions were evaporated in vacuo, azeotroping with EtOH to give a white solid. The residue was dissolved in DMSO:MeOH (1:1, 0.9 mL) and purified by MDAP. The product containing fractions were evaporated to dryness, azeotroping with EtOH and PhMe to give the title compounds as white solids. The total yield of Example 92 was 25%. LCMS (System C): $t_{RET}$=0.57 min, MH$^+$=529. The total yield of Example 93 was 5%. LCMS (System C): $t_{RET}$=0.40 min, MH$^+$=473.

Example 94a: (2S,3R)-2-(((2-(1,5-dimethyl-6-oxo-1,6-dihydropyridin-3-yl)-1-(1-(tetrahydro-2H-pyran-4-ylethyl)-1H-benzo[d]imidazol-5-yl)methylamino)-3-hydroxybutanoic acid, Hydrochloride— Diastereomer 1

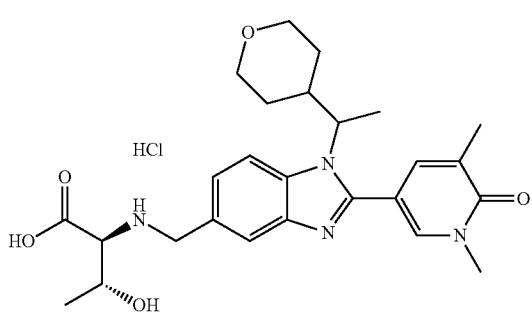 [SMILES: Cc1cc(-c2nc3cc(CN[C@H](C(=O)O)[C@@H](C)O)ccc3n2C(C)C2CCOCC2)cn(C)c1=O ; Cl]

(2S,3R)-tert-butyl 2-(((2-(1,5-dimethyl-6-oxo-1,6-dihydropyridin-3-yl)-1-(1-(tetrahydro-2H-pyran-4-yl)ethyl)-1H-benzo[d]imidazol-5-yl)methyl)amino)-3-hydroxybutanoate (182a) (12.5 mg, 0.023 mmol) was dissolved in 2M aq. HCl (2 mL, 4.00 mmol). The reaction mixture was heated to 40° C. for 4 days. The reaction mixture was evaporated in vacuo to give the title compound as a white solid. Total yield of the reaction was 58%. LCMS (System C): $t_{RET}$=0.40 min, MH$^+$=483.

Example 94b: (2S,3R)-2-(((2-(1,5-dimethyl-6-oxo-1,6-dihydropyridin-3-yl)-1-(1-(tetrahydro-2H-pyran-4-ylethyl)-1H-benzo[d]imidazol-5-yl)methyl)amino)-3-hydroxybutanoic acid, Hydrochloride— Diastereomer 2

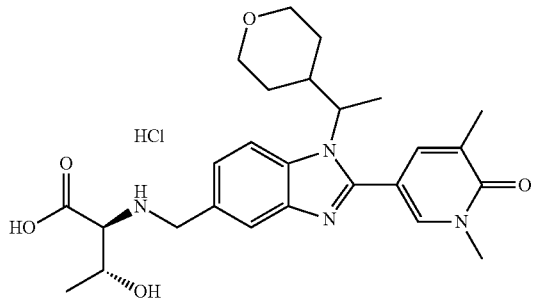 [SMILES: Cc1cc(-c2nc3cc(CN[C@H](C(=O)O)[C@@H](C)O)ccc3n2C(C)C2CCOCC2)cn(C)c1=O ; Cl]

(2S,3R)-tert-butyl 2-(((2-(1,5-dimethyl-6-oxo-1,6-dihydropyridin-3-yl)-1-(1-(tetrahydro-2H-pyran-4-yl)ethyl)-1H-benzo[d]imidazol-5-yl)methyl)amino)-3-hydroxybutanoate (182b) (12.5 mg, 0.023 mmol) was dissolved in 2M aq. HCl (2 mL, 4.00 mmol). The reaction mixture was heated to 40° C. for 4 days. The reaction mixture was evaporated in vacuo to give the title compound as a white solid. Total yield of the reaction was 80%. LCMS (System C): $t_{RET}$=0.40 min, MH$^+$=483.

Example 95: (2S,3R)-cyclopentyl 2-(((1-ethyl-2-(5-methyl-6-oxo-1,6-dihydropyridin-3-yl)-1H benzo[d]imidazol-5-yl)methyl)amino)-3-hydroxybutanoate

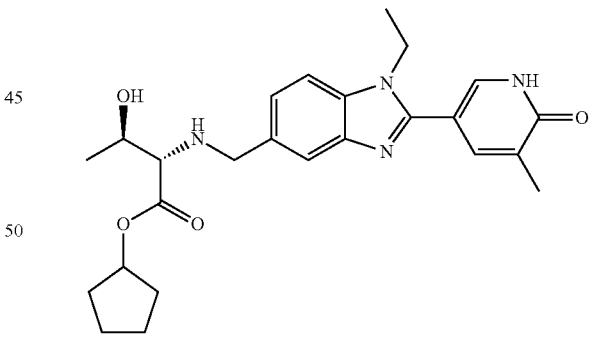

To a mixture of 1-ethyl-2-(5-methyl-6-oxo-1,6-dihydropyridin-3-yl)-1H-benzo[d]imidazole-5-carbaldehyde (For a preparation, see Intermediate 198, 134 mg, 0.476 mmol) in DCM (5 mL) was added (2S,3R)-cyclopentyl 2-amino-3-hydroxybutanoate 4-methylbenzenesulfonate (For a preparation see Intermediate 31, N27467-41-1, 342 mg, 0.953 mmol) and triethylamine (0.166 mL, 1.191 mmol), and the reaction mixture stirred at room temperature for 15 mins. Sodium triacetoxyborohydride (202 mg, 0.953 mmol) was added, and the reaction mixture stirred at room temperature for 2.5 hours. Saturated sodium bicarbonate solution (10 mL) was added and the organic layer separated. The aqueous layer was extracted with further dichloromethane (10 mL), and the organic layers were combined, dried using a hydrophobic frit and blown down under a stream of nitrogen. The sample was dissolved in DMSO (2×1 mL) and purified twice by MDAP (Method B). The solvent was blown down under a stream of nitrogen to give the title compound (126 mg) as an off-white solid. LCMS (System B): $t_{RET}$=0.89 min; MH$^+$ 453

The following Examples were prepared in a similar manner to Example 95:

Example 96: (S)-tetrahydro-2H-pyran-4-yl 2-(((1-(2-methoxyethyl)-2-(5-methyl-6-oxo-1,6-dihydropyridin-3-yl)-1H-benzo[d]imidazol-5-yl)methyl)amino)-4-methylpentanoate (prepared from: Intermediate 201 and Intermediate 14) System B, 0.96 min, MH$^+$ = 511, Yield: 113 mg, 61%

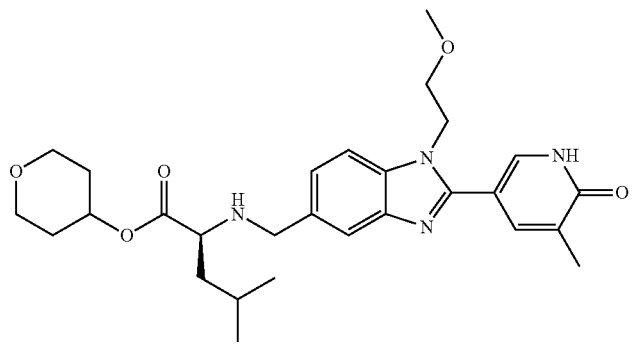 [SMILES: COCCn1c(-c2c[nH]c(=O)c(C)c2)nc2cc(CN[C@@H](CC(C)C)C(=O)OC3CCOCC3)ccc21]

Example 97: (2S,3R)-neopentyl 2-(((2-(1,5-dimethyl-6-oxo-1,6-dihydropyridin-3-yl)-1-isopropyl-1H-benzo[d]imidazol-5-yl)methyl)amino)-3-hydroxybutanoate (prepared from: Intermediate 274 and Intermediate 10) System B, 1.04 min, MH$^+$ = 483, Yield: 90 mg, 43%

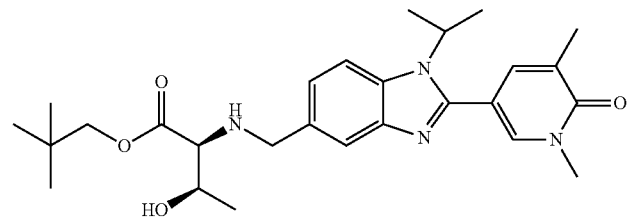 [SMILES: Cc1cc(-c2nc3cc(CN[C@H](C(=O)OCC(C)(C)C)[C@@H](C)O)ccc3n2C(C)C)cn(C)c1=O]

Example 98: (2S,3R)-isobutyl 2-(((2-(1,5-dimethyl-6-oxo-1,6-dihydropyridin-3-yl)-1-isopropyl-1H-benzo[d]imidazol-5-yl)methyl)amino)-3-hydroxybutanoate (prepared from: Intermediate 274 and Intermediate 11) System B, 0.98 min, MH$^+$ = 469, Yield: 31 mg, 20%

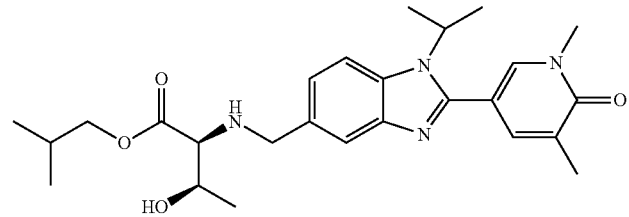 [SMILES: Cc1cc(-c2nc3cc(CN[C@H](C(=O)OCC(C)C)[C@@H](C)O)ccc3n2C(C)C)cn(C)c1=O]

Example 99: (S)-cyclopentyl 2-(((2-(1,5-dimethyl-6-oxo-1,6-dihydropyridin-3-yl)-1-isopropyl-1H-benzo[d]imidazol-5-yl)methyl)amino)-3-methoxypropanoate (prepared from: Intermediate 274 and Intermediate 196) System B, 1.03 min, MH$^+$ = 481, Yield: 110 mg, 67%

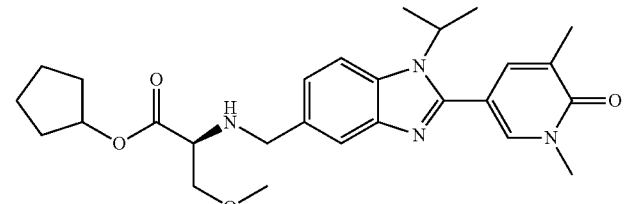

Example 100: (2S,3R)-isobutyl 2-(((2-(1,5-dimethyl-6-oxo-1,6-dihydropyridin-3-yl)-1-(((S)-tetrahydrofuran-2-yl)methyl)-1H-benzo[d]imidazol-5-yl)methyl)amino)-3-hydroxybutanoate (prepared from: Intermediate 118 and Intermediate 11) System B, 0.96 min, MH$^+$ = 511, Yield: 36 mg, 22%

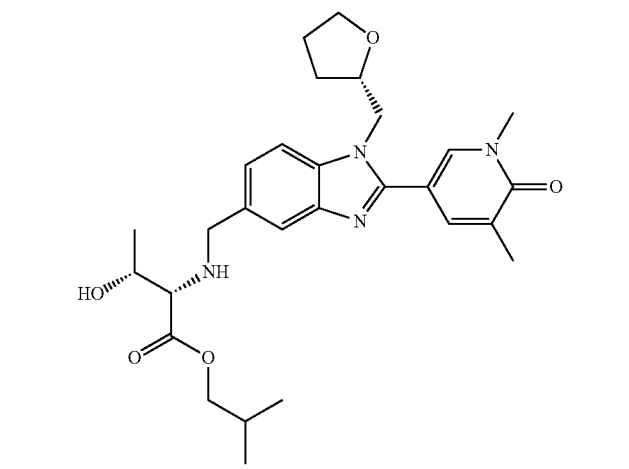 [SMILES: Cc1cc(-c2nc3cc(CN[C@H](C(=O)OCC(C)C)[C@@H](C)O)ccc3n2C[C@@H]2CCCO2)cn(C)c1=O]

-continued

Example 101: (2S,3R)-isobutyl 2-(((2-(1,5-dimethyl-6-oxo-1,6-dihydropyridin-3-yl)-1-(((R)-tetrahydrofuran-2-yl)methyl)-1H-benzo[d]imidazol-5-yl)methyl)amino)-3-hydroxybutanoate (prepared from: Intermediate 119 and Intermediate 11) System B, 0.96 min, MH$^+$ = 511, Yield: 29 mg, 36%

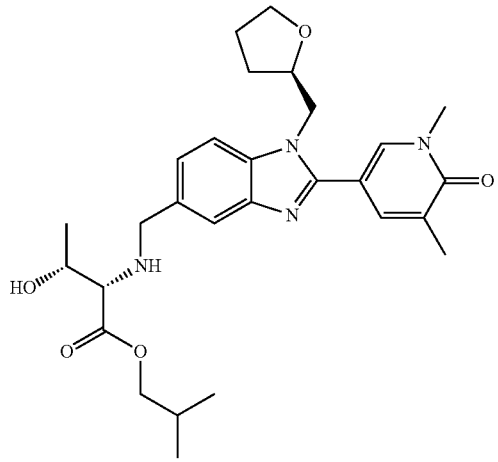 [SMILES: Cc1cc(-c2nc3cc(CN[C@H](C(=O)OCC(C)C)[C@@H](C)O)ccc3n2C[C@H]2CCCO2)cn(C)c1=O]

Example 102: (2S,3R)-isobutyl 2-(((2-(1,5-dimethyl-6-oxo-1,6-dihydropyridin-3-yl)-1-((tetrahydro-2H-pyran-4-yl)methyl)-1H-benzo[d]imidazol-6-yl)methyl)amino)-3-hydroxybutanoate (prepared from: Intermediate 121 and Intermediate 11) System B, 0.89 min, MH$^+$ = 525, Yield: 170 mg, 28%

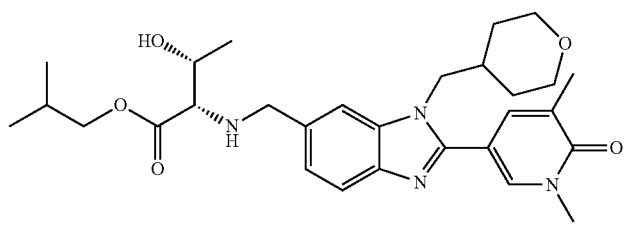 [SMILES: Cc1cc(-c2nc3ccc(CN[C@H](C(=O)OCC(C)C)[C@@H](C)O)cc3n2CC2CCOCC2)cn(C)c1=O]

Example 103: (2S,3R)-(S)-tetrahydrofuran-3-yl 2-(((2-(1,5-dimethyl-6-oxo-1,6-dihydropyridin-3-yl)-1-((tetrahydro-2H-pyran-4-yl)methyl)-1H-benzo[d]imidazol-6-yl)methyl)amino)-3-hydroxybutanoate (prepared from: Intermediate 121 and Intermediate 40) System A, 0.48 min, MH$^+$ = 539, Yield: 40 mg, 11%

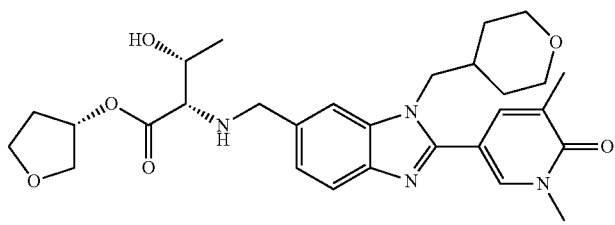 [SMILES: Cc1cc(-c2nc3ccc(CN[C@H](C(=O)O[C@H]4CCOC4)[C@@H](C)O)cc3n2CC2CCOCC2)cn(C)c1=O]

Example 104: (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-6-yl)methyl)amino)-3-hydroxybutanoate (prepared from: Intermediate 121 and Intermediate 31) System B, 0.82 min, MH$^+$ = 511, Yield: 145 mg, 52%

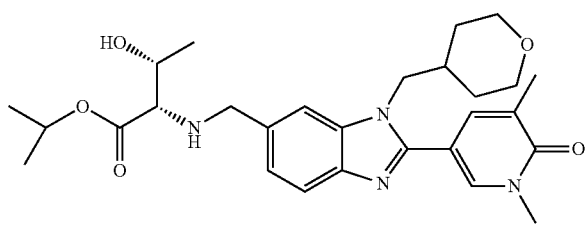 [SMILES: Cc1cc(-c2nc3ccc(CN[C@H](C(=O)OC(C)C)[C@@H](C)O)cc3n2CC2CCOCC2)cn(C)c1=O]

Example 105: (2S,3R)-cyclopentyl 2-(((2-(1,5-dimethyl-6-oxo-1,6-dihydropyridin-3-yl)-1-((tetrahydro-2H-pyran-4-yl)methyl)-1H-benzo[d]imidazol-6-yl)methyl)amino)-3-hydroxybutanoate (prepared from: Intermediate 121 and Intermediate 137) System B, 0.89 min, MH$^+$ = 537, Yield: 197 mg, 67%

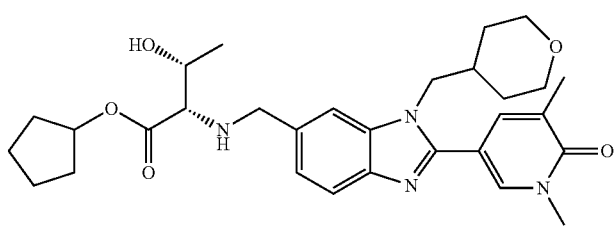

Example 106: (2S,3R)-tert-butyl 2-(((2-(1,5-dimethyl-6-oxo-1,6-dihydropyridin-3-yl)-1-((tetrahydro-2H-pyran-4-yl)methyl)-1H-benzo[d]imidazol-6-yl)methyl)amino)-3-hydroxybutanoate (prepared from: Intermediate 121) System B, 0.88 min, MH$^+$ = 525, Yield 207 mg, 72%

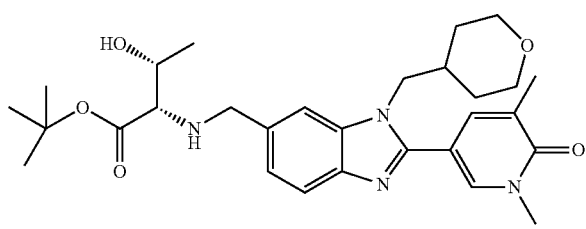 [SMILES: Cc1cc(-c2nc3ccc(CN[C@H](C(=O)OC(C)(C)C)[C@@H](C)O)cc3n2CC2CCOCC2)cn(C)c1=O]

Example 107: (2S,3R)-neopentyl 2-(((2-(1,5-dimethyl-6-oxo-1H-dihydropyridin-3-yl)-1-((tetrahydro-2H-pyran-4-yl)methyl)-1H-benzo[d]imidazol-6-yl)methyl)amino)-3-hydroxybutanoate (prepared from: Intermediate 121 and Intermediate 10) System B, 0.96 min, MH⁺ = 539, Yield: 110 mg, 75%

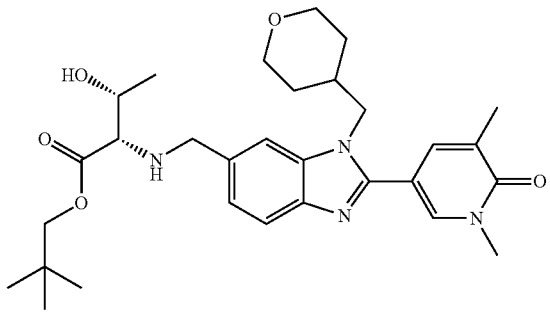 [SMILES: Cc1cc(-c2nc3ccc(CN[C@H](C(=O)OCC(C)(C)C)[C@@H](C)O)cc3n2CC2CCOCC2)cn(C)c1=O]

Example 108: (2S,3R)-isopropyl 3-hydroxy-2-(((2-(5-methyl-6-oxo-1,6-dihydropyridin-3-yl)-1-((tetrahydro-2H-pyran-3-yl)methyl)-1H-benzo[d]imidazol-5-yl)methyl)amino)butanoate (prepared from: Intermediate 211 and Intermediate 31) System B, 0.82 min, MH⁺ = 497, Yield: 136 mg, 43%

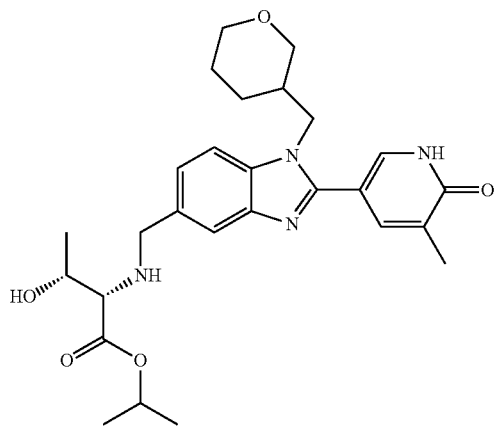 [SMILES: Cc1cc(-c2nc3cc(CN[C@H](C(=O)OC(C)C)[C@@H](C)O)ccc3n2CC2CCCOC2)c[nH]c1=O]

Example 109a: (2S,3R)-isobutyl 2-(((1-((1,4-dioxan-2-yl)methyl)-2-(1,5-dimethyl-6-oxo-1H-dihydropyridin-3-yl)-1H-benzo[d]imidazol-5-yl)methyl)amino)-3-hydroxybutanoate (single diastereomer, of unknown configuration at dioxane chiral centre, Isomer 1) (prepared from: Intermediate 120 and Intermediate 11) System B, 0.88 min, MH⁺ = 527, Yield: 158 mg, 65%

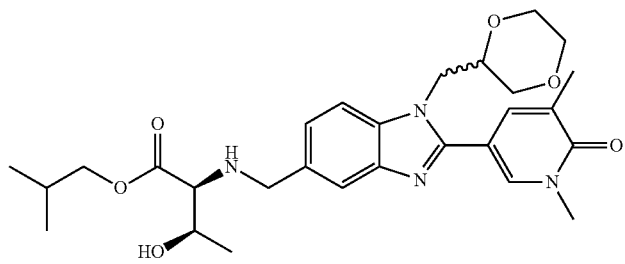 [SMILES: Cc1cc(-c2nc3cc(CN[C@H](C(=O)OCC(C)C)[C@@H](C)O)ccc3n2CC2COCCO2)cn(C)c1=O]

Example 109b: (2S,3R)-isopropyl 2-(((1-((1,4-dioxan-2-yl)methyl)-2-(1,5-dimethyl-6-oxo-1,6-dihydropyridin-3-yl)-1H-benzo[d]imidazol-5-yl)methyl)amino)-3-hydroxybutanoate (single diastereomer, of unknown configuration at dioxane chiral centre, isomer 2) (prepared from: Intermediate 120 and Intermediate 31) System B, 0.80 min, MH⁺ = 513, Yield: 83 mg, 75%

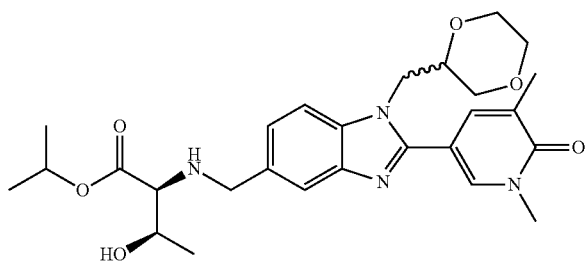 [SMILES: Cc1cc(-c2nc3cc(CN[C@H](C(=O)OC(C)C)[C@@H](C)O)ccc3n2CC2COCCO2)cn(C)c1=O]

Example 110: (2S,3R)-isopropyl 2-(((2-(1,5-dimethyl-6-oxo-1,6-dihydropyridin-3-yl)-1-(((S)-tetrahydrofuran-2-yl)methyl)-1H-benzo[d]imidazol-5-yl)methyl)amino)-3-hydroxybutanoate (prepared from: Intermediate 118 and Intermediate 31) System B, 0.87 min, MH$^+$ = 497, Yield: 7 mg, 5.2%

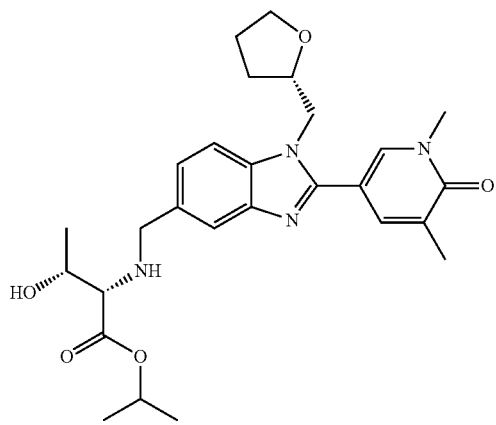 [SMILES: Cc1cc(-c2nc3cc(CN[C@H](C(=O)OC(C)C)[C@@H](C)O)ccc3n2C[C@@H]2CCCO2)cn(C)c1=O]

Example 111: (2S,3R)-tert-butyl 2-(((1-((1,4-dioxan-2-yl)methyl)-2-(1,5-dimethyl-6-oxo-1,6-dihydropyridin-3-yl)-1H-benzo[d]imidazol-5-yl)methyl)amino)-3-hydroxybutanoate (single diastereomer, of unknown configuration at dioxane chiral centre) (prepared from: Intermediate 120 and (2S,3R)-tert-butyl 2-amino-3-hydroxybutanoate hydrochloride (commercially available)) System B, 0.87 min, MH$^+$ = 527, Yield: 21 mg, 73%

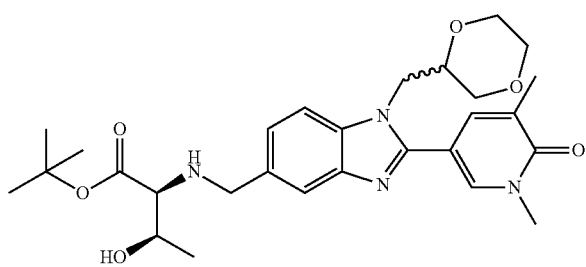 [SMILES: Cc1cc(-c2nc3cc(CN[C@H](C(=O)OC(C)(C)C)[C@@H](C)O)ccc3n2CC2COCCO2)cn(C)c1=O]

Example 112: (2S,3R)-2-hydroxy-2-methylpropyl 2-(((2-(1,5-dimethyl-6-oxo-1,6-dihydropyridin-3-yl)-1-((tetrahydro-2H-pyran-4-yl)methyl)-1H-benzo[d]imidazol-6-yl)methyl)amino)-3-hydroxybutanoate (prepared from: Intermediate 121 and Intermediate 7) System J, 0.74 min, MH$^+$ = 541, Yield: 35 mg, 47%

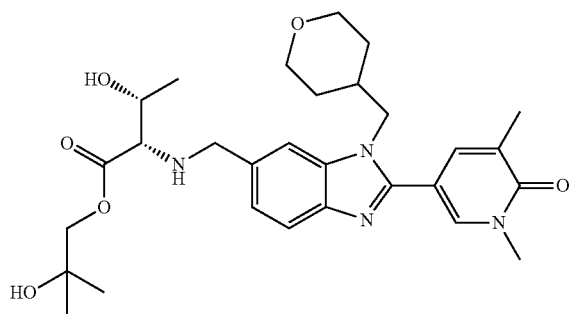 [SMILES: Cc1cc(-c2nc3ccc(CN[C@H](C(=O)OCC(C)(C)O)[C@@H](C)O)cc3n2CC2CCOCC2)cn(C)c1=O]

Example 113: (2S,3R)-tert-butyl 2-(((2-(1,5-dimethyl-6-oxo-1,6-dihydropyridin-3-yl)-1-(((S)-tetrahydrofuran-2-yl)methyl)-1H-benzo[d]imidazol-5-yl)methyl)amino)-3-hydroxybutanoate (prepared from: Intermediate 118 and (2S,3R)-tert-butyl 2-amino-3-hydroxybutanoate hydrochloride (commercially available)) System J, 0.99 min, MH$^+$ = 511, Yield: 89 mg, 61%

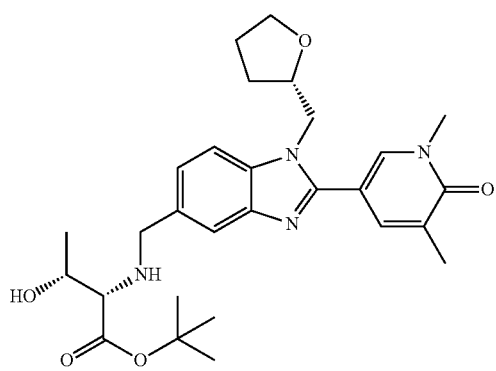 [SMILES: Cc1cc(-c2nc3cc(CN[C@H](C(=O)OC(C)(C)C)[C@@H](C)O)ccc3n2C[C@@H]2CCCO2)cn(C)c1=O]

| | |
|---|---|
| Example 114: (2S,3R)-(S)-tetrahydrofuran-3-yl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-methoxybutanoate (prepared from: Intermediate 116 and Intermediate 9) System J, 0.84 min, MH⁺ = 553, Yield: 218 mg, 72% | 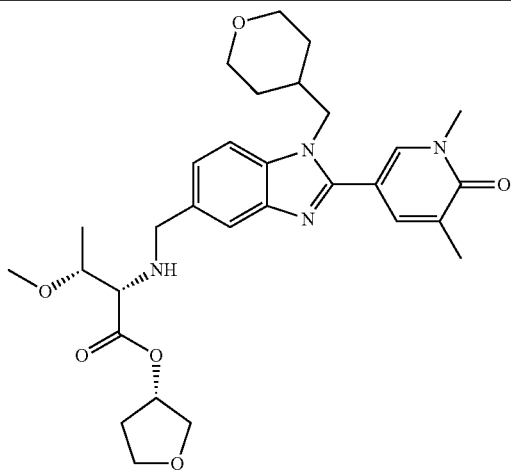 |
| Example 115: (2S,3R)-(S)-tetrahydrofuran-3-yl 2-(((2-(1,5-dimethyl-6-oxo-1,6-dihydropyridin-3-yl)-1-(((S)-tetrahydrofuran-2-yl)methyl)-1H-benzo[d]imidazol-5-yl)methyl)amino)-3-methoxybutanoate (prepared from: Intermediate 118 and Intermediate 9) System J, 0.88 min, MH⁺ = 539, Yield: 189 mg, 49% | 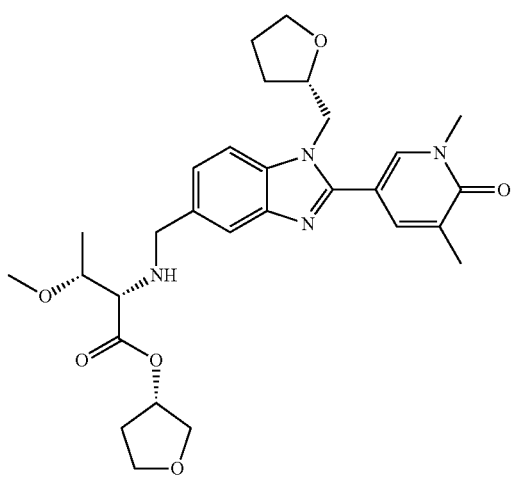 [SMILES: CO[C@H](C)[C@H](NCc1ccc2c(c1)nc(-c1cc(C)c(=O)n(C)c1)n2C[C@@H]1CCCO1)C(=O)O[C@H]1CCOC1] |
| Example 116: (2S,3R)-isobutyl 2-(((2-(1,5-dimethyl-6-oxo-1,6-dihydropyridin-3-yl)-1-((S)-1-methoxypropan-2-yl)-1H-benzo[d]imidazol-6-yl)methyl)amino)-3-hydroxybutanoate (prepared from: Intermediate 123 and Intermediate 11) System J, 0.96 min, MH⁺ = 499, Yield: 324 mg, 60% | 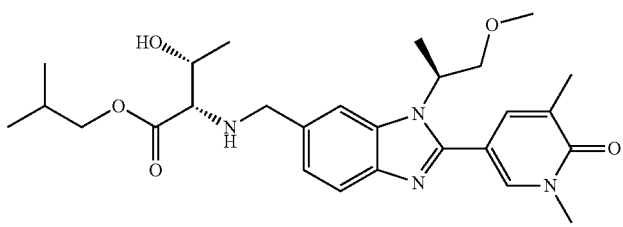 [SMILES: COC[C@H](C)n1c(-c2cc(C)c(=O)n(C)c2)nc2ccc(CN[C@H](C(=O)OCC(C)C)[C@@H](C)O)cc21] |
| Example 117: (2S,3R)-tert-butyl 2-(((2-(1,5-dimethyl-6-oxo-1,6-dihydropyridin-3-yl)-1-(((S)-tetrahydrofuran-2-yl)methyl)-1H-benzo[d]imidazol-6-yl)methyl)amino)-3-hydroxybutanoate (prepared from: Intermediate 124 and (2S,3R)-tert-butyl 2-amino-3-hydroxybutanoate hydrochloride(commercially available)) System J, 0.54 min, MH⁺ = 511, Yield: 22 mg, 15% | 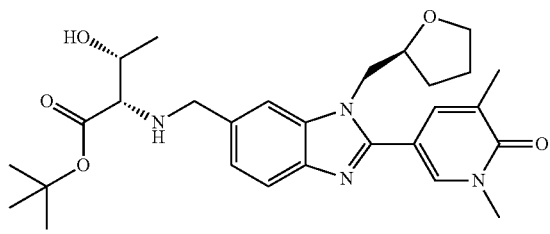 [SMILES: Cc1cc(-c2nc3ccc(CN[C@H](C(=O)OC(C)(C)C)[C@@H](C)O)cc3n2C[C@@H]2CCCO2)cn(C)c1=O] |

Example 118: (2S,3R)-
isobutyl 2-(((2-(1,5-dimethyl-6-
oxo-1,6-dihydropyridin-3-
yl)-1-(((S)-tetrahydrofuran-2-
yl)methyl)-1H-benzo[d]
imidazol-6-yl)methyl)amino)-3-
hydroxybutanoate (prepared
from: Intermediate 124 and
Intermediate 11) System I,
0.56 min, MH$^+$ = 511, Yield:
55 mg, 38%

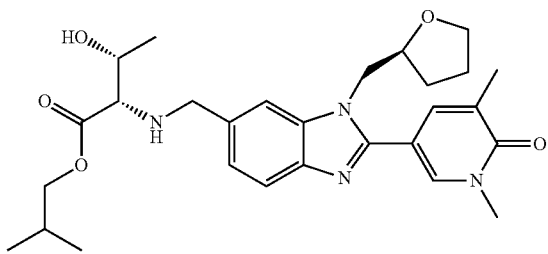 [SMILES: Cc1cc(-c2nc3ccc(CN[C@H](C(=O)OCC(C)C)[C@@H](C)O)cc3n2C[C@@H]2CCCO2)cn(C)c1=O]

Example 119: (2S,3R)-isopropyl
2-(((2-(1,5-dimethyl-6-
oxo-1,6-dihydropyridin-3-yl)-
1-(((S)-tetrahydrofuran-2-
yl)methyl)-1H-benzo[d]
imidazol-6-yl)methyl)amino)-3-
hydroxybutanoate (prepared
from: Intermediate 124 and
Intermediate 31) System I,
0.51 min, MH$^+$ = 497, Yield: 49 mg, 34%

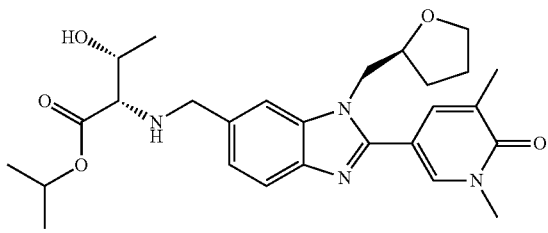 [SMILES: Cc1cc(-c2nc3ccc(CN[C@H](C(=O)OC(C)C)[C@@H](C)O)cc3n2C[C@@H]2CCCO2)cn(C)c1=O]

Example 120: (2S,3R)-isopropyl
2-(((2-(1,5-dimethyl-6-
oxo-1,6-dihydropyridin-3-yl)-
1-((S)-1-methoxypropan-2-
yl)-1H-benzo[d]imidazol-6-
yl)methyl)amino)-3-
hydroxybutanoate (prepared
from: Intermediate 123 and
Intermediate 31) System J,
0.88 min, MH$^+$ = 485, Yield: 41 mg, 35%

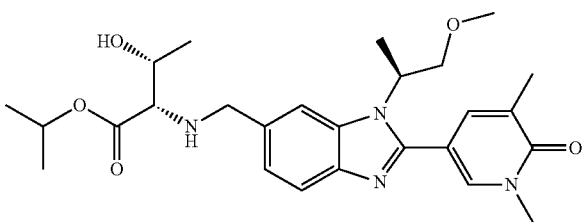 [SMILES: COC[C@H](C)n1c(-c2cc(C)c(=O)n(C)c2)nc2ccc(CN[C@H](C(=O)OC(C)C)[C@@H](C)O)cc21]

Example 123: (2S,3R)-tert-butyl
2-(((2-(1,5-dimethyl-6-
oxo-1,6-dihydropyridin-3-yl)-
1-((S)-1-methoxypropan-2-
yl)-1H-benzo[d]imidazol-6-
yl)methyl)amino)-3-
hydroxybutanoate (prepared
from: Intermediate 123 and
(2S,3R)-tert-butyl 2-
amino-3-hydroxybutanoate
hydrochloride (commercially
available)) System J, 0.95
min, MH$^+$ = 499, Yield: 66 mg, 56%

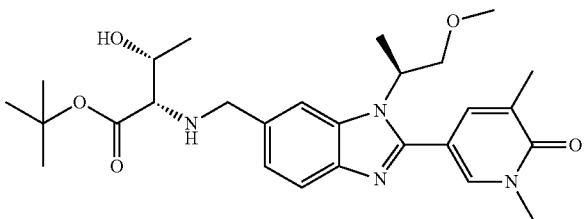 [SMILES: COC[C@H](C)n1c(-c2cc(C)c(=O)n(C)c2)nc2ccc(CN[C@H](C(=O)OC(C)(C)C)[C@@H](C)O)cc21]

Example 124: (2S,3R)-isopropyl 2-
(((1-(((R)-1-
acetylpiperidin-3-yl)methyl)-
2-(1,5-dimethyl-6-oxo-1,6-
dihydropyridin-3-yl)-1H-benzo[d]imidazol-6-
yl)methyl)amino)-3-
hydroxybutanoate (prepared from:
Intermediate 125 and
Intermediate 31) System J, 0.83
min, MH$^+$ = 552, Yield: 85 mg, 41%

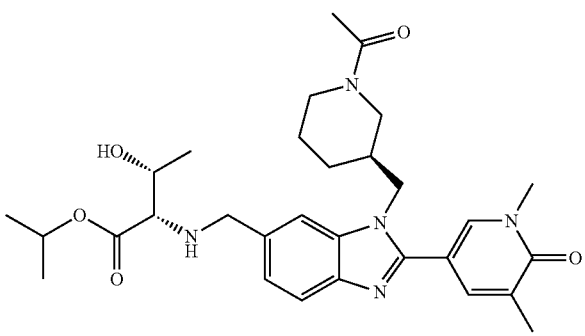 [SMILES: CC(=O)N1CCC[C@H](Cn2c(-c3cc(C)c(=O)n(C)c3)nc3ccc(CN[C@H](C(=O)OC(C)C)[C@@H](C)O)cc32)C1]

Example 125: (2S,3R)-isobutyl 2-(((1-(((R)-1-acetylpiperidin-3-yl)methyl)-2-(1,5-dimethyl-6-oxo-1,6-dihydropyridin-3-yl)-1H-benzo[d]imidazol-6-yl)methyl)amino)-3-hydroxybutanoate (prepared from: Intermediate 125 and Intermediate 11) System J, 0.90 min, MH$^+$ = 566, Yield: 52 mg, 47%

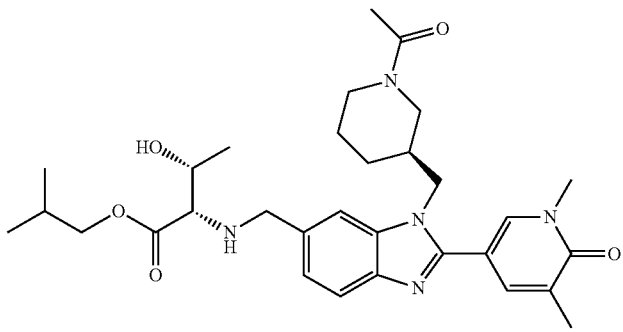 [SMILES: CC(=O)N1CCC[C@H](Cn2c(-c3cc(C)c(=O)n(C)c3)nc3ccc(CN[C@H](C(=O)OCC(C)C)[C@@H](C)O)cc32)C1]

Example 126: (2S,3R)-tert-butyl 2-(((1-(((R)-1-acetylpiperidin-3-yl)methyl)-2-(1,5-dimethyl-6-oxo-1,6-dihydropyridin-3-yl)-1H-benzo[d]imidazol-6-yl)methyl)amino)-3-hydroxybutanoate #(prepared from: Intermediate 125 and (2S,3R)-tert-butyl 2-amino-3-hydroxybutanoate hydrochloride (commercially available)) System J, 0.88 min, MH$^+$ = 566, Yield: 58 mg, 83%

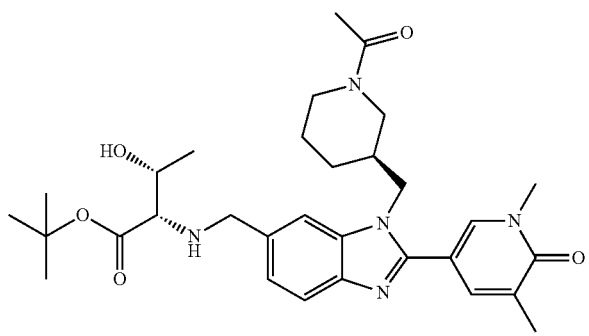 [SMILES: CC(=O)N1CCC[C@H](Cn2c(-c3cc(C)c(=O)n(C)c3)nc3ccc(CN[C@H](C(=O)OC(C)(C)C)[C@@H](C)O)cc32)C1]

Example 127: (2S,3R)-cyclobutyl 2-(((2-(1,5-dimethyl-6-oxo-1,6-dihydropyridin-3-yl)-1-((S)-1-methoxypropan-2-yl)-1H-benzo[d]imidazol-6-yl)methyl)amino)-3-hydroxybutanoate (prepared from: Intermediate 123 and Intermediate 32) System J, 0.93 min, MH$^+$ = 497, Yield: 40 mg, 55%

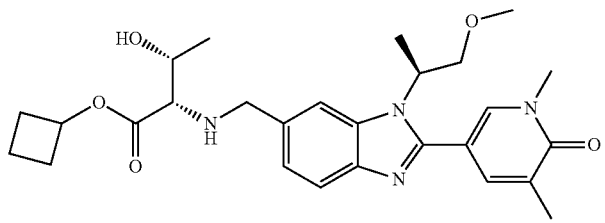 [SMILES: COC[C@H](C)n1c(-c2cc(C)c(=O)n(C)c2)nc2ccc(CN[C@H](C(=O)OC3CCC3)[C@@H](C)O)cc21]

Example 128: (2S,3R)-isopropyl 2-(((1-(((S)-1-acetylpiperidin-3-yl)methyl)-2-(1,5-dimethyl-6-oxo-1,6-dihydropyridin-3-yl)-1H-benzo[d]imidazol-6-yl)methyl)amino)-3-hydroxybutanoate (prepared from: Intermediate 127 and Intermediate 31) System J, 0.83 min, MH$^+$ = 552, Yield: 87 mg, 53%

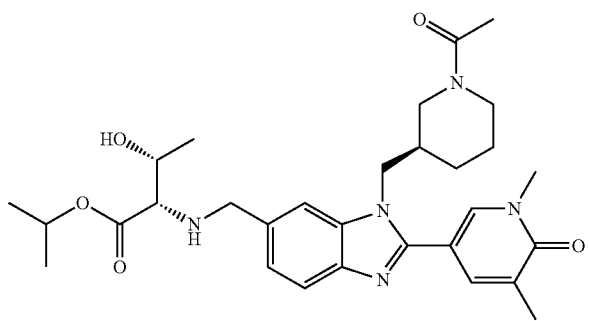 [SMILES: CC(=O)N1CCC[C@@H](Cn2c(-c3cc(C)c(=O)n(C)c3)nc3ccc(CN[C@H](C(=O)OC(C)C)[C@@H](C)O)cc32)C1]

Example 129: (2S,3R)-tert-butyl 2-(((1-(((S)-1-acetylpiperidin-3-yl)methyl)-2-(1,5-dimethyl-6-oxo-1,6-dihydropyridin-3-yl)-1H-benzo[d]imidazol-6-yl)methyl)amino)-3-hydroxybutanoate (prepared from: Intermediate 127 and (2S,3R)-tert-butyl 2-amino-3-hydroxybutanoate hydrochloride (commercially available)) System B, 0.88 min, MH$^+$ = 566, Yield: 19 mg, 34%

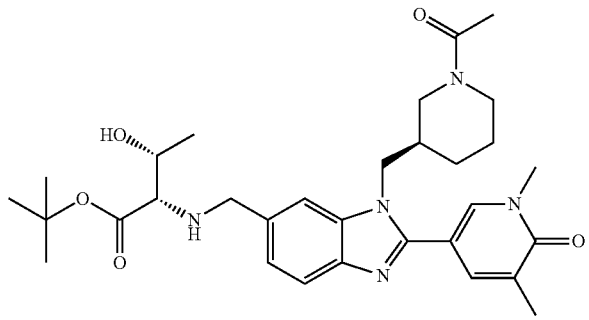

-continued

Example 130: (2S,3R)-isopropyl 2-(((2-(1,5-dimethyl-6-oxo-1,6-dihydropyridin-3-yl)-1-(1-methoxybutan-2-yl)-1H-benzo[d]imidazol-5-yl)methyl)amino)-3-hydroxybutanoate (prepared from: Intermediate 117 and Intermediate 31) System I, 0.61 min, MH+ = 499, Yield: 278 mg, 66%

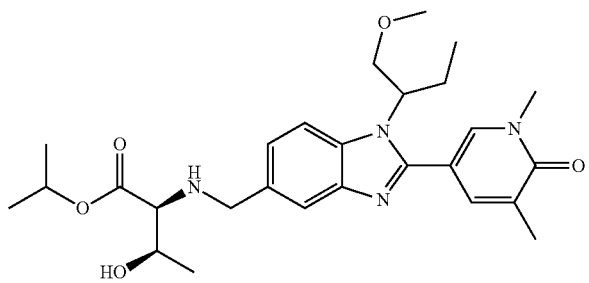 [SMILES: CCC(COC)n1c(-c2cc(C)c(=O)n(C)c2)nc2cc(CN[C@H](C(=O)OC(C)C)[C@@H](C)O)ccc21]

Example 131: (2S,3R)-cyclobutyl 2-(((2-(1,5-dimethyl-6-oxo-1,6-dihydropyridin-3-yl)-1-(1-methoxybutan-2-yl)-1H-benzo[d]imidazol-5-yl)methyl)amino)-3-hydroxybutanoate (prepared from: Intermediate 117 and Intermediate 32) System I, 0.62 min, MH+ = 511, Yield: 297 mg, 69%

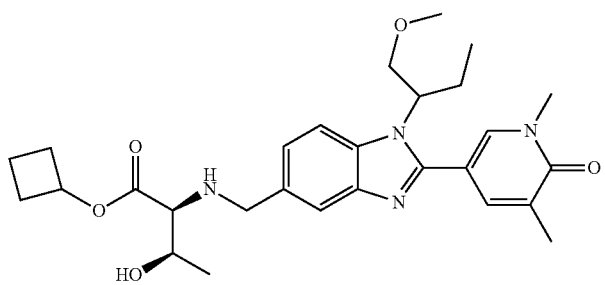 [SMILES: CCC(COC)n1c(-c2cc(C)c(=O)n(C)c2)nc2cc(CN[C@H](C(=O)OC3CCC3)[C@@H](C)O)ccc21]

Example 132: (2S,3R)-tert-butyl 2-(((2-(1,5-dimethyl-6-oxo-1,6-dihydropyridin-3-yl)-1-(1-methoxybutan-2-yl)-1H-benzo[d]imidazol-5-yl)methyl)amino)-3-hydroxybutanoate (prepared from: Intermediate 117 and (2S,3R)-tert-butyl 2-amino-3-hydroxybutanoate hydrochloride (commercially available)) System I, 0.63 min, MH+ = 513, Yield: 55 mg, 58%

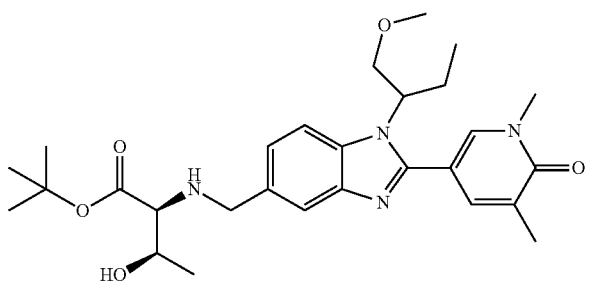 [SMILES: CCC(COC)n1c(-c2cc(C)c(=O)n(C)c2)nc2cc(CN[C@H](C(=O)OC(C)(C)C)[C@@H](C)O)ccc21]

Example 133: (2S,3R)-isopropyl 2-(((2-(1,5-dimethyl-6-oxo-1,6-dihydropyridin-3-yl)-1-((tetrahydrofuran-3-yl)methyl)-1H-benzo[d]imidazol-6-yl)methyl)amino)-3-hydroxybutanoate (prepared from: Intermediate 129 and Intermediate 31) System I, 0.84 min, MH+ = 497, Yield: 338 mg, 60%

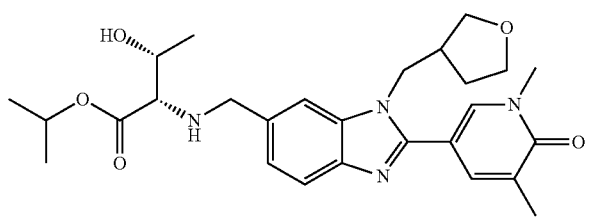

Example 134: (2S,3R)-tert-butyl 2-(((2-(1,5-dimethyl-6-oxo-1,6-dihydropyridin-3-yl)-1-((tetrahydrofuran-3-yl)methyl)-1H-benzo[d]imidazol-6-yl)methyl)amino)-3-hydroxybutanoate (prepared from: Intermediate 129 and (2S,3R)-tert-butyl 2-amino-3-hydroxybutanoate hydrochloride (commercially available)) System J, 0.91 min, MH+ = 511, Yield: 224 mg, 77%

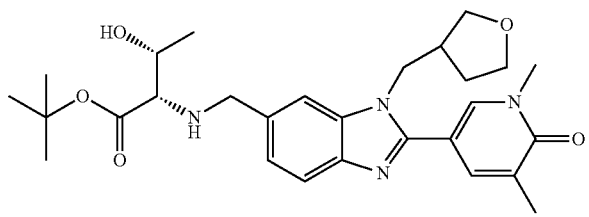 [SMILES: Cc1cc(-c2nc3ccc(CN[C@H](C(=O)OC(C)(C)C)[C@@H](C)O)cc3n2CC2CCOC2)cn(C)c1=O]

Example 135: (2S,3R)-isopropyl 2-(((2-(1,5-dimethyl-6-oxo-1,6-dihydropyridin-3-yl)-1-((S)-1-hydroxypropan-2-yl)-1H-benzo[d]imidazol-5-yl)methyl)amino)-3-hydroxybutanoate (prepared from: Intermediate 236 and Intermediate 31) System I, 0.48 min, MH⁺ = 471, Yield: 67 mg, 47%

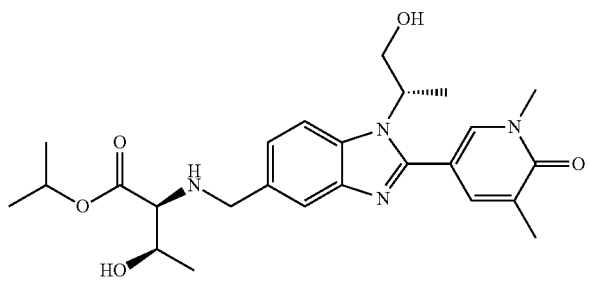 [SMILES: Cc1cc(-c2nc3cc(CN[C@H](C(=O)OC(C)C)[C@@H](C)O)ccc3n2[C@@H](C)CO)cn(C)c1=O]

Example 136: (S)-tert-butyl 4-methyl-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)pentanoate (prepared from: Intermediate 151 and Intermediate X) System B, 1.14 min, MH⁺ = 523, Yield: 18 mg, 88%

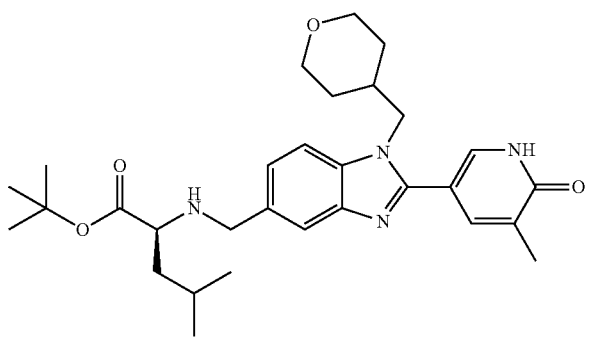 [SMILES: Cc1cc(-c2nc3cc(CN[C@@H](CC(C)C)C(=O)OC(C)(C)C)ccc3n2CC2CCOCC2)c[nH]c1=O]

Example 137: (S)-cyclopentyl 3-hydroxy-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)propanoate (prepared from: Intermediate 151 and Intermediate 276) System B, 0.81 min, MH⁺ = 509, Yield: 234 mg, 81%

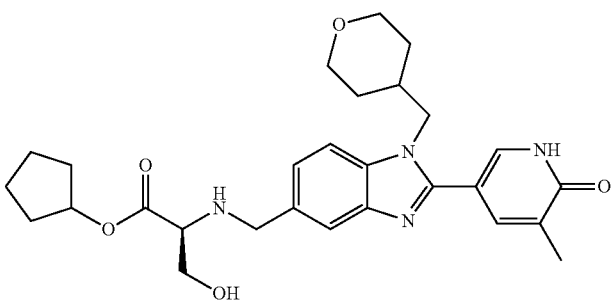 [SMILES: Cc1cc(-c2nc3cc(CN[C@@H](CO)C(=O)OC4CCCC4)ccc3n2CC2CCOCC2)c[nH]c1=O]

Example 138: (2S,3R)-cyclopentyl 3-hydroxy-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)butanoate (prepared from: Intermediate 151 and Intermediate 137) System B, 0.87 min, MH⁺ = 523, Yield: 261 mg, 88%

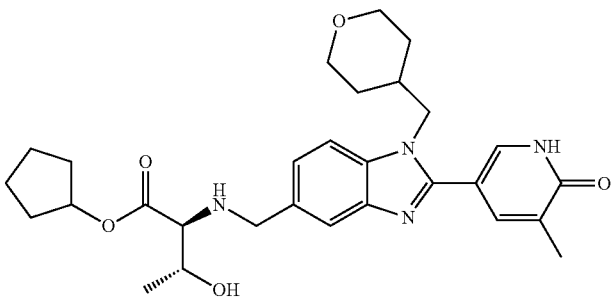 [SMILES: Cc1cc(-c2nc3cc(CN[C@H](C(=O)OC4CCCC4)[C@@H](C)O)ccc3n2CC2CCOCC2)c[nH]c1=O]

Example 139: (2S)-tetrahydrofuran-3-yl 4-methyl-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)pentanoate (Prepared from: Intermediate 151 and Intermediate 17) System B, 0.93 min, MH⁺ = 537, Yield: 243 mg, 80%

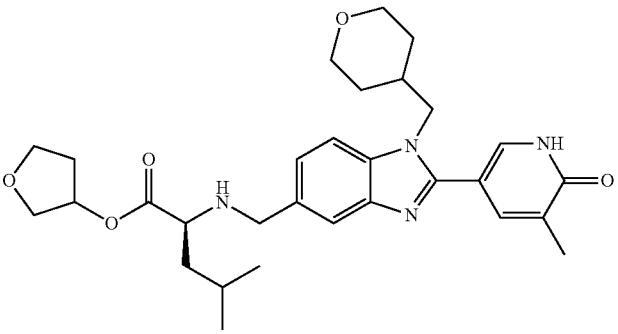 [SMILES: Cc1cc(-c2nc3cc(CN[C@@H](CC(C)C)C(=O)OC4CCOC4)ccc3n2CC2CCOCC2)c[nH]c1=O]

-continued

Example 140: (S)-cyclopentyl 2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)propanoate (prepared from: Intermediate 151 and Intermediate 277) System B, 0.94 min, MH$^+$ = 493, Yield: 176 mg, 63%

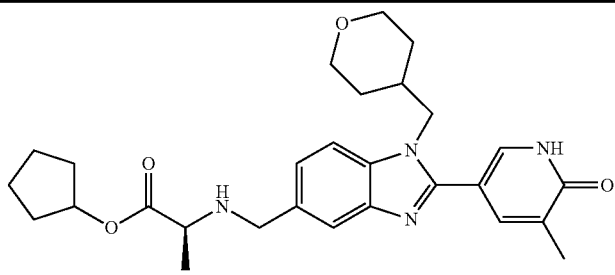

Example 141: (S)-neopentyl 4-methyl-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)pentanoate (prepared from: Intermediate 151 and Intermediate 19) System B, 1.20 min, MH$^+$ = 537, Yield: 209 mg, 69%

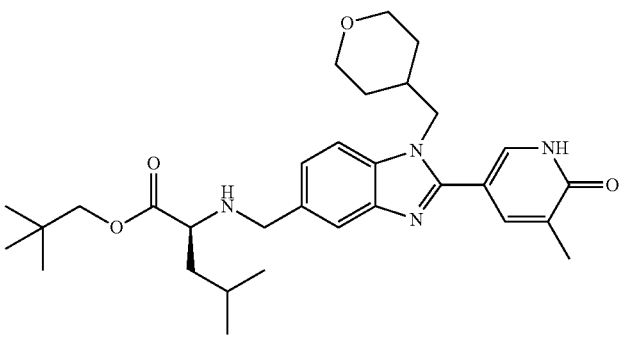 [SMILES: Cc1cc(-c2nc3cc(CN[C@@H](CC(C)C)C(=O)OCC(C)(C)C)ccc3n2CC2CCOCC2)c[nH]c1=O]

Example 142: (S)-cyclopentyl 2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)-2-(tetrahydro-2H-pyran-4-yl)acetate (prepared from: Intermediate 151 and Intermediate 22) System B, 0.98 min, MH$^+$ = 563, Yield: 122 mg, 64%

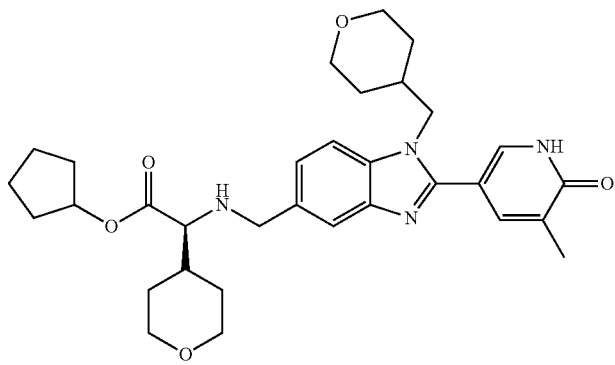 [SMILES: Cc1cc(-c2nc3cc(CN[C@H](C(=O)OC4CCCC4)C4CCOCC4)ccc3n2CC2CCOCC2)c[nH]c1=O]

Example 143: (S)-cyclopentyl 4-methoxy-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)butanoate (prepared from: Intermediate 151 and Intermediate 23) System B, 0.96 min, MH$^+$ = 537, Yield: 96 mg, 52%

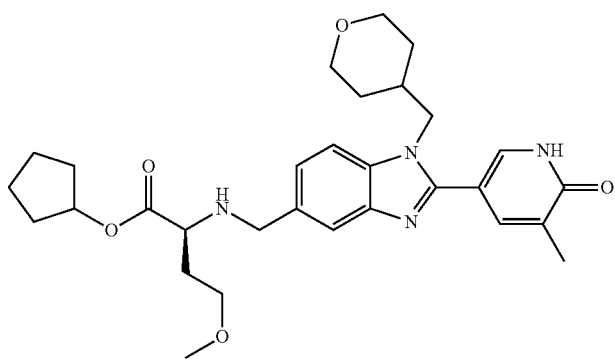 [SMILES: COCC[C@H](NCc1ccc2c(c1)nc(-c1c[nH]c(=O)c(C)c1)n2CC1CCOCC1)C(=O)OC1CCCC1]

Example 144: (S)-cyclopentyl 2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)butanoate (prepared from: Intermediate 151 and Intermediate 13) System B, 1.02 min, MH$^+$ = 507, Yield: 112 mg, 60%

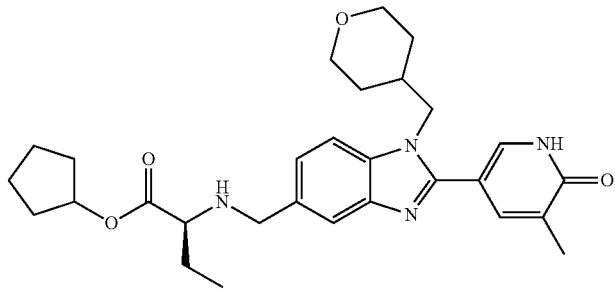 [SMILES: CC[C@H](NCc1ccc2c(c1)nc(-c1c[nH]c(=O)c(C)c1)n2CC1CCOCC1)C(=O)OC1CCCC1]

Example 145: (S)-cyclopentyl 2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)pentanoate (prepared from: Intermediate 151 and Intermediate 281) System B, 1.09 min, MH$^+$ = 521, Yield 112 mg, 60%

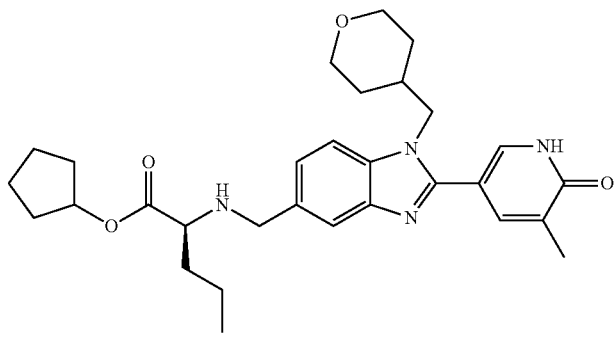 [SMILES: CCC[C@H](NCc1ccc2c(c1)nc(-c1c[nH]c(=O)c(C)c1)n2CC1CCOCC1)C(=O)OC1CCCC1]

Example 146: (S)-cyclopentyl 3-methoxy-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)propanoate (prepared from: Intermediate 151 and Intermediate 196) System B, 0.92 min, MH$^+$ = 522, Yield: 127 mg, 71%

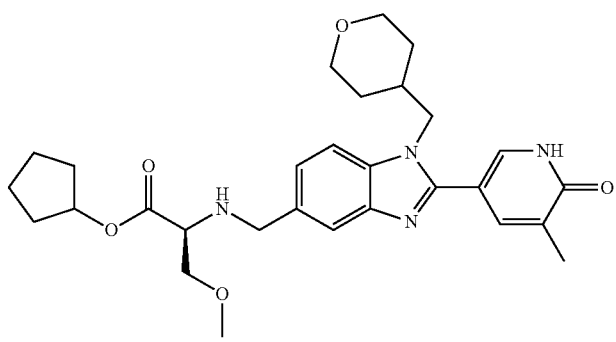

Example 147: (S)-(S)-1-methoxypropan-2-yl 3-methyl-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)butanoate (prepared from: Intermediate 151 and Intermediate 63) System A, 0.63 min, MH$^+$ = 525, Yield: 52 mg, 28%

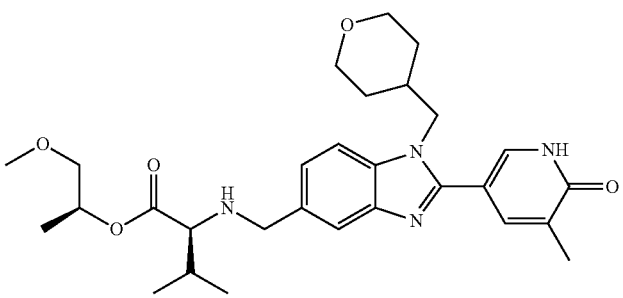 [SMILES: COC[C@H](C)OC(=O)[C@@H](NCc1ccc2c(c1)nc(-c1c[nH]c(=O)c(C)c1)n2CC1CCOCC1)C(C)C]

Example 148: (S)-(R)-1-methoxypropan-2-yl 3-methyl-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)butanoate (prepared from: Intermediate 151 and Intermediate 280) System A, 0.62 min, MH$^+$ = 525, Yield: 103 mg, 57%

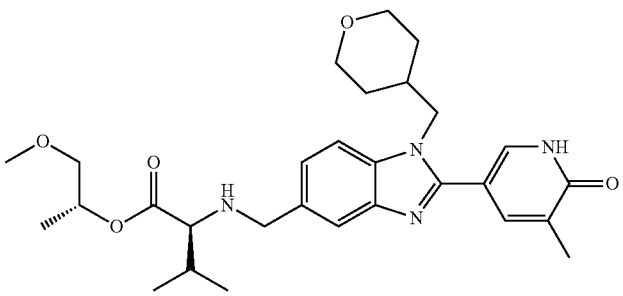 [SMILES: COC[C@@H](C)OC(=O)[C@@H](NCc1ccc2c(c1)nc(-c1c[nH]c(=O)c(C)c1)n2CC1CCOCC1)C(C)C]

Example 149: (2S,3R)-isobutyl 3-hydroxy-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)butanoate (prepared from: Intermediate 151 and Intermediate 11) System A, 0.87 min, MH$^+$ = 511, Yield: 72 mg, 28%

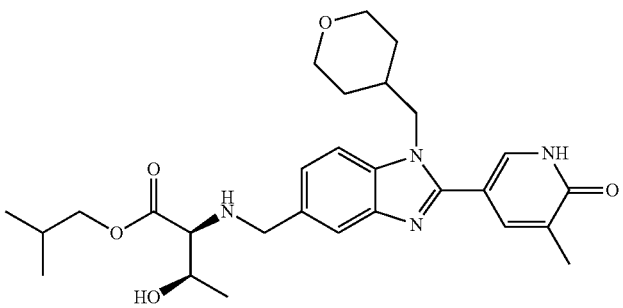 [SMILES: Cc1cc(-c2nc3cc(CN[C@H](C(=O)OCC(C)C)[C@@H](C)O)ccc3n2CC2CCOCC2)c[nH]c1=O]

Example 150: (2S)-tert-butyl 4-methyl-2-(((2-(5-methyl-6-oxo-1,6-dihydropyridin-3-yl)-1-((4-methylmorpholin-2-yl)methyl)-1H-benzo[d]imidazol-5-yl)methyl)amino)pentanoate (prepared from: Intermediate 275 and (S)-tert-butyl 2-amino-4-methylpentanoate hydrochloride (commercially available)) System B, 1.09 min, MH$^+$ = 538, Yield: 3.1 mg, 4%

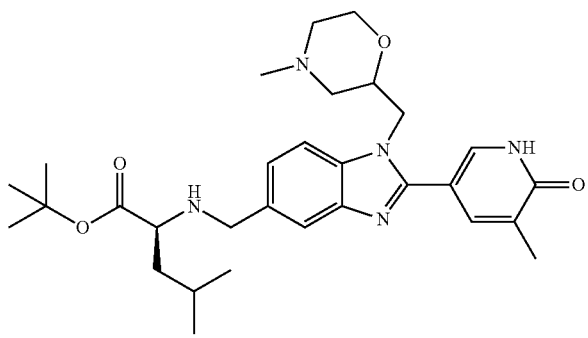 [SMILES: Cc1cc(-c2nc3cc(CN[C@@H](CC(C)C)C(=O)OC(C)(C)C)ccc3n2CC2CN(C)CCO2)c[nH]c1=O]

Example 151: (S)-cyclopentyl 2-(((1-ethyl-2-(5-methyl-6-oxo-1,6-dihydropyridin-3-yl)-1H-benzo[d]imidazol-5-yl)methyl)amino)-4-methylpentanoate (prepared from: Intermediate 113 and Intermediate 3) System B, 1.16 min, MH$^+$ = 465, Yield: 65 mg, 33%

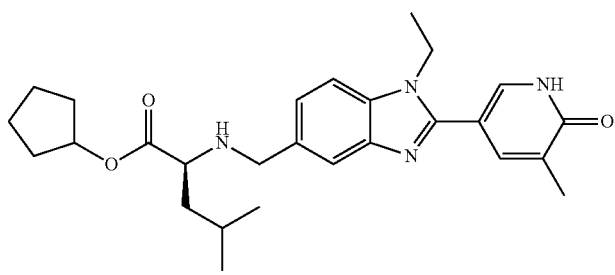 [SMILES: CCn1c(-c2c[nH]c(=O)c(C)c2)nc2cc(CN[C@@H](CC(C)C)C(=O)OC3CCCC3)ccc21]

Example 152: (2S)-cyclopentyl 4-methyl-2-(((1-((1-methyl-5-oxopyrrolidin-3-yl)methyl)-2-(5-methyl-6-oxo-1,6-dihydropyridin-3-yl)-1H-benzo[d]imidazol-5-yl)methyl)amino)pentanoate (prepared from: Intermediate 153 and Intermediate 3) System B, 1.03 min, MH$^+$ = 548, Yield: 23 mg, 13%

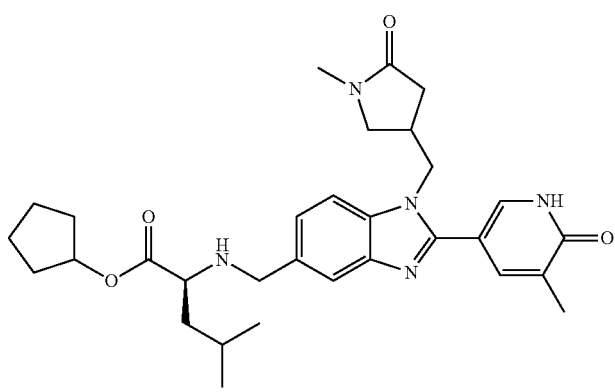 [SMILES: Cc1cc(-c2nc3cc(CN[C@@H](CC(C)C)C(=O)OC4CCCC4)ccc3n2CC2CC(=O)N(C)C2)c[nH]c1=O]

Example 153: (2S)-cyclopentyl 2-(((1-((1-acetylpyrrolidin-3-yl)methyl)-2-(5-methyl-6-oxo-1,6-dihydropyridin-3-yl)-1H-benzo[d]imidazol-5-yl)methyl)amino)-4-methylpentanoate (prepared from: Intermediate 156 and Intermediate 3) System B, 1.04 min, MH$^+$ = 562, Yield: 74 mg, 38%

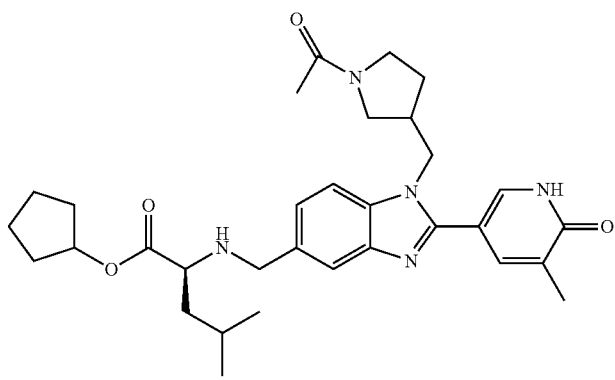 [SMILES: CC(=O)N1CCC(Cn2c(-c3c[nH]c(=O)c(C)c3)nc3cc(CN[C@@H](CC(C)C)C(=O)OC4CCCC4)ccc32)C1]

Example 154: (2S,3R)-neopentyl 2-(((2-(1,5-dimethyl-6-oxo-1,6-dihydropyridin-3-yl)-1-methyl-1H-benzo[d]imidazol-5-yl)methyl)amino)-3-hydroxybutanoate (prepared from: Intermediate 273 and Intermediate 10) System B, 0.95 min, MH$^+$ = 455, Yield: 137 mg, 85%

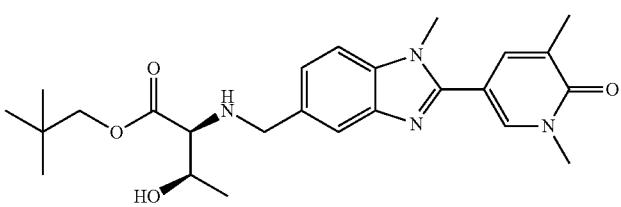 [SMILES: Cc1cc(-c2nc3cc(CN[C@H](C(=O)OCC(C)(C)C)[C@@H](C)O)ccc3n2C)cn(C)c1=O]

Example 155: (2S,3R)-isobutyl 2-(((2-(1,5-dimethyl-6-oxo-1,6-dihydropyridin-3-yl)-1-methyl-1H-benzo[d]imidazol-5-yl)methyl)amino)-3-hydroxybutanoate (prepared from: Intermediate 273 and Intermediate 11) System B, 0.89 min, MH+ = 441, Yield: 137 mg, 85%

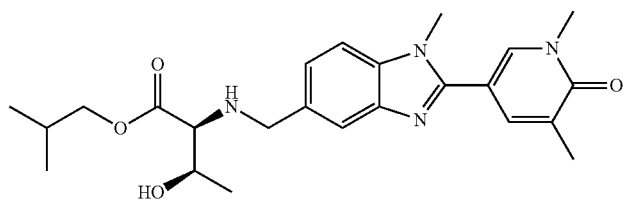 [SMILES: Cc1cc(-c2nc3cc(CN[C@H](C(=O)OCC(C)C)[C@@H](C)O)ccc3n2C)cn(C)c1=O]

Example 156: (2S,3R)-cyclopentyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate (prepared from: Intermediate 116 and Intermediate 137) System B, 0.91 min, MH+ = 537, Yield: 119 mg, 75%

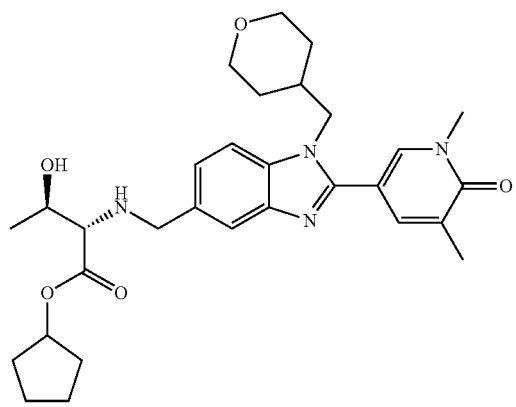 [SMILES: Cc1cc(-c2nc3cc(CN[C@H](C(=O)OC4CCCC4)[C@@H](C)O)ccc3n2CC2CCOCC2)cn(C)c1=O]

Example 157: (2S,3R)-(S)-tetrahydrofuran-3-yl 2-(((2-(1,5-dimethyl-6-oxo-1,6-dihydropyridin-3-yl)-1-isopropyl-1H-benzo[d]imidazol-5-yl)methyl)amino)-3-hydroxybutanoate (prepared from: Intermediate 274 and Intermediate 40) System A, 0.47 min, MH+ = 483, Yield: 111 mg, 71%

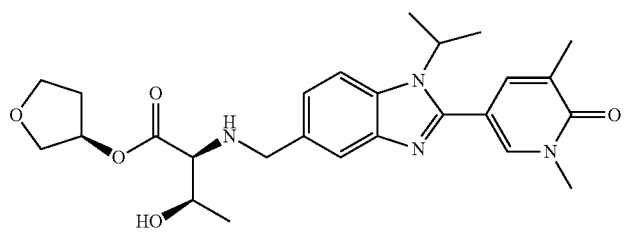 [SMILES: Cc1cc(-c2nc3cc(CN[C@H](C(=O)O[C@@H]4CCOC4)[C@@H](C)O)ccc3n2C(C)C)cn(C)c1=O]

Example 158: (2S,3R)-cyclopentyl 2-(((2-(1,5-dimethyl-6-oxo-1,6-dihydropyridin-3-yl)-1-isopropyl-1H-benzo[d]imidazol-5-yl)methyl)amino)-3-hydroxybutanoate (prepared from: Intermediate 274 and Intermediate 137) System A, 0.60 min, MH+ = 481, Yield: 83 mg, 53%

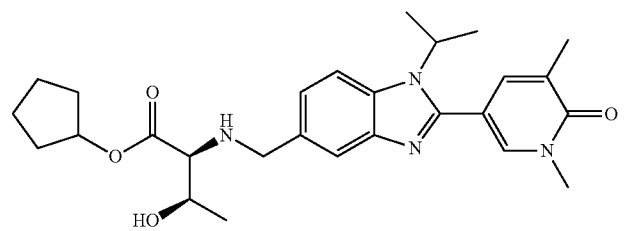 [SMILES: Cc1cc(-c2nc3cc(CN[C@H](C(=O)OC4CCCC4)[C@@H](C)O)ccc3n2C(C)C)cn(C)c1=O]

Example 159: (2S,3R)-(S)-tetrahydrofuran-3-yl 2-(((2-(1,5-dimethyl-6-oxo-1,6-dihydropyridin-3-yl)-1-(tetrahydro-2H-pyran-4-yl)-1H-benzo[d]imidazol-5-yl)methyl)amino)-3-hydroxybutanoate (prepared from: Intermediate 161 and Intermediate 40) System A, 0.48 min, MH+ = 525, Yield: 33 mg, 25%

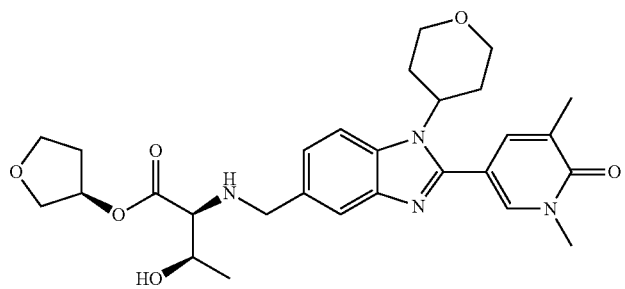 [SMILES: Cc1cc(-c2nc3cc(CN[C@H](C(=O)O[C@@H]4CCOC4)[C@@H](C)O)ccc3n2C2CCOCC2)cn(C)c1=O]

Example 160: (2S,3R)-isobutyl 2-(((2-(1,5-dimethyl-6-oxo-1,6-dihydropyridin-3-yl)-1-(tetrahydro-2H-pyran-4-yl)-1H-benzo[d]imidazol-5-yl)methyl)amino)-3-hydroxybutanoate (prepared from: Intermediate 161 and Intermediate 11) System B, 0.89 min, MH$^+$ = 511, Yield: 35 mg, 27%

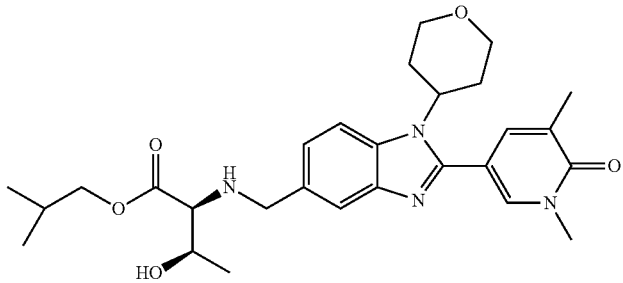 [SMILES: Cc1cc(-c2nc3cc(CN[C@H](C(=O)OCC(C)C)[C@@H](C)O)ccc3n2C2CCOCC2)cn(C)c1=O]

Example 161: (2S,3R)-isopropyl 2-(((2-(1,5-dimethyl-6-oxo-1,6-dihydropyridin-3-yl)-1-(tetrahydro-2H-pyran-4-yl)-1H-benzo[d]imidazol-5-yl)methyl)amino)-3-hydroxybutanoate (prepared from: Intermediate 161 and Intermediate 31) System I, 0.54 min, MH$^+$ = 497, Yield: 25 mg, 19%

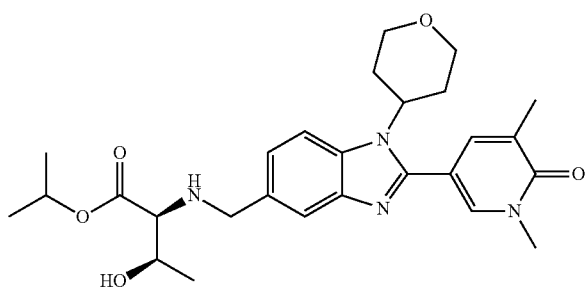 [SMILES: Cc1cc(-c2nc3cc(CN[C@H](C(=O)OC(C)C)[C@@H](C)O)ccc3n2C2CCOCC2)cn(C)c1=O]

Example 162: (2S,3R)-isobutyl 2-(((2-(1,5-dimethyl-6-oxo-1,6-dihydropyridin-3-yl)-1-((4-methylmorpholin-2-yl)methyl)-1H-benzo[d]imidazol-5-yl)methyl)amino)-3-hydroxybutanoate 9prepared from: Intermediate 164 and Intermediate 11) System B, 0.87 min, MH$^+$ = 540, Yield: 84 mg, 59%

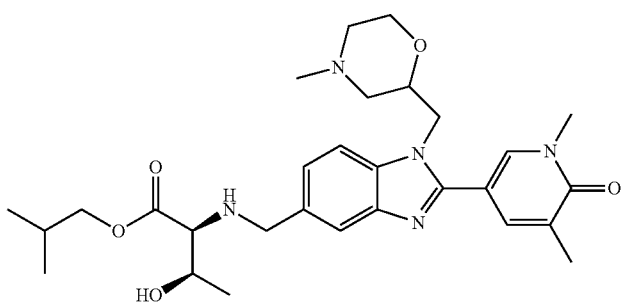 [SMILES: Cc1cc(-c2nc3cc(CN[C@H](C(=O)OCC(C)C)[C@@H](C)O)ccc3n2CC2CN(C)CCO2)cn(C)c1=O]

Example 163: (2S,3R)-(S)-tetrahydrofuran-3-yl 2-(((2-(1,5-dimethyl-6-oxo-1,6-dihydropyridin-3-yl)-1-((4-methylmorpholin-2-yl)methyl)-1H-benzo[d]imidazol-5-yl)methyl)amino)-3-hydroxybutanoate (prepared from: Intermediate 164 and Intermediate 40) System B, 0.69 min, MH$^+$ = 554, Yield: 85 mg, 58%

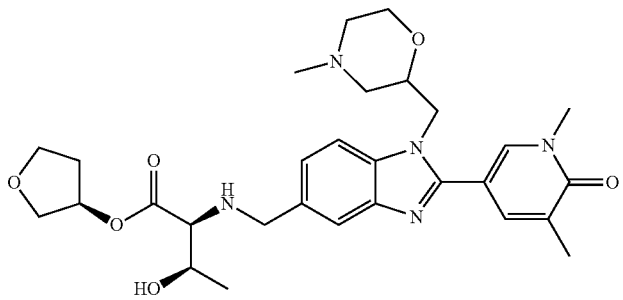 [SMILES: Cc1cc(-c2nc3cc(CN[C@H](C(=O)O[C@@H]4CCOC4)[C@@H](C)O)ccc3n2CC2CN(C)CCO2)cn(C)c1=O]

Example 164: (2S)-cyclopentyl 2-(((2-(1,5-dimethyl-6-oxo-1,6-dihydropyridin-3-yl)-1-((4-methylmorpholin-2-yl)methyl)-1H-benzo[d]imidazol-5-yl)methyl)amino)-3-methoxypropanoate (prepared from: Intermediate 164 and Intermediate 196) System B, 0.92 min, MH$^+$ = 552, Yield: 13 mg, 9%

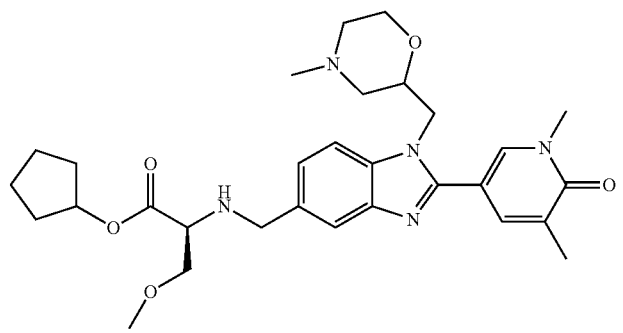 [SMILES: COC[C@H](NCc1ccc2c(c1)nc(-c1cc(C)c(=O)n(C)c1)n2CC1CN(C)CCO1)C(=O)OC1CCCC1]

-continued

Example 165: (2S,3R)-isobutyl 2-(((2-(1,5-dimethyl-6-oxo-1,6-dihydropyridin-3-yl)-1-((4-methylmorpholin-3-yl)methyl)-1H-benzo[d]imidazol-5-yl)methyl)amino)-3-hydroxybutanoate (prepared from: Intermediate 167 and Intermediate 11) System B, 0.84 min, $MH^+$ = 540, Yield: 30 mg, 21%

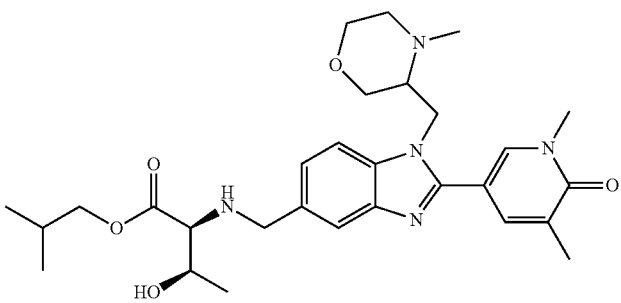 [SMILES: Cc1cc(-c2nc3cc(CN[C@H](C(=O)OCC(C)C)[C@@H](C)O)ccc3n2CC2COCCN2C)cn(C)c1=O]

Example 166: (2S)-cyclopentyl 2-(((2-(1,5-dimethyl-6-oxo-1,6-dihydropyridin-3-yl)-1-((4-methylmorpholin-3-yl)methyl)-1H-benzo[d]imidazol-5-yl)methyl)amino)-3-methoxypropanoate (prepared from: Intermediate 167 and Intermediate 196) System B, 0.89 min, $MH^+$ = 552, Yield: 39 mg, 27%

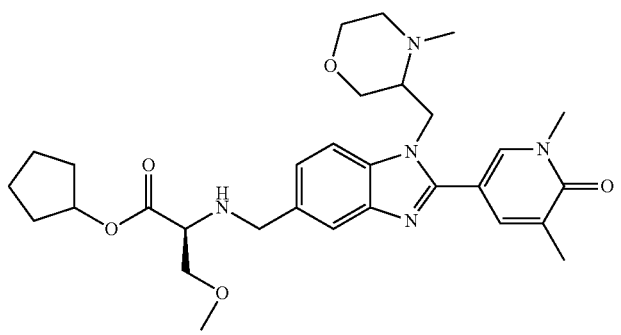 [SMILES: COC[C@H](NCc1ccc2c(c1)nc(-c1cc(C)c(=O)n(C)c1)n2CC1COCCN1C)C(=O)OC1CCCC1]

Example 167: (2S,3R)-(S)-tetrahydrofuran-3-yl 2-(((2-(1,5-dimethyl-6-oxo-1,6-dihydropyridin-3-yl)-1-((4-methylmorpholin-3-yl)methyl)-1H-benzo[d]imidazol-5-yl)methyl)amino)-3-hydroxybutanoate (prepared from: Intermediate 167 and Intermediat 40) System B, 0.66 min, $MH^+$ = 554, Yield: 11 mg, 8%

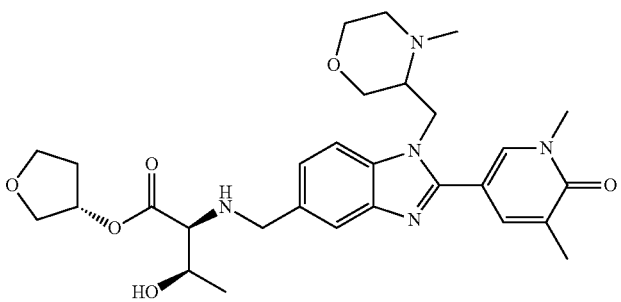 [SMILES: Cc1cc(-c2nc3cc(CN[C@H](C(=O)O[C@H]4CCOC4)[C@@H](C)O)ccc3n2CC2COCCN2C)cn(C)c1=O]

Example 168: (2S,3R)-isopropyl 2-(((1-(cyclopropyl methyl)-2-(1,5-dimethyl-6-oxo-1,6-dihydropyridin-3-yl)-1H-benzo[d]imidazol-6-yl)methyl)amino)-3-hydroxybutanoate (prepared from: Intermediate 173 and Intermediate 31) System J, 0.94 min, $MH^+$ = 467, Yield: 76 mg, 51%

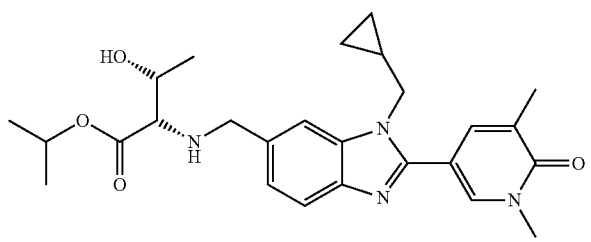

Example 169: (2S,3R)-isobutyl 2-(((1-(cyclopropylmethyl)-2-(1,5-dimethyl-6-oxo-1,6-dihydropyridin-3-yl)-1H-benzo[d]imidazol-6-yl)methyl)amino)-3-hydroxybutanoate (prepared from: Intermediate 173 and Intermediate 11) System J, 1.02 min, $MH^+$ = 481, Yield: 90 mg, 60%

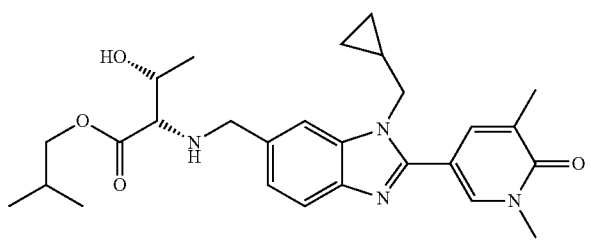

-continued

Example 170: (2S,3R)-tert-butyl 2-(((1-(cyclopropylmethyl)-2-(1,5-dimethyl-6-oxo-1,6-dihydropyridin-3-yl)-1H-benzo[d]imidazol-6-yl)methyl)amino)-3-hydroxybutanoate (prepared from: Intermediate 173 and (2S,3R)-tert-butyl 2-amino-3-hydroxybutanoate hydrochloride (commercially available)) System J, 1.01 min, MH$^+$ = 481, Yield: 90 mg, 60%

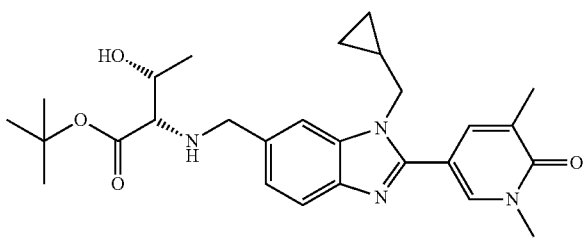

Example 171a: (2S,3R)-isopropyl 2-(((2-(1,5-dimethyl-6-oxo-1,6-dihydropyridin-3-yl)-1-((tetrahydro-2H-pyran-3-yl)methyl)-1H-benzo[d]imidazol-6-yl)methyl)amino)-3-hydroxybutanoate (single diastereomer of unknown configuration at tetrahydropyran centre, Isomer 1) (prepared from: Intermediate 177a and Intermediate 31) System I, 0.53 mins, MH$^+$ = 511, Yield: 68 mg, 49%

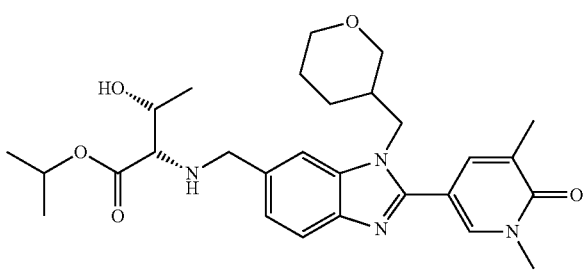

Example 171b: (2S,3R)-isopropyl 2-(((2-(1,5-dimethyl-6-oxo-1,6-dihydropyridin-3-yl)-1-((tetrahydro-2H-pyran-3-yl)methyl)-1H-benzo[d]imidazol-6-yl)methyl)amino)-3-hydroxybutanoate (single diastereomer of unknown configuration at tetrahydropyran centre, Isomer 2) (prepared from: Intermediate 177b and Intermediate 31) System I, 0.51 mins, MH$^+$ = 511, Yield: 70 mg, 49%

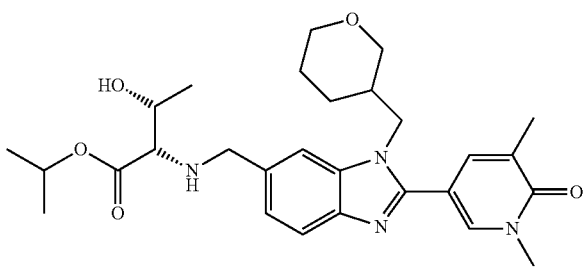

Example 172a: (2S,3R)-cyclobutyl 2-(((2-(1,5-dimethyl-6-oxo-1,6-dihydropyridin-3-yl)-1-((tetrahydro-2H-pyran-3-yl)methyl)-1H-benzo[d]imidazol-6-yl)methyl)amino)-3-hydroxybutanoate (single diastereomer of unknown configuration at tetrahydropyran centre, Isomer 1) (prepared from: Intermediate 177a and Intermediate 32) System I, 0.55 min, MH$^+$ = 523, Yield: 70 mg, 49%

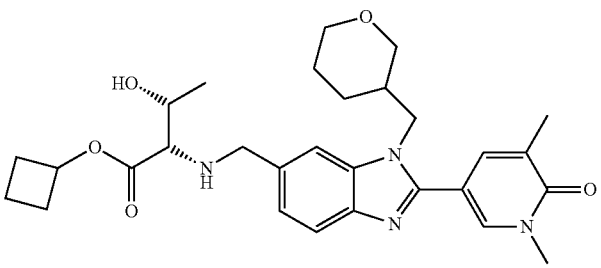

Example 172b: (2S,3R)-cyclobutyl 2-(((2-(1,5-dimethyl-6-oxo-1,6-dihydropyridin-3-yl)-1-((tetrahydro-2H-pyran-3-yl)methyl)-1H-benzo[d]imidazol-6-yl)methyl)amino)-3-hydroxybutanoate (single diastereomer of unknown configuration at tetrahydropyran centre, Isomer 2) (prepared from: Intermediate 177b and Intermediate 32) System I, 0.55 min, MH$^+$ = 523, Yield: 25 mg, 18%

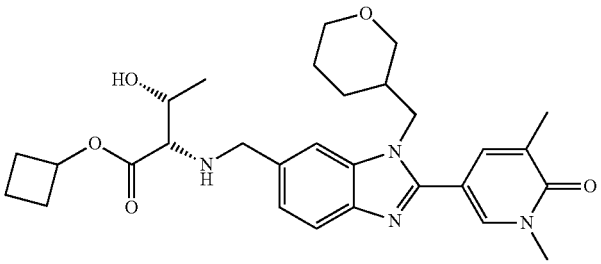

| | |
|---|---|
| Example 173: (2S,3R)-isopropyl 2-(((2-(1,5-dimethyl-6-oxo-1,6-dihydropyridin-3-yl)-1-(tetrahydro-2H-pyran-4-yl)-1H-benzo[d]imidazol-6-yl)methyl)amino)-3-hydroxybutanoate (prepared from: Intermediate 131 and Intermediate 31) System I, 0.51 min, MH$^+$ = 497, Yield: 60 mg, 41% | 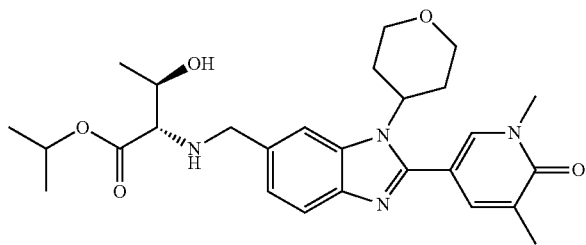 |
| Example 174: (2S,3R)-isopropyl 2-(((2-(1,5-dimethyl-6-oxo-1,6-dihydropyridin-3-yl)-1-((tetrahydro-2H-pyran-2-yl)methyl)-1H-benzo[d]imidazol-6-yl)methyl)amino)-3-hydroxybutanoate (prepared from: Intermediate 132 and Intermediate 31) System J, 0.98 min, MH$^+$ = 511, Yield: 238 mg, 54% | 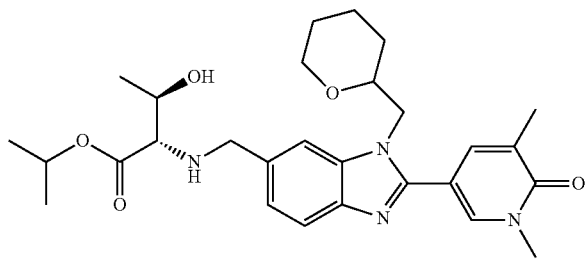 [SMILES: Cc1cc(-c2nc3ccc(CN[C@H](C(=O)OC(C)C)[C@@H](C)O)cc3n2CC2CCCCO2)cn(C)c1=O] |
| Example 175: (2S,3R)-isobutyl 2-(((2-(1,5-dimethyl-6-oxo-1,6-dihydropyridin-3-yl)-1-((tetrahydro-2H-pyran-2-yl)methyl)-1H-benzo[d]imidazol-6-yl)methyl)amino)-3-hydroxybutanoate (prepared from: Intermediate 132 and Intermediate 11) System J, 1.05 min, MH$^+$ = 525, Yield: 234 mg, 77% | 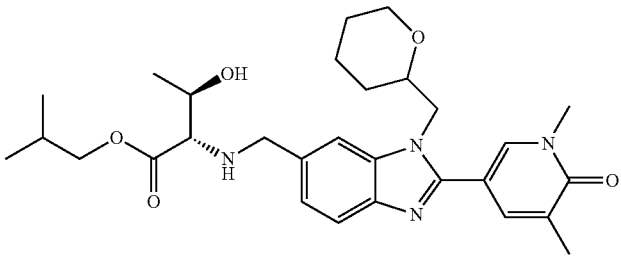 [SMILES: Cc1cc(-c2nc3ccc(CN[C@H](C(=O)OCC(C)C)[C@@H](C)O)cc3n2CC2CCCCO2)cn(C)c1=O] |
| Example 176: (2S,3R)-isobutyl 2-(((2-(1,5-dimethyl-6-oxo-1,6-dihydropyridin-3-yl)-1-(tetrahydro-2H-pyran-4-yl)-1H-benzo[d]imidazol-6-yl)methyl)amino)-3-hydroxybutanoate (prepared from: Intermediate 131 and Intermediate 11) System I, 0.57 min, MH$^+$ = 511, Yield: 55 mg, 72% | 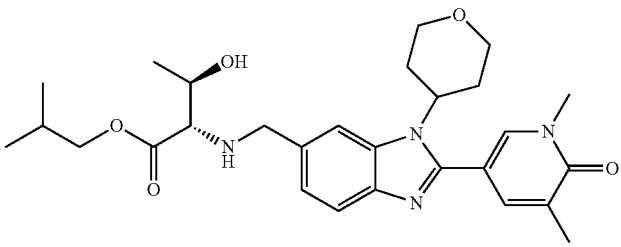 [SMILES: Cc1cc(-c2nc3ccc(CN[C@H](C(=O)OCC(C)C)[C@@H](C)O)cc3n2C2CCOCC2)cn(C)c1=O] |
| Example 177: (2S,3R)-tert-butyl 2-(((2-(1,5-dimethyl-6-oxo-1,6-dihydropyridin-3-yl)-1-(tetrahydro-2H-pyran-4-yl)-1H-benzo[d]imidazol-6-yl)methyl)amino)-3-hydroxybutanoate (prepared from: Intermediate 131 and (2S,3R)-tert-butyl 2-amino-3-hydroxybutanoate hydrochloride (commercially available)) System J, 0.90, MH$^+$ = 511, Yield: 48 mg, 63% | 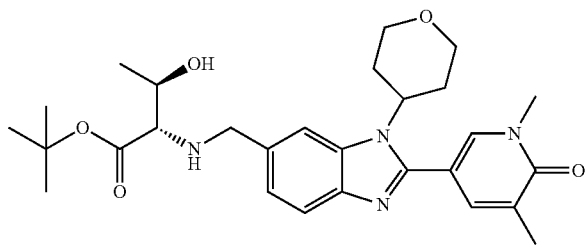 [SMILES: Cc1cc(-c2nc3ccc(CN[C@H](C(=O)OC(C)(C)C)[C@@H](C)O)cc3n2C2CCOCC2)cn(C)c1=O] |
| Example 178: (2S,3R)-tert-butyl 2-(((2-(1,5-dimethyl-6-oxo-1,6-dihydropyridin-3-yl)-1-((tetrahydro-2H-pyran-2-yl)methyl)-1H-benzo[d]imidazol-6-yl)methyl)amino)-3-hydroxybutanoate (prepared from: Intermediate 132 and (2S,3R)-tert-butyl 2-amino-3-hydroxybutanoate hydrochloride (commercially available)) System J, 1.05 min, MH$^+$ = 525, Yield: 116 mg, 77% | 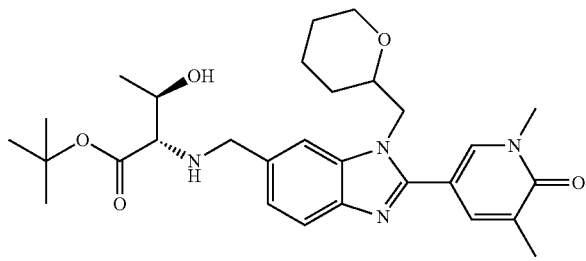 [SMILES: Cc1cc(-c2nc3ccc(CN[C@H](C(=O)OC(C)(C)C)[C@@H](C)O)cc3n2CC2CCCCO2)cn(C)c1=O] |

Example 179: (2S,3R)-isopropyl 2-(((2-(1,5-dimethyl-6-oxo-1,6-dihydropyridin-3-yl)-1-(3-methoxy-2-(methoxymethyl)propyl)-1H-benzo[d]imidazol-6-yl)methyl)amino)-3-hydroxybutanoate (prepared from: Intermediate 134 and Intermediate 31a) System C, 0.53 min, MH⁺ = 515, Yield: 54 mg, 43%

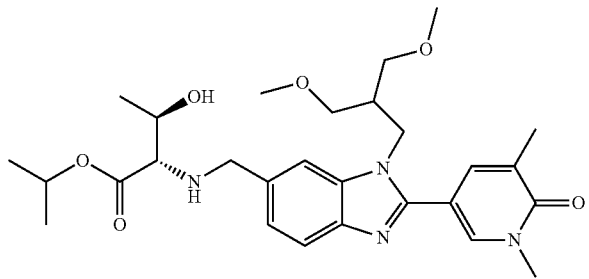 [SMILES: COCC(COC)Cn1c(-c2cc(C)c(=O)n(C)c2)nc2ccc(CN[C@H](C(=O)OC(C)C)[C@@H](C)O)cc21]

Example 180: (2S,3R)-(S)-tetrahydrofuran-3-yl 2-(((2-(1,5-dimethyl-6-oxo-1,6-dihydropyridin-3-yl)-1-((tetrahydro-2H-pyran-2-yl)methyl)-1H-benzo[d]imidazol-6-yl)methyl)amino)-3-hydroxybutanoate (prepared from: Intermediate 132 and Intermediate 40) System I, 0.51 min, MH⁺ = 539, Yield: 147 mg, 63%

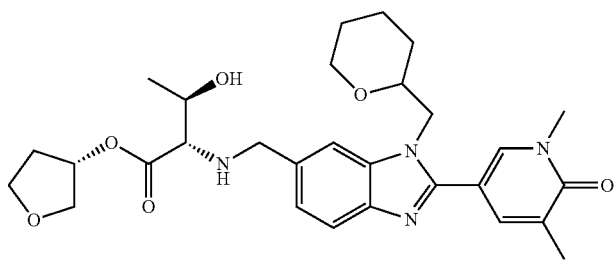 [SMILES: Cc1cc(-c2nc3ccc(CN[C@H](C(=O)O[C@H]4CCOC4)[C@@H](C)O)cc3n2CC2CCCCO2)cn(C)c1=O]

Example 181: (2S,3R)-isopropyl 2-(((2-(1,5-dimethyl-6-oxo-1,6-dihydropyridin-3-yl)-1-(1-(tetrahydro-2H-pyran-4-yl)ethyl)-1H-benzo[d]imidazol-5-yl)methyl)amino)-3-hydroxybutanoate (prepared from: Intermediate 133 and Intermediate 31) System I, 0.55 min, MH⁺ = 525, Yield: 111 mg, 25%

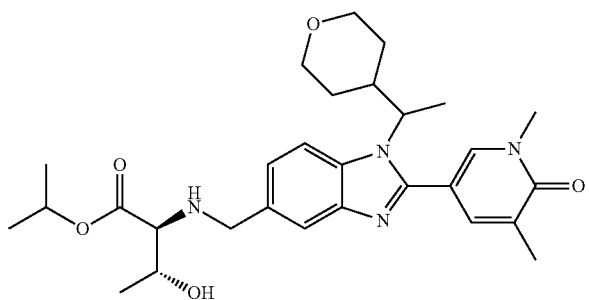 [SMILES: Cc1cc(-c2nc3cc(CN[C@H](C(=O)OC(C)C)[C@@H](C)O)ccc3n2C(C)C2CCOCC2)cn(C)c1=O]

Example 182: (2S,3R)-tert-butyl 2-(((2-(1,5-dimethyl-6-oxo-1,6-dihydropyridin-3-yl)-1-(1-(tetrahydro-2H-pyran-4-yl)ethyl)-1H-benzo[d]imidazol-5-yl)methyl)amino)-3-hydroxybutanoate (prepared from: Intermediate 133 and (2S,3R)-tert-butyl 2-amino-3-hydroxybutanoate hydrochloride (commercially available)) System I, 0.59 min, MH⁺ = 539, Yield: 65 mg; 62%

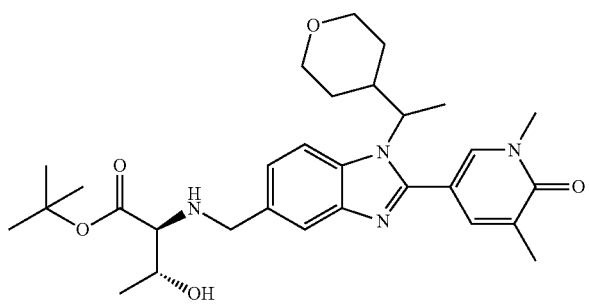 [SMILES: Cc1cc(-c2nc3cc(CN[C@H](C(=O)OC(C)(C)C)[C@@H](C)O)ccc3n2C(C)C2CCOCC2)cn(C)c1=O]

Example 183: (2S,3R)-tert-butyl 2-(((1-(((R)-1-acetylpiperidin-3-yl)methyl)-2-(1,5-dimethyl-6-oxo-1,6-dihydropyridin-3-yl)-1H-benzo[d]imidazol-5-yl)methyl)amino)-3-hydroxybutanoate (prepared from: Intermediate 136 and (2S,3R)-tert-butyl 2-amino-3-hydroxybutanoate hydrochloride (commercially available)) System I, 0.55 min, MH⁺ = 566, Yield 53 mg, 36%

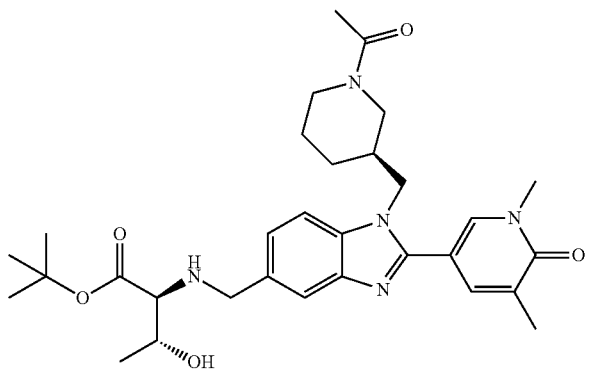 [SMILES: CC(=O)N1CCC[C@H](Cn2c(-c3cc(C)c(=O)n(C)c3)nc3cc(CN[C@H](C(=O)OC(C)(C)C)[C@@H](C)O)ccc32)C1]

Example 184: (S)-cyclobutyl 4-methyl-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)pentanoate (prepared from: Intermediate 151 and Intermediate 20) System B, 1.08 min, MH+ = 521, Yield: 31 mg, 28%

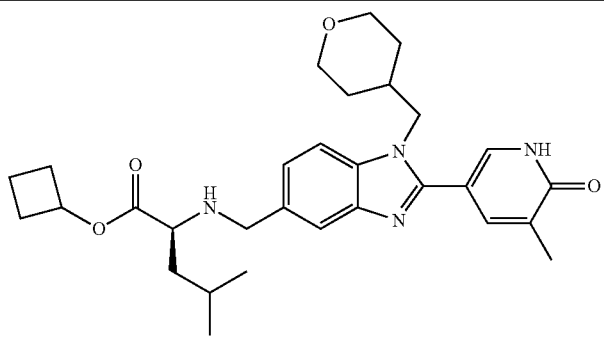

Example 185: (S)-tetrahydro-2H-pyran-4-yl 4-methyl-2 (((2-(5-methyl-6-oxo-1,6-dihydropyridin-3-yl)-1-((tetrahydro-2H-pyran-4-yl) methyl)-1H-benzo[d]imidazol 5-yl)methyl)amino)pentanoate (prepared from: Intermediate 151 and Intermediate 16) System B, 0.96 min, MH+ = 551, Yield: 61 mg, 52%

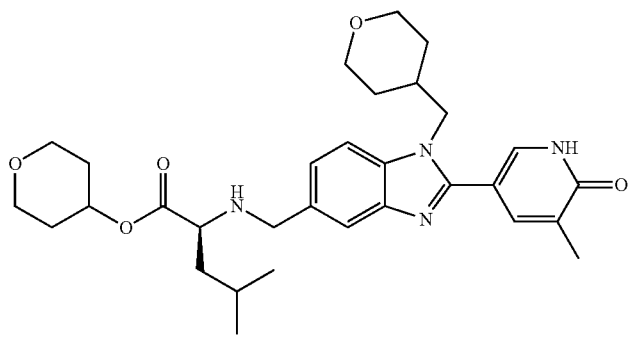 [SMILES: Cc1cc(-c2nc3cc(CN[C@@H](CC(C)C)C(=O)OC4CCOCC4)ccc3n2CC2CCOCC2)c[nH]c1=O]

Example 186: (S)-neopentyl 3-methyl-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)butanoate (prepared from: Intermediate 151 and Intermediate 15) System B, 1.16 min, MH+ = 523, Yield: 56 mg, 50%

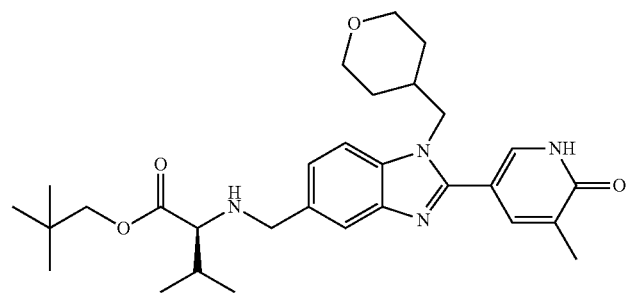 [SMILES: Cc1cc(-c2nc3cc(CN[C@H](C(=O)OCC(C)(C)C)C(C)C)ccc3n2CC2CCOCC2)c[nH]c1=O]

Example 187: (2S)-1-methoxypropan-2-yl 4-methyl-2-(((2-(5-methyl-6-oxo-1,6-dihydropyridin-3-yl)-1-((tetrahydro-2H-pyran-4-yl) methyl)-1H-benzo[d]imidazol-5-yl)methyl)amino)pentanoate (prepared from: Intermediate 151 and Intermediate 18) System B, 1.0 min, MH+ = 539, Yield: 46 mg, 40%

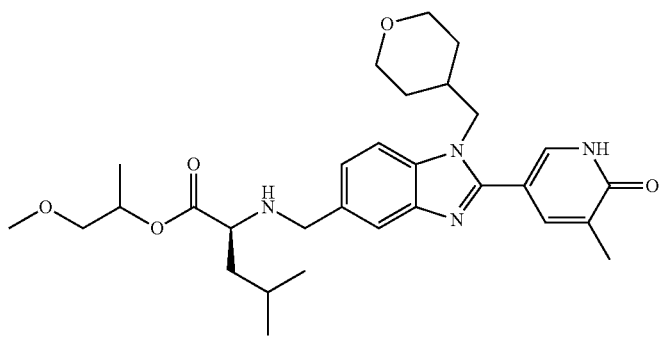 [SMILES: COCC(C)OC(=O)[C@H](CC(C)C)NCc1ccc2c(c1)nc(-c1c[nH]c(=O)c(C)c1)n2CC1CCOCC1]

Example 189: (2S,3R)-neopentyl 3-hydroxy-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)butanoate (prepared from: Intermediate 151 and Intermediate 10) System B, 0.93 min, MH+ = 525, Yield: 35 mg, 31%

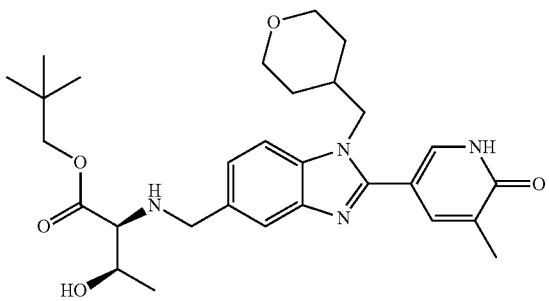 [SMILES: Cc1cc(-c2nc3cc(CN[C@H](C(=O)OCC(C)(C)C)[C@@H](C)O)ccc3n2CC2CCOCC2)c[nH]c1=O]

-continued

Example 190: (S)-isopropyl 4-methyl-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)pentanoate (prepared from: Intermediate 151 and Intermediate 21) System B, 1.07 min, MH⁺ = 509, Yield: 60 mg, 55%

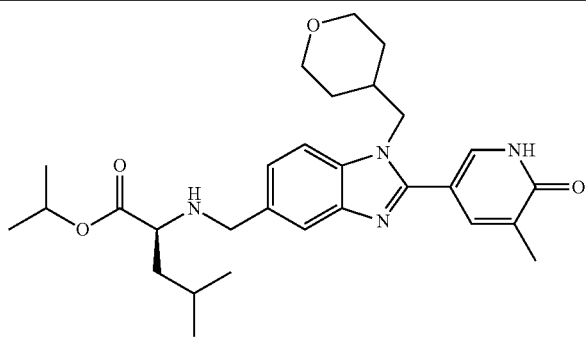

Example 191: (2S,3R)-neopentyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate (prepared from: Intermediate 116 and Intermediate 10) System B, 0.97 min, MH⁺ = 539, Yield: 82 mg, 74%

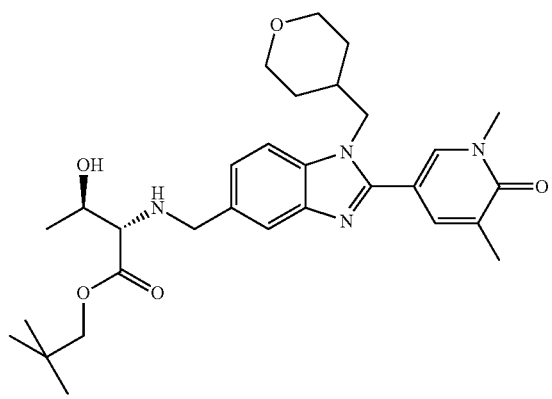 [SMILES: Cc1cc(-c2nc3cc(CN[C@H](C(=O)OCC(C)(C)C)[C@@H](C)O)ccc3n2CC2CCOCC2)cn(C)c1=O]

Example 192: (S)-cyclopentyl 3-(1H-imidazol-5-yl)-2-(((2-(5-methyl-6-oxo-1,6-dihydropyridin-3-yl)-1-((tetrahydro-2H-pyran-4-yl)methyl)-1H-benzo[d]imidazol 5-yl)methyl)amino)propanoate (prepared from: Intermediate 116 and Intermediate 286) System B, 0.79 min, MH⁺ = 558, Yield: 57 mg, 24%

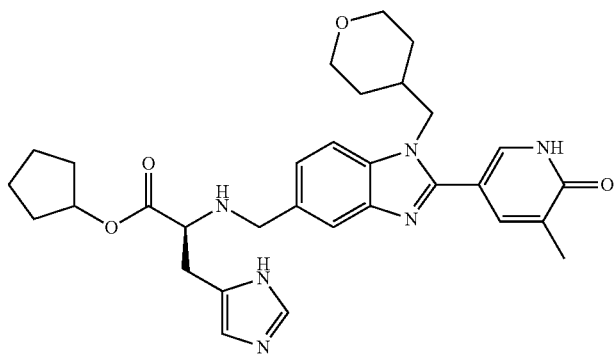 [SMILES: Cc1cc(-c2nc3cc(CN[C@@H](Cc4cnc[nH]4)C(=O)OC4CCCC4)ccc3n2CC2CCOCC2)c[nH]c1=O]

Example 193: (S)-neopentyl 3-methoxy-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)propanoate (prepared from: Intermediate 151 and Intermediate 192) System B, 0.96 min, MH⁺ = 525, Yield: 70 mg, 63%

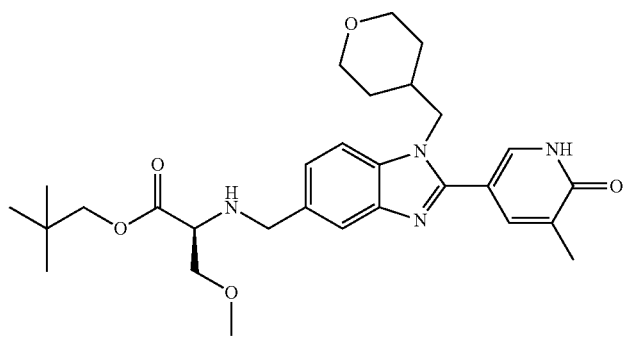 [SMILES: COC[C@H](NCc1ccc2c(c1)nc(-c1c[nH]c(=O)c(C)c1)n2CC1CCOCC1)C(=O)OCC(C)(C)C]

| | |
|---|---|
| Example 194: (S)-cyclopentyl 3-methoxy-2-(((2-(5-methyl-6-oxo-1,6-dihydropyridin-3-yl)-1-(oxetan-3-ylmethyl)-1H-benzo[d]imidazol-5-yl)methyl)amino)propanoate (prepared from: Intermediate 195 and Intermediate 196) System B, 0.85 min, MH⁺ = 495, Yield: 69 mg, 61% | 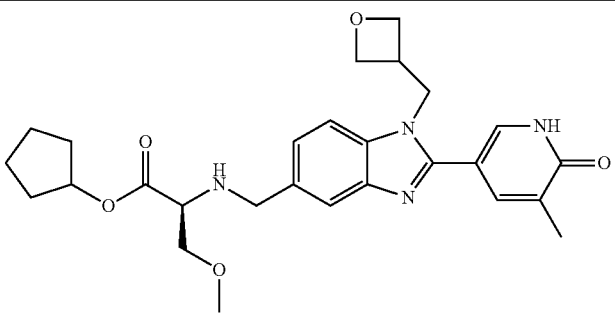 |
| Example 195: (S)-cyclopentyl 2-(((2-(1,5-dimethyl-6-oxo-1,6-dihydropyridin-3-yl)-1-ethyl-1H-benzo[d]imidazol-5-yl)methyl)amino)-3-methoxypropanoate (prepared from: Intermediate 198 and Intermediate 196) System B, 0.99 min, MH⁺ = 467, Yield: 155 mg, 73% | 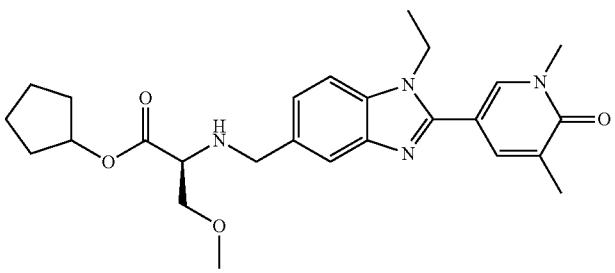 [SMILES: CCn1c(-c2cc(C)c(=O)n(C)c2)nc2cc(CN[C@@H](COC)C(=O)OC3CCCC3)ccc21] |
| Example 196: (2S,3R)-cyclopentyl 2-(((2-(1,5-dimethyl-6-oxo-1,6-dihydropyridin-3-yl)-1-ethyl-1H-benzo[d]imidazol-5-yl)methyl)amino)-3-hydroxybutanoate (prepared from: Intermediate 198 and Intermediate 137) System B, 0.94 min, MH⁺ = 467, Yield: 167 mg, 78% | 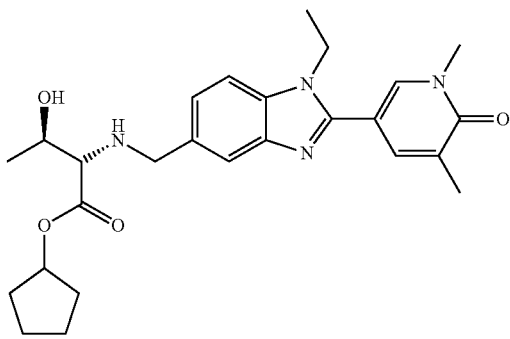 |
| Example 197: (2S,3R)-cyclopentyl 3-hydroxy-2-(((1-(2-methoxyethyl)-2-(5-methyl-6-oxo-1,6-dihydropyridin-3-yl)-1H-benzo[d]imidazol-5-yl)methyl)amino)butanoate (prepared from: Intermediate 201 and Intermediate 137) System B, 0.87 min, MH⁺ = 483, Yield: 141 mg, 67% | 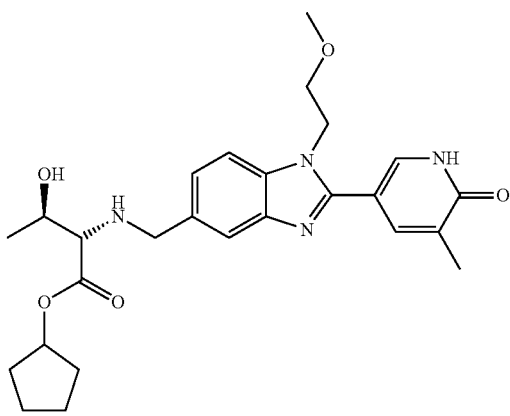 |
| Example 198: (S)-(S)-tetrahydrofuran-3-yl 2-(((2-(1,5-dimethyl-6-oxo-1,6-dihydropyridin-3-yl)-1-ethyl-1H-benzo[d]imidazol-5-yl)methyl)amino)-4-methylpentanoate (prepared from: Intermediate 198 and Intermediate 30) System B, 0.99 min, MH⁺ = 481, Yield: 154 mg, 70% | 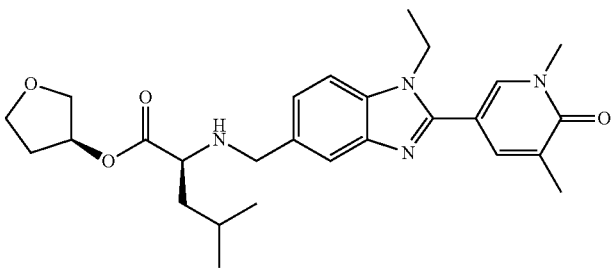 [SMILES: CCn1c(-c2cc(C)c(=O)n(C)c2)nc2cc(CN[C@@H](CC(C)C)C(=O)O[C@H]3CCOC3)ccc21] |

-continued

Example 199: (2S,3R)-neopentyl 2-(((2-(1,5-dimethyl-6-oxo-1,6-dihydropyridin-3-yl)-1-ethyl-1H-benzo[d]imidazol-5-yl)methyl)amino)-3-hydroxybutanoate (prepared from: Intermediate 198 and Intermediate 10) System B, 1.01 min, MH+ = 469, Yield: 153 mg, 71%

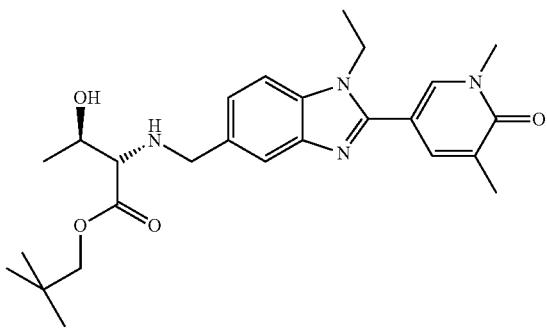

Example 200: (2S,3R)-neopentyl 3-hydroxy-2-(((2-(5-methyl-6-oxo-1,6-dihydropyridin-3-yl)-1-(oxetan-3-ylmethyl)-1H-benzo[d]imidazol-5-yl)methyl)amino)butanoate (prepared from: nd Intermediate 195 and Intermediate 10) System B, 0.87 min, MH+ = 497, Yield: 87 mg, 77%

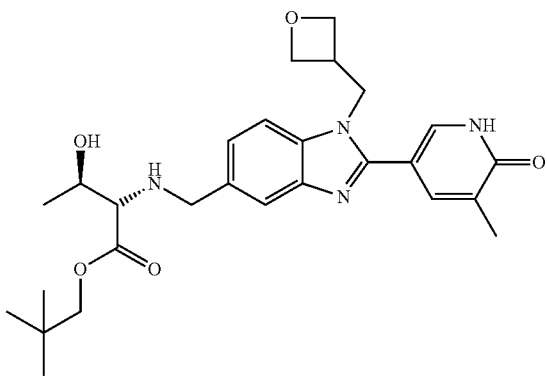

Example 201: (S)-cyclopentyl 2-(((2-(1,5-dimethyl-6-oxo-1,6-dihydropyridin-3-yl)-1-(2-methoxyethyl)-1H-benzo[d]imidazol-5-yl)methyl)amino)-3-methoxypropanoate (prepared from: Intermediate 203 and Intermediate 196) System B, 0.97 min, MH+ = 497, Yield: 125 mg, 61%

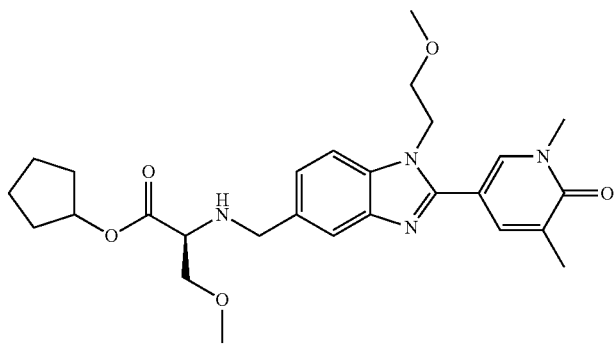 [SMILES: COCCn1c(-c2cc(C)c(=O)n(C)c2)nc2cc(CN[C@@H](COC)C(=O)OC3CCCC3)ccc21]

Example 202: (2S,3R)-cyclopentyl 2-(((2-(1,5-dimethyl-6-oxo-1,6-dihydropyridin-3-yl)-1-(2-methoxyethyl)-1H-benzo[d]imidazol-5-yl)methyl)amino)-3-hydroxybutanoate (prepared from: Intermediate 203 and Intermediate 137) System B, 0.91 min, MH+ = 497, Yield: 156 mg, 76%

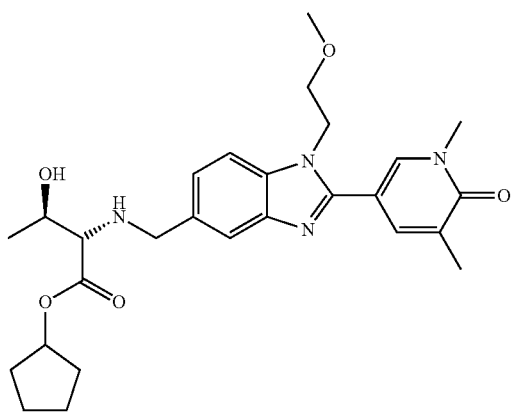

-continued

Example 203: (2S,3R)-cyclopentyl 2-(((1-(2-(dimethylamino)ethyl)-2-(5-methyl-6-oxo-1,6-dihydropyridin-3-yl)-1H-benzo[d]imidazol-5-yl)methyl)amino)-3-hydroxybutanoate (prepared from: Intermediate 206 and Intermediate 137)
System B, 0.86 min, MH$^+$ = 496, Yield: 163 mg, 79%

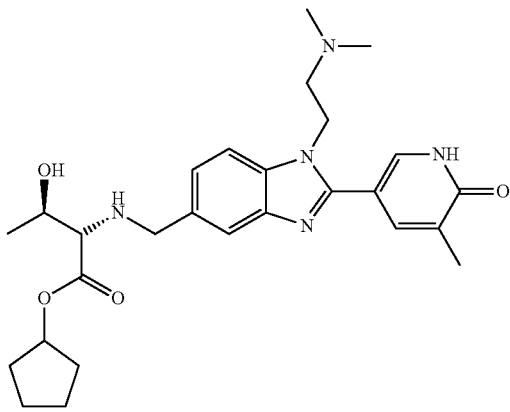

Example 204: (2S,3R)-neopentyl 2-(((2-(1,5-dimethyl-6-oxo-1,6-dihydropyridin-3-yl)-1-(2-methoxyethyl)-1H-benzo[d]imidazol-5-yl)methyl)amino)-3-hydroxybutanoate (prepared from: Intermediate 203 and Intermediate 10)
System B, 0.98 min, MH$^+$ = 499, Yield: 133 mg, 64%

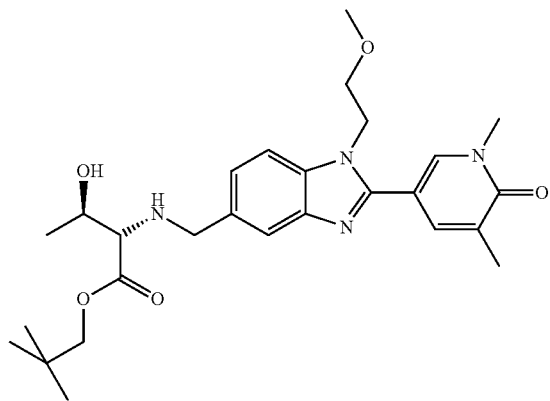

Example 205: (2S,3R)-neopentyl 2-(((1-(2-(dimethylamino)ethyl)-2-(5-methyl-6-oxo-1,6-dihydropyridin-3-yl)-1H-benzo[d]imidazol-5-yl)methyl)amino)-3-hydroxybutanoate (prepared from: Intermediate 206 and Intermediate 10)
System B, 0.92 min, MH$^+$ = 498, Yield: 164 mg, 79%

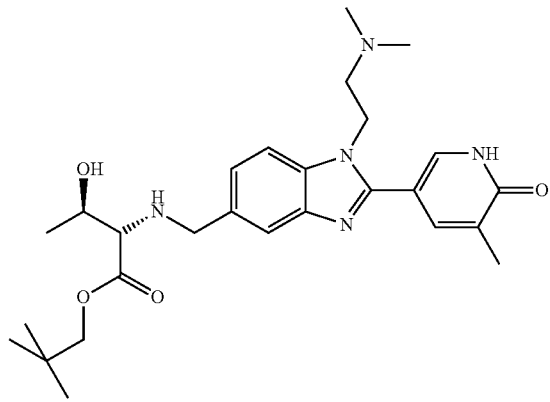

Example 206: (2S,3R)-isobutyl 2-(((2-(1,5-dimethyl-6-oxo-1,6-dihydropyridin-3-yl)-1-ethyl-1H-benzo[d]imidazol-5-yl)methyl)amino)-3-hydroxybutanoate (prepared from: Intermediate 198 and Intermediate 11) System B, 0.93 min, MH$^+$ = 455, Yield: 59 mg, 51%

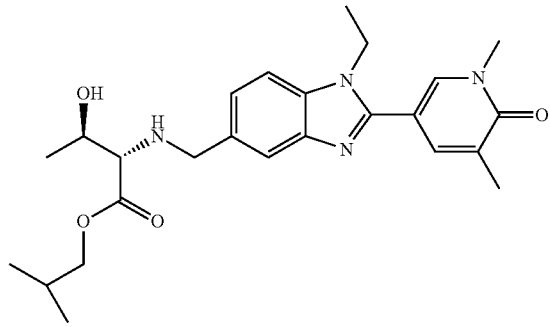 [SMILES: CCn1c(-c2cc(C)c(=O)n(C)c2)nc2cc(CN[C@H](C(=O)OCC(C)C)[C@@H](C)O)ccc21]

Example 207: (S)-cyclopentyl 3-methoxy-2-(((1-methyl-2-(5-methyl-6-oxo-1,6-dihydropyridin-3-yl)-1H-benzo[d]imidazol-5-yl)methyl)amino) propanoate (prepared from: Intermediate 208 and Intermediate 196) System B, 0.89 min, MH+ = 439, Yield: 18 mg, 7.3%

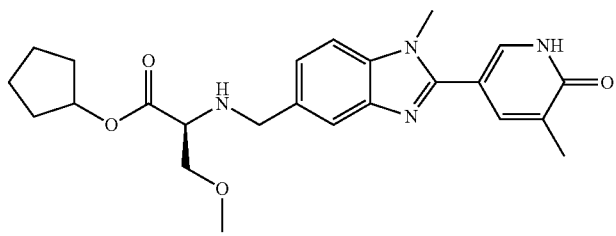 [SMILES: COC[C@H](NCc1ccc2c(c1)nc(-c1c[nH]c(=O)c(C)c1)n2C)C(=O)OC1CCCC1]

Example 208: (2S,3R)-neopentyl 3-hydroxy-2-(((1-methyl-2-(5-methyl-6-oxo-1,6-dihydropyridin-3-yl)-1H-benzo[d]imidazol-5-yl)methyl)amino)butanoate (prepared from: Intermediate 208 and Intermediate 10) System B, 0.90 min, MH+ = 441, Yield: 24 mg, 9.7%

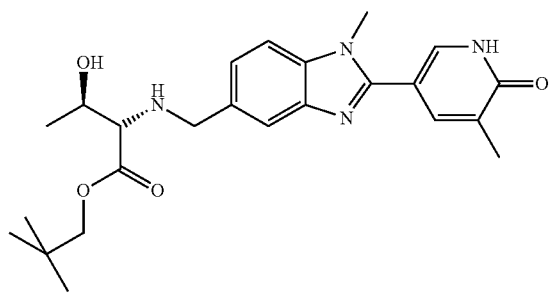

Example 209: (2S,3R)-isobutyl 3-hydroxy-2-(((1-methyl-2-(5-methyl-6-oxo-1,6-dihydropyridin-3-yl)-1H-benzo[d]imidazol-5-yl)methyl)amino)butanoate (prepared from: Intermediate 208 and Intermediate 11) System B, 0.84 min, MH+ = 427, Yield: 24 mg, 10%

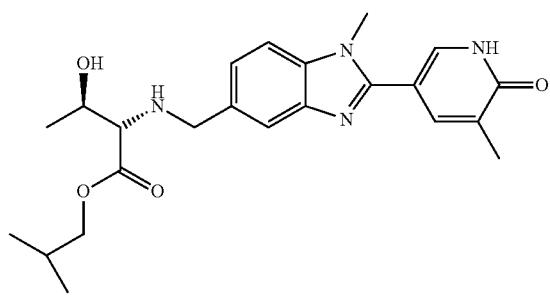

Example 210: (S)-(S)-tetrahydrofuran-3-yl 2-(((2-(1,5-dimethyl-6-oxo-1,6-dihydropyridin-3-yl)-1-ethyl-1H-benzo[d]imidazol-5-yl)methyl)amino)-3-methylbutanoate (prepared from: Intermediate 198 and Intermediate 283) System B, 0.93 min, MH+ = 467, Yield: 15 mg, 7%

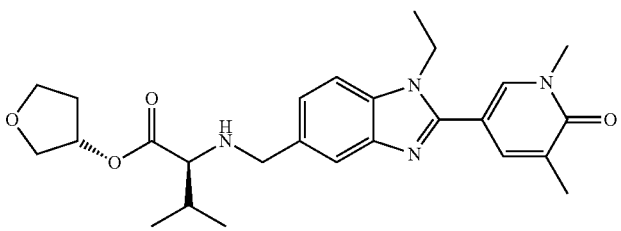

Example 211: (2S,3R)-isobutyl 2-(((2-(1,5-dimethyl-6-oxo-1,6-dihydropyridin-3-yl)-1-(2-methoxyethyl)-1H-benzo[d]imidazol-5-yl)methyl)amino)-3-hydroxybutanoate (prepared from: Intermediate 203 and Intermediate 11) System B, 0.91 min, MH+ = 485, Yield: 106 mg, 53%

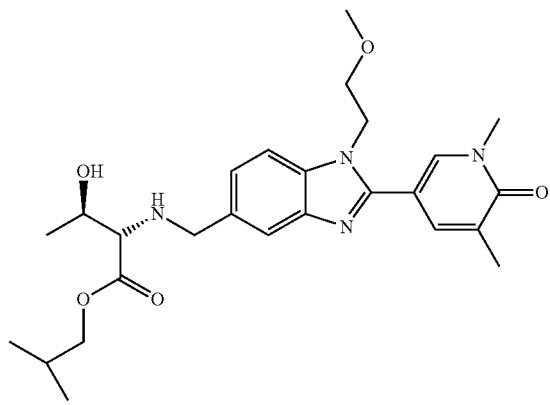

Example 212: (2S,3R)-tert-butyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate (prepared from: Intermediate 116 and (2S,3R)-tert-butyl 2-amino-3-hydroxybutanoate hydrochloride (commercially available)) System B, 0.89 min, MH$^+$ = 525, Yield: 67 mg, 62%

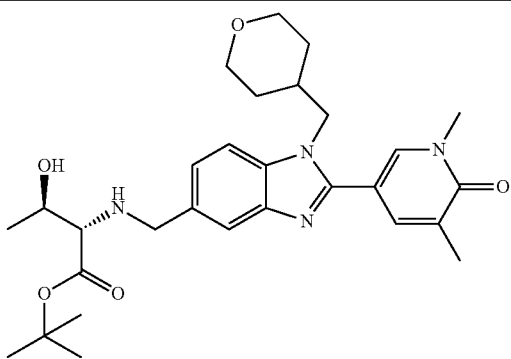

Example 213: (2S,3R)-isobutyl 2-(((2-(1,5-dimethyl-6-oxo-1,6-dihydropyridin-3-yl)-1-((tetrahydro-2H-pyran-3-yl)methyl)-1H-benzo[d]imidazol-5-yl)methyl)amino)-3-hydroxybutanoate (prepared from: Intermediate 212 and Intermediate 11) System C, 0.59, MH$^+$ = 525, Yield: 88 mg, 45%

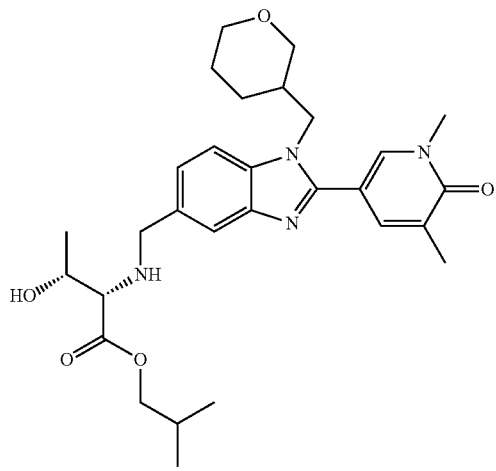 [SMILES: Cc1cc(-c2nc3cc(CN[C@H](C(=O)OCC(C)C)[C@@H](C)O)ccc3n2CC2CCCOC2)cn(C)c1=O]

Example 214: (2S,3R)-(S)-tetrahydrofuran-3-yl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate (prepared from: Intermediate 116 and Intermediate 40) System B; 0.71 min, MH$^+$ = 539, Yield: 3.2 mg, 4.3%

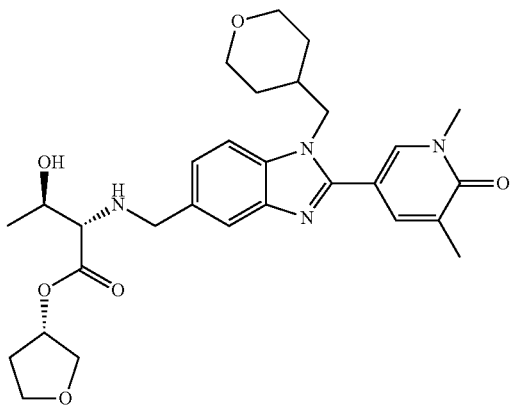 [SMILES: Cc1cc(-c2nc3cc(CN[C@H](C(=O)O[C@H]4CCOC4)[C@@H](C)O)ccc3n2CC2CCOCC2)cn(C)c1=O]

Example 215: (2S,3R)-isobutyl 2-(((2-(1,5-dimethyl-6-oxo-1,6-dihydropyridin-3-yl)-1-((S)-1-methoxypropan-2-yl)-benzo[d]imidazol-5-yl)methyl)amino)-3-hydroxybutanoate (prepared from: Intermediate 215 and Intermediate 11) System B, 0.96 min, MH$^+$ = 499, Yield: 53 mg, 48%

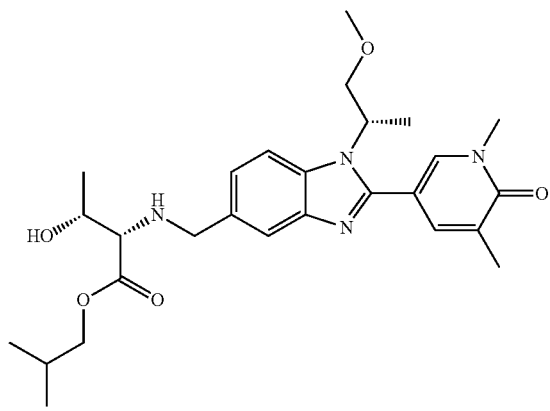 [SMILES: COC[C@H](C)n1c(-c2cc(C)c(=O)n(C)c2)nc2cc(CN[C@H](C(=O)OCC(C)C)[C@@H](C)O)ccc21]

Example 216: (2S,3R)-(S)-tetrahydrofuran-3-yl 2-(((2-(1,5-dimethyl-6-oxo-1,6-dihydropyridin-3-yl)-1-((S)-1-methoxypropan-2-yl)-1H-benzo[d]imidazol-5-yl)methyl)amino)-3-hydroxybutanoate
$^1$H NMR (d$_6$-DMSO): δ 1.12 (d, J = 6.3 Hz, 3 H), 1.53 (d, J = 7.1 Hz, 3 H), 1.79-1.87 (m, 1 H), 2.07-2.16 (m, 4 H), 3.15 (s, 3 H), 3.54 (s, 3 H), 3.65-3.87 (m, 9 H), 3.91 (d, J = 13.1 Hz, 1 H), 4.00 (t, J = 9.9 Hz, 1 H), 4.69-4.80 (m, 2 H), 5.21-5.27 (m, 1 H), 7.18 (dd, J = 8.3, 1.3 Hz, 1 H), 7.54 (s, 1 H), 7.60-7.65 (m, 1 H), 7.69 (d, J = 8.3 Hz, 1 H), 8.00 (d, J = 2.3 Hz, 1 H). (prepared from: Intermediate 215 and Intermediate 40) System B, 0.76 min, no MH$^+$

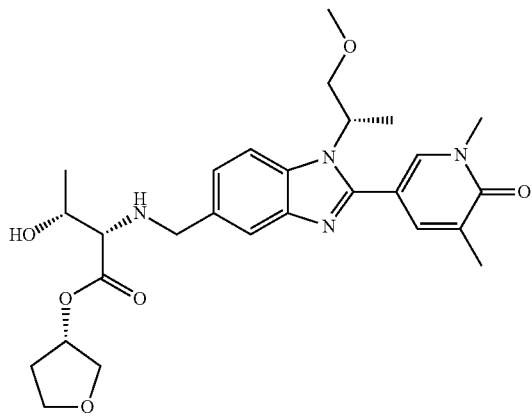 [SMILES: COC[C@H](C)n1c(-c2cc(C)c(=O)n(C)c2)nc2cc(CN[C@H](C(=O)O[C@H]3CCOC3)[C@@H](C)O)ccc21]

Example 217: (S)-cyclopentyl 2-(((2-(1,5-dimethyl-6-oxo-1,6-dihydropyridin-3-yl)-1-((S)-1-methoxypropan-2-yl)-1H-benzo[d]imidazol-5-yl)methyl)amino)-3-methoxypropanoate (prepared from: Intermediate 215 and Intermediate 196) System B, 1.02 min, MH$^+$ = 511, Yield: 152 mg, 72%

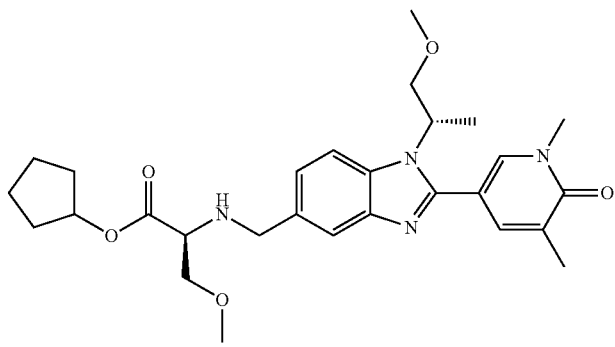 [SMILES: COC[C@H](NCc1ccc2c(c1)nc(-c1cc(C)c(=O)n(C)c1)n2[C@@H](C)COC)C(=O)OC1CCCC1]

Example 218: (2S,3R)-cyclopentyl 2-(((2-(1,5-dimethyl-6-oxo-1,6-dihydropyridin-3-yl)-1-((S)-1-methoxypropan-2-yl)-1H-benzo[d]imidazol-5-yl)methyl)amino)-3-hydroxybutanoate (prepared from: Intermediate 215 and Intermediate 137) System B, 0.96, MH$^+$ = 511, Yield: 121 mg, 57%

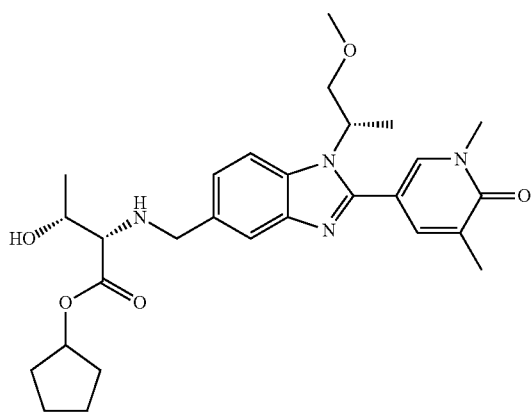 [SMILES: COC[C@H](C)n1c(-c2cc(C)c(=O)n(C)c2)nc2cc(CN[C@H](C(=O)OC3CCCC3)[C@@H](C)O)ccc21]

Example 219: (2S,3R)-isopropyl 2-(((2-(1,5-dimethyl-6-oxo-1,6-dihydropyridin-3-yl)-1-((S)-1-methoxypropan-2-yl)-1H-benzo[d]imidazol-5-yl)methyl)amino)-3-hydroxybutanoate (prepared from: Intermediate 215 and Intermediate 31) System B, 0.88 min, MH$^+$ = 485, Yield: 56 mg, 52%

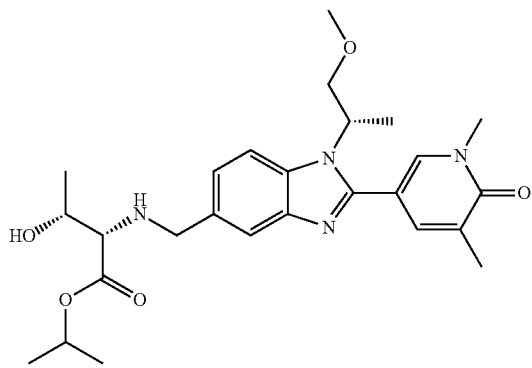 [SMILES: COC[C@H](C)n1c(-c2cc(C)c(=O)n(C)c2)nc2cc(CN[C@H](C(=O)OC(C)C)[C@@H](C)O)ccc21]

Example 220: (2S,3R)-(S)-sec-butyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate (prepared from: Intermediate 116 and Intermediate 34) System B, 0.89 min, MH$^+$ = 525, Yield: 34 mg, 48%

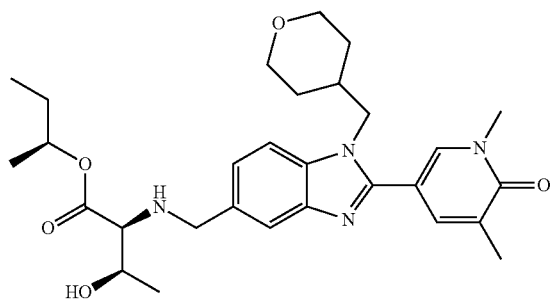 [SMILES: CC[C@H](C)OC(=O)[C@@H](NCc1ccc2c(c1)nc(-c1cc(C)c(=O)n(C)c1)n2CC1CCOCC1)[C@@H](C)O]

Example 221: (2S,3R)-cyclobutyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate (prepared from: Intermediate 116 and Intermediate 32) System B, 0.90 min, MH$^+$ = 523, Yield: 232 mg, 65%

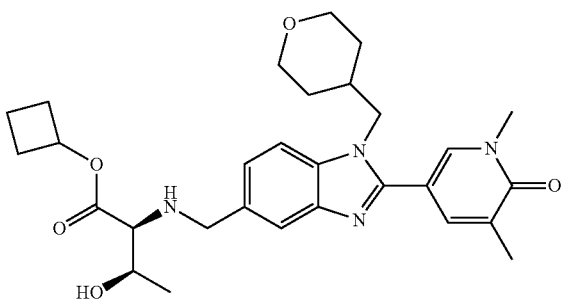 [SMILES: Cc1cc(-c2nc3cc(CN[C@H](C(=O)OC4CCC4)[C@@H](C)O)ccc3n2CC2CCOCC2)cn(C)c1=O]

Example 222: (2S,3R)-isopropyl 2-(((2-(1,5-dimethyl-6-oxo-1,6-dihydropyridin-3-yl)-1-((R)-1-methoxypropan-2-yl)-1H-benzo[d]imidazol-5-yl)methyl)amino)-3-hydroxybutanoate (prepared from: Intermediate 218 and Intermediate 31) System B, 0.87 min, MH$^+$ = 485, Yield: 61 mg, 61%

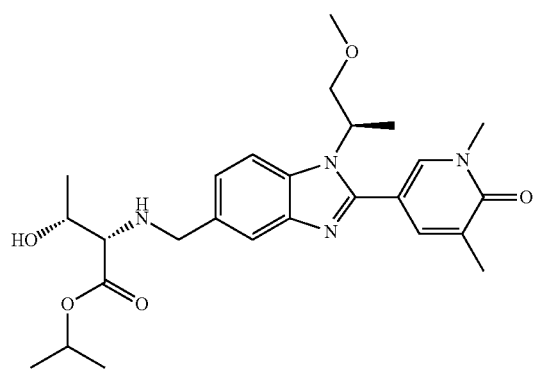 [SMILES: COC[C@@H](C)n1c(-c2cc(C)c(=O)n(C)c2)nc2cc(CN[C@H](C(=O)OC(C)C)[C@@H](C)O)ccc21]

Example 223: (2S,3R)-isobutyl 2-(((2-(1,5-dimethyl-6-oxo-1,6-dihydropyridin-3-yl)-1-((R)-1-methoxypropan-2-yl)-1H-benzo[d]imidazol-5-yl)methyl)amino)-3-hydroxybutanoate (prepared from: Intermediate 218 and Intermediate 11) System B, 0.96 min, MH$^+$ = 499, Yield: 80 mg, 52%

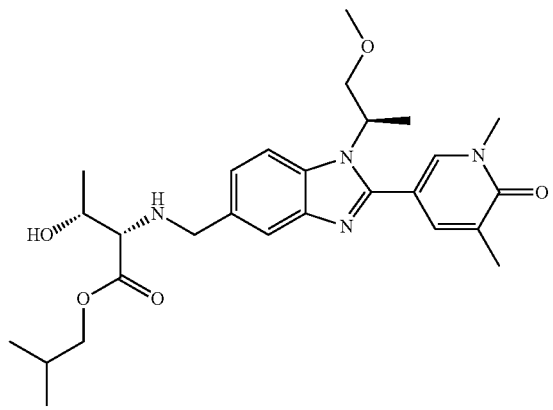 [SMILES: COC[C@@H](C)n1c(-c2cc(C)c(=O)n(C)c2)nc2cc(CN[C@H](C(=O)OCC(C)C)[C@@H](C)O)ccc21]

Example 224: (2S,3R)-(S)-tetrahydrofuran-3-yl 2-(((2-(1,5-dimethyl-6-oxo-1,6-dihydropyridin-3-yl)-1-(((S)-tetrahydrofuran-2-yl)methyl)-1H-benzo[d]imidazol-5-yl)methyl)amino)-3-hydroxybutanoate (prepared from: Intermediate 114 and Intermediate 40) System B, 0.75 min, MH$^+$ = 525, Yield: 231 mg, 77%

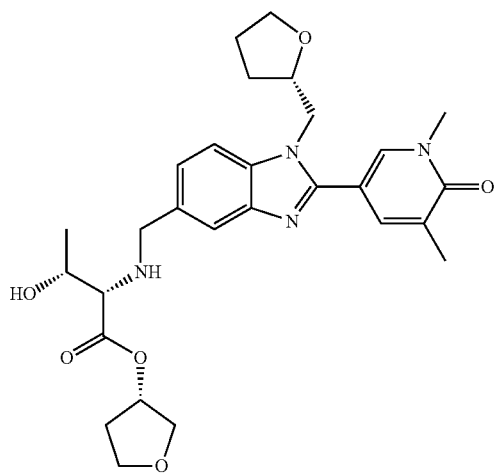 [SMILES: Cc1cc(-c2nc3cc(CN[C@H](C(=O)O[C@H]4CCOC4)[C@@H](C)O)ccc3n2C[C@@H]2CCCO2)cn(C)c1=O]

Example 225: (2R,3S)-isopropyl 2-(((2-(1,5-dimethyl-6-oxo-1,6-dihydropyridin-3-yl)-1-((tetrahydro-2H-pyran-3-yl)methyl)-1H-benzo[d]imidazol-5-yl)methyl)amino)-3-hydroxybutanoate (prepared from: Intermediate 212 and Intermediate 31) System J, 0.91 min, MH$^+$ = 511, Yield: 2.08 g 72%

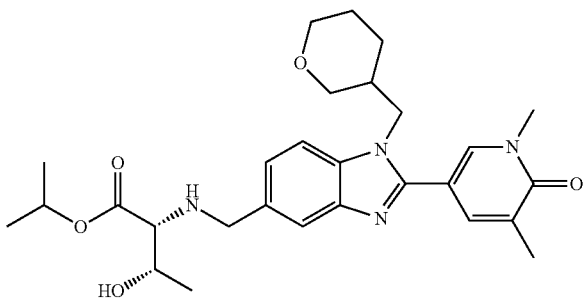 [SMILES: Cc1cc(-c2nc3cc(CN[C@@H](C(=O)OC(C)C)[C@H](C)O)ccc3n2CC2CCCOC2)cn(C)c1=O]

Example 226: (2S,3R)-cyclobutyl 2-(((2-(1,5-dimethyl-6-oxo-1,6-dihydropyridin-3-yl)-1-(((S)-tetrahydrofuran-2-yl)methyl)-1H-benzo[d]imidazol-5-yl)methyl)amino)-3-hydroxybutanoate (prepared from: Intermediate 114 and Intermediate 32) System J, 0.90 min, MH$^+$ = 509, Yield: 50 mg, 14%

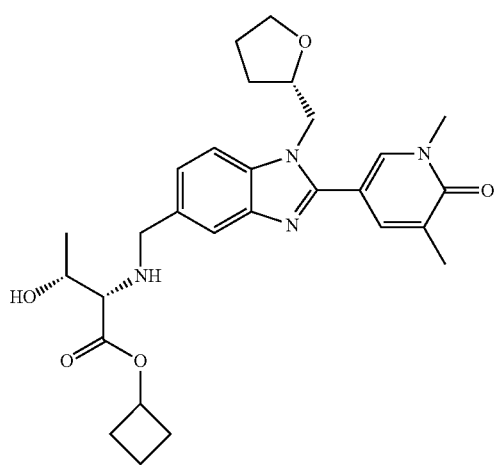 [SMILES: Cc1cc(-c2nc3cc(CN[C@H](C(=O)OC4CCC4)[C@@H](C)O)ccc3n2C[C@@H]2CCCO2)cn(C)c1=O]

Example 227: (2S,3R)-tert-butyl 2-(((2-(1,5-dimethyl-6-oxo-1,6-dihydropyridin-3-yl)-1-((S)-1-methoxypropan-2-yl)-1H-benzo[d]imidazol-5-yl)methyl)amino)-3-hydroxybutanoate (prepared from: Intermediate 215 and (2S,3R)-tert-butyl 2-amino-3-hydroxybutanoate hydrochloride (commercially available)) System J, 0.99 min, MH$^+$ = 499, Yield: 21 mg, 24%

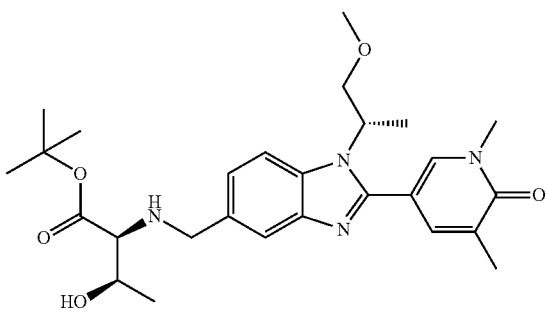 [SMILES: COC[C@H](C)n1c(-c2cc(C)c(=O)n(C)c2)nc2cc(CN[C@H](C(=O)OC(C)(C)C)[C@@H](C)O)ccc21]

| | |
|---|---|
| Example 228: (2S,3R)-cyclobutyl 2-(((2-(1,5-dimethyl-6-oxo-1,6-dihydropyridin-3-yl)-1-((tetrahydrofuran-3-yl)methyl)-1H-benzo[d]imidazol-5-yl)methyl)amino)-3-hydroxybutanoate (prepared from: Intermediate 221 and Intermediate 32) System J, 0.88 min, MH+ = 509, Yield: 312 mg, 60% | 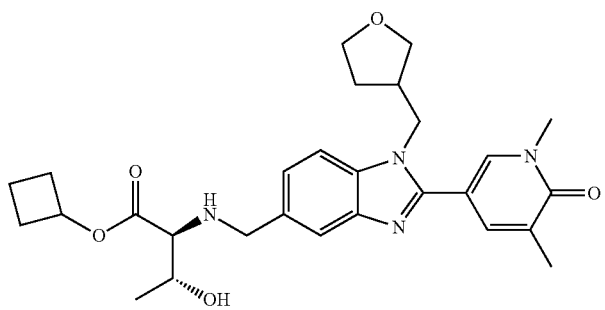 [SMILES: Cc1cc(-c2nc3cc(CN[C@H](C(=O)OC4CCC4)[C@@H](C)O)ccc3n2CC2CCOC2)cn(C)c1=O] |
| Example 229: (2S,3R)-isopropyl 2-(((2-(1,5-dimethyl-6-oxo-1,6-dihydropyridin-3-yl)-1-((tetrahydrofuran-3-yl)methyl)-1H-benzo[d]imidazol-5-yl)methyl)amino)-3-hydroxybutanoate (prepared from: Intermediate 221 and Intermediate 31) System J, 0.85 min, MH+ = 497, Yield: 236 mg, 42% | 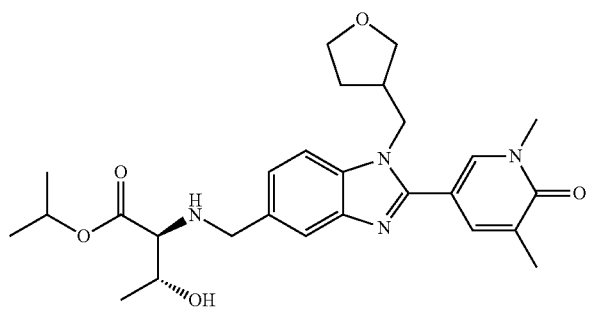 [SMILES: Cc1cc(-c2nc3cc(CN[C@H](C(=O)OC(C)C)[C@@H](C)O)ccc3n2CC2CCOC2)cn(C)c1=O] |
| Example 230: (2S,3R)-cyclobutyl 2-(((1-(1,3-dimethoxypropan-2-yl)-2-(1,5-dimethyl-6-oxo-1,6-dihydropyridin-3-yl)-1H-benzo[d]imidazol-5-yl)methyl)amino)-3-hydroxybutanoate (prepared from: Intermediate 224 and Intermediate 32) System J, 0.95 min; MH+ = 529, Yield: 147 mg; 76% | 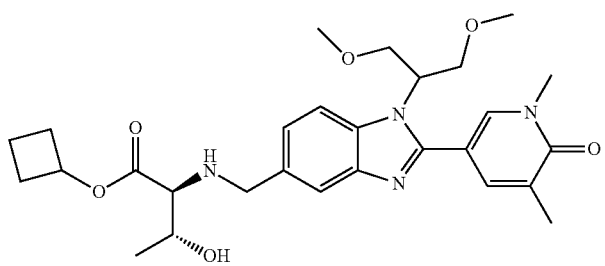 [SMILES: COCC(COC)n1c(-c2cc(C)c(=O)n(C)c2)nc2cc(CN[C@H](C(=O)OC3CCC3)[C@@H](C)O)ccc21] |
| Example 231: (2S,3R)-tert-butyl 2-(((1-(1,3-dimethoxypropan-2-yl)-2-(1,5-dimethyl-6-oxo-1,6-dihydropyridin-3-yl)-1H-benzo[d]imidazol-5-yl)methyl)amino)-3-hydroxybutanoate (prepared from: Intermediate 224 and (2S,3R)-tert-butyl 2-amino-3-hydroxybutanoate hydrochloride (commercially available)) System J, 0.98 min, MH+ = 529, Yield: 67 mg, 47% | 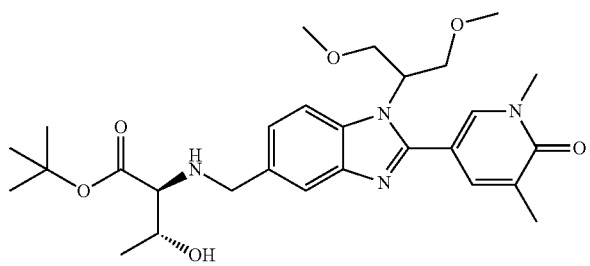 [SMILES: COCC(COC)n1c(-c2cc(C)c(=O)n(C)c2)nc2cc(CN[C@H](C(=O)OC(C)(C)C)[C@@H](C)O)ccc21] |
| Example 232: (2S,3R)-tert-butyl 2-(((2-(1,5-dimethyl-6-oxo-1,6-dihydropyridin-3-yl)-1-((tetrahydrofuran-3-yl)methyl)-1H-benzo[d]imidazol-5-yl)methyl)amino)-3-hydroxybutanoate (prepared from: Intermediate 221 and (2S,3R)-tert-butyl 2-amino-3-hydroxybutanoate hydrochloride (commercially available)) System J, 0.91 min, MH+ = 511, Yield: 93 mg, 40% | 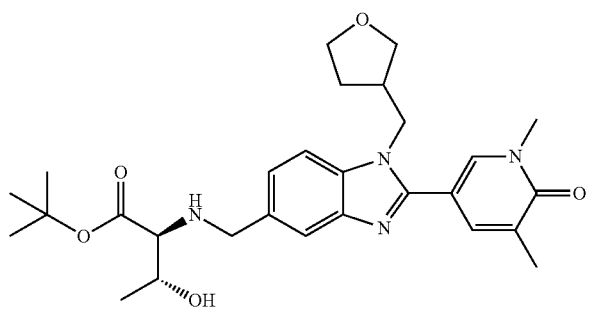 [SMILES: Cc1cc(-c2nc3cc(CN[C@H](C(=O)OC(C)(C)C)[C@@H](C)O)ccc3n2CC2CCOC2)cn(C)c1=O] |

Example 233: (S)-cyclopentyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxypropanoate 9preparing from: Intermediate 116 and Intermediate 276) System J, 0.89 min, MH$^+$ = 523, Yield: 142 mg, 76%

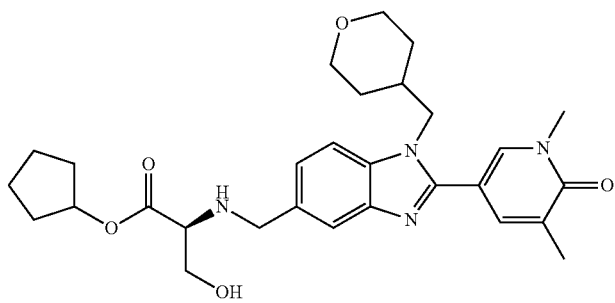 [SMILES: Cc1cc(-c2nc3cc(CN[C@@H](CO)C(=O)OC4CCCC4)ccc3n2CC2CCOCC2)cn(C)c1=O]

Example 234: (2S)-tetrahydrofuran-3-yl 2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)butanoate (prepared from: Intermediate 151 and Intermediate 35) System B, 0.90 min, MH$^+$ = 509, Yield: 154 mg, 89%

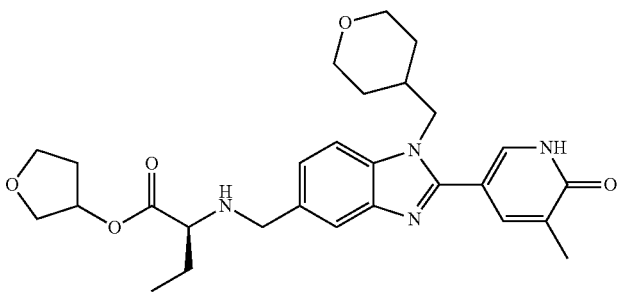 [SMILES: CC[C@H](NCc1ccc2c(c1)nc(-c1c[nH]c(=O)c(C)c1)n2CC1CCOCC1)C(=O)OC1CCOC1]

Example 235: (2S)-1-methoxypropan-2-yl 2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)butanoate (prepared from: Intermediate 151 and Intermediate 37) System B, 0.86 min, MH$^+$ = 511, Yield: 140 mg, 80%XXXXXXXXX

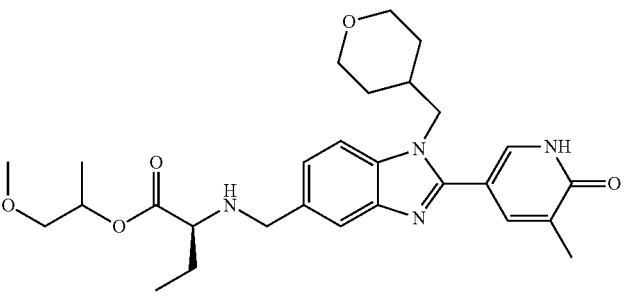 [SMILES: CC[C@H](NCc1ccc2c(c1)nc(-c1c[nH]c(=O)c(C)c1)n2CC1CCOCC1)C(=O)OC(C)COC]

Example 236: (2S)-tetrahydrofuran-3-yl 3-methyl-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)butanoate (prepared from: Intermediate 151 and Intermediate 5) System B, 0.88 min, MH$^+$ = 523, Yield: 84 mg; 47%

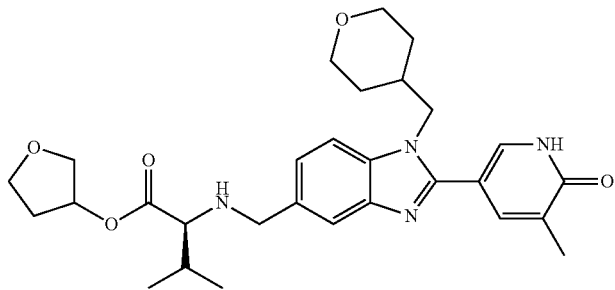 [SMILES: Cc1cc(-c2nc3cc(CN[C@H](C(=O)OC4CCOC4)C(C)C)ccc3n2CC2CCOCC2)c[nH]c1=O]

Example 237: (2S)-1-methoxypropan-2-yl 3-methyl-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)butanoate (prepared from: Intermediate 151 and Intermediate 41) System B, 0.96 min, MH$^+$ = 525, Yield: 96 mg, 54%

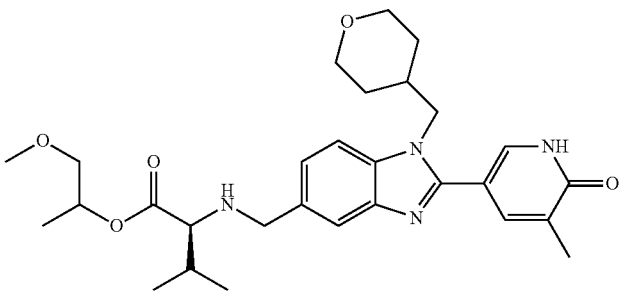 [SMILES: COCC(C)OC(=O)[C@@H](NCc1ccc2c(c1)nc(-c1c[nH]c(=O)c(C)c1)n2CC1CCOCC1)C(C)C]

Example 238: (2S)-1-methoxypropan-2-yl 3,3-dimethyl-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)butanoate (prepared from: Intermediate 151 and Intermediate 43) System B, 1.05 min, MH$^+$ = 539, Yield: 92 mg, 50%

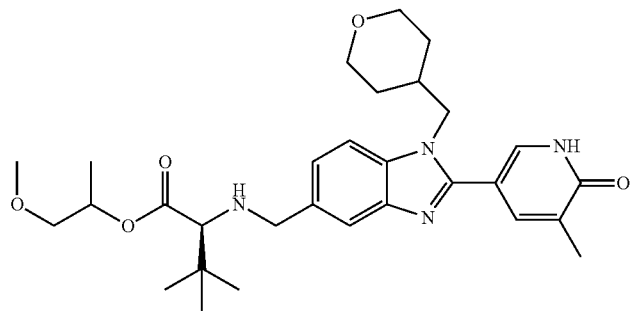 [SMILES: COCC(C)OC(=O)[C@@H](NCc1ccc2c(c1)nc(-c1c[nH]c(=O)c(C)c1)n2CC1CCOCC1)C(C)(C)C]

Example 239: (2S)-tetrahydrofuran-3-yl 3,3-dimethyl-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)butanoate (prepared from Intermediate 151 and Intermediate 45) System B, 0.96 min, MH$^+$ = 537, Yield: 130 mg, 71%

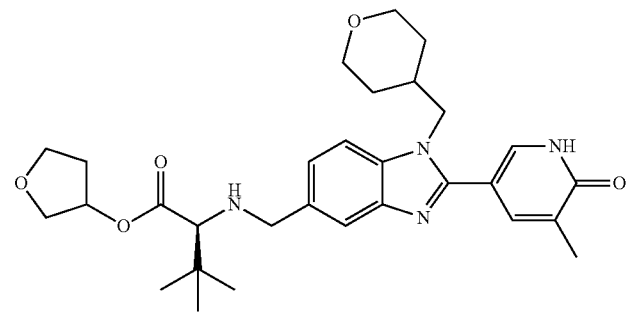 [SMILES: Cc1cc(-c2nc3cc(CN[C@H](C(=O)OC4CCOC4)C(C)(C)C)ccc3n2CC2CCOCC2)c[nH]c1=O]

Example 240: (2S)-tetrahydrofuran-3-yl 3-hydroxy-3-methyl-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)butanoate (prepared from: Intermediate 151 and Intermediate 47) System B, 0.73 min, MH$^+$ = 539, Yield: 33 mg, 18%

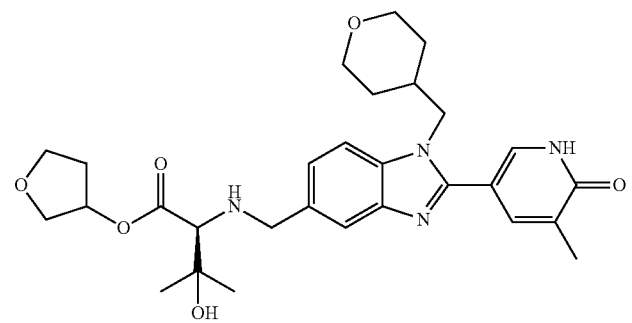 [SMILES: Cc1cc(-c2nc3cc(CN[C@H](C(=O)OC4CCOC4)C(C)(C)O)ccc3n2CC2CCOCC2)c[nH]c1=O]

Example 241: (S)-(S)-tetrahydrofuran-3-yl 3-methyl-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)butanoate (prepared from: Intermediate 151) and Intermediate 49) System B, 0.87 min, MH$^+$ = 523, Yield: 99 mg, 56%

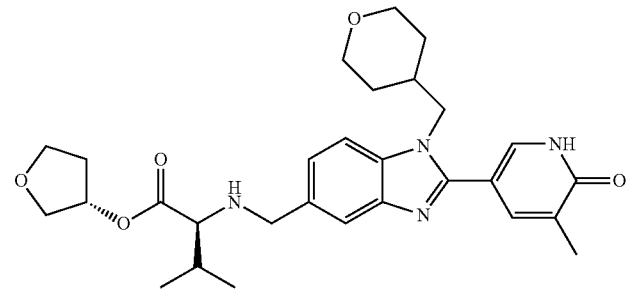 [SMILES: Cc1cc(-c2nc3cc(CN[C@H](C(=O)O[C@H]4CCOC4)C(C)C)ccc3n2CC2CCOCC2)c[nH]c1=O]

Example 242: (S)-ethyl 3-cyclopropyl-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)propanoate (prepared from: Intermediate 151 and (S)-ethyl 2-amino-3-cyclopropylpropanoate, Hydrochloride (commercially available)) System B, 0.93 min, MH$^+$ = 493, Yield: 37 mg, 53%

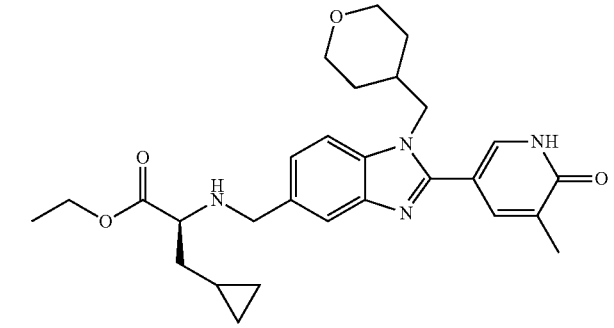 [SMILES: CCOC(=O)[C@H](CC1CC1)NCc1ccc2c(c1)nc(-c1c[nH]c(=O)c(C)c1)n2CC1CCOCC1]

-continued

Example 243: (S)-cyclopentyl 3-hydroxy-3-methyl-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)butanoate (prepared from: Intermediate 151 and Intermediate 47) System B, 0.93 min, MH+ = 537, Yield: 36 mg, 20%

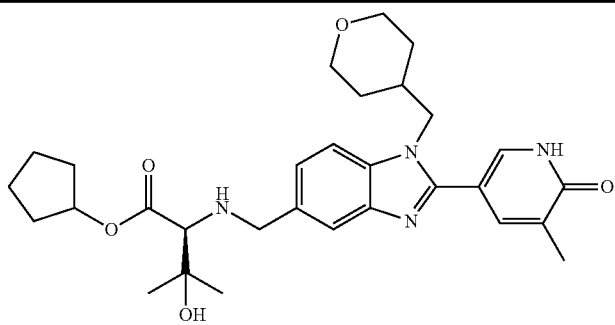

Example 244: (2S)-1-methoxypropan-2-yl 3-hydroxy-3-methyl-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)butanoate (prepared from: Intermediate 151 and Intermediate 53) System B, 0.81 min, MH+ = 541, Yield: 42 mg, 23%

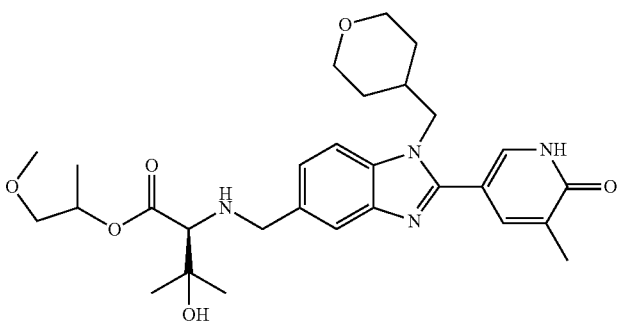 [SMILES: COCC(C)OC(=O)[C@@H](NCc1ccc2c(c1)nc(-c1c[nH]c(=O)c(C)c1)n2CC1CCOCC1)C(C)(C)O]

Example 245: (S)-cyclopentyl 2-cyclopropyl-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)acetate (Prepared from: Intermediate 151 and Intermediate 55) System B, 1.00 min, MH+ = 519, Yield: 61 mg, 60%

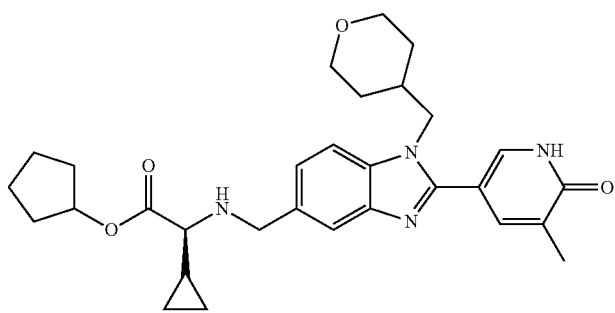 [SMILES: Cc1cc(-c2nc3cc(CN[C@H](C(=O)OC4CCCC4)C4CC4)ccc3n2CC2CCOCC2)c[nH]c1=O]

Example 246: (S)-cyclopentyl 3-cyclopropyl-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)propanoate (prepared from: Intermediate 151 and Intermediate 57) System B, 1.08 min, MH+ = 533, Yield: 48 mg, 45%

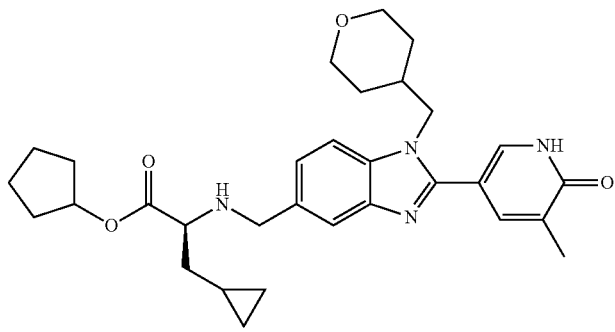 [SMILES: Cc1cc(-c2nc3cc(CN[C@@H](CC4CC4)C(=O)OC4CCCC4)ccc3n2CC2CCOCC2)c[nH]c1=O]

Example 247: (R)-cyclopentyl 3-cyclopropyl-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)propanoate (prepared from: Intermediate 151 and Intermediate 59) System B, 1.08 min, MH+ = 533, Yield: 57 mg, 54%

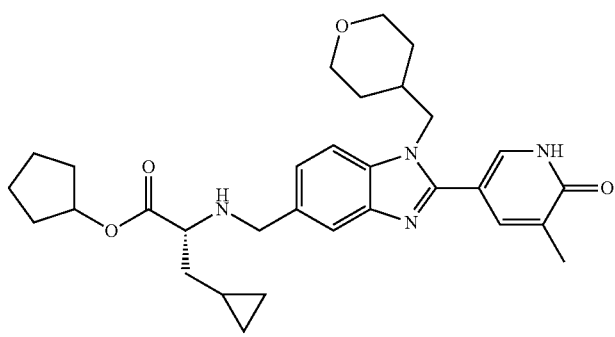 [SMILES: Cc1cc(-c2nc3cc(CN[C@H](CC4CC4)C(=O)OC4CCCC4)ccc3n2CC2CCOCC2)c[nH]c1=O]

Example 248: (2S,3R)-isobutyl 2-(((2-(1,5-dimethyl-6-oxo-1,6-dihydropyridin-3-yl)-1-((tetrahydro-2H-pyran-2-yl)methyl)-1H-benzo[d]imidazol-5-yl)methyl)amino)-3-hydroxybutanoate (prepared from: Intermediate 225 and Intermediate 11) System A, 0.67 min, MH$^+$ = 525, Yield: 138 mg, 58%

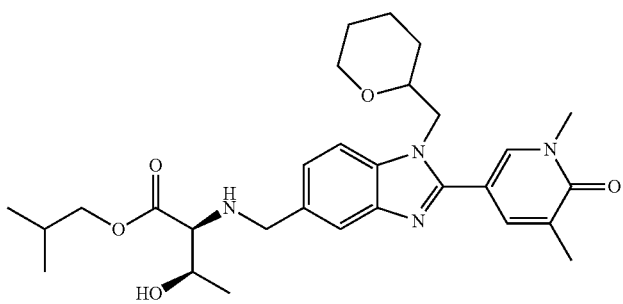 [SMILES: Cc1cc(-c2nc3cc(CN[C@H](C(=O)OCC(C)C)[C@@H](C)O)ccc3n2CC2CCCCO2)cn(C)c1=O]

Example 249: (2S,3R)-isobutyl 2-((2-((2-(1,5-dimethyl-6-oxo-1,6-dihydropyridin-3-yl)-1-ethyl-1H-benzo[d]imidazol-5-yl)oxy)ethyl)amino)-3-hydroxybutanoate (prepared from: Intermediate 228 and Intermediate 11) System B, 0.96 min, MH$^+$ = 485, Yield: 4.3 mg, 5.9%

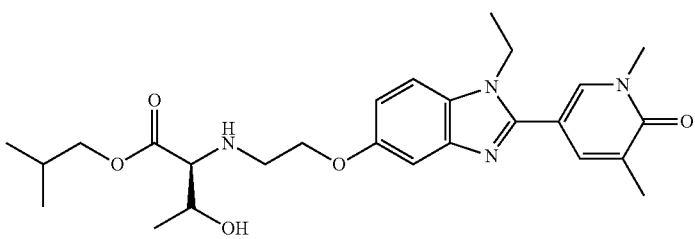 [SMILES: CCn1c(-c2cc(C)c(=O)n(C)c2)nc2cc(OCCN[C@H](C(=O)OCC(C)C)C(C)O)ccc21]

Example 250: (2S,3R)-isobutyl 2-(((2-(1,5-dimethyl-6-oxo-1,6-dihydropyridin-3-yl)-1-((R)-1-hydroxypropan-2-yl)-1H-benzo[d]imidazol-5-yl)methyl)amino)-3-hydroxybutanoate (prepared from: Intermediate 233 and Intermediate 11) System B, 0.85 min, MH$^+$ = 485, Yield: 59 mg, 40%

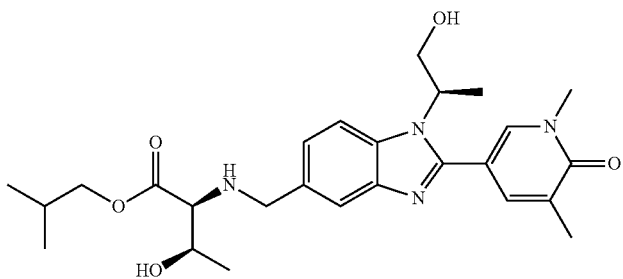 [SMILES: Cc1cc(-c2nc3cc(CN[C@H](C(=O)OCC(C)C)[C@@H](C)O)ccc3n2[C@H](C)CO)cn(C)c1=O]

Example 251: (2S,3R)-isopropyl 2-(((2-(1,5-dimethyl-6-oxo-1,6-dihydropyridin-3-yl)-1-((R)-1-hydroxypropan-2-yl)-1H-benzo[d]imidazol-5-yl)methyl)amino)-3-hydroxybutanoate (prepared from: Intermediate 233 and Intermediate 31) System B, 0.77 min, MH$^+$ = 471, Yield: 80 mg, 55%

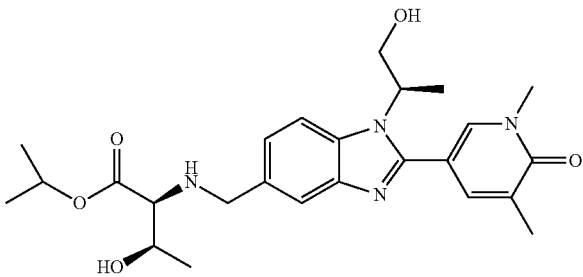 [SMILES: Cc1cc(-c2nc3cc(CN[C@H](C(=O)OC(C)C)[C@@H](C)O)ccc3n2[C@H](C)CO)cn(C)c1=O]

Example 252: (S)-cyclopentyl 2-((2-((2-(1,5-dimethyl-6-oxo-1,6-dihydropyridin-3-yl)-1-ethyl-1H-benzo[d]imidazol-5-yl)oxy)ethyl)amino)-4-methoxybutanoate (prepared from: Intermediate 228 and Intermediate 23) System B, 1.04 min, MH$^+$ = 511, Yield: 12 mg, 10%

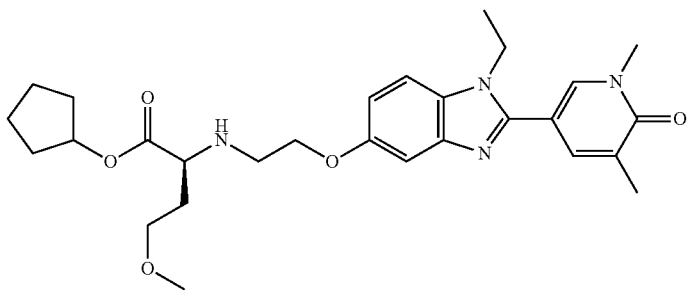 [SMILES: CCn1c(-c2cc(C)c(=O)n(C)c2)nc2cc(OCCN[C@@H](CCOC)C(=O)OC3CCCC3)ccc21]

Example 253: (S)-cyclopentyl 2-((2-((2-(1,5-dimethyl-6-oxo-1,6-dihydropyridin-3-yl)-1-((tetrahydro-2H-pyran-4-yl)methyl)-1H-benzo[d]imidazol-5-yl)oxy)ethyl)amino)-3-methoxypropanoate (prepared from: Intermediate 261 and Intermediate 196) System B, 0.99 min, MH$^+$ = 567, Yield: 9 mg, 16%

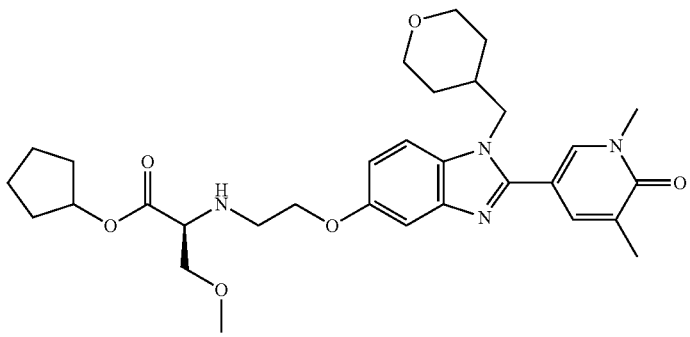 [SMILES: COC[C@H](NCCOc1ccc2c(c1)nc(-c1cc(C)c(=O)n(C)c1)n2CC1CCOCC1)C(=O)OC1CCCC1]

Example 254: (S)-cyclopentyl 2-((2-((2-(1,5-dimethyl-6-oxo-1,6-dihydropyridin-3-yl)-1-((tetrahydro-2H-pyran-4-yl)methyl)-1H-benzo[d]imidazol-5-yl)oxy)ethyl)amino)propanoate (prepared from: Intermediate 261 and Intermediate 61) System B, 1.00 min, MH$^+$ = 537, Yield: 15 mg, 13%

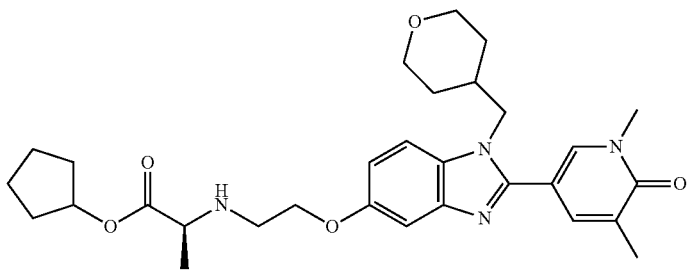 [SMILES: Cc1cc(-c2nc3cc(OCCN[C@@H](C)C(=O)OC4CCCC4)ccc3n2CC2CCOCC2)cn(C)c1=O]

Example 255: (2S,3R)-isopropyl 2-((2-((2-(1,5-dimethyl-6-oxo-1,6-dihydropyridin-3-yl)-1-ethyl-1H-benzo[d]imidazol-5-yl)oxy)ethyl)amino)-3-hydroxybutanoate (prepared from: Intermediate 228 and Intermediate 31) System B, 0.88 min, MH$^+$ = 471, Yield: 12 mg, 10%

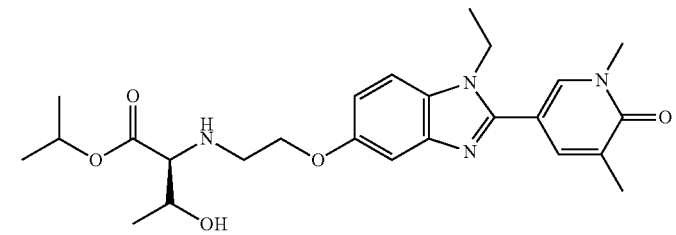 [SMILES: CCn1c(-c2cc(C)c(=O)n(C)c2)nc2cc(OCCN[C@H](C(=O)OC(C)C)C(C)O)ccc21]

Example 256: (S)-(S)-tetrahydrofuran-3-yl 2-((2-((2-(1,5-dimethyl-6-oxo-1,6-dihydropyridin-3-yl)-1-ethyl-1H-benzo[d]imidazol-5-yl)oxy)ethyl)amino)-3-methylbutanoate (prepared from: Intermediate 228 and Intermediate 49) System B, 0.95 min, MH$^+$ = 497, Yield: 13 mg, 11%

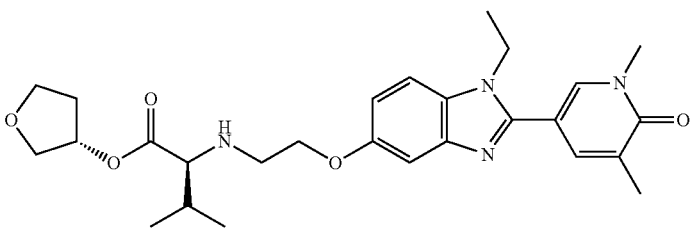 [SMILES: CCn1c(-c2cc(C)c(=O)n(C)c2)nc2cc(OCCN[C@H](C(=O)O[C@H]3CCOC3)C(C)C)ccc21]

Example 257: (2S,3R)-isobutyl 2-((2-((2-(1,5-dimethyl-6-oxo-1,6-dihydropyridin-3-yl)-1-((tetrahydro-2H-pyran-4-yl)methyl)-1H-benzo[d]imidazol-5-yl)oxy)ethyl)amino)-3-hydroxybutanoate (prepared from: Intermediate 261 and Intermediate 11) System B, 0.93 min, MH$^+$ = 555, Yield: 21 mg, 18%

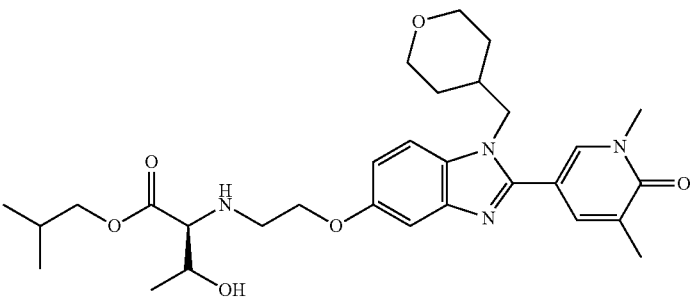 [SMILES: Cc1cc(-c2nc3cc(OCCN[C@H](C(=O)OCC(C)C)C(C)O)ccc3n2CC2CCOCC2)cn(C)c1=O]

Example 258: (2S,3R)-isopropyl 2-((2-((2-(1,5-dimethyl-6-oxo-1,6-dihydropyridin-3-yl)-1-((tetrahydro-2H-pyran-4-yl)methyl)-1H-benzo[d]imidazol-5-yl)oxy)ethyl)amino)-3-hydroxybutanoate (prepared from: Intermediate 261 and Intermediate 31) System B, 0.85 min, MH⁺ = 541, Yield: 24 mg, 21%

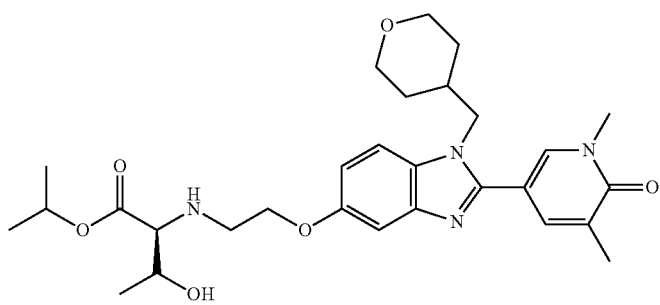 [SMILES: Cc1cc(-c2nc3cc(OCCN[C@H](C(=O)OC(C)C)C(C)O)ccc3n2CC2CCOCC2)cn(C)c1=O]

Example 259: (2S,3R)-isobutyl 2-(((2-(1,5-dimethyl-6-oxo-1,6-dihydropyridin-3-yl)-1-((S)-1-hydroxypropan-2-yl)-1H-benzo[d]imidazol-5-yl)methyl)amino)-3-hydroxybutanoate (prepared from: Intermediate 236 and Intermediate 11) System A, 0.51 min, MH⁺ = 485, Yield: 50 mg, 34%

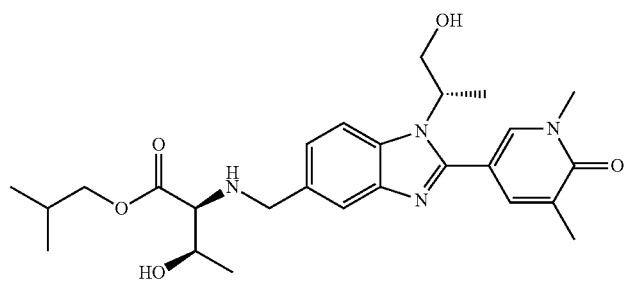 [SMILES: Cc1cc(-c2nc3cc(CN[C@H](C(=O)OCC(C)C)[C@@H](C)O)ccc3n2[C@@H](C)CO)cn(C)c1=O]

Example 260: (S)-(S)-tetrahydrofuran-3-yl 2-(((2-(1,5-dimethyl-6-oxo-1,6-dihydropyridin-3-yl)-1-((R)-1-hydroxypropan-2-yl)-1H-benzo[d]imidazol-5-yl)methyl)amino)-3-methylbutanoate (prepared from: Intermediate 233 and Intermediate 49) System B, 0.83 min, MH⁺ = 497, Yield: 47 mg, 31%

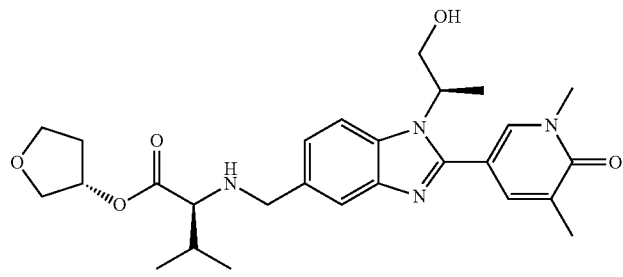 [SMILES: Cc1cc(-c2nc3cc(CN[C@H](C(=O)O[C@H]4CCOC4)C(C)C)ccc3n2[C@H](C)CO)cn(C)c1=O]

Example 261: (S)-(S)-tetrahydrofuran-3-yl 2-(((2-(1,5-dimethyl-6-oxo-1,6-dihydropyridin-3-yl)-1-(2-hydroxyethyl)-1H-benzo[d]imidazol-5-yl)methyl)amino)-3-methylbutanoate (prepared from: Intermediate 278 and Intermediate 49) System I, 0.41 min, MH⁺ = 483, Yield: 50 mg, 32%

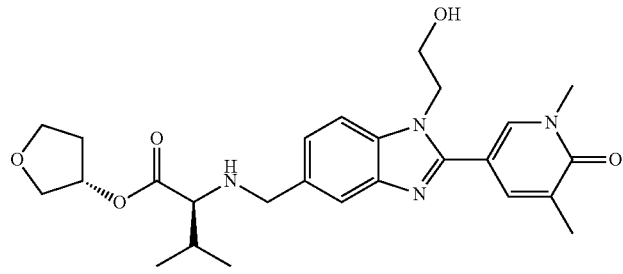 [SMILES: Cc1cc(-c2nc3cc(CN[C@H](C(=O)O[C@H]4CCOC4)C(C)C)ccc3n2CCO)cn(C)c1=O]

Example 262: (2S,3R)-isobutyl 3-hydroxy-2-(((2-(5-methyl-6-oxo-1,6-dihydropyridin-3-yl)-1-((tetrahydro-2H-pyran-2-yl)methyl)-1H-benzo[d]imidazol-5-yl)methyl)amino)butanoate (prepared from: Intermediate 245 and Intermediate 11) System I, 0.62 min, MH⁺ = 511, Yield: 49 mg, 34%

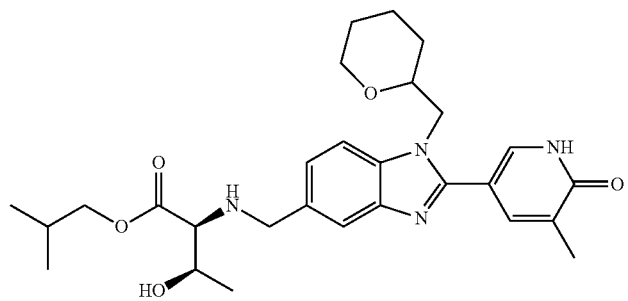 [SMILES: Cc1cc(-c2nc3cc(CN[C@H](C(=O)OCC(C)C)[C@@H](C)O)ccc3n2CC2CCCCO2)c[nH]c1=O]

Example 263: (S)-isopropyl 2-(((2-(1,5-dimethyl-6-oxo-1,6-dihydropyridin-3-yl)-1-((S)-1-hydroxypropan-2-yl)-1H-benzo[d]imidazol-5-yl)methyl)amino)-3-methylbutanoate (prepared from: Intermediate 236 and Intermediate 12) System I, 0.54 min, MH⁺ = 469, Yield: 58 mg, 40%

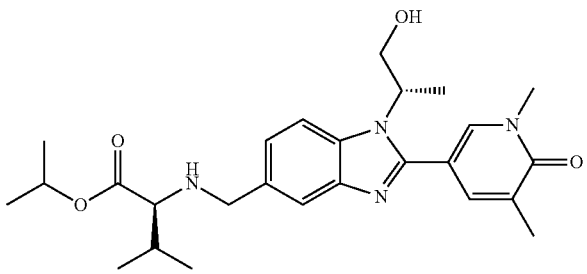 [SMILES: Cc1cc(-c2nc3cc(CN[C@H](C(=O)OC(C)C)C(C)C)ccc3n2[C@@H](C)CO)cn(C)c1=O]

Example 264: (S)-(S)-tetrahydrofuran-3-yl 2-(((2-(1,5-dimethyl-6-oxo-1,6-dihydropyridin-3-yl)-1-((S)-1-hydroxypropan-2-yl)-1H-benzo[d]imidazol-5-yl)methyl)amino)-3-methylbutanoate (prepared from: Intermediate 236 and Intermediate 49) System I, 0.46 min, MH⁺ = 497, Yield: 26 mg, 17%

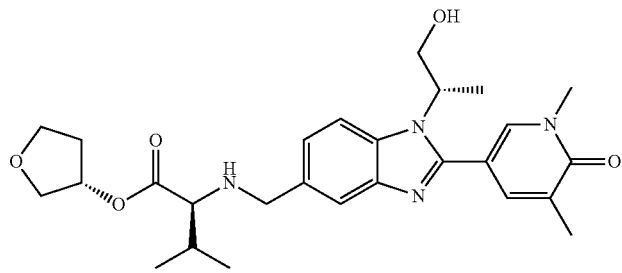 [SMILES: Cc1cc(-c2nc3cc(CN[C@H](C(=O)O[C@H]4CCOC4)C(C)C)ccc3n2[C@@H](C)CO)cn(C)c1=O]

Example 265a: tetrahydrofuran-3-yl 2-(((2-(1,5-dimethyl-6-oxo-1,6-dihydropyridin-3-yl)-1-((S)-1-hydroxypropan-2-yl)-1H-benzo[d]imidazol-5-yl)methyl)amino)-3-methoxybutanoate Diastereoisomer 1 (prepared from: Intermediate 236 and Intermediate 9) System I, 0.44 min, MH⁺ = 513, Yield: 4.4 mg, 2.8%

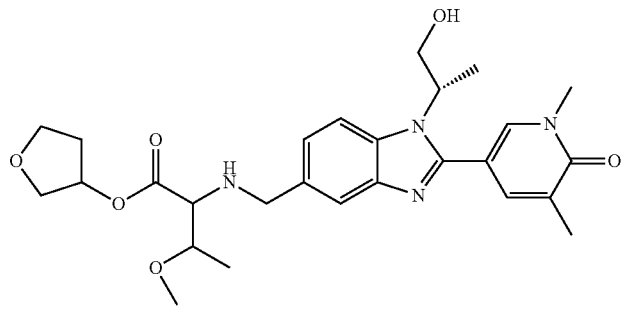 [SMILES: COC(C)C(NCc1ccc2c(c1)nc(-c1cc(C)c(=O)n(C)c1)n2[C@@H](C)CO)C(=O)OC1CCOC1]

Example 265b: tetrahydrofuran-3-yl 2-(((2-(1,5-dimethyl-6-oxo-1,6-dihydropyridin-3-yl)-1-((S)-1-hydroxypropan-2-yl)-1H-benzo[d]imidazol-5-yl)methyl)amino)-3-methoxybutanoate Diastereoisomer 2 (prepared from: Intermediate 236 and Intermediate 9) System J, 0.77 min, MH⁺ = 513, Yield: 35 mg, 22%

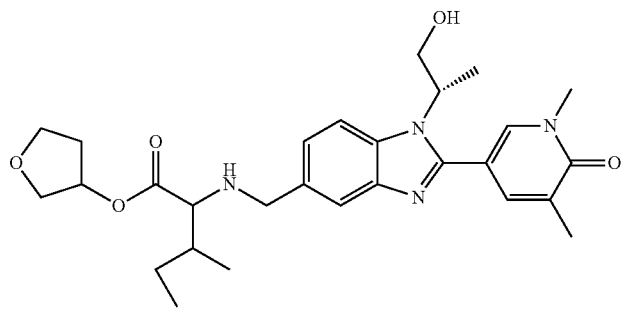 [SMILES: CCC(C)C(NCc1ccc2c(c1)nc(-c1cc(C)c(=O)n(C)c1)n2[C@@H](C)CO)C(=O)OC1CCOC1]

Example 266: (2S,3R)-isopropyl 2-(((2-(1,5-dimethyl-6-oxo-1,6-dihydropyridin-3-yl)-1-((tetrahydro-2H-pyran-2-yl)methyl)-1H-benzo[d]imidazol-5-yl)methyl)amino)-3-hydroxybutanoate (prepared from: Intermediate 225 and Intermediate 31) System I, 0.60 min, MH⁺ = 511, Yield: 85 mg, 30%

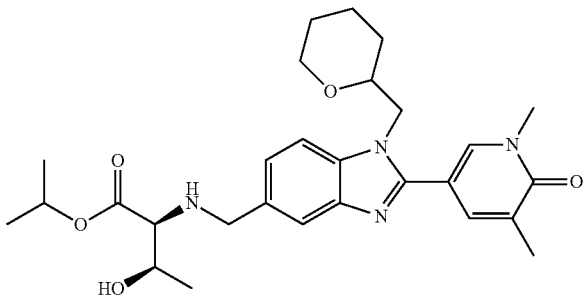 [SMILES: Cc1cc(-c2nc3cc(CN[C@H](C(=O)OC(C)C)[C@@H](C)O)ccc3n2CC2CCCCO2)cn(C)c1=O]

-continued

Example 267: (2S,3R)-isopropyl 3-hydroxy-2-(((2-(5-methyl-6-oxo-1,6-dihydropyridin-3-yl)-1-((tetrahydro-2H-pyran-2-yl)methyl)-1H-benzo[d]imidazol-5-yl)methyl)amino)butanoate (prepared from: Intermediate 245 and Intermediate 31 System I, 0.58 min, MH$^+$ = 497, Yield: 132 mg, 47%

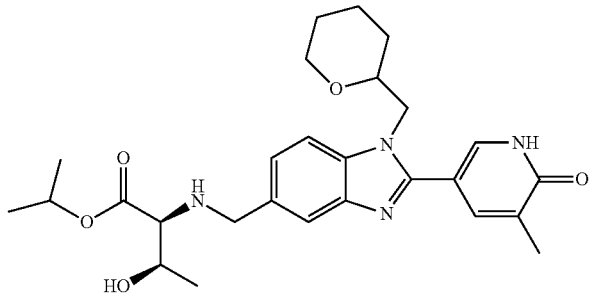 [SMILES: Cc1cc(-c2nc3cc(CN[C@H](C(=O)OC(C)C)[C@@H](C)O)ccc3n2CC2CCCCO2)c[nH]c1=O]

Example 268: (2S,3R)-isopropyl 2-((2-((2-(1,5-dimethyl-6-oxo-1,6-dihydropyridin-3-yl)-1-((S)-1-methoxypropan-2-yl)-1H-benzo[d]imidazol-5-yl)oxy)ethyl)amino)-3-hydroxybutanoate (prepared from: Intermediate 247 and Intermediate 31) System J, 0.97 min, MH$^+$ = 515, Yield: 7 mg, 7%

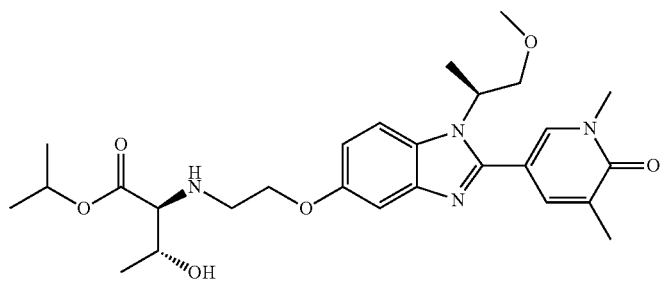 [SMILES: COC[C@H](C)n1c(-c2cc(C)c(=O)n(C)c2)nc2cc(OCCN[C@H](C(=O)OC(C)C)[C@@H](C)O)ccc21]

Example 269: (S)-isobutyl 2-((2-((2-(1,5-dimethyl-6-oxo-1,6-dihydropyridin-3-yl)-1-((S)-1-methoxypropan-2-yl)-1H-benzo[d]imidazol-5-yl)oxy)ethyl)amino)-3-methoxypropanoate (prepared from: Intermediate 247 and Intermediate 66) System J, 1.09 min, MH$^+$ = 529, Yield: 8 mg, 8%

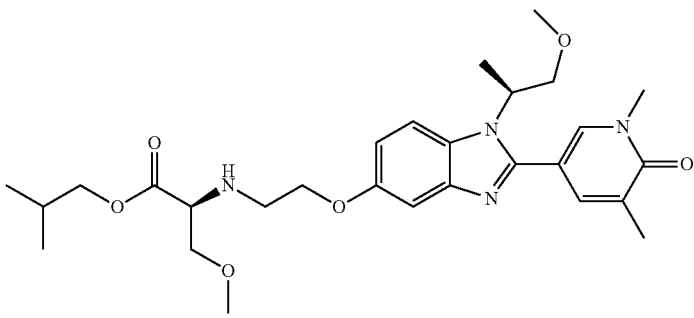 [SMILES: COC[C@H](NCCOc1ccc2c(c1)nc(-c1cc(C)c(=O)n(C)c1)n2[C@@H](C)COC)C(=O)OCC(C)C]

Example 270: (2S,3R)-isopropyl 2-(((2-1,5-dimethyl-6-oxo-1,6-dihydropyridin-3-yl)-1-(2-methoxypropyl)-1H-benzo[d]imidazol-5-yl)methyl)amino)-3-hydroxybutanoate (prepared from: Intermediate 256 and Intermediate 31) System I, 0.54 min, MH$^+$ = 485, Yield: 36 mg, 13%

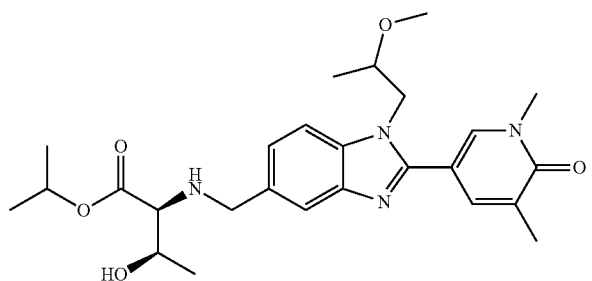 [SMILES: COC(C)Cn1c(-c2cc(C)c(=O)n(C)c2)nc2cc(CN[C@H](C(=O)OC(C)C)[C@@H](C)O)ccc21]

Example 271: (2S,3R)-neopentyl 2-(((2-(1,5-dimethyl-6-oxo-1,6-dihydropyridin-3-yl)-1-(2-methoxypropyl)-1H-benzo[d]imidazol-5-yl)methyl)amino)-3-hydroxybutanoate (prepared from: Intermediate 256 and Intermediate 10) System I, 0.65 min, MH$^+$ = 513, Yield: 311 mg, 82%

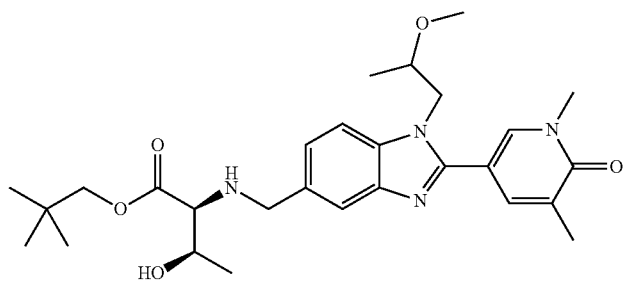 [SMILES: COC(C)Cn1c(-c2cc(C)c(=O)n(C)c2)nc2cc(CN[C@H](C(=O)OCC(C)(C)C)[C@@H](C)O)ccc21]

| | |
|---|---|
| Example 272: (2S,3R)-tert-butyl 2-(((2-(1,5-dimethyl-6-oxo-1,6-dihydropyridin-3-yl)-1-(2-methoxypropyl)-1H-benzo[d]imidazol-5-yl)methyl)amino)-3-hydroxybutanoate (prepared from: Intermediate 256 and (2S,3R)-tert-butyl 2-amino-3-hydroxybutanoate hydrochloride (commercially available)) System I, 0.59 min, MH+ = 499, Yield: 311 mg, 82% | 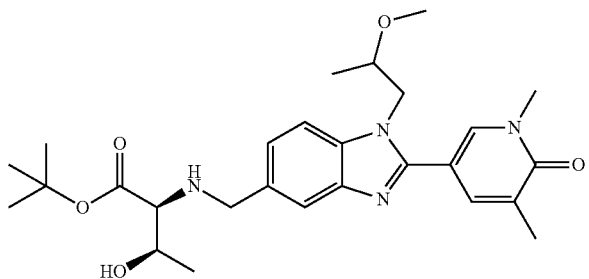 [SMILES: COC(C)Cn1c(-c2cc(C)c(=O)n(C)c2)nc2cc(CN[C@H](C(=O)OC(C)(C)C)[C@@H](C)O)ccc21] |
| Example 273: (2S,3R)-cyclobutyl 2-(((2-(1,5-dimethyl-6-oxo-1,6-dihydropyridin-3-yl)-1-(2-methoxypropyl)-1H-benzo[d]imidazol-5-yl)methyl)amino)-3-hydroxybutanoate (prepared from: Intermediate 256 and Intermediate 32) System I, 0.57 min, MH+ = 497, Yield: 290 mg, 66% | 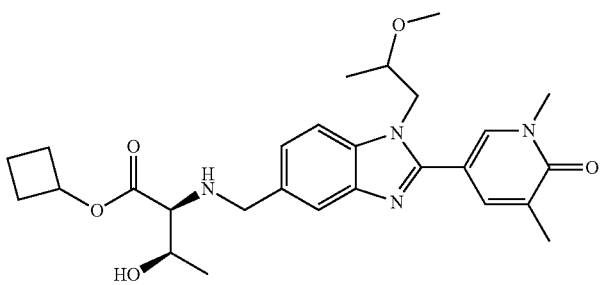 [SMILES: COC(C)Cn1c(-c2cc(C)c(=O)n(C)c2)nc2cc(CN[C@H](C(=O)OC3CCC3)[C@@H](C)O)ccc21] |
| Example 274: (2S,3R)-tert-butyl 2-((2-((2-(1,5-dimethyl-6-oxo-1,6-dihydropyridin-3-yl)-1-((tetrahydro-2H-pyran-4-yl)methyl)-1H-benzo[d]imidazol-5-yl)oxy)ethyl)amino)-3-hydroxy butanoate (prepared from: Intermediate 261 and (2S,3R)-tert-butyl 2-amino-3-hydroxybutanoate hydrochloride (commercially available)) System J, 0.96 min, MH+ = 545, Yield: 25 mg, 17% | 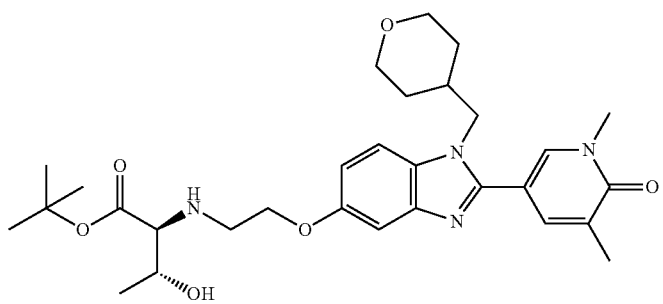 [SMILES: Cc1cc(-c2nc3cc(OCCN[C@H](C(=O)OC(C)(C)C)[C@@H](C)O)ccc3n2CC2CCOCC2)cn(C)c1=O] |
| Example 275: (2S,3R)-cyclobutyl 2-((2-((2-(1,5-dimethyl-6-oxo-1,6-dihydropyridin-3-yl)-1-((tetrahydro-2H-pyran-4-yl)methyl)-1H-benzo[d]imidazol-5-yl)oxy)ethyl)amino)-3-hydroxy butanoate (prepared from: Intermediate 261 and Intermediate 32) System J, 0.93 min, MH+ = 553, Yield: 9.2 mg, 3.3% | 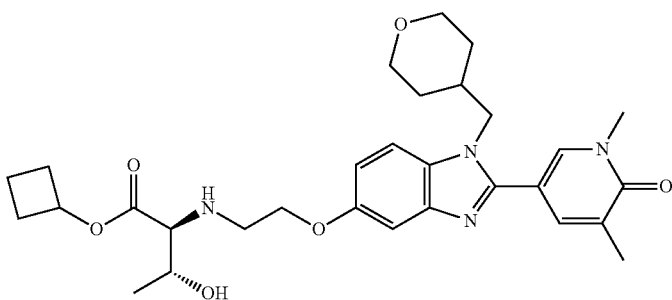 [SMILES: Cc1cc(-c2nc3cc(OCCN[C@H](C(=O)OC4CCC4)[C@@H](C)O)ccc3n2CC2CCOCC2)cn(C)c1=O] |
| Example 276: (2S,3R)-(S)-tetrahydrofuran-3-yl 2-((2-((2-(1,5-dimethyl-6-oxo-1,6-dihydropyridin-3-yl)-1-((tetrahydro-2H-pyran-4-yl)methyl)-1H-benzo[d]imidazol-5-yl)oxy)ethyl)amino)-3-hydroxy butanoate (prepared from: Intermediate 261 and Intermediate 40) System J, 0.79 min, MH+ = 569, Yield: 170 mg, 12% | 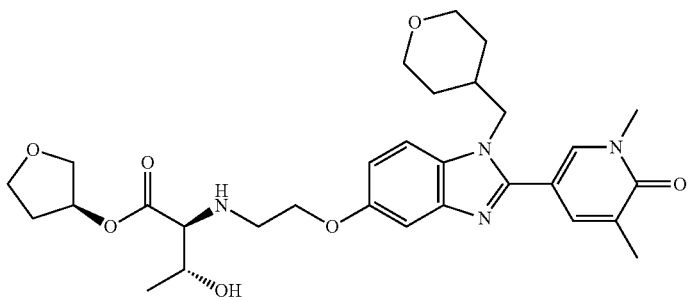 [SMILES: Cc1cc(-c2nc3cc(OCCN[C@H](C(=O)O[C@H]4CCOC4)[C@@H](C)O)ccc3n2CC2CCOCC2)cn(C)c1=O] |

Example 108a and Example 108b: (2S,3R)-Isopropyl 3-hydroxy-2-(((2-(5-methyl-6-oxo-1,6-dihydropyridin-3-yl)-1-((-tetrahydro-2H-pyran-3-yl)methyl)-1H-benzo[d]imidazol-5-yl)methyl)amino)butanoate (Isomer 1) and (2S,3R)-isopropyl 3-hydroxy-2-(((2-(5-methyl-6-oxo-1,6-dihydropyridin-3-yl)-1-((-tetrahydro-2H-pyran-3-yl)methyl)-1H-benzo[d]imidazol-5-yl)methyl)amino)butanoate (Isomer 2)

isomer 1

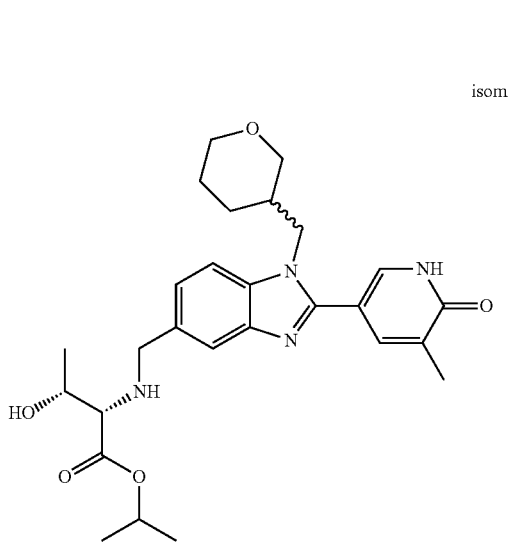

isomer 2

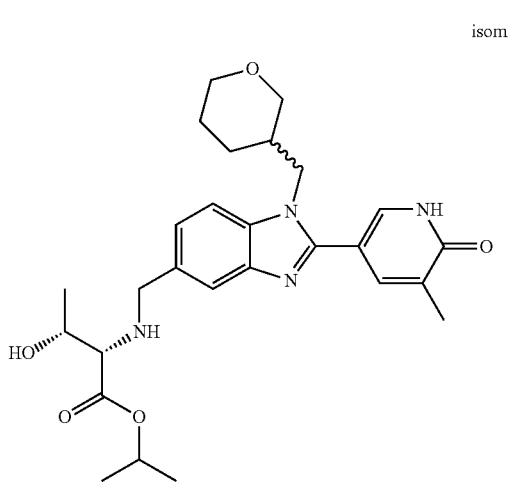

The racemic (2S,3R)-Isopropyl 3-hydroxy-2-(((2-(5-methyl-6-oxo-1,6-dihydropyridin-3-yl)-1-((-tetrahydro-2H-pyran-3-yl)methyl)-1H-benzo[d]imidazol-5-yl)methyl)amino)butanoate (For a preparation see Example 108, 120 mg) was separated by chiral HPLC. The HPLC purification was carried out on a Chiralcel OD-H column (Lot. No. ODH11158-01, 250×30 mm). The purification was run using 30% EtOH in heptane, with a flow rate of 30 mL/min. UV detection was at 215 nm. The first eluting enantiomer was collected, and the fractions evaporated under reduced pressure, to give the title compound "Isomer 1", Example 108a (41 mg). The second eluting enantiomer was collected, and the fractions evaporated under reduced pressure, to give the title compound "Isomer 2", Example 108b (38 mg). Isomer 1: LCMS (System J): $t_{RET}$=0.85 min; MH$^+$ 497. Isomer 2: LCMS (System J): $t_{RET}$=0.85 min; MH$^+$ 497.

Example 130a: (2S,3R)-isopropyl 2-(((2-(1,5-dimethyl-6-oxo-1,6-dihydropyridin-3-yl)-1-(1-methoxybutan-2-yl)-1H-benzo[d]imidazol-5-yl)methyl)amino)-3-hydroxybutanoate (Single Diastereomer of Unknown Configuration at Marked Centre, Isomer 1)

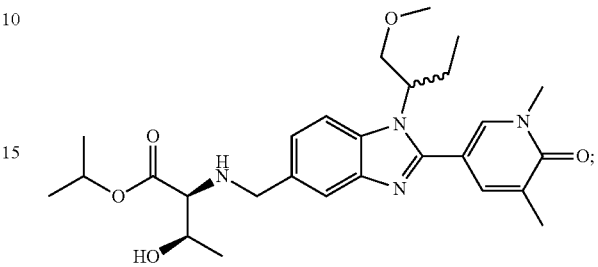

Example 130b: (2S,3R)-isopropyl 2-(((2-(1,5-dimethyl-6-oxo-1,6-dihydropyridin-3-yl)-1-(1-methoxybutan-2-yl)-1H-benzo[d]imidazol-5-yl)methyl)amino)-3-hydroxybutanoate (Single Diastereomer of Unknown Configuration at Marked Centre, Isomer 2)

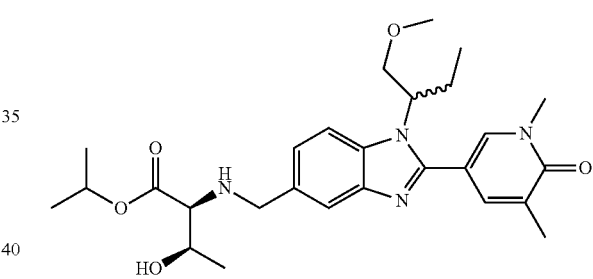

A sample of (rac)-(2S,3R)-isopropyl 2-(((2-(1,5-dimethyl-6-oxo-1,6-dihydropyridin-3-yl)-1-(1-methoxybutan-2-yl)-1H-benzo[d]imidazol-5-yl)methyl)amino)-3-hydroxybutanoate_(for a preparation see Example 130, 290 mg) was separated by chiral chromatography using a 30 mm×25 cm Chiralcel OD-H column, eluting with 60% EtOH/Heptane at a flowrate of 30 mL/min. The appropriate fractions for each isomer were combined and evaporated under reduced pressure to give the title compounds Example 130a: Isomer 1 (107 mg)

LCMS (System I): $t_{RET}$=0.59 min; MH$^+$ 499. Chiral analysis carried out on a 4.6 mmid×25 cm Chiralcel OD-H column, eluting with 60% EtOH/Heptane at a flowrate of 1 mL/min, chiral purity>99.5%.

Example 130b: Isomer 2 (96 mg)

LCMS (System I): $t_{RET}$=0.59 min; MH$^+$ 499. Chiral analysis carried out on a 4.6 mmid×25 cm Chiralcel OD-H column, eluting with 60% EtOH/Heptane at a flowrate of 1 mL/min, chiral purity=98.5%.

Example 131a: (2S,3R)-cyclobutyl 2-(((2-(1,5-dimethyl-6-oxo-1,6-dihydropyridin-3-yl)-1-(1-methoxybutan-2-yl)-1H-benzo[d]imidazol-5-yl)methyl)amino)-3-hydroxybutanoate (Single Diastereomer of Unknown Configuration at Marked Centre, Isomer 1)

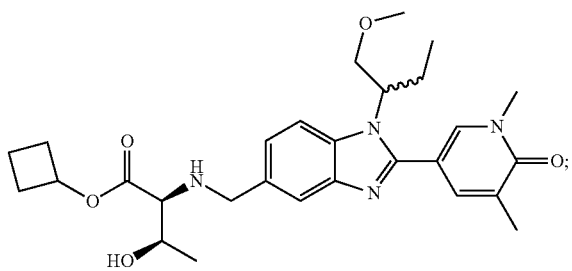 [SMILES: CCC(COC)n1c(-c2cc(C)c(=O)n(C)c2)nc2cc(CN[C@H](C(=O)OC3CCC3)[C@@H](C)O)ccc21]

and

Example 131b: (2S,3R)-cyclobutyl 2-(((2-(1,5-dimethyl-6-oxo-1,6-dihydropyridin-3-yl)-1-(1-methoxybutan-2-yl)-1H-benzo[d]imidazol-5-yl)methyl)amino)-3-hydroxybutanoate (Single Diastereomer of Unknown Configuration at Marked Centre, Isomer 2)

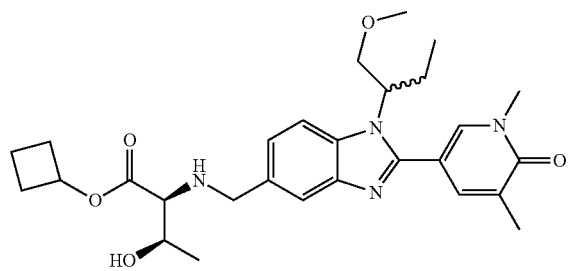 [SMILES: CCC(COC)n1c(-c2cc(C)c(=O)n(C)c2)nc2cc(CN[C@H](C(=O)OC3CCC3)[C@@H](C)O)ccc21]

A sample of (rac)-(2S,3R)-cyclobutyl 2-(((2-(1,5-dimethyl-6-oxo-1,6-dihydropyridin-3-yl)-1-(1-methoxybutan-2-yl)-1H-benzo[d]imidazol-5-yl)methyl)amino)-3-hydroxybutanoate (for a preparation see Example 131, 300 mg) was separated by chiral chromatography using a 30 mm×25 cm Chiralcel OD-H column, eluting with 10% EtOH/Heptane at a flowrate of 30 mL/min. The appropriate fractions for each isomer were combined and evaporated under reduced pressure to give the title compounds Example 131a: Isomer 1 (58 mg)

LCMS (System I): $t_{RET}$=0.61 min; MH$^+$ 511. Chiral analysis carried out on a 4.6 mmid×25 cm Chiralcel OD-H column, eluting with 10% EtOH/Heptane at a flowrate of 1 mL/min, chiral purity=97.3%%.

Example 131b: Isomer 2 (92 mg)

LCMS (System I): $t_{RET}$=0.61 min; MH$^+$ 511. Chiral analysis carried out on a 4.6 mmid×25 cm Chiralcel OD-H column, eluting with 10% EtOH/Heptane at a flowrate of 1 mL/min, chiral purity>99.5%.

Example 132a: (2S,3R)-tert-butyl 2-(((2-(1,5-dimethyl-6-oxo-1,6-dihydropyridin-3-yl)-1-(1-methoxybutan-2-yl)-1H-benzo[d]imidazol-5-yl)methyl)amino)-3-hydroxybutanoate (Signal Diastereomer of Unknown Configuration at Marked Centre, Isomer 1)

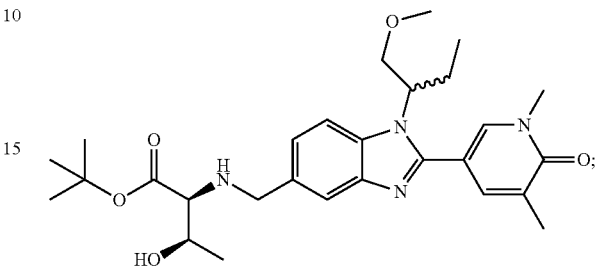

and

Example 132b: (2S,3R)-tert-butyl 2-(((2-(1,5-dimethyl-6-oxo-1,6-dihydropyridin-3-yl)-1-(1-methoxybutan-2-yl)-1H-benzo[d]imidazol-5-yl)methyl)amino)-3-hydroxybutanoate (Single Diastereomer of Unknown Configuration at Marked Centre, Isomer 2)

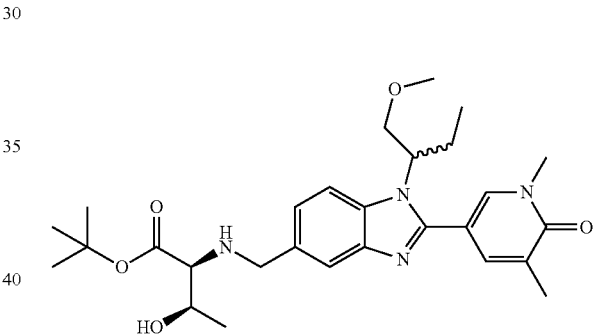

A sample of (rac)-(2S,3R)-tert-butyl 2-(((2-(1,5-dimethyl-6-oxo-1,6-dihydropyridin-3-yl)-1-(1-methoxybutan-2-yl)-1H-benzo[d]imidazol-5-yl)methyl)amino)-3-hydroxybutanoate (for a preparation see Example 132, 50 mg) was separated by chiral chromatography using a 30 mm×25 cm Chiralcel OD-H column, eluting with 70% EtOH/Heptane at a flowrate of 30 mL/min. The appropriate fractions for each isomer were combined and evaporated under reduced pressure to give the title compounds Example 132a: Isomer 1 (18 mg)

LCMS (System I): $t_{RET}$=0.62 min; MH$^+$ 513. Chiral analysis carried out on a 4.6 mmid×25 cm Chiralcel OD-H column, eluting with 70% EtOH/Heptane at a flowrate of 1 mL/min, chiral purity=97.3%.

Example 132b: Isomer 2 (14 mg)

LCMS (System I): $t_{RET}$=0.62 min; MH$^+$ 513. Chiral analysis carried out on a 4.6 mmid×25 cm Chiralcel OD-H column, eluting with 10% EtOH/Heptane at a flowrate of 1 mL/min, chiral purity>99.5%.

Example 133a: (2S,3R)-isopropyl 2-(((2-(1,5-dimethyl-6-oxo-1,6-dihydropyridin-3-yl)-1-((tetrahydrofuran-3-yl)methyl)-1H-benzo[d]imidazol-6-yl)methyl)amino)-3-hydroxybutanoate (Single Diastereomer of Unknown Configuration at Marked Centre, Isomer 1)

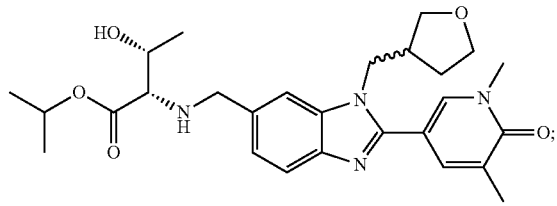 [SMILES: Cc1cc(-c2nc3ccc(CN[C@H](C(=O)OC(C)C)[C@@H](C)O)cc3n2CC2CCOC2)cn(C)c1=O]

and

Example 133b: (2S,3R)-isopropyl 2-(((2-(1,5-dimethyl-6-oxo-1,6-dihydropyridin-3-yl)-1-((tetrahydrofuran-3-yl)methyl)-1H-benzo[d]imidazol-6-yl)methyl)amino)-3-hydroxybutanoate (Single Diastereomer of Unknown Configuration at Marked Centre, Isomer 2)

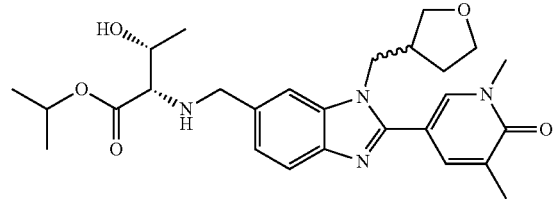 [SMILES: Cc1cc(-c2nc3ccc(CN[C@H](C(=O)OC(C)C)[C@@H](C)O)cc3n2CC2CCOC2)cn(C)c1=O]

A sample of (rac)-(2S,3R)-isopropyl 2-(((2-(1,5-dimethyl-6-oxo-1,6-dihydropyridin-3-yl)-1-((tetrahydrofuran-3-yl)methyl)-1H-benzo[d]imidazol-6-yl)methyl)amino)-3-hydroxybutanoate (for a preparation see Example 133, 285 mg) was separated by chiral chromatography using a 30 mm×25 cm Chiralcel OD-H column, eluting with 50% EtOH/Heptane at a flowrate of 25 mL/min. The appropriate fractions for each isomer were combined and evaporated under reduced pressure to give the title compounds Example 133a: Isomer 1 (159 mg)

LCMS (System J): $t_{RET}$=0.84 min; MH$^+$ 497. Chiral analysis carried out on a 4.6 mmid×25 cm Chiralcel OD-H column, eluting with 70% EtOH/Heptane at a flowrate of 1 mL/min, chiral purity>99.5%.

Example 133b: Isomer 2 (145 mg)

LCMS (System J): $t_{RET}$=0.84 min; MH$^+$ 497. Chiral analysis carried out on a 4.6 mmid×25 cm Chiralcel OD-H column, eluting with 70% EtOH/Heptane at a flowrate of 1 mL/min, chiral purity=99.2%.

Example 134a: (2S,3R)-tert-butyl 2-(((2-(1,5-dimethyl-6-oxo-1,6-dihydropyridin-3-yl)-1-((tetrahydrofuran-3-yl)methyl)-1H-benzo[d]imidazol-6-yl)methyl)amino)-3-hydroxybutanoate (Single Diastereomer of Unknown Configuration at Marked Centre, Isomer 1)

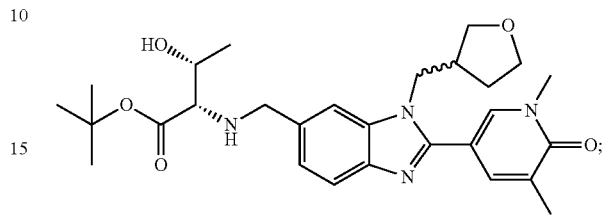

Example 134b: (2S,3R)-tert-butyl 2-(((2-(1,5-dimethyl-6-oxo-1,6-dihydropyridin-3-yl)-1-((tetrahydrofuran-3-yl)methyl)-1H-benzo[d]imidazol-6-yl)methyl)amino)-3-hydroxybutanoate (Single Diastereomer of Unknown Configuration at Marked Centre, Isomer 2)

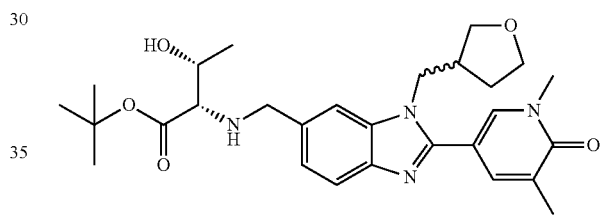

A sample of (rac)-(2S,3R)-tert-butyl 2-(((2-(1,5-dimethyl-6-oxo-1,6-dihydropyridin-3-yl)-1-((tetrahydrofuran-3-yl)methyl)-1H-benzo[d]imidazol-6-yl)methyl)amino)-3-hydroxybutanoate (for a preparation see Example 134, 200 mg) was separated by chiral chromatography using a 30 mm×25 cm Chiralcel OD-H column, eluting with 50% EtOH/Heptane at a flowrate of 25 mL/min. The appropriate fractions for each isomer were combined and evaporated under reduced pressure to give the title compounds.

Example 134a: Isomer 1 (100 mg)

LCMS (System J): $t_{RET}$=0.84 min; MH$^+$ 511. Chiral analysis carried out on a 4.6 mmid×25 cm Chiralcel OD-H column, eluting with 70% EtOH/Heptane at a flowrate of 1 mL/min, chiral purity>99.5%.

Example 134b: Isomer 2 (85 mg)

LCMS (System J): $t_{RET}$=0.91 min; MH$^+$ 511. Chiral analysis carried out on a 4.6 mmid×25 cm Chiralcel OD-H column, eluting with 70% EtOH/Heptane at a flowrate of 1 mL/min, chiral purity=99.5%.

Example 139a and 139b: (S)-(S)-tetrahydrofuran-3-yl 4-methyl-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)pentanoate and (S)-(R)-tetrahydrofuran-3-yl 4-methyl-2-(((2-(5-methyl-6-oxo-1,6-dihydropyridin-3-yl)-1-((tetrahydro-2H-pyran-4-yl)methyl)-1H-benzo[d]imidazol-5-yl)methyl)amino)pentanoate

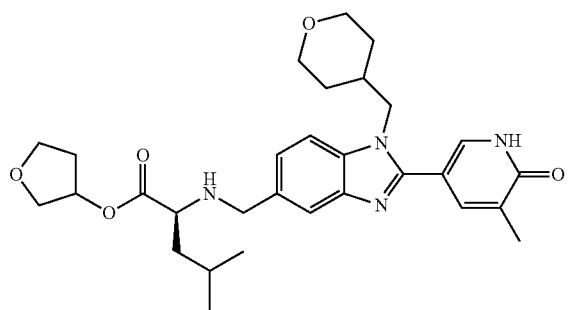 [SMILES: Cc1cc(-c2nc3cc(CN[C@@H](CC(C)C)C(=O)OC4CCOC4)ccc3n2CC2CCOCC2)c[nH]c1=O]

Example 139 (85 mg) was dissolved in Ethanol/Heptane (1:1, 1 mL) and purified by chiral chromatography (stationary phase: Chiralpak IA, mobile phase: heptane/ethanol) (N28112-60). The combined fractions containing pure Isomer 1 (Example 139a) were concentrated in vacuo to give pure Isomer 1 as a colourless solid (25 mg). LCMS (System B): $t_{RET}$=0.92 min, MH$^+$=537. The combined fractions containing pure Isomer 2 (Example 139b) were concentrated in vacuo to give pure Isomer 2 as a colourless solid (45 mg). LCMS (System B): $t_{RET}$=0.93 min, MH$^+$=537.

Example 162a and 162b: (2S,3R)-isobutyl 2-(((2-(1,5-dimethyl-6-oxo-1,6-dihydropyridin-3-yl)-1-(((R)-4-methylmorpholin-2-yl)methyl)-1H-benzo[d]imidazol-5-yl)methyl)amino)-3-hydroxybutanoate and (2S,3R)-isobutyl 2-(((2-(1,5-dimethyl-6-oxo-1,6-dihydropyridin-3-yl)-1-(((S)-4-methylmorpholin-2-yl)methyl)-1H-benzo[d]imidazol-5-yl)methyl)amino)-3-hydroxybutanoate

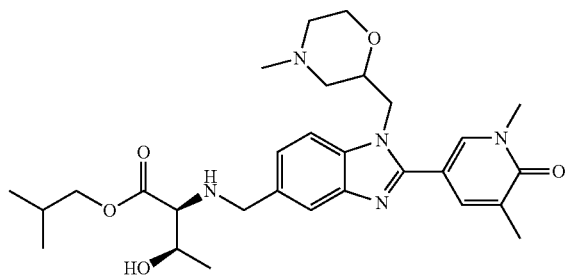 [SMILES: Cc1cc(-c2nc3cc(CN[C@H](C(=O)OCC(C)C)[C@@H](C)O)ccc3n2CC2CN(C)CCO2)cn(C)c1=O]

Example 162 (26 mg) was dissolved in Ethanol (1 mL) and purified by chiral chromatography (stationary phase: Chiralcel OD-H, mobile phase: 60% heptane/40% ethanol) (N31661-32). The combined fractions containing pure Isomer 1 were concentrated in vacuo to give pure Isomer 1 (Example 162a) as a colourless solid (11 mg). LCMS (System B): $t_{RET}$=0.88 min, MH$^+$=540. The combined fractions containing pure Isomer 2 were concentrated in vacuo to give pure Isomer 2 (Example 162b) as a colourless solid (11 mg). LCMS (System B): $t_{RET}$=0.87 min, MH$^+$=540.

Example 174a: (2S,3R)-isopropyl 2-(((2-(1,5-dimethyl-6-oxo-1,6-dihydropyridin-3-yl)-1-((tetrahydro-2H-pyran-2-yl)methyl)-1H-benzo[d]imidazol-6-yl)methyl)amino)-3-hydroxybutanoate—diastereomer 1 and Example 174b: (2S,3R)-isopropyl 2-(((2-(1,5-dimethyl-6-oxo-1,6-dihydropyridin-3-yl)-1-((tetrahydro-2H-pyran-2-yl)methyl)-1H-benzo[d]imidazol-6-yl)methyl)amino)-3-hydroxybutanoate—Diastereomer 2

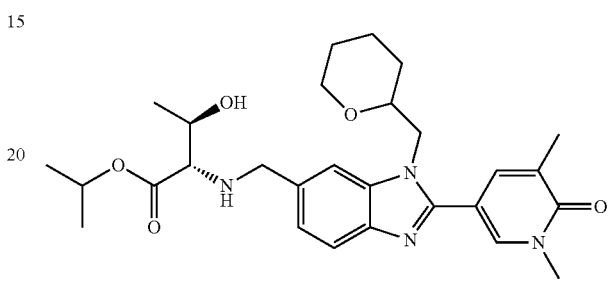

Example 174 (203 mg) was dissolved in EtOH (2 mL) and purified by chiral chromatography (stationary phase Chiralpak AD-H, mobile phase 40% EtOH/Heptane). The combined fractions were evaporated in vacuo to give pure diastereomer 1 (Example 174a) as a colourless solid (81 mg). HPLC-UV: RT~8.2 minutes, >99.5% isomeric purity by area HPLC @ 215 nm. LCMS (System I): $t_{RET}$=0.57 min, MH$^+$=511. The combined fractions were evaporated in vacuo to give pure diastereomer 2 (Example 174b) as a colourless solid (99 mg). HPLC-UV: RT~15.0 minutes, 99.3% isomeric purity by area HPLC @ 215 nm. LCMS (System I): $t_{RET}$=0.58 min, MH$^+$=511.

Example 175: (2S,3R)-isobutyl 2-(((2-(1,5-dimethyl-6-oxo-1,6-dihydropyridin-3-yl)-1-((tetrahydro-2H-pyran-2-yl)methyl)-1H-benzo[d]imidazol-6-yl)methyl)amino)-3-hydroxybutanoate—Diastereoisomer 2 and Example 175: (2S,3R)-isobutyl 2-(((2-(1,5-dimethyl-6-oxo-1,6-dihydropyridin-3-yl)-1-((tetrahydro-2H-pyran-2-yl)methyl)-1H-benzo[d]imidazol-6-yl)methyl)amino)-3-hydroxybutanoate—Diastereoisomer 1

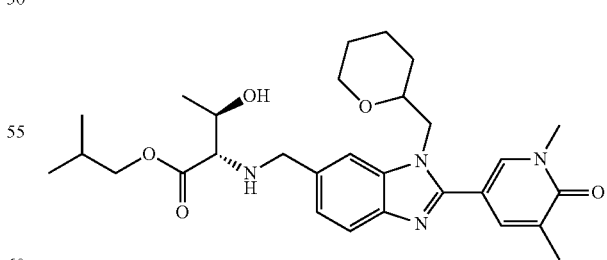

Example 175 (220 mg) was dissolved in EtOH (2 mL) and purified by chiral chromatography (stationary phase: Chiralpak AD-H, mobile phase: 40% EtOH/Heptane). The combined fractions containing pure diastereomer 1 were concentrated in vacuo to give pure diastereomer 1 (Example 175a) as a colourless solid (91 mg). HPLC-UV: RT~8.3 minutes, >95% isomeric purity by area HPLC @ 215 nm. LCMS (System I): $t_{RET}$=0.63 min, MH$^+$=525. The combined fractions containing pure diastereomer 2 were concentrated in vacuo to give pure diastereomer 2 (Example 175b) as a colourless solid (89 mg). HPLC-UV: RT~12.4 minutes, >95% isomeric purity by area HPLC @ 215 nm. LCMS (System I): $t_{RET}$=0.63 min, MH$^+$=525.

Example 178a: (2S,3R)-tert-butyl 2-(((2-(1,5-dimethyl-6-oxo-1,6-dihydropyridin-3-yl)-1-((tetrahydro-2H-pyran-2-yl)methyl)-1H-benzo[d]imidazol-6-yl)methyl)amino)-3-hydroxybutanoate—diastereoisomer 1 and Example 178b: (2S,3R)-tert-butyl 2-(((2-(1,5-dimethyl-6-oxo-1,6-dihydropyridin-3-yl)-1-((tetrahydro-2H-pyran-2-yl)methyl)-1H-benzo[d]imidazol-6-yl)methyl)amino)-3-hydroxybutanoate—diastereoisomer 2

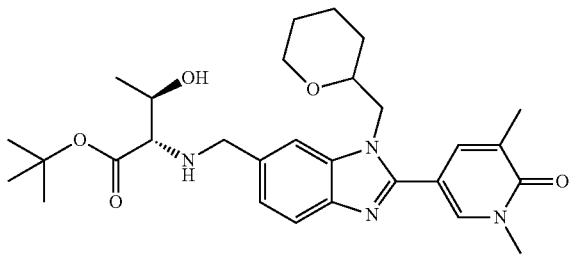 [SMILES: Cc1cc(-c2nc3ccc(CN[C@H](C(=O)OC(C)(C)C)[C@@H](C)O)cc3n2CC2CCCCO2)cn(C)c1=O]

Example 178 (100 mg) was dissolved in EtOH (2 mL) and purified by chiral chromatography (stationary phase: Chiralpak AD-H, mobile phase: 40% EtOH/Heptane). The combined fractions containing pure diastereomer 1 were concentrated in vacuo to give pure diastereomer 1 as a colourless solid (50 mg). HPLC-UV: RT~8.1 minutes, >99.5% isomeric purity by area HPLC @ 215 nm. LCMS (System I): $t_{RET}$=0.61 min, MH$^+$=525. The combined fractions containing pure diastereomer 2 were concentrated in vacuo to give pure diastereomer 2 as a colourless solid (41 mg). HPLC-UV: RT~17.7 minutes, ca.>99.5% isomeric purity by area HPLC @ 215 nm. LCMS (System I): $t_{RET}$=0.61 min, MH$^+$=525.

Example 180a: (2S,3R)—(S)-tetrahydrofuran-3-yl 2-(((2-(1,5-dimethyl-6-oxo-1,6-dihydropyridin-3-yl)-1-((tetrahydro-2H-pyran-2-yl)methyl)-1H-benzo[d]imidazol-6-yl)methyl)amino)-3-hydroxybutanoate—Diastereomer 1 and Example 180b: (2S,3R)—(S)-tetrahydrofuran-3-yl 2-(((2-(1,5-dimethyl-6-oxo-1,6-dihydropyridin-3-yl)-1-((tetrahydro-2H-pyran-2-yl methyl-1H-benzo[d]imidazol-6-yl)methyl)amino)-3-hydroxybutanoate—Diastereomer 2

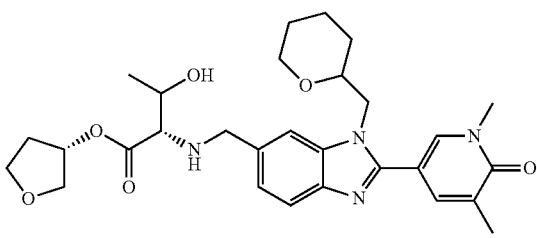 [SMILES: Cc1cc(-c2nc3ccc(CN[C@H](C(=O)O[C@H]4CCOC4)C(C)O)cc3n2CC2CCCCO2)cn(C)c1=O]

Example 180 (140 mg) was dissolved in EtOH (2 mL) and purified by chiral chromatography (stationary phase: Chiralcel OD-H, mobile phase: 30% EtOH/Heptane). The combined fractions containing pure diastereomer 1 (Example 180a) were concentrated in vacuo to give pure diastereomer 1 as a colourless solid (64 mg). HPLC-UV: RT~6.2 minutes, >99.5% isomeric purity by area HPLC @ 215 nm. LCMS (System I): $t_{RET}$=0.52 min, MH$^+$=539. The combined fractions containing pure diastereomer 2 (Example 180b) were concentrated in vacuo to give pure diastereomer 2 as a colourless solid (64 mg). HPLC-UV: RT~9.8 minutes, ca.>99.5% isomeric purity by area HPLC @ 215 nm. LCMS (System I): $t_{RET}$=0.52 min, MH$^+$=539.

Example 181a: (2S,3R)-isopropyl 2-(((2-(1,5-dimethyl-6-oxo-1,6-dihydropyridin-3-yl)-1-(1-(tetrahydro-2H-pyran-4-yl)ethyl)-1H-benzo[d]imidazol-5-yl)methylamino)-3-hydroxybutanoate—Diastereomer 1 and Example 181b: (2S,3R)-isopropyl 2-(((2-(1,5-dimethyl-6-oxo-1,6-dihydropyridin-3-yl)-1-(1-(tetrahydro-2H-pyran-4-yl)ethyl)-1H-benzo[d]imidazol-5-yl)methylamino)-3-hydroxybutanoate—Diastereomer 2

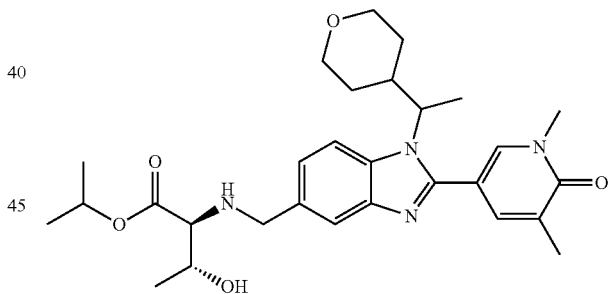

Example 181 (107 mg) was dissolved in EtOH (2 mL) and purified by chiral chromatography (stationary phase: Chiralpak AD-H, mobile phase: EtOH).

The combined fractions containing pure Isomer 1 were concentrated in vacuo to give pure Isomer 1 as a colourless solid (48 mg). HPLC-UV: RT~8.4 minutes, >99.5% isomeric purity by area HPLC @215 nm. LCMS (System J): $t_{RET}$=0.55 min, MH$^+$=525. The combined fractions containing pure Isomer 2 were concentrated in vacuo to give pure Isomer 2 as a colourless solid (36 mg). HPLC-UV: RT~11.4 minutes, ca. 99.1% isomeric purity by area HPLC @ 215 nm. LCMS (System J): $t_{RET}$=0.56 min, MH$^+$=525.

Example 182a: (2S,3R)-tert-butyl 2-(((2-(1,5-dim-ethyl-6-oxo-1,6-dihydropyridin-3-yl)-1-(1-(tetra-hydro-2H-pyran-4-yl)ethyl)-1H-benzo[d]imidazol-5-yl)methyl)amino)-3-hydroxybutanoate—Diastereomer 1 and Example 182b: (2S,3R)-tert-butyl 2-(((2-(1,5-dimethyl-6-oxo-1,6-dihydropyridin-3-yl)-1-(1-(tetrahydro-2H-pyran-4-yl)ethyl)-1H-benzo[d]imidazol-5-yl)methyl)amino)-3-hydroxybutanoate—Diastereomer 2

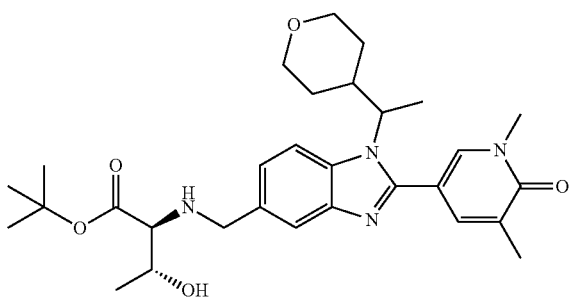 [SMILES: Cc1cc(-c2nc3cc(CN[C@H](C(=O)OC(C)(C)C)[C@@H](C)O)ccc3n2C(C)C2CCOCC2)cn(C)c1=O]

Example 182 (ca. 56 mg) was dissolved in EtOH (2 mL) and purified by chiral chromatography (stationary phase: Chiralpak IC, mobile phase: EtOH).
The combined fractions containing pure Isomer 1 were concentrated in vacuo to give pure Isomer 1 as a colourless solid (27 mg). HPLC-UV: RT~19.5 minutes, >99.5% isomeric purity by area HPLC @ 215 nm. LCMS (System J): $t_{RET}$=0.59 min, MH$^+$=539. The combined fractions containing pure Isomer 2 were concentrated in vacuo to give pure Isomer 2 as a colourless solid (29 mg). HPLC-UV: RT~25.5 minutes, >99.5% isomeric purity by area HPLC @ 215 nm. LCMS (System J): $t_{RET}$=0.56 min, MH$^+$=539.

Example 213a (2S,3R)-isobutyl 2-(((2-(1,5-dim-ethyl-6-oxo-1,6-dihydropyridin-3-yl)-1-(((R)-tetra-hydro-2H-pyran-3-yl)methyl)-1H-benzo[d]imidazol-5-ylmethyl)amino)-3-hydroxybutanoate and 213b: (2S,3R)-isobutyl 2-(((2-(1,5-dimethyl-6-oxo-1,6-dihydropyridin-3-yl)-1-(((S)-tetrahydro-2H-pyran-3-yl)methyl)-1H-benzo[d]imidazol-5-yl)methyl)amino)-3-hydroxybutanoate

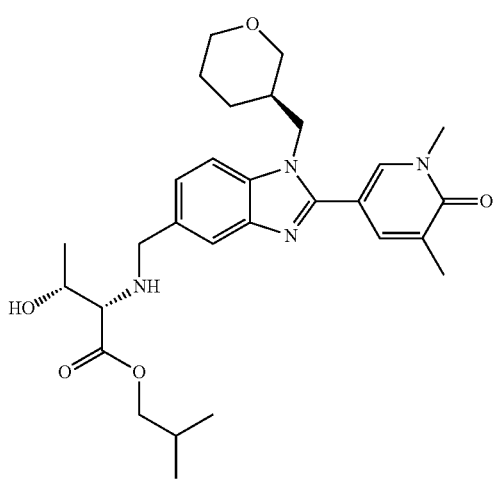 [SMILES: Cc1cc(-c2nc3cc(CN[C@H](C(=O)OCC(C)C)[C@@H](C)O)ccc3n2C[C@H]2CCCOC2)cn(C)c1=O]

Example 213a

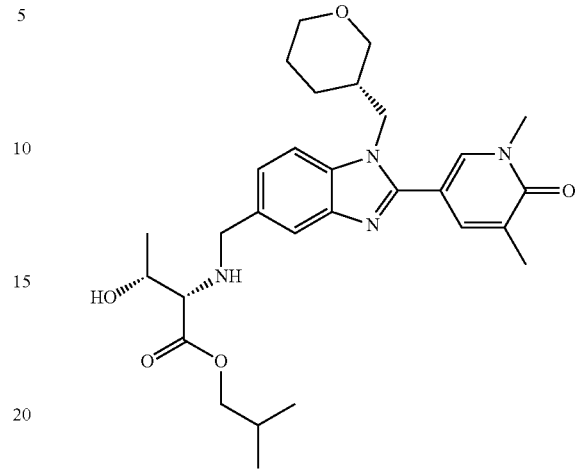

Example 213b

A sample of (2S,3R)-isobutyl 2-(((2-(1,5-dimethyl-6-oxo-1,6-dihydropyridin-3-yl)-1-((tetrahydro-2H-pyran-3-yl)methyl)-1H-benzo[d]imidazol-5-yl)methyl)amino)-3-hydroxybutanoate (For a preparation see Example 213, 125 mg) was purified by chiral chromatography on a Chiralpak IA (250×430 mm, 5 micron) column, Flowrate: 40 mL/min, detection: UV DAD (250 nm (bandwidth 80 nm, reference 375 nm (bandwidth 50 nm)). Eluting with a 50:50 mixture of Acetonitrile containing 0.2% v/v isopropylamine and Propan-2-ol containing 0.2% v/v isopropylamine. Appropriate fractions were combined and evaporated under a stream of nitrogen to give the title compounds.

Isomer 1, Example 213a: (52 mg)

Chiral analysis carried out on a Chiralpak IA (250×4.6 mm, 5 micron) column, flowrate: 1 mL/min, detection: UV DAD (250 nm (bandwidth 40 nm, reference 375 nm (bandwidth 50 nm)). Eluting with a 50:50 mixture of Acetonitrile containing 0.2% v/v isopropylamine and Propan-2-ol containing 0.2% v/v isopropylamine. Chiral purity is >99.5%. LCMS (System J): $t_{RET}$=0.99 min; MH$^+$ 525

Isomer 2, Example 213b: (53 mg)

Chiral analysis carried out on a Chiralpak IA (250×4.6 mm, 5 micron) column, flowrate: 1 mL/min, detection: UV DAD (250 nm (bandwidth 40 nm, reference 375 nm (bandwidth 50 nm)). Eluting with a 50:50 mixture of Acetonitrile containing 0.2% v/v isopropylamine and Propan-2-ol containing 0.2% v/v isopropylamine. Chiral purity is 99.7%. LCMS (System J): $t_{RET}$=0.99 min; MH$^+$ 525.

Example 225a and Example 225b: (2S,3R)-isopropyl 2-(((2-(1,5-dimethyl-6-oxo-1,6-dihydropyridin-3-yl)-1-(((R)-tetrahydro-2H-pyran-3-yl)methyl)-1H-benzo[d]imidazol-5-yl)methyl)amino)-3-hydroxybutanoate "R-DIASTEREOISOMER" and (2S,3R)-isopropyl 2-(((2-(1,5-dimethyl-6-oxo-1,6-dihydropyridin-3-yl)-1-(((S)-tetrahydro-2H-pyran-3-yl)methyl)-1H-benzo[d]imidazol-5-yl)methyl)amino)-3-hydroxybutanoate "S-DIASTEREOISOMER"

Example 228a and Example 228b: (2S,3R)-cyclobutyl 2-(((2-(1,5-dimethyl-6-oxo-1,6-dihydropyridin-3-yl)-1-((tetrahydrofuran-3-yl)methyl)-1H-benzo[d]imidazol-5-yl)methyl)amino)-3-hydroxybutanoate DIASTEREOMER 1 and (2S,3R)-cyclobutyl 2-(((2-(1,5-dimethyl-6-oxo-1,6-dihydropyridin-3-yl)-1-((tetrahydrofuran-3-yl)methyl)-1H-benzo[d]imidazol-5-yl)methylamino)-3-hydroxybutanoate DIASTEREOMER 2

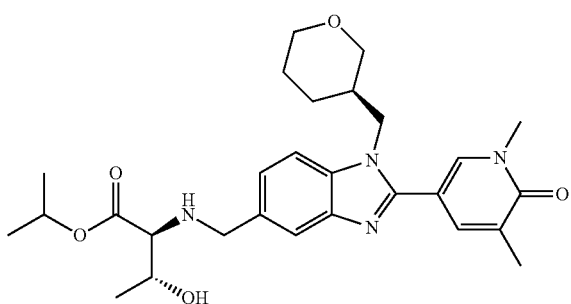

Diastereoisomer 1

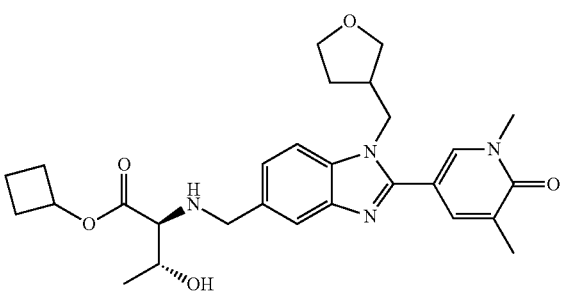

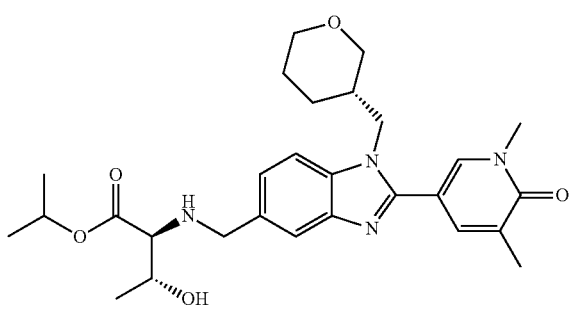

Diastereoisomer 2

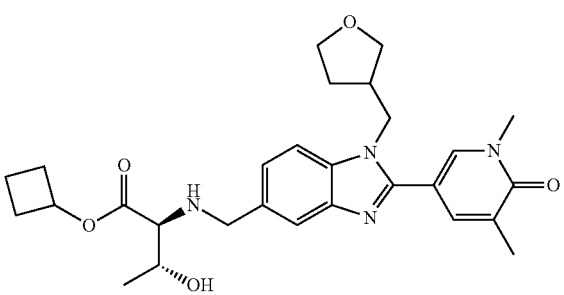

The racemic (2R,3S)-isopropyl 2-(((2-(1,5-dimethyl-6-oxo-1,6-dihydropyridin-3-yl)-1-((tetrahydro-2H-pyran-3-yl)methyl)-1H-benzo[d]imidazol-5-yl)methyl)amino)-3-hydroxybutanoate (For a preparation see Example 225, 2.1 g) was separated by chiral HPLC. The HPLC purification was carried out on a Chiralpak ID column (Lot. No. ID12179-01, 250×30 mm). The purification was run using 80% EtOH in cyclohexane with 0.2% IPA added, with a flow rate of 30 mL/min. UV detection was at 215 nm. The first eluting enantiomer was collected, and the fractions evaporated under reduced pressure to give the title compound "R-DIASTEREOISOMER" Example 225a (858 mg). The second eluting enantiomer was collected, and the fractions evaporated under reduced pressure, to give the title compound "S-DIASTEREOISOMER", Example 225b (836 mg). DIASTEREOISOMER 1: LCMS (System J): $t_{RET}$=0.91 min; MH$^+$ 511. DIASTEREOISOMER 2: LCMS (System J): $t_{RET}$=0.90 min; MH$^+$ 511.

racemic (2S,3R)-cyclobutyl 2-(((2-(1,5-dimethyl-6-oxo-1,6-dihydropyridin-3-yl)-1-((tetrahydrofuran-3-yl)methyl)-1H-benzo[d]imidazol-5-yl)methyl)amino)-3-hydroxybutanoate (For a preparation see Example 228, 250 mg) was separated by chiral HPLC. The HPLC purification was carried out on a Chiralpak AD-H column (Lot. No. ADH12143-01, 250×30 mm). The purification was run using 100% EtOH, with a flow rate of 25 mL/min. UV detection was at 215 nm. The first eluting enantiomer was collected, and the fractions evaporated under reduced pressure. The sample was purified by MDAP (Method B). The fractions were combined, evaporated under reduced pressure, and dried in a vacuum oven overnight to give the title compound "DIASTEREOISOMER 1" (98 mg). The second eluting enantiomer was collected, and the fractions evaporated under reduced pressure, to give the title compound "DIASTEREOISOMER 2" (90 mg). DIASTEREOISOMER 1: LCMS (System J): $t_{RET}$=0.52 min; MH$^+$ 509. DIASTEREOISOMER 2: LCMS (System J): $t_{RET}$=0.52 min; MH$^+$ 509.

Example 229a and Example 229b: (2S,3R)-isopropyl 2-(((2-(1,5-dimethyl-6-oxo-1,6-dihydropyridin-3-yl)-1-((tetrahydrofuran-3-yl)methyl)-1H-benzo[d]imidazol-5-yl)methylamino)-3-hydroxybutanoate DIASTEREOISOMER 1 and (2S,3R)-isopropyl 2-(((2-(1,5-dimethyl-6-oxo-1,6-dihydropyridin-3-yl)-1-((tetrahydrofuran-3-yl)methyl)-1H-benzo[d]imidazol-5-yl)methylamino)-3-hydroxybutanoate DIASTEREOISOMER 2

Example 232a and Example 232b: (2S,3R)-tert-butyl 2-(((2-(1,5-dimethyl-6-oxo-1,6-dihydropyridin-3-yl)-1-((tetrahydrofuran-3-yl)methyl)-1H-benzo[d]imidazol-5-yl)methylamino)-3-hydroxybutanoate DIASTEREOISOMER 1 and (2S,3R)-tert-butyl 2-(((2-(1,5-dimethyl-6-oxo-1,6-dihydropyridin-3-yl)-1-((tetrahydrofuran-3-yl)methyl)-1H-benzo[d]imidazol-5-yl)methylamino)-3-hydroxybutanoate DIASTEREOISOMER 2

Diastereoisomer 1

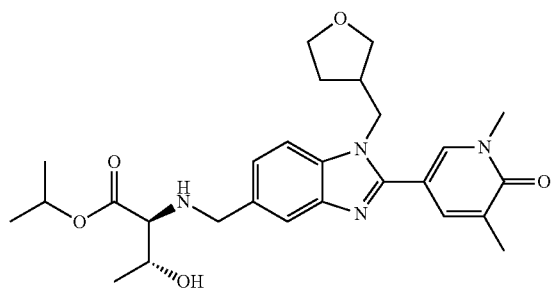

Diastereoisomer 2

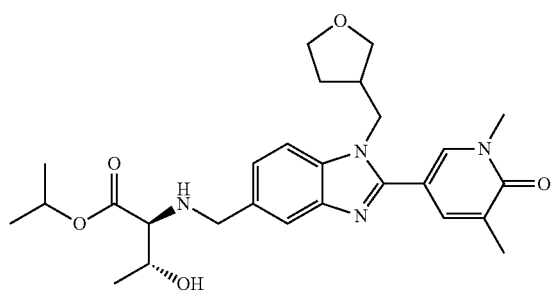

The racemic (2S,3R)-isopropyl 2-(((2-(1,5-dimethyl-6-oxo-1,6-dihydropyridin-3-yl)-1-((tetrahydrofuran-3-yl)methyl)-1H-benzo[d]imidazol-5-yl)methyl)amino)-3-hydroxybutanoate (for a preparation see Example 229, 200 mg) was separated by chiral HPLC. The HPLC purification was carried out on a Chiralpak AD-H column (Lot. No. ADH12143-01, 250×30 mm). The purification was run using 100% EtOH, with a flow rate of 25 mL/min. UV detection was at 215 nm. The first eluting enantiomer was collected, and the fractions evaporated under reduced pressure to give the title compound "DIASTEREOISOMER 1", Example 229a (21 mg). The second eluting enantiomer was collected, and the fractions evaporated under reduced pressure, to give the title compound "DIASTEREOISOMER 2", Example 229b (20 mg). DIASTEREOISOMER 1: LCMS (System J): $t_{RET}$=0.86 min; MH$^+$ 497. DIASTEREOISOMER 2: LCMS (System J): $t_{RET}$=0.86 min; MH$^+$ 497.

The racemic (2S,3R)-tert-butyl 2-(((2-(1,5-dimethyl-6-oxo-1,6-dihydropyridin-3-yl)-1-((tetrahydrofuran-3-yl)methyl)-1H-benzo[d]imidazol-5-yl)methyl)amino)-3-hydroxybutanoate (For a preparation see Example 232, 80 mg) was separated by chiral HPLC. The HPLC purification was carried out on a Chiralpak AD-H column (Lot. No. ADH12143-01, 250×30 mm). The purification was run using 100% EtOH, with a flow rate of 25 mL/min. UV detection was at 215 nm. The first eluting enantiomer was collected, and the fractions evaporated under reduced pressure to give the title compound "DIASTEREOISOMER 1", Example 232a (21 mg). The second eluting enantiomer was collected, and the fractions evaporated under reduced pressure, to give the title compound "DIASTEREOISOMER 2", Example 232b (20 mg). DIASTEREOMER 1: LCMS (System J): $t_{RET}$=0.92 min; MH$^+$ 511. DIASTEREOMER 2: LCMS (System J): $t_{RET}$=0.92 min; MH$^+$ 511.

Example 248a: (2S,3R)-isobutyl 2-(((2-(1,5-dimethyl-6-oxo-1,6-dihydropyridin-3-yl)-1-((tetrahydro-2H-pyran-2-yl)methyl)-1H-benzo[d]imidazol-5-yl)methyl)amino)-3-hydroxybutanoate (enantiomer 1) and Example 248b: (2S,3R)-isobutyl 2-(((2-(1,5-dimethyl-6-oxo-1,6-dihydropyridin-3-yl)-1-((tetrahydro-2H-pyran-2-yl)methyl)-1H-benzo[d]imidazol-5-yl)methyl)amino)-3-hydroxybutanoate (enantiomer 2)

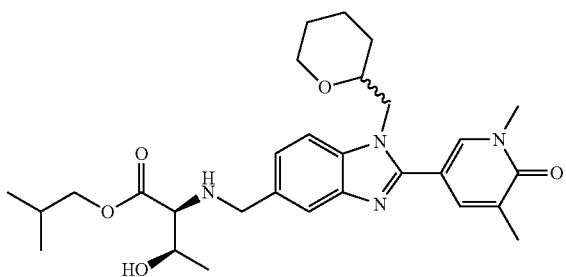 [SMILES: Cc1cc(-c2nc3cc(CN[C@H](C(=O)OCC(C)C)[C@@H](C)O)ccc3n2CC2CCCCO2)cn(C)c1=O]

The enantiomers were obtained by the chiral separation of Example 248.
Analytical Method: Approx 0.5 mg dissolved in 50% EtOH/Heptane (1 mL) 20 uL injected on column.
  40% EtOH/Heptane, f=1.0 mL/min, wavelength 215 nm, 4. Ref 550,100
  Column 4.6 mmid×25 cm Chiralcel OD-H
  Lot No. ODHOCE-PD027
Prep Method: Approx 110 mg dissolved in 1.5 mL of EtOH.
  Injection; 1.5 mL the solution was injected onto the column.
  40% EtOH/Heptane, f=30 mL/min, wavelength 215 nm, 4. Ref 550,100
  Column 30 mm×25 cm Chiralcel OD-H
  Lot No. ODH11158-01
Enantiomer 1 Rt=5.0 min.>99% ee by UV.
Enantiomer 2 Rt=12.0 min.>99% ee by UV.

Example 266a: (2S,3R)-isopropyl 2-(((2-(1,5-dimethyl-6-oxo-1,6-dihydropyridin-3-yl)-1-((tetrahydro-2H-pyran-2-yl)methyl)-1H-benzo[d]imidazol-5-yl)methyl)amino)-3-hydroxybutanoate (enantiomer 1) and Example 266b: (2S,3R)-isopropyl 2-(((2-(1,5-dimethyl-6-oxo-1,6-dihydropyridin-3-yl)-1-((tetrahydro-2H-pyran-2-yl)methyl)-1H-benzo[d]imidazol-5-yl)methyl)amino)-3-hydroxybutanoate (enantiomer 2)

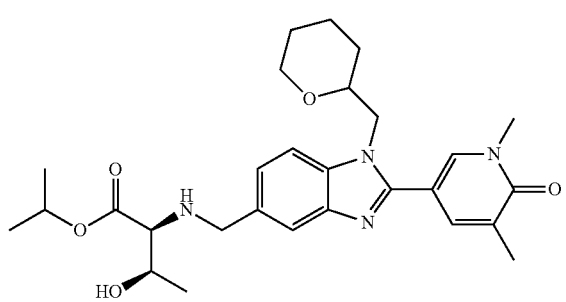 [SMILES: Cc1cc(-c2nc3cc(CN[C@H](C(=O)OC(C)C)[C@@H](C)O)ccc3n2CC2CCCCO2)cn(C)c1=O]

The enantiomers were obtained by the chiral separation of Example 266.
Quantity: Approx 70 mg.
Analytical Method: Approx 0.5 mg dissolved in 50% EtOH/Heptane (1 mL) 20 ul injected on column.
  30% EtOH/Heptane, f=1.0 mL/min, wavelength 215 nm, 4. Ref 550,100
  Column 4.6 mmid×25 cm Chiralcel OD-H
  Lot No. ODHOCE-PD027
Prep Method: Approx 70 mg dissolved in 1 mL EtOH.
  Injection; 1 mL of the solution was injected onto the column.
  30% EtOH/Heptane, f=30 mL/min, wavelength, 215 nm, 4. Ref 550,100
  Column 30 mm×25 cm Chiralcel OD-H
  Lot No ODH11158-01
Enantiomer 1 Rt=6.0 min.>99% ee by UV.
Enantiomer 2 Rt=11.5 min.>99% ee by UV.

Example 267a: (2S,3R)-isopropyl 3-hydroxy-2-(((2-(5-methyl-6-oxo-1,6-dihydropyridin-3-yl)-1-((tetrahydro-2H-pyran-2-yl)methyl)-1H-benzo[d]imidazol-5-yl)methyl)amino)butanoate (enantiomer 1) and Example 267b: (2S,3R)-isopropyl 3-hydroxy-2-(((2-(5-methyl-6-oxo-1,6-dihydropyridin-3-yl)-1-((tetrahydro-2H-pyran-2-yl)methyl)-1H-benzo[d]imidazol-5-yl)methyl)amino)butanoate (enantiomer 2)

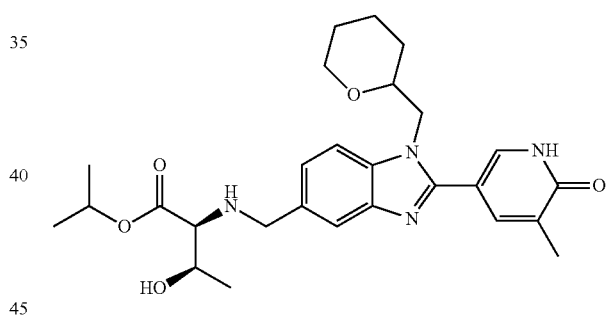

The enantiomers were obtained by the chiral separation of Example 267
Quantity: Approx 120 mg.
Analytical Method: Approx 0.5 mg dissolved in 50% EtOH/Heptane (1 mL) 20 ul injected on column.
  20% EtOH/Heptane, f=1.0 mL/min, wavelength 215 nm, 4. Ref 550,100
  Column 4.6 mmid×25 cm Chiralcel OD-H
  Lot No. ODHOCE-PD027
Prep Method: Approx 120 mg dissolved in 1 mL EtOH.
  Injection; 1 mL of the solution was injected onto the column.
  20% EtOH/Heptane, f=30 mL/min, wavelength 215 nm, 4. Ref 550,100
  Column 30 mm×25 cm Chiralcel OD-H
  Lot No ODH11158-01
Enantiomer 1 Rt=8.5 min.>99% ee by UV.
Enantiomer 2 Rt=12.2 min.>99% ee by UV.

Example 270a: (2S,3R)-isopropyl 2-(((2-(1,5-dimethyl-6-oxo-1,6-dihydropyridin-3-yl)-1-(2-methoxypropyl)-1H-benzo[d]imidazol-5-yl)methyl)amino)-3-hydroxybutanoate (enantiomer 1) and Example 270b: (2S,3R)-isopropyl 2-(((2-(1,5-dimethyl-6-oxo-1,6-dihydropyridin-3-yl)-1-(2-methoxypropyl)-1H-benzo[d]imidazol-5-yl)methyl)amino)-3-hydroxybutanoate (enantiomer 2)

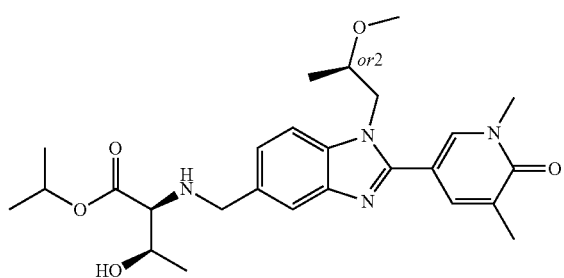 [SMILES: CO[C@H](C)Cn1c(-c2cc(C)c(=O)n(C)c2)nc2cc(CN[C@H](C(=O)OC(C)C)[C@@H](C)O)ccc21]

The enantiomers were obtained by the chiral separation of Example 270.
Quantity: Approx 150 mg.
Analytical Method: Approx 0.5 mg dissolved in 50% EtOH/Heptane (1 mL) 20 ul injected on column.
  30% EtOH/Heptane, f=1.0 mL/min, wavelength 215 nm, 4. Ref 550,100
  Column 4.6 mmid×25 cm Chiralcel OD-H
  Lot No. ODHOCE-PD027 Prep Method: Approx 150 mg dissolved in 2 mL EtOH.
Injection; 1 mL of the solution was injected onto the column.
  30% EtOH/Heptane, f=30 mL/min, wavelength, 215 nm, 4. Ref 550,100
  Column 30 mm×25 cm Chiralcel OD-H
  Lot No ODH11158-01
Enantiomer 1 Rt=6.0 min.>99% ee by UV.
Enantiomer 2 Rt=11.5 min.>99% ee by UV.

Example 271a: (2S,3R)-neopentyl 2-(((2-(1,5-dimethyl-6-oxo-1,6-dihydropyridin-3-yl)-1-(2-methoxypropyl)-1H-benzo[d]imidazol-5-yl)methyl)amino)-3-hydroxybutanoate (Single diastereomer of unknown configuration at marked centre, Isomer 1) and Example 271b: (2S,3R)-neopentyl 2-(((2-(1,5-dimethyl-6-oxo-1,6-dihydropyridin-3-yl)-1-(2-methoxypropyl)-1H-benzo[d]imidazol-5-yl)methyl)amino)-3-hydroxybutanoate (Single Diastereomer of Unknown Configuration at Marked Centre, Isomer 2)

Example 271a: Isomer 1

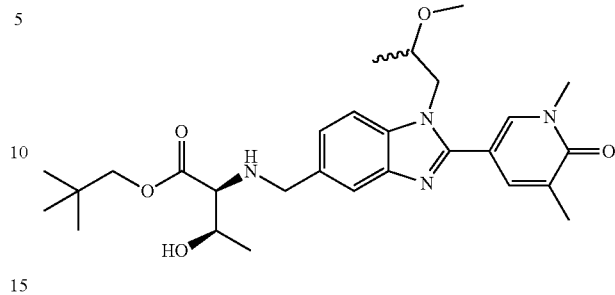

Example 271b: Isomer 2

A sample of (rac)-(2S,3R)-neopentyl 2-(((2-(1,5-dimethyl-6-oxo-1,6-dihydropyridin-3-yl)-1-(2-methoxypropyl)-1H-benzo[d]imidazol-5-yl)methyl)amino)-3-hydroxybutanoate (for a preparation see Example 271, 280 mg) was separated by chiral column chromatography using a 30 mm×25 cm Chiralcel OD-H column, eluting with 50% EtOH/Heptane at a flowrate of 30 mL/min. The appropriate fractions for each isomer were combined and evaporated under reduced pressure to give the title compounds

Example 271a: Isomer 1 (140 mg)

LCMS (System I): $t_{RET}$=0.66 min; MH$^+$ 513
Chiral analysis carried out on a 4.6 mmid×25 cm Chiralcel OD-H column, eluting with 50% EtOH/Heptane at a flowrate of 1 mL/min, chiral purity>99.5%

Example 271b: Isomer 2 (140 mg)

LCMS (System I): $t_{RET}$=0.65 min; MH$^+$ 513
Chiral analysis carried out on a 4.6 mmid×25 cm Chiralcel OD-H column, eluting with 50% EtOH/Heptane at a flowrate of 1 mL/min, chiral purity>99.5%

Example 272a: (2S,3R)-tert-butyl 2-(((2-(1,5-dimethyl-6-oxo-1,6-dihydropyridin-3-yl)-1-(2-methoxypropyl)-1H-benzo[d]imidazol-5-yl)methyl)amino)-3-hydroxybutanoate (Single diastereomer of unknown configuration at marked centre, Isomer 1) and Example 272b: (2S,3R)-tert-butyl 2-(((2-(1,5-dimethyl-6-oxo-1,6-dihydropyridin-3-yl)-1-(2-methoxypropyl)-1H-benzo[d]imidazol-5-yl)methyl)amino)-3-hydroxybutanoate (Single Diastereomer of Unknown Configuration at Marked Centre, Isomer 2)

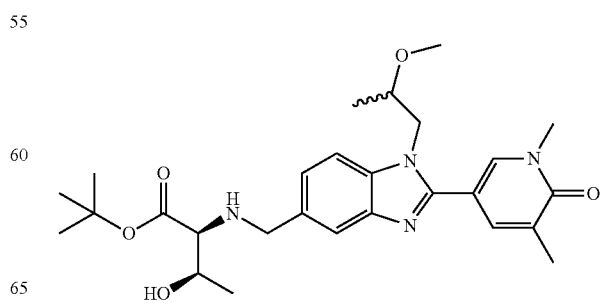

Example 272a: Isomer 1

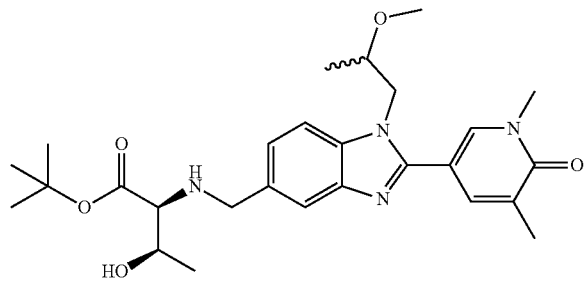 [SMILES: COC(C)Cn1c(-c2cc(C)c(=O)n(C)c2)nc2cc(CN[C@H](C(=O)OC(C)(C)C)[C@@H](C)O)ccc21]

Example 272b: Isomer 2

A sample of (rac)-(2S,3R)-tert-butyl 2-(((2-(1,5-dimethyl-6-oxo-1,6-dihydropyridin-3-yl)-1-(2-methoxypropyl)-1H-benzo[d]imidazol-5-yl)methyl)amino)-3-hydroxybutanoate (for a preparation see Example 272, 300 mg) was separated by chiral chromatography using a 30 mm×25 cm Chiralcel OD-H column, eluting with 30% EtOH/Heptane at a flow-rate of 30 mL/min. The appropriate fractions for each isomer were combined and evaporated under reduced pressure to give the title compounds Example 272a: Isomer 1 (120 mg)

LCMS (System I): $t_{RET}$=0.58 min; MH$^+$ 499
Chiral analysis carried out on a 4.6 mmid×25 cm Chiralcel OD-H column, eluting with 40% EtOH/Heptane at a flow-rate of 1 mL/min, chiral purity>99.5%

Example 272b: Isomer 2 (120 mg)

LCMS (System I): $t_{RET}$=0.57 min; MH$^+$ 499
Chiral analysis carried out on a 4.6 mmid×25 cm Chiralcel OD-H column, eluting with 40% EtOH/Heptane at a flow-rate of 1 mL/min, chiral purity>99.5%

Example 273a: (2S,3R)-cyclobutyl 2-(((2-(1,5-dimethyl-6-oxo-1,6-dihydropyridin-3-yl)-1-(2-methoxypropyl)-1H-benzo[d]imidazol-5-yl)methyl)amino)-3-hydroxybutanoate (Single diastereomer of unknown configuration at marked centre, Isomer 1) and
Example 273b: (2S,3R)-cyclobutyl 2-(((2-(1,5-dimethyl-6-oxo-1,6-dihydropyridin-3-yl)-1-(2-methoxypropyl)-1H-benzo[d]imidazol-5-yl)methyl)amino)-3-hydroxybutanoate (Single Diastereomer of Unknown Configuration at Marked Centre, Isomer 2)

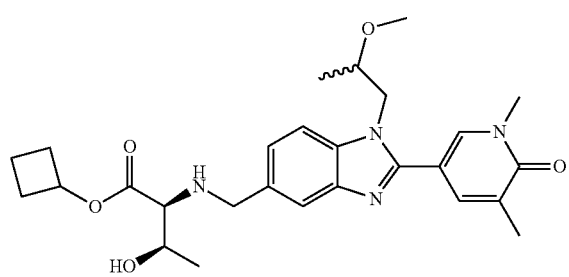 [SMILES: COC(C)Cn1c(-c2cc(C)c(=O)n(C)c2)nc2cc(CN[C@H](C(=O)OC3CCC3)[C@@H](C)O)ccc21]

Example 273a: Isomer 1

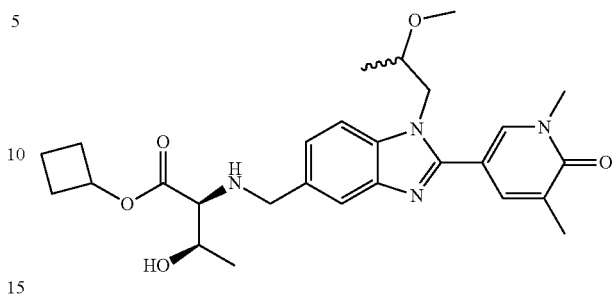

Example 273b: Isomer 2

A sample of (rac)-(2S,3R)-cyclobutyl 2-(((2-(1,5-dimethyl-6-oxo-1,6-dihydropyridin-3-yl)-1-(2-methoxypropyl)-1H-benzo[d]imidazol-5-yl)methyl)amino)-3-hydroxybutanoate (for a preparation see Example 273, 290 mg) was separated by chiral chromatography using a 30 mm×25 cm Chiralcel OD-H column, eluting with 40% EtOH/Heptane at a flow-rate of 30 mL/min. The appropriate fractions for each isomer were combined and evaporated under reduced pressure to give the title compounds Example 273a: Isomer 1 (120 mg)

LCMS (System I): $t_{RET}$=0.56 min; MH$^+$ 497
Chiral analysis carried out on a 4.6 mmid×25 cm Chiralcel OD-H column, eluting with 40% EtOH/Heptane at a flow-rate of 1 mL/min, chiral purity>99.5%

Example 273b: Isomer 2 (120 mg)

LCMS (System I): $t_{RET}$=0.57 min; MH$^+$ 497
Chiral analysis carried out on a 4.6 mmid×25 cm Chiralcel OD-H column, eluting with 40% EtOH/Heptane at a flow-rate of 1 mL/min, chiral purity>99.5%

Example 277: (S)-cyclopentyl 2-((2-((2-(1,5-dimethyl-6-oxo-1,6-dihydropyridin-3-yl)-1-((tetrahydro-2H-pyran-4-yl)methyl)-1H-benzo[d]imidazol-6-yl)oxy)ethyl)amino)-3-methoxypropanoate hydrochloride

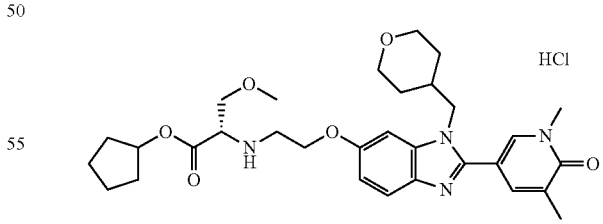

A mixture of 2-((2-(1,5-dimethyl-6-oxo-1,6-dihydropyridin-3-yl)-1-((tetrahydro-2H-pyran-4-yl)methyl)-H-benzo[d]imidazol-6-yl)oxy)acetaldehyde (intermediate 239, 116 mg, 0.229 mmol), (S)-cyclopentyl 2-amino-3-methoxypropanoate hydrochloride (intermediate 196, 131 mg, 0.587 mmol) and triethylamine (89 mg, 123 µL, 0.88 mmol) in dichloromethane (5 mL) was stirred at room temperature for 30 minutes. Sodium triacetoxyborohydride (187 mg, 0.88 mmol) was added and the reaction mixture stirred at room temperature for 18 hours. Saturated NaHCO$_3$ solution (15 mL) was added and the mixture stirred for 15 minutes. The organic phase was separated and the aqueous phase was extracted with dichloromethane (2×10 mL). The combined organics were washed with brine, dried and evaporated. The residue was purified by MDAP (method B). The product was dissolved in ethyl acetate (5 mL) and treated with 1.0M hydrogen chloride in diethyl ether (1.0 mL). The solvent was removed to give the title compound (53 mg, 0.088 mmol, 30.0% yield), as a colourless solid. LCMS (System B): $t_{RET}$=0.97 min; MH$^+$ 567.

The following Examples were prepared in a similar manner to Example 277:

Example 278: S)-cyclopentyl 2-((2-((2-(1,5-dimethyl-6-oxo-1,6-dihydropyridin-3-yl)-1-((tetrahydro-2H-pyran-4-yl)methyl)-1H-benzo[d]imidazol-6-yl)oxy)ethyl)-amino)propanoate hydrochloride (prepared from: Intermediate 239 and Intermediate 61) System B, 0.98 min, MH$^+$ = 537, Yield: 67 mg 40%

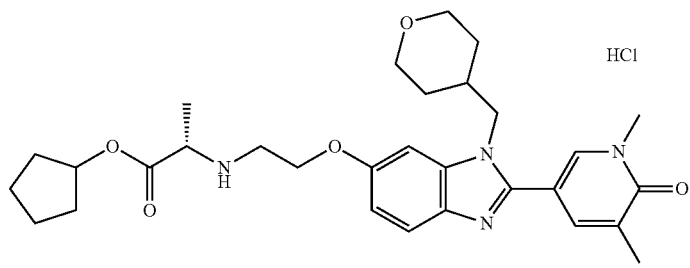 [SMILES: Cc1cc(-c2nc3ccc(OCCN[C@@H](C)C(=O)OC4CCCC4)cc3n2CC2CCOCC2)cn(C)c1=O ; Cl]

Example 279: (S)-(S)-tetrahydrofuran-3-yl 2-((2-((2-((1,5-dimethyl-6-oxo-1,6-dihydropyridin-3-yl)-1-((tetrahydro-2H-pyran-4-yl)methyl)-1H-benzo[d]imidazol-6-yl)oxy)ethyl)amino)-3-methylbutanoate hydrochloride (prepared from: Intermediate 239 and Intermediate 49) System B, 0.91 min, MH$^+$ = 567, Yield: 46 mg 26%

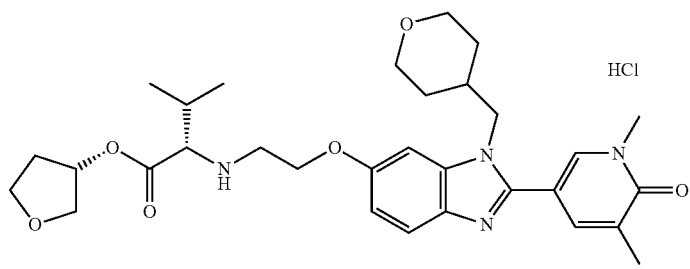

Example 280: (S)-(S)-1-methoxypropan-2-yl 2-((2-((2-(1,5-dimethyl-6-oxo-1,6-dihydropyridin-3-yl)-1-((tetrahydro-2H-pyran-4-yl)-methyl)-1H-benzo[d]-imidazol-6-yl)oxy)ethyl)amino)-3-methylbutanoate hydrochloride (prepared from: Intermediate 239 and Intermediate 63) System B, 1.01 min, MH$^+$ = 569, Yield: 58 mg 33%

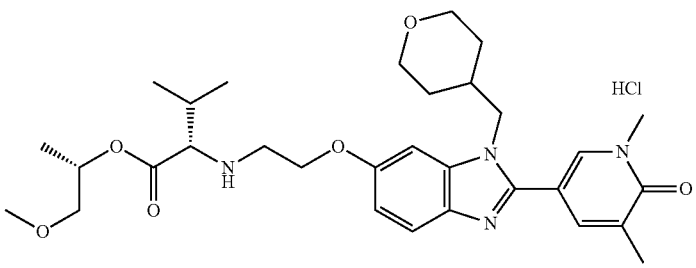 [SMILES: COC[C@H](C)OC(=O)[C@@H](NCCOc1ccc2nc(-c3cc(C)c(=O)n(C)c3)n(CC3CCOCC3)c2c1)C(C)C ; Cl]

Example 281a: (2S,3R)-isopropyl 3-hydroxy-2-(((2-(5-methyl-6-oxo-1,6-dihydropyridin-3-yl)-1-((tetrahydrofuran-3-yl)methyl)-1H-benzo[d]imidazol-5-yl)methyl)amino)butanoate, hydrochloride (enantiomer 1) (prepared from: Intermediate 255 and Intermediate 31) System J, 0.81 min, MH$^+$ = 483, Yield: 44 mg 36%

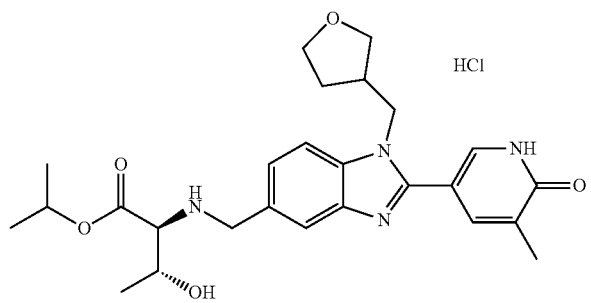 [SMILES: Cc1cc(-c2nc3cc(CN[C@H](C(=O)OC(C)C)[C@@H](C)O)ccc3n2CC2CCOC2)c[nH]c1=O ; Cl]

Example 281b: (2S,3R)-isopropyl 3-hydroxy-2-(((2-(5-methyl-6-oxo-1,6-dihydropyridin-3-yl)-1-((tetrahydrofuran-3-yl)methyl)-1H-benzo[d]imidazol-5-yl)methyl)amino)butanoate hydrochloride (Enantiomer 2) (prepared from: Intermediate 255 and Intermediate 31) System J, 0.81 min, MH$^+$ = 483, Yield: 53 mg 43%

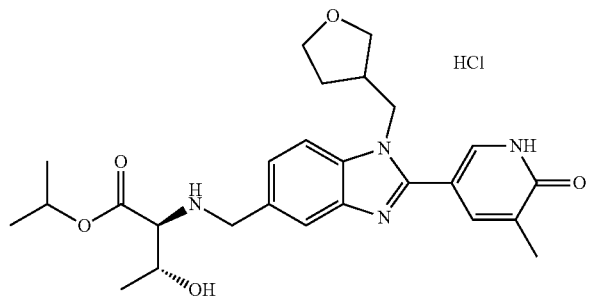 [SMILES: Cc1cc(-c2nc3cc(CN[C@H](C(=O)OC(C)C)[C@@H](C)O)ccc3n2CC2CCOC2)c[nH]c1=O ; Cl]

| | |
|---|---|
| Example 282a: (2S,3R)-isobutyl 3-hydroxy-2-(((2-(5-methyl-6-oxo-1,6-dihydropyridin-3-yl)-1-((tetrahydrofuran-3-yl)methyl)-1H-benzo[d]-imidazol-5-yl)methyl)amino)butanoate hydrochloride (enantiomer 1) (prepared from: Intermediate 251 and Intermediate 11) System J, 0.89 min, MH⁺ = 497, Yield; 42 mg 33% | 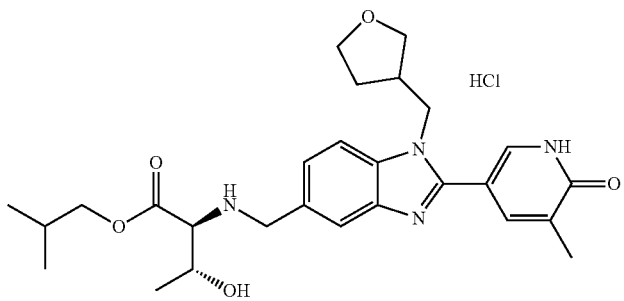 [SMILES: Cc1cc(-c2nc3cc(CN[C@H](C(=O)OCC(C)C)[C@@H](C)O)ccc3n2CC2CCOC2)c[nH]c1=O ; Cl] |
| Example 282b: (2S,3R)-isobutyl 3-hydroxy-2-(((2-(5-methyl-6-oxo-1,6-dihydropyridin-3-yl)-1-((tetrahydrofuran-3-yl)methyl)-1H-benzo[d]-imidazol-5-yl)methyl)amino)butanoate, Hydrochloride (Enantiomer 2) (prepared from: Intermediate 255 and Intermediate 11) System J, 0.89 min, MH⁺ = 497, Yield: 30 mg 24% | 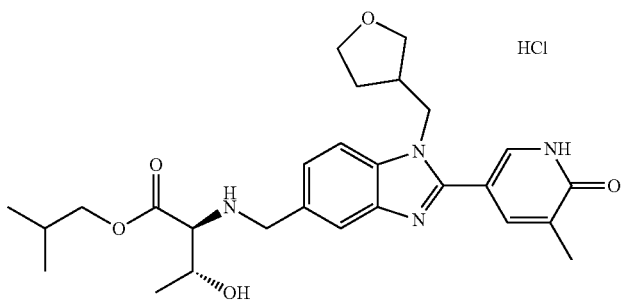 [SMILES: Cc1cc(-c2nc3cc(CN[C@H](C(=O)OCC(C)C)[C@@H](C)O)ccc3n2CC2CCOC2)c[nH]c1=O ; Cl] |
| Example 283a: (2S)-isobutyl 3-methoxy-2-(((2-(5-methyl-6-oxo-1,6-dihydropyridin-3-yl)-1-((tetrahydrofuran-3-yl)methyl)-1H-benzo[d]imidazol-5-yl)methyl)amino)propanoate hydrochloride (Enantiomer 1) (prepared from: Intermediate 251 and Intermediate 66) System J, 0.94 min, MH⁺ = 497, Yield: 72 mg 57% | 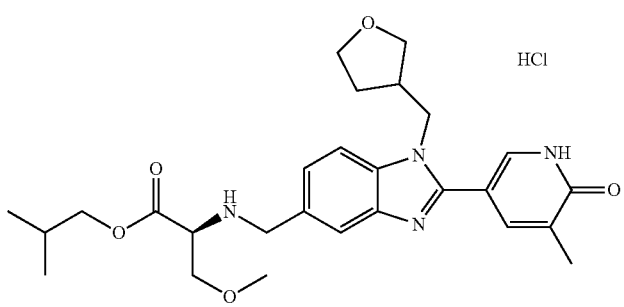 [SMILES: COC[C@H](NCc1ccc2c(c1)nc(-c1c[nH]c(=O)c(C)c1)n2CC1CCOC1)C(=O)OCC(C)C ; Cl] |
| Example 283b: (2S)-isobutyl 3-methoxy-2-(((2-(5-methyl-6-oxo-1,6-dihydropyridin-3-yl)-1-((tetrahydrofuran-3-yl)methyl)-1H-benzo[d]imidazol-5-yl)methyl)amino)propanoate hydrochloride (Enantiomer 2) (prepared from: Intermediate 255 and Intermediate 66) System J, 0.94 min, MH⁺ = 497, Yield: 48 mg 38% | 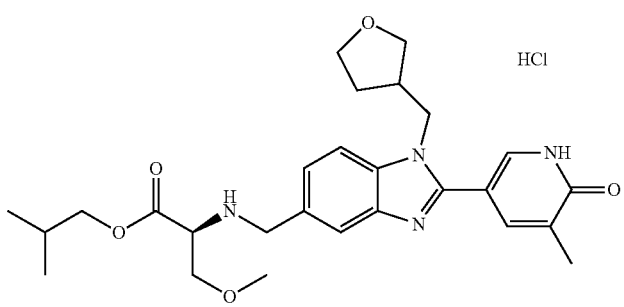 [SMILES: COC[C@H](NCc1ccc2c(c1)nc(-c1c[nH]c(=O)c(C)c1)n2CC1CCOC1)C(=O)OCC(C)C ; Cl] |
| Example 284: (S)-isopropyl 4-chloro-2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)butanoate, hydrochloride (prepared from: Intermediate 116 and Intermediate 69) System J, 1.06 min, MH⁺ = 529, (1 Cl) Yield: 280 mg 60% | 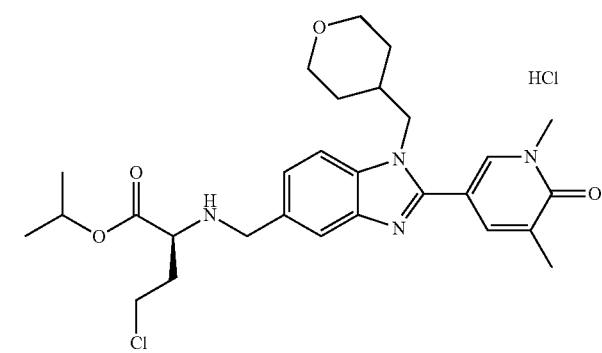 [SMILES: Cc1cc(-c2nc3cc(CN[C@@H](CCCl)C(=O)OC(C)C)ccc3n2CC2CCOCC2)cn(C)c1=O ; Cl] |

| | |
|---|---|
| Example 285: (2S)-tetrahydrofuran-3-yl 2-(((2-(1,5-dimethyl-6-oxo-1,6-dihydro-pyridin-3-yl)-1-methyl-1H-benzo[d]-imidazol-5-yl)methyl)amino)-3-methyl-butanoate hydrochloride (prepared from: Intermediate 273 and Intermediate 39) System B, 0.88 min, MH+ = 453, Yield: 50 mg, 29% | 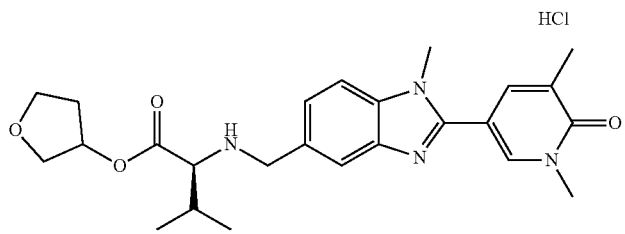 [SMILES: Cl ; Cc1cc(-c2nc3cc(CN[C@H](C(=O)OC4CCOC4)C(C)C)ccc3n2C)cn(C)c1=O] |
| Example 286: (S)-(S)-tetrahydrofuran-3-yl 4-methyl-2-(((2-(5-methyl-6-oxo-1,6-dihydropyridin-3-yl)-1-((tetrahydro-2H-pyran-4-yl)methyl)-1H-benzo[d]-imidazol-5-yl)methyl)amino)pentanoate (prepared from: Intermediate 115 and Intermediate 30) System B, 0.91 min, MH+ = 537, Yield: 40 mg, 44% | 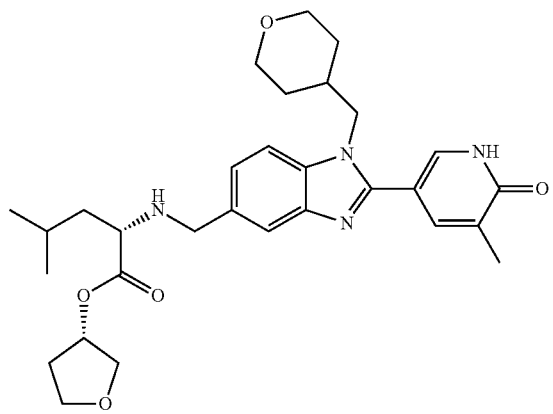 [SMILES: Cc1cc(-c2nc3cc(CN[C@@H](CC(C)C)C(=O)O[C@H]4CCOC4)ccc3n2CC2CCOCC2)c[nH]c1=O] |
| Example 287: (2S,3R)-isobutyl 2-(((2-(1,5-dimethyl-6-oxo-1,6-dihydropyridin-3-yl)-1-((tetrahydro-2H-pyran-4-yl)-methyl)-1H-benzo[d]imidazol-5-yl)-methyl)amino)-3-hydroxybutanoate (prepared from: Intermediate 116 and Intermediate 11) System C, 0.60 min, MH+ = 525, Yield: 80 mg, 40% | 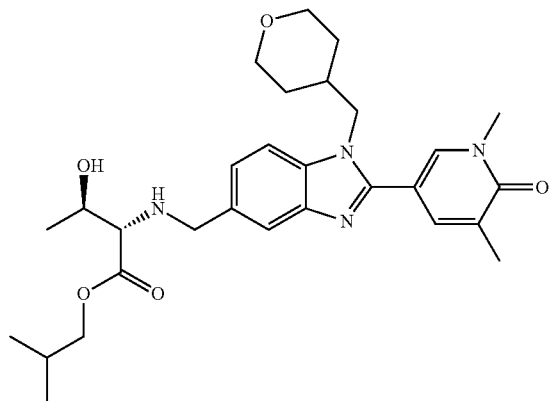 [SMILES: Cc1cc(-c2nc3cc(CN[C@H](C(=O)OCC(C)C)[C@@H](C)O)ccc3n2CC2CCOCC2)cn(C)c1=O] |

Example 288: (2S,3R)-isobutyl 2-((2-((2-(1,5-dimethyl-6-oxo-1,6-dihydropyridin-3-yl)-1-((tetrahydro-2H-pyran-4-yl)methyl)-1H-benzo[d]imidazol-6-yl)oxyethyl)amino)-3-hydroxybutanoate, hydrochloride Example 290: (2S,3R)-isopropyl 2-((2-(2-(1,5-dimethyl-6-oxo-1,6-dihydropyridin-3-yl)-1-((tetrahydro-2H-pyran-4-yl)methyl)-1H-benzo[d]imidazol-5-yl)ethyl)amino)-3-hydroxybutanoate

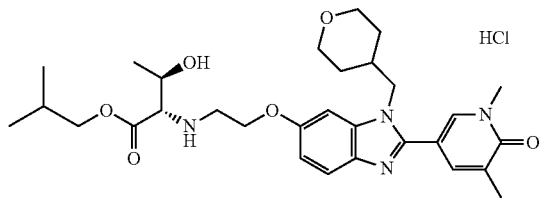 [SMILES: Cc1cc(-c2nc3ccc(OCCN[C@H](C(=O)OCC(C)C)[C@@H](C)O)cc3n2CC2CCOCC2)cn(C)c1=O ; Cl]

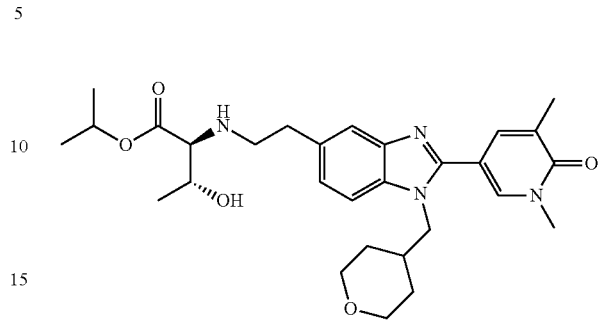

Stage i)
A mixture of 2-((2-(1,5-dimethyl-6-oxo-1,6-dihydropyridin-3-yl)-1-((tetrahydro-2H-pyran-4-yl)methyl)-1H-benzo[d]imidazol-6-yl)oxy)acetaldehyde (Intermediate 239) (116 mg, 0.293 mmol), (2S,3R)-isobutyl 2-amino-3-hydroxybutanoate 4-methylbenzenesulphonic acid salt (Intermediate 11) (204 mg, 0.587 mmol) and triethylamine (89 mg, 123 µL, 0.88 mmol) in dichloromethane (5 mL) was stirred at room temperature for 30 minutes. Sodium triacetoxyborohydride (187 mg, 0.88 mmol) was added and the reaction mixture stirred at room temperature for 18 hours. Saturated NaHCO₃ solution (15 mL) was added and the mixture stirred for 15 minutes. The organic phase was separated and the aqueous phase was extracted with dichloromethane (2×10 mL). The combined organics were washed with brine, dried and evaporated to give stage i) product. LCMS Mass ion [M-2] with respect to expected observed. Suggests enamine has formed.
Stage ii)
The stage i) product was dissolved in isopropanol (10 mL). The solution was treated with ammonium formate (92 mg, 1.47 mmol) and 10% palladium on carbon, 50% water paste (23 mg, 20% wt). The reaction mixture was refluxed for 4 hours. The cooled reaction mixture was filtered through 'celite'. The solvent was evaporated from the filtrate and the residue purified by high pH MDAP (Method B). Not pure enough, repurified by formic acid MDAP (Method A). The product was dissolved in ethyl acetate (5 mL) and treated with 1.0M hydrogen chloride in diethyl ether (1 mL). The solvent was removed to give the title compound (2 mg, 3.38 µmol, 1.153% yield), as a colourless solid. LCMS (System B): $t_{RET}$=0.92 min; MH⁺ 555.
The following Example was prepared in a similar manner to Example 288:

1,3-dimethyl-5-(5-(oxiran-2-yl)-1-((tetrahydro-2H-pyran-4-yl)methyl)-1H-benzo[d]imidazol-2-yl)pyridin-2(1H)-one (for a preparation see Intermediate 266, 0.1 g, 0.264 mmol) was dissolved in THF (3 mL) under nitrogen. The solution was cooled down to 0° C. and BF₃.OEt₂ (0.017 mL, 0.132 mmol) was added. The mixture was stirred at 0° C. for 5 min, then (2S,3R)-isopropyl 2-amino-3-hydroxybutanoate hydrochloride (Intermediate 31a, 0.057 g, 0.290 mmol), triethylamine (0.110 mL, 0.791 mmol) and p-toluenesulfonic acid monohydrate (0.050 g, 0.264 mmol) were added. The reaction mixture was stirred under nitrogen at room temperature for 1 hr. Sodium triacetoxyborohydride (0.223 g, 1.054 mmol) was added. The reaction mixture was stirred under nitrogen for 2 hours. The reaction mixture was stirred 10 min with a saturated solution of sodium bicarbonate, it was then diluted with ethyl acetate. The layers were separated. The aqueous was extracted with ethyl acetate. The organics were combined and dried over a phase separator, and concentrated. The oil was purified by flash column chromatography eluted with 0-10% MeOH in DCM. The fractions were concentrated to dryness. The residue was purified by MDAP (method B). The solvent was evaporated in vacuo to give the title compound as a white solid (40% yield). LCMS (System J): $t_{RET}$=0.91 min; MH⁺ 525.
The following Example was prepared in a similar manner to Example 290:

Example 289: (2S,3R)-isopropyl 2-((2-((2-(1,5-dimethyl-6-oxo-1,6-dihydropyridin-3-yl)-1-((tetrahydro-2H-pyran-4-yl)methyl)-1H-benzo[d]imidazol-6-yl)oxy)ethyl)-amino)-3-hydroxybutanoate hydrochloride (prepared from: Intermediate 239 and Intermediate 31) System B, 0.84 min, MH⁺ = 541, Yield: 4 mg, 2.3%

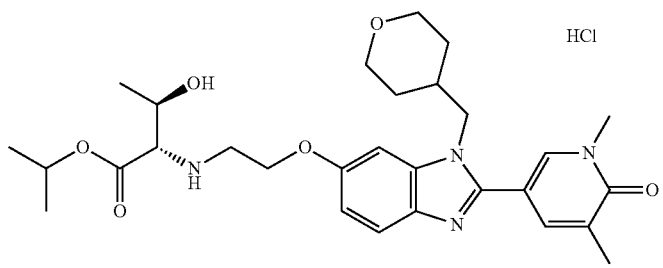 [SMILES: Cc1cc(-c2nc3ccc(OCCN[C@H](C(=O)OC(C)C)[C@@H](C)O)cc3n2CC2CCOCC2)cn(C)c1=O ; Cl]

Example 291: (2S,3R)-tert-butyl 2-((2-(2-(1,5-dimethyl-6-oxo-1,6-dihydro-pyridin-3-yl)-1-((tetrahydro-2H-pyran-4-yl)methyl)-1H-benzo[d]imidazol-5-yl)ethyl)amino)-3-hydroxybutanoate (prepared from: Intermediate 266 and (2S,3R)-tert-butyl 2-amino-3-hydroxy-butanoate hydrochloride (commercially available)) System J, 0.96 min, MH⁺ = 539, Yield: 23 mg, 11%

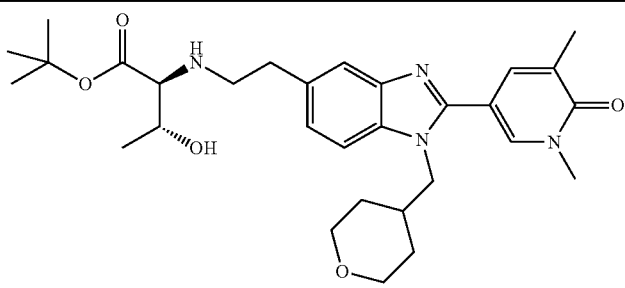

Example 292: (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate hydrochloride

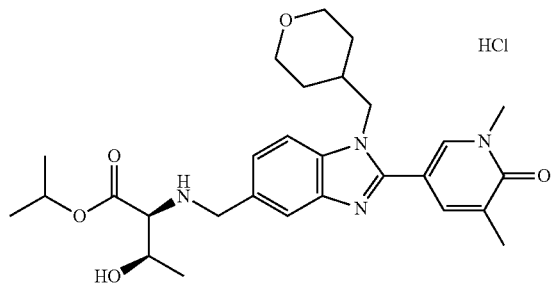 [SMILES: Cc1cc(-c2nc3cc(CN[C@H](C(=O)OC(C)C)[C@@H](C)O)ccc3n2CC2CCOCC2)cn(C)c1=O ; Cl]

(2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate (Example 303, 400 mg, 0.788 mmol) was dissolved in ethyl acetate (3 mL) and treated with 1.0M hydrogen chloride in diethyl ether (1 mL). Diethyl ether (20 mL) was added, the solid was filtered off, washed with diethyl ether and dried to give the title compound (409 mg, 0.748 mmol), as a colourless solid. LCMS (System I): $t_{RET}$=0.51 min; MH⁺ 511. ¹H NMR (400 MHz, DMSO-d6) • ppm 9.78 (br s, 2H), 8.44 (s, 1H), 8.02-8.10 (m, 1H), 7.83 (s, 1H), 7.67 (d, J=12.0 Hz, 1H), 4.88-4.97 (m, 1H), 4.38-4.49 (m, 4H), 4.08-4.14 (m, 1H), 3.70-3.77 (m, 2H), 3.61-3.67 (m, 1H), 3.58 (s, 3H), 3.07-3.16 (m, 2H), 2.13 (s, 3H), 1.93-2.06 (m, 1H), 1.15-1.32 (m, 13H).

Example 293: (2S,3R)₂-(((2-(1,5-dimethyl-6-oxo-1,6-dihydropyridin-3-yl)-1-((tetrahydro-2H-pyran-2-yl)methyl)-1H-benzo[d]imidazol-5-yl)methyl)amino)-3-hydroxybutanoic acid, Hydrochloride

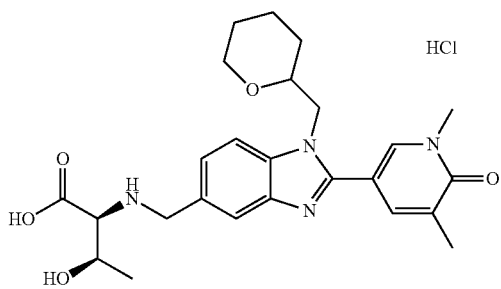 [SMILES: Cc1cc(-c2nc3cc(CN[C@H](C(=O)O)[C@@H](C)O)ccc3n2CC2CCCCO2)cn(C)c1=O ; Cl]

(2S,3R)-2-(((2-(1,5-dimethyl-6-oxo-1,6-dihydropyridin-3-yl)-1-((tetrahydro-2H-pyran-2-yl)methyl)-1H-benzo[d]imidazol-5-yl)methyl)amino)-3-hydroxybutanoic acid (Example 82, 8 mg, 0.017 mmol) was triturated with 1M hydrogen chloride in diethyl ether (17 mL, 0.017 mmol) and stirred under nitrogen for 5 hours. Solvents were then removed in vacuo, the white solid obtained was dried in a vacuum oven at 40° C. for 24 hours to give the title compound (5.6 mg, 0.011 mmol, 64.9% yield) and appeared as a white solid. LCMS (System I): $t_{RET}$=0.51 min; MH⁺ 469.

Example 294: (2S,3R)-cyclobutyl 2-(((1-(((S)-1-acetylpiperidin-3-yl)methyl)-2-(1,5-dimethyl-6-oxo-1,6-dihydropyridin-3-yl)-1H-benzo[d]imidazol-5-yl)methyl)amino)-3-hydroxybutanoate hydrochloride

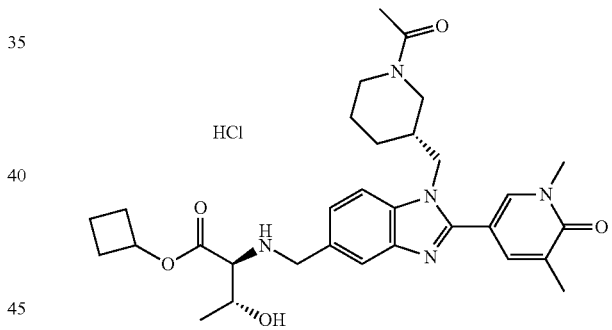

(2S,3R)-cyclobutyl 2-amino-3-hydroxybutanoate, 4-Methylbenzenesulphonic acid salt (for a preparation see intermediate 32, 170 mg, 0.492 mmol) was added to a solution of (S)-1-((1-acetylpiperidin-3-yl)methyl)-2-(1,5-dimethyl-6-oxo-1,6-dihydropyridin-3-yl)-1H-benzo[ ]imidazole-5-carbaldehyde (Intermediate 135) (100 mg, 0.246 mmol) in DCM (5 mL) and the resulting solution stirred overnight under N₂. Sodium triacetoxyborohydride (156 mg, 0.738 mmol) was added and the resulting suspensions stirred for 3 h. The reaction mixture was solubilised with MeOH and loaded on to a 10 g SCX cartridge. The cartridge was eluted with MeOH, followed by 2M methanolic ammonia. The basic fractions were evaporated in vacuo to dryness and the residues purified by MDAP (HPH method B). The product containing fractions were evaporated in vacuo azeotroping with EtOH to give a colourless oil. The residues were dissolved in DCM (1 mL) and 1 M HCl in diethyl ether added with stirring. The resulting suspension was evaporated in vacuo to give the title compound as a white solid. The total yield of the reaction was 53%.

LCMS (System C): $t_{RET}$=0.52 min, MH⁺=564

The following Examples were prepared in a similar manner to Example 294:

Example 295: (2S,3R)-tert-butyl 2-(((1-(((S)-1-acetylpiperidin-3-yl)-methyl)-2-(1,5-dimethyl-6-oxo-1,6-dihydropyridin-3-yl)-1H-benzo[d]-imidazol-5-yl)methyl)amino)-3-hydroxybutanoate, Hydrochloride (prepared from: Intermediate 135 and (2S,3R)-tert-butyl 2-amino-3-hydroxybutanoate hydrochloride (commercially available)) System C, 0.54 min, MH$^+$ = 566, Yield: 69 mg, 42%

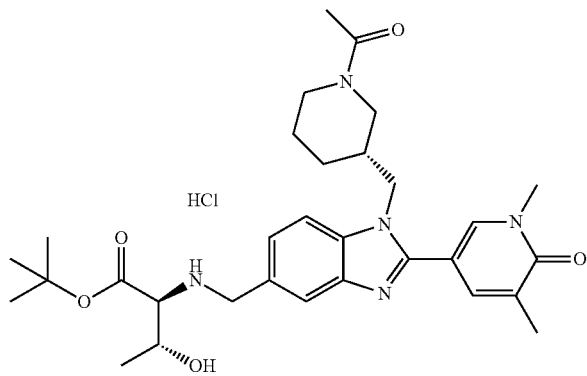 [SMILES: CC(=O)N1CCC[C@@H](Cn2c(-c3cc(C)c(=O)n(C)c3)nc3cc(CN[C@H](C(=O)OC(C)(C)C)[C@@H](C)O)ccc32)C1 ; Cl]

Example 296: (2S,3R)-isopropyl 2-(((1-(((S)-1-acetylpiperidin-3-yl)-methyl)-2-(1,5-dimethyl-6-oxo-1,6-dihydropyridin-3-yl)-1H-benzo[d]imidazol-5-yl)methyl)-amino)-3-hydroxybutanoate, Hydrochloride (prepared from: Intermediate 135 and Intermediate 31) System C, 0.50, MH$^+$ = 552, Yield: 20 mg, 13%

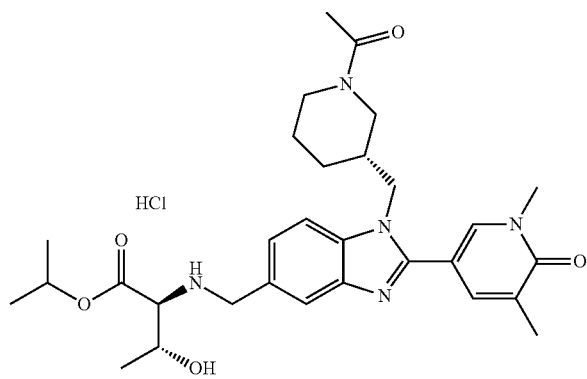 [SMILES: CC(=O)N1CCC[C@@H](Cn2c(-c3cc(C)c(=O)n(C)c3)nc3cc(CN[C@H](C(=O)OC(C)C)[C@@H](C)O)ccc32)C1 ; Cl]

Example 297: (2S,3R)-isopropyl 2-(((1-(((R)-1-acetylpiperidin-3-yl)-methyl)-2-(1,5-dimethyl-6-oxo-1,6-dihydropyridin-3-yl)-1H-benzo-[c]imidazol-5-yl)methyl)amino)-3-hydroxybutanoate, Hydrochloride (prepared from: Intermediate 136 and Intermediate 31) System I, 0.51 min, MH$^+$ = 552, Yield: 78 mg, 48%

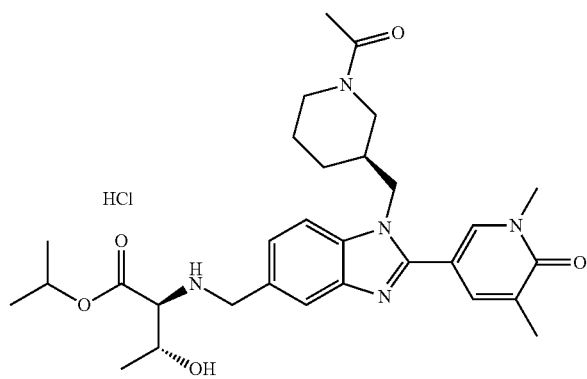 [SMILES: CC(=O)N1CCC[C@H](Cn2c(-c3cc(C)c(=O)n(C)c3)nc3cc(CN[C@H](C(=O)OC(C)C)[C@@H](C)O)ccc32)C1 ; Cl]

Example 298: (2S,3R)-cyclobutyl 2-(((1-(((R)-1-acetylpiperidin-3-yl)-methyl)-2-(1,5-dimethyl-6-oxo-1,6-dihydropyridin-3-yl)-1H-benzo[d]imidazol-5-yl)methyl)-amino)-3-hydroxybutanoate, Hydrochloride (prepared from: Intermediate 136 and Intermediate 32) System I, 0.54 min, MH$^+$ = 564, Yield: 34 mg, 22%

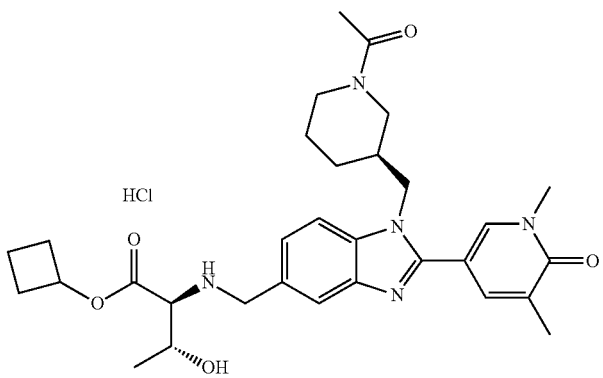 [SMILES: CC(=O)N1CCC[C@H](Cn2c(-c3cc(C)c(=O)n(C)c3)nc3cc(CN[C@H](C(=O)OC4CCC4)[C@@H](C)O)ccc32)C1 ; Cl]

| Example 299: (S)-isopropyl 2-(((1-(((S)-1-acetylpiperidin-3-yl)-methyl)-2-(1,5-dimethyl-6-oxo-1,6-dihydropyridin-3-yl)-1H-benzo[d]imidazol-5-yl)methyl)-amino)-3-methylbutanoate, Hydrochloride (prepared from: Intermediate 135 and Intermediate 12) System C, 0.56 min, MH⁺ = 550, Yield: 126 mg, 79% | 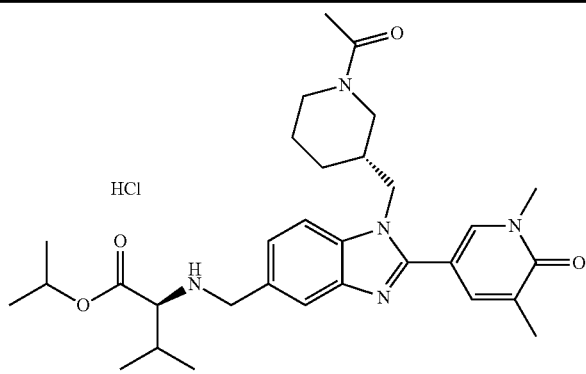 |
|---|---|

Example 300: (S)-cyclopentyl 2-(((2-(1,5-dimethyl-6-oxo-1,6-dihydropyridin-3-yl)-1-methyl-1H-benzo[d]imidazol-5-yl)methyl)amino)-3-methoxypropanoate, hydrochloride Example 301: (S)-cyclopentyl 2-(((2-(1,5-dimethyl-6-oxo-1,6-dihydropyridin-3-yl)-1-methyl-1H-benzo[d]imidazol-5-yl)methyl)amino)-3-hydroxy-3-methylbutanoate, hydrochloride

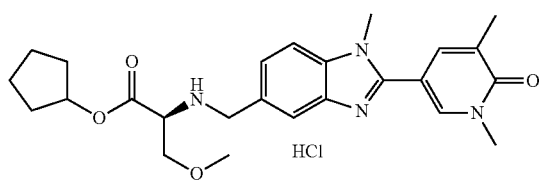 [SMILES: COC[C@H](NCc1ccc2c(c1)nc(-c1cc(C)c(=O)n(C)c1)n2C)C(=O)OC1CCCC1 ; Cl]

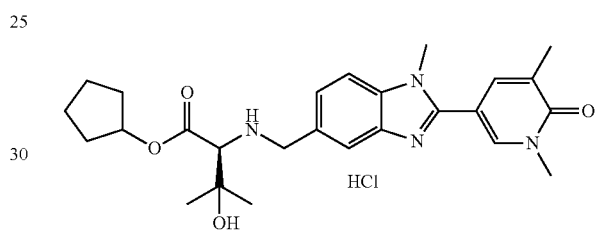

2-(1,5-dimethyl-6-oxo-1,6-dihydropyridin-3-yl)-1-methyl-H-benzo[d]imidazole-5-carbaldehyde (102 mg, 0.363 mmol, Intermediate 273) was dissolved in DCM (5 mL) and treated with (S)-cyclopentyl 2-amino-3-methoxypropanoate, hydrochloride (162 mg, 0.725 mmol, Intermediate 196) and triethylamine (0.151 mL, 1.088 mmol). To the stirred solution was added sodium triacetoxyborohydride (384 mg, 1.813 mmol). The mixture was then stirred for 18 hrs under nitrogen. Saturated sodium bicarbonate (15 mL) was then added to the mixture and stirred for 15 min. The layers were then separated, the aqueous layer extracted twice with dichloromethane (10 mL×2) and the organics combined and dried with a hydrophobic frit. The solvent was then removed under vacuum. The residue was dissolved in minimum amount of dichloromethane and loaded onto a 10 g silica cartridge and eluted using the following method: 0% ethyl acetate for 2 column volumes, 0-25% ethanol/ethyl acetate for 10 column volumes then 25% ethanol/ethyl acetate for 5 column volumes. The appropriate fractions were combined and the solvent removed in vacuo producing (S)-cyclopentyl 2-(((2-(1,5-dimethyl-6-oxo-1,6-dihydropyridin-3-yl)-1-methyl-1H-benzo[d]imidazol-5-yl)methyl)amino)-3-methoxypropanoate as a colourless oil. The sample was dissolved in a minimum amount of diethyl ether and then treated with a few drops of 1M hydrochloric acid in diethyl ether and the solvent and HCl removed under vacuum. This yielded the title compound (68 mg, 0.139 mmol, 38.4% yield) as a white solid. LCMS (System B): $t_{RET}$=0.94 min, MH⁺=453.

2-(1,5-dimethyl-6-oxo-1,6-dihydropyridin-3-yl)-1-methyl-1H-benzo[d]imidazole-5-carbaldehyde (100 mg, 0.355 mmol, Intermediate 273) was dissolved in DCM (5 mL) and treated with (S)-cyclopentyl 2-amino-3-hydroxy-3-methylbutanoate, hydrochloride (110 mg, 0.463 mmol, Intermediate 51) and triethylamine (0.148 mL, 1.066 mmol) and stirred for 2 hrs. Sodium triacetoxyborohydride (377 mg, 1.777 mmol) was then added and the reaction stirred overnight. After this time, another 3 equivalents of sodium triacetoxyborohydride (377 mg, 1.777 mmol) was added and the mixture stirred for 2 hrs. To the mixture was added sodium bicarbonate (25 mL) and the reaction stirred for 15 min. The phases were then separated and the aqueous layer extracted twice with dichloromethane (2×10 mL) and the organics combined and dried using a hydrophobic frit. The solvent was then removed under vacuum and the residue dissolved in minimum of dichloromethane. The solution was then loaded onto a Biotage SNAP 10 g cartridge and automated chromatography run using the following method: 0% ethyl acetate for 2 column volumes, 0-25% ethanol in ethyl acetate over 10 column volumes, 25% ethanol for 5 column volumes. The appropriate fractions were then combined and solvent removed under vacuum. The residue was then dissolved in a minimum of dichloromethane and then loaded onto a Biotage SNAP 10 g cartridge and automated chromatography run using the following method: 15% ethanol in ethyl acetate for 2 column volumes, 15-40% ethanol in ethyl acetate for 10 column volumes, 40% ethanol in ethyl acetate for 5 column volumes. The residue was then dissolved in dimethyl sulphoxide (0.4 mL) and dichloromethane (0.4 mL) and purified by high pH mass directed autopurification. The appropriate fractions were then combined and the solvent removed under vacuum. This yielded (S)-cyclopentyl 2-(((2-(1,5-dimethyl-6-oxo-1,6-dihydropyridin-3-yl)-1-methyl-1H-benzo[d]imidazol-5-yl)methyl)amino)-3-hydroxy-3-methylbutanoate (26.5 mg, 0.057 mmol, 15.98% yield) as a yellow oil. The oil was then dissolved in diethyl ether and a few drops of 1M HCl in diethyl ether added and the solvent removed under vacuum yielding the title compound (26.5 mg, 0.053 mmol, 14.82% yield) as a white solid. LCMS (System B): $t_{RET}$=0.95 min, MH$^+$=467.

Example 302: (S)-4-methyl-2-(((2-(5-methyl-6-oxo-1,6-dihydropyridin-3-yl)-1-(1-methylpiperidin-4-yl)-1H-benzo[d]imidazol-5-yl)methylamino)pentanoic acid, hydrochloride

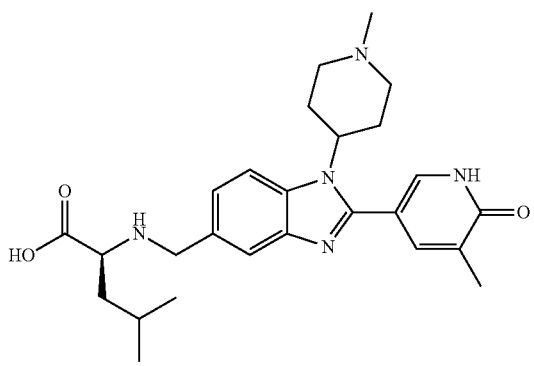 [SMILES: Cc1cc(-c2nc3cc(CN[C@@H](CC(C)C)C(=O)O)ccc3n2C2CCN(C)CC2)c[nH]c1=O]

To a solution of (S)-cyclopentyl 4-methyl-2-(((2-(5-methyl-6-oxo-1,6-dihydropyridin-3-yl)-1-(1-methylpiperidin-4-yl)-1H-benzo[d]imidazol-5-yl)methyl)amino)pentanoate (For a preparation see Example 2, 17 mg, 0.032 mmol) in Methanol (1 mL) and THF (1 mL) was added 1 M aqueous lithium hydroxide solution (0.032 mL, 0.032 mmol) and the reaction mixture stirred at room temperature overnight. Stirring was continued for three days at room temperature. The reaction mixture was heated at 50° C. for two days. Further 1 M aqueous lithium hydroxide solution (0.16 mL, 0.16 mmol) was added, and the reaction mixture heated at 50° C. overnight. The sample was evaporated under reduced pressure, and the residue dissolved in water (5 mL) and loaded onto an isolute 103 cartridge. The cartridge was washed with water, and then eluted with methanol. The methanol fractions were combined and blown down under a stream of nitrogen to give the title compound (13 mg). LCMS (System B): $t_{RET}$=0.57 min; MH$^+$ 466.

Example 303: (2S,3R)-Isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate

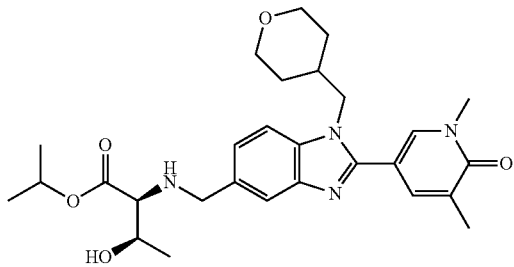 [SMILES: Cc1cc(-c2nc3cc(CN[C@H](C(=O)OC(C)C)[C@@H](C)O)ccc3n2CC2CCOCC2)cn(C)c1=O]

A mixture of 2-(1,5-dimethyl-6-oxo-1,6-dihydropyridin-3-yl)-1-((tetrahydro-2H-pyran-4-yl)methyl)-1H-benzo[d]imidazole-5-carbaldehyde (for an example preparation see Intermediate 116, 10.0 g, 27.4 mmol), (2S,3R)-isopropyl 2-amino-3-hydroxybutanoate hydrochloride (for an example preparation see Intermediate 31a, 10.82 g, 54.7 mmol) and triethylamine (6.92 g, 9.54 mL, 68.4 mmol) in DCM (100 mL) was stirred at room temperature overnight. Sodium triacetoxyborohydride (17.4 g, 82 mmol) was added and the reaction mixture was stirred at room temperature for 4 hours. The reaction mixture was diluted with DCM (100 mL) and poured onto saturated sodium bicarbonate (300 mL). The mixture was stirred at room temperature for 30 minutes, the organic phase was separated and the aqueous phase was extracted with DCM (2×100 mL). The combined organics were dried and evaporated. The residue was chromatographed using a gradient of 2.5-10% MeOH in DCM to give the title compound (11.57 g, 22.66 mmol, 83% yield), as a colourless foam. LCMS (System J): $t_{RET}$=0.87 min; MH$^+$ 511. $^1$H NMR (d$_6$-DMSO): δ 1.06-1.26 (m, 13H), 1.90-2.02 (m, 1H), 2.11 (s, 3H), 2.20-2.41 (m, 1H), 3.00 (d, J=4.9 Hz, 1H), 3.05-3.16 (m, 2H), 3.56 (s, 3H), 3.66 (d, J=1.32 Hz, 1H), 3.76-3.86 (m, 1H), 3.90 (d, J=13.2 Hz, 1H), 4.26 (d, J=7.3 Hz, 2H), 4.67 (d, J=5.4 Hz, 1H), 4.93 (sept, J=6.2 Hz, 1H), 7.22 (dd, J=8.3, 1.2 Hz, 1H), 7.53 (s, 1H), 7.61 (d, J=8.3 Hz, 1H), 7.73 (dd, J=2.3, 1.1 Hz, 1H), 8.12 (d, J=2.2 Hz, 1H).

Alternative Process for the Preparation of Example 303: (2S,3R)-Isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate

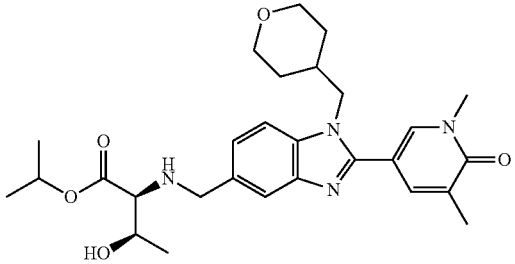 [SMILES: Cc1cc(-c2nc3cc(CN[C@H](C(=O)OC(C)C)[C@@H](C)O)ccc3n2CC2CCOCC2)cn(C)c1=O]

(3-Nitro-4-(((tetrahydro-2H-pyran-4-yl)methyl)amino)phenyl)methanol (4-fluoro-3-nitrophenyl)methanol (2.4 g, 14.02 mmol) and (tetra hydro-2H-pyran-4-yl)methanamine (2.423 g, 21.04 mmol) were suspended in water (30 ml) and potassium carbonate (2.52 g, 18.23 mmol) was added, then the mixture was stirred at 80° C. for 24 h, then allowed to cool while stirring. The resulting mixture was extracted with EtOAc (50 ml) and the organic layer washed with water (50 ml), dried and evaporated in vacuo to give the title compound (3.60 g, 13.52 mmol, 96% yield) as a dark yellow solid. LCMS (System D): $t_{RET}$=0.82 min; MH$^+$ 267. The title compound was used in the next step without purification.

(3-Amino-4-(((tetrahydro-2H-pyran-4-yl)methyl)amino)phenyl)methanol (3-Nitro-4-(((tetrahydro-2H-pyran-4-yl)methyl)amino)phenyl)methanol (48 g, 180 mmol) was dissolved in ethanol (400 ml) and hydrogenated over Pd/C 5% by weight (3 g, 28.2 mmol) at atmospheric pressure for 18 h, then the mixture was filtered through Celite under nitrogen, and the filtrate evaporated in vacuo to give the title compound (50 g, 212 mmol, 117% yield) as a dark brown oil. LCMS (System D): $t_{RET}$=0.62 min; MH$^+$ 237. Product was carried through to the next step without further purification.

5-(5-(Hydroxymethyl)-1-((tetrahydro-2H-pyran-4-yl)methyl)-1H-benzo[d]imidazol-2-yl)-1,3-dimethyl-pyridin-2-(1H)-one (3-Amino-4-(((tetrahydro-2H-pyran-4-yl)methyl)amino) phenyl)methanol (50 g, 190 mmol) was suspended in water (500 ml) and 1,5-dimethyl-6-oxo-1,6-dihydropyridine-3-carbaldehyde (31.7 g, 209 mmol) and cetylpyridinium bromide (14.64 g, 38.1 mmol) were added, then the mixture was stirred vigorously overnight. The mixture was extracted with DCM (3×300 ml) and the combined organics were washed with brine (500 ml), then dried and evaporated to give a dark brown solid. This was suspended in EtOAc (500 ml) and heated to reflux for 2 h, then cooled and the product collected by filtration. The crude was resuspended in EtOAc (500 ml) and heated to reflux again, then cooled in an ice bath and the product collected by filtration and washed with ether (300 ml) to give a brown solid (64 g). LCMS showed clean product, but the NMR spectrum shows the presence of 0.2 eq of the cetylpyridinium salt remaining in the product. Carried through to the next step without purification. The title compound was 90% Wt purity. LCMS (System D): $t_{RET}$=0.66 min; MH$^+$ 368.

(2S,3R)-isopropyl 2-amino-3-hydroxybutanoate, hydrochloride

AcCl (96 ml, 1343 mmol) was added dropwise to 2-propanol (500 ml, 6490 mmol) and the mixture was then stirred for 20 min before addition of (2S,3R)-2-amino-3-hydroxybutanoic acid (40 g, 336 mmol). The resulting suspension was heated to reflux overnight, then cooled and evaporated in vacuo to give a colourless oil. This was triturated with ether (300 ml) and the product collected by filtration to give (2S,3R)-isopropyl 2-amino-3-hydroxybutanoate as a colourless solid.
$^1$H NMR (400 MHz, DMSO-d$_6$) δ 8.49 (br. s., 3H), 5.66 (br. s., 1H), 4.99 (td, J=6.24, 12.47 Hz, 1H), 4.09 (br. s., 1H), 3.80 (d, J=4.16 Hz, 1H), 1.17-1.29 (m, 9H)

2-(1,5-dimethyl-6-oxo-1,6-dihydropyridin-3-yl)-1-((tetrahydro-2H-pyran-4-yl)methyl)-1H-benzo[d]imidazole-5-carbaldehyde 5-(5-(Hydroxymethyl)-1-((tetrahydro-2H-pyran-4-yl) methyl)-1H-benzo[d]imidazol-2-yl)-1,3-dimethylpyridin-2 (1H)-one (64 g, 122 mmol) was dissolved in DCM (600 ml) and manganese dioxide (42.4 g, 488 mmol) was added, then the mixture was heated at reflux for 18 h. LCMS showed complete conversion, and the mixture was filtered and the solid washed with DCM. The filtrate was evaporated in vacuo to give a brown gum, which was dissolved in DCM (100 ml) and loaded onto a 340 g silica column, then eluted with 0-50% EtOH/EtOAc and product-containing fractions were evaporated in vacuo to give a brown solid. This was triturated with ether (200 ml) and the solid collected by filtration, then suspended in EtOAc (300 ml) and heated to reflux for 1 h, then cooled in an ice bath and the product collected by filtration to give 2-(1,5-dimethyl-6-oxo-1,6-dihydropyridin-3-yl)-1-((tetrahydro-2H-pyran-4-yl)methyl)-1H-benzo[d]imidazole-5-carbaldehyde (42.5 g, 116 mmol, 95% yield) as a sand-coloured solid. LCMS (System D): $t_{RET}$=0.74 min; MH$^+$ 366. The filtrate was evaporated in vacuo and the residue triturated in EtOAc (50 ml) at reflux for 30 min, then cooled and filtered to give an additional portion of the product (3 g) as a beige solid, NMR consistent with the desired aldehyde. The title compound was 80% Wt purity.

(2S,3R)-isopropyl 2-(((2-(1,5-dimethyl-6-oxo-1,6-dihydropyridin-3-yl)-1-((tetrahydro-2H-pyran-4-yl) methyl)-1H-benzo[d]imidazol-5-yl)methyl)amino)-3-hydroxybutanoate 2-(1,5-dimethyl-6-oxo-1,6-dihydropyridin-3-yl)-1-((tetrahydro-2H-pyran-4-yl)methyl)-1H-benzo[d]imidazole-5-carbaldehyde (42 g, 115 mmol) and (2S,3R)-isopropyl 2-amino-3-hydroxybutanoate hydrochloride (34.1 g, 172 mmol) were dissolved in DCM (500 ml), then Et$_3$N (48.1 ml, 345 mmol) was added, followed by sodium triacetoxyborohydride (73.1 g, 345 mmol) and the mixture was stirred at room temperature for 24 h. The mixture was added to 1.5 liters of saturated sodium bicarbonate solution in a 5 liter conical flask and stirred vigorously for 1 h, then the organic layer was separated, the aqueous extracted with DCM (500 ml) and the combined organics washed with water (500 ml) and brine (500 ml), dried over sodium sulphate and evaporated in vacuo to give a brown foam. The crude product was dissolved in DCM (200 ml) and loaded onto a 750 g silica column, then eluted with 0-30% EtOH/EtOAc and clean product-containing fractions were evaporated in vacuo to give (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate (51 g, 100 mmol, 87% yield) as a beige foam. LCMS (System D): $t_{RET}$=0.86 min; MH$^+$ 511.
$^1$H NMR (d6-DMSO): δ 1.06-1.26 (m, 13H), 1.90-2.02 (m, 1H), 2.11 (s, 3H), 2.20-2.41 (m, 1H), 3.00 (d, J=4.9 Hz, 1H), 3.05-3.16 (m, 2H), 3.56 (s, 3H), 3.66 (d, J=1.32 Hz, 1H), 3.76-3.86 (m, 1H), 3.90 (d, J=13.2 Hz, 1H), 4.26 (d, J=7.3 Hz, 2H), 4.67 (d, J=5.4 Hz, 1H), 4.93 (sept, J=6.2 Hz, 1H), 7.22 (dd, J=8.3, 1.2 Hz, 1H), 7.53 (s, 1H), 7.61 (d, J=8.3 Hz, 1H), 7.73 (dd, J=2.3, 1.1 Hz, 1H), 8.12 (d, J=2.2 Hz, 1H).

Preparation of the edisylate salt of Example 303 (without seeding): (2S,3R)-Isopropyl 2-(((2-(1,5-dimethyl-6-oxo-1,6-dihydropyridin-3-yl)-1-((tetrahydro-2H-pyran-4-yl)methyl)-1H benzo[d]imidazol-5-yl)methyl)amino)-3-hydroxybutanoate, 1,2-ethanedisulphonic acid salt To a carousel tube was added (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl) amino)-3-hydroxybutanoate (For a preparation see Example 303, 100 mg, 0.196 mmol) and isopropanol (1.35 mL). The stirred mixture was heated to 40° C. and a solution of ethane-1,2-disulfonic acid (44.7 mg, 0.235 mmol) in isopropanol (557 µL) was added. The mixture was stirred at 40° C. for 15 hr. After this time, solid had formed. The reaction was removed from the carousel, cooled directly to 24° C. and stirred for 6 h. After this time, the suspension was filtered and dried under vacuum for 5 min. The solid, transferred into a vial was further dried in the vacuum oven at 40° C. for 3 days to yield (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl) amino)-3-hydroxybutanoate, 1,2-ethanedisulphonic acid salt (91 mg, 66.3% yield) as a white crystalline solid. $^1$H NMR (400 MHz, DMSO-d$_6$) δ ppm 9.61 (1H, br. s.), 9.29 (1H, br. s.), 8.35 (1H, br. s.), 8.02 (1H, d, J=8.6 Hz), 7.92 (1H, s), 7.82-7.75 (1H, m), 7.58 (1H, d, J=8.6 Hz), 4.94 (1H, spt, J=6.2 Hz), 4.46-4.34 (4H, m), 4.05 (1H, quin, J=6.4 Hz), 3.77-3.69 (2H, m), 3.66 (1H, br. s.), 3.59 (3H, s), 3.17-3.08 (2H, m), 2.66 (4H, s), 2.13 (3H, s), 2.06-1.93 (1H, m), 1.31-1.16 (13H, m). LCMS (System D): $t_{RET}$=0.88 min; MH$^+$ 511.

Preparation of the edisylate salt of Example 303 (with seeding): (2S,3R)-Isopropyl 2-(((2-(1,5-dimethyl-6-oxo-1,6-dihydropyridin-3-yl)-1-((tetra hydro-2H-pyran-4-yl methyl)-1H benzo[d]imidazol-5-yl)methyl)amino)-3-hydroxybutanoate, 1,2-ethanedisulphonic acid salt To an EasyMax 400 mL reactor was added (2S,3R)-Isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate (for an example preparation see Example 303 (alternative process))(10 g, 19.58 mmol) and Isopropanol (135 mL). In a separate flask was prepared a solution of ethane-1,2-disulfonic acid (4.47 g, 23.50 mmol) in Isopropanol (28 mL) warmed at 40° C. and filtered. To the solution of (2S,3R)-Isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate (for an example preparation see Example 303 (alternative process), stirred at 250 rpm was added 40% of the ethane-1,2-disulfonic acid solution (11.2 mL). A seed of (2S,3R)-Isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate (for an example preparation see above 'Preparation of the edisylate salt of Example 303 (without seeding)') (131 mg) was added and the mixture was stirred at 40° C. for 1.5 h. After this time, the remaining 60% of the ethane-1,2-disulfonic acid solution (16.8 mL) was added dropwise over 6 h. On complete addition of ethane-1,2-disulfonic acid solution the mixture was slowly cooled to 20° C. over 3.5 h and stirred for a further 11 h at RT. The resulting suspension was filtered with filter cup and paper filter, with the filtrate running clear. The filter cake was washed with IPA (2×20 mL and 10 mL) and further dried under with vacuum to yield the wet filter cake (24.06 g). The solids were collected and dried in a vacuum oven (44° C.) for 22 h to yield the title compound (11.337 g, 16.02 mmol, 82% yield) as a white crystalline solid. LCMS (System D): $t_{RET}$=0.88 min; MH$^+$ 511.

Example 304: (2S,3R)$_2$-(((2-(1,5-Dimethyl-6-oxo-1,6-dihydropyridin-3-yl)-1-(((S)-tetrahydrofuran-2-yl)methyl)-1H-benzo[d]imidazol-5-yl)methyl)amino)-3-hydroxybutanoic acid

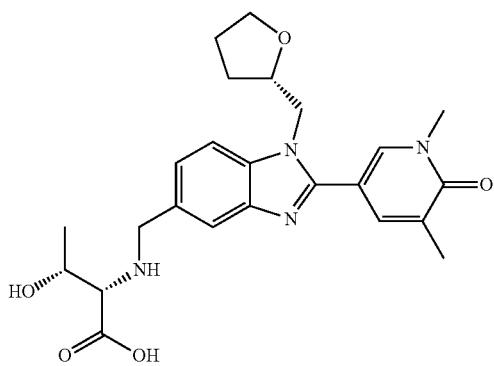 [SMILES: Cc1cc(-c2nc3cc(CN[C@H](C(=O)O)[C@@H](C)O)ccc3n2C[C@@H]2CCCO2)cn(C)c1=O]

(2S,3R)—(S)-tetrahydrofuran-3-yl-2-(((2-(1,5-dimethyl-6-oxo-1,6-dihydropyridin-3-yl)-1-(((S)-tetrahydrofuran-2-yl)methyl)-1H-benzo[d]imidazol-5-yl)methyl)amino)-3-hydroxybutanoate (For a preparation see Example 224, 190 mg, 0.362 mmol) was dissolved in THF (3 mL) and methanol (3 mL). Lithium hydroxide (26.0 mg, 1.087 mmol) was dissolved in water (1 mL) and the solution was added. The reaction mixture was stirred for 5 hours at 40° C. 2M hydrochloric acid (0.543 mL, 1.087 mmol) was added and the solvents were removed under reduced pressure. The residue was dissolved in water (1 mL) and DMSO (0.8 mL), the solution was filtered, and purified by MDAP (Method B). The appropriate fractions were combined and concentrated under reduced pressure. The residue was suspended in THF (3 mL) and 2 M HCl (0.2 mL) was added. The solvents were removed under a stream of nitrogen. The sample was dissolved in water (0.7 mL) and DMSO (0.7 mL) and purified by MDAP (Method B). The appropriate fractions were blown under a stream of nitrogen and the resultant residues were treated with THF (4 mL) and 2 M sodium hydroxide (0.04 mL). The solvents were blown down under a stream of nitrogen. The sample was dissolved in ethyl acetate, filtered, and the solid which was isolated during filtration was dissolved in water and concentrated under reduced pressure. The residue was dissolved in water (0.8 mL) and purified by MDAP (Method B). The appropriate fractions were blown under a stream of nitrogen to yield the title compound (16 mg) as a white solid. LCMS (System J): $t_{RET}$=0.54 min; MH$^+$ 455.

Example 305: (2S,3R)-Isopropyl 2-(((1-(1,3-dimethoxypropan-2-yl)-2-(1,5-dimethyl-6-oxo-1,6-dihydropyridin-3-yl)-1H-benzo[d]imidazol-5-yl)methylamino)-3-hydroxybutanoate

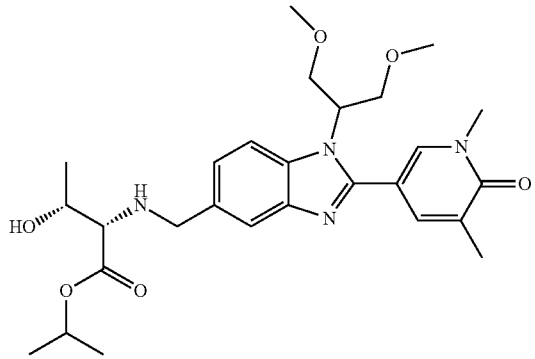 [SMILES: COCC(COC)n1c(-c2cc(C)c(=O)n(C)c2)nc2cc(CN[C@H](C(=O)OC(C)C)[C@@H](C)O)ccc21]

To a mixture of 1-(1,3-dimethoxypropan-2-yl)-2-(1,5-dimethyl-6-oxo-1,6-dihydropyridin-3-yl)-1H-benzo[d]imidazole-5-carbaldehyde (for an example preparation see Intermediate 224, 6.3 g, 17.05 mmol) and (2S,3R)-isopropyl 2-amino-3-hydroxybutanoate hydrochloride (for an example preparation see Intermediate 31a, 6.74 g, 34.1 mmol) in Dichloromethane (DCM) (200 mL) was added triethylamine (5.94 mL, 42.6 mmol) and the reaction mixture stirred at room temperature overnight. Sodium triacetoxyborohydride (10.84 g, 51.2 mmol) was added and the reaction mixture stirred at room temperature for four hours. Saturated aqueous sodium bicarbonate solution was added (200 mL) and the organic layer separated. The aqueous layer was re-extracted with dichloromethane (2×100 mL), and the organic layers combined, dried using a hydrophobic frit and evaporated under reduced pressure. The sample was loaded in dichloromethane and purified by column chromatography (silica) using a gradient of 0-5% methanol in dichloromethane. The appropriate fractions were combined and evaporated under reduced pressure. The sample was purified by HPLC (Xselect CSH C18 column, eluted using water/acetonitrile with 0.1% formic acid modifier) and the fractions evaporated under reduced pressure to give isolated material (5.7 g). 2.1 g of material was removed for subsequent reactions. The remaining material (3.6 g), a colourless gum, was dried in a vacuum oven for 3 nights whereupon it became a scratchable glass. As much material as possible was removed from the flask and returned to a vacuum oven for a further 2 nights to give the title compound (3.2 g, 6.22 mmol). LCMS (System J): $t_{RET}$=0.92 min; MH$^+$ 515. $^1$H NMR (d$_6$-DMSO): δ 1.11 (d, J=6.4 Hz, 3H), 1.19 (d, J=6.1 Hz, 6H), 2.09 (s, 3H), 3.00 (d, J=4.9 Hz, 1H), 3.16 (d, J=1.5 Hz, 6H), 3.54 (s, 3H), 3.65 (d, J=13.2 Hz, 1H), 3.70-3.86 (m, 3H), 3.91 (d, J=13.0 Hz, 1H), 3.96-4.07 (m, 2H), 4.70 (d, J=5.4 Hz, 1H), 4.78-4.86 (m, 1H), 4.94 (sept, J=6.2 Hz, 1H), 7.18 (dd, J=8.4, 1.3 Hz, 1H), 7.55 (s, 1H), 7.67-7.70 (s, 1H), 7.72 (d, J=8.6 Hz, 1H), 8.05 (d, J=2.2 Hz, 1H).

Example 306: (2S,3S)—(S)-tetrahydrofuran-3-yl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate

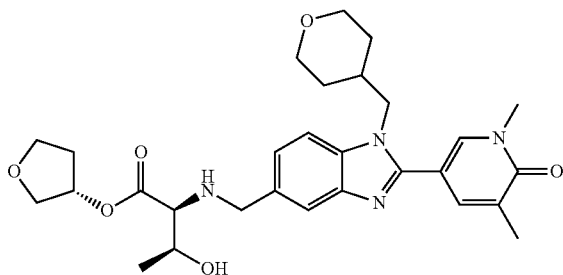 [SMILES: Cc1cc(-c2nc3cc(CN[C@H](C(=O)O[C@H]4CCOC4)[C@H](C)O)ccc3n2CC2CCOCC2)cn(C)c1=O]

To a stirred solution of 2-(1,5-dimethyl-6-oxo-1,6-dihydropyridin-3-yl)-1-((tetrahydro-2H-pyran-4-yl)methyl)-1H-benzo[d]imidazole-5-carbaldehyde (0.438 mmol, 160 mg) (for an example preparation see Intermediate 116) and ((2S,3S)—(S)-tetrahydrofuran-3-yl 2-amino-3-hydroxybutanoate hydrochloride (98.8 mg, 0.525 mmol) (for an example preparation see Intermediate 40) in DCM (5 mL) was added triethylamine (0.182 mL). The resulting mixture was stirred for 1 h and sodium triacetoxyborohydride (278 mg, 1.374 mmol) was added. The reaction mixture was stirred for 30 min and allowed to stand overnight The reaction mixture was partitioned between DCM and aq. sat. NaHCO$_3$. The organic layer was removed and the aqueous extracted twice with DCM. The organic phases were combined and concentrated in vacuo to give a brown oil. The oil was dissolved in DCM and purified by silica gel chromatography eluting with EtOAc:EtOH (3-25%). The appropriate fractions were combined and evaporated in vacuo to give the title compound as a colourless oil. The total yield of the reaction was 46%. LCMS (System C): $t_{RET}$=0.45 min, MH$^+$=539.

Example 307: (2S,3R)-isopropyl 2-(((2-(1,5-dimethyl-6-oxo-1,6-dihydropyridin-3-yl)-1-((S)-piperidin-3-ylmethyl)-1H-benzo[d]imidazol-6-yl)methyl)amino-3-hydroxybutanoate

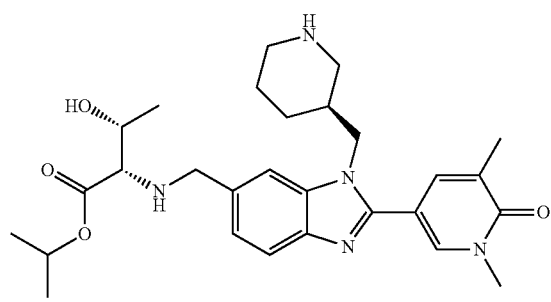 [SMILES: Cc1cc(-c2nc3ccc(CN[C@H](C(=O)OC(C)C)[C@@H](C)O)cc3n2C[C@H]2CCCNC2)cn(C)c1=O]

5-6N HCl in isopropanol (0.2 mL) was added to a solution of (R)-tert-butyl 3-((2-(1,5-dimethyl-6-oxo-1,6-dihydropyridin-3-yl)-6-(((((2S,3R)-3-hydroxy-1-isopropoxy-1-oxobutan-2-yl)amino)methyl)-1H-benzo[d]imidazol-1-yl)methyl)piperidine-1-carboxylate (For a preparation see Intermediate 267, 31.4 mg, 51.5 mmol), in isopropanol (1 mL). Resulting mixture was stirred at r.t. overnight (17 hrs). 5-6N HCl in isopropanol (0.8 mL) was added to reaction mixture and resulting solution was stirred for 5 hours. Volatiles were removed under a stream of nitrogen and mixture was purified by MDAP (Method B) Fractions were combined, volatiles removed under reduce pressure and crude was loaded on a 2 g pre equilibrated SCX cartridge, eluted with 3CV of methanol and 3CV of 2M ammonia in Methanol. Basic fractions were combined and volatiles were removed under reduced pressure to afford a yellow oil. The oil was purified by MDAP (Method B). Relevant fractions combined and volatiles were removed under reduce pressure to give the title compound (15.5 mg) as a translucent/white solid.

LCMS (System J): $t_{RET}$=0.79 min; MH$^+$ 510

Example 308: (2S,3R)-tert-butyl 2-(((2-(1,5-dimethyl-6-oxo-1,6-dihydropyridin-3-yl)-1-((S)-piperidin-3-methyl)-1H-benzo imidazol-6-yl)methyl)amino)-3-hydroxybutanoate

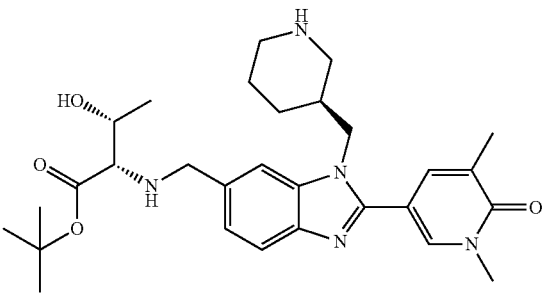 [SMILES: Cc1cc(-c2nc3ccc(CN[C@H](C(=O)OC(C)(C)C)[C@@H](C)O)cc3n2C[C@H]2CCCNC2)cn(C)c1=O]

5-6N HCl in isopropanol (0.2 mL) was added to a solution of (R)-tert-butyl 3-((6-(((((2S,3R)-1-(tert-butoxy)-3-hydroxy-1-oxobutan-2-yl)amino)methyl)-2-(1,5-dimethyl-6-oxo-1,6-dihydropyridin-3-yl)-1H-benzo[d]imidazol-1-yl)methyl)piperidine-1-carboxylate (For a preparation see Intermediate 268, 21 mg, 33.7 mmol) in isopropanol (1 mL). Resulting mixture was stirred at r.t. overnight (17 hrs). 5-6N HCl in isopropanol (0.8 mL) was added to reaction mixture and resulting solution was stirred for 5 hours. Volatiles were removed using blow down unit and mixture was purified by MDAP (Method B). Fractions were combined, volatiles removed under reduced pressure and crude was loaded on a 2 g pre equilibrated SCX cartridge, eluted with 3CV of methanol and 3CV of 2M ammonia in Methanol. Basic fractions were combined and volatiles were removed under reduce pressure to afford a yellow oil. This oil was purified by MDAP (Method B). Relevant fractions combined and volatiles were removed under reduce pressure to afford the title compound (13.5 mg) as a translucent/white solid. LCMS (System J): $t_{RET}$=0.85 min; MH$^+$ 524.

Example 309: (S)-isopropyl 2-(((2-(1,5-dimethyl-6-oxo-1,6-dihydropyridin-3-yl)-1-((R)-piperidin-3-ylmethyl)-1H-benzo[d]imidazol-6-yl)methylamino)-3-methylbutanoate dihydrochloride

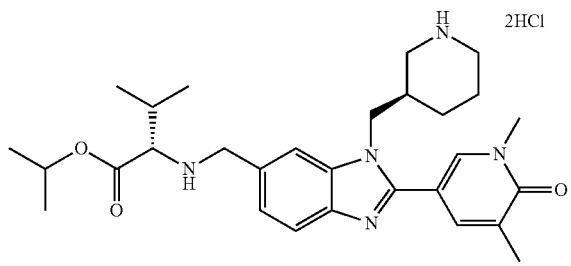 [SMILES: Cc1cc(-c2nc3ccc(CN[C@H](C(=O)OC(C)C)C(C)C)cc3n2C[C@@H]2CCCNC2)cn(C)c1=O]

HCl 5M in IPA (1 mL, 5.00 mmol) was added to (S)-tert-butyl 3-((2-(1,5-dimethyl-6-oxo-1,6-dihydropyridin-3-yl)-6-((((S)-1-isopropoxy-3-methyl-1-oxobutan-2-yl)amino)methyl)-1H benzo[d]imidazol-1-yl)methyl)piperidine-1-carboxylate (For a preparation see Intermediate 269, 56 mg, 0.092 mmol) and the resulting solution was stirred at rt for 21 hr. The solution was evaporated under reduced pressure to obtain the crude product (51.5 mg) as a yellow solid. The sample was dissolved in MeOH 1 mL and purified by MDAP (method B). The solvent was dried down to give 37 mg of a yellow oil. The oil was dried in the vacuum oven overnight. The solid (28 mg) was then was suspended in EtOH:ACN 1:1 2 mL and 80 μL of HCl in Et$_2$O 1 M were poured in. The volatiles were removed under vacuo to obtain the title compound (35 mg) as a yellow solid. LCMS (System J): $t_{RET}$=1.02 min; MH$^+$ 508.

Example 310: (S)-cyclopentyl 2-(((1-(azetidin-3-ylmethyl)-2-(5-methyl-6-oxo-1,6-dihydropyridin-3-yl)-1H-benzo[d]imidazol-5-yl)methyl)amino)-4-methylpentanoate

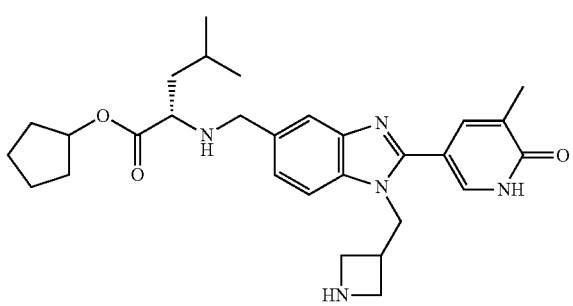 [SMILES: Cc1cc(-c2nc3cc(CN[C@@H](CC(C)C)C(=O)OC4CCCC4)ccc3n2CC2CNC2)c[nH]c1=O]

A round bottom flask was charged with (S)-tert-butyl 3-((5-(((1-(cyclopentyloxy)-4-methyl-1-oxopentan-2-yl)amino)methyl)-2-(5-methyl-6-oxo-1,6-dihydropyridin-3-yl)-1H-benzo[d]imidazol-1-yl)methyl)azetidine-1-carboxylate (Intermediate 270, 60 mg, 0.099 mmol), 1,4-dioxane (10 mL) and TFA (0.5 mL, 6.49 mmol). The vessel was capped and stirred at room temperature for 2 days. The volatiles were removed in vacuo to give a yellow oil. The oil was dissolved in DMSO (1 mL) and purified MDAP (Method B). The solvent was evaporated in vacuo to give the title compound (34 mg, 0.067 mmol, 67.9% yield). LCMS (System B): $t_{RET}$=0.93 min; MH$^+$ 506.

Example 311: (S)-isopropyl 2-(((2-(1,5-dimethyl-6-oxo-1,6-dihydropyridin-3-yl)-1-((R)-piperidin-3-ylmethyl)-1H-benzo[d]imidazol-5-yl)methyl)amino)-3-methylbutanoate

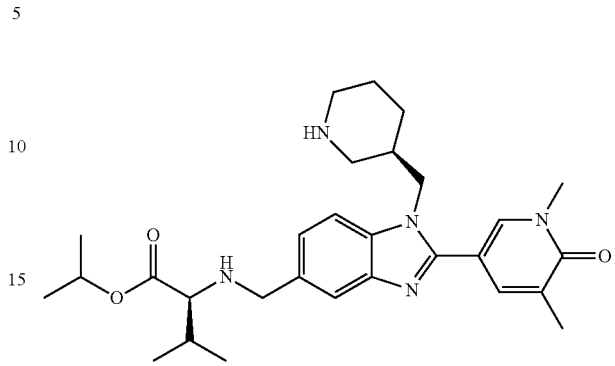

A solution of 5M HCl in IPA (10 mL, 50.0 mmol) was added to (S)-tert-butyl 3-((2-(1,5-dimethyl-6-oxo-1,6-dihydropyridin-3-yl)-5-((((S)-1-isopropoxy-3-methyl-1-oxobutan-2-yl)amino)methyl)-1H-benzo[d]imidazol-1-yl)methyl)piperidine-1-carboxylate (180 mg, 0.296 mmol) (for an example preparation see Intermediate 272) and the resulting solution stirred for 1 h and stirring stopped over the weekend. The reaction mixture was evaporated in vacuo to a brown gum, dissolved in MeOH and loaded on to a 5 g SCX cartridge. The cartridge was eluted with MeOH (50 mL) followed by 2 M methanolic ammonia (25 mL). The basic fractions were evaporated in vacuo to dryness and purified by MDAP (N31339-85-1, Formic method A). The clean, product containing fractions had 2 M aq. HCl (5 mL) added and were evaporated in vacuo to a white solid. N31339-85-A1 was dissolved in MeOH and loaded on to a 5 g SCX cartridge. The cartridge was eluted with MeOH (20 mL), followed by 2M methanolic ammonia (15 mL). The basic fractions were evaporated in vacuo to give the title compound as a white solid. The total yield of the reaction was 67%. LCMS (System C): $t_{RET}$=0.48 min, MH$^+$=508.

Example 312: (S)-isopropyl 2-(((2-(1,5-dimethyl-6-oxo-1,6-dihydropyridin-3-yl)-1-((R)-piperidin-3-ylmethyl)-1H-benzo[d]imidazol-5-yl)methyl)amino)-3-methylbutanoate, dihydrochloride

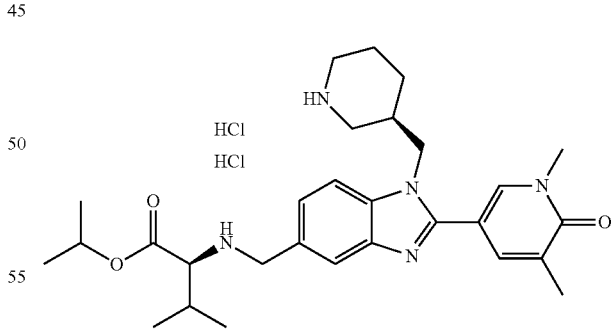

(S)-isopropyl 2-(((2-(1,5-dimethyl-6-oxo-1,6-dihydropyridin-3-yl)-1-((R)-piperidin-3-ylmethyl)-1H-benzo[d]imidazol-5-yl)methyl)amino)-3-methylbutanoate (see for a preparation Example 311) (96 mg, 0.189 mmol) was dissolved in DCM (2 mL) and 1M HCl in diethyl ether (0.5 mL, 0.500 mmol) added with stirring. The resulting suspension was evaporated in vacuo to give the title compound as a white solid. The total yield of the reaction was 97%. LCMS (System C): $t_{RET}$=0.48 min, MH$^+$=508.

The following Example was prepared in a similar manner to Example 17:

| | |
|---|---|
| Example 313: (2S,3R)-2-((2-(2-(1,5-dimethyl-6-oxo-1,6-dihydro-pyridin-3-yl)-1-((tetrahydro-2H-pyran-4-yl)methyl)-1H-benzo[d]imidazol-5-yl)ethyl)amino)-3-hydroxybutanoic acid hydrochloride (prepared from: Example 290) System D, 0.56 min, MH+ = 483, Yield 10 mg, 38%. | 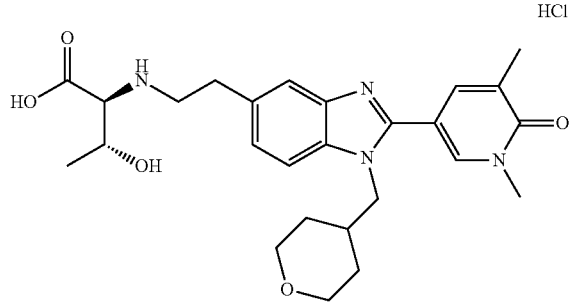 [SMILES: Cl ; Cc1cc(-c2nc3cc(CCN[C@H](C(=O)O)[C@@H](C)O)ccc3n2CC2CCOCC2)cn(C)c1=O] |

The following Examples were prepared in a similar manner to Example 95:

| | |
|---|---|
| Example 314: (2R,3S)-isopropyl 2-(((2-(1,5-dimethyl-6-oxo-1,6-dihydropyridin-3-yl)-1-((tetrahydro-2H-pyran-4-yl)methyl)-1H-benzo[d]-imidazol-5-yl)methyl)amino)-3-hydroxybutanoate (prepared from: Intermediate 116 and Intermediate 287) System E, 3.07 min, MH+ = 511, Yield 78 mg, 11%. | 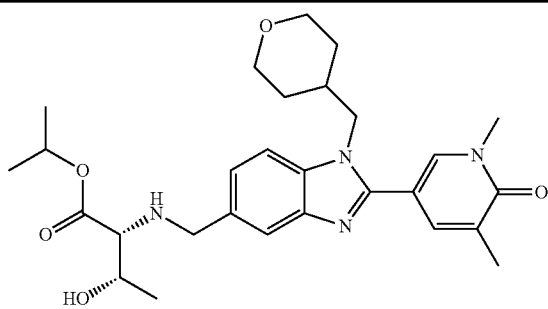 |
| Example 315: (2R,3S)-isopropyl 2-(((1-(1,3-dimethoxypropan-2-yl)-2-(1,5-dimethyl-6-oxo-1,6-dihydro-pyridin-3-yl)-1H-benzo[d]imidazol-5-yl)methyl)amino)-3-hydroxy-butanoate (prepared from: Intermediate 224 and Intermediate 287) System E, 3.15 min, MH+ = 515, Yield 85 mg, 30%. | 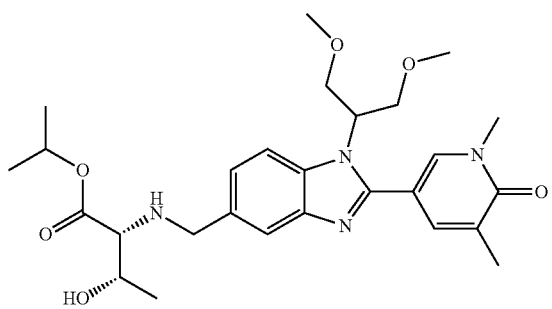 [SMILES: COCC(COC)n1c(-c2cc(C)c(=O)n(C)c2)nc2cc(CN[C@@H](C(=O)OC(C)C)[C@H](C)O)ccc21] |
| Example 316: (2S,3S)-isopropyl 2-(((2-(1,5-dimethyl-6-oxo-1,6-dihydropyridin-3-yl)-1-((tetrahydro-2H-pyran-4-yl)methyl)-1H-benzo[d]-imidazol-5-yl)methyl)amino)-3-hydroxybutanoate (prepared from: Intermediate 116 and Intermediate 288) System D, 0.84 min, MH+ = 511, Yield 61.8 mg, 56%. | 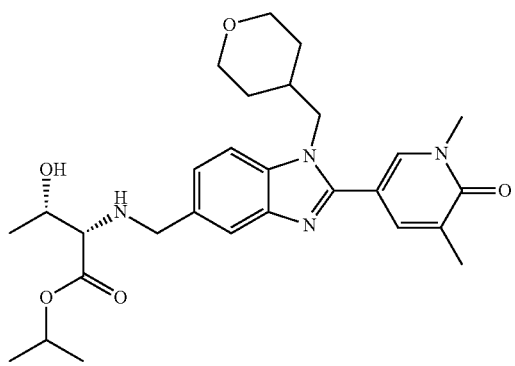 [SMILES: Cc1cc(-c2nc3cc(CN[C@H](C(=O)OC(C)C)[C@H](C)O)ccc3n2CC2CCOCC2)cn(C)c1=O] |

| Example | | |
|---|---|---|
| Example 317: (2R,3R)-isopropyl 2-(((2-(1,5-dimethyl-6-oxo-1,6-dihydropyridin-3-yl)-1-((tetrahydro-2H-pyran-4-yl)methyl)-1H-benzo[d]-imidazol-5-yl)methyl)amino)-3-hydroxybutanoate (prepared from: Intermediate 116 and Intermediate 289) System D, 0.85 min, MH+ = 511, Yield 78.3 mg, 71%. | 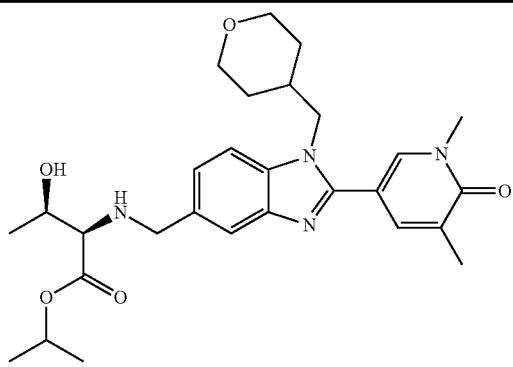 | |
| Example 318: Isopropyl 2-(((1-(1,3-dimethoxypropan-2-yl)-2-(1,5-dimethyl-6-oxo-1,6-dihydropyridin-3-yl)-1H-benzo[d]imidazol-5-yl)-methyl)amino)-3-hydroxybutanoate (prepared from: Intermediate 224 and Intermediate 290) System F, 1.40 min, MH+ = 515, Yield 480 mg, 35%. | 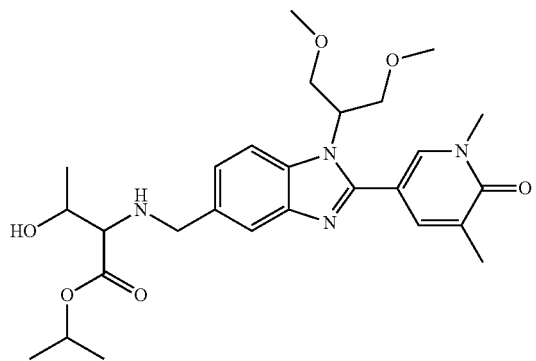 | |
| Example 319: Isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino-3-hydroxybutanoate (prepared from: Intermediate 116 and Intermediate Intermediate 290) System F, 1.33 min, MH+ = 511, Yield 449 mg, 33%. | 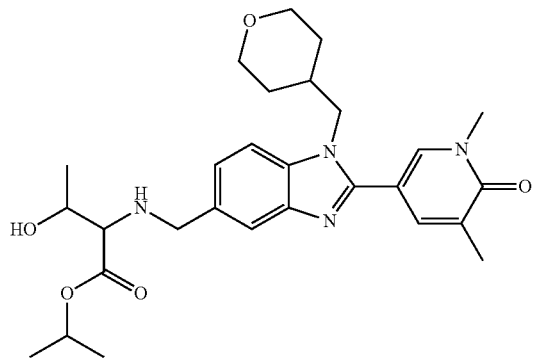 [SMILES: Cc1cc(-c2nc3cc(CNC(C(=O)OC(C)C)C(C)O)ccc3n2CC2CCOCC2)cn(C)c1=O] | |

Example 320: (2S,3R)-tert-butyl 2-((2-(1-(1,3-dimethoxypropan-2-yl)-2-(1,5-dimethyl-6-oxo-1,6-dihydropyridin-3-yl)-1H-benzo[d]imidazol-5-yl)ethyl)amino)-3-hydroxybutanoate

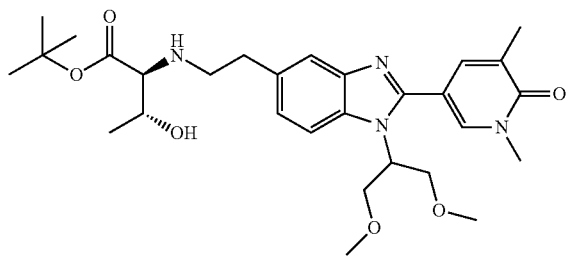 [SMILES: COCC(COC)n1c(-c2cc(C)c(=O)n(C)c2)nc2cc(CCN[C@H](C(=O)OC(C)(C)C)[C@@H](C)O)ccc21]

To a solution of 5-(1-(1,3-dimethoxypropan-2-yl)-5-(oxiran-2-yl)-1H-benzo[d]imidazol-2-yl)-1,3-dimethylpyridin-2(1H)-one (for a preparation see Intermediate 291, 500 mg, 1.304 mmol) in THF (13 mL) was added BF$_3$.OEt$_2$ (0.165 mL, 1.304 mmol) at 0° C. and the solution was stirred for 15 min. Then triethylamine (0.545 mL, 3.91 mmol) was added to the reaction mixture followed by (2S,3R)-tert-butyl 2-amino-3-hydroxybutanoate hydrochloride (304 mg, 1.434 mmol) and TsOH (248 mg, 1.304 mmol) and reaction mixture was stirred overnight at room temp. Then sodium triacetoxyborohydride (276 mg, 1.304 mmol) was added and stirring continued for another 12 hours. Sat. NaHCO$_3$ (20 mL) was added to the reaction mixture and extracted with ethyl acetate (30 mL×2). The combined organics were washed with brine (20 mL) dried (Na$_2$SO$_4$), filtered and concentrated to get the crude product. The crude product was purified by preparative HPLC using a kinetexc8 (150*30) mm 5µ column, eluting with 5 Mm Ammonium bicarbonate(Aq)/Acetonitrile. The appropriate fractions were lyophilized to get the title compound (2S,3R)-tert-butyl 2-((2-(1-(1,3-dimethoxypropan-2-yl)-2-(1,5-dimethyl-6-oxo-1,6-dihydropyridin-3-yl)-1H-benzo[d]imidazol-5-yl)ethyl)amino)-3-hydroxybutanoate (67 mg, 9.4% yield). LCMS (System E): t$_{RET}$=1.46 min; MH+ 543.

The following Examples were prepared in a similar manner to Example 320:

Example 321: (2S,3R)-isopropyl 2-((2-(1-(1,3-dimethoxypropan-2-yl)-2-(1,5-dimethyl-6-oxo-1,6-dihydropyridin-3-yl)-1H-benzo[d]imidazol-5-yl)ethyl)amino)-3-hydroxybutanoate (prepared from Intermediate 291 and Intermediate 31a) System E, 1.39 min, MH$^+$ = 529, Yield 45 mg, 6.4%

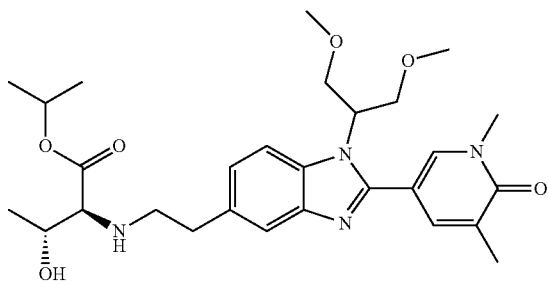 [SMILES: COCC(COC)n1c(-c2cc(C)c(=O)n(C)c2)nc2cc(CCN[C@H](C(=O)OC(C)C)[C@@H](C)O)ccc21]

Example 322: (2S,3R)-cyclobutyl 2-((2-(1-(1,3-dimethoxypropan-2-yl)-2-(1,5-dimethyl-6-oxo-1,6-dihydropyridin-3-yl)-1H-benzo[d]imidazol-5-yl)ethyl)amino)-3-hydroxybutanoate hydroxybutanoate (prepared from: Intermediate 291 and Intermediate 32) System E, 1.50 min, MH$^+$ = 541, Yield 46 mg, 6.3%

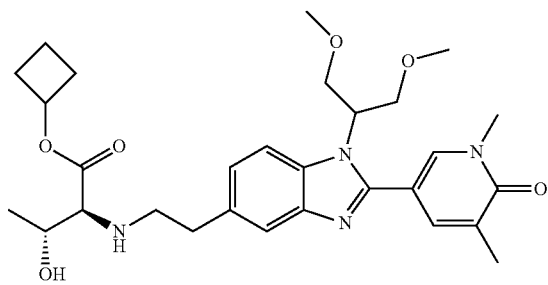 [SMILES: COCC(COC)n1c(-c2cc(C)c(=O)n(C)c2)nc2cc(CCN[C@H](C(=O)OC3CCC3)[C@@H](C)O)ccc21]

Example 323: (2S,3R)-cyclobutyl 2-((2-(2-(1,5-dimethyl-6-oxo-1,6-dihydropyridin-3-yl)-1-((tetrahydro-2H-pyran-4-yl)methyl)-1H-benzo[d]imidazol-5-yl)ethyl)amino)-3-hydroxybutanoate (prepared from: Intermediate 292 and Intermediate 32) System E, 1.33 min, MH$^+$ = 537, Yield 75 mg, 14%

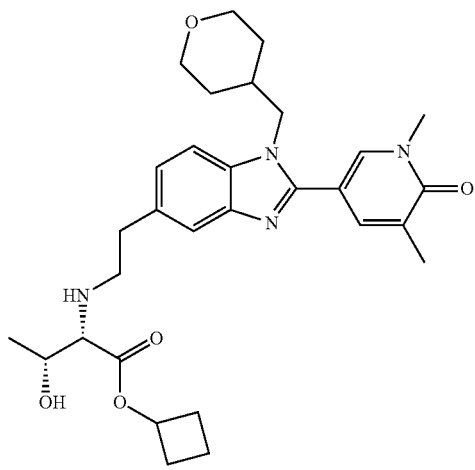 [SMILES: Cc1cc(-c2nc3cc(CCN[C@H](C(=O)OC4CCC4)[C@@H](C)O)ccc3n2CC2CCOCC2)cn(C)c1=O]

The following Examples were prepared in a similar manner to Example 71:

Example 324: (2S,3R)-2-((2-(1-(1,3-dimethoxypropan-2-yl)-2-(1,5-dimethyl-6-oxo-1,6-dihydropyridin-3-yl)-1H-benzo[d]imidazol-5-yl)ethyl)amino)-3-hydroxybutanoic acid (prepared from: Example 320) System E, 1.15 min, MH$^+$ = 487, Yield 45 mg, 64%

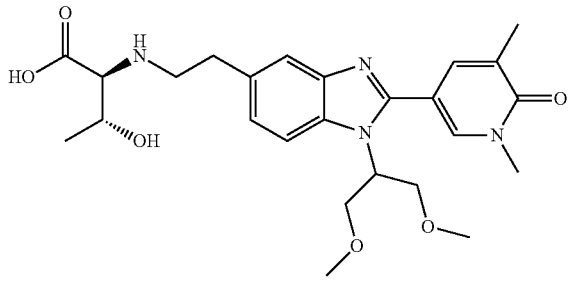 [SMILES: COCC(COC)n1c(-c2cc(C)c(=O)n(C)c2)nc2cc(CCN[C@H](C(=O)O)[C@@H](C)O)ccc21]

Biological Data
Time Resolved Fluorescence Resonance Energy Transfer (TR-FRET) Assay
Binding was assessed using a time resolved fluorescent resonance energy transfer binding assay. This utilises a 6 His purification tag at the N-terminal of the proteins as an epitope for an anti-6 His antibody labeled with Europium chelate (PerkinElmer AD0111) allowing binding of the Europium to the proteins which acts as the donor fluorophore. A small molecule, high affinity binder of the bromodomains BRD2, BRD3, BRD4 and BRDT has been labeled with Alexa Fluor647 (Reference Compound X) and this acts as the acceptor in the FRET pair.

Reference Compound X: 4-((Z)-3-(6-((5-(2-((4S)-6-(4-chlorophenyl)-8-methoxy-1-methyl-4H-benzo[f][1,2,4]triazolo[4,3-a][1,4]diazepin-4-yl)acetamido)pentyl)amino)-6-oxohexyl)-2-((2E,4E)-5-(3,3-dimethyl-5-sulfo-1-(4-sulfobutyl)-3H-indol-1-ium-2-yl)penta-2,4-dien-1-ylidene)-3-methyl-5-sulfoindolin-1-yl)butane-1-sulphonate)

Analytical HPLC (Sphersisorb ODS2, 1 to 35% B over 60 min): MSM10520-1: [M+H]⁺ (obs): 661.8/– corresponding with M-29. This equates to [(M+2H)/2]⁺ for a calculated mass of 1320.984 which is M-29. This is a standard occurrence with the Alexa Fluor 647 dye and represents a theoretical loss of two methylene groups under the conditions of the mass spectrometer.

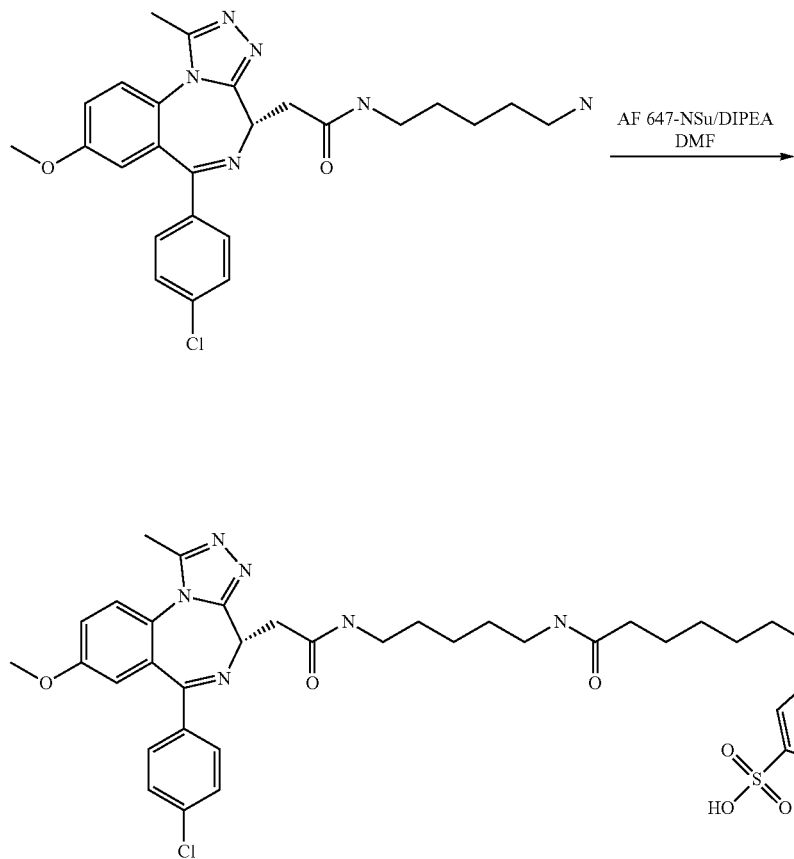

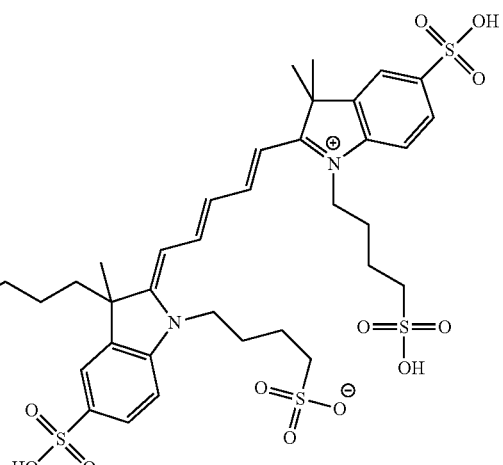

To a solution of N-(5-aminopentyl)-2-((4S)-6-(4-chlorophenyl)-8-methoxy-1-methyl-4H-benzo[f][1,2,4]triazolo[4,3-a][1,4]diazepin-4-yl)acetamide (for a preparation see Reference Compound J, WO2011/054848A1, 1.7 mg, 3.53 μmol) in DMF (40 μl) was added a solution of AlexaFluor647-ONSu (2.16 mg, 1.966 μmol) also in DMF (100 μl). The mixture was basified with DIPEA (1 μl, 5.73 μmol) and agitated overnight on a vortex mixer. The reaction mixture was evaporated to dryness. The solid was dissolved in acetonitrile/water/acetic acid (5/4/1, <1 mL) filtered and was applied to a Phenomenex Jupiter C18 preparative column and eluted with the following gradient (A=0.1% trifluoroacetic acid in water, B=0.1% TFA/90% acetonitrile/10% water): Flow rate=10 ml/min., AU=20/10 (214 nm): 5-35%, t=0 min: B=5%; t=10 min: B=5%; t=100 min: B=35%; t=115 min: B=100% (Sep. grad: 0.33%/min)

The major component was eluted over the range 26-28% B but appeared to be composed of two peaks. The middle fraction (F1.26) which should contain "both" components was analysed by analytical HPLC (Spherisorb ODS2, 1 to 35% over 60 min): single component eluting at 28% B. Fractions F1.25/26&27 were combined and evaporated to dryness. Transferred with DMF, evaporated to dryness, triturated with dry ether and the blue solid dried overnight at <0.2 mbar: 1.54 mg.

Assay Principle:

In the absence of a competing compound, excitation of the Europium causes the donor to emit at λ618 nm which excites the Alexa labelled bromodomain binding compound leading to an increased energy transfer that is measurable at λ647 nM. In the presence of a sufficient concentration of a compound that can bind these proteins, the interaction is disrupted leading to a quantifiable drop in fluorescent resonance energy transfer.

The binding of compounds of the invention to Bromodomains BRD2, BRD3, BRD4 and BRDT was assessed using mutated proteins to detect differential binding to either Binding Domain 1 (BD1) or Binding Domain 2 (BD2) on the bromodomain. These single residue mutations in the acetyl lysine binding pocket greatly lower the affinity of the fluoroligand (Reference Compound X) for the mutated domain (>1000 fold selective for the non-mutated domain). Therefore in the final assay conditions, binding of the fluoroligand to the mutated domain cannot be detected and subsequently the assay is suitable to determine the binding of compounds to the single non-mutated bromodomain.

Protein Production:

Recombinant Human Bromodomains [(BRD2 (1-473) (Y113A) and (Y386A), BRD3 (1-435) (Y73A) and (Y348A)

BRD4 (1-477) (Y97A) and (Y390A) and BRDT (1-397) (Y66A) and (Y309A)] were expressed in *E. coli* cells (in pET15b vector for BRD2/3/4 and in pET28a vector for BRDT) with a 6-His tag at the N-terminal. The His-tagged Bromodomain pellet was resuspended in 50 mM HEPES (pH7.5), 300 mM NaCl, 10 mM imidazole & 1 μl/ml protease inhibitor cocktail and extracted from the *E. coli* cells using sonication and purified using a nickel sepharose high performance column, the proteins were washed and then eluted with a linear gradient of 0-500 mM imidazole with buffer 50 mM HEPES (pH7.5), 150 mM NaCl, 500 mM imidazole, over 20 column volumes. Final purification was completed by Superdex 200 prep grade size exclusion column. Purified protein was stored at −80° C. in 20 mM HEPES pH 7.5 and 100 mM NaCl. Protein identity was confirmed by peptide mass fingerprinting and predicted molecular weight confirmed by mass spectrometry.

Protocol for Bromodomain BRD2, 3, 4 and T, BD1+BD2 Mutant Assays:

All assay components were dissolved in buffer composition of 50 mM HEPES pH7.4, 50 mM NaCl, 5% Glycerol, 1 mM DTT and 1 mM CHAPS. The final concentration of bromodomain proteins were 10 nM and the Alexa Fluor647 ligand was at Kd. These components were premixed and 5 μl of this reaction mixture was added to all wells containing 50 nl of various concentrations of test compound or DMSO vehicle (0.5% DMSO final) in Greiner 384 well black low volume microtitre plates and incubated in dark for 30 minutes at rt. 5 μl of detection mixture containing 1.5 nM final concentration anti-6His Europium chelate was added to all wells and a further dark incubation of at least 30 minutes was performed. Plates were then read on the Envision platereader, (•ex=317 nm, donor. •m=615 nm; acceptor •em=665 nm; Dichroic LANCE dual). Time resolved fluorescent intensity measurements were made at both emission wavelengths and the ratio of acceptor/donor was calculated and used for data analysis. All data was normalized to the mean of 16 high (inhibitor control—Example 11 of WO 2011/054846A1) and 16 low (DMSO) control wells on each plate. A four parameter curve fit of the following form was then applied:

$$y = a + ((b-a)/(1+(10^x/10^c)^d)$$

Where 'a' is the minimum, 'b' is the Hill slope, 'c' is the $pIC_{50}$ and 'd' is the maximum.

Results:

All the Examples, with the exception of Examples 82, 92, 93, 271, 286 and 304, were tested in the above BRD4 assay and were found to have a mean $pIC_{50}$ in the range of 4.5 to 8.0 in the BRD4 BD1 assay and a mean $pIC_{50}$ in the range of 4.4 to 7.2 in the BRD4 BD2 assay, with the exception of Examples 21, 24, 48, 60 and 302 which had a $pIC_{50}$ of <4.3 in the BRD4 BD2 assay. Example 303 was found to have a mean $pIC_{50}$ of 7.3 in the BRD4 BD1 assay and a mean $pIC_{50}$ of 6.8 in the BRD4 BD2 assay. Example 68 was found to have a mean $pIC_{50}$ of 6.6 in the BRD4 BD1 assay and a mean $pIC_{50}$ of 6.2 in the BRD4 BD2 assay. Example 305 was found to have a mean $pIC_{50}$ of 7.3 in the BRD4 BD1 assay and a mean $pIC_{50}$ of 6.4 in the BRD4 BD2 assay. Example 66 was found to have a mean $pIC_{50}$ of 6.7 in the BRD4 BD1 assay and a mean $pIC_{50}$ of 5.9 in the BRD4 BD2 assay. The edisylate salt of Example 303 was found to have a mean $pIC_{50}$ of 7.3 in the BRD4 BD1 assay and a mean $pIC_{50}$ of 6.6 in the BRD4 BD2 assay.

Measurement of LPS Induced MCP-1 Production from Human Whole Blood

Activation of monocytic cells by agonists of toll-like receptors such as bacterial lipopolysaccharide (LPS) results in production of key inflammatory mediators including MCP-1. Such pathways are widely considered to be central to the pathophysiology of a range of auto-immune and inflammatory disorders. Blood is collected in a tube containing Sodium heparin (Leo Pharmaceuticals) (10 units of heparin/mL of blood). 96-well compound plates containing 1 μL test sample in 100% DMSO were prepared (two replicates on account of donor variability). 130 μL of whole blood was dispensed into each well of the 96-well compound plates and incubated for 30 min at 37° C., 5% $CO_2$. 10 μL of lipopolysaccharide (from *Salmonella typhosa*; L6386) made up in PBS (200 ng/mL final assay concentration) was added to each well of the compound plates. The plates were then placed in the humidified primary cell incubator for 18-24 hours at 37° C., 5% $CO_2$. 140 μL of PBS was added to all wells of the compound plates containing blood. The plates were then sealed and centrifuged for 10 mins at 2500 rpm. 25 μL of cell supernatant was placed in a 96-well MSD plate pre-coated with human MCP-1 capture antibody. The plates were sealed and placed on a shaker at 600 rpm for 1 hour (r.t). 25 μL of Anti-human MCP-1 antibody labelled with MSD SULFO-TAG™ reagent is added to each well of the MSD plate (stock 50× was diluted 1:50 with Diluent 100, final assay concentration is 1 μg/mL). The plates were then re-sealed and shaken for another hour before washing with PBS. 150 μL of 2×MSD Read Buffer T (stock 4×MSD Read Buffer T was diluted 50:50 with de-ionised water) was then added to each well and the plates read on the MSD Sector Imager 6000. Concentration response curves for each compound were generated from the data and an $pIC_{50}$ value was calculated.

Results:

All the Examples (with the exception of Examples 2-11, 13, 15-36, 38-62, 65, 67, 69-79, 81-88, 90, 91, 93-94a, 95-99, 137-143, 145, 147, 150-156, 184-190, 192-210, 234-247, 271, 285-286, 288, 293, 301-302, 304, 310, 313 and 324) were tested in the above assay and were found to have a mean $pIC_{50}$ in the range of 4.6 to 8.8. Example 303 had a mean $pIC_{50}$ of 7.6. Example 68 had a mean $pIC_{50}$ of 5.4. Example 305 had a mean $pIC_{50}$ of 8.0. Example 66 had a mean $pIC_{50}$ of 6.0. The edisylate salt of Example 303 had a mean $pIC_{50}$ of 7.5.

These data demonstrate that bromodomain inhibitors tested in the above whole blood assay inhibited the production of key inflammatory mediator MCP-1.

Hydrolysis by hCES-1

Hydrolysis of ESM-containing BET inhibitors by carboxylesterase 1 (CES1) is one aspect of delivering a targeted molecule. Rates of hydrolysis of certain compounds of the invention by recombinant human CES1 were determined using an HPLC assay. Recombinant human CES1 (Gly18-Glu563, bearing a polyhistidine tag at the C-terminus) expressed in human cells and purified to homogeneity was obtained from Novoprotein, Summit, N.J., USA (catalogue number C450). Reactions were run in 384 well plates at 20° C. in a buffer of 50 mM sodium phosphate pH 7.5/100 mM NaCl. Assays used a fixed concentration of test compound (50 μM) and CES1 (50 nM) and a time course of the reaction was obtained by stopping samples at increasing times by addition of formic acid to lower the pH. Stopped samples were subsequently analysed by HPLC to resolve product acid from unhydrolysed ester, using a 50×2 mm C18 5 μM reversed-phase column (Phenomenex Gemini) at a flow rate of 1 ml/min using a gradient of acetonitrile in water, containing 0.1% formic acid. Chromatography was monitored using absorbance at 300 nm wavelength. The % of product formed was determined using integrated peak areas and used to determine the initial rate of the reaction. The specific activity of the CES1 against each test compound under these conditions (in units of μM/min/μM) was obtained by dividing the initial rate of the reaction by the CES1 concentration.

Results:

Examples 1, 5, 13, 14, 98, 100, 102, 104, 109a, 110, 112, 116, 119, 120, 124, 125, 127, 128, 136, 139, 139a/b, 140, 141, 143, 146, 147, 155, 157, 159, 160, 168, 173, 181a, 184, 187, 189, 211, 219-222, 225a/b, 228, 228a/b, 229a/b, 230, 250, 258-259, 263, 268, 287, 289, 303, and 305 had rates of hydrolysis of 0.05 to 30.92 (ρM of test compound hydrolysed per minute per μM of CES1) in the above assay. Example 303 had a mean rate of hydrolysis of 0.21 (n=2) in the above assay. Example 305 had a mean rate of hydrolysis of 0.31 (n=2) (μM of test compound hydrolysed per minute per μM of CES1) in the above assay. Examples 16, 138, 156, 212, 214, 216 and 162a were tested but had no detectable level of hydrolysis in this assay.

The invention claimed is:

1. A compound of formula (I), or a salt thereof:

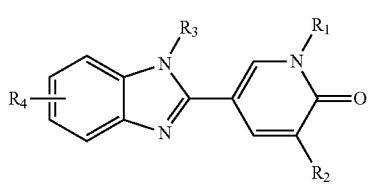

(I)

wherein $R_1$ and $R_2$ are each independently hydrogen or methyl with the proviso that at least one of $R_1$ and $R_2$ is methyl;

$R_3$ is $C_{1-6}$alkyl, $C_{1-6}$alkoxy, cycloalkyl, heterocycloalkyl, or —$CHR_5(CH_2)_aR_6$;

$R_4$ is attached at the 5 or 6 position of the benzimidazole and represents

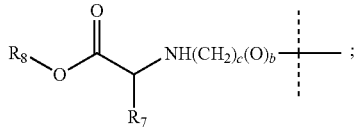

$R_5$ is hydrogen, $C_{1-3}$alkyl, $C_{1-3}$alkoxy, or —$(CH_2)_dOR_9$;
$R_6$ is hydrogen, $C_{1-3}$alkyl, $C_{1-3}$alkoxy, —$(CH_2)_eOR_{10}$, hydroxyl, —$NR_{11}R_{12}$, halo, cycloalkyl, heterocycloalkyl, aryl, or heteroaryl, wherein said $C_{1-3}$alkyl, $C_{1-3}$alkoxy, —$(CH_2)_eOR_{10}$, cycloalkyl, heterocycloalkyl, aryl or heteroaryl is optionally substituted with one or two substituents independently selected from the group consisting of $C_{1-3}$alkyl, $C_{1-3}$alkoxy, halo, —$CH_2OH$, —COOH, and —$COCH_3$;
$R_7$ is hydrogen, $C_{1-6}$alkyl, —$(CH_2)_g$cycloalkyl, —$(CH_2)_h$heterocycloalkyl, or —$CR_{13}R_{14}R_{15}$;
$R_8$ is hydrogen, $C_{1-6}$alkyl, cycloalkyl, heterocycloalkyl, or —$CHR_{16}R_{17}$ wherein said $C_{1-6}$alkyl is optionally substituted with $C_{1-3}$alkoxy, and wherein $R_{16}$ is hydrogen or $C_{1-3}$alkyl and $R_{17}$ is cycloalkyl or heterocycloalkyl;

$R_9$, $R_{10}$, $R_{11}$, $R_{12}$, $R_{14}$, $R_{15}$, and $R_{18}$ are each independently hydrogen or $C_{1-3}$alkyl;

$R_{13}$ is hydrogen, hydroxyl, —$CH_2OR_{18}$, halo, —COOH, —$CONH_2$, 1H-imidazol-4-yl, —SH, —SeH, $C_{1-3}$alkyl, $C_{1-3}$alkoxy, phenyl, or 4-hydroxyphenyl wherein said $C_{1-3}$alkyl or $C_{1-3}$alkoxy is optionally substituted with halo, hydroxyl, —NHC(=$NH_2$)$NH_2$, —$NH_2$, —COOH, —$CONH_2$, or —$SCH_3$;

a is 0, 1, 2 or 3;

b is 0 or 1;

c is 1, 2 or 3 with the proviso that when b is 1, c is 2 or 3;

d and e are each independently 1 or 2; and g and h are each independently 0, 1 or 2.

2. The compound according to claim 1, wherein $R_1$ and $R_2$ are each methyl.

3. The compound according to claim 1, wherein $R_3$ represents a 5 or 6 membered heterocycloalkyl or the group —$CHR_5R_6$ wherein $R_5$ represents hydrogen or $C_{1-3}$alkyl and $R_6$ represents 5 or 6 membered heterocycloalkyl, wherein said heterocycloalkyl is optionally substituted with $C_{1-3}$alkyl or —$COCH_3$.

4. The compound according to claim 3, wherein $R_6$ is:

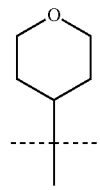

5. The compound according to claim 3, wherein $R_5$ is hydrogen.

6. The compound according to claim 1, wherein $R_3$ is —$CHR_5(CH_2)_aR_6$, $R_5$ is —$(CH_2)_dOR_9$, a is 0 and $R_6$ is —$(CH_2)_eOR_{10}$.

7. The compound according to claim 1, wherein b is 0 and c is 1.

8. The compound according to claim 1, wherein $R_4$ represents:

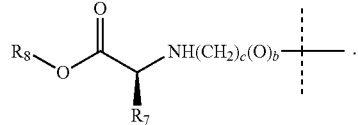

9. The compound according to claim 8, wherein $R_7$ is hydrogen, methyl, isopropyl, sec-butyl, isobutyl, —$CH_2$-phenyl, —$CH_2$-4-hydroxyphenyl, —$CH_2OH$, —$CH(CH_3)$OH, —$CH_2SH$, —$CH_2SeH$, —$(CH_2)_2SCH_3$, —$CH_2COOH$, —$(CH_2)_2COOH$, —$CH_2CONH_2$, —$(CH_2)_2CONH_2$, —$(CH_2)_4NH_2$, —$(CH_2)_3NHC(=NH_2)NH_2$, or —$CH_2$-1H-imidazol-4-yl.

10. The compound according to claim 8, wherein $R_7$ is —$CH(CH_3)OH$.

11. The compound according to claim 8, wherein $R_8$ is isopropyl, isobutyl or cyclopentyl.

12. The compound according to claim 1, selected from the group consisting of:

tert-butyl (2S,3R)-2-{[(1-{[(3R)-1-acetylpiperidin-3-yl]methyl}-2-(1,5-dimethyl-6-oxo-1,6-dihydropyridin-3-yl)-1H-1,3-benzodiazol-6-yl)methyl]amino}-3-hydroxybutanoate;

tert-butyl (2S,3R)-2-({[2-(1,5-dimethyl-6-oxo-1,6-dihydropyridin-3-yl)-1-(oxan-4-ylmethyl)-1H-1,3-benzodiazol-6-yl]methyl}amino)-3-hydroxybutanoate;

2-methylpropyl (2S)-2-[(2-{[2-(1,5-dimethyl-6-oxo-1,6-dihydropyridin-3-yl)-1-(oxan-4-ylmethyl)-1H-1,3-benzodiazol-5-yl]oxy}ethyl)amino]-3-hydroxybutanoate;

2-methylpropyl (2S,3R)-2-({[2-(1,5-dimethyl-6-oxo-1,6-dihydropyridin-3-yl)-1-[(3S)-oxan-3-ylmethyl]-1H-1,3-benzodiazol-5-yl]methyl}amino)-3-hydroxybutanoate;

tert-butyl (2S,3R)-2-{[(1-{[(3R)-1-acetylpiperidin-3-yl]methyl}-2-(1,5-dimethyl-6-oxo-1,6-dihydropyridin-3-yl)-1H-1,3-benzodiazol-5-yl)methyl]amino}-3-hydroxybutanoate;

propan-2-yl (2S,3R)-2-{[(1-{[(3R)-1-acetylpiperidin-3-yl]methyl}-2-(1,5-dimethyl-6-oxo-1,6-dihydropyridin-3-yl)-1H-1,3-benzodiazol-5-yl)methyl]amino}-3-hydroxybutanoate;

2-methylpropyl (2S,3R)-2-({[2-(1,5-dimethyl-6-oxo-1,6-dihydropyridin-3-yl)-1-(oxan-3-ylmethyl)-1H-1,3-benzodiazol-5-yl]methyl}amino)-3-hydroxybutanoate;

cyclopentyl (2S)-2-[(2-{[2-(1,5-dimethyl-6-oxo-1,6-dihydropyridin-3-yl)-1-(oxan-4-ylmethyl)-1H-1,3-benzodiazol-5-yl]oxy}ethyl)amino]propanoate;

propan-2-yl (2S)-2-[(2-{[2-(1,5-dimethyl-6-oxo-1,6-dihydropyridin-3-yl)-1-(oxan-4-ylmethyl)-1H-1,3-benzodiazol-5-yl]oxy}ethyl)amino]-3-hydroxybutanoate;

propan-2-yl (2S,3R)-2-{[(1-{[(3R)-1-acetylpiperidin-3-yl]methyl}-2-(1,5-dimethyl-6-oxo-1,6-dihydropyridin-3-yl)-1H-1,3-benzodiazol-6-yl)methyl]amino}-3-hydroxybutanoate;

propan-2-yl (2S,3R)-2-({[2-(1,5-dimethyl-6-oxo-1,6-dihydropyridin-3-yl)-1-[(3R)-oxan-3-ylmethyl]-1H-1,3-benzodiazol-6-yl]methyl}amino)-3-hydroxybutanoate;

cyclobutyl (2S,3R)-2-{[(1-{[(3R)-1-acetylpiperidin-3-yl]methyl}-2-(1,5-dimethyl-6-oxo-1,6-dihydropyridin-3-yl)-1H-1,3-benzodiazol-5-yl)methyl]amino}-3-hydroxybutanoate;

propan-2-yl (2S)-2-{[(1-{[(3R)-1-acetylpiperidin-3-yl]methyl}-2-(1,5-dimethyl-6-oxo-1,6-dihydropyridin-3-yl)-1H-1,3-benzodiazol-5-yl)methyl]amino}-3-methylbutanoate;

cyclopentyl (2S)-2-[(2-{[2-(1,5-dimethyl-6-oxo-1,6-dihydropyridin-3-yl)-1-(oxan-4-ylmethyl)-1H-1,3-benzodiazol-5-yl]oxy}ethyl)amino]-3-methoxypropanoate;

2,2-dimethylpropyl (2S,3R)-2-({[2-(1,5-dimethyl-6-oxo-1,6-dihydropyridin-3-yl)-1-(oxan-4-ylmethyl)-1H-1,3-benzodiazol-6-yl]methyl}amino)-3-hydroxybutanoate;

propan-2-yl (2S,3R)-2-({[2-(1,5-dimethyl-6-oxo-1,6-dihydropyridin-3-yl)-1-[(3R)-oxan-3-ylmethyl]-1H-1,3-benzodiazol-5-yl]methyl}amino)-3-hydroxybutanoate;

cyclobutyl (2S,3R)-2-[(2-{[2-(1,5-dimethyl-6-oxo-1,6-dihydropyridin-3-yl)-1-(oxan-4-ylmethyl)-1H-1,3-benzodiazol-5-yl]oxy}ethyl)amino]-3-hydroxybutanoate;

cyclopentyl (2S)-2-[(2-{[2-(1,5-dimethyl-6-oxo-1,6-dihydropyridin-3-yl)-1-(oxan-4-ylmethyl)-1H-1,3-benzodiazol-6-yl]oxy}ethyl)amino]propanoate;

propan-2-yl (2S,3R)-2-({[2-(1,5-dimethyl-6-oxo-1,6-dihydropyridin-3-yl)-1-(oxan-3-ylmethyl)-1H-1,3-benzodiazol-5-yl]methyl}amino)-3-hydroxybutanoate;

propan-2-yl (2S,3R)-2-{[(1-{[(3S)-1-acetylpiperidin-3-yl]methyl}-2-(1,5-dimethyl-6-oxo-1,6-dihydropyridin-3-yl)-1H-1,3-benzodiazol-6-yl)methyl]amino}-3-hydroxybutanoate;

propan-2-yl (2S,3R)-2-({[2-(1,5-dimethyl-6-oxo-1,6-dihydropyridin-3-yl)-1-[(3R)-oxan-3-ylmethyl]-1H-1,3-benzodiazol-6-yl]methyl}amino)-3-hydroxybutanoate;

propan-2-yl (2S,3R)-2-({[2-(1,5-dimethyl-6-oxo-1,6-dihydropyridin-3-yl)-1-[(3R)-oxan-3-ylmethyl]-1H-1,3-benzodiazol-5-yl]methyl}amino)-3-hydroxybutanoate;

cyclobutyl (2R,3S)-2-({[2-(1,5-dimethyl-6-oxo-1,6-dihydropyridin-3-yl)-1-[(3R)-oxan-3-ylmethyl]-1H-1,3-benzodiazol-6-yl]methyl}amino)-3-hydroxybutanoate; and (3S)-oxolan-3-yl (2S,3R)-2-[(2-{[2-(1,5-dimethyl-6-oxo-1,6-dihydropyridin-3-yl)-1-(oxan-4-ylmethyl)-1H-1,3-benzodiazol-5-yl]oxy}ethyl)amino]-3-hydroxybutanoate, or a salt thereof.

13. The compound according to claim 1, which is (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate, of formula:

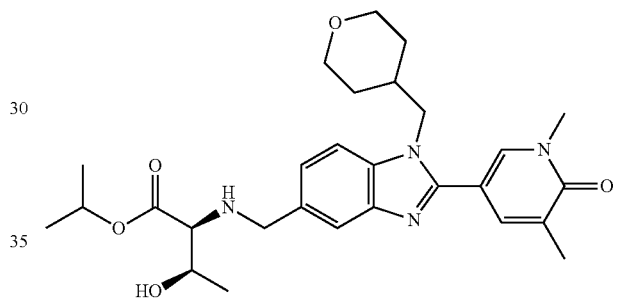

or a salt thereof.

14. The compound according to claim 1, which is (2S,3R)-2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoic acid, of formula:

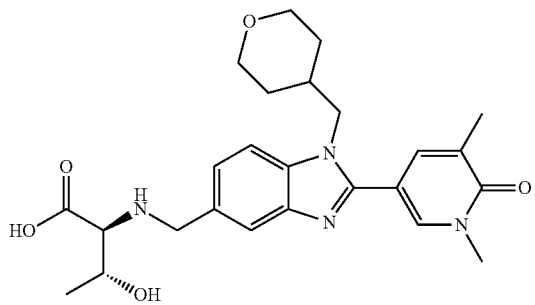 [SMILES: Cc1cc(-c2nc3cc(CN[C@H](C(=O)O)[C@@H](C)O)ccc3n2CC2CCOCC2)cn(C)c1=O]

or a salt thereof.

15. The compound according to claim 1, which is in the form of a pharmaceutically acceptable salt.

16. The compound according to claim 1, which is the 1,2-ethanedisulphonic acid salt of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate, of formula:

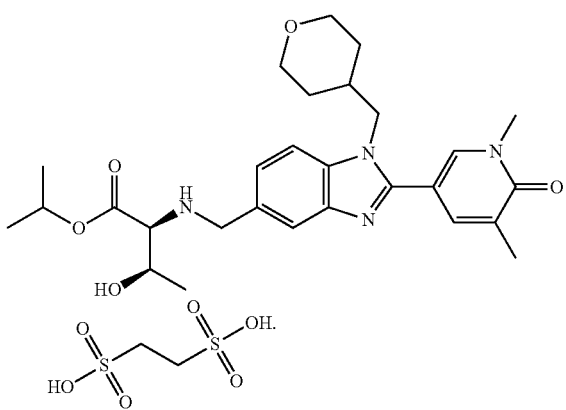

17. The compound according to claim 16, which is in crystalline form and is characterised by having significant X-ray powder diffraction (XRPD) peaks at 2θ values, +0.10 2 θ experimental error, of 5.4, 8.8, 9.9, 11.6, 13.8, 16.9, 18.0, 16.6, 19.1, 19.4, 19.8, 20.4, 20.9, 21.3, 22.0, 22.4, 22.9, 23.4, 24.9, and 25.1 degrees.

18. A pharmaceutical composition comprising the compound according to claim 15, and one or more pharmaceutically acceptable excipients.

19. A method of ameliorating or stabilizing rheumatoid arthritis and/or reducing or eliminating rheumatoid arthritis symptoms, which method comprises administering to a human subject in need thereof, a therapeutically effective amount of the compound according to claim 15.

20. The compound according to claim 1, which is (2S, 3R)-isopropyl 2-(((2-(1,5-dimethyl-6-oxo-1, 6-dihydropyridin-3-yl)-1-((tetrahydro-2H-pyran-4-yl)methyl)-1H-benzo[d]imidazol-5-yl) methyl)amino)-3-hydroxybutanoate, of formula:

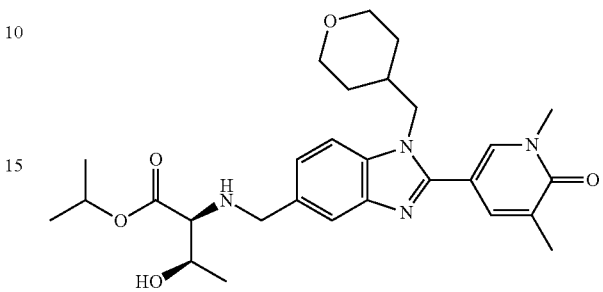

or a pharmaceutically acceptable salt thereof.

21. A pharmaceutical composition comprising the compound according to claim 20, and one or more pharmaceutically acceptable excipients.

22. A method of ameliorating or stabilizing rheumatoid arthritis and/or reducing or eliminating rheumatoid arthritis symptoms, which method comprises administering to a human subject in need thereof, a therapeutically effective amount of the compound according to claim 20.

* * * * *